(12) United States Patent
Zhou et al.

(10) Patent No.: US 12,421,523 B2
(45) Date of Patent: Sep. 23, 2025

(54) PLANTS WITH MODIFIED TRAITS

(71) Applicant: Nuseed Global Innovation Ltd, Manchester (GB)

(72) Inventors: XueRong Zhou, Harrison (AU); Qing Liu, Giraland (AU); Anna El Tahchy, Moncrieff (AU); Srinivas Belide, Moncrieff (AU); Madeline Claire Mitchell, Turner (AU); Uday Kumar Divi, Moncrieff (AU); Thomas Vanhercke, Kaleen (AU); James Robertson Petrie, Goulburn (AU); Surinder Pal Singh, Downer (AU); Allan Graham Green, Cremorne Point (AU)

(73) Assignee: NUSEED GLOBAL INNOVATION LTD., Manchester (GB)

( * ) Notice: Subject to any disclaimer, the term of this patent is extended or adjusted under 35 U.S.C. 154(b) by 0 days.

(21) Appl. No.: 18/516,336

(22) Filed: Nov. 21, 2023

(65) Prior Publication Data

US 2024/0200087 A1    Jun. 20, 2024

Related U.S. Application Data

(62) Division of application No. 16/329,939, filed as application No. PCT/AU2017/050948 on Sep. 1, 2017, now Pat. No. 11,859,193.

(30) Foreign Application Priority Data

Sep. 2, 2016    (AU) .................. 2016903541
Sep. 6, 2016    (AU) .................. 2016903577
Nov. 11, 2016   (AU) .................. 2016904611
Jan. 6, 2017    (WO) ............. PCT/AU2017/050012
Jul. 13, 2017   (AU) .................. 2017902756

(51) Int. Cl.
| | | |
|---|---|---|
| C12N 15/82 | (2006.01) | |
| A23K 10/12 | (2016.01) | |
| A23K 10/30 | (2016.01) | |
| C10L 1/02 | (2006.01) | |
| C11B 1/04 | (2006.01) | |
| C11B 1/06 | (2006.01) | |
| C11B 1/10 | (2006.01) | |
| C11C 3/00 | (2006.01) | |
| C12Q 1/6895 | (2018.01) | |

(52) U.S. Cl.
CPC .......... *C12N 15/8247* (2013.01); *A23K 10/12* (2016.05); *A23K 10/30* (2016.05); *C10L 1/026* (2013.01); *C11B 1/04* (2013.01); *C11B 1/06* (2013.01); *C11B 1/10* (2013.01); *C11C 3/003* (2013.01); *C12N 15/8218* (2013.01); *C12N 15/8251* (2013.01); *C12Q 1/6895* (2013.01); *C10L 2200/0476* (2013.01); *C10L 2200/0484* (2013.01); *C10L 2270/026* (2013.01); *C10L 2290/04* (2013.01); *C10L 2290/24* (2013.01); *C10L 2290/26* (2013.01); *C12Q 2600/13* (2013.01)

(58) Field of Classification Search
None
See application file for complete search history.

(56) References Cited

U.S. PATENT DOCUMENTS

| | | | |
|---|---|---|---|
| 4,670,613 | A | 6/1987 | Ruyter |
| 4,948,811 | A | 8/1990 | Spinner |
| 4,992,605 | A | 2/1991 | Craig |
| 5,500,361 | A | 3/1996 | Kinney |
| 5,807,893 | A | 9/1998 | Voelker |
| 5,912,416 | A | 6/1999 | Weisker |
| 6,100,077 | A | 8/2000 | Sturley |
| 6,344,548 | B1 | 2/2002 | Farese |
| 6,432,684 | B1 | 8/2002 | Mukerji |
| 6,998,516 | B2 | 2/2006 | Brar |
| 7,001,771 | B1 | 2/2006 | Morell |
| 7,045,326 | B2 | 5/2006 | Cases |
| 7,109,392 | B1 | 9/2006 | Broglie |
| 7,135,617 | B2 | 11/2006 | Lardizabal |
| 7,244,599 | B2 | 7/2007 | Tanner |
| 7,417,176 | B2 | 8/2008 | Lardizabal |
| 7,429,473 | B2 | 9/2008 | Milcamps |
| 7,521,593 | B2 | 4/2009 | Regina |
| 7,589,253 | B2 | 9/2009 | Green |

(Continued)

FOREIGN PATENT DOCUMENTS

| | | |
|---|---|---|
| EP | 1806398 | 7/2007 |
| EP | 1813664 A1 | 8/2007 |

(Continued)

OTHER PUBLICATIONS

Smith et al. (Nature Biotechnology, 15:1222-1223, 1997).*

(Continued)

*Primary Examiner* — Vinod Kumar

(74) *Attorney, Agent, or Firm* — Gary J. Gershik

(57) ABSTRACT

The present invention relates, inter alia, to vegetative plant parts, such as from a *Sorghum* sp. and/or a *Zea mays* plant, which comprise a total fatty acid (TFA) content which comprises fatty acids esterified in the form of triacylglycerols (TAG) and fatty acids in the form of lipids other than TAG, wherein the vegetative plant parts comprise greatly increased levels of TFA, for example a TFA content of about 5% (w/w dry weight). The present invention also relates to the use of the vegetative plant parts as a feedstuff, and/or to produce a feedstuff, for animal consumption.

5 Claims, 20 Drawing Sheets

Figure 1:
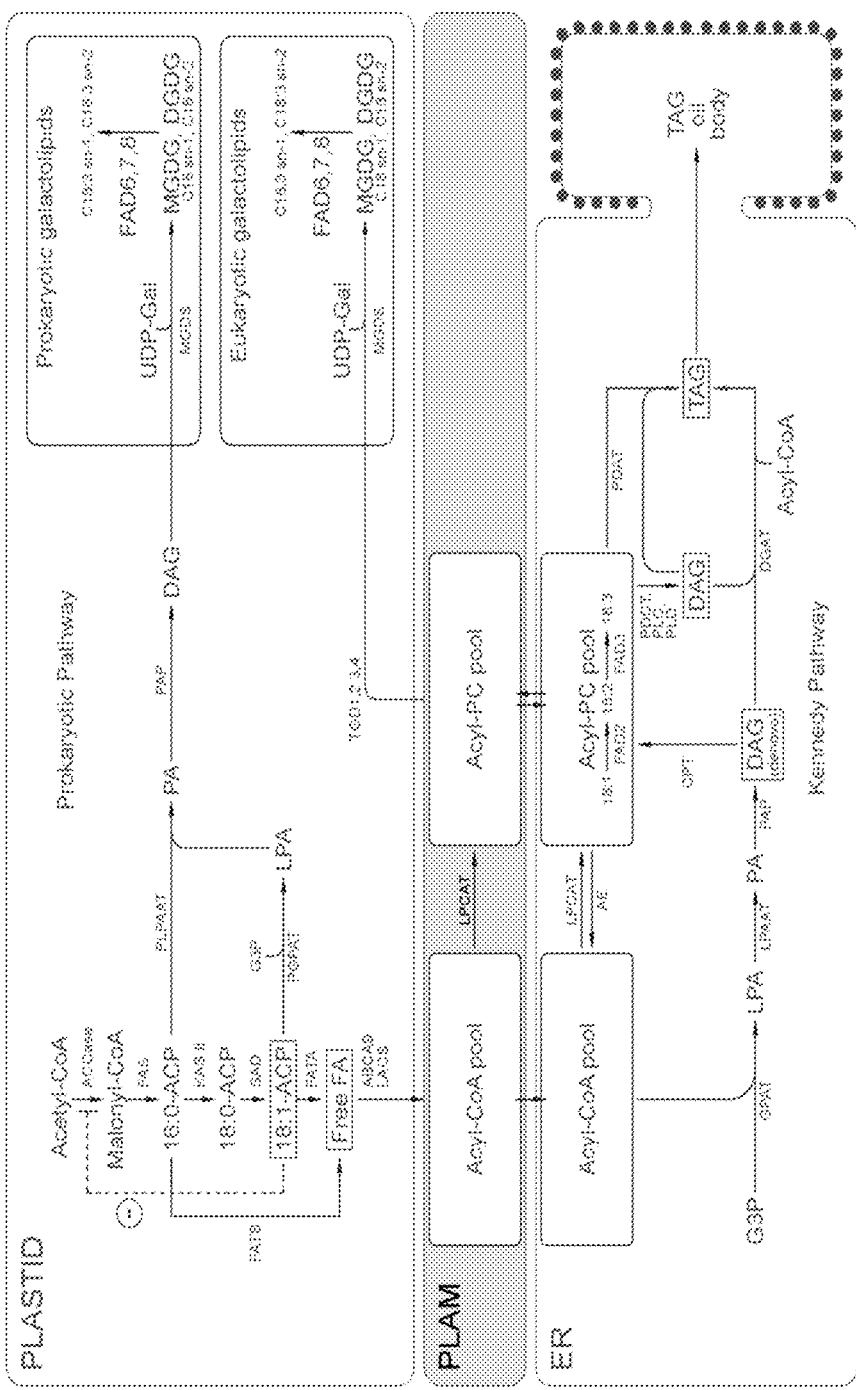

Specification includes a Sequence Listing.

(56) References Cited

U.S. PATENT DOCUMENTS

| | | |
|---|---|---|
| 7,619,105 B2 | 11/2009 | Green |
| 7,667,114 B2 | 2/2010 | Morell |
| 7,700,139 B2 | 4/2010 | Bird |
| 7,700,826 B2 | 4/2010 | Morell |
| 7,741,532 B2 | 6/2010 | Lardizabal |
| 7,790,955 B2 | 9/2010 | Li |
| 7,807,849 B2 | 10/2010 | Singh |
| 7,812,221 B2 | 10/2010 | Morell |
| 7,834,248 B2 | 11/2010 | Green |
| 7,834,250 B2 | 11/2010 | Singh |
| 7,888,499 B2 | 2/2011 | Regina |
| 7,892,803 B2 | 2/2011 | Tanner |
| 7,919,132 B2 | 4/2011 | Regina |
| 7,932,438 B2 | 4/2011 | Singh |
| 7,932,440 B2 | 4/2011 | Reid |
| 7,993,686 B2 | 8/2011 | Bird |
| 8,049,069 B2 | 11/2011 | Wu |
| 8,071,341 B2 | 12/2011 | Singh |
| 8,106,226 B2 | 1/2012 | Singh |
| 8,115,087 B2 | 2/2012 | Regina |
| 8,158,392 B1 | 4/2012 | Singh |
| 8,178,759 B2 | 5/2012 | Morell |
| 8,188,336 B2 | 5/2012 | Li |
| 8,269,082 B2 | 9/2012 | Millar |
| 8,288,572 B2 | 10/2012 | Singh |
| 8,501,262 B2 | 8/2013 | Bird |
| 8,530,724 B2 | 9/2013 | Whitelaw |
| 8,535,917 B2 | 9/2013 | Singh |
| 8,575,377 B2 | 11/2013 | Singh |
| 8,716,555 B2 | 5/2014 | Liu |
| 8,735,111 B2 | 5/2014 | Vanhercke |
| 8,778,644 B2 | 7/2014 | Singh |
| 8,809,026 B2 | 8/2014 | Vanhercke |
| 8,809,559 B2 | 8/2014 | Petrie |
| 8,816,106 B2 | 8/2014 | Damcevski |
| 8,853,432 B2 | 10/2014 | Singh |
| 8,921,652 B2 | 12/2014 | Liu |
| 9,057,075 B2 | 6/2015 | Liu |
| 9,061,992 B2 | 6/2015 | Vanhercke |
| 9,127,288 B2 | 9/2015 | Petrie |
| 9,512,438 B2 | 12/2016 | Vanhercke |
| 11,859,193 B2 | 1/2024 | Zhou |
| 2002/0104124 A1 | 8/2002 | Green |
| 2004/0221335 A1 | 11/2004 | Shewmaker |
| 2005/0106697 A1 | 5/2005 | Cases |
| 2005/0193446 A1 | 9/2005 | Zou |
| 2005/0262588 A1 | 11/2005 | Dehesh |
| 2006/0053512 A1 | 3/2006 | Bao |
| 2006/0094088 A1 | 5/2006 | Picataggio |
| 2006/0206963 A1 | 9/2006 | Voelker |
| 2008/0268539 A1 | 10/2008 | Singh |
| 2008/0289248 A1 | 11/2008 | Gao |
| 2008/0311580 A1 | 12/2008 | Abrahams |
| 2009/0061492 A1 | 3/2009 | Benning |
| 2009/0308041 A1 | 12/2009 | Whitelaw |
| 2010/0105078 A1 | 4/2010 | Benning |
| 2010/0184130 A1 | 7/2010 | Koprowski |
| 2010/0192457 A1 | 8/2010 | Tsurutani |
| 2010/0221400 A1 | 9/2010 | Chapman |
| 2010/0257639 A1 | 10/2010 | Bruccoleri |
| 2011/0015415 A1 | 1/2011 | Singh |
| 2011/0045127 A1 | 2/2011 | Ral |
| 2011/0054198 A1 | 3/2011 | Singh |
| 2011/0126325 A1 | 5/2011 | Zhou |
| 2011/0190521 A1 | 8/2011 | Damcevski |
| 2011/0201065 A1 | 8/2011 | Singh et al. |
| 2011/0218348 A1 | 9/2011 | Zhou |
| 2011/0223311 A1 | 9/2011 | Liu |
| 2011/0229623 A1 | 9/2011 | Liu |
| 2011/0281818 A1 | 11/2011 | Jenkins et al. |
| 2011/0314725 A1 | 12/2011 | Petrie |
| 2012/0016144 A1 | 1/2012 | Petrie et al. |
| 2012/0029252 A1 | 2/2012 | Lissianski |
| 2012/0041218 A1 | 2/2012 | Singh et al. |
| 2012/0055077 A1 | 3/2012 | Savage |
| 2012/0114770 A1 | 5/2012 | Regina |
| 2012/0129805 A1 | 5/2012 | Li |
| 2012/0208198 A1 | 8/2012 | Bogs et al. |
| 2012/0237949 A1 | 9/2012 | Benning |
| 2012/0278951 A1 | 11/2012 | Roberts |
| 2013/0059351 A1 | 3/2013 | Tojo |
| 2013/0115362 A1 | 5/2013 | Regina |
| 2013/0164798 A1 | 6/2013 | Vanhercke |
| 2013/0247451 A1 | 9/2013 | Vanhercke |
| 2013/0288318 A1 | 10/2013 | Wood |
| 2014/0020133 A1 | 1/2014 | Benning |
| 2014/0031573 A1 | 1/2014 | Shanklin |
| 2014/0120225 A1 | 5/2014 | Whitelaw |
| 2014/0228585 A1 | 8/2014 | Benning |
| 2014/0256006 A1 | 9/2014 | Vanhercke |
| 2014/0371477 A1 | 12/2014 | Wood |
| 2015/0037457 A1 | 2/2015 | Vanhercke |
| 2015/0176017 A1 | 6/2015 | Liu |
| 2015/0267216 A1 | 9/2015 | Vanhercke |
| 2015/0337017 A1 | 11/2015 | Xu |
| 2015/0353863 A1 | 12/2015 | Petrie |
| 2016/0002566 A1 | 1/2016 | Vanhercke |
| 2016/0002651 A1 | 1/2016 | Xu |
| 2017/0037320 A1 | 2/2017 | Vanhercke |

FOREIGN PATENT DOCUMENTS

| | | |
|---|---|---|
| EP | 1837397 | 9/2007 |
| EP | 1944375 | 7/2008 |
| JP | H06-504439 | 8/1992 |
| JP | H10-509863 | 3/1996 |
| JP | 2003-508061 | 3/2001 |
| WO | WO 1998/55631 | 12/1998 |
| WO | WO 1999/049050 | 9/1999 |
| WO | WO 1999/67268 | 12/1999 |
| WO | WO 1999/67403 | 12/1999 |
| WO | WO 2000/01713 | 1/2000 |
| WO | WO 2000/011176 | 3/2000 |
| WO | WO 2000/32756 | 6/2000 |
| WO | WO 2000/32793 | 6/2000 |
| WO | WO 2000/36114 | 6/2000 |
| WO | WO 2000/60095 | 10/2000 |
| WO | WO 2000/66750 | 10/2000 |
| WO | WO 2000/66749 | 11/2000 |
| WO | WO 2001/070777 | 9/2001 |
| WO | WO 2002/004648 | 1/2002 |
| WO | WO 2002/072775 | 9/2002 |
| WO | WO 2004/011671 | 2/2004 |
| WO | WO 2004/042014 | 5/2004 |
| WO | WO 2005/003322 | 1/2005 |
| WO | WO 2005/063988 | 5/2005 |
| WO | WO 2005/103253 | 11/2005 |
| WO | WO 2006/007432 | 1/2006 |
| WO | WO 2007/045019 | 4/2007 |
| WO | WO 2007/101273 | 9/2007 |
| WO | WO 2007/103738 | 9/2007 |
| WO | WO 2007/107738 | 9/2007 |
| WO | WO 2007/141257 | 12/2007 |
| WO | WO 2007/149583 | 12/2007 |
| WO | WO 2008/006207 | 1/2008 |
| WO | WO 2008/060595 | 5/2008 |
| WO | WO 2008/025068 | 6/2008 |
| WO | WO 2008/068498 A2 | 6/2008 |
| WO | WO 2008/119082 | 10/2008 |
| WO | WO 2008/130248 | 10/2008 |
| WO | WO 2008/147935 | 12/2008 |
| WO | WO 2008/157226 | 12/2008 |
| WO | WO 2008/157827 | 12/2008 |
| WO | WO 2009/027335 | 3/2009 |
| WO | WO 2009/073822 | 6/2009 |
| WO | WO 2009/085169 | 7/2009 |
| WO | WO 2003/078639 | 9/2009 |
| WO | WO 2009/129582 | 10/2009 |
| WO | WO 2009/143397 | 11/2009 |
| WO | WO 2009/143398 | 11/2009 |
| WO | WO 2009/143401 | 11/2009 |
| WO | WO 2009/147409 | 12/2009 |
| WO | WO 2010/009499 | 1/2010 |
| WO | WO 2010/009500 | 1/2010 |

(56) References Cited

FOREIGN PATENT DOCUMENTS

| | | |
|---|---|---|
| WO | WO 2010/057246 | 5/2010 |
| WO | WO 2010/088426 | 8/2010 |
| WO | WO 2011/048119 A2 | 4/2011 |
| WO | WO 2011/053169 | 5/2011 |
| WO | WO 2011/062748 | 5/2011 |
| WO | WO 2011/082253 | 7/2011 |
| WO | WO 2011/123897 A1 | 10/2011 |
| WO | WO 2011/127118 | 10/2011 |
| WO | WO 2012/000033 A1 | 1/2012 |
| WO | WO 2012/000026 | 5/2012 |
| WO | WO 2012/092644 A1 | 7/2012 |
| WO | WO 2013/003608 | 1/2013 |
| WO | WO 2013/022353 | 2/2013 |
| WO | WO 2013/033369 A2 | 3/2013 |
| WO | WO 2013/096562 | 6/2013 |
| WO | WO 2013/096993 A | 7/2013 |
| WO | WO 2013/096993 A1 | 7/2013 |
| WO | WO 2013/185184 | 12/2013 |
| WO | WO 2014/068437 | 5/2014 |
| WO | WO 2014/068438 | 5/2014 |
| WO | WO 2014/068439 | 5/2014 |
| WO | WO 2014/100467 A1 | 6/2014 |
| WO | WO-2016004473 A1 * | 1/2016 ............. C10B 53/02 |

OTHER PUBLICATIONS

Bork et al. (TIG, 12:425-427, 1996).*
Doerks et al., (TIG, 14:248-250, 1998).*
Gutterson (HortScience 30:964-966, 1995).*
Bruening (Proc. Natl. Acad. Sci., 95:13349-13351, 1998).*
Elomaa et al. (Molecular Breeding, 2:41-50, 1996).*
Colliver et al. (Plant molecular Biology, 35:509-522, 1997).*
Emery et al. (Current Biology 13:1768-1774, 2003).*
Nunes et al. (Planta 224:125-132; 2006).*
Arziman et al. (Nucleic Acids Research, 33:582-588, 2005).*
Bonawitz et al.,(Annu. Rev. Genet. 44: 337-363, 2010).*
Paul et al. (Plant Cell Reports; 35:1417-1427; 2016).*
Nov. 14, 2017 International Search Report issued in connection with International Application No. PCT/AU2017/050948.
Nov. 14, 2017 Written Opinion issued in connection with International Application No. PCT/AU2017/050948.
Divi et al., Plant & Cell Physiology (2015) 57(1): 125-137.
John Moran, Tropical Dairy Farming: Feeding Management for Small Holder Dairy Farmers in Humid Topics 83-97 (2005).
Feb. 28, 2021 Partial European Search Report issued in connection with corresponding European Patent Application No. 17844702.5.
Jan. 20, 2021 Office Action issued in connection with corresponding Russian Patent Application No. 2019109455.
Kelly, A.A. et al. "The Sugar-Dependent1 Lipase Limits Triacylglycerol Accumulation in Vegetative Tissues of *Arabidopsis*", Plant Physiology, 162: 1282-1289 (Jul. 2013).
Vanhercke, T. et al. "Metabolic engineering of biomass for high energy density: oilseed-like triacylglycerol yields from plant leaves", Plant Biotechnology, 12: 231-239 (2014).
Sep. 6, 2021 Office Action issued in relation to the counterpart Ukrainian Patent Application No. a201903090 including English translation thereof.
Apr. 20, 2021 Request for Further Processing and Response to Communication under Rule 70(2) and Rule 70a (2) EPC filed in connection with European Patent Application No. 17844702.5.
Jun. 17, 2021 Office Action and Search Report issued in connection with corresponding Russian Patent Application No. 2019109455 including English language translation thereof.
Jul. 1, 2022 Office Action and Search Report issued in connection with corresponding Argentinian Patent Application No. 20170102448.
Alvarez, M. L., et al. (2000). Silencing of HMW glutenins in transgenic wheat expressing extra HMW subunits. *Theoretical and Applied Genetics*, 100(2), 319-327.
Bartlett, J. G., et al. (2008). High-throughput Agrobacterium-mediated barley transformation. *Plant Methods*, 4(1), 22.

Bates, P. D. (2016). Understanding the control of acyl flux through the lipid metabolic network of plant oil biosynthesis. Biochimica et Biophysica Acta(BBA)—Molecular and Cell Biology of Lipids, 1861(9), 1214-1225.
Baud, S., et al. (2007). Wrinkled1 specifies the regulatory action of Leafy COTYLEDON2 towards fatty acid metabolism during seed maturation in *Arabidopsis*. The Plant Journal, 50(5), 825-838.
Bäumlein, H., et al. (1992). Cis-analysis of a seed protein gene promoter: the conservative RY repeat CATGCATG within the legumin box is essential for tissue-specific expression of a legumin gene. The Plant Journal, 2(2), 233-239.
Belide, S., et al. (2013). Rapid expression and validation of seed-specific constructs in transgenic LEC2 induced somatic embryos of *Brassica napus*. Plant Cell, Tissue and Organ Culture (PCTOC), 113(3), 543-553.
Bibikova, M., et al. (2002). Targeted chromosomal cleavage and mutagenesis in *Drosophila* using zinc-finger nucleases. Genetics, 161 (3), 1169-1175.
Bihmidine, S., et al. (2015). Sucrose accumulation in sweet sorghum stems occurs by apoplasmic phloem unloading and does not involve differential sucrose transporter expression. BMC plant biology, 15 (1), 186.
Bihmidine, S., et al. (2016). Tonoplast Sugar Transporters (SbTSTs) putatively control sucrose accumulation in sweet sorghum stems. Plant signaling & behavior, 11(1), e1117721.
Bourque, J. E. (1995). Antisense strategies for genetic manipulations in plants. Plant Science, 105(2), 125-149.
Boutilier, K., et al. (2002). Ectopic expression of Baby Boom triggers a conversion from vegetative to embryonic growth. The Plant Cell, 14(8), 1737-1749.
Bradford, M. M. (1976). A rapid and sensitive method for the quantitation of microgram quantities of protein utilizing the principle of protein-dye binding. Analytical biochemistry, 72(1-2), 248-254.
Braun, D. M., & Slewinski, T. L. (2009). Genetic control of carbon partitioning in grasses: roles of sucrose transporters and tie-dyed loci in phloem loading. Plant Physiology, 149(1), 71-81.
Broothaerts, W., et al. (2005). Gene transfer to plants by diverse species of bacteria. Nature, 433(7026), 629-633.
Browse, J., et al. (1986). Fluxes through the prokaryotic and eukaryotic pathways of lipid synthesis in the '16: 3' plant *Arabidopsis thaliana*. Biochemical Journal, 235(1), 25-31.
Buchanan-Wollaston, V. (1994). Isolation of cDNA clones for genes that are expressed during leaf senescence in *Brassica napus* (identification of a gene encoding a senescence-specific metallothionein-like protein). Plant Physiology, 105(3), 839-846.
Busk, P. K., et al. (1997). Regulatory elements in vivo in the promoter of the abscisic acid responsive gene rab17 from maize. The Plant Journal, 11(6), 1285-1295.
Capuano, F., et al. (2007). Properties and exploitation of oleosins. Biotechnology advances, 25(2), 203-206.
Chikwamba, R. K., et al. (2003). Localization of a bacterial protein in starch granules of transgenic maize kernels. Proceedings of the National Academy of Sciences, 100 (19), 11127-11132.
Chung, B. Y., et al. (2006). Effect of 5'UTR introns on gene expression in *Arabidopsis thaliana*. BMC genomics, 7(1), 120.
Cong, L., et al. (2013). Multiplex genome engineering using CRISPR/Cas systems. Science, 339 (6121), 819-823.
Coutu, C., et al. (2007). pORE: a modular binary vector series suited for both monocot and dicot plant transformation. Transgenic research, 16(6), 771-781.
Dahlqvist, A., et al. (2000). Phospholipid: diacylglycerol acyltransferase: an enzyme that catalyzes the acyl-CoA-independent formation of triacylglycerol in yeast and plants. Proceedings of the National Academy of Sciences, 97 (12), 6487-6492.
Damaj, M. B., et al. (2010). Sugarcane Dirigent and O-methyltransferase promoters confer stem-regulated gene expression in diverse monocots. Planta, 231(6), 1439-1458.
Dauk, M., et al. (2007). A FAD2 homologue from Lesquerella lindheimeri has predominantly fatty acid hydroxylase activity. Plant science, 173 (1), 43-49.

(56) References Cited

OTHER PUBLICATIONS

Ellerström, M., et al. (1996). Functional dissection of a napin gene promoter: identification of promoter elements required for embryo and endosperm-specific transcription. Plant molecular biology, 32(6), 1019-1027.
Fan, J., et al. (2013). Phospholipid: diacylglycerol acyltransferase-mediated triacylglycerol biosynthesis is crucial for protection against fatty acid-induced cell death in growing tissues of *Arabidopsis*. The Plant Journal, 76(6), 930-942.
Fan, J., et al. (2014). *Arabidopsis* lipins, PDAT1 acyltransferase, and SDP1 triacylglycerol lipase synergistically direct fatty acids toward β-oxidation, thereby maintaining membrane lipid homeostasis. The Plant Cell, 26(10), 4119-4134.
Fan, J., et al. (2015). *Arabidopsis* Trigalactosyldiacylglycerol5 interacts with TGD1, TGD2, and TGD4 to facilitate lipid transfer from the endoplasmic reticulum to plastids. The Plant Cell, 27(10), 2941-2955.
Protein Sources for the Animal Feed Industry. Proceedings of the Food And Agriculture Organization of the United Nations Protein Sources, Expert Consultation and Workshop Bangkok, Apr. 29, 2002 Uto May 3, 2002.
Finkelstein, R. R., et al. (1998). The *Arabidopsis* abscisic acid response locus ABI4 encodes an APETALA2 domain protein. The Plant Cell, 10(6), 1043-1054.
Gazzarrini, S., et al. (2004). The transcription factor FUSCA3 controls developmental timing in *Arabidopsis* through the hormones gibberellin and abscisic acid. Developmental cell, 7(3), 373-385.
Ghosh, A. K., et al. (2009). At4g24160, a soluble acyl-coenzyme A-dependent lysophosphatidic acid acyltransferase. Plant physiology, 151(2), 869-881.
Gidda, S. K., et al. (2013). Lipid droplet-associated proteins (LDAPs) are involved in the compartmentalization of lipophilic compounds in plant cells. Plant signaling & behavior, 8 (11), e27141.
Girijashankar, V., & Swathisree, V. (2009). Genetic transformation of Sorghum bicolor. Physiology and molecular biology of plants, 15(4), 287-302.
Gould, J., et al. (1991). Transformation of *Zea mays* L. using Agrobacterium tumefaciens and the shoot apex. Plant physiology, 95(2), 426-434.
Guan, H. P., et al. (2015). Glucagon receptor antagonism induces increased cholesterol absorption. Journal of lipid research, 56(11), 2183-2195.
Gurel, S., et al. (2009). Efficient, reproducible Agrobacterium-mediated transformation of sorghum using heat treatment of immature embryos. Plant cell reports, 28(3), 429-444.
Gutiérrez, S. P., et al. (2013). Protein body formation in stable transgenic tobacco expressing elastin-like polypeptide and hydrophobin fusion proteins. BMC biotechnology, 13(1), 40.
Hinchee, M. A., et al. (1988). Production of transgenic soybean plants using Agrobacterium-mediated DNA transfer. Bio/technology, 6(8), 915-922.
Horvath, H., et al. (2000). The production of recombinant proteins in transgenic barley grains. Proceedings of the National Academy of Sciences, 97(4), 1914-1919.
Huang, A. H. (1996). Oleosins and oil bodies in seeds and other organs. Plant physiology, 110(4), 1055.
Huang, M. D., & Huang, A. H. (2016). Subcellular lipid droplets in vanilla leaf epidermis and avocado mesocarp are coated with oleosins of distinct phylogenic lineages. Plant physiology, 171(3), 1867-1878.
Ikeda, M., et al. (2006). Embryogenesis-related genes; its expression and roles during somatic and zygotic embryogenesis in carrot and *Arabidopsis*. Plant Biotechnology, 23(2), 153-161.
Iwabuchi, M., et al. (2003). Δ12-oleate desaturase-related enzymes associated with formation of conjugated trans-Δ11, cis-Δ13 double bonds. Journal of Biological Chemistry, 278 (7), 4603-4610.
Jiang, W., et al. (2013). Demonstration of CRISPR/Cas9/sgRNA-mediated targeted gene modification in *Arabidopsis*, tobacco, sorghum and rice. Nucleic acids research, 41(20), e188-e188.
Kereszt, A., et al. (2007). Agrobacterium rhizogenes-mediated transformation of soybean to study root biology. Nature protocols, 2(4), 948.
Kim, Y. G., et al. (1996). Hybrid restriction enzymes: zinc finger fusions to Fok I cleavage domain. Proceedings of the National Academy of Sciences, 93(3), 1156-1160.
Kim, M. J., et al. (2016). The mediator complex MED15 subunit mediates activation of downstream lipid-related genes by the Wrinkled1 transcription factor. Plant physiology, 171(3), 1951-1964.
Klemens, P. A., et al. (2013). Overexpression of the vacuolar sugar carrier AtSWEET16 modifies germination, growth, and stress tolerance in *Arabidopsis*. Plant Physiology, 163(3), 1338-1352.
Kwong, R. W., et al. (2003). Leafy Cotyledon1-Like defines a class of regulators essential for embryo development. The Plant Cell, 15(1), 5-18.
Lacroix, B., et al. (2008). Association of the Agrobacterium T-DNA-protein complex with plant nucleosomes. Proceedings of the National Academy of Sciences, 105(40), 15429-15434.
Laemmli, U. K. (1970). Cleavage of structural proteins during the assembly of the head of bacteriophage T4. nature, 227(5259), 680-685.
Laibach, N., et al. (2018). Small rubber particle proteins from Taraxacum brevicorniculatum promote stress tolerance and influence the size and distribution of lipid droplets and artificial poly (cis-1, 4-isoprene) bodies. The Plant Journal, 93(6), 1045-1061.
Larkin, P. J., et al. (1996). Transgenic white clover. Studies with the auxin-responsive promoter, GH3, in root gravitropism and lateral root development. Transgenic research, 5(5), 325-335.
Laux, T., et al. (1996). The WUSCHEL gene is required for shoot and floral meristem integrity in *Arabidopsis*. Development, 122(1), 87-96.
Li, S. F., et al. (1996). A novel myb-related gene from *Arabidopsis thaliana*. FEBS letters, 379(2), 117-121.
Li, Y., et al. (2006). Oil content of *Arabidopsis* seeds : the influence of seed anatomy, light and plant-to-plant variation. Phytochemistry, 67(9), 904-915.
Li, J., et al. (2016). Development of a Simple and Efficient Method for Agrobacterium-Mediated Transformation in Sorghum. International Journal of Agriculture & Biology, 18(1).
Linder, M. B., Szilvay, G. R., Nakari-Setälä, T., & Penttila, M. E. (2005). Hydrophobins: the protein-amphiphiles of filamentous fungi. FEMS microbiology reviews, 29(5), 877-896.
Liu, G., & Godwin, I. D. (2012). Highly efficient sorghum transformation. Plant cell reports, 31(6), 999-1007.
Liu, Y. F., et al. (2014). Soybean GmMYB73 promotes lipid accumulation in transgenic plants. BMC plant biology, 14(1), 73.
Liu, G., et al. (2015. A robust tissue culture system for sorghum [*Sorghum* bicolor (L.) *Moench*]. South African Journal of Botany, 98, 157-160.
Lu, B., et al. (2007). A small ATPase protein of *Arabidopsis*, TGD3, involved in chloroplast lipid import. Journal of Biological Chemistry, 282(49), 35945-35953.
Ma, W., et al. (2016). 14-3-3 protein mediates plant seed oil biosynthesis through interaction with AtWRI1. The Plant Journal, 88(2), 228-235.
Maceachran, D. P., et al. (2010). The Rhodococcus opacus PD630 heparin-binding hemagglutinin homolog TadA mediates lipid body formation. Appl. Environ. Microbiol., 76(21), 7217-7225.
Matsuoka, M., & Minami, E. I. (1989). Complete structure of the gene for phosphoenolpyruvate carboxylase from maize. European journal of biochemistry, 181(3), 593-598.
Matsuoka, M., et al. (1994). The promoters of two carboxylases in a C4 plant (maize) direct cell-specific, light-regulated expression in a C3 plant (rice). The Plant Journal, 6(3), 311-319.
McCleary, B. V., et al. (2010). Determination of total dietary fiber (CODEX definition) by enzymatic-gravimetric method and liquid chromatography: Collaborative study. Journal of AOAC international, 93(1), 221-233.
McCleary, B. V., et al. (2015). Determination of total dietary fibre and available carbohydrates: A rapid integrated procedure that simulates in vivo digestion. Starch-Stärke, 67(9-10), 860-883.
McElroy, D., et al. (1990). Isolation of an efficient actin promoter for use in rice transformation. The plant cell, 2(2), 163-171.

(56) References Cited

OTHER PUBLICATIONS

McKinley, B., et al. (2016). Dynamics of biomass partitioning, stem gene expression, cell wall biosynthesis, and sucrose accumulation during development of Sorghum bicolor. The Plant Journal, 88(4), 662-680.
Meier, I., et al. (1997). The tomato RBCS3A promoter requires integration into the chromatin for correct organ-specific regulation. FEBS letters, 415(1), 91-95.
Mizuno, H., et al. (2016). The sorghum SWEET gene family: stem sucrose accumulation as revealed through transcriptome profiling. Biotechnology for biofuels, 9(1), 127.
Mojica, F. J., et al. (2000). Biological significance of a family of regularly spaced repeats in the genomes of Archaea, Bacteria and mitochondria. Molecular microbiology, 36(1), 244-246.
Mudge, S. R., et al. (2013). Mature-stem expression of a silencing-resistant sucrose isomerase gene drives isomaltulose accumulation to high levels in sugarcane. Plant biotechnology journal, 11(4), 502-509.
Murashige, T., & Skoog, F. (1962). A revised medium for rapid growth and bio assays with tobacco tissue cultures. Physiologia plantarum, 15(3), 473-497.
Murphy, D. J. (2012). The dynamic roles of intracellular lipid droplets: from archaea to mammals. Protoplasma, 249(3), 541-585.
Nishida, I., Tasaka, Y., Shiraishi, H., & Murata, N. (1993). The gene and the RNA for the precursor to the plastid-located glycerol-3-phosphate acyltransferase of Arabidopsis thaliana. Plant molecular biology, 21(2), 267-277.
Padidam, M. (2003). Chemically regulated gene expression in plants. Current opinion in plant biology, 6(2), 169-177.
Padidam, M., et al. (2003). Chemical-inducible, ecdysone receptor-based gene expression system for plants. Transgenic research, 12(1), 101-109.
Parthibane, V., et al. (2012). Oleosin is bifunctional enzyme that has both monoacylglycerol acyltransferase and phospholipase activities. Journal of Biological Chemistry, 287(3), 1946-1954.
Parthibane, V., et al. (2012). Serine/threonine/tyrosine protein kinase phosphorylates oleosin, a regulator of lipid metabolic functions. Plant physiology, 159(1), 95-104.
Perrin, Y., et al. (2000). Transgenic pea seeds as bioreactors for the production of a single-chain Fv fragment (scFV) antibody used in cancer diagnosis and therapy. Molecular Breeding, 6(4), 345-352.
Potenza, C., et al. (2004). Targeting transgene expression in research, agricultural, and environmental applications: promoters used in plant transformation. In Vitro Cellular & Developmental Biology-Plant, 40(1), 1-22.
Qiu, X., et al. (2001). Identification of a Δ4 Fatty Acid Desaturase from Thraustochytrium sp. Involved in the Biosynthesis of Docosahexanoic Acid by Heterologous Expression in Saccharomyces cerevisiae and Brassica juncea. Journal of Biological Chemistry, 276(34), 31561-31566.
Robson, P. R., et al. (2004). Leaf senescence is delayed in maize expressing the Agrobacterium IPT gene under the control of a novel maize senescence-enhanced promoter. Plant Biotechnology Journal, 2(2), 101-112.
Ruuska, S. A., et al. (2002). Contrapuntal networks of gene expression during Arabidopsis seed filling. The Plant Cell, 14(6), 1191-1206.
Saad, R. B., et al. (2011). Promoter of the AlSAP gene from the halophyte grass Aeluropus littoralis directs developmental-regulated, stress-inducible, and organ-specific gene expression in transgenic tobacco. Transgenic research, 20(5), 1003-1018.
Saha, S., et al. (2006). Cytosolic triacylglycerol biosynthetic pathway in oilseeds. Molecular cloning and expression of peanut cytosolic diacylglycerol acyltransferase. Plant Physiology, 141(4), 1533-1543.
Scott, R. W., et al. (2010). Elevation of oil body integrity and emulsion stability by polyoleosins, multiple oleosin units joined in tandem head-to-tail fusions. Plant biotechnology journal, 8(8), 912-927.

Shimada, T. L., & Hara-Nishimura, I. (2010). Oil-body-membrane proteins and their physiological functions in plants. Biological and Pharmaceutical Bulletin, 33(3), 360-363.
Stalker, D. M., et al. (1988). Purification and properties of a nitrilase specific for the herbicide bromoxynil and corresponding nucleotide sequence analysis of the bxn gene. Journal of Biological Chemistry, 263(13), 6310-6314.
Tai, S. S., et al. (2002). Gene family of oleosin isoforms and their structural stabilization in sesame seed oil bodies. Bioscience, biotechnology, and biochemistry, 66(10), 2146-2153.
Tan, H., et al. (2011). Enhanced Seed Oil Production in Canola by Conditional Expression of Brassica napus Leafy COTYLEDON1 (BnLEC1) and LEC1-LIKE (BnL1L) in Developing Seeds 1.
Taylor, C. B. (1997). Comprehending cosuppression. The Plant Cell, 9(8), 1245.
Thillet, J., et al. (1988). Site-directed mutagenesis of mouse dihydrofolate reductase. Mutants with increased resistance to methotrexate and trimethoprim. Journal of Biological Chemistry, 263(25), 12500-12508.
Tingay, S., et al. (1997). Agrobacterium tumefaciens-mediated barley transformation. The Plant Journal, 11(6), 1369-1376.
Ulmasov, T., et al. (1995). The soybean GH2/4 gene that encodes a glutathione S-transferase has a promoter that is activated by a wide range of chemical agents. Plant physiology, 108(3), 919-927.
Vieler, A., et al. (2012). A lipid droplet protein of Nannochloropsis with functions partially analogous to plant oleosins. Plant physiology, 158(4), 1562-1569.
Voinnet, O., et al. (2003). Retracted: An enhanced transient expression system in plants based on suppression of gene silencing by the p19 protein of tomato bushy stunt virus. The Plant Journal, 33(5), 949-956.
Wang, H., et al. (2002). A chromatin immunoprecipitation (ChIP) approach to isolate genes regulated by AGL15, a MADS domain protein that preferentially accumulates in embryos. The Plant Journal, 32(5), 831-843.
Wormit, A., et al. (2006). Molecular identification and physiological characterization of a novel monosaccharide transporter from Arabidopsis involved in vacuolar sugar transport. The Plant Cell, 18(12), 3476-3490.
Wu, E., et al. (2014). Optimized Agrobacterium-mediated sorghum transformation protocol and molecular data of transgenic sorghum plants. In Vitro Cellular & Developmental Biology-Plant, 50(1), 9-18.
Xie, K., et al. (2014). Genome-wide prediction of highly specific guide RNA spacers for CRISPR-Cas9-mediated genome editing in model plants and major crops. Molecular plant, 7(5), 923-926.
Yamagishi, K., et al. (2005). TANMEI/EMB2757 encodes a WD repeat protein required for embryo development in Arabidopsis. Plant physiology, 139(1), 163-173.
Yamasaki, K., et al. (2004). Solution structure of the B3 DNA binding domain of the Arabidopsis cold-responsive transcription factor RAV1. The Plant Cell, 16(12), 3448-3459.
Yang, D., et al. (2003). Expression and localization of human lysozyme in the endosperm of transgenic rice. Planta, 216(4), 597-603.
Yen, C. L. E., et al. (2005). The triacylglycerol synthesis enzyme DGAT1 also catalyzes the synthesis of diacylglycerols, waxes, and retinyl esters. Journal of lipid research, 46(7), 1502-1511.
Yokoyama, R., et al. (1994). The rolC promoter of Agrobacterium rhizogenes Ri plasmid is activated by sucrose in transgenic tobacco plants. Molecular and General Genetics MGG, 244(1), 15-22.
Zale, J., et al. (2016). Metabolic engineering of sugarcane to accumulate energy-dense triacylglycerols in vegetative biomass. Plant biotechnology journal, 14(2), 661-669.
Zheng, Y., et al. (2009). Global identification of targets of the Arabidopsis MADS domain protein AGAMOUS-Like15. The Plant Cell, 21(9), 2563-2577.
Zolman, B. K., et al. (2001). The Arabidopsis pxa1 mutant is defective in an ATP-binding cassette transporter-like protein required for peroxisomal fatty acid β-oxidation. Plant Physiology, 127(3), 1266-1278.

(56) References Cited

OTHER PUBLICATIONS

Sep. 16, 2022 Office Action issued in connection with corresponding Russian Federation Patent Application 2019109455 including English language thereof.
Abdullah, R., Cocking, E. C., & Thompson, J. A. (Dec. 1986). Efficient plant regeneration from rice protoplasts through somatic embryogenesis. Biotechnology, 4, 1087-1090.
Agarwal et el. (2003) "Cottonseed Oil Quality, Utilization and Processing" CICR Technical Bulletin No. 25, pp. 1-16.
Aghoram, K., Wilson, R. F., Burton, J. W., Dewey, R. E. 2006. A mutation in a 3-keto-acyl-acp synthase ii gene is associated with elevated palmitic acid levels in soybean seeds. Crop Sci. 46:2453-2459.
Akagi et al. (1995) Nucleotide Sequence of a Stearoyl-Acel carrier Protein Desaturase cDNA from Developing Seeds of Rice. Plant Physiol. 108, 845-846.
Alemanno et al. (2008) "Characterization of leafy cotyledon1-like during embryogenesis in *Theobroma cacao* L." Planta 227:853-866.
Almeida and Allshire, (2005) "RNA silencing and genome regulation." Trends in Cell Biology, 15:251-258.
Alonso et al. (2010) "Catalytic conversion of biomass to biofuels" Green Chem. 12:1493-1513.
Anai et al. (2003) Improvement of rice (*Oryza sativa* L.) seed oil quality through introduction of a soybean microsomal omega-3 fatty acid desaturase gene. Plant Cell Rep. 21, 988-992.
Andrianov et al. (2010) "Tobacco as a production platform for biofuel: overexpression of *Arabidopsis* DGAT and LEC2 genes increases accumulation and shifts the composition of lipids in green biomass" Plant Biotech. J. 8:277-287.
Apr. 15, 2016 Response to Office Action issued Jan. 15, 2016, filed in connection with U.S. Appl. No. 14/729,754, filed Jun. 3, 2015.
Apr. 17, 2018 Second Office Action issued in connection with Mexican Patent Application MX/a/2014/007964.
Apr. 20, 2018 Examination Report issued in connection with Philippine Patent Application No. 1/2014/501474.
Apr. 26, 2017 Office Action, issued in connection with Ukrainian Patent Application No. 201408514, including English language translation.
Apr. 28, 2015 Notice of Allowance, issued in connection with U.S. Appl. No. 14/283,728, filed May 21, 2014.
Apr. 30, 2013 Office Action, issued in connection with U.S. Appl. No. 13/725,404, filed Dec. 21, 2012.
Ascherio and Willett (1997) "Health effects of trans fatty acids" Am. J. Clin. Nutr. 66: 1006S-1010S.
Aug. 1, 2018 Second Office Action issued in connection with Ukrainian Patent Application No. a 2014 08514, including English language translation thereof.
Aug. 17, 2016 Response to the Rules 70 (2) and 70a (2) Communication, filed in connection with European patent application 12863568.7.
Aug. 17, 2018 Office Action issued in connection with Canadian Patent Application No. 2,860,434.
Aug. 20, 2018 Response to the Apr. 20, 2018 Office Action issued in connection with Philippine Patent Application No. 1-2014-501474.
Aug. 22, 2016 Second Examination Report, issued in connection with Australian Patent Application No. 2013205482.
Aug. 27, 2015 First Office Action, issued in connection with Chinese Patent Application No. 201280070729. 5, including English language translation.
Aug. 8, 2016 Response to First Examination Report, filed in connection with Australian Patent Application No. 2013205482.
Awai et al., (2006) "A phosphatidic acid-binding protein of the chloroplast inner envelope membrane involved in lipid trafficking" PNAS 103 (28):10817-22.
Bao and Ohlrogge, (1999) "Supply of Fatty Acid is One Limiting Factor in the Accumulation of Triacylglycerol in Developing Embryos." Plant Physiology, 120:1057-1062.
Barthole et al. (2011) "Controlling lipid accumulation in cereal grains" Plant Sci. 185-186:33-39.

Baumlein, H., et al., (1991) "A Novel Seed Protein Gene From Vicia faba Is Developmentally Regulated In Transgenic Tobacco And Arabidopsis Plants," Molecular And General Genetics, 225(3): 459-467.
Benning, (2008) "A role for lipid trafficking in chloroplast biogenesis" Progress in Lipid Research 47, 381-389.
Benning, (2009) "Mechanisms of Lipid Transport Involved in Organelle Biogenesis in Plant Cells" Annu. Rev. Cell Dev. Biol. 25:71-91.
Bligh and Dyer (1959) "A Rapid Method of Total Lipid Extraction and Purification" Canadian Journal of Biochemistry and Physiology 37:911-917.
Bligh and Dyer, (1959) "Orange-red Flesh in Cod and Haddock" J. Fish. Res. Bd. Canada, 16(4):449-452.
Boggs et al. (1964) "Relation of Hexanal in Vapor Above Stored Potato Granules to Subjective Flavor Extimates." J. Food Sci. 29: 487-48.
Bonanome and Grundy (1988) "Effect of Dietary Stearic Acid on Plasma Cholesterol and Lipoprotein Levels" N. Engl. Med. 318: 1244-1248.
Bouvier-Nave et al. (2000) "Expression in yeast and tobacco of plant cDNAs encoding acyl CoA: diacylglycerol acyltransferase" European Journal of Biochemistry/FEBS 267:85-96.
Brandt et al., (1985) "Primary Structure of a B1 Hordein Gene from Barley" Carlsberg Res. Commun., 50:333-345.
Broun et al. (1998) "A bifunctional oleate 12-hydroxylase: desaturase from Lesquerella fenleri." The Pant Journal, 13(2):201-210.
Buhr et al. (2002) "Ribozyme termination of RNA transcripts down-regulate seed fatty acid genes in transgenic soybean" Plant J. 30: 155-163.
Burgal et al., (2008) "Metabolic engineering of hydroxy fatty acid production in plants: RcDGAT2 drives dramatic increases in ricinoleate levels in seed oil" Plant Biotechnology Journal 6(8):819-831.
Cao et al. (2007) "Catalytic properties of MGAT3, a putative triacylglycerol synthase" Journal of Lipid Research (48): 583-591.
Cao et al., (2003) "Properties of the Mouse Intestinal Acyl-CoA:Monoacylglycerol Acyltransferase, MGAT2." The Journal of Biological Chemistry, 278(28)25657-25669;.
Cases et al., (1998) "Identification of a gene encoding an acyl CoA:diacylglycerol acyltransferase, a key enzyme in triacylglycerol synthesis" PNAS 95:13018-13023.
Cases et al., J. Biol. Chem. (2001) "Cloning of DGAT2, a Second Mammalian Diacylglycerol Acyltransferase, and Related Family Members" 276(42):38870-38876;.
Cernac and Benning (2004) "Wrinkled1 encodes an AP2/EREB domain protein involved in the control of storage compound biosynthesis in *Arabidopsis*" Plant J. 40:575-585.
Champagne et al. (1995) "Stabilization of Brown Rice Products Using Ethanol Vapors as an Antioxidant Delivery System" Cereal Chem 72:255-258.
Chang et al., (1978) "Chemical Reactions Involved in the Deep-Fat Frying of Foods." Journal of American Oil Chemists' Society, 55:718-727.
Chapman et al. (2001) "Transgenic Cotton Plants with Increased Seed Oleic Acid Content" Journal of American Chemists' Chemistry; vol. 78 No. 9, 941-947.
Chappell et al. (1998) "Vegetable Oil Production: Industry Profile," Preliminary Final Report, EPA Contract # 68-04-0099, RTU Project # 7018-54, p. 1-1—5-26, retrieved from http://www.epa.gov/ttnecas1/regdata/IPs/Vegetable%20Oil_IP.pdf Apr. 23, 2013.
Cheng et al., (2003) "Identification of Acyl Coenzyme A:Monoacylglycerol Acyltransferase 3, an Intestinal Specific Enzyme Implicated in Dietary Fat Absorption." The Journal of Biological Chemistry, 278(126):13611-13614.
Cherry, (1983) "Cottonseed Oil" J. Am. Oil Chem. Soc. 60:360-367.
Choudhury et al. (1980) "Lipids in Developing and Mature Rice Grain" Phytochemistry 19: 1063-1069.
Cicero et al. (2001) "Rice bran oil and [gamma]-oryzanol in the treatment of hyperlipoproteinaemias and other conditions" Phytotherapy Research; vol. 15 No. 4, 277-289.
Clapp et al., (1993) "The 16-Kilodalton N-Terminal Fragment of Human Prolactin is a Potent Inhibitor of Angiogenesis" Endocrinology, 133(3):1292-1299.

(56) References Cited

OTHER PUBLICATIONS

Colot et al., (1987) "Localization of sequences in wheat endosperm protein genes which confer tissue-specific expression in tobacco" The EMBO Journal, 6(12):3559-3564.
Comai et al., (2004) "Efficient discovery of DNA polymorphisms in natural populations by Ecotilling" The Plant Journal, 37:778-786.
Connolly et al. (1998) GenBank Accession No. AC004236, NCBI, pp. 1-11.
Dec. 27, 2016 Examination Report, issued in connection with Russian Federation Patent Application No. 2014131059, including English Language Translation.
Dec. 31, 2013 Office Action, issued in connection with U.S. Appl. No. 13/725,404, filed Dec. 21, 2012.
Domergue et al., (2005) "In vivo characterization of the first acyl-CoA Δ6-desaturase from a member of the plant kingdom, the microalga *Ostreococcus tauri*." Biochem J. 389, 483-490.
Dougherty et al. (1995). Effects of diets containing high or low amounts of stearic acid on plasma lipoprotein fractions and fecal fatty acid excretion of men. Am. J. Clin. Nutr. 61:1120-1128.
Dowd et al., (2004) "Gene Expression Profile Changes in Cotton Root and Hypocotyl Tissues in Response to Infection with *Fusarium oxysporum* f. sp. *vasinfectum*" Molecular Plant-Microbe Interactions. 17: 654-667.
Dubois et al. (2007) "Fatty acid profiles of 80 vegetable oils with regard to their nutritional potential" European Journal of Lipid Science Technology 109(7):710-732.
Dulermo and Nicaud (2011) "Involvement of the G3P shuttle and β-oxidation pathway in the control of TAG synthesis and lipid accumulation in Yarrowia lipolytica" Metab. Eng. 13:482-491.
Durrett et al. (2008) "Plant triacylglycerols as feedstocks for the production of biofuels" Plant J. 54:593-607.
Eastmond, (2006) "Sugar-dependent1 Encodes a Patatin Domain Triacylglycerol Lipase That Initiates Storage oil Breakdown in Germinating *Arabidopsis* Seeds" The Plant Cell, vol. 18, 665-675.
Endalew et al. (2011) "Inorganic heterogeneous catalysts for biodiesel production from vegetable oils" Biomass and Bioenergy 35:3787-3809.
English translation of May 7, 2018 Office Action, issued in connection with Japanese Patent No. 2014-549274.
English translation of the Aug. 23, 2017 Office Action, issued in connection with Mexican Patent Application No. MX/a/2014/007964.
English translation of the Oct. 24, 2017 Office Action, issued in connection with Russian Patent Application No. 2014131059.
English translation of the Oct. 24, 2017 Office Action, issued in connection with Chinese Patent Application No. 201280070729.5; Feb. 18, 2014 Notice of Allowance, issued in connection with U.S. Appl. No. 13/725,404, filed Dec. 21, 2012.
File History for U.S. Pat. No. 2009-0308041, Whitelaw et al., Dec. 17, 2009 (U.S. Appl. No. 12/309,276, filed Jul. 6, 2009).
File History of U.S. Patent Application Publication No. 2011/0314725, Petrie et al., published Dec. 29, 2011 (U.S. Appl. No. 13/171,032, filed Jun. 28, 2011).
File History of U.S. Patent Application Publication No. 2013/0164798, Vanhercke et al., published Jun. 27, 2013 (U.S. Appl. No. 13/841,641, filed Mar. 15, 2013).
File History of U.S. Patent Publication No. 2011-0223311, Liu et al., published Sep. 15, 2011 (U.S. Appl. No. 13/011,773, filed Jan. 21, 2011).
File History of U.S. Patent Publication No. 2011-0229623, Liu et al., Sep. 22, 2011 (U.S. Appl. No. 13/011,779, filed Jan. 21, 2011).
Folch et al., (1957) "A Simple Method for the Isolation and Purification of total Lipides From Animal Tissues" J. Biol. Chem. 226: 497.
Fuller et al., (1966) "A Gas Chromatographic Method for Continuous Accelerated Study of 02 Uptake in Fats" JAOCS. 43: 477-478.
Ghosal et al. (2007) "*Saccharomyces cerevisiae* phospholipid: diacylglycerol acyl transferase (PDAT) devoid of its membrane anchor region is a soluble and active enzyme retaining its substrate specificities" Biochimica et Biophysica Acta 1771:1457-1463.
Goffman et al., (2003) "Genetic Diversity for Lipid Content and Fatty Acid Profile in Rice Bran, " Journal of the American Oil Chemists' Society 80:485-490.
Gong and Jiang (2011) "Biodiesel production with microalgae as feedstock: from strains to biodiesel" Biotechnol. Lett. 33:1269-1284.
Greenwell et al. (2010) "Placing microalgae on the biofuels priority list: a review of the technological challenges" J. R. Soc. Interface 7:703-726.
Ha (2005) "Bioactive components in rice bran oil improve lipid profiles in rats fed on high-cholesterol diet" Nutrition research 25, 597-606.
Haseloff, J. and Gerlach, W. L., (1988) "Simple RNA Enzymes With New And Highly Specific Endoribonuclease Activities," Nature, 334: 585-591.
Henikoff et al., (2004) "Tilling. Traditional Mutagenesis Meets Functional Genomics." Plant Physiology, 2004, 135:630-636.
Hu et al. (1997) "Dietary Fat Intake and the Rist of Coronary Heart Disease in Women." N. Engl. J. Med. 337:1491-1499.
Hutchins et al., (1968) "A New Process for the Selective Hydrogenation Cyclopropenoids in Cottonseed Oil" Journal of American Oil Chemists Society 45: 397-399.
International Search Report and Written Opinion of the International Searching Authority issued Apr. 8, 2013 in connection with PCT International Patent Application No. PCT/AU2012/001598, which claims priority of U.S. Appl. No. 61/718,563 filed Oct. 25, 2012 and U.S. Appl. No. 61/580,590, filed Dec. 27, 2011.
Jain et al., (2000) "Enhancement of seed oil content by expression of glycerol-3-phosphate acyltransferase genes" Biochemical Society Transactions 28(6):958-961.
Jako et al., (2001) "Seed-Specific Over-Expression of an *Arabidopsis* cDNA Encoding a Diacylglycerol Acyltransferase Enhances Seed Oil Content and Seed Weight" Plant Physiology 126:861-874.
James et al.(2010) "Disruption of the *Arabidopsis* CGI-58 homologue produces Chanarin-Dorfman-like lipid droplet accumulation in plants," 107(41):17833-17838 and supporting information pp. 1-3.
Jan. 13, 2017 Examination Report, issued in connection with Chilean Patent Application No. 201401715, including English Language Translation.
Jan. 15, 2016 Office Action, issued in connection with U.S. Appl. No. 14/729,754, filed Jun. 3, 2015.
Jan. 23, 2015 First Examination Report, issued in connection with Australian Patent Application No. 2013205482.
Jan. 27, 2014 Response to Office Action issued Dec. 31, 2013, filed in connection with U.S. Appl. No. 13/725,404, filed Dec. 21, 2012.
Jennings and Akoh (2000) "Lipase-Catalyzed Modification of Rice Bran Oil to Incorporate Capric Acid." Journal of Agricultural and Food Chemistry, 48:4439-4443.
Jolivet et al. (2004) "Protein composition of oil bodies in *Arabidopsis thaliana* ecotype WS" Plant Physiology and Biochemistry 42: 501-509.
Jones et al. (1995) "Palmitoyl-Acyl Carrier Protein (ACP) Thioesterase and the Evolutionary Origin of Plant Acyl-ACP Thioesterases." Plant Cell 7: 359-371.
Jul. 6, 2016 Notice of Allowance, issued in connection with U.S. Appl. No. 14/729,754, filed Jun. 3, 2015.
Jul. 8, 2013 Response to Office Action issued Apr. 30, 2013, in connection with U.S. Appl. No. 13/725,404, filed Dec. 21, 2012.
Jun. 19, 2013 Examiner Interview Summary, issued in connection with U.S. Appl. No. 13/725,404, filed Dec. 21, 2012.
Jun. 20, 2017 Communication from the EPO Examining Division, issued in connection with European Patent Application No. 12863568.7.
Jun. 28, 2016 Office Action, issued in connection with Chinese Patent Application No. 201280070729.5, including English language translation.
Kargiotidou et al., (2008) "Low temperature and light regulate delta 12 fatty acid desaturases (FAD2) at a transcriptional level in cotton (*Gossypium hirsutum*)" Journal of Experimental Botany 2008 59 (8): 2043-2056.
Karmakar et al. (2010) "Properties of various plants and animals feedstocks for biodiesel production" Bioresource Technology 101:7201-7210.

(56) References Cited

OTHER PUBLICATIONS

Kelly et al., (2011) "Seed Storage Oil Mobilization Is Important But Not Essential for Germination or Seedling Establishment in *Arabidopsis*" Plant Physiology, vol. 157, pp. 866-875.
Kelly et al.(2013). Suppression of the Sugar-dependent 1 triacylglycerol lipase family during seed development enhances oil yield in oilseed rape (*Brassica napus* L. ). Plant Biotech. J. 11:355-361.
Kim et al., (1999) GenBank Accesion No. AF213480, NCBI, p. 1.
Kinney (1996) "Development of Genetically Engineered Soybean Oils for Food Applications." J. Food Lipids 3:273-292.
Klahre et al. (2002) "High molecular weight RNAs and small interfering RNAs induce systemic posttranscriptional gene silencing in plants." PNAS 99 (18): 11981-11986.
Kodama et al. (1997) "Structure, chromosomal location and expression of a rice gene encoding the microsome ω-3 fatty acid desaturase." Plant Molecular Biology 33:493-502.
Kohno-Murase et al. (2006) "Production of trans-10, cis-12 conjugated linoleic acid in rice." Transgenic Research 15:95-100.
Kozeil et al. (1996) "Optimizing expression of transgenes with an emphasis on post-transcriptional events." Plant Molecular Biology, 32:393-405.
Langridge et al., Trends in genetic and genome analysis in wheat: a review. Aust. J. Agric. Res., 2001, 52:1043-1077.
Lardizabal et al. (2001) "DGAT2 Is a New Diacylglycerol Acyltransferase Gene Family" J. Biol. Chem. 276:38862-3886.
Lardizabal et al. (2008) "Expression of Umbelopsis ramanniana DGAT2A in Seed Increases Oil in Soybean" Plant Physiol. 148: 89-96.
Lee, M., et al., (1998) "Identification Of Non-Heme Diiron Proteins That Catalyze Triple Bond And Epoxy Group Formation," Science, 280(5365): 915-918.
Lemieux B., (2000) "High Throughput Single Nucleotide Polymorphism Genotyping Technology." Current Genomics, 2000, 1:301-311.
Leonard et al. (1997) "Cuphea wrightii thioesterases have unexpected broad specificities on saturated fatty acids." Plant Molecular Biology, vol. 34, Issue 4: 669-679.
Li et al., (1997) "Comparison of promoters and selectable marker genes for use in Indica rice transformation." Molecular Breeding, 3:1-14.
Liu et al. (1997) EMBL Nucleotide Sequence Database as X97016.
Liu et al. (1999) "Molecular cloning and expression of a CDNA encoding a microsomal ω-6 fatty acid desaturase from cotton (*Gossypium hirsutum*)" Aust. J. Plant Physiol. 26:101-106 .
Liu et al. (2002) "High-Oleic and High-Stearic Cottonseed Oils : Nutritionally Improved Cooking Oils Developed Using Gene Silencing." J. Am. Coll. Nutr. 21: 205S-211S.
Liu et al. (2010) "Increasing Seed Mass and Oil Content in Transgenic Arabidopsis by the Overexpression of wril-like gene from *Brassica napus*" Plant Physiology and Biochemistry 48(1): 9-15.
Liu et al. (2010) "Producing biodiesel from high free fatty acids waste cooking oil assisted by radio frequency heating" Fuel 89: 2735-2740.
Liu et al., (1999) "Cloning and Sequence Analysis of A Novel Member (Accession No. Y10112) of the Microsomal w-6 Fatty Acid Desaturase Family from Cotton" Plant Physiol. (PGR 99-063) 120: 339.
Liu et al., (2000) "Genetic modification of cotton seed oil using inverted-repeat gene-silencing techniques." Biochemical Society Transations, 28(6):927-929.
Liu et al., (2002) "High-Stearic and High-Oleic Cottonseed Oils Produced by Hairpin RNA-Mediated Post-Transcriptional Gene Silencing." Plant Physiology, 129 (4):1732-1743.
Liu et al., (2005) GenBank Accession No. AY574036.
Liu et al., (2005) GenBank Accession No. AY574037.
Liu et al., (2005) GenBank Accession No. AY574038.
Lu et al. (1993) "High efficiency retroviral mediated gene transduction into single isolated immature and replatable CD343+ hematopoietic stem/progenitor cells from human umbilical cord blood." J. Exp. Med., 178, 2089-2096.
Lu et al., (2011) "New frontiers in oilseed biotechnology: meeting the global demand for vegetable oils for food, feed, biofuel, and industrial applications" Current Opinion in Biotechnology, 22:252-259.
Maher and Bressler (2007) "Pyrolysis of triglyceride materials for the production of renewable fuels and chemicals" Bioresource Technology 98:2351-2368.
Mar. 25, 2015 First Examination Report, issued in connection with New Zealand Patent Application No. 627107.
Mar. 3, 2017 Third Office Action, issued in connection with Chinese Patent Application 201280070729.5, including English language translation.
Mensink and Katan (1990) "Effect of Dietary Trans Fatty Acids on High-Density and Low-Density Lipoprotein Cholesterol Levels in Healthy Subjects." N. Engl. J. Med. 323: 439-445.
Mikkilineni and Rocheford (2003) "Sequence variation and genomic organization of fatty acid desaturase-2 (fad2) and fatty acid desaturase-6 (fad6) cDNAs in maize." Theor. Applied Genetics, 106, 1326-1332.
Millar and Waterhouse (2005) "Plant and animal microRNAs: similarities and differences." Funct Integr Genomics, 2005, 5:129-135.
Miquel et al. (1992) "*Arabidopsis* mutants deficient in polyunsaturated fatty acid synthesis: Biochemical and genetic characterization of a plant oleoyl-phosphatidylcholine desaturase" Journal of Biological Chemistry; vol. 267 No. 3, 1502-1509.
Moghadasian and Frohlich (1999) "Effects of Dietary Phytosterols on Cholesterol Metabolism and Atherosclerosis: Clinical and Experimental Evidence." Am. J. Med. 107: 588-94.
Mojovic et al., (1993) "Rhizopus arrhizus lipase-catalyzed interesterification of the midfraction of palm oil to a cocoa butter equivalent fat" Enzyme Microb Technol. 15: 438-443.
Morrison (1988) "Lipids in Cereal Starches: A Review." J Cereal Sci. 8:1-15.
Most et al. (2005) "Rice bran oil, not fiber, lowers cholesterol in humans." Am J Clin Nutr 81:64-8.
Mounts et al., (1998) "Effect of Altered Fatty Acid Composition on Soybean Oil Stability" J Am. Oil Chem. Soc. 65: 624-628.
Needleman & Wunsch (1970) "A general method applicable to the search for similarities in the amino acid sequence of two proteins." J. Mol. Biol., 48, 443-453.
Nielsen et al. (2004) Formation of Volatile Compounds in Model Experiments with Crude Leek (*Allium ampeloprasum* Var. Lancelot) Enzyme Extract and Linoleic Acid or Linolenic Acid. Journal of Agricultural and Food Chemistry 52:2315-2321.
Noakes and Clifton (1998) "Oil blends containing partially hydrogenated or interesterified fats: differential effects on plasma lipids." Am. J. Clin. Nutr. 98: 242-247.
Nov. 14, 2016 Office Action, issued in connection with Japanese Patent Application No. 2014-549274, including Engligh Language Translation.
O'Brien (2005) "Cottonseed Oil" Bailey's Industrial Oil and Fat Products, 6th Edition, edited by Fereidoon Shahidi.
O'Brien, (2002) Cottonseed Oil. In: F.D. Gunstone (Ed. ) Vegetable Oils in Food Technology: Composition, Properties and Uses. Blackwell Publishing, Oxford, pp. 203-230.
Oct. 10, 2016 Response to Second Examination Report, filed in connection with Australian Patent Application No. 2013205482.
Oct. 14, 2015 Application to Amend a Complete Specification, filed in connection with South African Patent Application No. 2014/05075).
Oct. 17, 2016 Third Examination Report, issued in connection with Australian Patent Application No. 2013205482.
Oct. 18, 2013 Amendment, filed in connection with U.S. Appl. No. 13/725,404, filed Dec. 21, 2012.
Oct. 20, 2016 Response to Third Examination Report, filed in connection with Australian Patent Application No. 2013205482.
Ohlrogge and Jaworski (1997) "Regulation of Fatty Acid Synthesis. Annu Rev Plant Physiol Plant Mol Biol." 48:109-136.

(56) References Cited

OTHER PUBLICATIONS

Okuley et al. (1994) "*Arabidopsis* FAD2 Gene Encodes the Enzyme that is Essential for Polyunsaturated Lipid Synthesis." Plant Cell, 6:147-158.
PCT International Patent Application International Search Report, issued Dec. 6, 2011 for the related application PCT/AU2001/000794.
Perez-Vich et al. (1998) "Determination of Seed Oil Content and Fatty Acid Composition in Sunflower Through the Analysis of Intact Seeds, Husked Seeds, Meal and Oil by Near-Infrared Reflectance Spectroscopy" JAOCS 75:547-555.
Perriman, R., et al., (1992) "Extended Target-Site Specificity For A Hammerhead Ribozyme," Gene, 113 (2):157-163.
Petrie et al., (2012) "Recruiting a New Substrate for Triacylglycerol Synthesis in Plants: The Monoacylglycerol Acyltransferase Pathway" PLoS One 7 (4): e35214, pp. 1-8.
Pirtle et al. (1999) "Characterization of a Palmitoyl-Acyl Carrier Protein Thioesterase (FatB1) in Cotton" Plant Cell Physiology 40:2 p. 155-163.
Pirtle et al., (2001) "Molecular cloning and functional expression of the gene for a cotton v-12 fatty acid desaturase (FAD2)" Biochim. Biophys. Acta 1522: 122-129.
Pokharkar et al., (2008) "Synthesis and Characterization of Fatty Acid Methyl Ester by In-Situ Transesterification in Capparis Deciduas Seed" Leonardo Electronic Journal of Practices and Technologies 13:12-18.
Radcliffe et al. (1997) "Serum Lipids in Rats Fed Diets Containing Rice Bran Oil or High-Linolenic Acid Safflower Oil." Biochemical Archives 13:87-95.
Rajasekharan et al., (2006) "Monoacylglycerol as an intermediate in triacylglycerol biosynthesis in plants" International Symposium on Plant Lipids, Abstract.
Resurreccion et al. (1979) "Nutrient Content and Distribution in Milling Fractions of Rice Grain." Journal of the Science of Food and Agriculture, 30: 475-481.
Roche and Gibney (2000) "Effect of long-chain n-3 polyunsaturated fatty acids on fasting and postprandial triacylglycerol metabolism." Am. J. Clin. Nutr. 71: 232S-237S.
Roston et al., (2012) "TGD1, -2, and -3 Proteins Involved in Lipid Trafficking Form ATP-binding Cassette (ABC) Transporter with Multiple Substrate-binding Proteins" The Journal of Biological Chemistry vol. 287, No. 25, pp. 21406-21415.
Rukmini and Raghuram (1991) "Nutritional and Biochemical Aspects of the Hypolipidemic Action of Rice Bran Oil: A Review." Journal of the American College of Nutrition 10(6):593-601.
Sanjaya et al.(2013) "Altered Lipid Composition and Enhanced Nutritional Value of Arabidopsis Leaves following Introduction of an Algal Diacylglycerol Acyltransferase 2" Plant Cell, 1-17.
Sanjaya et al. (2011) "Increasing the energy density of vegetative tissues by diverting carbon from starch to oil biosynthesis in transgenic *Arabidopsis* " Plant Biotech. J. 9:874-883.
Sasaki et al., (1999) GenBank Accession No. AP000399, NCBI, pp. 1-33.
Sasaki et al., (2001) GenBank Accession No. AP004047, NCBI, pp. 1-36.
Sasaki et al., (2001) Genbank Accession No. AP004236, NCBI, pp. 1-37.
Sasaki et al., (2002) GenBank Accession No. AP005168, NCBI, pp. 1-31.
Sasaki et al., (2002) GenBank Accession No. AP005291, NCBI, pp. 1-38.
Sasaki et al., (2002) GenBank Accession No. BAC45170.1, NCBI.
Sasaki et al., (2002) GenBank Accession No. BAC45173.1, NCBI.
Semwal et al. (2011) "Biodiesel production using heterogeneous catalysts" Bioresource Technology 102:2151-2161.
Senior I.J., (1998) "Uses of Plant Gene Silencing." Biotechnology & Genetic Engineering Reviews, Ed. Tombs, M. P., 15:79-119;
Sep. 10, 2018 Office Action issued in connection with Mexican Patent Application No. MX/a/2014/007964.

Sep. 23, 2013 Notice of Allowance, issued in connection with U.S. Appl. No. 13/725,404, filed Dec. 21, 2012.
Sep. 23, 2015 Partial Supplementary European Search Report, issued in connection with European Patent Application No. 12863568.7.
Sharma et al., (2003) GenBank Accesion No. AC108870, NCBI, pp. 1-27.
Sheikh et al (2002) "Fatty Acids Composition in Germinating Cotton Seedlings Affected by High Temperature Stress" Pakistan Journal of Applied Sciences 2:1 p. 97-99.
Shen, B., et al. (2010) . Expression of ZmLEC1 and ZmWRI1 increases seed oil production in maize. Plant physiology, 153 (3), 980-987.
Shenstone and Vickery, (1961) "Occurrence of Cyclo-Propene Acids in Some Plants of the Order Malvales" Nature 190: 68-169.
Shiina et al. (1997) "Identification of Promoter Elements Involved in Cytosolic Ca2+-Mediated Photoregulation of Maize cab-m1 Expression" Plant Physiol. 115:477-483.
Shin et al. (1986) "Correlation Between Oxidative Deterioration of Unsaturated Lipid and n-Hexanal during Storage of Brown Rice." J. Food Sci. 51:460-463.
Shippy, R., et al., (1999) "The Hairpin Ribozyme—Discovery, Mechanism, And Development For Gene Therapy," Molecular Biotechnology, 12(1): 117-129.
Singh et al. (2012) "Accumulating Triacylglycerol in leaves via the Monoacylglycerol Acyltransferase Pathway" 20th International Symposium on Plant Lipids.
Sivaraman et al. (2004) "Development of high oleic and low linoleic acid transgenics in a zero erucic acid *Brassica juncea* L. (Indian mustard) line by antisense suppression of the fad2 gene" Molecular Breeding, Kluwer Academic Publishers, DO; vol. 13 No. 1, 365-375.
Slade and Knauf, (2005) "Tilling moves beyond functional genomics into crop improvement." Transgenic Research, 14:109-115.
Slocombe et al.(2009) "Oil accumulation in leaves directed by modification of fatty acid breakdown and lipid synthesis pathways" Plant Biotechnology Journal, 7, 694-703.
Smith et al. (2000) "Total silencing by intron-spliced hairpin RNAs" Nature 407:319-320.
Srinivasan et al. (2007) "Heterologous expression of the Baby Boom AP2/ERF transcription factor enhances the regeneration capacity of tobacco (*Nicotiana tabacum* L. )" Planta 225:341-51.
St Angelo et al. (1980) "Identification of Lipoxygenase- Linoleate Decomposition Products by Direct Gas Chromatography-Mass Spectrometry." J Lipids 1:45-49.
Stalberg et al., (1993) "Deletion Analysis of a 2S Seed Storage Protein Promoter of *Brassica napus* in Transgenic Tobacco," Plant Molecular Biology, 23(4): 671-683.
Stoutjesdijk et al. (2002) "hpRNA-mediated targeting of the Arabidopsis FAD2 gene gives highly efficient and stable silencing" Plant Physiology, American Society of Plant Physiologists, Rockville, MD, US; vol. 129, 1723-31.
Stoutjesdijk et al., (2000) "High-oleic acid Australian *Brassica napus* and *B. juncea* varieties produced by co-suppression of endogenous Δ12-desaturases." Biochem. Soc. Trans. 28: 938-940.
Suzuki et al. (1999) "Volatile Components in Stored Rice [*Oryza sativa* (L.)] of Varieties with and without Lipoxygenase-3 in Seeds." J. Agric. Food Chem. 47: 1119-1124.
Taira et al. (1986) "Lipid Content and Fatty-Acid Composition of Indica and Japonica Types of Nonglutinous Brown Rice" Journal of Agriculture and Food Chemistry; vol. 34 No. 3, 542-545.
Taira et al. (1988) "Fatty Acid Composition of Indica Sinica Javanica and Japonica Groups of Nonglutinous Brown Rice" Journal of Agricultural and Food Chemistry; vol. 36 No. 1, 45-47.
Taira et al. (1989) "Fatty Acid Composition of Indica-Types and Japonica-Types of Rice Bran and Milled Rice" Journal of the American Oil Chemists' Society; vol. 66 No. 9, 1326-1329.
Takeyama, H., et al., (1997) "Expression Of The Eicosapentaenoic Acid Synthesis Gene Cluster From *Shewanella* sp. In A Transgenic Marine Cyanobacterium, *Synechococcus* sp., " Microbiology, 143 (Pt 8): 2725-2731.
Thelen and Ohlrogge (2002) "Metabolic Engineering of Fatty Acid Biosynthesis in Plants." Metabolic Engineering 4: 12-21.

(56) References Cited

OTHER PUBLICATIONS

Theriault et al. (1999) . "Tocotrienol: A Review of its Therapeutic Potential." Clin. Biochem. 32: 309-19.
Tholstrup et al. (1994) "Fat high in stearic acid favorably affects blood lipids and factor VII coagulant activity in comparison with fats high in palmitic acid or high in myristic and lauric acids." Am. J. Clin. Nutr. 59: 371-377.
To et al., (2012) "Wrinkled Transcription Factors Orchestrate Tissue-Specific Regulation of Fatty Acid Biosynthesis in *Arabidopsis*" The Plant Cell, vol. 24: 5007-5023.
Toriyama et al., "Haploid and diploid plant regeneration from protoplasts of anther callus in rice." Theor Appl Genet, 1986, 73:16-19.
Trautwein, E.A., (2001) "n-3 Fatty Acids—Physiological And Technical Aspects For Their Use In Food," European Journal of Lipid Science and Technology, 103(1): 45-55.
Tsugita et al (1983) "Cooking Flavor and Texture of Rice Stored under Different Conditions." Agricultural and Biological Chemistry 47: 543-549.
Tsuzuki et al.(2004) "Oxidation Rate of Conjugated Linoleic Acid and Conjugated Linolenic Acid is Slowed by Triacylglycerol Esterification and α-Tocopherol." Lipids 39:475-480.
Valvekens, D., et al., (1988) "Agrobacterium tumefaciens-Mediated Transformation Of *Arabidopsis thaliana* Root Explants By Using Kanamycin Selection," Proceedings Of the National Academy of Sciences of the United States of America, 85(15) 5536-5540.
Van de Loo, F. J., Broun, P., Turner, S., & Somerville, C. (1995) "An oleate 12-hydroxylase from *Ricinus communis* L. is a fatty acyl desaturase homolog." Proc. Natl. Acad. Sci. USA, 92, 6743-6747.
Vanhercke et al (2013) "Metabolic engineering of biomass for high energy density: oilseed-like triacylglycerol yields from plant leaves" Plant Biotechnol. J., doi: 10.1111/pbi.12131 (pp. 1-9).
Vanhercke et al. (2012) "Maximizing lipid accumulation in vegetative plant tissues" 8th International Symposium on Biocatalysis and Agricultural Biotechnology.
Vanhercke et al. (2013) "Synergistic effect of WRI1 and DGAT1 coexpression on triacylglycerol biosynthesis in plants" FEBS Letters 587:364-369.
Voelker et al. (1996) "Genetic engineering of a quantitative trait: metabolic and genetic parameters influencing the accumulation of laurate in rapeseed." Plant J. 9: 229-241.
Wagner et al. (1992) "Coupling of adenovirus to transferrin-polylysine/DNA complexes greatly enhances receptor-mediated gene delivery and expression of transfected genes." Proc. Natl. Acad. Sci. USA, 89, 6099-6103.
Wang et al., (1998) "Improved Vectors for Agrobacterium tumefaciens-Mediated Transformation of Monocot Plants." Acta Hort, 1998, 461:401-407.
Waterhouse, P.M., et al., (1998) "Virus Resistance And Gene Silencing In Plants Can Be Induced By Simultaneous Expression Of Sense And Antisense RNA," Proceedings of the National Academy of Sciences of the United States of America, 95 (23): 13959-13964.
Weselake et al. (2009) "Increasing the flow of carbon into seed oil" Biotechnology Advances 27:866-878.
Whitelaw et al. (1986) "A Rice FATB Insertional Mutant Exhibits Improved Growth and Reduced Photoinhibition at High Temperatures" Proceedings of the 55th Australian Cereal Chemistry Conference, 55th Australian Cereal Chemistry Conference, Jul. 3-7, 2008, Sydney Australia, Jul. 3, 2005, pates 101-104.
Whitelaw et al., (2004) "Investigation of lipid synthesis in the rice grain: modification of fatty acids in rice bran oil." In C.K. Black, J.F. Panozzo, and G.J. Rebetzke (Eds. ), Cereals 2004: Proceedings of the 54th Australian Cereal Chemistry Conference and 11th Wheat Breeders Assembly, 21st-245th Sep. 2004, Canberra ACT, North Melbourne VIC: Cereal Chemistry Division, Royal Australian Chemical Institute, AU (pp. 418-420).
Williams et al. (1999) "Impaired Endothelial Function Following a Meal Rich in Used Cooking Fat." J. Am. Coll. Cardiol. 33:1050-1055.

Wood et al. (2009) "A leaf-based assay using interchangeable design principles to rapidly assemble multistep recombinant pathways" Plant Biotech. J. 7: 914-924.
Xu et al., (2005) "Mutation of the TGD1 Chloroplast Envelope Protein Affects Phosphatidate Metabolism in *Arabidopsis*" The Plant Cell, vol. 17, 3094-3110.
Xu et al., (2008) "Cloning and characterization of an acyl-CoA-dependent diacylglycerol acyltransferase 1 (DGAT1) gene from Tropaeolum majus, and a study of the functional motifs of the DGAT protein using site-directed mutagenesis to modify enzyme activity and oil content" Plant Biotechnology Journal 6, pp. 799-818.
Xu et al., (2008) "Lipid Trafficking between the Endoplasmic Reticulum and the Plastid in *Arabidopsis* Requires the Extraplastidic TGD4 Protein" The Plant Cell, vol. 20: 2190-2204.
Xu et al., (2010) "Lipid Transport Mediated by *Arabidopsis* TGD Proteins is Unidirectional from the Endoplasmic Reticulum to the Plastid" Plant Cell Physiol, 51(6): 1019-1028.
Yang & Ohlrogge (2009) "Turnover of Fatty Acids during Natural Senescence of *Arabidopsis*, Brachypodium, and Switchgrass and in *Arabidopsis* b-Oxidation Mutants" Plant Physiology, 150, 1981-1989.
Yang et al. (2010) "A distinct type of glycerol-3-phosphate acyltransferase with sn-2 preference and phosphatase activity producing 2-monoacylglycerol" PNAS 107:12040-12045.
Yasumatsu et al. (1966) "Studies on Cereals Part V Stale Flavor of Stored Rice." Agric. Biol. Chem. 30:483-486.
Yen et al. (2003) "MGAT2, a Monoacylglycerol Acyltransferase Expressed in the Small Intestine" The Journal of Biological Chemistry 278 (20): 18532-18537.
Yen et al., (2002) "Identification of a gene encoding MGAT1, a monoacylglycerol acyltransferase" PNAS USA 99 (13):8512-8517.
Zhou et al. (2002) "Ageing of Stored Rice: Changes in Chemical and Physical Attributes." Journal of Cereal Science 35:65-78.
Zock et al. (1994) "Impact of myristic acid versus palmitic acid on serum lipid and piloprotein levels in healthy women and men." Arterioscler Thromb. 14: 567-575.
Andre, C, et al. (2012) . Feedback regulation of plastidic acetyl-CoA carboxylase by 18: 1-acyl carrier protein in *Brassica napus*. Proceedings of the National Academy of Sciences, 109 (25), 10107-10112.
Apr. 16, 2013 Chinese Notice of Rejection, issued in connection with Chinese Patent Application No. 200780033971.4, including English Language Translation.
Apr. 16, 2013 Response, filed in connection with Japanese Patent Application No. 2009-519744.
Aug. 1, 2013 Request for Re-Examination, filed in connection with Chinese Patent Application No. 200780033971.4.
Aug. 1, 2013 Response, filed in connection with Chinese Patent Application No. 200780033971.4, including English Language copy of pending claims.
Aug. 21, 2014 Response to Search Report, filed in connection with European Patent Publication No. 11799957.3.
Aug. 21, 2014 Response, filed in connection with Canadian Patent Application No. 2,693,630.
Aug. 27, 2013 Response, filed in connection with European Patent Application No. 07763775.9.
Aug. 28, 2018 Written Opinion issued in connection with Chilean patent application 201700049, including English language translation.
Aug. 30, 2016 Examination Report, issued in connection with Chinese Patent Application No. 201510550052.0, including English Language Translation.
Awai et al.(2006). Lipid trafficking between the endoplasmic reticulum and the chloroplast. Biochem. Soc. Trans. 34:395-398.
Bao and Ohlrogge, (1999) Supply of Fatty Acid is One Limiting Factor in the Accumulation of Triacylglycerol in Developing Embryos. Plant Physiology, 1999, 120:1057-1062.
Baud and Lepiniec (2010). Physiological and developmental regulation of seed oil production. Progr. Lipid Res. 49:235-249.
Benning et al.(2009). A 25-amino acid sequence of the *Arabidopsis* TGD2 protein is sufficient for specific binding of phosphatidic acid. J. Biol. Chem 284:17420-17427.

(56) References Cited

OTHER PUBLICATIONS

Chen et al (2011). Three homologous genes encoding sn-glycerol-3-phosphate acyltransferase 4 exhibit different expression patterns and functional divergence in *Brassica napus*. Plant Physiol. 155:851-865.
CHristie (1993) . Preparation of ester derivatives of fatty acids for chromatographic analysis. Advances in Lipid Methodology-Two, Oily Press, Dundee, pp. 195-213.
Amended Claims filed on Oct. 19, 2015 in connection with PCT International Application No. PCT/AU2014/050433, filed Dec. 18, 2014.
Dec. 2, 2014 Fifth Chinese Office Action, issued in connection with Chinese Patent Application No. 200780033971.4, including English Language Translation.
Dec. 21, 2018 Response filed to the Aug. 1, 2018 Examination Report which issued in connection with corresponding European Patent Application No. 15175769.7.
Dec. 28, 2015 Response to Second Office Action, filed in connection with Russian Patent Application No. 2013102419, including English Language Translation.
Dec. 6, 2013 Response, filed in connection with Australian Patent Application No. 2007272316.
Demand for International Preliminary Examination filed on Oct. 19, 2015 in connection with PCT International Application No. PCT/AU2014/050433, filed Dec. 18, 2014.
Dyer J et al., "Molecular Analysis of a Bifunctional Fatty Acid Conjugase/Desaturase from Tung. Implications for the Evolution of Plant Fatty Acid Diversity" Plant Physiol. 130 pp. 2027-2038 (2002).
English Language Translation of Apr. 16, 2013 Grounds of Rejection, issued in connection with Chinese Patent Application No. 200780033971.4.
English language translation of Jan. 6, 2014 First Office Action, issued in connection with Chinese Patent Application No. 201180041568.2.
English Language translation of May 21, 2013 Office Action, issued in connection with Japanese Patent Application No. 2009-519744.
English Language Translation of May 21, 2013 Second Japanese Office Action, issued in connection with Japanese Patent Application No. 2009-519744.
English Translation of Feb. 19, 2016 Office Action, issued in connection with Russian Federation Patent Application No. 2013102419.
English Translation of Jun. 26, 2013 Office Action, issued in connection with Chinese Patent Application No. 200980134226.8.
English Translation of Office Action issued Aug. 27, 2010 in connection with Chinese Patent Application No. 200780033971.4.
European Examination Report issued Apr. 1, 2011 by the European Patent Office in connection with European Patent Application No. 07763775.9.
European Examination Report issued Jun. 8, 2010 by the European Patent Office in connection with European Patent Application No. 07763775.9.
European Patent Office Communication Pursuant to Rules 70(2) and 70a (2) EPC issued Dec. 11, 2015 in connection with European Patent Application No. EP13782495.9, filed Apr. 24, 2013.
Examination Report dated Aug. 1, 2018 which issued in connection with corresponding European patent application 15175769.7.
Examination Report which issued on Jun. 8, 2012 in connection with Australian Patent Application No. 2007272316.
Extended European Search Report issued Nov. 25, 2015 in connection with European Patent Application No. EP13782495.9, filed Apr. 24, 2013.
Extended European Search Report, completed Nov. 19, 2015 in connection with European Patent Application No. 15175769.7, filed Jul. 7, 2015.
Fan J., & Xu, C. (2011) . Genetic analysis of *Arabidopsis* mutants impaired in plastid lipid import reveals a role of membrane lipids in chloroplast division. Plant signaling & behavior, 6(3), 458-460.
Fan. J. et al. "Dual Role for Phospholipid: Diacylglycerol Acyltransferase: Enhancing Fatty Acid Synthesis and Diverting Fatty Acids from Membrane Lipids to Triacylglycerol in *Arabidopsis* Leaves", The Plant Cell, 2013, vol. 25, pp. 3506-3518. Whole document.
Feb. 13, 2014 Amendments, filed in connection with South African Patent Application No. 2013/00684.
Feb. 20, 2019 Office Action and its English translation which issued in connection with corresponding Russian Patent Application No. 2017102934.
Feb. 21, 2014 Office Action, issued in connection with Canadian Patent Application No. 2,693,630.
Feb. 23, 2016 Proposed Amendments, filed in connection with European Patent Application No. 07763775.9.
Feb. 29, 2016 Communication Pursuant to Article 94 (3) EPC, issued in connection with European Patent Application No. 11799957. 3.
Feeney, M. et al. (2013). Following Vegetative to Embryonic Cellular Changes in Leaves of *Arabidopsis thaliana* Over-Expressing Leafy COTYLEDON2. Plant physiology, pp. 113.
Fourth Office Action which issued on Aug. 3, 2012 in connection with Chinese Patent Application No. 200780033971.4, including English language translation.
Froissard et al. (2009) Heterologous expression of AtClo1, a plant oil body protein, induces lipid accumulation in yeast. FEMS yeast research, 9(3), 428-438.
Hartman, B.E. & Hatcher, P.G. "Hydrothermal liquefaction of isolated cuticle of Agave americana and Capsicum annuum: Chemical characterization of petroleum-like products", Fuel, Apr. 2015 , vol. 156, pp. 225-233. Abstract, pp. 225-227.
Horn et al. (2013). Identification of a new class of lipid droplet-associated proteins in plants. Plant physiology, pp. 113.
Ichihara et al.(1988). Diacylglycerol acyltransferase in maturing safflower seeds: its influences on the fatty acid composition of triacylglycerol and on the rate of triacylglycerol synthesis. Biochimica et Biophysica Acta (BBA)—Lipids and Lipid Metabolism, 958 (1), 125-129.
International Preliminary Report issued on Jan. 25, 2011 by International Searching Authority (ISA/US) in connection with International Application No. PCT/AU2006/000930.
International Preliminary Report on Patentability issued on Jan. 14, 2009 in connection with PCT International Patent Application No. PCT/AU2007/000977.
International Search Report issued Aug. 13, 2013 in connection with International Patent Application No. PCT/AU2013/000426, filed Apr. 24, 2013.
International Search Report issued by International Searching Authority (ISA.AU) on Oct. 25, 2007 in connection with International Application No. PCT/AU2007/000977.
International Search Report issued on Sep. 8, 2009 by the International Searching Authority (ISA/US) in connection with International Application No. PCT/AU2006/000930.
International Search Report issued on Sep. 8, 2009 in Connection with International Application No. PCT/AU2009/000929.
International Search Report, mailed Aug. 19, 2015 in connection with PCT International Application No. PCT/AU2015/050380, filed Jul. 7, 2015.
Jan. 12, 2016 Office Action, issued in connection with Japanese Patent Application No. 2013-240977, including English Language Translation;.
Jan. 14, 2019 Office Action issued in connection with corresponding Philippine Patent Application No. 1-2016-502588.
Jan. 28, 2014 Extended European Search Report, issued in connection with European Patent Publication No. 11799957.3.
Jan. 28, 2016 Response to the Summons to Oral Proceedings, filed in connection with European Patent Application No. 07763775.9.
Jan. 4, 2016 Response, filed in connection with European Patent Application No. 1179957.3.
Jessen et al (2015). Two Activities of Long-Chain Acyl-Coenzyme A Synthetase Are Involved in Lipid Trafficking between the Endoplasmic Reticulum and the Plastid in *Arabidopsis*. Plant Physiology, 2015, vol. 167, pp. 351-366 (published Dec. 2014).
Jul. 10, 2014 Third Party Observations, filed in connection with European Patent Publication No. 11799957.3.

(56) References Cited

OTHER PUBLICATIONS

Jul. 17, 2019 Office Action issued in connection with Russian Patent Application No. 2017102934, including the English Language Translation.
Jul. 17, 2019 Search Report, issued in connection with Russian Patent Application No. 201702934, including the English Language Translation.
Jul. 31, 2013 Declaration, filed in connection with Chinese Patent Application No. 200780033971.4.
Jun. 6, 2019 Office Action issued in connection with Chilean Patent Application No. 201700049, including the English Language Translation.
Kelly, A.A. et al. "The Sugar-Dependent1 Lipase Limits Triacylglycerol Accumulation in Vegetative Tissues of *Arabidopsis*", Plant Physiology, 2013, vol. 162, pp. 1282-1289. Abstract, pp. 1283-1286, Figure 6, Materials and Methods.
Knutzon et al. (1995). Cloning of a coconut endosperm CDNA encoding a 1-acyl-sn-glycerol-3-phosphate acyltransferase that accepts medium-chain-length substrates. Plant Physiol. 109:999-1006.
Kruse, A. et al. "Hydrothermal conversion of biomass to fuels and energetic materials", Current Opinion in Chemical Biology, 2013, vol. 17, pp. 515-521. Abstract, pp. 515-517.
Kuhn et al. (2009). The Ostreococcus tauri ADP-glucose pyrophosphorylase reveals alternative paths for the evolution of subunit roles. J. Biol. Chem. 284:34092-34102.
Kunst et al. (1988). Altered regulation of lipid biosynthesis in a mutant of *Arabidopsis* deficient in chloroplast glycerol-3-phosphate acyltransferase activity. Proc. Natl. Acad. Sci. U.S.A. 85:4143-4147.
Lee et al., (2003) . *Arabidopsis* Leafy COTYLEDON1 represents a functionally specialized subunit of the CCAAT binding transcription factor. Proc. Natl. Acad. Sci. U.S.A. 100:2152-2156.
Letter to the International Preliminary Examination Authority filed on Oct. 19, 2015 in connection with PCT International Application No. PCT/AU2014/050433, filed Dec. 18, 2014.
Li-Beisson et al (2013). Acyl-Lipid Metabolism. The *Arabidopsis* Book, 2013, Published By: The American Society of Plant Biologists.
Liu et al (2012). Hyperoside protects cortical neurons from oxygen-glucose deprivation-reperfusion induced injury via nitric oxide signal pathway. Prog. Lipid Res. 51:350-377.
Lotan et al. (1998) . *Arabidopsis* Leafy COTYLEDON1 Is Sufficient to Induce Embryo Development in Vegetative Cells. Cell 93: 1195-1205.
Lu et al (2007). A Small ATPase Protein of Arabidopsis, TGD3, Involved in Chloroplast Lipid Import. J. Biol. Chem. 282: 35945-35953.
Luerssen et al. (1998). FUSCA3 encodes a protein with a conserved VP1/ABI3-like B3 domain which is of functional importance for the regulation of seed maturation in *Arabidopsis thaliana*. Plant J. 15: 755-764.
Mar. 17, 2016 Decision, issued in connection with European Patent No. 07763755.9.
Mar. 20, 2015 Response to Jan. 14, 2015 Communication, filed in connection with European Patent Application No. EP 07763775.9.
May 13, 2019 Response filed to the Jan. 14, 2019 Office Action issued in connection with corresponding Philippine Patent Application No. 1-2016-502588.
May 16, 2013 Response to Japanese Office Action, filed in connection with Japanese Patent Application No. 2009-519744.
May 21, 2013 Response to Office Action, filed in connection with Chinese Patent Application No. 201180041568.2.
Mongrand et al (1998). The C16: 3\C18: 3 fatty acid balance in photosynthetic tissues from 468 plant species. Phytochemistry 49:1049-1064.
Moreno-Perez (2012). Reduced expression of FatA thioesterases in *Arabidopsis* affects the oil content and fatty acid composition of the seeds. Planta (2012) 235:629-639.

Moreno-Perez et al (2014) . Effect of a mutagenized acyl-ACP thioesterase FATA allele from sunflower with improved activity in tobacco leaves and *Arabidopsis* seeds. Planta, 2014, vol. 239, pp. 667-677.
Mu et al. (2008). Leafy COTYLEDON1 Is a Key Regulator of Fatty Acid Biosynthesis in *Arabidopsis* Plant Physiol. 148:1042-1054.
Naim et al. (2012). Advanced engineering of lipid metabolism in Nicotiana benthamiana using a draft genome and the V2 viral silencing-suppressor protein. PLoS One 7: e52717.
Nov. 15, 2013 Office Action, issued in connection with Australian Patent Application No. 2007272316.
Oct. 9, 2013 European Examination Report, issued in connection with European Patent Application No. 07763775.9.
Ohlrogge and Browse (1995). Lipid biosynthesis. Plant Cell 7: 957-970.
Pasquinelli et al., MicroRNAs: a developing story. Current Opinion in Genetics & Development, 2005, 15:200-205.
Phillips et al. (2002). Free and Esterified Sterol Composition of Edible Oils and Fats. Journal of Food Composition and Analysis 12:123-142.
Response filed to the third Office Action filed on Apr. 5, 2012 in connection with Chinese Patent Application No. 200780033971.4, including English language copy of the claims.
Response to European Examination Report, filed with the European Patent Office in Connection on Dec. 16, 2010 in connection with European Patent Application No. 07763775.9.
Response to European Examination Report, filed with the European Patent Office in Connection on Oct. 3, 2011 in connection with European Patent Application No. 07763775.9.
Response to First Office Action filed with the Chinese Patent Office on Jan. 11, 2011 in connection with Chinese Patent Application No. 200780033971.4, and an English Translation of the Claims.
Response to Second Office Action and English Translation of Claims, filed with the Chinese Patent Office on Aug. 3, 2011 in connection with Chinese Patent Application No. 200780033971.4, and an English Translation of the Claims.
Reynolds, K. B. et al. "Metabolic engineering of medium-chain fatty acid biosynthesis in *Nicotiana benthamiana* plant leaf lipids", Frontiers in Plant Science, Mar. 2015 , vol. 6: Article 164 (pp. 1-14). Whole document.
Santos-Mendoza et al. (2005). Leafy Cotyledon 2 activation is sufficient to trigger the accumulation of oil and seed specific mRNAs in *Arabidopsis* leaves. FEBS Lett. 579:4666-4670.
Santos-Mendoza et al. (2008) . Deciphering gene regulatory networks that control seed development and maturation in *Arabidopsis*. Plant J. 54:608-620.
Schnurr et al. (2002) . Fatty Acid Export from the Chloroplast. Molecular Characterization of a Major Plastidial Acyl-Coenzyme A Synthetase from *Arabidopsis*. Plant Physiol. 129:1700-1709.
Sep. 12, 2014 Second Chinese Office Action, issued in connection with Chinese Patent Application No. 201180041568.2, including English language translation thereof.
Sep. 12, 2016 Response to Feb. 29, 2016 Examination Report, filed in connection with European Patent Application No. 11799957.3.
Sep. 2, 2013 First Examination Report, issued in connection with Australian Patent Application No. 2011274301.
Sep. 2, 2016 First Examination Report issued in connection with Indian patent application 107/MUMNP/2009.
Sep. 25, 2015 Summons to Oral Proceedings, issued in connection with European Patent Application No. EP 07763775.9.
Sep. 9, 2015 Response to Examination Report, filed in connection with Canadian Patent Application No. 2,693,630 First Office Action which issued on Oct. 16, 2012 in connection with Japanese Patent Application No. 2009-519744.
Shimada et al. (2014). Leaf Oil Body Functions as a Subcellular Factory for the Production of a Phytoalexin in *Arabidopsis*. Plant Physiol. 164:105-118.
Shockey et al. (2002) . *Arabidopsis* Contains Nine Long-Chain Acyl-Coenzyme A Synthetase Genes That Participate in Fatty Acid and Glycerolipid Metabolism. Plant Physiol. 129:1710-1722.
Stone et al. (2001). Leafy Cotyledon2 encodes a B3 domain transcription factor that induces embryo development. Proc. Natl. Acad. Sci. U.S.A. 98: 11806-11811.

(56) References Cited

OTHER PUBLICATIONS

Stone et al. (2008) . Arabidopsis Leafy Cotyledon2 induces maturation traits and auxin activity: Implications for somatic embryogenesis. Proc. Natl. Acad. Sci. U.S.A.105:3151-3156.
Supplementary European Search Report issued Feb. 23, 2010 in connection with corresponding European Patent Application No. 07763775.9.
Third Office Action which issued on Nov. 16, 2011 in connection with Chinese Patent Application No. 200780033971.4, including English language translation.
Timothy Durrett et al., "Plant triacylglycerols as feedstocks for the production of biofuels", The Plant Journal, May 1, 2008, vol. 54, No. 4, pp. 593-607.
Van Erp, H. et al. "Mul tigene Engineering of Triacylglycerol Metabolism Boosts Seed Oil Content in *Arabidopsis*", Plant Physiology, 2014, vol. 165, pp. 30-36. Abstract, pp. 31-33, Materials and Methods.
Vanhercke et al.(2013) "Metabolic engineering of biomass for high energy density: oilseed-like triacylglycerol yields from plant leaves" Plant Biotechnol. J., doi: 10.1111/pbi.12131.
Vanhercke, T. et al. "Synergistic effect of WRil and DGATI coexpression on triacylglycerol biosynthesis in plants", FEBS Letters, 2013, vol. 587, pp. 364-369. Whole document.
Voelker et al. (1992). Fatty Acid Biosynthesis Redirected to Medium Chains in Transgenic Oilseed Plants. Science 257:72-74.
Wang and Benning (2012). TGD4 involved in endoplasmic reticulum-to-chloroplast lipid trafficking is a phosphatidic acid binding protein. Plant J 70:614-623.
Weselake et al. (2008). Metabolic control analysis is helpful for informed genetic manipulation of oilseed rape (*Brassica napus*) to increase seed oil content. J. Exp. Botany 59: 3543-3549.
Winichayakul et al. (2013). In Vivo Packaging of Triacylglycerols Enhances Arabidopsis Leaf Biomass and Energy Density. Plant Physiol. 162:626-639.
Written Opinion issued on Aug. 18, 2009 by the International Searching Authority (ISA/US) in connection with International Application No. PCT/AU2006/000930.
Written Opinion of the International Search Authority, issued on Sep. 8, 2009 in Connection with International Application No. PCT/AU2009/000929.
Written Opinion of the International Searching Authority issued Aug. 13, 2013 in connection with International Patent Application No. PCT/AU2013/000426, filed Apr. 24, 2013.
Written Opinion of the International Searching Authority, mailed Aug. 19, 2015 in connection with PCT International Application No. PCT/AU2015/050380, filed Jul. 7, 2015.
Written Opinion, issued Dec. 6, 2011 for the related application PCT/2001/000794.
Wu et al. (1994) "A Mutant *Arabidopsis* Deficient in the Elongation of Palmitic Acid" Plant Physiol. 106: 143-150.
Wu et al. (1997) "Low-Temperature Damage and Subsequent Mutant *Arabidopsis* Exposed to Recovery of fabl 2OC'" Plant Physiol, 113: 347-356.
Mar. 27, 2017 International Search Report issued in connection with PCT International Application No. PCT/AU2017/050012.
Mar. 27, 2017 Written Opinion of the International Searching Authority issued in connection with PCT International Application No. PCT/AU2017/050012.
Jul. 10, 2018 International Preliminary Report on Patentability issued in connection with PCT International Application No. PCT/AU2017/050012.
Kelly, A. A., et al. (2013) . The sugar-dependent1 lipase limits triacylglycerol accumulation in vegetative tissues of *Arabidopsis*. Plant physiology, 162(3), 1282-1289.
Vanhercke, T., et al. (2014) . Metabolic engineering of biomass for high energy density: oilseed-like triacylglycerol yields from plant leaves. Plant biotechnology journal, 12(2), 231-239.
Reynolds, K. B., et al. (2015). Metabolic engineering of medium-chain fatty acid biosynthesis in *Nicotiana benthamiana* plant leaf lipids. Frontiers in plant science, 6, 164.

Nookaraju, A., et al. (2014). Enhanced accumulation of fatty acids and triacylglycerols in transgenic tobacco stems for enhanced bioenergy production. Plant cell reports, 33(7), 1041-1052.
Vanhercke, T., et al. (2017). Step changes in leaf oil accumulation via iterative metabolic engineering. Metabolic engineering, 39, 237-246.
Liu, Q., et al. (2017). Genetic enhancement of oil content in potato tuber (*Solanum tuberosum* L.) through an integrated metabolic engineering strategy. Plant biotechnology journal, 15(1), 56-67.
Jun. 23, 2021 Office Action issued in connection with corresponding Argentinian Patent Application No. 20170102448, including English language translation thereof.
El Tahchy, A., et al. (2017). Thioesterase overexpression in *Nicotiana benthamiana* leaf increases the fatty acid flux into triacylglycerol. FEBS letters, 591 (2), 448-456.
Yee, S., et al. (2021) . Sesamum indicum Oleosin L improves oil packaging in *Nicotiana benthamiana* leaves. Plant direct, 5(9), e343.
May 2, 2022 First Examination Report issued in connection with corresponding Australian patent application 2017204957.
U.S. Appl. No. 13/093,252, filed Apr. 25, 2011, Singh.
Aug. 30, 2023 Second Office Action issued in connection with Chinese Patent Application No. 201780068087.8 and English language translation thereof.
Feb. 24, 2024 Third Office Action issued in connection with Chinese Patent Application No. 201780068087.8 and English language translation thereof.
Jul. 10, 2024 Decision of Rejection issued in connection with Chinese Patent Application No. 201780068087.8 and English language translation thereof.
Jul. 18, 2024 Office Action issued in connection with European Patent Application No. 17844702.5.
Nov. 18, 2024 Response to Jul. 18, 2024 Communication pursuant to Article 94(3) EPC filed in connection with European Patent Application No. EP17844702.
Bartlett, J. et G., al. (2008). High-throughput Agrobacterium-mediated barley transformation. Plant Methods, 4(1), 22.
Yokoyama, R. et al. (1994). The rolC promoter of Agrobacterium rhizogenes Ri plasmid is activated by sucrose in transgenic tobacco plants. Molecular and General Genetics MGG, 244(1), 15-22. et al.
Boggs et al. (1964) "Relation of Hexanal in Vapor Above Stored Potato Granules to Subjective Flavor Extimates." J. Food Sci. 29:487-489.
Bouvier-Nave et al. (2000) "Expression in yeast and tobacco of plant CDNAS encoding acyl CoA: diacylglycerol acyltransferase" European Journal of Biochemistry/FEES 267:85-96.
Chappell et al. (1998) "Vegetable Oil Production: Industry Profile," Preliminary Final Report, EPA Contract # 68-D4-0099, RTU Project # 7018-54, p. 1-1—5-26, retrieved from http://www.epa.gov/ttnecas1/regdata/IPs/Vegetable&200il IP.pdf Apr. 23, 2013.
File History for U.S. Patent Publication No. 2009-0308041, Whitelaw et al., Dec. 17, 2009 (U.S. Appl. No. 12/309,276, filed Jul. 6, 2009).
Fuller et al., (1966) "A Gas Chromatographic Method for Continuous Accelerated Study of O2 Uptake in Fats" JAOCS. 43: 477-478.
First Examination Jan. 23, 2015 Report, issued in connection with Australian Patent Application No. 2013205482.
Liu et al., (2000) "Genetic modification of cotton seed oil inverted-repeat gene-silencing using techniques." Biochemical Society Transations, 28(6):927-929.
Oct. 16, 2016 Response to Third Examination Report, filed in connection with Australian Patent Application No. 2013205482.
Whitelaw et al., (2004) "Investigation of lipid synthesis in the rice grain: modification of fatty acids in rice bran oil." In C.K. Black, J.F. Panozzo, and G. J. Rebetzke (Eds.), Cereals 2004: Proceedings of the 54th Australian Cereal Chemistry Conference and 11th Wheat Breeders Assembly, Sep. 21-25, 2004, Canberra ACT, North Melbourne VIC: Cereal Chemistry Division, Royal Australian Chemical Institute, AU (pp. 418-420).
Demand for International Preliminary Examination filed on Oct. 19, 2015 in with connection PCT International Application No. PCT/AU2014/050433, filed Dec. 18, 2014.
English Translation of Office Action issued Aug. 27, 2010 in connection Chinese with Patent Application No. 200780033971.4.

(56) References Cited

OTHER PUBLICATIONS

Li-Beisson et al Acyl-Lipid (2013). Metabolism. The *Arabidopsis Book*, 2013, Published By: The American Society of Plant Biologists.
Mar. 17, 2016 Decision, issued in connection with European Patent Application No. 07763755.9.
Reynolds, K. B. et al. "Metabolic engineering of medium-chain fatty acid biosynthesis in *NicotianabBenthamiana* plant leaf lipids", Frontiers in Plant Science, Mar. 2015, vol. 6: Article 164 (pp. 1-14). Whole document.
Wang and Benning Wang (2012). TGD4 involved in endoplasmic reticulum-to-chloroplast lipid trafficking is a phosphatidic acid binding protein. Plant J 70:614-623.
Wu et al. (1997) "Low-Temperature Damage and Subsequent Mutant Arabidopsis Exposed to Recovery of fab1 2OC'" Plant Physiol, 113: 347-356.
Mar. 27, 2017 International Search Report issued in connection with International Application No. PCT/AU2017/050012.
PCT International Patent Application Publication No. WO 2011/123897 A1, published Oct. 13, 2011.
PCT International Patent Application Publication No. WO 2016/004473 A1, published Jan. 14, 2016.
PCT International Application Publication No. WO 1998/55631, Lardiazabal et al., published Dec. 10, 1998.
PCT International Application Publication No. WO 1999/67268, Farese et al., Dec. 29, 1999.
PCT International Application Publication No. WO 1999/67403, Farese et al., Dec. 29, 1999.
PCT International Application Publication No. WO 2000/01713, Lardiazabal et al., published Jan. 13, 2000.
PCT International Application Publication No. WO 2000/32756, DuPont, Jun. 8, 2000.
PCT International Application Publication No. WO 2000/32793, Metz et al., Jun. 8, 2000.
PCT International Application Publication No. WO 2000/36114, Zou et al., Jun. 22, 2000.
PCT International Application Publication No. WO 2000/60095, BASF Plant Science GMBH, Oct. 12, 2000.
PCT International Application Publication No. WO 2000/66749, Shorrosh et al., Nov. 9, 2000.
PCT International Application Publication No. WO 2003/078639, Graham et al., Sep. 25, 2009.
PCT International Application Publication No. WO 2004/011671, Lardizabal et al., Feb. 5, 2004.
PCT International Application Publication No. WO 2005/003322, DuPont, Jan. 13, 2005.
PCT International Application Publication No. WO 2008/130248, Cookson et al., published Oct. 30, 2008.
PCT International Application Publication No. WO 2008/157226, Koprowski et al., published Dec. 24, 2008.
PCT International Application Publication No. WO 2008/157827, Ohlrooge et al., published Dec. 24, 2008.
PCT International Application Publication No. WO 2009/027335, Zank et al., Mar. 5, 2009.
PCT International Application Publication No. WO 2009/143397, Meyer et al., Nov. 26, 2009.
PCT International Application Publication No. WO 2012/000026, Petrie et al., Jan. 5, 2012.
PCT International Publication No. WO 2005/063988, Pioneer Hi-Bred International, Inc.; E.I. Du Pont De Nemours and Company, published Jul. 14, 2005.
PCT International Publication No. WO 2000/011176, E.I. Du Pont De Nemours and Company, Mar. 2, 2000.
PCT International Publication No. WO 2007/107738, Pioneer Hi-Bred International, Inc; E.I. Du Pont De Nemours and Company, published Sep. 13, 2007.
PCT International Application Publication No. WO 2010/009499, Commonwealth Scientific and Industrial Research Organisation, published Jan. 28, 2010.

PCT International Application Publication No. WO 2000/66750, Dahesh et al., published Oct. 9, 2000.
PCT International Application Publication No. WO 2005/103253, Singh et al., published Nov. 3, 2005.
PCT International Application Publication No. WO 2010/009500, Commonwealth Scientific and Industrial Research Organisation, published Jan. 28, 2010.
PCT International Application Publication No. WO 2010/057246, Commonwealth Scientific and Industrial Research Organisation, published May 27, 2010.
PCT International Application Publication No. WO 2008/025068, Commonwealth Scientific and Industrial Research Organisation, published Jun. 3, 2008.
PCT International Application Publication No. WO 2009/129582, Commonwealth Scientific and Industrial Research Organisation, published Oct. 29, 2009.
PCT International Application Publication No. WO 1999/049050, E. I. Du Pont De Nemours and Company, published Sep. 30, 1999.
PCT International Application No. WO 2013/022353 A1, Agresearch Limited, published Feb. 14, 2013.
PCT International Application No. WO 2009/073822 A2, The Ohio State University Research Foundation, published Jun. 11, 2009.
European Patent Application No. 1944375, Monsanto S.A.S., published Jul. 16, 2008.
European Patent Application No. 1837397, Monsanto S.A.S., published Sep. 26, 2007.
European Patent Application No. 1806398, Monsanto S.A.S., published Jul. 11, 2007.
PCT International Publication No. WO 2007/103738 (Pioneer Hi-Bred International, Inc; E.I. Du Pont De Nemours and Company) published Sep. 13, 2007.
PCT International Patent Application Publication No. WO 2011/062748, E.I. Du Pont De Nemours and Company, May 26, 2011.
Published Japanese Translation No. H10-509863 of the PCT International Publication, including corresponding English language application Canadian Patent Application Publication No. 2,200,357.
Published Japanese Translation No. 2003-508061 of the PCT International Publication, including corresponding English language application Canadian Patent Application Publication No. 2 382 845.
Published Japanese Translation No. H06-504439 of the PCT International Publication, including corresponding English language application PCT International Publication No. WO 92/13082.
PCT International Publication No. WO 2011/123897 A1, published Oct. 13, 2011 to Licella Pty Ltd.
PCT International Publication No. WO 2012/092644 A1, published Jul. 12, 2012 to Licella Pty Ltd.
PCT International Application Publication No. WO 2012/000033 A1, published Jan. 5, 2012 to Ignite Energy Resources Limited.
PCT International Publication No. WO 2013/096993 A1, published Jul. 4, 2013 to Commonwealth Scientific and Industrial Research Organisation.
PCT International Application Publication No. WO 2014/100467 A1, published Jun. 26, 2004 to Boston Medical Center Corporation et al.
PCT International Application Publication No. WO 2011/048119 A2, published Apr. 28, 2011 to Georg-August-Universitat Gottingen Stiftung Offentlichen Rechts.
PCT International Application No. WO 2008/068498 A2, published Jun. 12, 2008 to The University of York.
PCT International Application Publication No. WO 2013/033369 A2, published Mar. 7, 2013 to Tyton Biosciences.
European Patent Application Publication No. 1,813,664 A1, published Aug. 1, 2007 (Sapporo Breweries Limited).
PCT International Patent Application Publication No. WO2001/070777, published Sep. 27, 2001 (The Regents of the University of California).
PCT International Patent Application Publication No. WO2002/004648, published Jan. 17, 2002 (Pioneer Hi-Bred International, Inc.).
PCT International Patent Application Publication No. WO2002/072775, published Sep. 19, 2002 (Michigan State University).

(56) References Cited

OTHER PUBLICATIONS

PCT International Patent Application Publication No. WO2004/042014, published May 21, 2004 (The J. David Gladstone Institutes).
PCT International Patent Application Publication No. WO2006/007432, published Jan. 19, 2006 (BASF Plant Science GMBH).
PCT International Patent Application Publication No. WO2007/045019, published Apr. 26, 2007 (Agriculture Victoria Services Pty Ltd).
PCT International Patent Application Publication No. WO2007/101273, published Sep. 7, 2007 (Pioneer Hi-Bred International, Inc.).
PCT International Patent Application Publication No. WO2007/141257, published Dec. 13, 2007 (Total Raffinage Marketing et al.).
PCT International Patent Application Publication No. WO2007/149583, published Dec. 27, 2007 (The Board of Trustees Operating Michigan State University).
PCT International Patent Application Publication No. WO2008/006207, published Jan. 17, 2008 (National Research Council of Canada).
PCT International Patent Application Publication No. WO2008/060595, published May 22, 2008 (The Board of Trustees of Michigan State University).
PCT International Patent Application Publication No. WO2008/119082, published Oct. 2, 2008 (LS9, Inc.).
PCT International Patent Application Publication No. WO2008/147935, published Dec. 4, 2008 (E. I. Du Pont De Nemours and Company).
PCT International Patent Application Publication No. WO2009/085169, published Jul. 9, 2009 (National Research Council of Canada).
PCT International Patent Application Publication No. WO2009/143398, published Nov. 26, 2009 (E. I. Du Pont De Nemours and Company).
PCT International Patent Application Publication No. WO2009/143401, published Nov. 26, 2009 (E. I. Du Pont De Nemours and Company).
PCT International Patent Application Publication No. WO2009/147409, published Dec. 10, 2009 (The University of York).
PCT International Patent Application Publication No. WO2010/088426, published Aug. 5, 2010 (Board of Regents, The University of Texas System).
PCT International Patent Application Publication No. WO2011/053169, published May 5, 2011 (Agresearch Limited).
PCT International Patent Application Publication No. WO2011/082253, published Jul. 7, 2011 (Board of Trustees of Michigan State University).
PCT International Patent Application Publication No. WO2011/127118, published Oct. 13, 2011 (Algenetix, Inc.).
PCT International Patent Application Publication No. WO2013/003608, published Jan. 3, 2013 (Brookhaven Science Associates, LLC).
PCT International Patent Application Publication No. WO2013/096562, published Jun. 27, 2013 (E. I. Du Pont De Nemours and Company).
PCT International Patent Application Publication No. WO2013/185184, published Dec. 19, 2013 (Commonwealth Scientific and Industrial Research Organisation).
PCT International Patent Application Publication No. WO2014/068437, published May 8, 2014 (Agresearch Limited).
PCT International Patent Application Publication No. WO2014/068438, published May 8, 2014 (Agresearch Limited).
PCT International Patent Application Publication No. WO2014/068439, published May 8, 2014 (Agresearch Limited).
PCT International Application Publication No. WO 2013/096993 A1, Commonwealth Scientific and Industrial Research Organisation, published Jul. 4, 2013.
PCT International Application Publication No. WO 2014/100467 A1, Boston Medical Center Corporation et al., published Jun. 26, 2014.
PCT International Application Publication No. WO 2016/004473 A1, Commonwealth Scientific and Industrial Research Organisation, published Jan. 14, 2016.
U.S. Appl. No. 13/093,252, filed Apr. 25, 2011.
Aug. 30, 2023 Second Office Action issued in connection with Chinese Patent Application No. 201780068087.8 and English language translation thereof (Exhibit 1).
Feb. 24, 2024 Third Office Action issued in connection with Chinese Patent Application No. 201780068087.8 and English language translation thereof (Exhibit 2).
Jul. 10, 2024 Decision of Rejection issued in connection with Chinese Patent Application No. 201780068087.8 and English language translation thereof (Exhibit 3).
Jul. 18, 2024 Office Action issued in connection with European Patent Application No. 17844702.5 (Exhibit 4).

* cited by examiner

A

Neutral and polar leaf lipids

- [PEPC::ZmWRI1] (pOIL103) + [Ubi::UrDGAT2+Act::SiOleosin+Ubi::NPTII] (pOIL197)
- Vegetative stage

B

Polar leaf lipid classes

- [PEPC::ZmWRI1] (pOIL103) + [Ubi::UrDGAT2+Act::SiOleosin+Ubi::NPTII] (pOIL197)
- Vegetative stage

SEQUENCE LISTING

```
Sequence total quantity: 323
SEQ ID NO: 1            moltype = AA  length = 520
FEATURE                 Location/Qualifiers
source                  1..520
                        mol_type = protein
                        organism = Arabidopsis thaliana
SEQUENCE: 1
MAILDSAGVT TVTENGGGEF VDLDRLRRRK SRSDSSNGLL LSGSDNNSPS DDVGAPADVR   60
DRIDSVVNDD AQGTANLAGD NNGGGDNNGG GRGGGEGRGN ADATFTYRPS VPAHRRARES  120
PLSSDAIFKQ SHAGLFNLCV VVLIAVNSRL IIENLMKYGW LIRTDFWFSS RSLRDWPLFM  180
CCISLSIFPL AAFTVEKLVL QKYISEPVVI FLHIIITMTE VLYPVYVTLR CDSAFLSGVT  240
LMLLTCIVWL KLVSYAHTSY DIRSLANAAD KANPEVSYYV SLKSLAYFMV APTLCYQPSY  300
PRSACIRKGW VARQFAKLVI FTGFMGFIIE QYINPIVRNS KHPLKGDLLY AIERVLKLSV  360
PNLYVWLCMF YCFFHLWLNI LAELLCFGDR EFYKDWWNAK SVGDYWRMWN MPVHKWMVRH  420
IYFPCLRSKI PKTLAIIIAF LVSAVFHELC IAVPCRLFKL WAFLGIMFQV PLVFITNYLQ  480
ERFGSTVGNM IFWFIFCIFG QPMCVLLYYH DLMNRKGSMS                        520

SEQ ID NO: 2            moltype = AA  length = 314
FEATURE                 Location/Qualifiers
source                  1..314
                        mol_type = protein
                        organism = Arabidopsis thaliana
SEQUENCE: 2
MGGSREFRAE EHSNQFHSII AMAIWLGAIH FNVALVLCSL IFLPPSLSLM VLGLLSLFIF   60
IPIDHRSKYG RKLARYICKH ACNYFPVSLY VEDYEAFQPN RAYVFGYEPH SVLPIGVVAL  120
CDLTGFMPIP NIKVLASSAI FYTPFLRHIW TWLGLTAASR KNFTSLLDSG YSCVLVPGGV  180
QETFHMQHDA ENVFLSRRRG FVRIAMEQGS PLVPVFCFGQ ARVYKWWKPD CDLYLKLSRA  240
IRFTPICFWG VFGSPLPCRQ PMHVVVGKPI EVTKTLKPTD EEIAKFHGQY VEALRDLFER  300
HKSRVGYDLE LKIL                                                   314

SEQ ID NO: 3            moltype = AA  length = 340
FEATURE                 Location/Qualifiers
source                  1..340
                        mol_type = protein
                        organism = Ricinus communis
SEQUENCE: 3
MGEEANHNNN NNNINSNDEK NEEKSNYTVV NSRELYPTNI FHALLALSIW IGSIHFNLFL   60
LFISYLFLSF PTFLLIVGFF VVLMFIPIDE HSKLGRRLCR YVCRHACSHF PVTLHVEDMN  120
AFHSDRAYVF GYEPHSVFPL GVSVLSDHFA VLPLPKMKVL ASNAVFRTPV LRHIWTWCGL  180
TSATKKNFTA LLASGYSCIV IPGGVQETFY MKHGSEIAFL KARRGFVRVA MEMGKPLVPV  240
FCFGQSNVYK WWKPDGELFM KIARAIKFSP IVFWGVLGSH LPLQRPMHVV VGKPIEVKQN  300
PQPTVEEVSE VQGQFVAALK DLFERHKARV GYADLTLEIL                        340

SEQ ID NO: 4            moltype = AA  length = 322
FEATURE                 Location/Qualifiers
source                  1..322
                        mol_type = protein
```

```
                        organism = Vernicia fordii
SEQUENCE: 4
MGMVEVKNEE EVTIFKSGEI YPTNIFQSVL ALAIWLGSFH FILFLVSSSI FLPFSKFLLV    60
IGLLLFFMVI PINDRSKLGQ CLFSYISRHV CSYFPITLHV EDINAFRSDR AYVFGYEPHS   120
VPPIGVMILS LGLIPLPNIK FLASSAVFYT PFLRHIWSWC GLTPATRKNF VSLLSSGYSC   180
ILVPGGVQET FYMKQDSEIA FLKARRGFIR IAMQTGTPLV PVFCFGQMHT FKWWKPDGEL   240
FMKIARAIKF TPTIFWGVLG TPLPFKNPMH VVVGRPIEVK QNPQPTAEEV AEVQREFIAS   300
LKNLFERHKA RVGYSDLKLE IF                                           322

SEQ ID NO: 5            moltype = AA  length = 355
FEATURE                 Location/Qualifiers
source                  1..355
                        mol_type = protein
                        organism = Mortierella ramanniana
SEQUENCE: 5
MASKDQHLQQ KVKHTLEAIP SPRYAPLRVP LRRRLQTLAV LLWCSMMSIC MFIFFFLCSI    60
PVLLWFPIIL YLTWILVWDK APENGGRPIR WLRNAAWWKL FAGYFPAHVI KEADLDPSKN   120
YIFGYHPHGI ISMGSFCTFS TNATGFDDLF PGIRPSLLTL TSNFNIPLYR DYLMACGLCS   180
VSKTSCQNIL TKGGPGRSIA IVVGGASESL NARPGVMDLV LKRRFGFIKI AVQTGASLVP   240
TISFGENELY EQIESNENSK LHRWQKKIQH ALGFTMPLFH GRGVFNYDFG LLPHRHPIYT   300
IVGKPIPVPS IKYGQTKDEI IRELHDSYMH AVQDLDRYK DIYAKDRVKE LEFVE         355

SEQ ID NO: 6            moltype = AA  length = 388
FEATURE                 Location/Qualifiers
source                  1..388
                        mol_type = protein
                        organism = Homo sapiens
SEQUENCE: 6
MKTLIAAYSG VLRGERQAEA DRSQRSHGGP ALSREGSGRW GTGSSILSAL QDLFSVTWLN    60
RSKVEKQLQV ISVLQWVLSF LVLGVACSAI LMYIFCTDCW LIAVLYFTWL VPDWNTPKKG   120
GRRSQWVRNW AVWRYFRDYF PIQLVKTHNL LTTRNYIFGY HPHGIMGLGA FCNFSTEATE   180
VSKKFPGIRP YLATLAGNFR MPVLREYLMS GGICPVSRDT IDYLLSKNGS GNAIIIVVGG   240
AAESLSSMPG KNAVTLRNRK GFVKLALRHG ADLVPIYSFG ENEVYKQVIF EEGSWGRWVQ   300
KKFQKYIGFA PCIFHGRGLF SSDTWGLVPY SKPITTVVGE PITIPKLEHP TQQDIDLYHT   360
MYMEALVKLF DKHKTKFGLP ETEVLEVN                                     388

SEQ ID NO: 7            moltype = AA  length = 328
FEATURE                 Location/Qualifiers
source                  1..328
                        mol_type = protein
                        organism = Homo sapiens
SEQUENCE: 7
MAHSKQPSHF QSLMLLQWPL SYLAIFWILQ PLFVYLLFTS LWPLPVLYFA WLFLDWKTPE    60
RGGRRSAWVR NWCVWTHIRD YFPITILKTK DLSPEHNYLM GVHPHGLLTF GAFCNFCTEA   120
TGFSKTFPGI TPHLATLSWF FKIPVREYL MAKGVCSVSQ PAINYLLSHG TGNLVGIVVG    180
GVGEALQSVP NTTTLILQKR KGFVRTALQH GAHLVPTFTF GETEVYDQVL FHKDSRMYKF   240
QSCFRRIFGF YCCVFYGQSF CQGSTGLLPY SRPIVTVVGE PLPLPQIEKP SQEMVDKYHA   300
LYMDALHKLF DQHKTHYGCS ETQKLFFL                                     328

SEQ ID NO: 8            moltype = AA  length = 361
FEATURE                 Location/Qualifiers
source                  1..361
                        mol_type = protein
                        organism = Bos taurus
SEQUENCE: 8
MKTLIAAYSG VLRGTGSSIL SALQDLFSVT WLNRAKVEKQ LQVISVLQWV LSFLVLGVAC    60
SVILMYTFCT DCWLIAVLYF TWLVPDWNTP KKGGRRSQWV RNWAVWRYFR DYFPIQLVKT   120
HNLLTSRNYI FGYHPHGIMG LGAFCNFSTE ATEVSKKFPG IRPYLATLAG NFRMPVLREY   180
LMSGGICPVN RDTIDYLLSK NGSGNAIIIV VGGAAESLSS MPGKNAVTLR NRKGFVKLAL   240
RHGADLVPTY SFGENEVYKQ VIFEEGSWGR WVQKKFQKYI GFAPCIFHGR GLFSSDTWGL   300
VPYSKPITTV VGEPITIPRL ERPTQQDIDL YHAMYVQALV KLFDQHKTKF GLPETEVLEV   360
N                                                                  361

SEQ ID NO: 9            moltype = AA  length = 388
FEATURE                 Location/Qualifiers
source                  1..388
                        mol_type = protein
                        organism = Mus musculus
SEQUENCE: 9
MKTLIAAYSG VLRGERRAEA ARSENKNKGS ALSREGSGRW GTGSSILSAL QDIFSVTWLN    60
RSKVEKQLQV ISVLQWVLSF LVLGVACSVI LMYTFCTDCW LIAVLYFTWL AFDWNTPKKG   120
GRRSQWVRNW AVWRYFRDYF PIQLVKTHNL LTTRNYIFGY HPHGIMGLGA FCNFSTEATE   180
VSKKFPGIRP YLATLAGNFR MPVLREYLMS GGICPVNRDT IDYLLSKNGS GNAIIIVVGG   240
AAESLSSMPG KNAVTLKNRK GFVKLALRHG ADLVPTYSFG ENEVYKQVIF EEGSWGRWVQ   300
KKFQKYIGFA PCIFHGRGLF SSDTWGLVPY SKPITTVVGE PITVPKLEHP TQKDIDLYHA   360
MYMEALVKLF DNHKTKFGLP ETEVLEVN                                     388

SEQ ID NO: 10           moltype =    length =
SEQUENCE: 10
```

```
SEQ ID NO: 11           moltype = AA   length = 4
FEATURE                 Location/Qualifiers
REGION                  1..4
                        note = conserved sequence
source                  1..4
                        mol_type = protein
                        organism = synthetic construct
SEQUENCE: 11
HPHG                                                                       4

SEQ ID NO: 12           moltype = AA   length = 4
FEATURE                 Location/Qualifiers
REGION                  1..4
                        note = conserved sequence
source                  1..4
                        mol_type = protein
                        organism = synthetic construct
SEQUENCE: 12
EPHS                                                                       4

SEQ ID NO: 13           moltype = AA   length = 24
FEATURE                 Location/Qualifiers
REGION                  1..24
                        note = conserved sequence
SITE                    2
                        note = X - any amino acid
SITE                    5
                        note = X - any amino acid
SITE                    6
                        note = X - Lysine (K) or Arginine (R)
SITE                    7
                        note = X - any amino acid
REGION                  9..11
                        note = X - any amino acid
REGION                  13..15
                        note = X - any amino acid
SITE                    16
                        note = X - Leucine (L) or Valine (V)
REGION                  19..21
                        note = X - any amino acid
SITE                    24
                        note = X - Glutamic Acid (E) or Glutamine (Q)
source                  1..24
                        mol_type = protein
                        organism = synthetic construct
SEQUENCE: 13
RXGFXXXAXX XGXXXXVPXX XFGX                                                24

SEQ ID NO: 14           moltype = AA   length = 8
FEATURE                 Location/Qualifiers
REGION                  1..8
                        note = conserved sequence
SITE                    3
                        note = X - any amino acid
REGION                  5..7
                        note = X - any amino acid
source                  1..8
                        mol_type = protein
                        organism = synthetic construct
SEQUENCE: 14
FLXLXXXN                                                                   8

SEQ ID NO: 15           moltype = AA   length = 118
FEATURE                 Location/Qualifiers
REGION                  1..118
                        note = conserved sequence
source                  1..118
                        mol_type = protein
                        organism = synthetic construct
SEQUENCE: 15
ALVVANHQSF LDPLVLSALL PRKGGRVRFV AKKELFYVPL GWLLRLLGA IFIDRENGRL           60
ARAALREAVR LLRDGGWLLI FPEGTRSRPG KLLPFKKGAA RLALEAGVPI VPVAIRGT           118

SEQ ID NO: 16           moltype = AA   length = 187
FEATURE                 Location/Qualifiers
REGION                  1..187
                        note = conserved sequence
```

```
SITE                    15
                        note = X - any amino acid
SITE                    18
                        note = X - any amino acid
SITE                    23
                        note = X - any amino acid
REGION                  25..26
                        note = X - any amino acid
REGION                  28..30
                        note = X - any amino acid
REGION                  32..33
                        note = X - any amino acid
REGION                  35..38
                        note = X - any amino acid
SITE                    41
                        note = X - any amino acid
REGION                  46..48
                        note = X - any amino acid
SITE                    53
                        note = X - any amino acid
REGION                  55..57
                        note = X - any amino acid
SITE                    61
                        note = X - any amino acid
SITE                    67
                        note = X - any amino acid
SITE                    72
                        note = X - any amino acid
REGION                  74..77
                        note = X - any amino acid
SITE                    79
                        note = X - any amino acid
SITE                    114
                        note = X - any amino acid
REGION                  127..128
                        note = X - any amino acid
SITE                    136
                        note = X - any amino acid
REGION                  139..142
                        note = X - any amino acid
SITE                    144
                        note = X - any amino acid
SITE                    150
                        note = X - any amino acid
REGION                  164..165
                        note = X - any amino acid
REGION                  167..172
                        note = X - any amino acid
source                  1..187
                        mol_type = protein
                        organism = synthetic construct
SEQUENCE: 16
AVFDKDGTLT EDDTXFLXYL LKXLXXLXXX LXXDXXXXGS XLTLSXXXDL LEXLXXXGGI   60
XVIGLAXRYL EXLXXXXEXA KLFEGFIKPD AAELLKELHE AGLRVVVLTG DPRXIAKPVA  120
KELGIDXXNV LATELXDEXX XXVXGRITGX LDKARAVERL VVLXXKXXXX XXVVAIGDSA  180
NDLPALK                                                           187

SEQ ID NO: 17           moltype = AA  length = 190
FEATURE                 Location/Qualifiers
REGION                  1..190
                        note = conserved sequence
source                  1..190
                        mol_type = protein
                        organism = synthetic construct
SEQUENCE: 17
IKAVVFDKDG TLTDGEPPIA EAIVEAAAEL GLPLLLPLEE VEKLLGRGVE GIERILLEGG   60
LTAELLLELE GELAAGKTAV LVALDGEVLG LIALADKLYP GAREALKALK ERGIKVAILT  120
NGDRANAEAV LEALGLADLF DVIVDSDDVG PVKPKPEIFL KALERLGVKP EEVLMVGDGV  180
NDAPALAAAG                                                        190

SEQ ID NO: 18           moltype = AA  length = 15
FEATURE                 Location/Qualifiers
REGION                  1..15
                        note = conserved sequence
source                  1..15
                        mol_type = protein
                        organism = synthetic construct
SEQUENCE: 18
GDLVICPEGT TCREP                                                   15
```

```
SEQ ID NO: 19            moltype =    length =
SEQUENCE: 19
000

SEQ ID NO: 20            moltype =    length =
SEQUENCE: 20
000

SEQ ID NO: 21            moltype = AA   length = 356
FEATURE                  Location/Qualifiers
source                   1..356
                         mol_type = protein
                         organism = Arabidopsis thaliana
SEQUENCE: 21
MDWEIRGSSL GQKLLEFDSE QERQTRFRAY DSEEAAAHTY DLAALKYWGP DTILNFPAET    60
YTKELEEMQR VTKEEYLASL RRQSSGFSRG VSKYRGVARH HHNGRWEARI GRVFGNKYLY   120
LGTYNTQEEA AAAYDMAAIE YRGANAVTNF DISNYIDRLK KKGVFPFPVN QANHQEGILV   180
EAKQEVETRE AKEEPREEVK QQYVEEPPQE EEEKEEEKAE QQEAEIVGYS EEAAVVNCCI   240
DSSTIMEMDR CGDNNELAWN FCMMDTGFSP FLTDQNLANE NPIEYPELFN ELAFEDNIDF   300
MFDDGKHECL NLENLDCCVV GRESPPSSSS PLSCLSTDSA SSTTTTTTSV SCNYLV       356

SEQ ID NO: 22            moltype = AA   length = 430
FEATURE                  Location/Qualifiers
source                   1..430
                         mol_type = protein
                         organism = Arabidopsis thaliana
SEQUENCE: 22
MKKRLTTSTC SSSPSSSVSS STTTSSPIQS EAPRPKRAKR AKKSSPSGDK SHNPTSPAST    60
RRSSIYRGVT RHRWTGRFEA HLWDKSSWNS IQNKKGKQVY LGAYDSEEAA AHTYDLAALK   120
YWGPDTILNF PAETYTKELE EMQRVTKEEY LASLRRQSSG FSRGVSKYRG VARHHHNGRW   180
EARIGRVFGN KYLYLGTYNT QEEAAAAYDM AAIEYRGANA VTNFDISNYI DRLKKKGVFP   240
FPVNQAHQE GILVEAKQEV ETREAKEEPR EEVKQQYVEE PPQEEEEKEE EKAEQQEAEI   300
VGYSEEAAVV NCCIDSSTIM EMDRCGDNNE LAWNFCMMDT GFSPFLTDQN LANENPIEYP   360
ELFNELAFED NIDFMFDDGK HECLNLENLD CCVVGRESPP SSSSPLSCLS TDSASSTTTT   420
TTSVSCNYLV                                                        430

SEQ ID NO: 23            moltype = AA   length = 430
FEATURE                  Location/Qualifiers
source                   1..430
                         mol_type = protein
                         organism = Arabidopsis lyrata
SEQUENCE: 23
MKRRLTTSTS SSSPSSSVSS STTTSSPIQS EAPRPKRAKR AKKSSPSGDK SHNPTSPAST    60
RRSSIYRGVT RHRWTGRFEA HLWDKSSWNS IQNKKGKQGA YDSEEAAAHT YDLAALKYWG   120
PDTILNFPAE TYTKELEEMQ RVTKEEYLAS LRRQSSGFSR GVSKYRGVAR HHHNGRWEAR   180
IGRVFGNKYL YLGTYNTQEE AAAAYDMAAI EYRGANAVTN FDISNYIDRL KKKGVFPFPV   240
NQPNHQEAIL VEAKQEIETR EAKEEPREEV KQQYVEEPPQ EEKEEEKAEQ QEAEFVGYKD   300
EGAVVNCCID SSAIMEMNRC GDNNELAWNF CMMDSGFAPF LTDQNLSNEN PIEYPELFNE   360
LAFEDNIDFM FDEAKNDCLS LENLDCCVVG RESPTSSSSP LSCFSTDSAS STTTTTSVSC   420
NYLGLFVGSE                                                        430

SEQ ID NO: 24            moltype = AA   length = 413
FEATURE                  Location/Qualifiers
source                   1..413
                         mol_type = protein
                         organism = Brassica napus
SEQUENCE: 24
MKRPLTTSPS SSSSTSSSAC ILPTQSETPR PKRAKRAKKS SLRSDVKPQN PTSPASTRRS    60
SIYRGVTRHR WTGRYEAHLW DKSSWNSIQN KKGKQVYLGA YDSEEAAAHT YDLAALKYWG   120
PNTILNFPVE TYTKELEEMQ RCTKEEYLAS LRRQSSGFSR GVSKYRGVAR HHHNGRWEAR   180
IGRVFGNKYL YLGTYNTQEE AAAAYDMAAI EYRGANAVTN FDIGNYIDRL KKKGVFPFPV   240
SQANHQEAVL AETKQEVEAK EEPTEEVKQC VEKEEEAKEE TEKKQQQEVE EAVITCCIDS   300
SESNELAWDF CMMDSGFAPF LTDSNLSSEN PIEYPELFNE MGFEDNIDFM FEEGKQDCLS   360
LENLDCCDGV VVVGRESPTS LSSSPLSCLS TDSASSTTTT ATTVTSVSWN YSV         413

SEQ ID NO: 25            moltype = AA   length = 415
FEATURE                  Location/Qualifiers
source                   1..415
                         mol_type = protein
                         organism = Brassica napus
SEQUENCE: 25
MKRPLTTSPS TSSSTSSSAC ILPTQPETPR PKRAKRAKKS SIPTDVKPQN PTSPASTRRS    60
SIYRGVTRHR WTGRYEAHLW DKSSWNSIQN KKGKQVYLGA YDSEEAAAHT YDLAALKYWG   120
PDTILNFPAE TYTKELEEMQ RCTKEEYLAS LRRQSSGFSR GVSKYRGVAR HHHNGRWEAR   180
IGRVFGNKYL YLGTYNTQEE AAAAYDMAAI EYRGANAVTN FDISNYIDRL KKKGVFPFPV   240
SQANHQEAVL AEAKQEVEAK EEPTEEVKQC VEKEEPQEAK EEKTEKKQQQ QEVEEAAVTC   300
CIDSSESNEL AWDFCMMDSG FAPFLTDSNL SSENPIEYPE LFNEMGFEDN IDFMFEEGKQ   360
DCLSLENLDC CDGVVVVGRE SPTSLSSSPL SCLSTDSASS TTTTTITSVS CNYSV        415
```

```
SEQ ID NO: 26            moltype = AA   length = 285
FEATURE                  Location/Qualifiers
source                   1..285
                         mol_type = protein
                         organism = Glycine max
SEQUENCE: 26
MKRSPASSCS SSTSSVGFEV HHPIEKRRPK HPRRNNLKSQ KCKQNQTTTG GRRSSIYRGV   60
TRHRWTGRFE AHLWDKSSWN NIQSKKGKQV YLGAYDTEES AARTYDLAAL KYWGKDATLN  120
FPIETYTKDL EEMDKVSREE YLASLRRQSS GFSRGISKYR GVARHHHNGR WEARIGRVCG  180
NKYLYLGTYK TQEEAAVAYD MAAIEYRGVN AVTNFDISNY MDKIKKKNDQ TLQQQQTEVQ  240
TETVPNSSDS EEAEVEQQHT TTITTPPPSE NLHMLPQEHQ VGGWV                 285

SEQ ID NO: 27            moltype = AA   length = 417
FEATURE                  Location/Qualifiers
source                   1..417
                         mol_type = protein
                         organism = Jatropha curcas
SEQUENCE: 27
MKRSSASSCS SSSSSSSSPS SSSSACSAS SSCLDSVSPP NHHQLRSEKS KSKRIRKIQT   60
KQDKCQTTAT TTSPSGGGRR SSIYRGVTRH RWTGRFEAHL WDKSSWNNIQ NKKGRQVYLG  120
AYDNEEAAAH TYDLAALKYW GQDTTLNFPI ETYSKELEEM QKMSKEEYLA SLRRRSSGFS  180
RGVSKYRGVA RHHHNGRWEA RIGRVFGNKY LYLGTYNTQE EAAAAYDMAA IEYRGANAVT  240
NFDVSHYIDR LKKKGIPLDK ILPETLSKGS KESEEIERTS PLPLPSPPSP SITPLHEEIV  300
SPQLLETECP QHPPCMDTCT MIVMDPIEEH ELTWSFCLDS GLVPLPVPDL PLANGCELPD  360
LLDDTGFEDN IDLIFDACCF GNDANPADEN GKERLSSAST SPSCSTTLTS VSCNYSV    417

SEQ ID NO: 28            moltype = AA   length = 443
FEATURE                  Location/Qualifiers
source                   1..443
                         mol_type = protein
                         organism = Ricinus communis
SEQUENCE: 28
MKRSPTSPCS SSSSSYSSS SASSSCVGPD DTPVAPGSHH HHDHHQLRSQ KSSKRIRKVK   60
KKQQNHNIDQ NNTNTTITAP TSARRSSIYR GVTRHRWTGR FEAHLWDKSS WNNIQNKKGR  120
QGAYDNEEAA AHTYDLAALK YWGPETTLNF PIETYPKELE EMQKMSKEEY LASLRRQSSG  180
FSRGVSKYRG VARHHHNGRW EARIGRVFGN KYLYLGTYNT QEEAAAAYDM AAIEYRGANA  240
VTNFDISNYI DRLKKKGILL DQILPDQPLR KCSSESEEEA AEAEVERLPS LPSSILPQEQ  300
DTISPQLQCT QLLPSMDSCT MINMDPIEDN ELTWSFCLDS GLTLFSVPEL PLENACELPD  360
LFDDTGFEDN IDLIFDGCCF GNDDDGGGGA NHQEFMVESR GCRVGEVGIS GSMEEENGKE  420
MCCSSSSPSC STTTSVSCCN YSV                                        443

SEQ ID NO: 29            moltype = AA   length = 402
FEATURE                  Location/Qualifiers
source                   1..402
                         mol_type = protein
                         organism = Populus trichocarpa
SEQUENCE: 29
MKRSSSCSSS SSSSSSCVA SESIHKPKAK RIRKNQKSNQ GKSQNAAAAA ANNSHNSGKR   60
SSIYRGVTRH RWTGRFEAHL WDKSSWNSIQ NKKGKQGAYD NEEAAAHTYD LAALKYWGSE  120
TTLNFPIETY TKEIEEMQKV TKEEYLASLR RQSSGFSRGV SKYRGVARHH HNGRWEARIG  180
RVYGNKYLYL GTYNTQEEAA AAYDMAAIQY RGANAVTNFD VSNYIERLRK KGIPIDRILQ  240
EQQLLNNSVD SSVEVEVEQP TPPPQQQQEE QEQKIVSSSS QLQCSQLNSS LDGTPPMVIM  300
DTIEEHELAW SFCMDSGLSL TMPDLPLENS CELPDLFDHT GFEDNIDLIF DACCYGKEAN  360
PAGYTLEDNS TGGVEEDRLS SDSVSNSPTS STTTSVSCNY SV                   402

SEQ ID NO: 30            moltype = AA   length = 409
FEATURE                  Location/Qualifiers
source                   1..409
                         mol_type = protein
                         organism = Vitis vinifera
SEQUENCE: 30
MVKRSSPGSS SSPSSSSTSS DAASRPAPPS GGKPKSRKKE AKKNSNGNGS NSKNKRTSIY   60
RGVTKHRWTG RFEAHLWDKS SWNDISNKRG RQGAYYNEEA AARTYDLAAL KYWGPTTPLN  120
FPLETYQKDA EEMEKMSKEE YLALLRRQSN GFSRGVSKHH HNGRWEARIG RVLGNKYLYL  180
GTYSTQEEAA AAYDMAAIEY RGLNAVTNFD ISNYVKLGRV EAQVQELAQQ LQPNTPIGPQ  240
NELQKEEEEQ LQEPVLSSSQ HLPSMDSSAM EIMDPADDPD LPWNFCAYST LLVPDVPLGK  300
GGELSDLFYE KGFEDNIDYM FEGAAGNEEE SNSAENGVKE NGFMHELEVD GKLQNVVGFF  360
FLSFFFLPKR AGIRKRGVDS CMQLFLYFVF LFYPPFLPEVS KFLFHLSLD            409

SEQ ID NO: 31            moltype = AA   length = 420
FEATURE                  Location/Qualifiers
source                   1..420
                         mol_type = protein
                         organism = Brachypodium distachyon
SEQUENCE: 31
MKRSPPQPSP SPSSSPASSS SSPSSSDSSS SIAIPRKRAR TAAAAGGGK ARAAAAKRPK   60
KDGKDSGSSS NGGGGGGGKR SSIYRGVTRH RWTGRFEAHL WDKNCFTSLQ NKKKGRQVYL  120
GAYDTEEAAA RAYDLAALKY WGPETTLNFS ADDYGKERSE MEAVSREEYL AALRRRSSGF  180
```

```
SRGVSKYRGV ARHHHNGRWE ARIGRVLGNK YLYLGTFDTQ EEAARAYDLA AIQYRGANAV    240
TNFDISRYLD QPQLLEQLQQ QQGPQVVAAL QEEAQRDHQS DNAVQELNSG EAQTPGGIDE    300
PIAIGDSTED INTSLTVDDI IEESLWSPYE FDIMAGVNVS NSMNLSELFS DVAFEGNIGC    360
LFEECSGIDD CSSRHGAGLA AFGLFTEGDD KLKDVSEMEM EVNPQANDVS CPPKMITVCN    420

SEQ ID NO: 32             moltype = AA  length = 423
FEATURE                   Location/Qualifiers
source                    1..423
                          mol_type = protein
                          organism = Hordeum vulgare
SEQUENCE: 32
MKRSPPPQPS PSSSPACSPS PSSPSSSDSS SIAIPRKRAR TQKAGSAKAK AAPKRAKKDS     60
GRSTKDSDAS ANGAAASGKR SSIYRGVTRH RWTGRFEAHL WDKNCFTSIQ NKKKGRQVYL    120
GAYDTEEAAA RAYDLAALKY WGPETTLNFT VDEYAKERSE MEAVSREEYL AALRRRSSGF    180
SRGVSKYRGV ARHHHNGRWE ARIGRVLGNK YLYLGTFDTQ EEAARAYDLA AIEYRGANAV    240
TNFDISRYLD QPQLLAQLEQ GPQVVPALQE ELQHDHQSDN AVQELNSGEA QKPGSVSEPI    300
AVDDTDNTGD IGAPLVFDSG VEENLWSPCM DYDVDPIFGP NISSSMNLSE WFNDPAFESN    360
IGYMFEGCSD VDDCSTRHGA GLSALGFLKE GDDKLKDGSD MEAEITPQAN DVSCPPKMIT    420
VCN                                                                 423

SEQ ID NO: 33             moltype = AA  length = 443
FEATURE                   Location/Qualifiers
source                    1..443
                          mol_type = protein
                          organism = Oryza sativa
SEQUENCE: 33
MAKRSSPDPA SSSPSASSSP SSPSSSSSED SSSPMSMPCK RRARPRTDKS TGKAKRPKKE     60
SKEVVDPSSN GGGGGKRSSI YRGVTRHRWT GRFEAHLWDK NCSTSLQNKK KGRQGAYDSE    120
EAAARAYDLA ALKYWGPETV LNFPLEEYEK ERSEMEGVSR EEYLASLRRR SSGFSRGVSK    180
YRGVARHHHN GRWEARIGRV LGNKYLYLGT FDTQEEAAKA YDLAAIEYRG ANAVTNFDIS    240
CYLDQPQLLA QLQQEPQLLA QLQQEPQVVP ALHEEPQDDD RSENAVQELS SSEEANTSSDN   300
NEPLAADDSA ECMNEPLPIV DGIEESLWSP CLDYELDTMP GAYFSNSMNF SEWFNDEAFE    360
GGMEYLFEGC SSITEGGNSM DNSGVTEYNL FEECNMLEKD ISDFLDKDIS DFLDKDISIS    420
DGERISPQAN NISCPQKMIS VCN                                           443

SEQ ID NO: 34             moltype = AA  length = 420
FEATURE                   Location/Qualifiers
source                    1..420
                          mol_type = protein
                          organism = Sorghum bicolor
SEQUENCE: 34
MDMERSQQQK SPTESPPPPS PSSSSSSVSA DTVLPPPGKR RRAATTAKAK AGAKPKRARK     60
DAAAAADPPP PPAAAAAGKR SSVYRGVTRH RWTGRFEAHL WDKHCLAALH NKKKGRQVYL    120
GAYDSEEAAA RAYDLAALKY WGPETLLNFP VEDYSSEMPE MEGVSREEYL ASLRRRSSGF    180
SRGVSKYRGV ARHHHNGRWE ARIGRVFGNK YLYLGTFDTQ EEAAKAYDLA AIEYRGVNAV    240
TNFDISCYLD HPLFLAQLQQ EPQVVPALNQ EAQPDQSETE TIAQESVSSE AKTPDDNAEP    300
DDNAEPDDIA EPLITVDDSI EESLWSPCMD YELDTMSRSN FGSSINLSEW FNDADFDSNI    360
GCLFDGCSAV DEGGKDGVGL ADFSLLEDFS LFEAGDGQLK DVLSDMEEGI QPPTMISVCN    420

SEQ ID NO: 35             moltype = AA  length = 395
FEATURE                   Location/Qualifiers
source                    1..395
                          mol_type = protein
                          organism = Zea mays
SEQUENCE: 35
MERSQRQSPP PPSPSSSSSS VSADTVLVPP GKRRRAATAK AGAEPNKRIR KDPAAAAGK      60
RSSVYRGVTR HRWTGRFEAH LWDKHCLAAL HNKKKGRQVY LGAYDSEEAA ARAYDLAALK    120
YWGPETLLNF PVEDYSSEMP EMEAVSREEY LASLRRRSSG FSRGVSKYRG VARHHHNGRW    180
EARIGRVFGN KYLYLGTFDT QEEAAKAYDL AAIEYRGVNA VTNFDISCYL DHPLFLAQLQ    240
QEPQVVPALN QEPQPDQSET GTTEQEPESS EAKTPDGSAE PDENAVPDDT AEPLSTVDDS    300
IEEGLWSPCM DYELDTMSRP NFGSSINLSE WFADADFDCN IGCLFDGCSA ADEGSKDGVG    360
LADFSLFEAG DVQLKDVLSD MEEGIQPPAM ISVCN                              395

SEQ ID NO: 36             moltype = AA  length = 413
FEATURE                   Location/Qualifiers
source                    1..413
                          mol_type = protein
                          organism = Brachypodium distachyon
SEQUENCE: 36
MEAYCSTLVK DELINGGGGG SAGGMRYCEA APRVSPPVAI KSVKRRKREP PAVSGMTTVS     60
GGGKDGDKSA GNAAAKRSSR FRGVSRHRWT GRFEAHLWDK GTWNPTQKKK GKQVYLGAYN    120
EEEAAARAYD LAALKYWGPT TYTNFPVVDY EKELKVMQGV SREEYLASIR RKSNGFSRGV    180
SKYRGVARHH HNGRWEARIG RVFGNKYLYL GTYSTQEEAA RAYDIAAIEY RGINAVTNFD    240
LSSYIRWLKP NSTINTNTPA AELAILGGGG TPAALITPPP TMHVPRLLPP LVKGRGSSIA    300
DDVSAGSCVF GGPSPSPSPT TTALSLLLRS SVFQELVAQQ QPPSTVDDDD DIGGHAAVSD    360
AAQRAAEENE ESFGEVLYGA GEGEAATAFS CSMYELGLDD NFARIEESLW GCL           413

SEQ ID NO: 37             moltype = AA  length = 423
FEATURE                   Location/Qualifiers
```

```
source                    1..423
                          mol_type = protein
                          organism = Brachypodium sylvaticum
SEQUENCE: 37
MEAYCSSLVK DELINGGGGG AGGMRYCEAA PRVSPPVAIK SVKRRKREPP AVSGMTTVSG    60
GGGGNGKDGD KSAGNAAAAK RSSRFRGVSR HRWTGRFEAH LWDKGTWNPT QKKKGKQVYL   120
GAYNEEEAAA RAYDLAALKY WGPTTYTNFP VVDYEKELKV MQGVSREEYL ASIRRKSNGF   180
SRGVSKYRGV ARHHHNGRWE ARIGRVFGNK YLYLGTYSTQ EEAARAYDIA AIEYRGINAV   240
TNFDLSSYIR WLKPNSAANT NTPPAAAAEL AILGGAPAAL ISPAPAPTTM RVPRLLPPLV   300
RGRGGSIPDD VSAGGSCVFG SPSPSPSPTT TSALSLLLRS SVFQELVAQQ QPPSIVDDDD   360
GVGGQEAVSD AAERAAEENE ESFGEVLYGA GEGEAAAAFS CSMYELGLDD SFARIEESLW   420
GCL                                                                 423

SEQ ID NO: 38             moltype = AA  length = 399
FEATURE                   Location/Qualifiers
source                    1..399
                          mol_type = protein
                          organism = Oryza sativa
SEQUENCE: 38
METYGLVKDE LLHGIGGGQG RLYCEVKPTA APAVITAAGG GAKSVKRRKR EPSAAAMSAV    60
TVAGNGKEAG GSNAANKRSS RFRGVSRHRW TGRFEAHLWD KGTWNPTQKK KGKQVYLGAY   120
NEEDAAARAY DLAALKYWGP TTYTNFPVAD YEKELKLMQG VSKEEYLASI RRKSNGFSRG   180
VSKYRGVARH HHNGRWEARI GRVFGNKYLY LGTYSTQEEA ARAYDIAAIE YRGINAVTNF   240
DLSTYIRWLK PPSSSSAAGT PHHHGGGMVV GADRVLAPAQ SYPISAAADD DVAGCWRPLP   300
SPSSSTTTAL SLLLRSSMFQ ELVARQPVVE GDDGQLAVVS GDDADADADS DVKEPPPESE   360
YGEVFASDEA AAAAYGCSM YELDDSFALI DDSVWNCLI                          399

SEQ ID NO: 39             moltype = AA  length = 488
FEATURE                   Location/Qualifiers
source                    1..488
                          mol_type = protein
                          organism = Sorghum bicolor
SEQUENCE: 39
METYSLQVKD ELHGGGIGIG GGGQGLYCGA TPRPAAPAAT GGGGGGGGDGA VKSNKRSRKR    60
EPPPPPPSSL VTMSNGGKDE AVAGSGDKSA SSNSNASKRS SRFRGVSRHR WTGRFEAHLW   120
DKGTWNPTQK KKGKQVYLGA YNEEDAAARA YDLAALKYWG PTTYTNFPVV DYERELKVMQ   180
NVSKEEYLAS IRRKSNGFSR GVSKYRGVAR HHHNGRWEAR IGRVFGNKYL YLGTYSTQEE   240
AARAYDIAAI EYRGINAVTN FDLSTYIRWL KPGGGVEDSA AGTPTSGVRA PGIPPASLSL   300
QAGGLLQHPH GAAAGMLQVD VDDLYRGQLA AARGAALFSG GIDDVGSVYA AGSAGPSPTA   360
LCAGRPSPSP SPSSSTTALS LLLRSSVFQE LVARNAGGGA AQQQQLVVAD DDGAVSPADV   420
VDAKVEQPEA EGELGRHGDQ LYGAARADED EDAFACSMYE LDDSFARMEQ SLWGCLRSSD   480
APDNMNNL                                                            488

SEQ ID NO: 40             moltype = AA  length = 443
FEATURE                   Location/Qualifiers
source                    1..443
                          mol_type = protein
                          organism = Sorghum bicolor
SEQUENCE: 40
MESSGMMMVK SEIESCGYPG PSSSTAPAAG VVIGGSATTE RGEGGHHHHH HQVVVRRRRR    60
EPPLLAPIAG GGIGKPLPSI TVKRSSRFRG VSRHRWTGRF EAHLWDKNSW NPTQRKKGKQ   120
VYLGAYDEEE AAARAYDLAA LKYWGPTTYT NFPVMDYEKE LKIMENLTKE EYLASLRRKS   180
SGFSRGVSKY RGVARHHQNG RWEARIGRVF GNKYLYLGTY STQEEAARAY DIAAIEYKGV   240
NAVTNFDLRS YITWLKPSGA PAAFNPEAAL LMQAAPAEQL LHPAETAQML PRVGNPFLLD   300
HGAAPPGSSG GGGQDASMSS MVSPGAGGGM RRRGSSTALS LLLKSSMFRQ LVEKNSDAEE   360
GVRDREDAAA AAAAAHPAGP GDAYEYHNFF QGEAPPDMCD LFSSGGGGDH ARNAGFHGEI   420
AACYDDGEGL DGWNGFGNMS SLQ                                           443

SEQ ID NO: 41             moltype = AA  length = 407
FEATURE                   Location/Qualifiers
source                    1..407
                          mol_type = protein
                          organism = Glycine max
SEQUENCE: 41
MELAPVKSEL SPRSHRLLMI DGSEVIGTKC VKRRRRDSST AVLGGNGQQG EQLEEQKQLG    60
GQSTATTVKR SSRFRGVSRH RWTGRFEAHL WDKGTWNPTQ KKKGKQVYLG AYNDEEAAAR   120
AYDLAALKYW GISTFTNFPV SDYEKEIEIM KTVTKEEYLA SLRRRSSGFS RGVSKYRGVA   180
RHHHNGRWEA RIGRVFGNKY LYLGTYSTQE EAARAYDIAA IEYRGINAVT NPDLSTYIRW   240
LRPGTHPTAS HDQKPSTDAQ PFATSNSMQA RGNIEVSNSN KNSFPSGKLD STKKRDFSKY   300
MNPLSPCNKP SSPTALGLLL KSSVFRELMQ RNLNSSSEEA EEVELKYPHE GNDGVGGIYD   360
NENTNNSYFC SSNISRLPNL ESSEEESPLPM YHGTVQSLWN SAFNMSN                407

SEQ ID NO: 42             moltype = AA  length = 406
FEATURE                   Location/Qualifiers
source                    1..406
                          mol_type = protein
                          organism = Glycine max
SEQUENCE: 42
MELAPVKSEL SPRSHRLVII DGSDVISTKC AKRRRRDSSM AVLGGNGQQG EQLEEQKQLG    60
```

```
GQSTATTVKR SSRFRGVSRH RWTGRFEAHL WDKGTWNPTQ KKKGKQVYLG AYNDEEAAAR    120
AYDLAALKYW GTSTFTNFPV SDYEKEIEIM KTVTKEEYLA SLRRRSSGFS RGVSKYRGVA    180
RHHHNGRWEA RIGRVFGNKY LYLGTYSTQE EAARAYDIAA IEYRGINAVT NFDLSTYIRW    240
LRPGTHPTAS HDQKPSTDAQ LFATSNSMQT RGNIEVSNSN MHSFPSGELD STKKRDFSKY    300
MNPLSPCNKP SSPTALGLLL KSSVFRELMQ RNLNSSSEEA DVELKYPQEG NDGVGGIYDN    360
DNTSNSYFCS SNISRLPNLE SSEECPLPMY HGTMQSLWNS AFNMSN                   406

SEQ ID NO: 43              moltype = AA  length = 418
FEATURE                    Location/Qualifiers
source                     1..418
                           mol_type = protein
                           organism = Populus trichocarpa
SEQUENCE: 43
MEMTRNTGDQ ISLGRRRLCM IEEERRAGEA GKCIKRRRRD PSTFALSCNI NDQQSDQQQQ    60
QQSLGDRTAA VATTVKRSSR FRGVSRHRWT GRFEAHLWDK GTWNPTQRKK GKQGAYDEEE    120
SAARAYDLAA LKYWGTSTFT NFPASDYEKE IEIMKTVTKE EYLASLRRRS SGFSRGVSKY    180
RGVARHHHNG RWEARIGRVF GNKYLYLGTY STQEEAAHAY DIAAIEYRGI NAVTNFDLST    240
YIRWLKPEAS LPAPQTQESK PASDPLPMAT FSNHLPSEKP TQLSVLQMDP SLMDNLTPNK    300
NEDIFHRKTL PVSPLTRSSS STALSLLFKS SIFKELVEKN LNTTSEEIEE NDSKNPHNGN    360
NNAGEAFYDG LSPIPHTGTS TEDPFLCSEQ GETNTLPPYS GMEQSLWNGA LSMPSRFH     418

SEQ ID NO: 44              moltype = AA  length = 336
FEATURE                    Location/Qualifiers
source                     1..336
                           mol_type = protein
                           organism = Vitis vinifera
SEQUENCE: 44
MEMTTVKSEL GLERGRLCTA ETDALEVTKC VKRRRRDPSA VTPGCSKQGE QQKQVLLQAG    60
QSITAIATTM KRSSRFRGVS RHRWTGRFEA HLWDKGSWNV TQRKKGKQVY LGAYDEEESA    120
ARAYDLAALK YWGPSTFTNF PVSDYEKEIE IMQGLTKEEY LASLRRRSSG FSRGVSKYRG    180
VARHHHNGRW EARIGRVFGN KYLYLGTYST QEEAAHAYDI AAIEYRGINA VTNFELSTYV    240
RWLRPRATAL TPQEPRSNSI MQASSNCLPN EEVELSFLSP NPFTVDDLAT PLKQEKFQRE    300
VSISPCTKSS SPTALSLLHR SSVFRQLVEK NSNSIE                              336

SEQ ID NO: 45              moltype = AA  length = 389
FEATURE                    Location/Qualifiers
source                     1..389
                           mol_type = protein
                           organism = Glycine max
SEQUENCE: 45
MAMMKENIIE VSLGRRQMSM TEGEFQGTRS VKRRRREVAA AAGSGDDNHQ QQLPQQEVGE    60
NTTVNTTKRS SRFRGVSRHR WTGRYEAHLW DKLSWNITQK KKGKQGAYDE EESAARAYDL    120
AALKYWGTST FTNFPISDYE KEIQIMQTMT KEEYLATLRR KSSGFSRGVS KYRGVSKYRG    180
NGRWEARIGR VFGNKYLYLG TYSTQEEAAR AYDIAAIEYR GIHAVTNFDL STYIKWLKPS    240
GGGTLEANLE SHAALEHQKV ASPSNYALTE ESKSLAHNS FFSPYSLDSP VKHERFGNKT     300
YQFSSNKSSS PTALGLLLRS SLFRELVEKN SNVSGEEDDG EATKDQQTQI ATDDDLGGIF    360
FDSFSDIPFV CDPNRYDLEL QERDLHSIF                                      389

SEQ ID NO: 46              moltype = AA  length = 389
FEATURE                    Location/Qualifiers
source                     1..389
                           mol_type = protein
                           organism = Glycine max
SEQUENCE: 46
MVMMKENIIE EKLGRSQMSM VEGEFQGTWG VKRRRREVAA AASSGDDNHH QQLPQQEVGE    60
NSSISTTKRS SRFRGVSRHR WTGRYEAHLW DKLSWNITQK KKGKQGAYDE EESAARAYDL    120
AALKYWGNST FTNFPISDYE KEIEIMQTMT KEEYLATLRR KSSGFSRGVS KYRGVARHHH    180
NGRWEARIGR VFGNKYLYLG TYSTQEEAAR AYDIAAIEYR GIHAVTNFDL STYIKWLKPS    240
GGGTPEENLE SHAVLEHQKL ASPSNYALTE ESKSLVLPNS FISPDSLDSP VKHESFGNKT    300
YQFSRNKSSS PTALGLLLRS SLFRELVEKN SNVSGEEADG EVTKDQQPQL ASDDDLDGIF    360
FDSFGDIPFV CDPTRYNLEL QERDLHSIF                                      389

SEQ ID NO: 47              moltype = AA  length = 392
FEATURE                    Location/Qualifiers
source                     1..392
                           mol_type = protein
                           organism = Medicago truncatula
SEQUENCE: 47
MAMLIENEVM CLGKSQRSMD GKEVKGARRV KRQRRDAIVP KIGDDANKMA QKQVGENSTT    60
NTSKRSSRFR GVSRHRWTGR FEAHLWDKLS WNTTQKKKGK QGAYDEEESA ARAYDLAALK    120
YWGTSTFTNF PISDYDKEIE IMNTMTKEEY LATLRRKSSG FSRGVSKYRG VARHHHNGRW    180
EARIGRVFGN KYLYLGTYST QEEAARAYDI AAIEYRGIHA VTNFELSSYI KWLKPETTTE    240
ENHESQILQK ESRTLAPPNN STLLQESKLL ALQKSFFIPN DLNSTEKQES SFENKNYHFL    300
SNKSTSPTAL SLLLRSSLFR ELLEKNSNVS EDEVTKEQQQ QQITSDDELG GIFYDGIDNI    360
SPFDFDPNSCN IELQERDLHS ISCLYQYLNF GQ                                392

SEQ ID NO: 48              moltype = AA  length = 386
FEATURE                    Location/Qualifiers
source                     1..386
```

```
                          mol_type = protein
                          organism = Populus trichocarpa
SEQUENCE: 48
MMMIKNEENP GRRRGCIADS EAQVARCVKR RRRDPAIVAL GSDDNQSQQQ MPQKQTDQTS    60
AATTVKRSSR FRGVSRHRWT GRFEAHLWDK LSWNVTQKKK GKQGAYDEEE SAARAYDLAA   120
LKYWGTSTFT NFPISDYEKE IEIMQTVTKE EYLASLRRKS SGFSRGVSKY RGVARHHHNG   180
RWEARIGRVF GNKYLYLGTY STQEEAARAY DIAAIEYRGI NAVTNFDLST YIRWIKPGVA   240
AQAAANELQT VTDPQTAATL TDTYTPREET KPSLFLPNQF TADYLNSPPK LDAFQNNIFV   300
DSSNKTSSPT ALSLLLRSSV FRELVEKNSN VCEEETDGNE IKNQPMAGSD DEYGGIFYDG   360
IGDIPFVYSS NKYSLGLEER ELQFVL                                       386

SEQ ID NO: 49             moltype = AA  length = 372
FEATURE                   Location/Qualifiers
source                    1..372
                          mol_type = protein
                          organism = Ricinus communis
SEQUENCE: 49
MEMMMVKNEE ISGRRRASVT ESEAYVARCV KRRRRDAAVV TVGGDDSQSH QQQQQQQPEQ    60
QAHQISAATT VKRSSRYRGV SRHRWTGRFE AHLWDKLSWN VTQKKKGKQG AYDEEESAAR   120
AYDLAALKYW GTSTFTNFPI SDYEKEIEIM QTVTKEEYLA SLRRKSSGFS RGVSKYRGVA   180
RHHHNGRWEA RIGRVFGNKY LYLGTYSTQE EAARAYDIAA IEYRGINAVT NFDLSTYIRW   240
LKPEVAAQVA ANEPQTVAES RMLPSINNRI AREESKPSFF SATPFSLDCW SYPRKQEEFQ   300
NRTPITPCSK TSSPTALSLL LRSSIFRELV EKNSNVSEDE NEGEETKNQS QIGSDDEFGG   360
LFYERIGDIP FI                                                      372

SEQ ID NO: 50             moltype = AA  length = 404
FEATURE                   Location/Qualifiers
source                    1..404
                          mol_type = protein
                          organism = Vitis vinifera
SEQUENCE: 50
MEMMRVKSEE NLGRRRMCVA DAEAQGTRCV KRRRRDPAIV TLGCDDQSQQ QQLPNQQPDQ    60
ASAATTVKRS SRFRGVSRHR WTGRFEAHLW DKFSWNVTQK KGKQGAYDE EESAARAYDL    120
AALKYWGAST FTNFPVSDYE KEIEIMQSVT KEEYLACLRR KSSGFSRGVS KYRGVARHHH   180
NGRWEARIGR VFGNKYLYLG TYSTQEEAAR AYDIAAIEYR GINAVTNFDL STYIRWLNPA   240
ANNPVVPHES RANTEPQALA SSNFVLSEES EPLFFHSNSF TMDDLNPPHK QEVFQTKIPI   300
EPCSKSSSPT ALGLLLRSSI FRELVEKNSN APEDETDAED TKNQQQVGSD DEYGIFYDGI   360
GDIPFVCPSN GDRNELQERL PLPFTISQGN PYGTAVLTSM QSIN                   404

SEQ ID NO: 51             moltype = AA  length = 378
FEATURE                   Location/Qualifiers
source                    1..378
                          mol_type = protein
                          organism = Brachypodium distachyon
SEQUENCE: 51
MAKQRTDSAG TDAAVQLTK PKRTRKSVPR RESPSRRTSA YRGVTRHRWT GRFEAHLWDK     60
NTWTQSQRKK KGRQVYLGAY GGEEAAARAY DLAALKYWGR DTVLNFPLSN YDEEWKEMEG   120
QSREEYIGSL RRKSTGFSRG VSKYRGVARH HHNGKWEARI GRVYGNKYLY LGTYGTQEEA   180
AMAYDIAAIE HRGLNAVTNF DVSRYIDWHR RLCRDLGDNI ITPLTNPTVD LEEAMAGDDD   240
DGQFLLPSQA TTPPSTSSAL GLLLLSPRLK EVIEGSGAAS AMAASTSESS AAGSPPPSWS   300
SSSCSPSPPS PSHSPPETQQ KQQQQEYGAS AAAARCSFPD DVQTYFGCED GCAEVDTFLF   360
GDLSAYAAPM FQFELLDV                                                378

SEQ ID NO: 52             moltype = AA  length = 416
FEATURE                   Location/Qualifiers
source                    1..416
                          mol_type = protein
                          organism = Oryza sativa
SEQUENCE: 52
MAKRRSNGET AAASSDDSSS GVCGGGGGGE VEPRRQKRP RRSAPRDCPS QRSSAFRGVT     60
RHRWTGRFEA HLWDKNTWNE SQSKKGRQGA YDGEEAAARA YDLAALKYWG HDTVLNFPLS   120
TYDEELKEME GQSREEYIGS LRRKSSGFSR GVSKYRGVAR HHHNGKWEAR IGRVFGNKYL   180
YLGTYATQEE AAVAYDIAAI EHRGLNAVTN FDINLYIRWY HGSCRSSSAA AATTIEDDDF   240
AEEAIAAALQG VDEQPSSSPA TTRQLQTADD DDDDLVAQLP PQLRPLARAA STSPIGLLLR   300
SPKFKEIIEQ AAAAASSSG SSSSSSTDSP SSSSSSSLSP SPLPSPPPQQ QPTVPKDDQY   360
NVDMSSVAAA RCSFPDDVQT YFGLDDDGFG YPEVDTFLFG DLGAYAAPMF QFELDV       416

SEQ ID NO: 53             moltype = AA  length = 440
FEATURE                   Location/Qualifiers
source                    1..440
                          mol_type = protein
                          organism = Sorghum bicolor
SEQUENCE: 53
MARPRKNAGT DEDNPNAATG VSVTGKPPKL KRVRRKGEPR ESSTPSQRSS AYRGVTRHRW    60
TGRFEAHLWD KDARNGSRNK KGKQGAYDDE EAAARAHDLA ALKYWGPATV LNFPLCGYDE   120
ELREMEAQPR EEYIGSLRRR SSGFSRGVSK YRGVARHHHN GRWEARIGRV LGNKYLYLGT   180
FATQEEAAVA YDIAAIEHRG LNAVTNFDIS HYVNHWHRHC HGPSDDSLGV VVDDVAAFQL   240
PDDLPECPAA AIGVEETTGG DAEFHNGEEG YLQHHTSGPF GAQQQLPDET GALAAHQMAP   300
NSSALDMVLQ SPKFKELMEQ VSAAAAAVAS ESSIGGSMSS SSPSPSLSSF SPSPLQLPSP   360
```

```
SSLSSFSPSS PLQQPSPPLQ QPEFVEGAPA ARCSFPDDVQ TFFDFENESD MSFMYAEVDT    420
FLFGDLGAYA APIFHFDLDV                                               440

SEQ ID NO: 54               moltype = AA  length = 408
FEATURE                     Location/Qualifiers
source                      1..408
                            mol_type = protein
                            organism = Zea mays
SEQUENCE: 54
MARPRKNGGT DEDDANAATG ATGKPKKLMK RARRKSESPS PRSSAYRGVT RHRWTGRFEA    60
HLWDKDARNG SRSKKGKQVY LGAYDDEDAA ARAHDLAALK YWGPAGTVLN FPLSGYDEER    120
REMEGQPREE YVASLRRRSS GFARGVSKYR GVARHHHNGR WEARIGRVLG NKYLYLGTYA    180
TQEEAAVAYD MAAIEHRGFN AVTNFDISHY INHWHRHCHG PCDGSLGAMD VAPNVSLELD    240
LLECPATVGL GLEETTGDDE FHNREDYLGH LFGVQQLPDE MGPPAHQMAP ASSALDLVLQ    300
SPRFKELMQQ VSAAGASETN GGSMRSSPST SLCSFSPSPL ELPSPPLQQP TEFIDGAPPR    360
CSFPDDVQSF FDFKNDNDMS FVYAEVDTFL FGDLGAYAPP MFDFDLYE                408

SEQ ID NO: 55               moltype = AA  length = 304
FEATURE                     Location/Qualifiers
source                      1..304
                            mol_type = protein
                            organism = Arabidopsis lyrata
SEQUENCE: 55
MAKVSRRSKK TIVEDEISDK TASASEAASI VFKSKRKRKS PPRNAPPQRS SPYRGVTRHR    60
WTGRYEAHLW DKNSWNETQT KKGRQVYIGA YDEEEAAARA YDLAALKYWG RDTLLNFPLL    120
IYDEDVKEME GQSKEEYIGS LRRKSSGFSR GVSKYRGVAR HHHNGRWEAR IGRVFGNKYL    180
YLGTYATQEE AAIAYDIAAI EYRGLNAVTN FDVSRYLNPD AADSKPIRND PESSDDNKCP    240
KSEEIIEPST SPEAITTRRS FPDDIQTYFG CQDSGKLATE EDVIFGGLNS FINPGFYNEF    300
DYGP                                                                304

SEQ ID NO: 56               moltype = AA  length = 308
FEATURE                     Location/Qualifiers
source                      1..308
                            mol_type = protein
                            organism = Arabidopsis thaliana
SEQUENCE: 56
MAKVSGRSKK TIVDDEISDK TASASESASI ALTSKRKRKS PPRNAPLQRS SPYRGVTRWT    60
GRYEAHLWDK NSWNDTQTKK GRQGAYDEEE AAARAYDLAA LKYWGRDTLL NFPLPSYDED    120
VKEMEGQSKE EYIGSLRRKS SGFSRGVSKY RGVARHHHNG RWEARIGRVF GNKYLYLGTY    180
ATQEEAAIAY DIAAIEYRGL NAVTNFDVSR YLNPNAAADK ADSDSKPIRS PSREPESSDD    240
NKSPKSEEVI EPSTSPEVIP TRRSFPDDIQ TYFGCQDSGK LATEEDVIFD CFNSYINPGF    300
YNEFDYGP                                                            308

SEQ ID NO: 57               moltype = AA  length = 303
FEATURE                     Location/Qualifiers
source                      1..303
                            mol_type = protein
                            organism = Arabidopsis thaliana
SEQUENCE: 57
MAKVSGRSKK TIVDDEISDK TASASESASI ALTSKRKRKS PPRNAPLQRS SPYRGVTRHR    60
WTGRYEAHLW DKNSWNDTQT KKGRQVYLGA YDEEEAAARA YDLAALKYWG RDTLLNFPLL    120
SYDEDVKEME GQSKEEYIGS LRRKSSGFSR GVSKYRGVAR HHHNGRWEAR IGRVFATQEE    180
AAIAYDIAAI EYRGLNAVTN FDVSRYLNPN AAADKADSDS KPIRSPSREP ESSDDNKSPK    240
SEEVIEPSTS PEVIPTRRSF PDDIQTYFGC QDSGKLATEE DVIFDCFNSY INPGFYNEFD    300
YGP                                                                 303

SEQ ID NO: 58               moltype = AA  length = 332
FEATURE                     Location/Qualifiers
source                      1..332
                            mol_type = protein
                            organism = Arabidopsis lyrata
SEQUENCE: 58
MEEITRKSKK TSVENETGDD QSATSVVVKA KRKRRSQPRD APPQRSSVHR GVTRHRWTGR    60
YEAHLWDKNS WNETQSKKGR QGAYDEEDAA ARAYDLAALK YWGRDTILNF PLCNYEEDIK    120
EMESQSKEEY IGSLRRKSSG FSRGVSKYRG VAKHHHNGRW EARIGRVFGN KYLYLGTYAT    180
QEEAAIAYDI AAIEYRGLNA VTNFDISRYM KLPVPENPID AANNLESPHS DSSPFINPT     240
HESDLSQSQS SSDDNDDRKT KLLKSSPLNA EEVIGPSTPP EIAPPRRSFP EDIQTYFGCQ    300
NSGKLTTEED DVIFGDLDSF LTPDFYSELN DC                                 332

SEQ ID NO: 59               moltype = AA  length = 328
FEATURE                     Location/Qualifiers
source                      1..328
                            mol_type = protein
                            organism = Thellungiella halophila
SEQUENCE: 59
MAKVSQRSKK TIVNDEISDK KAVAVASVSS SAFLKSKRKR KLPPQNAPPQ RSSSYRGVTR    60
HRWTGRYEAH LWDKNCWNET QTKKGRQVYL GAYDEEEAAA RAYDLAALKY WGRDTLLNFP    120
LPTYEEDVKE MEGHSREEYI GSLRRKSSGF SRGVSKYRGV ARHHHNGRWE ARIGRVFGNK    180
YLYLGTYATQ EEAARAYDIA AIEYRGLNAV TNFDVSRYLN LPESKNPSAA ANHLPDESDY    240
```

```
YDSMPVRNPN HEPRSPDGQT SSEDNDYTKT EETLDPEAIP SRRSFPDDIQ TYFGCQDSGK    300
LATEEDVIFG GFNSFINPGF YNDFDYAP                                      328

SEQ ID NO: 60           moltype = AA  length = 345
FEATURE                 Location/Qualifiers
source                  1..345
                        mol_type = protein
                        organism = Arabidopsis thaliana
SEQUENCE: 60
MFIAVEVSPV MEDITRQSKK TSVENETGDD QSATSVVLKA KRKRRSQPRD APPQRSSVHR     60
GVTRHRWTGR YEAHLWDKNS WNETQTKKGR QVYLGAYDEE DAAARAYDLA ALKYWGRDTI    120
LNFPLCNYEE DIKEMESQSK EEYIGSLRRK SSGFSRGVSK YRGVAKHHHN GRWEARIGRV    180
FGNKYLYLGT YATQEEAAIA YDIAAIEYRG LNAVTNFDIS RYLKLPVPEN PIDTANNLLE    240
SPHSDLSPFI KPNHESDLSQ SQSSSEDNDD RKTKLLKSSP LVAEEVIGPS TPPEIAPPRR    300
SFPEDIQTYF GCQNSGKLTA EEDDVIFGDL DSFLTPDFYS ELNDC                   345

SEQ ID NO: 61           moltype = AA  length = 299
FEATURE                 Location/Qualifiers
source                  1..299
                        mol_type = protein
                        organism = Glycine max
SEQUENCE: 61
MAKKSQKSLK NNNNNNTTRK RTRKSVPRDS PPQRSSIYRG VTRHRWTGRY EAHLWDKNCW     60
NESQSKKGRQ VYLGAYDDEE AAARAYDLAA LKYWGQDTIL NFPLSNYEEK LKEMEGQSKE    120
EYIGSLRRKS SGFSRGVSKY RGVARHHHNG RWEARIGRVF GNKYLYLGTY ATQEEAAAAY    180
DMAAIEYRGL NAVTNFDLSR YINWPRPKTE ENHQNTPSNQ NVNSNAELEL GSASDEITEE    240
GVARSSESES NPSRRTFPED IQTIFENNQD SGIYIENDDI IFGDLGSFGA PIFHFELDV     299

SEQ ID NO: 62           moltype = AA  length = 393
FEATURE                 Location/Qualifiers
source                  1..393
                        mol_type = protein
                        organism = Brachypodium distachyon
SEQUENCE: 62
MAKPRKNSAA ANNNNNDNST NANNAVAEAA AADVRAKPKK RTRKSVPRES PSQRSSIYRG     60
VTRHRWTGRF EAHLWDKNSW NESQNKKGKQ VYLGAYDEEE AAARAYDLAA LKYWGPDTIL    120
NFPPLSVDDE LKEMEGQSRE EYIGSLRRKS SGFSRGVSKY RGVARHHHNG RWEARIGRVF    180
GNKYLYLGTY ATQEEAAMAY DMAAIEYRGL NAVTNFDLSR YIKWLRPGGG VDSAAAAAAR    240
NPHPMLAGLA TQEELPAIDH LLDGMAFQQH GLHSSSAAAA AAQEFPLPPA LGHAPTTSAL    300
SLLLQSPKFK EMIERTSAAE TTTTATTTSS SSSPRPAASP QCSFPEDIQT FFGCDDGVGV    360
GVGAVGYTDV DGLFFGDLSA YASSTAFHFE LDL                                393

SEQ ID NO: 63           moltype = AA  length = 379
FEATURE                 Location/Qualifiers
source                  1..379
                        mol_type = protein
                        organism = Oryza sativa
SEQUENCE: 63
MAKPRKNSTT TNTSSSGVAA AAAAAVKPK RTRKSVPRES PSQRSSVYRG VTRHRWTGRF      60
EAHLWDKNSW NESQNKKGKQ VYLGAYDEEE AAARAYDLAA LKYWGPDTIL NFPLSAYEGE    120
LKEMEGQSRE EYIGSLRRKS SGFSRGVSKY RGVARHHHNG RWEARIGRVF GNKYLYLGTY    180
ATQEEAAMAY DMAAIEYRGL NAVTNFDLSR YIKWLRPGAD GAGAAQNPHP MLGALSAQDL    240
PAIDLDAMAS SFQHDGHGAA AAAAQLIPAR HSLGHTPTTS ALSLLLQSPK FKEMIERTSA    300
AETTTTSSTT TSSSSPSPPQ ATKDDGASPQ CSFPKDIQTY FGCAAEDGAA GAGYADVDGL    360
FFGDLTAYAS PAFHFELDL                                                379

SEQ ID NO: 64           moltype = AA  length = 398
FEATURE                 Location/Qualifiers
source                  1..398
                        mol_type = protein
                        organism = Sorghum bicolor
SEQUENCE: 64
MAKPRKNSAA ANNNSSSNG AGDLTPRAKP KRTRKSVPRE SPTQRSSVYR GVTRHRWTGR      60
FEAHLWDKNS WNESQNKKGK QVYLGAYDDE EAAARAYDLA ALKYWGPDTI LNFPASAYEG    120
EMKGMEGQSR EEYIGSLRRK SSGFSRGVSK YRGVARHHHN GRWEARIGRV FGNKYLYLGT    180
YATQEEAAMA YDMAAIEYRG LNAVTNFDLS RYIKWLRPGA GGMAAAAAAA QNPHPMLGGL    240
AQQLLLPPPA DTTTTDGAGA AAFQHDHHGA EAFPLPPRTS LGHTPTTSAL SLLLQSPKFK    300
EMIQRTESGT TTTTTTTSSL SSSPPPTPSP SPPRRSPAPT QPPVQAAARD ASPHQRGFPE    360
DVQTFFGCED TAGIDVEALF FGDLAAYATP AFHFEMDL                           398

SEQ ID NO: 65           moltype = AA  length = 396
FEATURE                 Location/Qualifiers
source                  1..396
                        mol_type = protein
                        organism = Zea mays
SEQUENCE: 65
MARPRKNSAA AANNNNSNTT NAGNAAVDLA ARVKPKRTRK SVPRESPSQR SSVYRGVTRH     60
RWTGRFEAHL WDKNSWNESQ NKKGKQVYLG AYDDEDAAAR AYDLAALKYW GPDTILNFPA    120
SAYEAELKEM EGQSREEYIG SLRRKSSGFS RGVSKYRGVA RHHHNGRWEA RIGRVFGNKY    180
```

```
LYLGTYGTQE EAAMAYDMAA IEYRGLNAVT NFDLSRYIKW LRPGAGAAQN PHPMLDGLAQ      240
QLLLSPEGTI DGAAFHQQQH DHRQQGAAEL PLPPRASLGH TPTTSALGLL LQSSKFKEMI      300
QRASAAESGT TTVTTTSSSS SQPPTPTPTP SPSPPPTPPV QPARDASPQC SFPEDIQTFF      360
GCEDVAGVGA GVDVDALFFG DLAAYASPAF HFEMDL                                396

SEQ ID NO: 66           moltype = AA   length = 362
FEATURE                 Location/Qualifiers
source                  1..362
                        mol_type = protein
                        organism = Glycine max
SEQUENCE: 66
MAKKSQLRTQ KNNATNDDIN LNATNTVITK VKRTRRSVPR DSPPQRSSIY RGVTRHRWTG      60
RYEAHLWDKH CWNESQNKKG RQGAYDNEEA AAHAYDLAAL KYWGQDTILN FPLSNYLNEL      120
KEMEGQSREE YIGSLRRKSS GFSRGISKYR GVARHHHNGR WEARIGKVFG NKYLYLGTYA      180
TQEEAATAYD LAAIEYRGLN AVTNFDLSRY IKWLKPNNTN SNNDQISINL TNINNNCTNN      240
FIPNPDQEQE VSFFHNQDSL NNTIVEEATL VPHQPRPASA TLALELLLQS SKFKEMVEMT      300
SVANLSTQME SDQLPQCTFP DHIQTYFEYE DSNKYEEGDD LLFKFSEFSS IVPFYHCDEF      360
ES                                                                    362

SEQ ID NO: 67           moltype = AA   length = 370
FEATURE                 Location/Qualifiers
source                  1..370
                        mol_type = protein
                        organism = Glycine max
SEQUENCE: 67
MAKKSQLRTQ KNNVTTNDDN NLNVTNTVTT KVKRTRRSVP RDSPPQRSSI YRGVTRHRWT      60
GRYEAHLWDK HCWNESQNKK GRQVYLGAYD NEEAAAHAYD LAALKYWGQD TILNFPLSNY      120
LNELKEMEGQ SREEYIGSLR RKSSGFSRGI SKYRGVARHH HNGRWEARIG KVFGNKYLYL      180
GTYATQEEAA TAYDLAAIEY RGLNAVTNFD LSRYIKWLKP NNNTNNVIDD QISINLTNIN      240
NNNNCTNSFT PSPDQEQEAS FFHNKDSLNN TIVEEVTLVP HQPRPASATS ALELLLQSSK      300
FKEMMEMTSV ANLSSTQMES ELPQCTFPDH IQTYFEYEDS NRYEEGDDLM FKFNEFSSIV      360
PFYQCDEFES                                                            370

SEQ ID NO: 68           moltype = AA   length = 356
FEATURE                 Location/Qualifiers
source                  1..356
                        mol_type = protein
                        organism = Medicago truncatula
SEQUENCE: 68
MAKKSQKQIE KDDNASNDND NLNPSNTVTT KAKRTRKSVP RTSPPQRSSI YRGVTRHRWT      60
GRYEAHLWDK NCWNESQNKK GRQGAYDNEE TAAHAYDLAA LKYWGQDTII NFPLSNYQKE      120
LIEMESQSRE EYIGSLRRKS SGFSRGVSKY RGVARHHHNG RWEARIGKVF GNKYLYLGTY      180
ATQEEAATAY DMAAIEYRGL NAVTNFDLSR YIKWLKPNND NNKSNI NLCDINSNSS         240
ANDSNSNEEL EFSLVDNEIS LNNSIDEATL VQPRPTSATS ALELLLQSSK FKEMVEMASM      300
TSNVSTTLES DQLSQCAFPD DIQTYFEYEN FNDTMLEDLN SIMPTFHYDF EGAEVL         356

SEQ ID NO: 69           moltype = AA   length = 347
FEATURE                 Location/Qualifiers
source                  1..347
                        mol_type = protein
                        organism = Glycine max
SEQUENCE: 69
MAKQQTHKIN ASTNNNISTT NTVTAKVKRT RRSVPRDSPP QRSSIYRGVT RHRWTGRYEA      60
HLWDKNCWNE SQNKKGRQGA YDDEEAAAHA YDLAALKYWG QDTILNFPLS TYQNELKEME      120
GQSREEYIGS LRRKSSGFSR GVSKYRGVAR HHHNGRWEAR IGRVFGNKYL YLGTYATQEE      180
AATAYDMAAI EYRGVNAVTN FDLSRYIKWL KPNNNNTTVN SNLIDSNPNC ETNFTSNSNQ      240
QQGFNFPNRQ ESFNNEEAAM TQPRPAVATS ALGLLLQSSK FKEMMEMTSA TDLSTPPSES      300
ELPSCTFPDD IQTYFECEDS HRYGEGDDIM FSVLNGFVPP MFHCDDF                   347

SEQ ID NO: 70           moltype = AA   length = 351
FEATURE                 Location/Qualifiers
source                  1..351
                        mol_type = protein
                        organism = Glycine max
SEQUENCE: 70
MAKQQTHEIN ASTNNNINTT KTVTTKVKRT RRSVPRNSPP QRSSIYRGVT RHRWTGRYEA      60
HLWDKNCWNE SQNKKGRQGA YDDEEAAAHA YDLAALKYWG QDTILNFPLS TYQNELKEME      120
GQSREEYIGS LRRKSSGFSR GVSKYRGVAR HHHNGRWEAR IGVFGNKYL YLGTYATQEE       180
AATAYDMAAI EYRGLNAVTN FDLSRYIKWL KPNNNNNKVN SNNLIVSIPN CATNFTPNSN      240
QQQGFNFFNS QESFNNNEEA AMTQPRPAAA TSALGLLLQS SKFKEMMEMT SAIDLSTPPS      300
ESELPPCTFP DDIQTYFECE DSHRYGEGDD IMFSELNGFV PPMFHCDDFE A               351

SEQ ID NO: 71           moltype = AA   length = 353
FEATURE                 Location/Qualifiers
source                  1..353
                        mol_type = protein
                        organism = Populus trichocarpa
SEQUENCE: 71
MAKLSQKNTK NTASNNNNTT NGVTKVKRTR RSVPRDSPPQ RSSIYRGVTR HRWTGRYEAH      60
```

```
LWDKNCWNES QNKKGRQGAY DDEEAAAHAY DLAALKYWGP ETILNFPLST YQNELKEMEG    120
QSREECIGSL RRKSSGFSRG VSKYRGVARH HHNGRWEARI GRVFGNKYLY LGTYATQEEA    180
ATAYDMAAIE YRGLNAVTNF DLSRYIKWLK PNQNNTDNNN GLDLPNPIIG TDNSTHPNPN    240
QELGTTFLQI NQQTYQPSET TLTQPRPATN PSSALGLLLQ SSKFKEMMEM TAVTDCPPTP    300
PSGLDPTPCS FLEDVQTYFD CLDSSNYGDQ GDDMIFGDLN SFVPPMFQCD FET           353

SEQ ID NO: 72            moltype = AA   length = 323
FEATURE                  Location/Qualifiers
source                   1..323
                         mol_type = protein
                         organism = Vitis vinifera
SEQUENCE: 72
MAKLSQQNHK NSANSNATNT TLSVTKVKRT RKTVPRDSPP QRSSIYRGVT RHRWTGRYEA    60
HLWDKNCWNE SQNKKGRQVY LGAYHDEEAA AHAYDLAALK YWGPETILNF PLSTYEKELK    120
EMEGLSREEY IGSLRRRSSG FSRGVSKYRG VARHHHNGRW EARIGRVFGN KYLYLGTYAT    180
QEEAATAYDM AAIEYRGLNA VTNFDLSRYI KWLKPNQNNP CEQPNNPNLD SNLTPNPNHD    240
FGISFLNHPQ TSGTAACKMM EMTTAADHLS TPPESELPRC SFPDDIQTYF ECQDSGSYEE    300
GDDVIFSELN SFIPPMFQCD FSA                                            323

SEQ ID NO: 73            moltype = AA   length = 347
FEATURE                  Location/Qualifiers
source                   1..347
                         mol_type = protein
                         organism = Vitis vinifera
SEQUENCE: 73
MAKLSQQNHK NSANSNATNT TLSVTKVKRT RKTVPRDSPP QRSSIYRGVT RHRWTGRYEA    60
HLWDKNCWNE SQNKKGRQGA YHDEEAAAHA YDLAALKYWG PETILNFPLS TYEKELKEME    120
GLSREEYIGS LRRRSSGFSR GVSKYRGVAR HHHNGRWEAR IGRVFGNKYL YLGTYATQEE    180
AATAYDMAAI EYRGLNAVTN FDLSRYIKWL KPNQNNPCEQ PNNPNLDSNL TPNPNHDFGI    240
SFLNHPQTSG TAACSEPPLT QTRPPIASSA LGLLLQSSKF KEMMEMTTAA DHLSTPPESE    300
LPRCSFPDDI QTYFECQDSG SYEEGDDVIF SELNSFIPPM FQCDFSA                  347

SEQ ID NO: 74            moltype = AA   length = 275
FEATURE                  Location/Qualifiers
source                   1..275
                         mol_type = protein
                         organism = Populus trichocarpa
SEQUENCE: 74
MGKTSKQSLK NSANTSINPA TKVKRTRKSV PRDSPPQRSS IYRGVTRHRW TGRYEAHLWD    60
KNCWNESQNK KGRQGAYDDE EAAGHAYDLA ALKYWGQDTI LNFPLSTYEE EFKEMEGHSK    120
EEYIGSLRRK SSGFSRGVSK YRGVARHHHN GRWEARIGRV FGNKYLYLGT YATQEEAATA    180
YDMAAIEYRG LNAVTNFDLS RYSSKFKEML ERTSASDCPL TPPESDRDPP RRSFPDDIQT    240
YFDCQDSSSY TDGDDIIFGD LHSFASPIFH CELDG                               275

SEQ ID NO: 75            moltype = AA   length = 304
FEATURE                  Location/Qualifiers
source                   1..304
                         mol_type = protein
                         organism = Vitis vinifera
SEQUENCE: 75
MAKTSQKSQK TTGNSTNNNG GSVAKVKRTR KSVPRDSPPQ RSSIFRGVTR HRWTGRYEAH    60
LWDKNCWNES QNKKGRQVYL GAYDDEEAAA HAYDLAALKY WGQETILNFP LSAYQEELKE    120
MEGQSKEEYI GSLRRKSSGF SRGVSKYRGV ARHHHNGRWE ARIGRVFGNK YLYLGTYATQ    180
EEAATAYDMA AIEYRGLNAV TNFDLSRYIN SPAPNPNPSD HELGLSFLQQ QHGSDATELP    240
LSHARSDCPL TPPDQIEMPR SSFPDDIQTY FDCQETNSYG ESDDIIFGDL KYFSSPMFQC    300
ELDT                                                                 304

SEQ ID NO: 76            moltype = AA   length = 393
FEATURE                  Location/Qualifiers
source                   1..393
                         mol_type = protein
                         organism = Sorghum bicolor
SEQUENCE: 76
MASPNPEAAA GLQTVAVAAG GGEGGSSSSL GAVAGAAAVS SSGELVPRRS LAVRKERVCT    60
AKERISRMPP CAAGKRSSIY RGVTRHRWTG RYEAHLWDKS TWNQNQNKKG KQGAYDDEEA    120
AARAYDLAAL KYWGAGTQIN FPVSDYARDL EEMQMISKED YLVSLRRQLH NSRWDTSLGL    180
GNDYMSLSCG KDIMLDGKFA GSFGLERKID LTNYIRWWLP KKTRQSDTSK TEEIADEIRA    240
IESSMQQTEP YKLPSLGLGS PSKPSSVGLS ACSILSQSDA FKSFLEKSTK LSEECTLSKE    300
IVEGKTVASV PATGYDTGAI NINMNELLVQ RSTYSMAPVM PTPMKTTWSP ADPSVDPLFW    360
SNFVLPSSQP VTMATITTTT NEVSSSDPFQ SQE                                 393

SEQ ID NO: 77            moltype = AA   length = 428
FEATURE                  Location/Qualifiers
source                   1..428
                         mol_type = protein
                         organism = Lupinus angustifolius
SEQUENCE: 77
MASSSSDPGK SEIGGGAAET SEAAAVAVAV TNDQSLLYRG LKKAKKERGC TAKERISKMP    60
PCAAGKRSSI YRGVTRHRWT GRYEAHLRDK STWNQNQNKK GKQVYLGAYD DEEAAARAYD    120
```

```
LAALKYWGPG TLINFPVTDY TRDLEEMQNV SREEYLASLR RKSSGFSRGI SKYRALSSRW    180
EPSYSRFAGS DYFNSMHYGA GDDSAAESEY ASGFCIERKI DLTGHIKWWG SNKSRQPDAG    240
TRLSEEKRHG FAGDICSEPK TLEQKVQPTE PYQMPELGRS HNEKKHRSSA VSALSILSQS    300
AAYKSLQEKA SKKQENSTDN DENENKNTVN KLDHGKAVEK SSNHDGGSDR VDIEIGTTGA    360
LSLQRNIYPL TPFLSAPLLT AYNTVDPSLV DPVLWTSLVP MLSAGLSCPT QVTKTETSSS    420
YTIFQPEG                                                            428

SEQ ID NO: 78           moltype = AA  length = 440
FEATURE                 Location/Qualifiers
source                  1..440
                        mol_type = protein
                        organism = Ricinus communis
SEQUENCE: 78
MASSSSDPGL KPELGGGSGG ESSEAVIAND QLLLYRQLKK PKKERGCTAK ERISKMPPCT    60
AGKRSSIYRG VTRHRWTGRY EAHLWDKSTW NQNQNKKGKQ GAYDDEEAAA RAYDLAALKY   120
WGPGTLINFP VTDYSRDLEE MQNVSREEYL ASLRRKSSGF SRGISKYRGL SSQWDSSFGR   180
MPGSEYFSSI NYGAADDPAA ESEYVGSLCF ERKIDLTSYI RWWGFNKTRE SVSKSSDERK   240
HGYGEDISEL KSSEWAVQST EPYQMPRLGM PDNGKKHKCS KISALSILSH SAAYKNLQEK   300
ASKKQENCTD NDEKENKKTN KMDYGKAVEK STSHDGSNER LGAALGMSGG LSLQRNAYQL   360
APFLSAPLLT NYNAIDPLVD PILWTSLVPV LPAGFSRNSE VGMGLQIVSC HKDRDKFNLY   420
LLSAGGVSTF LLLVVHWRFC                                               440

SEQ ID NO: 79           moltype = AA  length = 428
FEATURE                 Location/Qualifiers
source                  1..428
                        mol_type = protein
                        organism = Lupinus angustifolius
SEQUENCE: 79
MASSSSDPGK SEIGGGAAET SEAAAVAVAV TNDQSLLYRG LKKAKKERGC TAKERISKMP    60
PCAAGKRSSI YRGVTRHRWT GRYEAHLRDK STWNQNQNKK GKQVYLGAYD DEEAAARAYD   120
LAALKYWGPG TLINFPVTDY TRDLEEMQNV SREEYLASLR RKSSGFSRGI SKYRALSSRW   180
EPSYSRFAGS DYFNSMHYGA GDDSAAESEY ASGFCIERKI DLTGHIKWWG SNKSRQPDAG   240
TRLSEEKRHG FAGDICSEPK TLEQKVQPTE PYQMPELGRS HNEKKHRSSA VSALSILSQS   300
AAYKSLQEKA SKKQENSTDN DENENKNTVN KLDHGKAVEK SSNHDGGSDR VDIEIGTTGA   360
LSLQRNIYPL TPFLSAPLLT AYNTVDPSLV DPVLWTSLVP MLSAGLSCPT QVTKTETSSS   420
YTIFQPEG                                                            428

SEQ ID NO: 80           moltype = AA  length = 508
FEATURE                 Location/Qualifiers
source                  1..508
                        mol_type = protein
                        organism = Aspergillus fumigatus
SEQUENCE: 80
MKMSASKTVT SSASAVSTSS GRSTPSKLVN GATRNGSAAA GNGSTGTAKG KRRSKYRHVA    60
AYHSELRHSS LSRETSVVPS FLGFRNLMVI VLVAMNLRLI IENFMKYGVL ICIKCHDYRK   120
QDVVLGSILF ALVPCHLFLA YIIELVAAQQ SKKTVGRQKK DLSTEERERE QQAFRSTWRY   180
TAFFHTVNAT LCLAVTSFVV YFYINHPGIG TICELHAIIV WLKNCSYAFT NRDLRQAMVD   240
PSAESALPEI YSTCPYPRNI TLGNLTYFWL APTLVYQPVY PRSSHIRWSF VAKRLAEFFG   300
LAVFIWLLSA QYAAPVLRNS IDKIAVMDIA SILERVMKLS TISLVIWLAG FFALFQSLLN   360
ALAEVMRFGD REFYTDWWNS PSLGAYWRSW NRPVYLFMKR HVFSPLVGRG WSPFAASFMV   420
FSLSAVLHEM LVGIPTHNLI GVAFAGMMFQ LPLIAVTAPF EKVNDALGKI VGNSIFWVSF   480
CLVGQPLGAL LYFFAWQAKY GSVSKIHV                                      508

SEQ ID NO: 81           moltype = AA  length = 521
FEATURE                 Location/Qualifiers
source                  1..521
                        mol_type = protein
                        organism = Ricinus communis
SEQUENCE: 81
MTILETPETL GVISSSATSD LNLSLRRRRT SNDSDGALAD LASKFDDDDD VRSEDSAENI    60
IEDPVAAVTE LATAKSNGKD CVANSNKDKI DSHGGSSDFK LAYRPSVPAH RSLKESPLSS   120
DLIFKQSHAG LFNLCIVVLV AVNSRLIIEN LMKYGWLIKT GFWFSSRSLR DWPLFMCCLS   180
LPVFPLAAYL VEKAAYRKYI SPPIVIFLHV IITSAAVLYP ASVLSCESA FLSGVTLMEL    240
ACMVWLKLVS YAHTNYDMRA IADTIHKEDA SNSSSTEYCH DVSFKTLAYF MVAPTLCYQP   300
SYPRTAFIRK GWVFRQFVKL IIFTGFMGFI IEQYINPIVQ NSQHPLKGDL LYAIERVLKL   360
SVPNLYVWLC LFYCFFHLWL NIVAELLRFG DREFYKDWWN AKTVEEYWRM WNMPVHKWMV   420
RHIYFPCLRR KIPRGVAIVI AFFVSAVFHE LCIAVPCHMF KLWAFFGIMF QIPLVVITNY   480
FQRKFRSSMV GNMIFWFFFC ILGQPMCVLL YYHDLMNRDG N                       521

SEQ ID NO: 82           moltype = AA  length = 526
FEATURE                 Location/Qualifiers
source                  1..526
                        mol_type = protein
                        organism = Vernicia fordii
SEQUENCE: 82
MTIPETPDNS TDATTSGGAE SSSDLNLSLR RRTASNSDG AVAELASKID ELESDAGGGQ     60
VIKDPGAEMD SGTLKSNGKD CGTVKDRIEN RENRGGSDVK FTYRPSVPAH RALKESPLSS   120
DNIFKQSHAG LFNLCIVVLV AVNSRLIIEN IMKYGWLIKT GFWFSSRSLR DWPLLMCCLT   180
LPIFSLAAYL VEKLACRKYI SAPTVVFLHI LFSSTAVLYP VSVILSCESA VLSGVALMLF   240
```

```
ACIVWLKLVS YAHTNFDMRA IANSVDKGDA LSNASSAESS HDVSFKSLVY FMVAPTLCYQ   300
PSYPRTASIR KGWVVRQFVK LIIFTGFMGF IIEQYINPIV QNSQHPLKGD LLYAIERVLK   360
LSVPNLYVWL CMFYCFFHLW LNILAELLRF GDREFYKDWW NARTVEEYWR MWNMPVHKWM   420
VRHIYFPCLR HKIPRGVALL ITFFVSAVFH ELCIAVPCHI FKLWAFIGIM FQIPLVGITN   480
YLQNKFRSSM VGNMIFWFIF CILGQPMCLL LYYHDLMNRK GTTESR                 526

SEQ ID NO: 83              moltype = AA  length = 523
FEATURE                    Location/Qualifiers
source                     1..523
                           mol_type = protein
                           organism = Vernonia galamensis
SEQUENCE: 83
MALLDTPQIG EITTTATTTI RRRTTVKPDA GIGDGLFDSS SSSKTNSSFE DGDSLNGDFN    60
DKFKEQIGAG DESKDDSKGN GQKIDHGGVK KGRETTVVHY AYRPSSPAHR RIKESPLSSD   120
AIFKQSHAGL FNLCIVVLVA VNGRLIIENL MKYGLLINSN FWFSSRSLRD WPLLMCCLTP   180
SDFPLAAYIV EKLAWKKRIS DPVVITLHVI ITTTAILYPV FMILRFDSVV LSGVSLMLCA   240
CINWLKLVSF VHTNYDMRSL LNSTDKGEVE PMSSNMDYFY DVNFKSLVYF MVAPTLCYQI   300
SYPRTAFIRK GWVLRQLIKL VIFTGFMGFI IEQYINPIVK NSRHPLKGDF LYAIERVLKL   360
SVPNLYVWLC MFYCFFHLWL NILAELLCFG DREFYKDWWN AQTIEEYWRL WNMPVHKWIV   420
RHLYFPCLRN GIPKGAAILV AFFMSAVFHE LCIAVPCHIF KFWAFIGIMF QVPLVLLTNY   480
LQHKFQNSMV GNMIFWCFFS IFGQPMCVLL YYHDVMNQKG KSK                    523

SEQ ID NO: 84              moltype = AA  length = 517
FEATURE                    Location/Qualifiers
source                     1..517
                           mol_type = protein
                           organism = Vernonia galamensis
SEQUENCE: 84
MALLDTPQIG EITTTATTTI RQHPLGKPDA GIGDGLFSSS SSKTNSSFED GDSLNGDFND    60
KPFKEQIGAGD ESKKGNGKID HGGVKKGRET TVVHYAYRPS SPAHRRIKES PLSSDAIFKQ  120
SHAGLFNLCI VVLVAVNGRL IIENLMKYGL LINSKFWFSS RSLRDWPLLM CWLTPSDFPL   180
AAYIVEKLAW KKRISDPVVI TLHVVITTTA ILYPIFMILR FDSVVLLGVS LMLCACINWL   240
KLVSFVHTNY DMRSLLNSTG KGEVEPMSSN MDYFYDINFK SLVYFMVAPT LCYQISYPRT   300
AFIRKGWVFR QLIKLVIFTG FMGFIIEQYI NPIVKNSRHP LKGDFLYAIE RVLKVSVPNL   360
YVWLCMFYCF FHLWLNILAE LLWFGDREFY KDWWNTQTIE EYWRLWNMPV HKWIVRHLYF   420
PCLRNGISKG AAILVAFFMS AVFHELCIAV PCHILKFWAF IGIMFQVPLV LLTNYLQHKF   480
QNSMVGNMIF WCFFSIFGQP MCVFLYYHEV NQKGKSK                           517

SEQ ID NO: 85              moltype = AA  length = 507
FEATURE                    Location/Qualifiers
source                     1..507
                           mol_type = protein
                           organism = Euonymus alatus
SEQUENCE: 85
MAANLNEASD LNFSLRRRTG GISSTTVPDS SSETSSSEAD YLDGGKGAAD VKDRGDGAVE    60
FQNSMKNVER IEKHESRVGL DSRFTYRPSV PAHRTIKESP LSSDAIFKQS HAGLFNLCIV   120
VLVAVNSRLI IENLMKYGWL IRSGFWFSSR SLRDWPLLRC CLTLPVFPLA AFLFEKLAQK   180
NLISEPVVVL LHIVNTTAAV LYPVLVILRC DSAFMSGVTL MLFACIVWLK LVSYAHTNYD   240
MRALTKSVEK GDTPLSSQNM DYSFDVNIKS LAYFMVAPTL CYQISYPRTP YVRKGWVVRQ   300
FVKLIIFTGL MGFIIEQYIN PIVQNSQHPL KGNFLYAIER VLKLSVPNLY VWLCMFYCLF   360
HLWNILAEL LCFGDREFYK DWWNAKTVEE YWRMWNMPVH KWMVRHIYFP CLRNGIPKGV   420
AFVISFLVSA VFHELCIAVP CHIFKLWAFF GIMLQVPLVL ITSYLQNKFR SSMVGNMMFW   480
FSFCIFGQPM CLLLYYHDLM NRNGKME                                     507

SEQ ID NO: 86              moltype = AA  length = 498
FEATURE                    Location/Qualifiers
source                     1..498
                           mol_type = protein
                           organism = Caenorhabditis elegans
SEQUENCE: 86
MQMRQQTGRR RRQPSETSNG SLASSRRSSF AQNGNSSRKS SEMRGPCEKV VHTAQDSLFS    60
TSSGWTNFRG FFNLSILLLV LSNGRVALEN VIKYGILITP LQWISTFVEH HYSIWSWPNL   120
ALILCSNIQI LSVFGMEKIL ERGWLGNGFA AVFYTSLVIA HLTIPVVVTL THKWKNPLWS   180
VVMMGVYVIE ALKFISYGHV NYWARDARRK ITELKTQVTD LAKKTCDPKQ FWDLKDELSM   240
HQMAAQYPAN LTLSNIYYFM AAPTLCYEFK FPRLLRIRKH FLIKRTVELI FLSFLIAALV   300
QQWVVPTVRN SMKPLSEMEY SRCLERLLKL AIPNHLIWLL FFYTFFHSFL NLIAELLRFA   360
DREFYRDFWN AETIGYFWKS WNIPVHRFAV RHIYSPMMRN NFSKMSAFFV VFFVSAFFHE   420
YLVSVPLKIF RLWSYYGMMG QIPLSIITDK VVRGGRTGNI IVWLSLIVGQ PLAILMYGHD   480
WYILNFGVSA VQNQTVGI                                               498

SEQ ID NO: 87              moltype = AA  length = 498
FEATURE                    Location/Qualifiers
source                     1..498
                           mol_type = protein
                           organism = Rattus norvegicus
SEQUENCE: 87
MGDRGGAGSS RRRRTGSRVS VQGGSGPKVE EDEVREAAVS PDLGAGGDAP APAPAPAHTR    60
DKDRQTSVGD GHWELRCHRL QDSLFSSDSG FSNYRGILNW CVVMLILSNA RLSLENLIKY   120
GILVDPIQVV SFLFKDPYSW PAPCLIIASN IFIVATFQIE KRLSVGALTE QMGLLLHVVN   180
```

```
LATIICFPAA VALLVESITP VGSLFALASY SIIFLKLSSY RDVNLWCRQR RVKAKAVSAG   240
KKVSGAAAQN TVSYPDNLTY RDLYYFIFAP TLCYELNFPR SPRIRKRFLL RRVLEMLFFT   300
QLQVGLIQQW MVPTIQNSMK PFKDMDYSRI IERLLKLAVP NHLIWLIFFY WLFHSCLNAV   360
AELLQFGDRE FYRDWWNAES VTYFWQNWNI PVHKWCIRHF YKPMLRLGSN KWMARTGVFW   420
ASAFFHEYLV SIPLRMFRLW AFTAMMAQVP LAWIVNRFFQ GNYGNAAVWV TLIIGQPVAV   480
LMYVHDYYVL NYDAPVGA                                                 498

SEQ ID NO: 88           moltype = AA  length = 488
FEATURE                 Location/Qualifiers
source                  1..488
                        mol_type = protein
                        organism = Homo sapiens
SEQUENCE: 88
MGDRGSSRRR RTGSRPSSHG GGGPAAAEEE VRDAAAGPDV GAAGDAPAPA PNKDGDAGVG    60
SGHWELRCHR LQDSLFSSDS GFSNYRGILN WCVVMLILSN ARLFLENLIK YGILVDPIQV   120
VSLFLKDPYS WPAPCLVIAA NVFAVAAFQV EKRLAVGALT EQAGLLLHVA NLATILCFPA   180
AVVLLVESIT PVGSLLALMA HTILFLKLFS YRDVNSWCRR ARAKAASAGK KASSAAAPHT   240
VSYPDNLTYR DLYYFLFAPT LCYELNFPRS PRIRKRFLLR RILEMLFFTQ LQVGLIQQWM   300
VPTIQNSMKP FKDMDYSRII ERLLKLAVPN HLIWLIFFYW LFHSCLNAVA ELMQFGDREF   360
YRDWWNSESV TYFWQNWNIP VHKWCIRHFY KPMLRRGSSK WMARTGVFLA SAFFHEYLVS   420
VPLRMFRLWA FTGMMAQIPL AWFVGRFFQG NYGNAAVWLS LIIGQPIAVL MYVHDYYVLN   480
YEAPAAEA                                                            488

SEQ ID NO: 89           moltype = AA  length = 11
FEATURE                 Location/Qualifiers
REGION                  1..11
                        note = conserved sequence
SITE                    4
                        note = X - Threonine (T) or Serine (S)
source                  1..11
                        mol_type = protein
                        organism = synthetic construct
SEQUENCE: 89
RGVXRHRWTG R                                                         11

SEQ ID NO: 90           moltype = AA  length = 8
FEATURE                 Location/Qualifiers
REGION                  1..8
                        note = conserved sequence
SITE                    1
                        note = X - Phenylalanine (F) or Tyrosine (Y)
source                  1..8
                        mol_type = protein
                        organism = synthetic construct
SEQUENCE: 90
XEAHLWDK                                                              8

SEQ ID NO: 91           moltype = AA  length = 9
FEATURE                 Location/Qualifiers
REGION                  1..9
                        note = conserved sequence
source                  1..9
                        mol_type = protein
                        organism = synthetic construct
SEQUENCE: 91
DLAALKYWG                                                             9

SEQ ID NO: 92           moltype = AA  length = 8
FEATURE                 Location/Qualifiers
REGION                  1..8
                        note = conserved sequence
SITE                    2
                        note = misc_feature - Xaa can be any naturally occurring
                         amino acid
SITE                    5
                        note = X - Serine (S) or Alanine (A)
SITE                    8
                        note = X - any amino acid
source                  1..8
                        mol_type = protein
                        organism = synthetic construct
SEQUENCE: 92
SXGFXRGX                                                              8

SEQ ID NO: 93           moltype = AA  length = 14
FEATURE                 Location/Qualifiers
REGION                  1..14
                        note = conserved sequence
SITE                    3
```

```
                              note = X - Histidine (H) or Gutamine (Q)
SITE                          6
                              note = X - Arginine (R) or Lysine (K)
SITE                          12
                              note = X - Arginine (R) or Lysine (K)
SITE                          13
                              note = misc_feature - Xaa can be any naturally occurring
                               amino acid
source                        1..14
                              mol_type = protein
                              organism = synthetic construct
SEQUENCE: 93
HHXNGXWEAR IGXV                                                             14

SEQ ID NO: 94                 moltype = AA   length = 9
FEATURE                       Location/Qualifiers
REGION                        1..9
                              note = conserved sequence
SITE                          7
                              note = X - any amino acid
source                        1..9
                              mol_type = protein
                              organism = synthetic construct
SEQUENCE: 94
QEEAAAXYD                                                                   9

SEQ ID NO: 95                 moltype = AA   length = 165
FEATURE                       Location/Qualifiers
source                        1..165
                              mol_type = protein
                              organism = Brassica napus
SEQUENCE: 95
MGILRKKKHE RKPSFKSVLT AILATHAATF LLLIAGVSLA GTAAAFIATM PLFVVFSPIL           60
VPAGITTGLL TTGLAAAGGA GATAVTIILW LYKRATGKAP PKVLEKVLKK IIPGAAAAPA           120
AAPGAAPAAA PAAAPAVAPA AAPAAAPAPK PAAPPAPKPA AAPSI                           165

SEQ ID NO: 96                 moltype = AA   length = 193
FEATURE                       Location/Qualifiers
source                        1..193
                              mol_type = protein
                              organism = Brassica napus
SEQUENCE: 96
MADVRTHAHQ VQVHPLRQQE GGIKVVYPQS GPSSTQVLAV IAGVPVGGTL LTLAGLTLAG           60
SVIGLMLAFP LFLIFSPVIV PAAFVIGLAM TGFMASGAIG LTGLSSMSWV LNHIRRVRER           120
MPDELEEAKQ RLADMAEYVG QRTKDAGQTI EEKAHDVRES KTYDVRDRDT KGHTATGGDR           180
DTKTTREVRV ATT                                                             193

SEQ ID NO: 97                 moltype = AA   length = 188
FEATURE                       Location/Qualifiers
source                        1..188
                              mol_type = protein
                              organism = Brassica napus
SEQUENCE: 97
MANVDRRVNV DRTDKGLQLQ PQYEDRVGYG YGYGGNTDYK SCGPSTNQIV ALIAGVPIGG           60
SLLALAGLTL AGSVIGFMLS IPLFLLFSPV IVPAALTIGL AVTGILASGL FGLTGLSSVS           120
WVLNYIRGRS DTVPEQLDYA KRRMADAVGY AGQKGKEMGQ YVQDKAHEAH DTSLTTETNG           180
KTRRAHIA                                                                   188

SEQ ID NO: 98                 moltype = AA   length = 180
FEATURE                       Location/Qualifiers
source                        1..180
                              mol_type = protein
                              organism = Brassica napus
SEQUENCE: 98
MADTARTHHD ITSRDQYPIL GRDRDQYPYG RSDYQTSGQD YSKTRQIAKA ATAVTAGGSL           60
LVLSSLTLVG TVIALTVATT LLVIFSPILV PALITVALLI TGFLSSGGFG IADITVFSWI           120
YKYATGEHPQ GSDKLDSARM KLGTKAQDIK DRAQYYGQQH TGGEHDRDRT RGTHHTTTTT           180

SEQ ID NO: 99                 moltype = AA   length = 210
FEATURE                       Location/Qualifiers
source                        1..210
                              mol_type = protein
                              organism = Brassica napus
SEQUENCE: 99
MADTHRVDRT DRHLQFQSPY EGGRVSIQYE GGGGAGGYGG RGGGYGAEGY KSMMPERGPS           60
STQVLSFLVG VPIVGSLLAI AGLLLAGSVI GLLISIPLFL LFSPVIVPAA LTIGLAATGF           120
LASGMFGLTG LSSVSWVLNY LRGTRKSSVP EQLEYAKKRM ADAVGYAGQK GKGMGQHVQN           180
KAQEAKQYDI SKTHDTTTKG HETTQRTAAA                                           210
```

```
SEQ ID NO: 100             moltype = AA  length = 149
FEATURE                    Location/Qualifiers
source                     1..149
                           mol_type = protein
                           organism = Brassica napus
SEQUENCE: 100
MANQTRTHQD IIVRDSRITL DRDHPKTGAQ MVKVATGVAA GGSLLVLSGL TLAGTVIAFA    60
VATPLLIIFS PVLVPAVITV VLIITGFLAS GGFGIAAITA FSWLYRHMTG SGSDQKIESA   120
RMKVGSRGYD TKYGQHNIGV HQQHQQAAS                                     149

SEQ ID NO: 101             moltype = AA  length = 137
FEATURE                    Location/Qualifiers
source                     1..137
                           mol_type = protein
                           organism = Arachis hypogaea
SEQUENCE: 101
MAEALYYGGR QRQEQPRSTQ LVKATTAVVA GGSLLILAGL VLAGTVIGLT TITPLFVIFS    60
PVLVPAVITV ALLGLGFLAS GGFGVAAITV LTWIYRYVTG KHPPGANQLD TARHKLMGKA   120
REIKDFGQQQ TSGAQAS                                                  137

SEQ ID NO: 102             moltype = AA  length = 150
FEATURE                    Location/Qualifiers
source                     1..150
                           mol_type = protein
                           organism = Arachis hypogaea
SEQUENCE: 102
MTDRTQPHAV QVHTTAGRFG DTAAGTNRYA DRGPSTSKVI AVITGLPIGG TLLLFAGLAL    60
AGTLLGLAVT TPLFILFSPV IVPATIVVGL SVAGFLTSGA CGLTGLSSFS WVMNYIRQTH   120
GSVPEQLEMA KHRMADVAGY VGQKTKDVGQ                                    150

SEQ ID NO: 103             moltype = AA  length = 166
FEATURE                    Location/Qualifiers
source                     1..166
                           mol_type = protein
                           organism = Arachis hypogaea
SEQUENCE: 103
MSDQTRTGYG GGGSYGSSYG GGGTYGSSYG TSYDPSTNQP IRQAIKFMTA STIGVSFLIL    60
SGLILTGTVI GLIIATPLLV IFSPILVPAA ITLALAAGGF LFSGGCGVAA IAALSWLYSY   120
VTGKHPAGSD RLDYAKGVIA DKARDVKDRA KDYAGAGRAQ EGTPGY                  166

SEQ ID NO: 104             moltype = AA  length = 176
FEATURE                    Location/Qualifiers
source                     1..176
                           mol_type = protein
                           organism = Arachis hypogaea
SEQUENCE: 104
MATATDRAPH QVQVHTPTTQ RVDVPRRGYD VSGGGIKTLL PERGPSTSQI IAVLVGVPTG    60
GTLLLLSGLS LLGTIIGLAI ATPVFIFFSP VIVPAVVTIG LAVTGILTAG ACGLTGLMSL   120
SWMINFIRQV HGTTVPDQLD SVKRRMADMA DYVGQKTKDA GQEIQTKAQD VKRSSS       176

SEQ ID NO: 105             moltype = AA  length = 153
FEATURE                    Location/Qualifiers
source                     1..153
                           mol_type = protein
                           organism = Ricinus communis
SEQUENCE: 105
MADRPQPHQV QVHRYDPTTG YKGQQKGPSA SKVLAVLTFL PVGGGLLSLS GITLTNTLIG    60
MAIATPLFIL FGPIILPAAV VIGLAMMAFM VAGALGLSGL TSQSWALKYF REGTAMPESL   120
DQAKKRMQDM AGYVGMKTKE VGQDIQRKAQ EGK                                153

SEQ ID NO: 106             moltype = AA  length = 138
FEATURE                    Location/Qualifiers
source                     1..138
                           mol_type = protein
                           organism = Ricinus communis
SEQUENCE: 106
MAEHQQSPVV SHRPRVNQLV KAGTAATAGS SLLFLSGLTL TGTVIALALA TPLMVLFSPV    60
LLPAVIIISL IGAGFLTSGG FGFGAILVLS WIYRYVTGKQ PPGAESLDQA RLKLAGKARE   120
MKDRAEQFGQ HVTGQQTS                                                 138

SEQ ID NO: 107             moltype = AA  length = 226
FEATURE                    Location/Qualifiers
source                     1..226
                           mol_type = protein
                           organism = Glycine max
SEQUENCE: 107
MTTQVPPHSV QVHTTTTHRY EAGVVPPGAR FETSYEAGVK AASIYHSERG PTTSQVLAVL    60
AGLPVGGILL LLAGLTLAGT LTGLAVATPL FVLFSPVLVP ATVAIGLAVA GFLTSGAFGL   120
TALSSFSWIL NYIRETQPAS ENLAAAAKHH LAEAAEYVGQ KTKEVGQKTK EVGQDIQSKA   180
```

```
QDTREAAARD AREAAARDAR EAAARDAKVE ARDVKRTTVT ATTATA            226

SEQ ID NO: 108          moltype = AA  length = 223
FEATURE                 Location/Qualifiers
source                  1..223
                        mol_type = protein
                        organism = Glycine max
SEQUENCE: 108
MTTVPPHSVQ VHTTTHRYEA GVVPPARFEA PRYEAGIKAP SSIYHSERGP TTSQVLAVVA  60
GLPVGGILLL LAGLTLAGTL TGLVVATPLF IIFSPVLIPA TVAIGLAVAG FLTSGVFGLT 120
ALSSFSWILN YIRETQPASE NLAAAAKHHL AEAAEYVGQK TKEVGQKTKE VGQDIQSKAQ 180
DTREAAARDA RDAREAAARD ARDAKVEARD VKRTTVTATT ATA                 223

SEQ ID NO: 109          moltype = AA  length = 155
FEATURE                 Location/Qualifiers
source                  1..155
                        mol_type = protein
                        organism = Linum usitatissimum
SEQUENCE: 109
MDQTHQTYAG TTQNPSYGGG GTMYQQQQPR SYQAVKAATA ATAGGSLIVL SGLILTATVI  60
SLIIATPLLV IFSPVLVPAL ITVGLLITGF LASGGFGVAA VTVLSWIYRY VTGGHPAGGD 120
SLDQARSKLA GKAREVKDRA SEFAQQHVTG GQQTS                          155

SEQ ID NO: 110          moltype = AA  length = 180
FEATURE                 Location/Qualifiers
source                  1..180
                        mol_type = protein
                        organism = Linum usitatissimum
SEQUENCE: 110
MADRTTQPHQ VQVHTQHHYP TGGAFGRYEG VLKGGPYHQQ GTSGSPSASK VLAVMTALPI  60
GGTLLALAGI TLAGTMIGLA ITTPIFVICS PVLVPAALLI GFAVSAFLAS GMAGLTGLTS 120
LSWFARYLQQ AGQGVGVGVP DSFDQAKRRM QDAAGYMGQK TKEVGQEIQR KSQDVKASDK 180

SEQ ID NO: 111          moltype = AA  length = 181
FEATURE                 Location/Qualifiers
source                  1..181
                        mol_type = protein
                        organism = Helianthus annuus
SEQUENCE: 111
TTTTYDRHFT TTQPHYRQDD RSRYDQQTHS QSTSRTLAII ALLPVGGILL GLAALTFIGT  60
LIGLALATPL FVIFSPIIVP AVLTIGLAVT GFLASGTFGL TGLSSLSYLF NMVRQTAGSV 120
PESLDYVKGT LQDAGEYAGQ KTKDFGQKIQ STAHEMGDQG QVGVHAQVGG GKEGRKSGDR 180
T                                                               181

SEQ ID NO: 112          moltype = AA  length = 156
FEATURE                 Location/Qualifiers
source                  1..156
                        mol_type = protein
                        organism = Zea mays
SEQUENCE: 112
MADHHRGATG GGGGYGDLQR GGGMHGEAQQ QQKQGAMMTA LKAATAATFG GSMLVLSGLI  60
LAGTVIALTV ATPVLVIFSP VLVPAAIALA LMAAGFVTSG GLGVAALSVF SWMYKYLTGK 120
HPPAADQLDH AKARLASKAR DVKDAAQHRI DQAQGS                         156

SEQ ID NO: 113          moltype = AA  length = 244
FEATURE                 Location/Qualifiers
source                  1..244
                        mol_type = protein
                        organism = Brassica napus
SEQUENCE: 113
VSKPDDCRRI VDETISHFGR LDHLVNNAGI MQISMFENIE EITRTRAVMD TNFWGSVYTT  60
RAALPYLRQS NGKIVAMSSS AAWLTAPRMS FYNASKAALL NFFETLRIEL GSDVHITIVT 120
PGYIESELTQ GKYFSGEGEL VVNQDIRDVQ IGAFPVTSVS GCAKGIVKGV CRKQRYVTEP 180
SWFKVTYLWK VFCPELIEWG CRLLFLSGHG TSEKNALNKK ILDIPGVRSA LYPESIRTPE 240
IKSE                                                            244

SEQ ID NO: 114          moltype = AA  length = 349
FEATURE                 Location/Qualifiers
source                  1..349
                        mol_type = protein
                        organism = Brassica napus
SEQUENCE: 114
MELINDFLNL TAPFFTFFGL CFFLPPFYFF KFVQSIFSTI FSENVYGKVV LITGASSGIG  60
EQLAYEYASK GACLALTARR KNRLEEVAEI AREVGSPNVV TVHADVSKPD DCRRIVDETI 120
SHFGRLDHLV NNAGIMQISM FENIEEITRT RAVMDTNFWG AVYTTRAALP YLRQSNGKIV 180
AMSSSAAWLT APRMSFYNAS KAALLNFFET LRIELGSDVH ITIVTPGYIE SELTQGKYVS 240
GEGELVVNQD IRDVQIGAFP VTSVSGRAKG IVKGVCRKER YVTEPSWFKV TYLWKVFCPE 300
LIEWGCRLMF LSGHGTPEEN ALNKKILDIP GVRSALYPEP IRTPEIKSE           349
```

```
SEQ ID NO: 115          moltype = AA  length = 456
FEATURE                 Location/Qualifiers
source                  1..456
                        mol_type = protein
                        organism = Brassica napus
SEQUENCE: 115
MVDLLNSVMN LVAPPATMVV MAFSWPLLCF ITFSERLYNS YFVTEDMEDK VVVITGASPA    60
IGEQIAYEYA KRGANLVLVA RREQRLRVVS NNARQIGANH VIIIAADVVK EDDCRRFITQ   120
AVNYYGRVDH LVNSASLGHT FYFDEVSDTT VFPHLLDINF WGNVYPTYVA LPHLQKTNGR   180
IVVNASVENW LPLPRMSLYS AAKAALVNFY ETLRFELNGD VGITIATHGW IGSEMSRGKF   240
MLEEGAEMQW KEEREVPANG GPLEEFAKMI VAGACRGDAY VKFPNWYDVF LLYRVFTPNV   300
LRWTFKLLLS SEGSRQSSLV GVGQGLPPEE SSSQMKLMLE GGSPRVTASP PRYTPSPSPP   360
HHTASPPRYT PSPSPPHHTS SPQRYTPSPS PPHYTSSRHR YTPSPSPPHY TESPPLYTES   420
PPHYTTSPNW YTESPPRYTP SPSPPRFSRF NIQELP                             456

SEQ ID NO: 116          moltype = AA  length = 348
FEATURE                 Location/Qualifiers
source                  1..348
                        mol_type = protein
                        organism = Sesamum indicum
SEQUENCE: 116
MDLIHTFLNL IAPPFTFFFL LFFLPPFQIF KFFLSILGTL FSEDVAGKVV VITGASSGIG    60
ESLAYEYAKR GACLVLAARR ERSLQEVAER ARDLGSPDVV VVRADVSKAE DCRKVVDQTM   120
NRFGRLDHLV NNAGIMSVSM LEEVEDITGY RETMDINFWG YVYMTRFAAP YLRNSRGRIV   180
VLSSSSSWMP TPRMSFYNAS KAAISQFFET LRVEFGPDIG ITLVTPGFIE SELTQGKFYN   240
AGERVIDQDM RDVQVSTTPI LRVESAARSI VRSAIRGERY VTEPAWFRVT YWWKLFCPEV   300
MEWVFRLMYL ASPGEPEKET FGKKVLDYTG VKSLLYPETV QVPEPKND                348

SEQ ID NO: 117          moltype = AA  length = 350
FEATURE                 Location/Qualifiers
source                  1..350
                        mol_type = protein
                        organism = Zea mays
SEQUENCE: 117
MLGMSRTGLA GAALRVALTA LLPLVLPAYY VYKLTTYLLG AVFPEDVAGK VVLITGASSG    60
IGEHLAYEYA KRGAYLALVA RREASLREVG DVALGLGSPG VLVLPADVSK PRDCEGFIDD   120
TISYFGRLDH LVNNASIWQV CKFEEIQDVR HLRALMDINF WGHVYPTRLA IPHLRRSRGR   180
IVGVTSNSSY IFIGRNTFYN ASKAAALSFY DTLRMELGSD IRITEVVPGV VESEITKGKM   240
LTKGGEMKVD QDERDAILGP TPAEPVGDFA RTVVRDVCRG ARYVFEPRWY MGVYLLRACL   300
PEVLAWNSRL LTVDTVGAST TDTLGKWLVE LPGVRRVVQP PSLRSPEIKD              350

SEQ ID NO: 118          moltype = AA  length = 245
FEATURE                 Location/Qualifiers
source                  1..245
                        mol_type = protein
                        organism = Brassica napus
SEQUENCE: 118
MGTATEIMER DAMATVAPYA PVTFHRRARV DLDDRLPKPY MPRALQAPDR EHPYGTPGHK    60
NYGLSVLQQH VAFFDIDDNG IIYPWETYSG LRMIGFNIIG SLIIAAVINL ALSYATLPGW   120
LPSPFFPIYI HNIHKSKHGS DSRTYDNEGR FMPVNLELIF SKYAKTLPDK LSLGELWDMT   180
EGQRDAWDIF GWFASKIEWG LLYLLARDEE GFLSKEAIRR CFDGSLFEYC AKIYVGINED   240
KTAYY                                                               245

SEQ ID NO: 119          moltype = AA  length = 244
FEATURE                 Location/Qualifiers
source                  1..244
                        mol_type = protein
                        organism = Brassica napus
SEQUENCE: 119
MVRESMGEES EAFATTAPLA PVTGERKVRN DLEETLPKPY LARALVAPDT EHPNGSEGHD    60
SKGMSVTQQH VAFFDQNGDG IVYPWETYAG FRDLGFNPIS SVFWAIFINF AFSYVTLPSW   120
LPSPLLPVYI DNIHKAKHGS DSSTYDTEGR YVPVNLENIF SKYALTAPNK ITLKELWNLT   180
EGNRMAIDPF GWLANKVEWL LVYLLAKDEE GFVSKEAVRG VFDASFFEYC AKKNKEKADS   240
RKQD                                                                244

SEQ ID NO: 120          moltype = AA  length = 245
FEATURE                 Location/Qualifiers
source                  1..245
                        mol_type = protein
                        organism = Sesamum indicum
SEQUENCE: 120
MATHVLAAAA ERNAALAPDA PLAPVTMERP VRTDLETSIP KPYMARGLVA PDMDHPNGTP    60
GHVHDNLSVL QQHCAFFDQD DNGIIYPWET YSGLRQIGFN VIASLIMAIV INVALSYPTL   120
PGWIPSPFFP IYLYNIHKAK HGSDSGTYDT EGRYLPMNFE NLFSKHARTM PDRLTLGELW   180
SMTEANREAF DIFGWIASKM EWTLLYILAR DQDGFLSKEA IRRCYDGSLF EYCAKMQRGA   240
EDKMK                                                               245

SEQ ID NO: 121          moltype = AA  length = 243
FEATURE                 Location/Qualifiers
```

```
source                   1..243
                         mol_type = protein
                         organism = Zea mays
SEQUENCE: 121
MSSYSPPPPP PRDQSMDTEA PNAPITRERR LNPDLQEQLP KPYLARALEA VDPSHPQGTK    60
GRDPRGMSVL QQHAAFFDRN GDGVIYPWET FQGLRAIGCG LTVSFAFSIL INLFLSYPTQ   120
PGWLPSPLLS IRIDNIHKGK HGSDSETYDT EGRFDPSKFD AIFSKYGRTH PNAITRDELS   180
SMLQGNRNTY DFLGWLAAAG EWLLLYSLAK DKDGLLQRET VRGLFDGSLF ERLEDDNNKK   240
KSS                                                                243

SEQ ID NO: 122           moltype = DNA   length = 11142
FEATURE                  Location/Qualifiers
misc_feature             1..11142
                         note = TDNA sequence
source                   1..11142
                         mol_type = other DNA
                         organism = synthetic construct
SEQUENCE: 122
tcctgtggtt ggcatgcaca tacaaatgga cgaacggata aacctttca cgcccttta      60
aatatccgat tattctaata aacgctcttt tctcttaggt ttacccgcca atatatcctg   120
tcaaacactg atagtttaaa ctgaaggcgg gaaacgacaa tctgctagtg gatctcccag   180
tcacgacgtt gtaaaacggg cgccctagaa tctaattatt ctattcagac taaattagta   240
taagtatttt tttaatcaat aaataataat taataattta ttagtaggag tgattgaatt   300
tataatatat tttttttaat catttaaaga atcttatatc tttaaattga caagagtttt   360
aaaatgggag agtgttatca tatcacaagt aggattaatg tgttatagtt tcacatgcat   420
tacgataagt tgtgaaagat aacattatta tatataacta tgcaatcac tagcgatcga   480
gtagtgagag tcgtcttatt acactttctt ccttcgatct gtcacatggc ggcggcccga   540
attctcacac aaggtagttg caagacactg aagtggtggt agtggtagta gaagaagcag   600
aatcggtaga aaggcaagac aatggagaag atgaagatgg tggagattct cttcccacaa   660
cgcacgaatc aaggttttca aggttaaggc actcgtgctt tccatcatcg aacatgaagt   720
cgatgttatc ctcgaaagca agtcgttga agagttctgg gtactcaatt gggttctcgt   780
tagcaaggtt ttgatcggta aggaatgggg agaatccagt atccatcatg cagaagttcc   840
aagcaagttc gttgttatct ccgcacctat ccatttccat gatggtggaa gaatcaatgc   900
agcagttaac aacggcagct tcctcagaat atcccacaat ttcacctct tgttgctaa   960
ccttctcttc ctcttttct tcttcctctt gaggtggttc ctcaacgtat tgttgcttaa  1020
cctcttccct aggttcctct ttagcttctc tagtctcaac ctcttgctta gcctcaacaa  1080
gaatacccct tgatggtta gcctggttaa ctgggaatgg gaaaacgccc ttcttcttaa  1140
gcctgtcgat gtagttggag atatcgaagt tggtaacagc gttagcacct ctgtactcaa  1200
tagcagccat atcataagca gctgcagcct cttcttgagt gttgtaagtt ccgaggtaga  1260
ggtacttgtt tccgaaaact cttccaatcc tagcttccca tcttccgtta tgatgatgcc  1320
tagcaactcc cctatactta gaaactcccc tagagaatcc agatgactgc cttctaaggg  1380
aagcaagata ctcttcttg gtcaccctct gcatctcttc aagttctttg gtgtaagtct  1440
cagctgggaa gttaagaatg gtatctgggc cccaatactt aagagcagca agatcataag  1500
tatgagcagc agcctcttca gaatcataag ctccaaggta aacctgcttg cccttcttgt  1560
tttggatgga gttccaagag gacttatccc aaaggtgagc ttcgaatctt ccagtccatc  1620
tatgcctagt aacacctctg tagatagatg accttctggt agaagctgga gaagttgggt  1680
tatgagactt atcgccagat ggagatgact tcttagccct cttagctcct tttggttcttg  1740
gagcttcaga ttgaattggg ctagaggtag tagtagaaga ggacactgaa gaagatggag  1800
aactagagca ggtagaggta gtgagcctct tcttcatgaa ttctgttctt ctttactctt  1860
tgtgtgactg aggtttggtc tagtgctttg gtcatctata taatgata acaacaatga  1920
gaacaagctt tggagtgatc ggagggtcta ggatacatga gattcaagtg gactaggatc  1980
tacaccgttg gattttgagt gtggatatgt gtgaggttaa ttttacttgg taacggccac  2040
aaaaggcctaa ggagaggtgt tgagaccctt atcggcttga accgctgaa taatgccacg  2100
tggaagataa ttccatgaat cttatcgtta tctatgagtg aaattgtgtg atggtggagt  2160
ggtgcttgct cattttactt gcctggtgga cttggcccctt tccttatgg gaattttat   2220
tttacttact atagagcttt catcctttt ttttaccttg gatttagtta atatataagtg  2280
gtatgattca tgaataaaaa tgggaaattt tgaatttgt actgctaaat gcataagatt  2340
aggtgaaact gtggaatata tattttttc atttaaaagc aaaatttgcc ttttactaga  2400
attataaata tagaaaaata tataacattc aaataaaaat gaaaataaga actttcaaaa  2460
aacagaacta tgtttaatgt gtaaagatta gtcgcacatc aagtcatctg ttacaatatg  2520
ttacaacaag tcataagccc aacaaagtta gcacgtctaa ataaactaaa gagtccacga  2580
aaatattaca aatcataagc ccaacaaagt tattgatcaa aaaaaaaaaa cgcccaacaa  2640
agctaaacaa agtccaaaaa aaacttctca agtctccatc ttcctttatg aacattgaaa  2700
actatacaca aaacaagtca gataaatctc tttctgggcc tgtcttccca acctcctaca  2760
tcacttccct atcggattga atgttttact tgtacctttt ccgttgcaat gatattgcaa  2820
gtatgtttgt gaaaactaat agggttaaca atcgaagtca tggaatatgg atttggtcca  2880
agattttccg agagctttct agtagaaagc ccatcaccag aaatttacta gtaaaataaa  2940
tcaccaatta ggtttcttat tatgtgccaa attcaatata attatagagg atattcaaa   3000
tgaaaacgta tgaatgttat tagtaaatgg tcaggtaaga cattaaaaaa atcctacgtc  3060
agatattcaa ctttaaaaat tcgatcagtg tggaattgta caaaaatttg ggatctacta  3120
tatatatata atgctttaca acacttggat ttttttttgg aggctggaat ttttaatcta  3180
catatttgtt ttggcatgc accaactcat tgtttagtgt aatactttga ttttgtcaaa  3240
tatatgtgtt cgtgtatatt tgtataagaa tttcttggac catacacaca cacacatata  3300
tatatatata tatatattaa atatcatgca cttttaattg aaaaataat atatatatat  3360
atagtgcatt ttttctaaca accatatatg ttgcgattga tctgcaaaaa tactgctaga  3420
gtaatgaaaa atataatcta ttgctgaaat tatctcagat gttaagattt tcttaaagta  3480
aattcttca aattttagct aaaagtcttg taataactaa agaataatac acaatctcga  3540
ccacggaaaa aaaacacata ataaattgg ggccctaga atctaattat tctattcaga  3600
ctaaattagt ataagtattt ttttaatcaa taaataataa ttaataattt attagtagga  3660
```

```
gtgattgaat ttataatata tttttttaa tcatttaaag aatcttatat ctttaaattg    3720
acaagagttt taaatgggga gagtgttatc atatcacaag taggattaat gtgttatagt    3780
ttcacatgca ttacgataag ttgtgaaaga taacattatt atatataaca atgcaatca    3840
ctagcgatcg agtagtgaga gtcgtcttat tacactttct tccttcgatc tgtcacatgg    3900
cggcggcccg cggccgcttc attactgag ccaggaggat ggatcgatgc tggtctgaga    3960
ccctgctacc ggttgctgac tgaactgctc ggcacggtcc ttcatttcac gggccttgct    4020
cgccaacttt gtcttggccg actccaactg atccgctccg ggtggatgtt tccccgtcag    4080
gtaacggtag atccaggaca gcacagacag agcggcaaca ccaaatcccc cgcttgccag    4140
aaaacccgct cccaacagga agatggtgat gactgcagat cagaaaaact cagattaatc    4200
gacaaattcg atcgcacaaa ctagaaacta acaccagatc tagatagaaa tcacaaatcg    4260
aagagtaatt attcgacaaa actcaaatta tttgaacaaa tcggatgata tctatgaaac    4320
cctaatcgag aattaagatg atatctaacg atcaaaccca gaaaatcgtc ttcgatctaa    4380
gattaacaga atctaaacca aagaacatat acgaaattgg gatcgaacga aaacaaaatc    4440
gaagattttg agagaataag gaacacagaa atttacctgc agggaccagt acaggcgaga    4500
agatcaccag gagaggtgtg gcgattgtca gcgcaatgac cgttccagcc agggtcaacc    4560
cggataacac caacaggcta cctccggcag taaccgcggt cgctgccttt acaacacgct    4620
gagcacgcgg ttgcagttgc aagtgggggg cacgtgtttg ttgctgctgc ccgtagtgct    4680
ctgccatggt ttttttaac ggagcaagcg gccgctgttc ttcttttactc tttgtgtgac    4740
tgaggtttgg tctagtgctt tggtcatcta tatataatga taacaacaat gagaacaagc    4800
tttggagtga tcggagggtc taggatacat gagattcaag tggactagga tctacaccgt    4860
tggatttga gtgtggatat gtgtgaggtt aattttactt ggtaacgcc acaaaggcct    4920
aaggagaggt gttgagaccc ttatcggctt gaaccgctga aataatgca cgtggaagat    4980
aattccatga atcttatcgt tatctatgag tgaaattgtg tgatggtgga gtggtgcttg    5040
ctcattttac ttgcctggtg gacttggccc tttccttatg gggaatttat attttactta    5100
ctatagagct ttcataccct tttttacct tggatttagt taatatataa tggtatgatt    5160
catgaataaa aatgggaaat ttttgaattt gtactgctaa atgcataaga ttaggtgaaa    5220
ctgtggaata tatatttttt tcatttaaaa gcaaatttg cctttactaa gaattataaa    5280
tatagaaaaa tatataacat tcaaataaaa atgaaaataa gaactttcaa aaaacagaac    5340
tatgtttaat gtgtaaagat tagtcgcaca tcaagtcatc tgttacaata tgttacaaca    5400
agtcataagc ccaacaaagt tagcacgtct aaataaacta aagagtccac gaaaatatta    5460
caaatcataa gcccaacaaa gttattgatc aaaaaaaaaa aacgcccaac aaagctaaac    5520
aaagtccaaa aaaacttct caagtctcca tcttccttta tgaacattga aaactataca    5580
caaaacaagt cagataaatc tcttttctggg cctgtcttcc caacctccta catcacttcc    5640
ctatcggatt gaatgtttta cttgtaccctt ttccgttgca atgatattga tagtatgttt    5700
gtgaaaacta ataggggttaa caatcgaagt catgaatat ggatttggtc caagattttc    5760
cgagagcttt ctagtagaaa gcccatcacc agaaatttac tagtaaaata aatcaccaat    5820
taggttttctt attatgtgcc aaattcaata taattataga ggatattca aatgaaaacg    5880
tatgaatgtt attagtaaat ggtcaggtaa gacattaaaa aaatcctacg tcagatattc    5940
aactttaaaa attcgatcag tgtggaattg tacaaaaatt tgggactac tatatatatat    6000
taatgcttta caacacttgg attttttttt ggaggctgga attttttaatc tacatatttg    6060
ttttggccat gcaccaactc attgtttagt gtaaatactt gattttgtca aatatatgtg    6120
ttcgtgtata tttgtataag aatttctttg accatataca cacacacata tatatatata    6180
tatatatatt atatatcatg cactttaat tgaaaaaata atatatatat atatagtgca    6240
tttttctaa caaccatata tgttgcgatt gatctgcaaa aatactgcta gagtaatgaa    6300
aaatataatc tattgctgaa attatctcag atgttaagat tttcttaaag taaattcttt    6360
caaattttag ctaaaagtct tgtaataact aaagaataat acacaatctc gaccacgaaa    6420
aaaaaacaca taatttttt gggcgcgcg cgtattggct agagcagctt gccaacatgg    6480
tggagcacga cactctcgtc tactccaaga atatcaaaga tacagtctca gaagaccaaa    6540
gggctattga gacttttcaa caaagggtaa tatcgggaaa cctcctcgga ttccattgcc    6600
cagctatctg tcacttcatc aaaaggacag tagaaaagga aggtggcacc tacaaatgcc    6660
atcattgcga taaaggaaag gctatcgttc aagatgcctc tgccgacagt tgtcccaaag    6720
atggaccccc acccacgagg agcatcgtg aaaaagaaga cgttccaacc acgtcttcaa    6780
agcaagtgga ttgatgtgat aacatggtgg agcacgacac tctcgtctac tccaagaata    6840
tcaaagatac agtctcagaa gaccaaaggg ctattgagac ttttcaacaa agggtaatat    6900
cgggaaacct cctcggattc cattgcccag ctatctgtca cttcatcaaa aggacagtag    6960
aaaaggaagg tggcacctac aaatgccatc attgcgataa aggaaaggct atcgttcaag    7020
atgcctctgc cgacagtggt cccaaagatg accccacc cacgaggagc atcgtggaaa    7080
aagaagacgt tccaaccacg tcttcaaagc aagtggattg atgtgatatc tccactgacg    7140
taagggatga cgcacaatcc cactatcctt cgcaagacct tcctctatat aaggaagttc    7200
atttcatttg gagaggacac gctgaaatca ccagtctctc tctacaaatc tatctctgcg    7260
atcgcatggc gattttggat tctgctggcg ttactacggt gacggagaac ggtggcggag    7320
agttcgtcga tcttgatagg cttcgtcgac ggaaatcgag atcggattct tctaacggac    7380
ttcttctctc tggttccgat aataattctc cttcggatga tgttggagct cccgccgacg    7440
ttagggatcg gattgattcc gttgttaacg atgacgctca gggaacagcc aatttggccg    7500
gagataataa cggtggtggc gataataacg gtggtggaag aggcggcgga gaaggaagag    7560
gaaacgccga tgctacgttt acgtatcgac cgtcggttcc agctcatcgg agggcgagag    7620
agagtccact tagctccgac gcaatcttca aacagagcca tgccggatta ttcaacctct    7680
gtgtagtagt tcttattgct gtaaacagta gactcatcat cgaaaatctt atgaagtatg    7740
gttggttgat cagaacggat ttctggttta gttcaagatc gctgcgagat tggccgcttt    7800
tcatgtgttg tatatccctt tcgatctttc ctttggctgc ctttacggtt gagaaattgg    7860
tacttcagaa atacatatca gaacctgttg tcatctttct tcatattatt atcaccatga    7920
cagaggtttt gtatccagtt tacgtcaccc taaggtgtga ttctgctttt ttatcaggtg    7980
tcactttgat gctcctcact tgcattgtgt ggctaaagtt ggtttcttat gctcatacta    8040
acacatgacat aagtcccta gccaatgcag caatcctgaa gtctcctact                 8100
acgttagctt gaaagagcttg gcatatttca tggtcgctcc cacattgtgt tatcagccaa    8160
gttatccacg ttctgcatgt atacggaagg gttgggtggc tcgtcaattt gcaaactgg    8220
tcatattcac cggattcatg ggatttataa tagaacaata tataaatcct attgtcagga    8280
actcaaagca tcctttgaaa ggcgatcttc tatatgctat tgaaagagtg ttgaagcttt    8340
cagttccaaa tttatatgtg tggctctgca tgttctactg cttcttccac ctttggttaa    8400
```

```
acatattggc agagcttctc tgcttcgggg atcgtgaatt ctacaaagat tggtggaatg 8460
caaaaagtgt gggagattac tggagaatgt ggaatatgcc tgttcataaa tggatggttc 8520
gacatatata cttcccgtgc ttgcgcagca agataccaaa gacactcgcc attatcattg 8580
ctttcctagt ctctgcagtc tttcatgagc tatgcatcgc agttccttgt cgtctcttca 8640
agctatgggc ttttcttggg attatgtttc aggtgccttt ggtcttcatc acaaactatc 8700
tacaggaaag gtttggctca acggtgggga acatgatcgt ctggttcatc ttctgcattt 8760
tcggacaacc gatgtgtgtg cttctttatt accacgacct gatgaaccga aaaggatcga 8820
tgtcatgagc gatcgcgatc gttcaaacat ttggcaataa agtttcttaa gattgaatcc 8880
tgttgccggt cttgcgttga ttatcatata atttctgttg aattacgtta agcatgtaat 8940
aattaacatg taatgcatga cgttatttat gagatgggtt tttatgatta gagtcccgca 9000
attatacatt taatacgcga tagaaaacaa aatatagcgc gcaaactagg ataaattatc 9060
gcgcgcggtg tcatctatgt tactagatcc ctgcagggcg tattggctag agcagcttgc 9120
caacatggtg gagcacgaca ctctcgtcta ctccaagaat atcaaagata cagtctcaga 9180
agaccaaagg gctattgaga cttttcaaca aagggtaata tcgggaaacc tcctcggatt 9240
ccattgccca gctatctgtc acttcatcaa aaggacagta gaaaaggaag gtggcaccta 9300
caaatgccat cattgcgata aggaaaggc tatcgttcaa gatgcctctg ccgacagtgg 9360
tcccaaagat ggaccccac ccacgaggag catcgtggaa aagaagacg ttccaaccac 9420
gtcttcaaag caagtggatt gatgtgataa catggtggag cacgacactc tcgtctactc 9480
caagaatatc aaagatacag tctcagaaga ccaaagggct attgagactt tcaacaaag 9540
ggtaatatcg ggaaacctcc tcggattcca ttgcccagct atctgtcact tcatcaaaag 9600
gacagtagaa aaggaaggtg gcacctacaa atgccatcat tgcgataaag gaaaggctat 9660
cgttcaagat gcctctgccg acagtggtcc caaagatgga cccccaccca cgaggagcac 9720
cgtggaaaaa gaagacgttc aaccacgtc ttcaaagcaa gtggattgat gtgatatctc 9780
cactgacgta agggatgacg cacaatccca ctatccttcg caagaccttc ctctatataa 9840
ggaagttcat ttcatttgga gaggacacgc tgaaatcacc agtctctctc tacaaatcta 9900
tctctctcga gatgattgaa caagatggat tgcacgcagg tctccggccg cgttgggtgg 9960
agaggctatt cggctatgac tgggcacaac agacaatcgg ctgctctgat gccgccgtgt 10020
tccggctgtc agcgcagggg aggccggttc tttttgtcaa gaccgacctg tccggtgccc 10080
tgaatgaact tcaagacgag gcagcgcggc tatcgtggct ggccacgacg ggcgttcctt 10140
gcgcagctgt gctcgacgtt gtcactgaag cgggaaggga ctggctgcta ttgggcgaag 10200
tgccggggca ggatctcctg tcatctcacc ttgctcctgc cgagaaagta tccatcatgg 10260
ctgatgcaat gcggcggctg catacgcttg atccggctac ctgcccattc gaccaccaag 10320
cgaaacatcg catcgagcga gcacgtactc ggatggaagc cggtcttgtc gatcaggatg 10380
atctggacga agagcatcag gggctcgcgc cagccgaact gttcgccagg ctcaaggcgc 10440
gcatgcccga cggcgaggat ctcgtcgtga cccatggcga tgcctgcttg ccgaatatca 10500
tggtggaaaa tggccgcttt tctggattca tcgactgtgg ccggctgggt gtggcggacc 10560
gctatcagga catagcgttg gctacccgtg atattgctga agagcttggc ggcgaatggg 10620
ctgaccgctt cctcgtgctt tacggtatcg ccgctcccga ttcgcagcgc atcgccttct 10680
atcgccttct tgacgagttc ttctgaaacg cgtgatcgtt caaacatttg gcaataaagt 10740
ttcttaagat tgaatcctgt tgccggtctt gcgatgatta tcatataatt tctgttgaat 10800
tacgttaagc atgtaataat taacatgtaa tgcatgacgt tatttatgag atgggttttt 10860
atgattagag tcccgcaatt atacatttaa tacgcgatag aaaacaaaat atagcgcgca 10920
aactaggata aattatcgcg cgcggtgtca tctatgttac tagatcgacg tccgtacggt 10980
taaaaccacc ccagtacatt aaaaacgtcc gcaatgtgtt attaagttgt ctaagcgtca 11040
atttgtttac accacaatat atcctgccac cagccagcca acagctcccc gaccggcagc 11100
tcggcacaaa atcaccactc gatacaggca gcccatcagt cc 11142
```

SEQ ID NO: 123          moltype = DNA   length = 16749
FEATURE                 Location/Qualifiers
misc_feature            1..16749
                        note = vector sequence
source                  1..16749
                        mol_type = other DNA
                        organism = synthetic construct
SEQUENCE: 123

```
gcttcctcgt gctttacggt atcgccgctc ccgattcgca gcgcatcgcc ttctatcgcc 60
ttcttgacga gttcttctga aacgcgtgat cgttcaaaca tttggcaata aagtttctta 120
agattgaatc ctgttgccgg tcttgcgatg attatcatat aatttctgtt gaattacgtt 180
aagcatgtaa taattaacat gtaatgcatg acgttatttt atgagatggg tttttatgatt 240
agagtcccgc aattatacat ttaatacgcg atagaaaaca aaatatagcg cgcaaactag 300
gataaattat cgcgcgcggt gtcatctatg ttactagatc gacgtccgta cggttaaaac 360
cacccccagta cattaaaaac gtccgcaatg tgttattaag ttgtctaagc gtcaatttgt 420
ttacaccaca atatatcctg ccaccagcca gccaacagct cccgaccgg cagctcggca 480
caaaatcacc actcgataca ggcagcccat cagtccacta gtctccacc ggtcgcggca 540
ccctcgccgc tgggctggcg gccgtctatg gccctgcaaa cgcgccagaa acgccgtcga 600
agccgtgtgc gagacaccgc agcgccggc gttgtggata cctcgcggaa aacttggccc 660
tcactgacag atgagggcg gacgttgaca cttgaggggc cgactcaccc ggcgcgggt 720
tgacagatga ggggcaggct cgatttcggc cggcgacgtg gagctggcca gcctcgcaaa 780
tcggcgaaaa cgcctgattt tacgcagtt tcccacagat gatgtggaca agcctgggga 840
taagtgccct gcggtattga cacttgaggg gcgcgactac tgacagatga ggggcgcgat 900
ccttgacact tgagggggcag agtgctgaca atgagggggc gcaccattg acatttgagg 960
ggctgtccac aggcagaaaa tccagcattt gcaagggttt ccgcccgttt tcggccacc 1020
gctaacctgt cttttaacct gcttttaaac caatatttat aaacctgtt tttaaccagg 1080
gctgcgccct gtgcgtga ccgcgcacg caagggggct tgccccccct tctcgaaccc 1140
tcccggcccg ctctcgcgtt ggcagcatca cccataattg tggtttcaaa atcggctccg 1200
tcgatactat gttatacgcc aactttgaaa acaactttga aaaagctgtt ttctggtatt 1260
taaggtttta gaatgcaagg aacagtgaat tggagttcgt cttgttataa ttagcttctt 1320
ggggtattta aatactgtag aaaagaggaa ggaaataata aatggctaaa atgagaatat 1380
caccggaatt gaaaaaactg atcgaaaaat accgctgcgt aaaagatacg gaaggaatgt 1440
```

```
ctcctgctaa ggtatataag ctggtgggag aaaatgaaaa cctatattta aaaatgacgg   1500
acagccggta taaagggacc acctatgatg tggaacggga aaaggacatg atgctatggc   1560
tggaaggaaa gctgcctgtt ccaaaggtcc tgcaccttga acggcatgat ggctggagca   1620
atctgctcat gagtgaggcc gatggcgtcc tttgctcgga agagtatgaa gatgaacaaa   1680
gccctgaaaa gattatcgag ctgtatgcgg agtgcatcag gctcttttcac tccatcgaca   1740
tatcggattg tccctatacg aatagcttag acagccgctt agccgaattg gattacttac   1800
tgaataacga tctggccgat gtggattgcg aaaactggga agaagacacc ccatttaaag   1860
atccgcgcga gctgtatgat tttttaaaga cggaaaagcc cgaagaggaa cttgtctttt   1920
cccacggcga cctgggagac agcaacatct ttgtgaaaga tggcaaagta agtggcttta   1980
ttgatcttgg gagaagcggc agggcggaca agtggtatga cattgccttc tgcgtccggt   2040
cgatcaggga ggatattggg gaagaacagt atgtcgagct attttttgac ttactgggga   2100
tcaagcctga ttgggagaaa ataaaatatt atattttact ggatgaattg ttttagtacc   2160
tagatgtggc gcaacgatgc tggcgacaag caggagcgca ccgacttctt ccgcatcaag   2220
tgttttggct ctcaggccga ggcccacggc aagtatttgg gcaaggggtc gctggtattc   2280
gtgcagggca agattcggaa taccaagtac gagaaggacg gccagacggt ctacgggacc   2340
gacttcattg ccgataaggt ggattatctg gacaccaagg caccaggcgg atcaaatcag   2400
gaataagggc acattgcccc ggcgtgagtc ggggcaatcc cgcaaggagg gtgaatgaat   2460
cggacgtttg accggaaggc atacaggcaa gaactgatcg acgcggggtt ttccgccgag   2520
gatgccgaaa ccatcgcaag ccgcaccgtc atgcgtgcgc cccgcgaaac cttccagtcc   2580
gtcggctcga tggcccagca agctacggcc aagatcgagc gcgacagcgt gcaactggct   2640
cccccctgccc tgcccgcgcc atcggccgcc gtggagcgtt cgcgtcgtct cgaacaggag   2700
gcggcaggtt tggcgaagtc gatgaccatc gacacgcggg gaactatgac gaccaagaag   2760
cgaaaaccg ccggcgagga cctggcaaaa caggtcagcg aggccaagca agccgcgttg   2820
ctgaaacaca cgaagcagca gatcaaggaa atgcagcttt ccttgttcga tattgcgccg   2880
tggccggaca cgatgcgagc gatgccaaac gacacggccc gctctgccct gttcaccacg   2940
cgcaacaaga aaatcccgcg cgaggcgctc caaaacaagg tcattttcac cgtcaacaag   3000
gacgtgaaga tcacctacac cggcgtcgag ctgcgggcac gatgacga actggtgtgg   3060
cagcaggtgt tggagtacgc gaagcgcacc cctatcggcg agccgatcac cttcacgttc   3120
tacgagcttt gccaggacct gggctggtcg atcaatggcc ggtattacac gaaggccgag   3180
gaatgcctgt cgcgcctaca ggcgacggcg atgggcttca cgtccgaccg cgttgggcac   3240
ctggaatcgg tgtcgctgct gcaccgcttc cgcgtcctgg accgtggcaa gaaaacgtcc   3300
cgttgccagg tcctgatcga cgaggaaatc gtcgtgctgt tgctggcga ccactacacg   3360
aaattcatat gggagaagta ccgcaagctg tcgccgacgg cccgacggat gttcgactat   3420
ttcagctcgc accgggagcc gtaccccgctc aagctggaaa ccttccgcct catgtgcgga   3480
tcggattcca cccgcgtgaa gaagtggcgc gagcaggtcg gcgaagcctg cgaagagttg   3540
cgaggcagcg gcctggtgga acacgcctgg gtcaatgatg acctggtgca ttgcaaacgc   3600
tagggccttg tgggtcagt tccggctggg ggttcagcag ccagcgcttt actgagatcc   3660
tcttccgctt cctcgctcac tgactcgctg cgctcggtcg ttcggctgcg gcgagcggta   3720
tcagctcact caaaggcggt aatacggtta cccacagaat cagggcgata cgcaggaaag   3780
aacatgtgag caaaaggcca gcaaaaggcc aggaaccgta aaaaggccgc gttgctggcg   3840
tttttccata ggctccgccc ccctgacgag catcacaaaa atcgacgctc aagtcagagg   3900
tggcgaaacc cgacaggact ataaagatac caggcgtttc ccctggaag ctccctcgtg   3960
cgctctcctg ttccgaccct gccgcttacc ggatacctgt ccgcctttct cccttcgggaa   4020
agcgtggcgc tttctcatag ctcacgctgt aggtatctca gttcggtgta ggtcgttcgc   4080
tccaagctgg gctgtgtgca cgaaccccc gttcagcccg accgctgcgc cttatccggt   4140
aactatcgtc ttgagtccaa cccggtaaga cacgacttat cgccactggc agcagccact   4200
ggtaacagga ttagcagagc gaggtatgta ggcggtgcta cagagttctt gaagtggtgg   4260
cctaactacg gctacactag aagaacagta tttggtatct gcgctctgct gaagccagtt   4320
accttcggaa aaagagttgg tagctcttga tccggcaaac aaaccaccgc tggtagcggt   4380
ggtttttttg tttgcaagca gcagattacg cgcagaaaaa aaggatctca agaagatcct   4440
ttgatcttttt ctacggggtc tgacgctcag tggaacgaaa actcacgtta agggattttg   4500
gtcatgagat tatcaaaaag gatcttcacc tagatccttt tggatctcct gtggttggca   4560
tgcacataca aatggacgaa cggataaaacc ttttcacgcc cttttaaata tccgattatt   4620
ctaataaacg ctcttttctc ttaggtttac ccgccaatat atcctgtcaa acactgatag   4680
tttaaactga aggcgggaaa cgacaatctg ctagtggatc tcccagtcac gacgttgtaa   4740
aacgggcgtc tgcgatcgct gaagttccta tacttttcag agaataggaa cttcggaata   4800
ggaacttccc atgggatcta gtaacataga tgacaccgcg cgcgataatt tatcctagtt   4860
tgcgcgctat attttgtttt ctatcgcgta ttaaatgtat aattgcggga ctctaatcat   4920
aaaaacccat ctcataaata acgtcatgca ttacatgtta attattcat gcttaacgta   4980
attcaacaga aattatatga taatcatcgc aagaccggca acaggattca atcttaagaa   5040
actttattgc caaatgtttg aacgatcacg ctagcggata acaatttcac acagggatat   5100
cactagtaaa aggtaccgag ctcctgcagt atcgatgcgg ccgcaaagtc gacgaattct   5160
cattagcaga actcaagatg ctgatcctct ggaacgttga acttgagctt gtgttcctcg   5220
aaaagcttgc acaactcttt gatgtaacgc tggtgaagtc tatcaacttc ctctctagaa   5280
ggctgaggag tcatttgaac ctcgataggc tttccaacga tagtagtgat aggctgtctg   5340
aaaggcatga gtccgaaaga gtattggaaa actccccttc catggaaaag tggaaggctg   5400
attcccataa tcttttggag tctgttctgg atccatctaa gccaagttcc aggagtgttc   5460
tcaacctggt tgaagaggtt gttctctccg aatgagaaga taggaacaag agcagcacca   5520
tgcataagag caagtctgat gaatccttta cggttcttca agagaagtct gtaagcacca   5580
ggtctagcat caagagcctc ttgagcacct ccaacgatga tagcaagaag gtttccacca   5640
cccttttctgc taaggatgtg atcagcagaa acttttctcgc tagacacgag tccaccagac   5700
atgatgtaat ctctgaagaa tggagccctg aaccaaacgg taagcatcat aaggtaggat   5760
ctgattccag ggaacaaaga ggtgaatcca gtagactcag tacagaggtt aaggaaagca   5820
ccagcagcaa gaacaccatg aggatgaat ccagcagtct agttacggct aggatcaagc   5880
tcagcagtct taacgagaga cacagggaag taatccttca tgtacttcca gatggccaat   5940
cttctgaaga attggatagg tctaccacct tgtctaggct tatcccaatc caagtaccac   6000
caggtagcgt aaagaacaga gaaaagccag aacctggtga acaagagtcc aacgaagata   6060
acgatgcaga gttgagcaag agcaaggaat gagaaacccc actgaagaac agcgaaagtc   6120
tgcaatcttc tctcccaagg aacaagaagt ggagcgaact cgaccatgaa ttcagtcccc   6180
```

```
cgtgttctct ccaaatgaaa tgaacttcct tatatagagg aagggtcttg cgaaggatag   6240
tgggattgtg cgtcatccct tacgtcagtg gagatatcac atcaatccac ttgctttgaa   6300
gacgtggttg gaacgtcttc tttttccacg atgctcctcg tgggtggggg tccatctttg   6360
ggaccactgt cggcagaggc atcttcaacg atggcctttc ctttatcgca atgatggcat   6420
ttgtaggagc caccttcctt ttccactatc ttcacaataa agtgacagat agctgggcaa   6480
tggaatccga ggaggtttcc ggatattacc ctttgttgaa aagtctcaat tgcccttgta   6540
tcttctgaga ctgtatcttt gatatttttg gagtagacaa gtgtgtcgtg ctccaccatg   6600
ttgacgaaga ttttcttctt gtcattgagt cgtaagagac tctgtatgaa ctgttcgcca   6660
gtcttacgg cgagttctgt taggtcctct atttgaatct ttgactccat gggatccaag    6720
ggccctagaa tctaattatt ctattcgac taaattagta taagtatttt tttaatcaat    6780
aaataataat taataattta ttagtaggag tgattgaatt tataatatat tttttttaat   6840
catttaaaga atcttatatc tttaaattga caagagtttt aaatgggag agtgttatca    6900
tatcacaagt aggattaatg tgttatagtt tcacatgcat tacgataagt tgtgaaagat   6960
aacattatta tatataacaa tgacaatcac tagcgatcga gtagtgagag tcgtcttatt   7020
acactttctt ccttcgatct gtcacatggc ggcggcccga attctcacac aaggtagttg   7080
caagacactg aagtggtggt agtggtagta gaagaagcag aatcggtaga aaggcaagac   7140
aatggagaag atgaagatgg tggagattct cttcccacaa cgcagcaatc aaggttttca   7200
aggttaaggc actcgtgctt tccatcatcg aacatgaagt cgatgttatc ctcgaaagca   7260
agctcgttga agagttctgg gtactcaatt gggttctcgt tagcaaggtt ttgatccgta   7320
aggaatgggg agaatccagt atccatcatg cagaagttcc aagcaagttc gttgttatct   7380
ccgcacctat ccatttccat gatggtggaa gaatcaatgc agcagttaac aacggcagct   7440
tcctcagaat atcccacaat ttcagcctct tgttgctcag ccttctcttc ctcttttttc   7500
tcttcctctt gaggtggttc ctcaacgtat tgttgcttaa cctcttccct aggttcctct   7560
ttagcttctc tagtctcaac ctcttgctta gcctcaacaa gaatacctc ttgatggtta    7620
gcctggttaa ctgggaatgg gaaaacgccc ttcttcttaa gcctgtcgat gtagttggag   7680
atatcgaagt tggtaacagc gttagcaccct ctgtactcaa tagcagccat atcataagca   7740
gctgcagcct cttcttgagt gttgtaagtt ccgaggtaga ggtacttgtt tccgaaaact   7800
cttccaatcc tagcttccca tcttccgtta tgatgatgcc tagcaactcc cctatactta   7860
gaaactcccc tagagaatcc agatgactgc cttctaaggg aagcaagata ctcttctttg   7920
gtcaccctct gcatctcttc aagttctttg gtgtaagtcc cgctgggaa gttaagaatg    7980
gtatctgggc cccaatactt aagagcagca agatcatagg tatgagcagc agcctcttca   8040
gaatcataag ctccaaggta aacctgcttg cccttcttgt tttggatgga gttccaagag   8100
gacttatccc aaaggtgagc ttcgaatctt ccagtccatc tatgcctagt aacacctctg   8160
tagatagatg acctctggt agaagctgga gaagttgggt tatgagactt atcgccagat    8220
ggagatgact tcttagccct cttagctctc tttggtcttg gagcttcaga ttgaattggg   8280
ctagaggtag tagtagaaga ggacactgaa gaagatggag aactagagca ggtagaggta   8340
gtgagcctct tcttcatgaa ttcactagtg attaaatttt gttggtgctt tgagcatata   8400
acaagcatgg tatatatagg cacgtaaaca agttgagaaa ttttactttg agtttgacat   8460
aaccaataaa agttagtgct gtttattacc tcactcagtt tgcaccgcaa ctgtcgttag   8520
tgatgtttac cttttctttt tctattattt attagtatta tataatatat atatatgtgt   8580
gatgagactt gaaattgttt agcaccgcaa atgtccttct tgaggggagg ttttcttttg   8640
ctgaggttgg ggtgtcacat acaccccct ctatggactc aacgtccttg ctgaggttta    8700
ccccacacta catgagattt ttctagactc aatactata tatttctcgc cttatcggaa    8760
ttggttaaac tcagttgaag ttagggtcat atcgataaaa ttgacacatg atcgactctg   8820
atattaaaca gattctctcc ctcgaacctc actcactttc cttttttctat tctttattag   8880
tattatataa tagatccgtt ccaaccattc acgtacataa gaagagagat attttttttt   8940
aatgactaa catgacaaat aaaacaaaca aaggagtaat gatcactaca acaaattaga   9000
ttatgagggga caaataattt catcatctat aaatcatgtt tcgtcactaa aaattttgtg   9060
tgacgaaaaa gatttcgtca atcagttgtc actaaaaata tacaaagacg atttaatgat   9120
gtttaccttt ccttttctat tctttattag tattatataa taaatatatg tgtgatgaga   9180
cttgaaattg tttagcaccg caaatgtcct tgttgaaggg aggttttctt ttgctgaggt   9240
tggggtgtca catacacccc ctctatggac tgaacgtcct ttttgaggtt tatttttacac   9300
tgcatgagat ttttctagat tcaacattat gatttctaga ctcaacacta cgatcgtcac   9360
taaagactat ttttatata taaaaaaat actttgtcct taaatgtata aattagggat   9420
aaatttatta ttataaaaaa ggttaataat tttgtgatta aatctattat tttgtcactg   9480
aaagtgtttg cttttaccga cgacatatat gtcactaaat attatcataa gtagtgacaa   9540
ttacaattgt cacaaaataa aaaaaattat tcatattcaa caaaaaaggg tactacgaca   9600
atacattttt tgtcactgaa agtaatcaag ttgtgataaa ttaatttatt taatgacaaa   9660
aatatttgta tcaaaattca cccatgatca tataataaaa ataactaaaa ttatactaaa   9720
gcataaatga caagaaaatc taactaaaac atatcaaata ttactcctaa acaaagacat   9780
ataagtaaaa atttcttcca aagtatcaat aacgtggtga cacatagctt gcaatcaatc   9840
ttgcttcaat tttcaccttt tatacctgta aaaagaaaga gaaataaaa caatgattta    9900
aaaatcgaat tcccgcggcc cctagaatct aattattcta ttcagactaa attagtataa   9960
gtattttttt aatcaataaa taattaataa taatttatta gtaggagtta ttgaattaa    10020
aatatatttt tttaatcat ttaaagaatc ttatatcttt aaattgacaa gagttttaaa    10080
tggggagagt gttatcatat cacaagtagg attaatgtgt tatagtttca catgcattac   10140
gataagttgt gaaagataac attattatat ataacaatga caatcactag cgatcgagta   10200
gtgagagtcg tcttattaca cttctttcct tcgatctgtc acatgcggc ggccgcggc     10260
cgcttcatta ctcgagccag gaggatggat cgatgctggt ctgagaccct gctaccggtt   10320
gctgactgaa ctgctcggca cggtccttca tttcacgggc cttgctcgcc aactttgtct   10380
tggccgactc caactgatcc gctccgggtg gatgtttccc cgtcaggtaa cggtagatcc   10440
aggacagcac agacagagcg gcaacaccaa atcccccgct tgccagaaaa cccgctccca   10500
acaggaagat ggtgatgact gcagatcaga aaaactcaga ttaatcgaca aattcgatcg   10560
cacaaactga aaactaacac cagatctaga tagaaatcac aaatcgaaga gtaattattc   10620
gacaaaactc aaattatttg aacaaatcgg atgatatcta tgaaaccccta atcgagaatt   10680
aagatgatat ctaacgatca aacccagaaa atcgtcttcg atctaagatt aacagaatct   10740
aaaccaaaga acatatacga aattgggatc gaacgaaaac aaaatcgaag attttgagag   10800
aataaggaac acagaaattt acctgcaggg accagtacag gcgagaagat caccaggaga   10860
ggtgtggcga ttgtcagcgc aatgaccgtt ccagccaggg tcaacccgga taacaccaac   10920
```

```
aggctacctc cggcagtaac cgcggtcgct gcctttacaa cacgctgagc acgcggttgc   10980
agttgcaagt gggggggcacg tgtttgttgc tgctgcccgt agtgctctgc catggaaatt   11040
ttgttggtgc tttgagcata taacaagcat ggtatatata ggcacgtaaa caagttgaga   11100
aattttactt tgagtttgac ataaccaata aaagttagtg ctgtttatta cctcactcag   11160
tttgcaccgc aactgtcgtt agtgatgttt accttttcct tttctattat ttattagtat   11220
tatataatat atatatatgt gtgatgagac ttgaaattgt ttagcaccgc aaatgtcctt   11280
cttgagggga ggttttcttt tgctgaggtt ggggtgtcac atacaccccc ctctatggac   11340
tcaacgtcct tgctgaggtt tacccccacac tacatgagat ttttctagac tcaatactat   11400
gatatttctc gccttatcgg aattgttaa actcagttga agttagggtc atatcgataa   11460
aattgacaca tgatcgactc tgatattaaa cagattctct ccctcgaacc tcactcactt   11520
tcctttttct attctttatt agtattatat aatagatccg ttccaaccat tcacgtacat   11580
aagaagagag atattttttt ttaatggact aacatgacaa ataaaacaaa caaaggagta   11640
atgatcacta caacaaatta gattatgagg dacaaataat ttcatcatct ataaatcatg   11700
tttcgtcact aaaaattttg tgtgacgaaa aagatttcgt caatcagttg tcactaaaaa   11760
tatacaaaga cgatttaatg atgtttacct ttccttttct attctttatt agtattatat   11820
aataaatata tgtgtgatga gacttgaaat tgtttagcac cgcaaatgtc cttgttgaag   11880
ggaggttttc ttttgctgag gttggggtgt cacatacacc ccctctatgg actgaacgtc   11940
cttttttgagg tttattttac actgcatgag attttttctag attcaacatt atgattttcta   12000
gactcaacac tacgatcgtc actaaagact attttttata tataaaaaaa atactttgtc   12060
cttaaatgta taaattaggg ataaatttat tattataaaa aaggttaata attttgtgat   12120
taaatctatt attttgtcac tgaaagtgtt tgcttttacc gacgacatat atgtcactaa   12180
atattatcat aagtagtgac aattacaatt gtcacaaaat aaaaaaaatt attcatattc   12240
aacaaaaaag ggtactacga caatacattt tttgtcactg aaagtaatca agttgtgata   12300
aattaattta tttaatgaca aaaatatttg tatcaaaatt cacccatgat catataataa   12360
aaataactaa aattatacta aagcataaat gacaagaaaa tctaactaaa acatatcaaa   12420
tattactcct aaacaaagac atataagtaa aaatttcttc caaagtatca ataacgtagt   12480
gacacatagc ttgcaatcaa tcttgcttca attttcacct tttatacctg taaaaagaaa   12540
gagaaaataa aacaatgatt taaggcgcg ccgcgtattg gctagagcag cttgccaaca   12600
tggtggagca cgacactctc gtctactcca agaatatcaa agatacagtc tcagaagacc   12660
aaagggctat tgagacttt caacaaaggg taatatcggg aaacctcctc ggattccatt   12720
gcccagctat ctgtcacttc atcaaaagga cagtagaaaa ggaaggtggc acctacaaat   12780
gccatcattg cgataaagga aaggctatcg ttcaagatgc ctctgccgac agtggtccca   12840
aagatggacc cccacccacg aggagcatcg tggaaaaaga agacgttcca accacgtctt   12900
caaagcaagt ggattgatgt gataacatgg tggagcacga cactctcgtc tactccagaa   12960
atatcaaaga tacagtctca gaagaccaaa gggctattga gacttttcaa caaagggtaa   13020
tatcgggaaa cctcctcgga ttccattgcc cagctatctg tcacttcatc aaaaggacag   13080
tagaaaagga aggtggcacc tacaaatgcc atcattgcga taaaggaaag gctatcgttc   13140
aagatgcctc tgccgacagt ggtcccaaag atggaccccc acccacgagg agcatcgtgg   13200
aaaaagaaga cgttccaacc acgtcttcaa agcaagtgga ttgatgtgat atcccactg   13260
acgtaaggga tgacgcacaa tcccactatc cttcgcaaga ccttcctcta tataaggaag   13320
ttcatttcat ttggagagga cacgctgaaa tcaccagtct ctctacaa atctatctct   13380
gcgatcgcat ggcgatttttg gattctgctg gcgttactac ggtgacgag aacggtggc   13440
gagagttcgt cgatcttgat aggcttcgtc gacggaaatc gagatcggat tcttctaacg   13500
gacttcttct ctctggttcc gataataatt ctccttcgga tgatgttgga gctcccgccg   13560
acgttaggga tcggattgat tccgttgtta acgatgacgc tcaggaaaca gccaatttgg   13620
ccggagataa taacggtggt ggcgataata acggtggtgg aagaggcggc ggagaaggaa   13680
gaggaaacgc cgatgctacg tttacgtatc gaccgtcgt tccagctcat cggagggcga   13740
gagagagtcc acttagctcc gacgcaatct tcaaacagag ccatgccgga ttattcaacc   13800
tctgtgtagt agttcttatt gctgtaaaca gtagactcat catcgaaaat cttatgaagt   13860
atggttggtt gatcagaacg gatttctggt ttagttcaag atcgctgcga gattggccgc   13920
ttttcatgtg ttgtatatcc cttttcgatct ttccttttacg tgcctttacg gttgagaat   13980
tggtacttca gaaatacata tcagaacctg ttgtcatctt tcttcatatt attatcacca   14040
tgacagaggt tttgtatcca gtttacgtca ccctaaggtg tgattctgct tttttatcag   14100
gtgtcacttt gatgctcctc acttgcattg tgtggctaaa gttggtttct tatgctcata   14160
ctagctatga cataagatcc ctagccaatg cagctgataa ggccaatcct gaagtctcat   14220
actacgttag cttgaagagc ttggcatatt tcatgtcgc tcccacattg tgttatcagc   14280
caagttatcc acgttctgca tgtatacgga aggggtgggt ggctcgtcaa tttgcaaaac   14340
tggtcatatt caccggattc atgggattta aatagaaca atatataaat cctattgtca   14400
ggaactcaaa acatcctttg aaaggcagtc ttctatatgc tattgaaaga gtgttgaagc   14460
tttcagttcc aaatttatat gtgtggctct gcatgtgtct ctgcttcttc caccttttggt   14520
taaacatatt ggcagagctt ctctgcttcg gggatcgtga attctacaaa gattggtgga   14580
atgcaaaaag tgtgggagat tactggagaa tgtggaatat gcctgttcat aaatggatgg   14640
ttcgacatat atacttcccg tgcttgcgca gcaagatacc aaagacactc gccattatca   14700
ttgcttttcct agtctctgca gtctttcatg agctatgcat cgcagttcct tgtcgtctct   14760
tcaagctatg ggcttttctt gggattatgt ttcaggtgcc tttggtcttc atcacaaact   14820
atctacagga aaggttggc tcaacggtgg gaacatgat cttctggttc atcttctgca   14880
ttttcggaca accgatgtgt gtgcttcttt attaccacga cctgatgaac cgaaaaggat   14940
cgatgtcatg agcgatcgcg atcgttcaaa catttggcaa taaagtttct taagattgaa   15000
tcctgttgcc ggtcttgcga tgattatcat ataatttctg ttgaattacg ttaagcatgt   15060
aataattaac atgtaatgca tgacgttatt tatgagatgg ggttttatga ttagagtccc   15120
gcaattatac atttaatacg cgatagaaaa caaaatatag cgcgcaaact aggataaatt   15180
atcgcgcgcg gtgtcatcta tgttactaga tccctgcagg gcgtattggc tagagcagct   15240
tgccaacatg gtggagcacg acactctcgt ctactccaag aatatcaaag atacagtctc   15300
agaagaccaa agggctattg agactttca caaaggtaa atacggaaa acctcctcgg   15360
attccattgc ccagctatct gtcacttcat caaaaggaca gtagaaaagg aaggtggcac   15420
ctacaaatgc catcattgcg ataaaggaaa ggctatcgtt caagatgcct ctgccgacag   15480
tggtcccaaa gatggacccc cacccacgag gagcatcgtg gaaaaagaag acgttccaac   15540
cacgtcttca aagcaagtgg attgatgtga taacatggtg gagcacgaca ctctcgtcta   15600
ctccaagaat atcaaagata cagtctcaga agaccaaagg gctattgaga cttttcaaca   15660
```

```
aagggtaata tcgggaaacc tcctcggatt ccattgccca gctatctgtc acttcatcaa    15720
aaggacagta gaaaaggaag gtggcaccta caaatgccat cattgcgata aaggaaaggc    15780
tatcgttcaa gatgcctctg ccgacagtgg tcccaaagat ggaccccac  ccacgaggag    15840
catcgtggaa aaagaagacg ttccaaccac gtcttcaaag caagtggatt gatgtgatat    15900
ctccactgac gtaagggatg acgcacaatc ccactatcct tcgcaagacg ttcctctata    15960
taaggaagtt catttcattt ggagaggaca cgctgaaatc accagtctct ctctacaaat    16020
ctatctctct cgagatgatt gaacaagatg gattgcacgc aggttctccg gccgcttggg    16080
tggagaggct attcggctat gactgggcac aacagacaat cggctgctct gatgccgccg    16140
tgttccggct gtcagcgcag gggaggccgg ttcttttgt  caagaccgac ctgtccggtg    16200
ccctgaatga acttcaagac gaggcagcgc ggctatcgtg gctgccacg  acgggcgttc    16260
cttgcgcagc tgtgctcgac gttgtcactg aagcgggaag ggactggctg ctattgggcg    16320
aagtgccggg gcaggatctc ctgtcatctc accttgctcc tgccgagaaa gtatccatca    16380
tggctgatgc aatgcggcgg ctgcatacgc ttgatccggc tacctgccca ttcgaccacc    16440
aagcgaaaca tcgcatcgag cgagcacgta ctcggatgga agccggtctt gtcgatcagg    16500
atgatctgga cgaagagcat caggggctcg cgccagccga actgttcgcc aggctcaagg    16560
cgcgcatgcc cgacggcgag gatctcgtcg tgactcatgg cgatgcctgc ttgccgaata    16620
tcatggtgga aaatggccgc ttttctggat tcatcgactg tggccggctg ggtgtggcgg    16680
accgctatca ggacatagcg ttggctaccc gtgatattgc tgaagagctt ggcggcgaat    16740
gggctgacc                                                             16749
```

```
SEQ ID NO: 124          moltype = DNA   length = 137
FEATURE                 Location/Qualifiers
misc_feature            1..137
                        note = linker sequence
source                  1..137
                        mol_type = other DNA
                        organism = synthetic construct
SEQUENCE: 124
atttaaatgc ggccgcgaat tcgtcgattg aggacgtccc tactagacct gctggacctc    60
ctcctgctac ttactacgat tctctcgctg tgcatatggt cagtcatgcc cgggcctgca   120
ggcggccgca tttaaat                                                  137

SEQ ID NO: 125          moltype = DNA   length = 434
FEATURE                 Location/Qualifiers
misc_feature            1..434
                        note = hpRNAi
source                  1..434
                        mol_type = other DNA
                        organism = synthetic construct
SEQUENCE: 125
gtgagcaatg aaccaagatt tatcaatacc gttactttg  atagcaaaga gggttctcct    60
actcttgtta tggtccacgg atatggtgcc tctcagggtt tcttctttcg gaatttttat   120
gccctttgcg a ggcatttcaa agttattgct attgatcagc ttggctgggg tggttcaagc  180
aggcctgact tcacatgcag aagtacagaa gagactgaag attggtttat tgattccttt   240
gaggagtggc gcaaagccaa aaaccttagc aactttattt tgcttgggca ctcctttgga   300
gggtatgtcg ctgcaaaata tgctctcaag catccagagc atgttcagca gttgattctg   360
gtaggaccag ctggatttac atcagagact gaacatatgt ccgagcggct tacccagttt   420
agagcaacat ggaa                                                     434

SEQ ID NO: 126          moltype = DNA   length = 593
FEATURE                 Location/Qualifiers
misc_feature            1..593
                        note = hpRNAi
source                  1..593
                        mol_type = other DNA
                        organism = synthetic construct
SEQUENCE: 126
actgctgatg ctgtcaggca gtatctatgg ttgtttgagg agcataatgt tcttgaattc    60
ctcgtacttg ctggagatca tctatatcga atggattatg aaaagttcat tcaagcccac   120
agagaaacag atgctgatat tactgttgcc gcactgccaa tggatgaaaa gcgagcacct   180
gcatttggtc tcatgaagat tgacgaagaa ggacgcatta ttgaatttgc agagaaaccg   240
aaaggagagc aattgaaagc aatgaaagtg atactacca ttttaggtct tgatgatgag    300
agagctaaag agatgccttt tatcgcaagt atgggtatat atgtcattag caaagatgtg   360
atgttaaact tacttcgtga taagttccct ggtgccaatc attttggcag tgaagttatt   420
cctggtgcaa cttcgcttgg gatgagagtg caagcttatt tatatgatgg atactgggaa   480
gatattggta ccatcgaagc tttctacaat gccaatttgg gcattaccaa aaagccagtc   540
ccagattta  gcttctatga ccgatcagct ccaatctaca cccaacctcg ata           593

SEQ ID NO: 127          moltype =     length =
SEQUENCE: 127
000

SEQ ID NO: 128          moltype =     length =
SEQUENCE: 128
000

SEQ ID NO: 129          moltype = AA   length = 7
FEATURE                 Location/Qualifiers
REGION                  1..7
```

```
                          note = probable lipid binding motif
REGION                    2..4
                          note = X - any amino acid
source                    1..7
                          mol_type = protein
                          organism = synthetic construct
SEQUENCE: 129
VXXXHGF                                                                    7

SEQ ID NO: 130            moltype = DNA  length = 1224
FEATURE                   Location/Qualifiers
source                    1..1224
                          mol_type = other DNA
                          organism = Arabidopsis thaliana
SEQUENCE: 130
atggcggaag aaatctcaaa gacgaaggtg ggatcttctt ctactgcttc ggtggctgat    60
tcatctgctg ctgcgtcggc tgcaacgaat gcggccaaat caagatggaa aattttgtgg   120
cctaattcgc tccggtggat tcctacgtcc accgattaca tcatcgccgc cgagaaacgt   180
cttctctcca tcctcaagac gccttatgta caagagcaag tcagtattgg ttcaggacca   240
ccaggttcta aaatcaggtg gtttaggtct acgagcaatg agtcacgtta catcaacact   300
gttacatttg atgccaagga gggagctcct acactcgtca tggttcatgg ttatggtgct   360
tctcaagggt ttttcttccg taattttgat gctcttgcca gtcgatttga agtgatcgct   420
attgatcaac ttgggtgggg tggttcaagt aggcctgatt ttacatgtag aagcacagaa   480
gaaactgagg catggtttat cgactccttt gaggaatggc gtaaagccca gaatctcagt   540
aactttattc tattaggaca ttcttttgga ggctatgttg ctgctaaata cgcgcttaag   600
catcctgaac atgttcaaca cttaattctg gtgggatctg ctgggttctc agcagaagca   660
gatgccaaat cagaatggct cactaaattt agagcaacat ggaaaggtgc agtcctaaat   720
catttatggg agtcaaattt cactcctcag aagctggtta aggattagg tccttgggt    780
ccaggtcttg taaatcggta tacaactgca agatttggtg cacattcgga gggaactggg   840
ctaacagaag aggaagccaa attgctaacc gattatgtga accatacttt ggctgcaaag   900
gctagtggag agttatgctt gaaatacatc ttctcatttg gagcatttgc taggaagccc   960
ctcttacaaa gtgcatcaga gtggaaagtg ccaacaacgt ttatctatgg aatgaatgat  1020
tggatgaact atcaaggtgc ggtggaagcg aggaaatcca tgaaggtccc ttgcgaaatc  1080
attcgggttc cacagggtgg tcattttgtg ttcatagaca cccaattgg ttttcattct   1140
gcagtgcttt atgcttgccg caagtttata tctcaagact cctctcatga tcaacaactc  1200
ctagatggtc tacgattggt ttag                                          1224

SEQ ID NO: 131            moltype = DNA  length = 1700
FEATURE                   Location/Qualifiers
source                    1..1700
                          mol_type = other DNA
                          organism = Brachypodium distachyon
SEQUENCE: 131
tccgcgcccg aaacgatccc aacagaagct ctaatctcca aagccgccgc gcgtgttgag    60
ggtggtgcgg ggaaaagctt ggtgtcgtga gccccgtgt cgcatgcgcc gcgctgccgc    120
cgtgacgagg atggcagcga ccgaggagat gaggcaggcg tccgccgccg ccgccgccac   180
ggtgaccgag gcctcggcgt cggcggcccc gcccgcgggg tccggtggg gcgggtgtg    240
gccggccgcg ctgcgctgga tccccactc caccgagcgc atcatcgccg ccgagaagcg   300
cctcctctcc gtactcaaaa ctgggtatgt ccaagaacaa gttaacattg gctcggctcc   360
accccgggtca aaagtaagat ggtttagatc atcaagtgat gagccaaggt tcatcaatac   420
agttgacattt gatagcaagg agaatgctcc cactcttgtc atggtccatg gttatggtgc   480
ttcacagggt ttcttcttta gaaatttga tgcccttgca agccgttcc gagtgattga    540
cattgatcag cttggttggg gtggatcaag tagacctgac ttcacctgta aaagtaccga   600
agaaactgag gcttggttca tagattcttt agaggaatgg cgtaaagcaa gaacctcag    660
taattttata ttgctcgtc attctttcg aggatatgt gcagcaaaat atgccttgca    720
gcatcctgaa cacgtgcagc acttaatttt ggtcggttct gctgggttt catcagaaac    780
agatcatagc tctgagtggt taaccaagtt tcgagcaaca tggaaaggca tgctagtgaa    840
ccaactatgg gagtccaatt ttactcctca agaattgta agaggattgg gtccttgggg    900
cccagatttg gttcgcagat ataccactgc taggtttggc tcatattcaa caggtgaatt    960
actaacagaa catgagtccg gcttgctgac agattacatt taccatacat tagctgccaa   1020
agctagtgga gagctgtgct tgaaatata tttttccttg ggggcatttg caaggaaacc    1080
tcttctgcag agtgcatctg actggaaagt gccgaccact ttcatatatg gccatgacga   1140
ttggatgaaa taccaggggg cacagcaagc acgcaaggat atgaaagttc cttgcgaaat   1200
catcagagtc ccacagggag gacatttttgt gttcatagat aacccttccg ggttccattc    1260
ggcagtcttc tatgcgtgcc ggaaattttt atctggagat gcagaggagg gtctctctct   1320
tcctgatggc ctgatatctg catgacagca tgaggcgcga tgtcatacca attagcggta   1380
tgaacacaaa gcaaagctat acggagctag gaaatgttac aaatgtcacg actcaccaga   1440
aatgttacaa atgtcaccac tcaccagttt cctttttgta tgtatgaatt gtgtgaatat   1500
acacgtcatt catatttgcc ggcgtatcag tacttcaata gtgataaaac atgatcatat   1560
atatatgtat gatttctcta gtcggttctc atcaagtcaa gttattgtga ttggtgaatg   1620
atatactttc caggtcaact ttgtgtttgc atgtacaaac tatcatggaa catatcagta   1680
tagtttatga tttgtcttcc                                              1700

SEQ ID NO: 132            moltype = DNA  length = 1484
FEATURE                   Location/Qualifiers
source                    1..1484
                          mol_type = other DNA
                          organism = Glycine max
SEQUENCE: 132
```

```
gtcatggatg cgcgtcactg ctcgcgttca ttataatggc ggaagagata accaagaacg   60
acgtcggagt aacctccaaa accaccagaa gcagctccag gttctggcct cgttggattc  120
ccacttccac cgatcacatc atcgctgccg agaagcgcct tctttccgtc gtcaagactg  180
gttatgttca agagcatgtt aacattggct ctggtcctcc tggctccaaa gtgaggtggt  240
tccgttcatc cagcaacgag ccgcggttta ttaacaccgt tacatttgac agtaaacccc  300
attctccaac gcttgtcatg attcatggtt atgctgcttc acaggggttc ttttttcgca  360
attttgacgc gcttgcgtct cgatttagag tcattgctgt tgatcaactt ggatggggtg  420
gatcgagcag acctgatttc acatgcaaaa gcactgaaga aactgaggca tggtttattg  480
attcttttga ggaatggaga aaagccaaaa acttgagcag ttttatactg ctcggacatt  540
cttttggtgg ttatgttgct gccaaatatg cgctcaagca ccctgagcat gtacaacact  600
tgattctggt tggatctgct ggattttcat ctgaatcaga tgcaaagtct gagtggataa  660
caaggtttcg agcaacatgg aagggggcag ttttgaacca tctttgggaa tcaaatttca  720
cacctcagaa acttgtcagg ggtttaggtc cttggggtcc aacatagtc cgcaagtata  780
caagtgctag gtttggtaca cattcaactg gggaaatact gactgaagag gaatcaacat  840
tgctgacaga ctatgtttac cacacattgg cggccaaagc tagtggagag ctgtgcttaa  900
aatatatttt ttcatttgga gcatttgcta ggatgcccct tcttctcagt gcctcagagt  960
ggaaggtgcc caccactttc atgtatggtt tccaagactg atgaattat caaggtgccc 1020
aagaagctcg caagcatatg aaggttccat gcgaaatcat caggattcct caggggtggc 1080
actttgcgtt cattgacaac ccaactgcct tccattcagc tgtttttat gcttgtcgaa 1140
ggtttcttac acctgatcca gacaatgaat ctcttcctaa agggctaacc tctgcatagg 1200
ttaggtctta attttgtgct attcctgtct atatgtattt taatatttt ttttactaat 1260
taaatttcat aattgaatga aatcatatgt atattgtttc agtaaagtgg aatttactga 1320
aaatatttgt aatagcaact tcaacaaaaa tcgatttgta ggagaaattt cttccctgga 1380
aattgttcta tttaaatct tgttgctcat aagatattat gacttcattc aactaataat 1440
tcatgtcgtt taggaaaagt agttagttat attaaatttg tcaa              1484

SEQ ID NO: 133           moltype = DNA  length = 1662
FEATURE                  Location/Qualifiers
source                   1..1662
                         mol_type = other DNA
                         organism = Zea mays
SEQUENCE: 133
accatacggg cggggccgca ccgaccgaac ctaaccgaga gcacgagcat acccgtcccg   60
actccgactg cagagcatca gccgaggaga aaagtcggga gaaacgcgcg tgacgtctgc  120
ccgcgtcgta tgccgccgcg ctgccgtcgc cgcgacgacc agacgccacc gatggcagcc  180
gaggagatga gacgggcctc cgcctcaacg gccacggcgg agatgccggc gtcgccggcg  240
ccggcgcaag cggggtcgag gtgggcgcgg gtgtggccgc gcgcgctccg gtggatcccc  300
acctccacgg accgcatcat cgccgccgag aagcgactcc tcacgatagt caaaactgga  360
tatgtccagg aacgagtcaa cattgctctc gctccacctg ggtcaaaagt aagatgggtt  420
aggtcagcaa gtgatgaacc aaggttcatt aatactgtaa catttgatag caaggagaat  480
gcccccaccc tggttatggt ccatggctat ggagcttcac aggggttctt ctttcgaaac  540
tttgatgccc ttgcaagccg ttttagggtg attgccattg atcagcttgg ctggggtggt  600
tcaagcagac ctgacttcac atgtaaaagt accgaagaaa ctgaggcatg gttcatagat  660
tctttcgagg agtggcgcaa ggccaagaac ctcagtaatt ttatattgct tggtcactct  720
tttgaggat atgttgctgc aaaatatgcg ctaaagcacc ctgaacacgt tcaacagttg  780
attttggttg gtcctgctgg cttctcatca gaaacagagc atagctctga gtggttaacc  840
aagtttcaag caacatggaa aggcatgcta atgaatcgtc tttgggagtc caatttttact  900
ccccaaaggg ttattagggg attgggtcct tggggtccag gtctagtaca gagatatacc  960
agtgccaggt ttggtacaag ttctactggt gaattactaa cagatgaaga atcggcattg 1020
atgacagatt atatgtacca tacgttagct gccaaagcta gtggagagct gtgcttgaaa 1080
tatatatttt ccttcgggc atttgcaagg aaacctcttc tgcagtgcgc gtccgattgg 1140
aaagtgccga ctactttcat atatgggcag caagattgga tgaactacca aggcgctcag 1200
caagcacgga aggacatgaa agttccttgt gaaataatca gggtgccgca gggtggacat 1260
tttgtgttca tagacaaccc ttcagggttc cactcggctg tctcctatgc gtgccgtaat 1320
cttctatcag taaatggaga ggagggattc acatttcctg atggcctaat atctgcgtga 1380
agtggcatgt tcaacaagct tgctcaacaa cagtttacat aaagcaaaga tatacgattg 1440
tggaaatcat tgcccatttc caccaatttg cttgtatacg gattatgctg tgtatatatt 1500
acataacaaa tgtattagta tcatttaatg cacgatttgt gaaagggcct gagttttgat 1560
ttagcgaatt ttaggttggt ttttttcccct ttttcttctt tcagtgcgct tgctagtcaa 1620
tcccatacta taagccgtga tcatttaaaa aaaaaaaaa aa                     1662

SEQ ID NO: 134           moltype = DNA  length = 1763
FEATURE                  Location/Qualifiers
source                   1..1763
                         mol_type = other DNA
                         organism = Sorghum bicolor
SEQUENCE: 134
actgcagatg cgcggtcgtc ggctccggct cgcggaggcg agaacggcga accagcccgt   60
gtctctgttc cctttcttcc ctttaaaaac acggcaaaaa aaaagctagc cggttacgct  120
accgaaccga acggctcggc acgcgggcac gggcgcgggg tcgcaccgga aaagcacgag  180
cagagcagac ctgacgtctc cagactgcag gagcatcatc agtcgaggag gaggaagtgt  240
ggggggggga aagggaaacg tgcgcgtcgt atgcgcctcg ctgccgtcgc caggacgacc  300
aggatggcag ccgaggagat gaggcgggcc tcggcctccg cggcggtcgc ggccacgacg  360
gaggcgcgcg cggcgcggc gcaagcgggg tccaggtggg tcggggtgtg gccgagcgcg  420
ctccggtgga tccccacctc cacgatcgc atcatcgccg cggagaagcg gctcctctcg  480
atagtcaaaa ctgggtatgt ccaggaacaa gtcaacattg gctcagctcc acctgggtca  540
aaagtaagat ggtttaggtc agcgagtgat gaaccaaggt tcattaatac tgtaacattt  600
gatggcaagg agaacgcccc cacctggtt atggtccatg gctatggagc ttcacagggg  660
ttcttctttc gaaactttga cgcccttgca agtcgtttta gggtgattgc cattgatcag  720
```

```
cttggctggg gtggttcaag cagacctgac ttcacatgta aaagtaccga agaaactgag    780
gcatggttca tagattcttt tgaggagtgg cgcaaggcca agaacctcag taattttata    840
ttgcttggtc actcctttgg aggatatgtt gcggcaaagt atgccctaaa gcaccctgaa    900
cacattcagc acttagtttt ggttggtcct gctggcttct cgtcagaaac agaccatagc    960
tctgagtggt taaccaagtt tcgagcaaca tggaaaggca tgctagtgaa tcatcctttgg    1020
gagtccaatt ttactcccca aagagttatt agaggattgg gcccttgggg tccaggtcta    1080
gtacaaagat ataccagtgc caggtttggt acacgttcaa ctggtgatat actaacagat    1140
caagaatcaa cattgttgac agattatatt taccatacct tagctgccaa agctagtgga    1200
gagctgtgct tgaaatatat attttccttc ggggcatttg caaggaaacc tcttctgcag    1260
tgcgcatccg attggaaagt gccgactact ttcatatatg gtcaggaaga ttggatgaac    1320
taccaagggg ctcagcaagc acggaaggac atgaaagttc cttgtgaaat aatcagggtg    1380
ccacagagtg gacattttgt gtttatagac aacccttcag ggttccactc ggctgtcttc    1440
tacgcgtgcc gtaatctttt atcccaaaat ggggaggagg gcttcacatt tcctggtggc    1500
ctaatatctg catgaagtgg catgttcaac aatcttatcg tgcccaacaa tagtttatat    1560
gaagcaaaga tatacgatgg tggaaatctt tgctcatttc caccaatctg gaaatatttg    1620
tgccctcttc caccaatttg tttgtatacg gattatgccg tgtatatatt ctgtgttgac    1680
tgtaagaaac ataatgtatt aacattatgt aatgtatgta cgattcttta tttgattttc    1740
aacttgcaat acgcaagaac cac                                              1763

SEQ ID NO: 135         moltype = DNA  length = 1399
FEATURE                Location/Qualifiers
source                 1..1399
                       mol_type = other DNA
                       organism = Ricinus communis
SEQUENCE: 135
cgcctttta ccagtcaatt tccattttta tatataagtg cttttgctta atttaagact    60
aactacagcg acgaattcgc gtttatgaaa ttgcttcgcc tacgactgct acgagtatct    120
agctcctcaa tatcatcaat aatggcggaa ggggctgctg ccacatcagc atcagcatca    180
gcgtcagcgt cagcgtcatg ggcaaaaaca agatctctac ggccatctgc tctccgttgg    240
atcccaactt caaccgatca catcatcgcc gccgaaaagc gtcttctctc cctcgtcaag    300
actcccctatg ttgtggaaca agtgaatata gggtctggcc caccggggtc gaaggtgagg    360
tggtttcgtt ctaaaagcga cgaggcacgg tttattaaca cggttacttt tgatagcaaa    420
gaggaggatt ctcctacact ggttatggtt catggatatg ctgcttctca aggcttcttc    480
tttcgcaatt ttgatgctct tgcttctcgt ttcaggctca ttgctattga tcagctcggt    540
tggggtggat caagtagacc tgattttacg tgtaagagca ctgaagaaac tgaggcatgg    600
ttcattgact ccttgaggc ttggcgtaaa gagaaaaacc tcagtaactt catcttactt    660
ggacattctt tcggagggta tattgcagct aaatatgcac tcaagcatcc tgagcatgtt    720
caacatctga ttttagtggg atctgctgga tttcatcag aatctgaaga caaatctgag    780
cagcttactc ggttcagagc aacatggaag ggagcagttt tgaatcattt atgggagtct    840
aattttactc ctcagaaggt tattagaggt ttaggtcctt ggggtccaga tctcgtacgc    900
aagtacacaa ctgctagatt tggttcatat tcaactggtg agatattaaa ggaggaggag    960
tccaaattgc ttacagacta tgtgtaccat acctagccg ccaaagctag tggagagcta    1020
tgcttgaaat atatatttc ttttggagca tttgctcgga tgcccttct acaaagcgcg    1080
tcacaatgga aagtgccaac tactttcata tatgggatgc aagattggat gaattatcaa    1140
ggggcccaaa gagctcgcaa agatatgaat gtccatgtg aaatcattag ggttcctcag    1200
ggcgggcact tcgttttcat agacaaccca actgggtttc attcagctgt gttatatgcc    1260
tgccggagat ttctctcacc cgatcctgat aatgaatctc ttcctgaagg tctgatatct    1320
gcgtaggaag tgtggtttgt aattatttct tttttatttg ttgtgtataa tttatctgag    1380
aatttccaat tctttcaat                                                  1399

SEQ ID NO: 136         moltype = DNA  length = 1480
FEATURE                Location/Qualifiers
source                 1..1480
                       mol_type = other DNA
                       organism = Medicago truncatula
SEQUENCE: 136
ggttggctca tagttccttt tacctgttga aaacaaaaca tatggagtaa cattttagtc    60
agaaattcaa agctacgcac ttgattaaac taattatcga aaaatggcgg aagaaattag    120
acaaaaggac gacgtcgatt catcttcgaa atctaaaagc ttctggtctt cactccgttg    180
gattcccact tctaccgatc atatcatcgc cgctgagaaa cgccttcttt ccattatcaa    240
gactgggtat gctcaagagc atgttaatat aggttctggt cctcctggct ctaaagttag    300
atggttccgt tcaaccagta acgagccacg cttctcaac actgttacat tgatagtaa    360
acccgattct cctacacttg ttatggttca tggatacgct gcttcagg gtttcttctt    420
tcgcaatttt gatgctctcg cctctcgttt cagaatcatt gtgtgatc aacttggttg    480
gggaggatca agcagacctg atttcacatg caaaagtacc gaagaaactg aggcatggtt    540
cattgattct ttcgaggaat ggagaaaagc caaaaatctt accaatttca tactgcttgg    600
acattctttt ggtggttatg ttgcttccaa atacgcgctc aagcaccctc agcacgtaca    660
acacttaatt ttggtgggac ctgccgggtt tacagaagaa acagatccaa agactgagtt    720
tgttactaag tttcgagcaa catggaaggg agcagttctg aaccatctat gggaatcatt    780
ttttacacct cagaaaattg tcagaggttt aggtccttgg ggtcctaaca tggtccgcaa    840
atatacaagt gctaggtttg gtacacattc aaccgggcaa aaactgattg acgaggaatc    900
aagtctgctg actgattatg tttatcatac attggcggcc aaagctagtg gggagctgtg    960
tttaaaatat atttttgcat ttggagcatt tgctaggatg cccttcttc aaagtgctca    1020
agagtggaag atgccaccca cattcatata tggttacgaa gattgatga attatgaagg    1080
tgcccaagaa gctcgcaagc atatgaaggt tccatgtgaa attatcaggg tccctaaggc    1140
cggccattt gtgttcattg acaacccaag tggcttccat tcagctgtgt tttatgcttg    1200
tcgaaggttt cttaccccaa attcggacaa tgaatctctt cccgaagggc tatcgtctgc    1260
ttaggattta attttgcatc aatccagtgt atattaaat ggttattaat ttttttttac    1320
ttcataactg aatgaagccg tgtcttgttt ctcagtgaag tggaatataa tggaaatata    1380
```

```
tgtaattgta ataacaataa tattgatttg ttggggaact ttgaggacaa aaacatattc   1440
tggtaaaatt tgttgcaca tgcgacaaac atatgctgtg                          1480

SEQ ID NO: 137          moltype = DNA  length = 1317
FEATURE                 Location/Qualifiers
source                  1..1317
                        mol_type = other DNA
                        organism = Arabidopsis thaliana
SEQUENCE: 137
gatctctctc cctctctctc tctctctctc cgggaaaaat ggataacttc ttaccctttc    60
cctcttctaa cgcaaactct gtccaagaac tctctatgga tcctaacaac aatcgctcgc   120
acttcacaac agtccctact tatgatcatc atcaggctca gcctcatcac ttcttgcctc   180
cgttttcata cccggtggag cagatggcgg cggtgatgaa tcctcagccg gtttacttat   240
cggagtgtta tcctcagatc ccggttacgc aaaccgtaag tgaattcggt tctctggttg   300
gtaatccttg tttgtggcaa gagagaggtg gttttcttga tccgcgtatg acgaagatgg   360
caaggatcaa caggaaaaac gccatgatga atcaagaaa caactctagc cctaattcta   420
gtccaagtga gttggttgat tcaaagagac agctgatgat gcttaacttg aaaaataacg   480
tgcagatctc cgacaagaaa gatagctacc aacagtccac atttgataac aagaagctta   540
gggttttgtg tgagaaggaa ttgaagaaca gcgatgttgg gtcactcggg aggatagttc   600
taccaaagag agatgcagaa gcaaatcttc cgaagctatc tgataaagaa ggaatcgttg   660
tacagatgag agatgttttc tctatgcagt cttggtcttt caaatacaag ttttggtcca   720
ataacaagag cagaatgtat gtcctcgaga acacaggaga atttgtgaag caaaatggag   780
ctgagatagg agactttta acaatatacg aggacgaaag caagaatctc tacttcgcca   840
tgaatggaaa ttcggaaaa caaaatgaag gaagagaaaa tgagtcgagg gaaaggaacc   900
actacgaaga ggcaatgctt gattacatac aagagacga gaggaagct tccattgcaa   960
tgctcatcgg aaatctaaac gatcactatc ccatccctaa cgatctcatg gacctcacca  1020
ctgaccttca gcaccatcaa gccacgtcct catcaatgcc acctgaggat cacgcgtacg  1080
tgggttcatc cgatgatcag gtgagcttta acgactttga gtggtggtga tatggtggtg  1140
gaagttctca agttcataac ccccttttatg aaaatagacc ttaagatata caaagagat  1200
taaaagaaaa aaaagttagt atatttcatc atatctctca ttgaagatga gattatatc  1260
tataattgtt taatagtgtt tttattactt ttctatcaat atattaaagt tttaatt     1317

SEQ ID NO: 138          moltype = DNA  length = 1439
FEATURE                 Location/Qualifiers
source                  1..1439
                        mol_type = other DNA
                        organism = Medicago truncatula
SEQUENCE: 138
tttcatcctt acatattttg catattgaaa cacgtaggat ggaataagat tgataacaaa    60
aattgcattg tttgcatatt gaaaacatgg gacaattgca tgggttcatg tgcttcatta   120
taagccacac attaggaaac acaggttgat attcaccact atttaacata gaatatctc   180
atgtgtaagc attcatacaa atatcacaat tgaattaaaa accaaagaaa tgtcttcctc   240
taacttctct tgtatcctat ccatctcctt aacattcttc atcttgctac tgaacaaggt   300
gaattcagca gaaacaactt cctttttccat cacaaaattt gtcccagatc aaaagaatct   360
catcttccaa ggcgatgcga aaactgcctc aacaggaag ttagaactct ccaaggcagt   420
caagaactct attggtagag ctctttattc cgcccctat cacatttggg atagcaaaac   480
cggtagtgtg gctaactttc aaactacctt caccttaca ataacggcgc ctaatactta   540
taatgttgca gacggtcttg cattcttcat tgcaccaatt gatactaagc cgaaatcaat   600
tcatcatgga ggatacctg gagttttcga tagcaaaact tacaaaaaat caattcaaac   660
tgttgcagtt gaaattgaca ctttctataa tgctcaatgg gatccaaatc ccggaaatat   720
aagtagcact ggtcgacata ttggaatcga tgtaaactct atcaaatcaa taagcaccgt   780
gccgtggagt ttggaaaaca ataaaaaggc taatgttgcg ataggttta atggtgcaac   840
aaatgtgttg agtgttgatg tggaatatcc tttgattcgt cattatacc taagtcatgt   900
tgtgcctttg aaggatgttg ttcctgagtg ggtaaggatt ggttttctctt cttctactgg   960
agccgaatat tcagcacatg atattttatc gtggtctttt gattcaaagt tgaacctagg  1020
ttttgagaac aatatcaatg ccaatgtttc aagctctact caagctgcat agttgaaaac  1080
ttatccatta tgtatgtgtg agtgtaacca accagtctaa gaaaactata ataagatacc  1140
tgaaataatg gttcattatc gtgtagtaga aatatggtca caccatatct tcttttttt   1200
ttaataaatt atggaataat gctattttct gcgagagtta tgtttcggaa agattcatga  1260
atagatgtta atcaattaga tctatatata tatatatata tatatatata tatatatat   1320
tagcattttc ttaaattatg catatgtaat atcgtgtaat gctattgttt atatcaatga  1380
atggtgttt gtagtcacat aattcgtaat ttctctccat gagaacagcg aaccaatta   1439

SEQ ID NO: 139          moltype = DNA  length = 1393
FEATURE                 Location/Qualifiers
source                  1..1393
                        mol_type = other DNA
                        organism = Brassica napus
SEQUENCE: 139
gagatgggta tccctataag gtgcagcatc gaaccatctg caacatttg actcgttttc    60
ttttgtgttt ttataacatc tgtctcttct tcactcgatc tccctctctt ttcttttca   120
atctccccaa cgaacctccc ttcataactc tctttctctc cccgggaaat atggataact   180
tcttgcccctt ttcctcttct aacgcaaact ctgtccaaga actctccatg gatcttaaca   240
agaatcgctc gcacttctcc atggcgcagc ctcagcactt gttgccgcct tactcgtacg   300
ttgcatgtcc ggcacttgat cagacggga ccatgaatca tcagcctctt cactcatcgg   360
atgcttttcc tcagatcccg gttgtacaaa ccggaggtga attcggctat tggtttgta   420
agccccggtgt gaggcaggaa cgaggtggat ttcttgatcc acactccact aagatggcta   480
ggatcaacag gaagaaggcg atgctaagat caagaaacaa ctctaaccct aattctagtt   540
cgaatgagtt ggttgattca aggagacaag tggctcttac catgaaaaat aatgccgaga   600
```

-continued

```
ttgctgctag aaaagatttt tatcgattct cctcattcga taacaagaaa cttagggttt    660
tgttggtgaa gcacttgaag aacagcgatg ttgggtcact tggaaggatt gttctaccaa    720
agagagaagc agaaggaaat cttccggagc tatctgataa agaaggaatg gtattagaga    780
tgagagatgt tgactctgtg cagtcttggt ctttcaaata caagtactgg tccaataaca    840
agagcagaat gtatgtcctc gaaaacacag gagaatttgt gagaaaaat ggagtattga     900
tgggagacta tctaacaatc tacgaggacg aaagcaagaa tctctacttc tccatcagaa    960
agcacccaca caaacaaaat gatggaagag gatgagtc gatggaagtt atcgagatga     1020
acttctatga agatataatg tttgattaca taccaaatga tgaagacgat tccattgcaa   1080
tgctcctcgg aaatctaaac gagcactatc cctacccaaa tgatcttatg gatctcactg   1140
tcaatcttga tcagcatcag caagccacct cctcgtcgcc acctgctgat cacatgagct   1200
cgaacgattt cttatggtga tgtgatggac gttgatatgg attcccttg agatgataata   1260
caagggatga aagaaaaga gtatcatatt catatccata tttgtttgat aaaatgtgtt    1320
tgttcccaat ctattattta tgaaaaactt atttgtgttt aactccagat taattaaata   1380
tttttcattt gac                                                     1393

SEQ ID NO: 140         moltype = DNA  length = 1755
FEATURE                Location/Qualifiers
source                 1..1755
                       mol_type = other DNA
                       organism = Arabidopsis thaliana
SEQUENCE: 140
atgaactcga tgaataactg gttaggcttc tctctctctc ctcatgatca aaatcatcac    60
cgtacggatg ttgactcctc caccaccaga accgccgtag atgttgccgg agggtactgt   120
tttgatctgg ccgctccctc cgatgaatct tctgccgttc aaacatcttt tctttctcct   180
ttcggtgtca ccctcgaagc tttcaccaga gacaataata gtcactccg agattgggac    240
atcaatggtg gtgcatgcaa taacattaac aataacgaaa aaaatggacc aaagcttgag   300
aatttcctcg gccgcaccac cacgatttac aataccaacg agaccgttgt agatggaaat   360
ggcgattgtg gaggaggaga cggtggtggt ggcggctcac taggcctttc gatgataaa    420
acatggctga gtaatcattc ggttgctaat gctaatcatc aagacaatgg taacggtgca   480
cgaggcttgt ccctctctat gaattcatct actagtgata gcaacaacta caacaacaat   540
gatgatgtcg tccaagagaa gactattgtt gatgtcgtag aaactacacc gaagaaaact   600
attgagagtt ttggacaaag gacgtctata taccgcggtg ttacaaggca tcggtggaca   660
ggtagatacg aggcacattt atgggacaat agttgcaaaa gagaaggcca gactcgcaaa   720
ggaagacaag tttatctggg aggttatgac aaagaagaaa agcagctag ggcttacgat    780
ttagccgcac taaagtattg gggaaccacc actactacta acttccctt gagtgaataat   840
gagaaagagg tagaagagat gaagcacatg acgaggcaag agtatgttgc ctctctgcgc   900
aggaaaagta gtggtttctc tcgtggtgca tcgatttatc gaggagtaac aaggcatcac   960
caacatggaa ggtggcaagc taggatcgga agagtcgccg gtaacaaaga cctctacttg  1020
ggaactttcg gcacacagga agagctgct gaggcttatg acattgcagc cattaaattc   1080
agaggattaa gcgcagtgac taacttcgac atgaacagat acaatgttaa agcaatcctc  1140
gagagcccga gtctacctat tggtagttct gcgaaacgtc tcaaggacgt taataatccg  1200
gttccagcta tgatgattag taataacgtt tcagagagtg caaataatgt tagcggttgg   1260
caaaacactg cgtttcagca tcatcaggga atggatttga gcttattgca caacagcag    1320
gagaggtacg ttggttatta caatggagga aacttgtcta ccgagagtac tagggtttgt   1380
ttcaaacaag aggaggaaca acaacacttc ttgagaaact cgccgagtca catgactaat  1440
gttgatcatc atagctcgac ctctgatgat tctgttaccg tttgtggaaa tgttgttagt   1500
tatggtggtt atcaaggatt cgcaatccct gttggaacat cggttaatta cgatcccttt   1560
actgctgctg agattgctta caacgcaaga aatcattatt actatgctca gcatcagcaa   1620
caacagcaga ttcagcagtc gccgggagga gattttccgg tggcgatttc gaataaccat   1680
agctctaaca tgtactttca cggggaaggt ggtggagaag gggctccaac gttttcagtt   1740
tggaacgaca cttag                                                  1755

SEQ ID NO: 141         moltype = DNA  length = 2061
FEATURE                Location/Qualifiers
source                 1..2061
                       mol_type = other DNA
                       organism = Medicago truncatula
SEQUENCE: 141
atgaacttgt taggtttctc tctatctcca caagaacaac atccatcaac acaagatcaa    60
acggtggctt cccgttttgg gttcaacct aatgaaatct caggctctga tgttcaagga    120
gatcactgct atgatctctc ttctcacaca actcctcatc attcactcaa cctttctcat   180
cctttttcca tttatgaagc tttccacaca ataacaacaa ttcacaccac tcaagattgg   240
aaggagaact acaacaacca aaaacctacta ttgggaacat catgcatgaa ccaaaatgtg   300
aacaacaaca accaacaaagc acaacaaaag ctagaaact tcctcggtgg acactcttc    360
accgaccatc aagaatacgg tggtagcaac tcatactctt cattacacct cccacctcat   420
cagccggaag catcctgtgg cggtggtgat ggtagtacaa gtaacaataa ctcaataggt   480
ttatctatga taaaaacatg gctcagaaac caacccaccac caccagaaaa caacaacaat   540
aacaacaatg aaaaagtggtgc acgtgtgcag acactatcag tttctatgag tactggctca   600
cagtcaagtt catctgtgcc tcttctcaat gcaaatgtga tgagtggtga gatttcctca   660
tcggaaaaca aacaaccacc cacaactgca gttgtacttg atagcaacca aacaagtgtc   720
gttgaaagtg ctgtgcctag aaaatccgtt gatacatttg acaaagaac ttccatttac    780
cgtggtgtaa caaggcatag atggacaggg agatatgaag ctcacctttg ggataatagt   840
tgtagaagag aggggcagag tcgcaaagga aggcaagttt acttgggagg ttatgacaaa   900
gaagaaaag cagctagagc ctatgatttg gcagcactaa aatattgggg aacaactact   960
acaacaaatt ttccaattag ccattatgaa aaagaagtgg aagaaatgaa gcatatgaca  1020
aggcaagagt acgttgcgtc attgagaagg aaaagtagtg gtttttcacg aggtgcatcc  1080
atttaccgag gagtaacaag acatcatcaa catggtagat ggcaagctag gattggaaga  1140
gttgcaggca acaaagatct ctacctagga actttcagca ctcaagaaga ggcagcagag  1200
gcatatgatg tggcagcaat aaaattcaga ggactgagtg cagttacaaa ctttgacatg  1260
```

```
agcagatatg atgtcaaaac catacttgag agcagcacat taccaattgg tggtgctgca  1320
aagcgtttaa aagacatgga gcaagttgaa ttgaatcatg tgaatgttga tattagccat  1380
agaactgaac aagatcatag catcatcaac aacactccc atttaacaga acaagccatc   1440
tatgcagcaa caaatgcatc taattggcat gcactttcat tccaacatca acaccacat   1500
catcattaca atgccaacaa catgcagtta cagaattcat cttatggaac tcaaactcaa  1560
aagctttggt gcaaacaaga acaagattcc gatgatcata gtacttatac tactgctact  1620
gatattcatc aactacagtt agggaataat aataacaata ctcacaattt ctttggttta  1680
caaaatatca tgagtatgga ttctgcttcc atggataata gttctggatc taattctgtt  1740
gtttatggtg gtggagatca tggtggttat ggaggaaatg gtggatatat gattccaatg  1800
gctattgcaa atgatggtaa ccaaaatcca agaagcaaca acaattttgg tgagagtgag  1860
attaaaggat ttggttatga aaatgttttt gggactacta ctgatcctta tcatgcacag  1920
gcagcaagga acttgtacta tcagccacaa caattatctg ttgatcaagg atcaaattgg  1980
gttccaactg ctattccaac acttgctcca aggactacca atgtctctct atgtcctcct  2040
ttcactttgt tgcatgaata g                                             2061

SEQ ID NO: 142              moltype = AA   length = 363
FEATURE                     Location/Qualifiers
source                      1..363
                            mol_type = protein
                            organism = Arabidopsis thaliana
SEQUENCE: 142
MDNFLPFPSS NANSVQELSM DPNNNRSHFT TVPTYDHHQA QPHHFLPPFS YPVEQMAAVM   60
NPQPVYLSEC YPQIPVTQTG SEFGSLVGNP CLWQERGGFL DPRMTKMARI NRKNAMMRSR  120
NNSSPNSSPS ELVDSKRQLM MLNLKNNVQI SDKKDSYQQS TFDNKKLRVL CEKELKNSDV  180
GSLGRIVLPK RDAEANLPKL SDKEGIVVQM RDVFSMQSWS FKYKFWSNNK SRMYVLENTG  240
EFVKQNGAEI GDFLTIYEDE SKNLYFAMNG NSGKQNEGRE NESRERNHYE EAMLDYIPRD  300
EEEASIAMLI GNLNDHYPIP NDLMDLTTDL QHHQATSSSP PPEDHAYVGS SDDQVSFNDF  360
EWW                                                                 363

SEQ ID NO: 143              moltype = AA   length = 280
FEATURE                     Location/Qualifiers
source                      1..280
                            mol_type = protein
                            organism = Medicago truncatula
SEQUENCE: 143
MSSSNFSCIL SISLTFFILL LNKVNSAETT SFSITKFVPD QKNLIFQGDA KTASTGKLEL   60
SKAVKNSIGR ALYSAPIHIW DSKTGSVANF QTTFTFTITA PNTYNVADGL AFFIAPIDTK  120
PKSIHHGGYL GVFDSKTYKK SIQTVAVEID TFYNAQWDPN PGNISSTGRH IGIDVNSIKS  180
ISTVPWSLEN NKKANVAIGF NGATNVLSVD VEYPLIRHYT LSHVVPLKDV VPEWVRIGFS  240
SSTGAEYSAH DILSWSFDSK LNLGFENNIN ANVSSSTQAA                         280

SEQ ID NO: 144              moltype = AA   length = 349
FEATURE                     Location/Qualifiers
source                      1..349
                            mol_type = protein
                            organism = Brassica napus
SEQUENCE: 144
MDNFLPFSSS NANSVQELSM DLNKNRSHFS MAQPQHLLPP YSYVACPALD QTGTMNHQPL   60
HSSDAFPQIP VVQTGGEFGY LVCKPGVRQE RGGFLDPHST KMARINRKKA MLRSRNNSNP  120
NSSSNELVDS RRQVALTMKN NAEIAARKDF YRFSSFDNKK LRVLLVKHLK NSDVGSLGRI  180
VLPKREAEGN LPELSDKEGM VLEMRDVDSV QSWSFKYKYW SNNKSRMYVL ENTGEFVKKN  240
GVLMGDYLTI YEDESKNLYF SIRKHPHKQN DGREDESMEV IEMNFYEDIM FDYIPNDEDD  300
SIAMLLGNLN EHYPYPNDLM DLTVNLDQHQ QATSSSPPAD HMSSNDFLW               349

SEQ ID NO: 145              moltype = AA   length = 584
FEATURE                     Location/Qualifiers
source                      1..584
                            mol_type = protein
                            organism = Arabidopsis thaliana
SEQUENCE: 145
MNSMNNWLGF SLSPHDQNHH RTDVSSTTR TAVDVAGGYC FDLAAPSDES SAVQTSFLSP    60
FGVTLEAFTR DNNSHSRDWD INGGACNTLT NNEQNGPKLE NFLGRTTTIY NTNETVVDGN  120
GDCGGGDGGG GGSLGLSMIK TWLSNHSVAN ANHQDNGNGA RGLSLSMNSS TSDSNNYNNN  180
DDVVQEKTIV DVVETTPKKT IESFGQRTSI YRGVTRHRWT GRYEAHLWDN SCKREGQTRK  240
GRQVYLGGYD KEEKAARAYD LAALKYWGPT TTTNFPLSEY EKEVEEMKHM TRQEYVASLR  300
RKSSGFSRGA SIYRGVTRHH QHGRWQARIG RVAGNKDLYL GTFGTQEEAA EAYDIAAIKF  360
RGLSAVTNFD MNRYNVKAIL ESPSLPIGSS AKRLKDVNNP VPAMMISNNV SESANNVSGW  420
QNTAFQHHQG MDLSLLQQQQ ERYVGYYNGG NLSTESTRVC FKQEEEEQQHF LRNSPSHMTN  480
VDHHSSTSDD SVTVCGNVVS YGGYQGFAIP VGTSVNYDPF TAAEIAYNAR NHYYYAQHQQ  540
QQQIQQSPGG DFPVAISNNH SSNMYFHGEG GGEGAPTFSV WNDT                   584

SEQ ID NO: 146              moltype = AA   length = 686
FEATURE                     Location/Qualifiers
source                      1..686
                            mol_type = protein
                            organism = Medicago truncatula
SEQUENCE: 146
MNLLGFSLSP QEQHPSTQDQ TVASRFGFNP NEISGSDVQG DHCYDLSSHT TPHHSLNLSH   60
PFSIYEAFHT NNNIHTTQDW KENYNNQNLL LGTSCMNQNV NNNNQQAQPK LENFLGGHSF  120
```

-continued

```
TDHQEYGGSN SYSSLHLPPH QPEASCGGGD GSTSNNNSIG LSMIKTWLRN QPPPPENNNN  180
NNNESGARVQ TLSLSMSTGS QSSSSVPLLN ANVMSGEISS SENKQPPTTA VVLDSNQTSV  240
VESAVPRKSV DTFGQRTSIY RGVTRHRWTG RYEAHLWDNS CRREGQTRKG RQVYLGGYDK  300
EEKAARAYDL AALKYWGTTT TTNFPISHYE KEVEEMKHMT RQEYVASLRR KSSGFSRGAS  360
IYRGVTRHHQ HGRWQARIGR VAGNKDLYLG TFSTQEEAAE AYDVAAIKFR GLSAVTNFDM  420
SRYDVKTILE SSTLPIGGAA KRLKDMEQVE LNHVNVDISH RTEQDHSIIN NTSHLTEQAI  480
YAATNASNWH ALSFQHQQPH HHYNANNMQL QNYPYGTQTQ KLWCKQEQDS DDHSTYTTAT  540
DIHQLQLGNN NNNTHNFFGL QNIMSMDSAS MDNSSGSNSV VYGGGDHGGY GGNGGYMIPM  600
AIANDGNQNP RSNNNFGESE IKGFGYENVF GTTTDPYHAQ AARNLYYQPQ QLSVDQGSNW  660
VPTAIPTLAP RTTNVSLCPP FTLLHE                                      686

SEQ ID NO: 147        moltype = DNA  length = 336
FEATURE               Location/Qualifiers
misc_feature          1..336
                      note = inducible promoter
source                1..336
                      mol_type = other DNA
                      organism = synthetic construct
SEQUENCE: 147
tcgatagttg tgatagttcc cacttgtccg tccgcatcgg catccgcagc tcgggatagt   60
tccgacctag gattggatgc atgcggaacc gcacgagggc ggggcggaaa ttgacacacc  120
actcctctcc acgcaccgtt caagaggtac gcgtatagag ccgtatagag cagagacgga  180
gcactttctg gtactgtccg cacgggatgt ccgcacggag agccacaaac gagcggggc   240
ccgtacgtgc tctcctaccc caggatcgca tccccgcata gctgaacatc tatataaaga  300
cccccaaggt tctcagtctc accaacatca tcaacc                            336

SEQ ID NO: 148        moltype = DNA  length = 2466
FEATURE               Location/Qualifiers
misc_feature          1..2466
                      note = inducer
source                1..2466
                      mol_type = other DNA
                      organism = synthetic construct
SEQUENCE: 148
atggccgaca ctagaagaag gcagaaccac tcttgtgacc catgccgtaa gggcaagaga   60
agatgtgatg ctccagagaa ccgtaacgag gctaatgaga acggatgggt gtcatgctct  120
aactgcaaga ggtggaacaa ggactgcacc ttcaactggc ttagctccca aaggtctaag  180
gctaaggggtg ctgctccaag agctaggact aagaaggcta ggactgctac tactacctcc  240
gagccttcta cttccgctgc tactattcca actcccgagt ccgataatca cgatgctcca  300
ccagtgatca actcccacga tgctttgcca tcttggactc agggacttct ttctcaccct  360
ggcgatctct tcgacttctc ccattctgct attccagcta acgctgagga tgctgctaac  420
gtgcaatctg atgctccatt cccatgggat cttgctatcc caggcgattt ctctatggga  480
cagcaacttg agaagcccct ctcccattg tctttccagg ctgttcttct tccaccacac  540
tccccaaaca ctgatgatct cattcgtgag cttgaggaac agactaccga tccagattcc  600
gtgactgaca ctaactccgt tcagcaagtt gctcaggatg gctctctttg gtctgatagg  660
cagtctccac tcctcccaga aaacagtttg tgcatggctt ccgactctac cgctagaagg  720
tatgctaggt ccaccatgac caagaacctc atgaggactg accacgactc catggaaaac  780
gcccttctt gctggcttac tgagcacaac tgcccatact ccgaccagat ttcttaccctc  840
ccaccaaagc aaagggctga gtggggacca aattggtcta acaggatgtg cattagggtg  900
tgcaggctcg atagggtgtc aacttctctt agaggaaggg ctctctccgc tgaagaagat  960
aaggcctgtg ctagggcact tcaccttgct atttgtgctt tcgcttctca gtggactcaa 1020
catgctcaaa ggggagctgg acttaacgtc ccagctgata ttgctgctga cgagcgttcc 1080
attaggcgta acgcttggaa tgaggctagg catgcacttc agcacactac tggaatccca 1140
tccttcaggg tgatcttcgc caacatcatc ttcagcctca ctcagtccgt gctcgatgat 1200
gatgacaac atggaatggg agctaggctc gataagcttc tcgagaatga tggtgctcca 1260
gtgttcctcg agactgctaa taggcagctc tacaccttca ggcacaagtt cgctaggatg 1320
cagagaaggg gtaaggcttt caataggctt cctggtggat ccgtggcttc tacttttcgct 1380
ggaatttttcg agactcccac cccctcatct gagtctccac aacttgatcc agtggtggct 1440
tctgaggaac acaggtctac tctgtctctc atgttctggc tcgggatcat gttcgacact 1500
ctgtctgctg ctatgtacca gaggccactt gttgtgtccg atgaggactc ccagatctct 1560
tctgcttctc caccaagaag aggtgccgag actcctatta accttgattg ctgggagcca 1620
ccaaggcagg tccatctaa tcaagagaag tctgatgtgt ggggcgacct gttccttagg 1680
acttctgatt ctttgcccga ccacgagtcc cacactcaaa tttctcaacc agctgctagg 1740
tggccatgca cttatgaaca agctgctgct gctctctcct ctgctactcc tgttaaggtg 1800
ttgctttaca ggcgtgtgac tcagctccaa actttgttgt ataggggagc ttctccagct 1860
aggcttgagg ctgctattca gaggactctc tacgtgtaca accactggac tgctaagtac 1920
cagccattca tgcaggattg cgttgccaac catgagcttc tcccatccag gatccagtct 1980
tggtacgtga tccttgatgg acactggcac cttgctgcta tgcttttggc tgatgtgctc 2040
gagtccatcg acagggattc ctactccgat atcaaccaca tcgacctcgt gactaagctc 2100
aggcttgata acgctcttgc tgtgtctgct ctcgctaggg catctcttag aggccaagaa 2160
ctcgatccag gcaaggcttc tccaatgtac aggcacttcc acgactccct tactgaggtt 2220
gcattccttg ttgagccatg gactgtggtg ctcatccact catttgctaa ggctgcttac 2280
atcctcctcg attgccttga tcttgatggt caggaaacg ctctcgctgg ataccttcaa 2340
cttaggcaga actgaactc ctgcatcagg gctctccagt tccttggccg taagtctgat 2400
atggctgctc tcgtggctaa ggatcttgag aggggactca acggaaaggt cgacagcttc 2460
ctctaa                                                            2466

SEQ ID NO: 149        moltype = AA  length = 208
FEATURE               Location/Qualifiers
```

```
source                  1..208
                        mol_type = protein
                        organism = Arabidopsis thaliana
SEQUENCE: 149
MTSSVIVAGA GDKNNGIVVQ QQPPCVAREQ DQYMPIANVI RIMRKTLPSH AKISDDAKET    60
IQECVSEYIS FVTGEANERC QREQRKTITA EDILWAMSKL GFDNYVDPLT VFINRYREIE   120
TDRGSALRGE PPSLRQTYGG NGIGFHGPSH GLPPPGPYGY GMLDQSMVMG GGRYYQNGSS   180
GQDESSVGGG SSSSINGMPA FDHYGQYK                                     208

SEQ ID NO: 150          moltype = AA   length = 236
FEATURE                 Location/Qualifiers
source                  1..236
                        mol_type = protein
                        organism = Arabidopsis lyrata
SEQUENCE: 150
MERGAPFSHY QLPKSISELN LDQHSNPNPM TSSVVVADAS DNNKGIVAQQ QPPCMAREQD    60
QYMPIANVIR IMRKILPSHA KISDDAKETI QECVSEYISF VTGEANERCQ REQRKTITAE   120
DILWAMSKLG FDNYVDPLTV FINRYREIET DRGSALREPP SLRQAYGGNG IGFHGPSHGL   180
PPPGPYGYGM LDQSMVMGGG RYYQNGSSGQ DESSAGGGSS SSINGMPAFD SYGQYK       236

SEQ ID NO: 151          moltype = AA   length = 230
FEATURE                 Location/Qualifiers
source                  1..230
                        mol_type = protein
                        organism = Brassica napus
SEQUENCE: 151
MERGAPLSHY QLPKSNSGLN LDQHNNSIPT MTGSISACDD KNKTILPQQQ PSMPREQDQY    60
MPIANVIRIM RKILPPHAKI SDDAKETIQE CVSEYISFVT GEANERCQRE QRKTITAEDI   120
LWAMSKLGFD DYVGPLNVFI NRYREFETDR GCSLRGESSF KPVYGGSGMG FHGPPPPGSY   180
GYGMLDQSMV MGGGRYYHNG SGQDGSVSGG GGSSSSMNGM PVYDQYGQYK              230

SEQ ID NO: 152          moltype = AA   length = 252
FEATURE                 Location/Qualifiers
source                  1..252
                        mol_type = protein
                        organism = Ricinus communis
SEQUENCE: 152
MERGGRVHRY RRHAKQPTPT TSATASTSPG MSSVQTTICS NINLPSTLSL SNSTAAPQAP    60
QQQQLQPSQC LVREQDQYMP IANVIRIMRR ILPPHAKISD DAKETIQECV SEYISFITGE   120
ANDRCQREQR KTITAEDVLW AMGKLGFDDY VEPLTLFLNR YREMENERST IRDPILKRSS   180
VGVVDYGNLG MNPFMPTFPM IPPPQGYFDS NMLGGYYRDA PDGASGAASG SNLAASSAPN   240
SLLHFDPFAQ FK                                                      252

SEQ ID NO: 153          moltype = AA   length = 198
FEATURE                 Location/Qualifiers
source                  1..198
                        mol_type = protein
                        organism = Glycine max
SEQUENCE: 153
MNMNMRQQQV ASSDQNCSNH SAAGEENECT VREQDRFMPI ANVIRIMRKI LPPHAKISDD    60
AKETIQECVS EYISFITGEA NERCQREQRK TITAEDVLWA MSKLGFDDYI EPLTMYLHRY   120
RELEGDRTSM RGEPLGKRTV EYATLATAFV PPPFHHHNGY FGAAMPMGTY VRETPPNAAS   180
SHHHHGISNA HEPNARSI                                                198

SEQ ID NO: 154          moltype = AA   length = 240
FEATURE                 Location/Qualifiers
source                  1..240
                        mol_type = protein
                        organism = Medicago truncatula
SEQUENCE: 154
METGGGFHGY RKLPTNTNSS AVAGTLKLSS VSEMNTRQQV GEQNNNGTEQ DNECIVREQD    60
RFMPIANVIR IMRKILPPHA KISDDAKETI QECVSEYISF ITGEANERCQ REQRKTITAE   120
DVLWAMSKLG FDDYIEPLTM YLHRYRELEG DRTSMRVEPL GKRGMEYGNL GGFVPQFHIG   180
HPNGGYYGNA APTYMMRDGN NNNNNNNNAP NAANAAGGSS HSQALANAEA NGHHHHHQYK   240

SEQ ID NO: 155          moltype = AA   length = 278
FEATURE                 Location/Qualifiers
source                  1..278
                        mol_type = protein
                        organism = Zea mays
SEQUENCE: 155
MDSSSFLPAA GAENGSAAGG ANNGGAAQQH AAPAIREQDR LMPIANVIRI MRRVLPAHAK    60
ISDDAKETIQ ECVSEYISFI TGEANERCQR EQRKTITAED VLWAMSRLGF DDYVEPLGAY   120
LHRYREFEGD ARGVGLVPGA APSRGGDHHP HSMSPAAMLK SRGPVSGAAM LPHHHHHHDM   180
QMHAAMYGGT AVPPPAGPPH HGGFLMPHPQ GSSHYLPYAY EPTYGGEHAM AAYYGGAAYA   240
PGNGGSGDGS GSGGGGSAS HTPQGSGGLE HPHPFAYK                            278

SEQ ID NO: 156          moltype = AA   length = 225
FEATURE                 Location/Qualifiers
```

```
                                       -continued
source                  1..225
                        mol_type = protein
                        organism = Arachis hypogaea
SEQUENCE: 156
METGGGFHGY RNLPTTTSGL KLSVSEMNMR AVENNTGSSN NNHTDDNECT VREQDRFMPI    60
ANVIRIMRKI LPPHAKISDD AKETIQECVS EYISFITGEA NERCQREQRK TITAEDVLWA   120
MSKLGFDDYI EPLTMYLHRY RELEGDRTSM RGEPLGKRTV DYGTLGVAAA STFVPPFHIG   180
HHHHHPHPSS YYGTPMGNYI RDAPNAGSSL QPPSLAHAEP NTQYK                   225

SEQ ID NO: 157          moltype = AA  length = 234
FEATURE                 Location/Qualifiers
source                  1..234
                        mol_type = protein
                        organism = Arabidopsis thaliana
SEQUENCE: 157
MERGGFHGYR KLSVNNTTPS PPGLAANFLM AEGSMRPPEF NQPNKTSNGG EEECTVREQD    60
RFMPIANVIR IMRRILPAHA KISDDSKETI QECVSEYISF ITGEANERCQ REQRKTITAE   120
DVLWAMSKLG FDDYIEPLTL YLHRYRELEG ERGVSCSAGS VSMTNGLVVK RPNGTMTEYG   180
AYGPVPGIHM AQYHYRHQNG FVFSGNEPNS KMSGSSSGAS GARVEVFPTQ QHKY         234

SEQ ID NO: 158          moltype = AA  length = 231
FEATURE                 Location/Qualifiers
source                  1..231
                        mol_type = protein
                        organism = Brassica napus
SEQUENCE: 158
MERGGFHGYR KFSLNTTNPS EPARFLMAEG SMQLAEPNQT NKTANGGEEE CVVREQDRFM    60
PIANVIRIMR RILPAHAKIS DDSKETIQEC VSEYISFITG EANERCQREQ RKTITAEDVL   120
WAMSKLGFDD YIEPLTLYLH RYRELEGDRG VGYNAGSVGM TSGMVVKRPN GTMGEYGAYG   180
VVPGMHMAPY HYRHQNGYAY SGNEPDSKMG GPSSAANGSR VELFPTQQHK Y            231

SEQ ID NO: 159          moltype = AA  length = 216
FEATURE                 Location/Qualifiers
source                  1..216
                        mol_type = protein
                        organism = Phaseolus coccineus
SEQUENCE: 159
MESGGFHGYR KLPNTTSPGL KLSVSDMNNV NTSRQVAGDN NHTADESNEC TVREQDRFMP    60
IANVIRIMRK ILPPHAKISG DAKETIQECV SEYISFITGE ANERCQREQR KTITAEDVLW   120
AMSKLGFDDY MEPLTMYLHR YRELEGDRTS MRGESLGKRT IEYAPMGVGV ATAFVPPQFH   180
PNGYYGPAMG AYVAPPNAAS SHHHGMPNTE PNARSM                             216

SEQ ID NO: 160          moltype = AA  length = 312
FEATURE                 Location/Qualifiers
source                  1..312
                        mol_type = protein
                        organism = Arabidopsis thaliana
SEQUENCE: 160
MVDENVETKA STLVASVDHG FGSGSGHDHH GLSASVPLLG VNWKKRRMPR QRRSSSSFNL    60
LSFPPPMPPI SHVPTPLPAR KIDPRKLRFL FQKELKNSDV SSLRRMILPK KAAEAHLPAL   120
ECKEGIPIRM EDLDGFHVWT FKYRYWPNNN SRMYVLENTG DFVNAHGLQL GDFIMVYQDL   180
YSNNYVIQAR KASEEEEVDV INLEEDDVYT NLTRIENTVV NDLLLQDFNH HNNNNNNNSN   240
SNSNKCSYYY PVIDDVTTNT ESFVYDTTAL TSNDTPLDFL GGHTTTTNNY YSKFGTFDGL   300
GSVENISLDD FY                                                       312

SEQ ID NO: 161          moltype = AA  length = 321
FEATURE                 Location/Qualifiers
source                  1..321
                        mol_type = protein
                        organism = Brassica napus
SEQUENCE: 161
MMADENVETK ASTLIASVGH QGHGFGSGSG GHHGLSASVP LLGVNSKKRR MPRQRRSSSS    60
FNLLSLPPPM PLSPHVPTPL SARKIDPRKL RFLFQKELKN SDVSSLRRMI LPKKAAEAHL   120
PALECKEGIP IRMEDLDGLH VWTFKYRYWP NNNSRMYVLE NTGDFVNAHG LQLGDFIMVY   180
LDLDSNNYVI QARKASEEEE EEEDVTIIEE DDVYTNLTKI ENTVVNDLLI QDFNHHNDNS   240
SNNNSNNNIN NNKCSYYYPV IDDITTNTAS FVYDTTTLTS NDSPLDFLGG HTTTTNTYY    300
SKFGSFEGLG SVENISLDDF Y                                             321

SEQ ID NO: 162          moltype = AA  length = 314
FEATURE                 Location/Qualifiers
source                  1..314
                        mol_type = protein
                        organism = Medicago truncatula
SEQUENCE: 162
MMMDEGEGKK KVVVQKTEAC GFMAGVEDEL GFVNVKGDNN NGSGQRIHHD HGFVAAAFGT    60
VHRKKRMARQ RRSSSSTITI HLKNLPSSTT TTTTTTTSHV PISPIPPLFH SLPPAREIDH   120
RRLRFLFQKE LKNSDVSSLR RMVLPKKAAE AFLPVLESKE GILLSMDDLD GLHVWSFKYR   180
FWPNNNSRMY VLENTGDFVS THGLRFGDSI MVYQDNQNHN YVIQAKKACD QDEYMEEAND   240
TINHIFVDDY EVNKSCFDVA YPAMNDTSMS FIYDTTISND SPLDFLGGSM TNYSRIGSVE   300
```

TFGSVENLSL DDFY                                                              314

SEQ ID NO: 163          moltype = DNA   length = 3275
FEATURE                 Location/Qualifiers
source                  1..3275
                        mol_type = other DNA
                        organism = Arabidopsis thaliana
SEQUENCE: 163
ggttggctat atggtccaaa ttttgatttg caatatgaga ttgcacagag agaacaatct   60
ttcattatga ttaattattg tacaagtaac aaacaccaat ctccgatata ctttggctct  120
ttagcacatt gttatgctag aagttagcgg aaatctatat gttgttaaac gcagcgttta  180
aattgaacag tgtaatttac cttgaaattt taagactaca tgctgtttag aatttcagat  240
gaaaacatct tgatgtttta gaaatccacg tgggaatagc gtaaatcttt atccaacgaa  300
cttattttgg ttttgttgta tttgtgcaag tcgtcacgct aatcgaaaaa agaaaagaaa  360
aaaagaagcc gtcatgatcg gccatttctc ggccgagtct gagtctgact ctgcgtccgt  420
gtcaccatta tcagatcgag cctgtcttat tcgttgcga ttccctatgc aaaaatcttc   480
ttctttttt tattccccca tttatctctg atctcttctc tcttctcaag taaacctctc   540
tgcttcacgt ctcttctttt cttgtcgatt ttccccagat aatcagttga aaacacaccc  600
aaattcatct tcgaatcaat aatggatata agtaatgagg ctagtgtcga tcccttttcg  660
attggaccat catctatcat gggtcgaacc attgctttca gagtcttgtt ctgtagatca  720
atgtcacagc ttaggcgtga tctctttcgg ttcttgttgc attggtttct tagatttaag  780
ctgaccgttt caccgtttgt ctcgtggttt catcctcaag accctcaagg gatttagcg   840
gtggttacaa tcattgcctt tgtgttgaaa cgatacacga atgtgaaaat aaaggcggaa  900
atggcttacc ggaggaagtt ttggaggaat atgatgcgga cggctttgac ttatgaggaa  960
tgggctcatg ctgctaagat gttagagaag gaaacaccaa agatgaatga atctgatctt 1020
tatgatgaag agttggttaa gaacaagctt caggagcttc gtcatcgtcg ccaagaaggc 1080
tcacttagag acattatgtt ttgtatgaga gctgatttgg tgaggaatct cggtaatatg 1140
tgtaattcgg agcttcataa aggtagactt caggttccta gacatatcaa agagtacatt 1200
gatgaggtgt ctactcagtt gagaatggtt tgtaactctg attcagagga gctttctttta 1260
gaagagaagc tttctttttat gcatgaaaca cggcatgcct ttggtagaac ggctttgctt 1320
ttgagtggtg gggcttctct tggtgcgttt catgttggtg tggttaggac tttggttgag 1380
cataagcttt tacctcgaat aattgctggt tctagtgttg gatccatcat ttgtgctgtt 1440
gtggcctcaa ggtcttggcc agaactcag agttctttg agaattcttt gcattcttta  1500
cagttctttg atcagctcgg aggcgtgttc tcaatagtga aacgggtaat gacacaaggg 1560
gctctacacg atatcagaca gttcaatgt atgcttagaa acctcacaag caatctcaca  1620
ttccaagaag cttatgacat acaggaagg attctcggga tcaccgtttg ctccccaaga  1680
aagcatgaac ctcctcggtg tcttaactat ttgacttcgc ctcatgtggt tatatggagc 1740
gcagtgactg cttcttgtgc ttttcctggt ctctttgaag ctcaagagct aatggctaaa 1800
gatcgaagtg gagagatcgt accgtatcat ccaccttcca atttggatcc agaagtaggc 1860
actaaatcat catctggacg ccggtggaga gatggtagtt tggaggttga tttaccaatg 1920
atgcagctta aagaactgtt caatgtcaat cattttattg tgagccaagc caatcctcac 1980
attgctccta tactgcgtct aaaggattta gttcgagctt atggtggtag attcgcagct 2040
aagctcgcgc atctagtgga gatggaggtc aaacataga gcaaccaggt attagagctc  2100
ggttttcctc tcggtggact cgcaaagctt tttgctcagg agtgggaagg tgatgttaca 2160
gttgtaatgc ctgctactct tgctcagtac tcgaagatta tacaaaatcc gactcatgtc 2220
gagcttcaga aagcggctaa ccaaggaaga agatgcactt gggagaagct ctcagccata 2280
aaatcaaact gcgggatcga gcttgcgctt gatgattctg tagctattct taaccatatg 2340
cggaggctca agaaaagtgc ggagagagc gccactgcca cgtcttcgtc tcatcacgga   2400
ttggcttcaa ccaccagatt caatgcttca agaagaatcc catcttggaa cgtccttgcc 2460
agagagaact caacaggctc actggatgat ctagtcactg acaataacct ccacgcttcc 2520
tcgggcagga atttaagcga cagtgaaaca gagagcgtgg agttgagttc ttggacaaga 2580
actggtggac ctttaatgag aacagcttct gctaataagt tcattgattt tgttcagagt 2640
cttgatatcg acattgcatt ggtcagagga tttagtagca gtcccaattc tccagcagtt 2700
cctcctggtg gtctcgtttac tccaagcccg agatccatag cggctcattc ggatatcgaa 2760
tcaaacagca atagcaacaa tctttggaaca agcacttcaa gcataacagt tactgaaggt 2820
gatcttctac agcctgagag aacgagtaac ggatttgtgt taaacgtcgt taaaagagag 2880
aacttgggaa tgccatcgat tgggaaccaa aatacagagt taccagagag tgtacagctc 2940
gatataccgg agaaggagat ggattgtagc tctgtatcag aacacgaaga agatgataac 3000
gacaatgaag aagaactaa cggctcgagt ctggttactg tttcttcaga agattccggt 3060
ttacaagaac cggtgtctgg tagtgttata gatgcttaga gtgtgattga ttcaagtgga 3120
tatagattct taattaaatt tgcagagttt ccaaagggtt tagtgcacca cttgtgtatg 3180
tttgtattgc ttattgtttg aaattcattt gtgaaatcga aatatatctg taaattcaga 3240
aaatattctc tcatccatta caaaatattt gagtc                           3275

SEQ ID NO: 164          moltype = DNA   length = 2795
FEATURE                 Location/Qualifiers
source                  1..2795
                        mol_type = other DNA
                        organism = Brassica napus
SEQUENCE: 164
tcccacgctc aggttctaat tgcaaaaaag gatcatactt tccttattaa aatcaatttc   60
ctgtgcttga tttctatctt aggaagctcg tagtagtttc tctgatagtg aatttgatga  120
aacaaagaaa aaaatgctga cttggtctca gattctaatt aaacacacac acacactaa   180
cctcaatgg atataagcaa cgaggccaat gtcgatccct tctcaatcgg accaacctcc  240
atcctcggcc gaaccatcgc cttcagagtc ctcttctgca aatcaatgct ccagctccgc  300
cgcgacctct tccgcttcct cctccactgg ttcctcacac tcaagctcgc cgtctccccc  360
tttgtctcct ggttccaccc ccggaacccc caggggatcc tcgccgtcgt cacgatcatc  420
gccttcgtcc tgaaacgcta caccaacgtg aaggccaagg ccgagatggc ctaccgtaga  480
aagttctgga ggaacatgat gcgcgcgcg ttgacttacg aggaatgggc tcacgccgct  540

```
aagatgttgg ataaagagac tccgaagatg aacgagtccg atctttacga tgaagagttg     600
gttaagaaca agctaatgga gcttcgtcat cgacgtcatg agggctctct tagagacatt     660
attttctgta tgagagctga tcttgtgaga aatctcggta atatgtgtaa ccctgagctt     720
cacaaggaa ggcttcacgt gccgagactc atcaaagagt atatcgatga ggtctctaca      780
cagcttagga tggtttgcga catggacact gaagagcttt ctctggagga gaaactttct     840
tttatgcatg agaccagaca cgcgtatgga agaacagctc tacttctcag tggaggagct     900
tctcttgggg cttccatct tggtgtggtc aagacgcttg tggaacataa gctattgcca      960
agaattatag ctggttcaag cgtggggtct gtaatgtgtg cggttgtggg gacaaggtca    1020
tggcccgagt tgcagagctt ctttgaaggg tcctggcatg ctctgcagtt ctttgatcag    1080
atgggaggaa ttttcactac tgtgaagcgg gttatgactc aaggcgcagt ccatgagatc    1140
cggcatctgc aatggaagtt gaggaatctc accaacaatc tcacagtccg gaatttccgg    1200
gtcgacgact tcgaggatac tcgggataac ggtttgctca ccgacgaagc actagccgcc    1260
tcggtgctta actatctcac ttctcctcac gtggtgatat ggagcgcggt gactgcttct    1320
tgcgcttttcc ctggtttgtt tgaagctcag gagctgattg ctaaagatag gagtggggag    1380
atagtgccgt atcatccgcc ttttaattt gaaccggagg aaggtgggga taagtcgtct    1440
acgaggaggt ggagagatgg gagtttggag gttgatttgc cgatgatgca gcttaaggag    1500
ctgttttaatg ttaatcattt tattgtgagc caggctaatc ctcacattgc tccgttgctg    1560
cgtttgaagg atatagttag agcttatgga ggtcgatttg cagcaaagct cgcgcaactc    1620
gcggagatgg aagtgaagca tagatgtaat caagtactag aactcgggct tcctctaaga    1680
gaagtagctt cactatttgc tcaagaatgg gaaggcgatg tcacaattgt catgccagct    1740
actttttctc agtacttgaa gatcatacaa gtcgacgatt tcgtcgagct tcaaaaagcc    1800
gctaaccaag gaaggagatg cacttgggag aagctatcag ccataaaagc aaactgtggg    1860
atcgagcttg cgcttgatga gtgtgtaact aatcttaacc atatgcgtag gctcaacaga    1920
agcgctgaga gagccgctgc tgctgctggc acgtcctcct cgtctcatca cggattagct    1980
tcaacgacaa gattcaatgc ttctagaaga atcccgtctt ggaacgtcat cgctagagag    2040
aactcaactg gctcactgga cgacctcgtc actgacagta acaataataa tctccacgcg    2100
gggaggaacc taagcgacag cgaaacggag agcgtggaga tgagttcttg gacgaggact    2160
ggtgaccgt tgatgagaac agcttctgct aataggttca ctgactttgt ccatggtctt    2220
gacgtggaca ttgcgttgac aagagggttt actagcagcc ctaactctcc agcggttcct    2280
ggcccggtta gtccgagttt tagtccaaga tcgagatcct tggcggctca atccgagagc    2340
gaatctgaca agagggaaag tagcaacagt tctagtatat cagctactga aggtgatctt    2400
ctgcagcctg agaaacgag taacggtttt gttttgaacg ttgttagaag agagaacttg    2460
gggatgcctg tggagaacca gagcggtgag ctgccggaga gtgtacagat agatatacct    2520
gagagggaga tggataatag ctctgtctca ggacatgaag atgataatga tgataatgat    2580
gatgaagaag aagaacataa gggctcggtt ccggttaaag attccggttt acaagattct    2640
tgtagtgtaa tagatgctta gactgatttg atccgagtga agagattctt gttcagcaaa    2700
gatcttggag tgtttagtg ctttgtaaat agtacaacta taggccgcaa gtaaggtgca    2760
tgttgtgtat gtttgcagtg attatgttga aaatt                              2795

SEQ ID NO: 165          moltype = DNA   length = 2670
FEATURE                 Location/Qualifiers
source                  1..2670
                        mol_type = other DNA
                        organism = Brachypodium distachyon
SEQUENCE: 165
atggaagaat ccggagaagc gagtattggg gccttcagga tcgggccgtc gacgcttctc       60
ggccgacgcg tcgcgcttcg cgtgctcctg ttcagctcgc tctggcgtct gcggggcgcg      120
gcgcgcgccg ctgtgtcgcg cgtgcgcagg gccacgctgc caatggccgc gtcctggctt      180
cacctcagga acacccatgg cgtcctcctg attctcgtgc tcttcgggtt gctcctcagg      240
aagctctccg gtgcgcggtc gcggctggcg ctggcgcgcc ggcgtaggct gtgcaagagc      300
gcgatgcgct acgcggcgac gtatgagcag tgggtgcgtc ccgccaaggt gctcgacaga      360
atgtctgagc aggtgaacga gtctgatttt tacgacgagg agctgatcaa gagtaggctt      420
gaggagctcc ggaggcggag ggaggaaggg tcgctccggg atgtggtgtt ctgtatcgcc      480
ggcgatctcg tgaggaactt ggggaacatg tgtaatcctg agcttcataa gggcaggctc      540
gaggtgccca ggctgataaa agatttcatt gatgaggttt caactcagct gaaaatggtg      600
tgtaatctgt acaccgatgc gttatttttg gaagagaagc ttgcctttgt tcaggaaacc      660
aggcatgcct atgggaggac agcactactc ttaagtgggg gcgcttcact gggctctttc      720
catgtaggta tagtgaaaac attagttgag cataagcttc tgcctcggat aatagcaggg      780
tctagcgttg gttccattat atgttcaatt gttgctactc gaacatggcc tgagattgag      840
agcttcttca tagactcatt acaaatctta cagttcttcg gtaggatagg tggaattttt     900
gctgtgacca aacgggttat gacttatggt gcacttcatg acattagcca gatgcaaagg      960
cttttgaggg atctcacaag taacttaaca tttcaagagg cttacgatat aactggccgt     1020
gttcttgggg tcactgtttg ctctcccaga aaaaacgagc caccctcgctg cctcaactac    1080
ctgacatcac cacatgttgt tatctgagt gctgtaactc cttcgtgtgc attcctggcc     1140
ctctttgaag ctcaggaatt gatggcaaag gataggtttg gccacatagt tccccttcca    1200
gcgccctttt ccacagatcc agaacaaggt cctggagcat caaagcggcg atggagggac    1260
ggaagtttgg agatggattt accgatgatg caactaaagg agttattcaa tgtgaatcat    1320
ttcatcgtca gccaagctaa tcctcacatc tctccactcc tccgaatgaa ggagattgtc    1380
agatcctatg gaggtcgctt tgcgggaaag ctcgctcgtc ttgctgtgat ggaggtgaag    1440
tatcgatgta accaagttct agaagttggc ctcccactgg gaggacttgc aaagttgttt    1500
gctcaggact gggagggtga tgtcactatg gttatgccag caacagtagc tcagtacttg    1560
aagattatac aagatccaac atatgcagaa ctccaaatgg ctgccaatca gggtcaaaga    1620
tgcacgtggg agaagctctc agcgatcaga gcaaactgtg caattgaact tgcattggat    1680
gaatccattg cggttctcaa ccacaaacga aggtaagaa cgacacaag ggcagcagct       1740
tcttcccagg aatataccag caatgttcga ctcagaacac caaggagggt accctcatgg    1800
agctgcatca gtcgagagaa ttcgtcagga tctctctcag aagatcactt tgcggtcgct    1860
atttcatcca gtcaccaagg tactatacga gttgatggcg caccaaacat gcctcatcat    1920
gttcgtcaca gttcacacga tggaagtgag agcgaatcag aaaccattga cttaaattca    1980
tggaccagga gtggtgggcc tctaatgagg acttcatcag ctgatcagtt catcagtttt    2040
```

```
atccagaatc tcgagattga atctgagttc gatagggttc gtactacaga ggatgacaat  2100
acaggtattt tatcaggatc tacattttca aaagatccat acccaaacat tagttctaga  2160
gtcactacac cagatagatg cacagaagtt tctgaaacag agtcgtgcaa cgccggcaac  2220
acaagcatca ctgtttctga aggagatttg ctacaacctg agaggactac caccggaatt  2280
ctactcaatt ttgtcagaag agaagatctg cttggtcagc ataacagtga tgctgacatg  2340
accgaaagct ccttagccga agcatatgtg gacacatcac atttggaatc ttgtgatgcc  2400
atctcagcct ctgacagttc tgaaggtaac aaagacgcag ctgactcaga gaatctcttg  2460
gtttctcatg cagatttagt aacttcgcat caatcttcag ttgatgataa caaaggtggc  2520
tagattttga aagaattctt ttagtggctt gctaagtcga tgctgtacag gaaaaactgt  2580
agtgtctccg tttcgtgagc actactgctg gtagcatagt gaatattgta ctttgtacca  2640
gatactaaat aaatttgatt gcttgccatt                                    2670

SEQ ID NO: 166        moltype = DNA  length = 3884
FEATURE               Location/Qualifiers
misc_feature          1..3884
                      note = Populus trichocarpa
source                1..3884
                      mol_type = other DNA
                      organism = synthetic construct
SEQUENCE: 166
gttttctttc ccttatccgc ctttgattgc aaaagtcaat gtcagagcca tcaccccctc   60
cttgctcaat ctttacgtaa ccgtatgtat atccttatct tcttctaaca tttcccaaga  120
ctccgatcct gtatttattg tattcacttc acccttcttc tctctttcct tcccgaacga  180
aaacaaagtc tcaatctttc attctctgtt tgtctaaagt ctgtacattc ttcactttct  240
cgagttgggt ttctttcttg aatttggttt cttgggtttg attttgtttt tcaagtggat  300
attgctattt attgggtggt gatattgaga ccctttttgtt agttttgtat attggttttt  360
gaggtggatg tagtttttttt aggggtttta gggtttggtt attgaaaact catatgtgca  420
ggttggcttc tggcaatctg gatttataag attctgtttt tcttgttgac acagtacagg  480
atcaaaaggg ttggattttt gttacttgtc aatatcttct tatttgtga tagctagtcc  540
ttttgcatta ggattgcata tctttattct atctacttca ttgtctctct atatattgcc  600
atcctatccg gggagagaca gattcaattg ttttattgtc cttctcattc tcattagaat  660
caaagtcttg acatacaatc ctttcacaat tgtgaaattt gattcctttag tgaccatcta  720
ttgtagctgt ttcatatttg tttcgttcaa gctaattctg ttgttagatt tgagacaaaa  780
gaaggccccg cttccaatta cagaccactt tcttgttttg gttttagcta agatatggat  840
ataagcaatg aggccagtgt tgacccttc aaaatcggac cttcatcgat cattgctagg  900
acaattgctt tcagattct gttctgtaaa tcaatctcac atttgaggca aaaaatctt   960
catgtgttgt tgaattacat ttatagagtt ggtgaatttc tggcgcctat gttatcatgg  1020
tttcatccaa ggaatccaca agggatattg gccatgatga cgataattgc atttttattg  1080
aaaagatatg cgaatgttaa attgagggcc gaaacagcgt ataggaggaa attttggagg  1140
aatacgatga gaactgcgtt gacatacgag gagtggtttc atgctgctaa aatgcttgat  1200
aaagagaccc caaagatgca tgaatgtgat ctctatgatg aagaactagt caggaacaag  1260
cttcaagagc tccaccaccg tcgccaagag ggatgtctta gagatataat cttttttatg  1320
agagccgatc ttgtaagaaa tctcggtaat atgtgtaacc ctgagcttca caagggtagg  1380
cttcaagtgc ccaagctcat aaaggaatat attgacgagg tctcaactca gttaagaatg  1440
gtttgtgact ccgattcaga ggagcttccg ttggaagaaa agcttgcttt catgcatgaa  1500
acgagacatg cttttgggag aacagctttg cttctgagtg gaggtgcttc acttggagcg  1560
tttcatgtgg gtgtggttaa aacactggtg gagcacaagc ttatgccccg aataattgct  1620
ggttctagtg tggggtcaat tatgtgttca gttgttgcca ccagatcgtg gccagagctg  1680
caaagttttt ttgaggattc ctggcactcg tttcagttttt tgaccaatt gggtggaatt  1740
ttcacagttg tgaagagggt catgagacaa ggagctgttc atgaaatccg gcagttgcaa  1800
tggatgttaa ggcatcttac aagtaatctt acatttcaag aagcttatga catgactggt  1860
cgaattcttg gatcacagt ttgctcacct aggaagcatg agcccctag atgccttaat  1920
taccttactt cccctcatgt tgttatatgg agtcagtca ctgcttcttg tgcttttcct  1980
ggccttttg aagcccagga actaatggca aaggacagaa gtggggaact tgtgccttat  2040
cacccaccct ttaatctgga tcctgaagaa ggatctgatg cacctatgcg taggtggagg  2100
gatggtagcc tggagattga tttaccaatg atacaattga aggaactatt caatgtcaat  2160
cattttattg taagtcaagc gaatcctcac attgctccat tgttgagact gaaggatata  2220
gtcagggcat atggggtag ctttgctgcc aagcttgctc atctcgctga gatggaggta  2280
aaacatagat gcaatcaggt attggaactt ggttttcaat taggtggact tgccaagctt  2340
tttgctcaag aatgggaagg tgatgttact gttgttatgc ctgccacact cgctcagtac  2400
tcaaaaatta ttcaaaaccc aaatcacttg gagcttcaaa aggcatcaaa ccaaggcaga  2460
aggtgcacat gggagaagct ttctgccata aaagctaatt gtggtattga gcttgctctt  2520
gatgagtgtg tttctgttct gaaccacatg cgtagactca aaaggagtgc tgagagagct  2580
gctgctgctt ctcatggcca agcaagctct gcgagcacat tgagatttag tgcttcaaaa  2640
agaattcctt cttggaattg catcgcaaga gaaaactcaa caggctcact gaagaagac  2700
ttccttgctg atgttgcttc aacattccat caaggagttg gtgtggctgg aggaacttct  2760
actggtagga atttgagaac acaacgcaac ctacatcatg atggaagtga tagtgaatct  2820
gaaagtgtag atttgaattc ttggacaaga tctggcgggc ctttgatgag gactgcttct  2880
gcaaataagt tcattgactt tgtccaaagt ctggatgttg attctgacgt aaggaaaggc  2940
ttcatggctc atcctaactc gcctgggggct cagatgggga gcaggatcc atataatcag  3000
atctcaagag tgacaacccc agatagaaat tcagaaagtg agtttgatca gagagatttt  3060
agcaatagaa attctactgg tggttctagc attacagtca ccgaaggaga ttttttgcag  3120
cctgaaagaa tccataacgg gtttgtgctg aatattgtaa agaaagaaga tttggcacat  3180
cccaatagtc catgatttt ggagaattac aatagtgaag ttcctgaatg tgttcagctt  3240
gattgtcctg aaaaggacat ggatgctagc tcagaatcgg actatgctgc agaggaagac  3300
gactcccctg caacagattc cttgcataaa tcagcttcca ctcttgatca cacagatgat  3360
tctgtcgttc atgacattca ggagaagcat gtcgtggatg ttaactttg agtttcttc   3420
gcattactgt accaaaatat tgggtggagt tgattcccgg gttactgtca atcaaaggtt  3480
tccgactttc cgtcacaact ggagtatcat agacgagatt tagaatctgt ttattttta  3540
```

```
ttttaaaaat attttgaaa aaaattttga tttattttg attttatttt tgttttaaat    3600
taatatttt ttggtgtttt tcatattatt ttgatatgtt gatattaaaa ataaattttt    3660
aatatcaatt attcaatcag atatatttt aagtaaaaca agacagtttg aaaagtaatc    3720
ggaactttta aaaggttgct cttagtagtg aattataaaa aacaattgaa agcaatctgg    3780
cagcgtcagg ctattgctgt tgtaaactaa ttttgtgcgc atactatgca acaattgtaa    3840
tccacatgct tagatttcag ccaacgagat ggaatttgac cctc                    3884

SEQ ID NO: 167         moltype = DNA   length = 2490
FEATURE                Location/Qualifiers
source                 1..2490
                       mol_type = other DNA
                       organism = Medicago truncatula
SEQUENCE: 167
atggatcgta taagtaatga agccactgtt gatcttttc caatcggtcc ttcaggaatt     60
cttgcccgaa caattgcatt cagagtcctt ttctgcaaat ccatttcaca tttaaggtat   120
caattattct taactttatt cgattcgttt catagattta gaaaattctg ggacccatt    180
atatcatcct tgcatccaaa aaaccctcaa gggatattag ccatcatcac cattctcgct   240
ttcttgttaa aacgttacag taatgtttaa gtaagagcta aattagcata caggagaaaa   300
ttttggagaa atatgatgag atcagctttg acttatgagg agtgggctca tgcagctaag   360
atgcttgata agagacgac attgaagacg atgaatgaat ccgattttta cgatgtagaa   420
ttggttagga ataaggttca agagttacga catcgtagac aagaggggtc tcttagagat   480
attatctttt gtatgagagc tgatcttgtt agaaatttag gtaatatgta taaccctcag   540
cttcataaag gtaggcttca tgtgccgaga cagattaagg agtatattga tgaggtggc   600
atgcagttga gaatggtttg tcattctgat tccgaggagc tttctttgga agaaaagctt   660
gctttcatgc atgaaactag acacgcgttt ggaggacgg ctttgttgtt gagtggtggt   720
gcttctcttg gagcttttca tgtcggtgta gttaaaacct tggtgaaaca taaacttatg   780
ccgaggataa tttctggttc gagtgtagga tccattatgt gctctattgt tgctactagg   840
tcttggcctg agcttcaaag ctttttgaa gattcgttgc actcgttaca gttttttgat   900
caaatggtg gatttttac gattgtcaag agggttacaa catttggtgc agttcatgag   960
atcagacagt tgcagattat gttgaggcat ctaacgagca atcttacatt tcaagaagct  1020
tacgacatga caggtcgagt tcttggatt acagtttgct cccaaggaa gcatgaaccg  1080
cctagagtgc ttaactactt gacttcaccc catgttgtta tatggagtgc agtcacagct  1140
tcttgtgcct ttcctggtct ttttgaggct caggaattga tggcaaagga tagaagtgga  1200
gagattgttc cttaccatcc tccatttaat ttgggtcctg aagagggttc ctcacaagtg  1260
cggcgttgga gggatggtag cttggagatc gatctaccta tgatgcagtt gaaagaattg  1320
ttcaatgtca atcattttat tgttagtcag gccaatcctc atattgcgcc attattgaga  1380
ttaaaagaat ttgtacgagc ttatggaggt aattttgctg ccaagctggc tcatctggta  1440
gagatggagg ttaaacatcg atgtaatcaa atactggaac ttggttttcc attaggtgga  1500
cttgccaagc tgtttgctca ggactgggaa ggtgatgtga cagttgttat gcctgctact  1560
cttgctcagt actcaaaaat tatccagaac ccttcttatg tggagcttca gaaggcagct  1620
aaccaaggga gaagatgcac ttgggagaag cttcagcca ttaaagcaaa ttgtggaatt  1680
gagcttgctc ttgatgagtg tgttcaatt ctcaatcata tgagaagact caaaagaagt  1740
gccgagagag tgcttctgc ttctcatggt ctttctagta ctgtcaaatt tagtgcttca  1800
aaaagaattc catcatgaa tgtcattgcg cgagagaatt ctacaggatc tcttgaagac  1860
tttcttgcag acactgctgc ttcatttcat acggggtta gtagttccag tggagccacg  1920
ggtaaaaatt ccaagcacca ccgcagcatg catgatgtaa gtgacagtga atccgaaagt  1980
gctgaattga atacctggac cagatctggt ggtccttga tgagaactgc ttcggcagat  2040
atgttcaccg actttgtcca aaacttagaa gttgatactg aactaaacag aggaatggga  2100
actaattta gccctcgtga ttcccagtat cacagtccca gattaacaac accgggataga  2160
tgctccgaga actcagaacc cgatcagaga gaaaatggca acaaggttgt catgaatgga  2220
tctagcataa tggtaactga aggtgatctt ttgcagcctg agagaatcca taatgaaatt  2280
gtgtttaatg ttgtcaagaa agaagactta acaccttcaa gtaggagtca tgattatgat  2340
agtgaaattg ctgagtgtct ccaaattgaa tgtccaggga aggagatgga tgatgctgct  2400
agctcagctt cagaaaacgg agatgacgat tctgcaacag ctaggcccct aactgaaaca  2460
ccagactcta atcctacaga taattcctga                                    2490

SEQ ID NO: 168         moltype = DNA   length = 2783
FEATURE                Location/Qualifiers
source                 1..2783
                       mol_type = other DNA
                       organism = Glycine max
SEQUENCE: 168
atggatcata ttagtaatga ggccagtgtt gaccgttttc caattggtcc ttctggcatt     60
cttggtagga caattgctt cagggttctt ttttgcaagt ctatctcaca ttttaggcac   120
cacatattta ttgtgttgtt agatctcttc tataggttta gggggggttt ggcatccttt   180
atatcatggt tgcatcccag gaaccctcaa gggatattgg caatgatgac aattgttgct   240
ttcttgttga aacgatacac aaatgtgaaa tcaaggctg aatggcata taggaggaag   300
ttttggagaa acatgatgag aagtgctttg acctatgagg agtgggctca tgcagctaag   360
atgcttgata aagagacaac aaagatgaat gaatcagacg tttatgatgt ggaattggtg   420
aggaacaagc ttcaagagct ccgccaccgt cgacaagagg gatctctcgg agatataatg   480
ttttttatgc gtgccgatct tattagaaat ttaggtaata tgtgtaaccc tgaactacac   540
aagggtaggc ttcaggtgcc taaattaatc aaggagtaca ttgatgaagt aacgactcaa   600
ttgagaatgg tctgtgattc tgattcagag agctatcatc tggaagaaaa gcttgctttc   660
atgcatgaaa ctaggcatgc atttgggagg actgcttttg tgttaagtgg gggtgcctct   720
cttgagcttt ctcatgtggg tgtagttaaa acactggtag aacataaaact catgcctagg   780
ataattgctg gttcaagtgt gggatccatt atgtgtgctg ttgttccac taggacttgg   840
cctgagctcc agagcttttt tgaggattca tggcactcat tgcaatttt tgatcaaatg   900
ggtgggattt tgcagttgt taagagagtc acaacattgg gtgctgttca tgagatcaga   960
cagttgcaaa tgatgttgag gcatctaaca agcaaccttc cattcaaga agcttatgac  1020
```

```
atgacaggca gaattcttgg gattactgtt tgttccccaa ggaagcatga accgcctaga   1080
tgtcttaact acttgacttc accccatgtg gttatatgga gtgcagtaac cgcttcttgt   1140
gcctttcctg gccttttga ggctcaagaa ttgatggcaa aggatagaag tggagagatt    1200
gttccttacc accctccttt taacttaggc cctgaagagg gctccacacc agtgcgccgt   1260
tggagggatg gtagcttgga gattgattta cctatgatgc agttgaaaga actattcaat   1320
gtcaatcatt ttatagttag tcaggccaac cctcatattg caccactatt gagattgaaa   1380
gaatttgtgc ggacttatgg gggcaacttt gctgccaagc ttgctcatct tgtggagatg   1440
gaggtgaaac ataggtgtca tcaaatactg gaacttggtt ttccattagg tggacttgct   1500
aaattgtttg ctcaagactg ggaaggtgat gtgactgttg ttattcccgc aactcttgt    1560
cagtacacca aaattataca gaaccctttca tatggagagc ttcaaaaggc agccaaccaa   1620
gggagaagat gtacctggga gaaactttca gccataaaag caaattgtgg cattgagctt   1680
gctcttgatg agtgtgttgt gattctcaat catatgagaa gactaaagag aattgctgag   1740
agagctgctt ctgcctctca tggtttgtcc agcactgtca ggtcagtgc ttcaaaaaga    1800
attccttcgt ggaattgcat tgcacgagag aattcgaccg gctcccttga ggacctact    1860
gatgttgcct cctcattgca tcaaggcatc ggcagttcca gcagagccaa tggcaaaact   1920
tggaagaccc accgtggcat acatgatgga agtgacagtg actctgaaag tgttgatttg   1980
cattcttgga caagaactgg cgggcctttg atgagaacta cttcagcaaa tatgttcgtt   2040
gattttctcc aaaacttaga aggttgatacg gatcctaata aaggcttagt gagtcacact   2100
atccataatg attttcagta tcatagcccc aggctcacaa cactagatag gaactctgat   2160
agcacagaat ctgagccaag ggaaactggc aacaggggttg tcaatgtgtc cagcatactt   2220
gtgaccgaag gtgatcttct gcagcctgaa aggatccata tgggattgt gtttaatgtt   2280
gtcaagaaag aagacttgtc acccttaagt agtagcagc atggttttga aaattacaac   2340
attgaagttg ctgaatgtgt ccaagatgag tgtccaggga aggagataga tgctgctagc   2400
tctgcatctg aacacggaga tgatgaagaa tccatgccag ccaggtcctt aactgacatg   2460
ccagattaca attccattga tcatcattcg ggcacagatt cgggtatgga tcaaagcatt   2520
gttgacagtt agtgtcaagt atcagttctt ttccagtgaa atttaatat tttgttccta    2580
ttgccctcca tattgtaaat agtactcatt ctagacttgg agaggtcttt attcatgatt   2640
ttgatgggaa tagcccacca attggtttg ctcataaatg taacaaagat aaagagtttg    2700
tatacataaa ttccacgaca acattgatat ttccttggtta ccacttctca gatgaatgaa   2760
atggagacat ggttttcata att                                           2783

SEQ ID NO: 169        moltype = DNA   length = 2724
FEATURE               Location/Qualifiers
source                1..2724
                      mol_type = other DNA
                      organism = Sorghum bicolor
SEQUENCE: 169
atggatgaca tcgccagcga ggcgccggtg ggggcgttcg ccatcggccc gtccacggcg    60
ctgggccgcg ccgtcgcgct ccgggtgctg ctctgcgcgt ccgcggcgcg cctgcggcac   120
cgcctggccg cggcgctccg cgccgcgctg cccgtcgcgg cggcgtggct gcacccgcgc   180
gacaacacgc gcgggatcct gctcgccgtc tgcgccgtcg cgctcctgct gcggggccga   240
cgcggcaggg ccgggctgcg ggcgagggtg cagtccgcct accgccgcaa gttctggcgg   300
aacatgatgc gcgccgcgct cacctacgag gagtgggcg atgctggag                360
cgcgaggccg ccccgcgccg cgccagcgac gccgacctct acgacgagga gctcgtccgc   420
aataagctcc gcgagctcag gcaccggcgc cacgagggat cgctcaggga catcgtcttc   480
tgcatgcgcg cggacctgct caggaacctc ggcaatatgt gcaaccccga actgcacaaa   540
gggagcgtgg aggtgcctag actcataaag gaatacattg aggaagtatc tactcaactg   600
aaaatggtct gtgattctga ttcagatgag ttgcctcttg aagagaaact cgcatttatg   660
catgagacaa ggcatgcctt tggtagaaca gccttgctgc taagtggagg tgcttcattg   720
ggatcctttc atgtgggtgt tgttaaaacc ttggtagagc ataaacttttt gccaaggata   780
atttacaggat caagtgttgg ctcgataatg tgttctataag tagcaacaag atcatggcat   840
gagctggaga gcttttttga agagtggcat tccctgaaat ttttttgatca gatgggtgga   900
atctttcctg tggttaaaag aattttgacg caaggcgctg ttcatgatat aaggcacttg   960
caggtgcttt tgagaaacct taccagcaat ttgacatttc aagaagctta tgacatgact   1020
ggtcggattc ttgttgtcac cgtgtgttct ccaaggaagc atgagccgcc tcgatgccta   1080
aactatttaa catcacctca tgttcttatc tggagtgcag taacagcttc ctgtgctttt   1140
cctggacttt tgaggcccca agaattgatg gcaaagata gatttggtca aaccattcct    1200
ttccatgctc cattcttatt aggcatagaa gaacgaactg ttgctccaac ccgccgctgg   1260
agagatggga gcttagaaag cgatttaccc atgaagcaat tgaaggaact attcaatgtg   1320
aatcatttca tagtaagcca agccaatcct cacatagctc cgctgttgag actaaaggaa   1380
atcgtcaggg cttatggagg cagcttcgct gccaagcttg ctgaacttgc tgagatggaa   1440
gtcaaacata ggtgtaatca agttttgaaa cttggatttc ctctaggagg attagctaaa   1500
ttatttgctc aagattggga aggcgatgtt acagttgtta tgccagccac tcttgcgcag   1560
tattccaaga tgatacagaa cccatcttat gctgagctcc aaggctgc gaatcaaggt    1620
aggagatgca cttgggaaaa gctatcagcc atcagggcaa attgtgctat tgagcttgca   1680
ctggatgaat gtgttgccct cctgaaccac ttgcgtaggc taaagaggag tgcagaaaga   1740
gcatccgcat cgcaaggata tggtccagca atcaggttct gcccatctag gaggattcca   1800
tcctggaatc tcatagcaag agaaaattca actggttctc ttgaagaaga aatgcttaca   1860
tctcctcaag gacctggagg agttgctgga acatctacca gaaaccagta tcctccagaga  1920
agtgcacatg agagcagcga cagtgaatct gagagtattg atttacactc ttggacaaga   1980
agtggtggcc ctcttatgag gacaacctca gccaataaat tcatcagctt tgttcagaat   2040
cttgagatcg acacagaatc cagaacaatt ccatcgaggg aagacataac tgatcttgtg   2100
acaccaaatg ctggtaccct tggcagctcat gcagtgagta gagaagcaat cgataggagc   2160
ttggacaatt cagctttaga tatccatgat accagtacca ctagatcgac atttggccct   2220
tcaacaagta ttgtggtttc tgaaggtgac ttgttgcagc ctgaaaagat tgaaaatggt   2280
attttgttta atgttgtaag gagggatact ctgctcgggt ctagtagtgg agttgagtct   2340
caaggatctc ctcgggaacc agatgttgaa acagtacaga cggagtgcct tgatggcgtg   2400
tctacttctg atgatgatga tgacaaggaa ctaaatgcca ttgatgatgg aggaactagt   2460
cccatgagca gaaataatct acaacatcag gggtcctcac tggaagaaaa attataccat   2520
```

```
ccctcttcct taaattctga agacgagaca aacacaaaca aaccagaagc tgcatcgatt   2580
tttgatatat gtacagatat gcatccggca tctattagcc tacctgaagg gtcttcagaa   2640
aagacagaac tggaaacaac aaagattcct gatgacaatt cagctgttat gaatgatgaa   2700
gttgcctcag gtgctggtaa ctaa                                          2724

SEQ ID NO: 170        moltype = DNA   length = 2985
FEATURE               Location/Qualifiers
source                1..2985
                      mol_type = other DNA
                      organism = Zea mays
SEQUENCE: 170
cattctctct ctctctctcc cttttcaatt tcggggcttt tatttctctc ctcccacgcc     60
ttgcatcttc ttgatgcgtt gcgtcccgac tcgaggcaga catcggaggc gcgccactga    120
cttagctcgc gatttctaga tccgcaaccc tgcgctgctc aactccgatt cttttagttc    180
ggattcgggt agcagcaggg cttcggtggc gatgacttga ttgatacgaa ttgggggattt   240
cttgctgttt gcgcctctct tcgtatcggc gctgaagggc tcagctcgag attagaacaa    300
tttgggtttt ggggtctttt cttcttctac tactgctggt caagttcaca gaaatcgctg    360
gctccgtggt ccaatggacg agtccgggga agcgagcgtc ggtccttca ggatcgggcc     420
gtcgacgctg ctgggccgcg gggtggcgtt ccgcgtgctc ctcttcagct cgctgtggcg    480
cctgcgggcg cgcgcgtacg cggccatctc gcgcgtgcgc agcgcggcgc tgccggtggc    540
ggcgtcctgg ctgcacctca ggaacagcca cggcgtcctc ctcatggccg tgctcctcgc    600
cctcttcctg aggaaactct cggccgcgcg gtcgcgggcg gcgctcgccg gccggcgcag    660
gcagcacgag aaggccatgc tgcatgccgg gacgtacgag gtctgggcgc gcgccgccaa    720
ggtgctcgac aagatgtctg agcaggtcca cgaggcggat ttctacgacg aggagctcat    780
caggaatagg ctcgaggaac tccggagacg gagggaggac gggtcgctcc gggacgtggt    840
gttctgtatg cgcggcgatc ttgttaggaa cttggggaac atgtgcaacc ctgaacttca    900
caagggcagg ctagaggttc ctaagcttat aaaggagtac attgaagagg tttctactca    960
actaagaatg tgtgcgaat ctgacactga cgagttgctg ttggaagaga aacttgcctt    1020
tgttcaggag accaggcatg cctttgggag gacagcgcta ctcttaagtg ggggtgcttc   1080
actcgggtct ttccatgtag gtgtagtgaa aacattggtt gagcataagc ttctgctcg    1140
gattatagca ggatcaagcg ttggttccat catatgttcg atcgttgcta cccgtacatg    1200
gcctgagatt gagagcttct tcacagactc attacagacc ttgcagtttt tcgacaggat   1260
gggcggaatt tttgcagtga tgaggcgtgt caccactat ggtgcactgc atgacattag    1320
ccagatgcaa aggcttttga gggatctcac aagtaactta acatttcaag aggcttatga   1380
catgaccggc cgtgttcttg ggatcaccgt ttgctctcct agaaaaaatg agccaccccg    1440
ctgcctcaac tacctgacgg caccacatgt tgttatttgg agtgcagtaa ccgcctcttg    1500
tgcatttcct gggctctttg aagctcagga actgatggca aaggataggt tcggcaacat    1560
cgttccctte catgcaccct ttgccacaga tcctgaacaa ggtcctggag catcgaagcg   1620
caggtggaga gacgggagct tggagatgga tttacccatg atgagactta aggagttgtt    1680
taatgtaaac catttcattg tgagccaaac taaccctcac atttctccac tcctccggat    1740
gaaagagctt gttagagcct atggagggcg ctttgctgga aagcttgctc gtcttgctga    1800
aatgaaggtt aagtatcgat gcaaccaaat cctagagatc ggtcttccaa tgggaggact    1860
tgcaaaattg tttgcccagg attgggaggg tgatgtgacc atggttatgc cagcaacact    1920
tgctcagtac ttgaagatca ttcagaatcc aacatacgcg gagctccaaa tggctgccaa    1980
ccaaggccgc aggtgcacat gggagaagct ctccgcaatc agagcgaact gcgccattga   2040
acttgcactt gacgaatcca tagcggttct aaaccacaaa cggaggctaa aacgaagcat    2100
ggagaggacg gcggcgggtt cgcagggtca ctctaactat gtccgaccca agactccgag   2160
gaggataccg tcatggagcc gcatcagtcg agagaactct ttggagtctc tctcggaaga    2220
gatctctgcg gttgctgctt cgtccatgca gcaaggcgct gctcttgttg tcggcgcacc    2280
accaacgact ctttctcagc atgttcggcg cagttctcat gacggaagtg agagtgagtc    2340
agaaaccatt gaccttaatt cctggaccag gagtggaggg atgacagcgtc               2400
cgccgacagg ttcatcagtt tcatccataa cattgagatt gacacagaat taagtaggcc    2460
ctgtgctgtg gaaggtgatg ctgcaggtat tttgtcagaa tctaccttcc caaacggtcc   2520
acgaccgaac aatagctcaa gtgttagtat gccaggtaga tgcacagaaa attctgggac    2580
cgagtcgtgc aacactgtca acaccagagc ttctactccc acaagcatgt cgttcgtga    2640
aggagatttg ctgccgcctg aaagcactac tgataatgtc ctacttaaca ttgtgaaaag   2700
agacgccctg caggatggtg taactgaatt ggcggaaagc tcctgcgctg aaggatatgc    2760
ggcaaactgt gacaccgtct cagggctaga ctgctgaagg taacaagacg ctcgctgctg    2820
acttgagcaa tcaacaatta gctgatgatt agattcttct tgattttgat gatgaaaggt    2880
catttatatg tagctcacta cagcaacgca gtgtaggaaa attgtacctg ctcgatttaa    2940
actttaaaga gcatgccatg agtagctttg ttaatgttaa tattc                   2985

SEQ ID NO: 171        moltype = DNA   length = 1998
FEATURE               Location/Qualifiers
source                1..1998
                      mol_type = other DNA
                      organism = Physcomitrella patens
SEQUENCE: 171
atgaattact tagacactga cgccgacgct gcgctagagc atttcggcat tggacctctg    60
actttggcgc aaaagttgt ggcctttcgc gtcctatttt gtcgttgggt gaaagagctt   120
cgtgttgccc tcgcaaagag gctgcagcgg acacggaggg tatggagaca ggtgttctat   180
atgtggtttg ggtggttgaa ccctcgaaat cccagcgtcc ttctgttagc tgccgttgta    240
gcaaccatgc tcatgagaag agcgaaggca gggtctcaga aagcagagat tgcgtacaga   300
cggaagttct gttccaattt aatgaaggca gctttgacgt atgaggaatg ggctcatgcg    360
gcgcggatgc tagagaagga gcagaatcgg aggaaagatt cagacttgta ccgatgaggat    420
ttggtgcgtt cgaagctcaa cgatcttcga ttgcgtcgtt tggagggtgg tgtggaggac    480
attcttttct gcattagggc cgatttagtg cgtaatttgg gtaacatgtg caatcccgaa    540
ctgcacaaag gccggctaca aactcccccc ctcatccagg aatacatcaa cgaagtgaga    600
taccatcttc gagctgtgtg tgggagcgac tcggacagct tcacacttga cgaaaaaatt    660
```

```
gcttttattc atgaaacccg ccatggtttt ggtcgcactg cacttcttct gagtggtgga   720
gcagctcttg gagcgtttca tcttggggtt gttcgaaccc ttgtcgagca tcgtttactt   780
ccccgagtga ttgccggtgc cagtgtggga tctgtcatat gctcatttgc tgcaactcga   840
acttggacag agctccagag cttttcgaa  gacaccatgc cccccatgca cttttcgaa    900
aacatgggga gcattttgc  tattgcgcac aggcttctga ctcgaggtgc tgtgcatgaa    960
attggtatgc tgcaaaggaa aatgagacag ctcattgggg atttgacctt tcaggaagct  1020
tacgatctat ctggccgcgt gcttggaatc tctgtatgct cacctcggag actcgagcct  1080
ccgagatgtt taaattattt aacttctccc catgtagtca tttggagcgc agtcactgca  1140
tcctgcgcat tcccaggcct ttttgaagca caggagctga tggcgaagga tcgaactggt  1200
caacttgtac cctatcattc gccacctcag gttggccccg aggacaagga catggaaaag  1260
gggattggga agcggcgatg gcgagacggc agtctggaaa gcgatttgcc aatgatgcag  1320
ttgaaggaac tgtttaatgt gaatcatttc attgtcagcc aggcgaatcc gcatattaca  1380
ccattttga  ggttcaagga ttttgttcgt gcatatggag gagatttcgc tggaaaattg  1440
gcacacttag cggagatgga ggttaagcac cggtgcaaga agatgatgga gatgggcttt  1500
gaggtgtttg gattggctaa gctcttcgca caagattggg aaggagatgt cacgcattgtg 1560
atgccggcca ctttgccca  gtttgccaag atcatcacga acctgacagc cacagatctt  1620
cgcaaggcag tgatgcaagg ccgacgctgc acctgggcga agctatcagc cattcaggcc  1680
aacttggca  tagaattgat gctagacgaa tgtgtctctg aattaaaccg tcgtaggaaa  1740
gccctgcgtg aaatagagcg cagcgcaatg cagagcagcc atggtgggat gcgcgggtta  1800
tcaggaacaa agcgtatccc atcctggaac atcatcgccc gagagaattc ctgcggttcg  1860
ctagatgaag agagtcttca cgaggtgcgg atcccacatg atggtagcga cagcgacgat  1920
aatctggacc aaaatcagct ttcgtggacg agagcaggtg gcccgctcat gcggaccgca  1980
tcagcagcca aattcgtg                                                 1998

SEQ ID NO: 172         moltype = DNA  length = 3439
FEATURE                Location/Qualifiers
source                 1..3439
                       mol_type = other DNA
                       organism = Hordeum vulgare
SEQUENCE: 172
gatcgcagtt agtttggctt gtacgtcgcg ttcccttcc  acccttatct ccttctccgg    60
ctgaccggga cgccgcattt gtcccatcca cggcacggca cggcacgggc acggaggga   120
gaagaagaag cccagctcga ctcctcctcc gcctcctcct ttcctctgat cccctccgtt   180
tgcccattcc ccagatccca gcacgccatg cccgggcgcg caggcgccaa gccgcaccgc   240
gcgcatttct cttccgccct gctccgatcc aaggccgcgg aggtgaccca gtgagctctc   300
ccgccacgcc cgtccgtccg ccggttcatc ggtcgcccat ggacgtcatc accaacgagg   360
cgcgcgtggg ggcgttcgcg atcggcccgt ccacggcggc gggccggggcg ctcgcgctgc  420
gcgtgctcct ctgcggctcc ctggcgcggc tgcggcaccg cctcgccgcc gcgctgcgcg   480
ccgcggccg  cctggcggcg gcctggctgc acccgcgcca caacacgcgg gggatcctgc   540
tggccgtctg cgccgtcgcg ctcctgctgc gcggccgcgg gggccgcgcc ggggtgcgcg   600
cgcgcgtgca gtccgcctac cgccgcaagt ctggcgcaa  catgatgcgc gccgcgctca   660
cctacgagga gtgggcgcac gccgcgcgga tgctcgagcg agacgccg   cgccgcgcca   720
ccgacgccga cctctacgac gaggagctcg tgcgcaacaa gctccgcgag ctcaggcacc   780
gtcgccagga gggctcgctc agggacatcg tcttctgcat gcgcgccgac ctgctcagga   840
accttggtaa catgtgcaac cccgagctcc acaagttgag gctgcaggtg cctaaactca   900
tcaaggaata cattgaggag gtatctactc aactgaaaat ggtttgcaat tctgattcag   960
acgagttacc tctcgaggag aaactggcat ttatgcatga gacaaggcat gcctttggta  1020
gatctgcctt actgctaagt ggaggagctt catttgggtc tttccatgta ggtgttgtga  1080
aaaccttggt agagcataag cttctaccta ggattatttc aggatcaagc gttggcgcaa  1140
taatgtgtgc tattgtcgcc acaaggtcat ggccagaact ggagagtttt tttgaggagt  1200
ggcattcctt gaaattcttt gaccaaatgg gtgggatctt tcctgtattt aaaagaattt  1260
tgacgcatgg ggctgttcat gacattaggc acttgcagac gcaattgaga atcttacaa   1320
gcaacttaac atttcaagag gcatatgaca tgactggccg ggttctcgtt gttaccgtgt  1380
gttctccaag aaaacatgag ccacctcgat gcctgaacta tttgacgtca cctcacgttc  1440
tcatctggag tgcggtaact gcttcctgtg cttttcccgtg acttttttgag gcccaggagt  1500
tgatggccaa agatagattc ggagaaacag ttcctttca  tgctccattc ttgtttgggcg  1560
tggaggaacg agctgatgct gctacacggc gatggagaga tgggagctta gaaagtgatt  1620
tgcccatgaa gcagttgaag gaattattca acgtaaatca cttcatagta agccaagcca  1680
atcctcacat tgctccatta ctgagactaa caggagctat cagggcttat ggggcagct   1740
ttgctgcaaa gcttgctgaa cttgctgaga tggaagttaa gcataggttc aatcaagttc  1800
tggaacttgg atttccatta ggaggaatag ctaagttatt tgctcaacat tgggaaggtg  1860
atgtgacaat tgttatgcca gccactcttg ctcagtattc gaagatcata cagaatcctt  1920
cgtattctga gcttcagaaa gcagcaagtc agggtaggcg atgcacttgg gaaaagctct  1980
ctgccatcag ggcaaactgc gctattgagc ttgcattaga tgaatgtgtt gcccttctga  2040
accacatgcg taggctgaag agaagtgcag aaagagcagc cgcttcacaa ggatatggtg  2100
ctacaattag actctgtcca tctagaagga ttccgtcatg aatctcata  gcaagagaaa  2160
attcaactgg ttctctcgat gaggagatgc tcacatctcc cactgttaca agccatcaag  2220
cagttggagg gactgctggg ccatctaaca gaaatcacca tctccaacat agtatacatg  2280
atagcagtga cagtgaatct gagagtatga acttgaactc atggacgaga agtggtggcc  2340
ctctcatgag gacagcctcg gctaataaat tcatcagctt tgttcagaac cttgagattg  2400
acccagagtt cagaacaatt tcaccaaagg ggagtgaagg tgatattttg acaccgaata  2460
gtaacttgtt tgctggtcac ccaattggta gagagccagt tgataatcat ccaaggcctg  2520
ttactcctgg taggacctca ggcaatacag gttccgatcc tcatgatact cctgttccta  2580
ggtctccatt tggtctttcc gcgagtatca tggtccctga ggtgacttg ctgcagcctg  2640
aaaagattga gaatggtatt ttattcaatg ttgtccgaag ggatactctc ctagcgtcta  2700
ctagcggagt tgaacctcat ggatcttcac atgaggcaga tgtggaaact gtaccgaccg  2760
agtgccttta tggtgcttcg gatgacgacg acaacgtgga actgaatgcc aatgatgaag  2820
cgctatctga tcgtggagat cagagatctt cagttgcagg aaatctagat tcgtccgctt  2880
ccatggaactg tcaagctgaa gcaagtacta ctcgatcaga agctccatct ctcttttgata 2940
```

```
tctgtgtgga gattcctcca gcaaccatga ccacagaaaa tagtcggcct gacgagcctt 3000
cttcagacat aagactggag actgtaaaga cagaatgccc tgatgagaat tctgctgctg 3060
ggaatgctga agttgactca gttcctgcca gtaaagaatc ttcctattgg tctcagacat 3120
cagaaattgg acagcagcat caagtggata tgggatctgt gaactcctgt actgtttcat 3180
tttcagaaga tgatagacat gtgagcctta tttcgaacga gaaaccgtc actacttcca 3240
gtggcggagc tgagagtatg acatctggaa gaagtgaagc tgactagcat agaacttgcc 3300
tgttgaccga cctaatgttt ttctgtgttg ggacttggta gtttgaacaa ttcagcttga 3360
tctgatccat gctatgtgtg caatttaaac tcgtgtcacg atcaaactga attgtgtcta 3420
tatgtaggtg ttgtaatcc                                              3439

SEQ ID NO: 173         moltype = DNA   length = 3470
FEATURE                Location/Qualifiers
source                 1..3470
                       mol_type = other DNA
                       organism = Nicotiana benthamiana
SEQUENCE: 173
gttatctgat ccaaacttct gacttttct atttccgaa tccctatgtt ttttaataaa   60
tccatctctg ccattgcagt gatatattca tttattgtta tcacctttctt catttattgg 120
tccctctgtg ttttccatat attgaaggag aaaacattaa cttatgcga ttttgtagtt 180
tttctggttg attcctacaa cccctttga cattgatctt gtgggttaca aaaacattg    240
aatctttatg tcaaaatttg atctttgtat ttcatttta attgaaattt gatttttggg  300
ggtattaagg attctttttgt cggttgattt tgtgcctttt ttgccaagtt ctgtcggtc  360
tctgagctga atttccataa tttgacaaaa agaaaaggct aaagcagaaa ggttgggagt 420
ttctttcttt gactttcaga aactaaggta ttttctttga tctaattctt gttaatatct  480
ggttcaatct gattccgttg aatcttgtga atagcctttg tttccctatt gtcagaaaat  540
tatttccttt tcactttcct cgactctcag aagttagtac aatctttgtt ctgctaaatc  600
ttgtgaataa cctttagctt agagttttag gtatctgtat attgggttct cttaacatttt 660
agcctagaag ccttctctag gattagtccc ccttttcatt gagatggata taagtaatga  720
ggctacaatt gacttctttt ccattggacc tactacgata ttgggtcgaa caatcgcctt  780
tagagtgttg ttctgtaaat caatttcaca attgaagcat caccctatttc atttcttatt 840
atattacttg tacaaattca agaatggttt gtcatactac ttgacacccct tgatctcgtg  900
gttgcacccct cgtaatccac aaggaatatt ggcattggta acgcttctcg ccttcttgtt 960
gaggcgatac acgaatgtaa aaatcaaggc tgagatggcc tataggagga agttttggag 1020
gaatatgatg agatctgcat tgacttatga ggagtgggct catgctgcca agatgctaga 1080
taaagagacc cctaaaatga atgaggcaga tctttatgat gtagaattag ttcgaaataa 1140
actccaagag cttcgacatc gtaggcaaga gggttctatg agggatatca tattctgtat 1200
gagagctgac cttgttagga atcttggtaa tatgtgtaat ccagaacttc acaagggaag 1260
gcttcatgtg cctagactga ttaaggatta tattgatgag gtttcaactc agttgagaat 1320
ggtatgcgac tctgattcgg aggagtctct cttggaagag aagcttgctt tcatgcatga 1380
aacaagacat gcctttggta ggacagcttt gcttttaagt ggaggtgctt ctttaggagc 1440
tttccatgtg ggcgtggtga aaacacttgt agaacacaaa ctgatgccac ggataattgc 1500
tggttcaagt gtcggctcga ttatgtgctc catagttgca actcgatctt ggcctgagct 1560
ccagagtttt ttcgaggact cctggcactc tttgcaattt ttcgatcagt tgggtgggat 1620
ttttactatt ttcaggaggg tcatgaccca gggtgctgta catgagatca gacagctgca 1680
ggtgctgtta cgtaatctca cgaataatct tactttccaa gaagcctatg acatgactgg 1740
tagagttctg gggattactg tttgctcgcc taggaaacat gaacctccta gatgcttgaa 1800
ctacttgact tcacctcatg ttgttatatg gagtgccgtt accgcttctt gtgcctttcc 1860
tggtctcttc gaagctcaag aacttatggc aaaggataga agtggagatc ttgttccata 1920
tcacccacca tttcatttgg gtcctgatgc cacttctagt gcatctgctc gtcgttggag 1980
ggatggtagc ttggaggttg atttgccaat gatgcagcta aaggagctct tcaatgtcaa 2040
tcactttatt gtgagccagg cgaatccgca tattgctcca ctgctgagga tcaaagagtt 2100
tgtaagagct tatggaggca acttttgctgc caagcttgct caacttacgg aaatggaggt 2160
gaagcacaga tgcaatcagg tattagaact tggttttccc ttgggaggat tagcaaagct 2220
ttttgctcaa gaatgggagg gtgatgtaac tgttgtaatg cctgccactc tagctcagta 2280
ctcaaaaatc atacagaatc cctcgactct ggagctgcaa aaagcagcaa atcaaggaag 2340
aaggtgcact tgggaaaaac tctcagccat gaaagcaaac tgtggaattg agcttgcact 2400
tgatgaatgc gttgctatac tgaatcacat gcgtagactg aaaaggagtg ctgagagggc 2460
ggctgctgct tcacatggct tggcaagcac tgtcagattt aacacttcca gaagaattcc 2520
ttcttggaac tgcattgcac gagagaactc aacaggctcc cttgaagatt ttcttgcgga 2580
tgttgctgct tcacatcatc aaggaggcag tggttcgggg gcgcatgtta accgtagttg 2640
gcgaacgcac cggaatgcac atgatggtag tgacagtgag ccggaaaatg tggaccttaa 2700
ttcttggaca agatcgggtg gtcctttgat gaggacaaca tcagctgata gtttattga   2760
ctttgtccag aacttggaaa ttggttcgcg attgaacaaa ggattgacta ttgacctcaa 2820
caatattatt cctcagatgg caagcaggga ccatttctcc ccgagcccaa ggtgaacaac 2880
acctgataga agttcagata cagaatttga tcaaagagat tttagttaca gggtccctgc 2940
gagtagttca agcattatgg taggcgaagg tgacttctg cagcctgaaa ggactaacag  3000
cggtattgtc ttcaatgtgg taaggaaagg agacttgacc ccatcgaaca gaagcattga 3060
ttcagaaaat aatagttccg tgcaggatgc agttgctgag tgcgtgcaac ttgaaagtcc 3120
agaaaaggag atggatatta gctcagtatc ggaggatggt gagaatgttg ttgggcaagg 3180
aagtagggta aatgaagttg attgtagtaa aaatcgttca tcaatcggtg atggcaacga 3240
taagcaagtt attgatactt gagagtttag ctttgattat tctacacagg ccattcgaat 3300
tattttttat actcaaatgg agcttctttc agagctaaca cactcagaat tggggttgta 3360
aatagtgcaa gtagcaaatc tgtaataaat gtttagtgta gtcatcaccc ttctactagt 3420
tcaaagtggc tcagttcaat tcaaattcag aacttcgata attcatgttt             3470

SEQ ID NO: 174         moltype = DNA   length = 713
FEATURE                Location/Qualifiers
source                 1..713
                       mol_type = other DNA
```

|  |  |  |  |  | |
|---|---|---|---|---|---|
| | | organism = Nicotiana benthamiana | | | |

SEQUENCE: 174

```
tgtatgagag ctgaccttgt taggaatctt ggtaatatgt gtaatccaga acttcacaag   60
ggaaggcttc atgtgcctag actgattaag gattatattg atgaggtttc aactcagttg  120
agaatggtat gcgactctga ttcggaggag ccttctcttgg aagagaagct tgctttcatg  180
catgaaacaa gacatgcctt tggtaggaca gctttgcttt taagtggagg tgcttcttta  240
ggagctttcc atgtgggcgt ggtgaaaaca cttgtagaac acaaactgat gccacggata  300
attgctggtt caagtgtcgg ctcgattatg tgctccatag ttgcaactcg atcttggcct  360
gagctccaga gtttttcga ggactcctgg cactctttga aattttttcga tcagttgggt  420
gggattttta ctattttcag gagggtcatg acccagggtg ctgtacatga gatcagacag  480
ctgcaggtgc tgttacgtaa tctcacgaat aatcttactt tccaagaagc ctatgacatg  540
actggtagag ttctggggat tactgtttgc tcgcctagga aacatgaacc tcctagatgc  600
ttgaactact tgacttcacc tcatgttgtt atatggagtg ccgttaccgc ttcttgtgcc  660
tttcctggtc tcttcgaagc tcaagaactt atggcaaagg atagaagtgg aga           713
```

| SEQ ID NO: 175 | moltype = DNA   length = 1500 |
|---|---|
| FEATURE | Location/Qualifiers |
| source | 1..1500 |
| | mol_type = other DNA |
| | organism = Arabidopsis thaliana |

SEQUENCE: 175

```
cgaaaaaaga agtagaatat atatatatat atatatatat atatatatat atatatattc   60
gtgtggacat cataaatgcc taaatgataa tagttgattt cgagtttat tttcgttact  120
tccaatcaaa ttctccttgc accatattta ttttttact gtgagaacat atataagtat  180
atattggaat tacgtatccg agaggttttt gcatatttcg tttatttatt ttcgatatcc  240
acactactgt attattaaaa atttgaaaaa ttcaactagg gctttcatc ttctctagaa  300
ttattcgttt atttatgtcg atgtccacac tattattaaa ataaaacgag aggatatggt  360
tggatcatcc aagtttcgtt tatgactctt tgttcattta caaacgttta gttttccact  420
taagttttga aaagagttaa tttccaatat attcggcaca gttttcaag tgtattcatc  480
tgtttttttt tttttttggtt ggctatatgg tccaaatttt gatttgcaat atgagattga  540
acagagagaa caatctttca ttatgattaa ttattgtaca agtaacaaac accaatctcc  600
gatatacttt ggctctttag cacattgtta tgctagaagt tagcggaaat ctatatgttg  660
ttaaacgcag cgtttaaatt gaacagtgta atttaccttg aaattttaag actacatgct  720
gtttagaatt tcagatgaaa acatcttgat gtttagaaaa tccacgtggg aatagcgtaa  780
aatcttatcc aacgaactta ttttggtttt gttgtatttg tgcaagtcgt cacgctaatc  840
gaaaaaagaa aagaaaaaaa gaagccgtca tgatcggcca tttctcggcc gagtctgagt  900
ctgactctgc gtccgtgtca ccattatcag atcgagcctg tcttatctcg ttgcgattcc  960
ctatgcaaaa atcttcttct tttttttatt cccccattta tctctgatct cttctctctt 1020
ctcaagtaaa cctctctgct tcacgtctct tcttttcttg tcgattttcc ccagataatc 1080
aggtaaataa ggctactttc ttatttgatc tggtggtctt tgtcgttgaaa tctctggggtt 1140
ttctctgttg atttcaaagt tctctctttt tttttttgtt tactgggtgc tgtgaaaaat 1200
gatcttgtca aagtctcctc ttttcatcga attgaaactc taattagaaa aaagatcata 1260
acttttatta aaaaaatgag tttgcttttgc ttaattttgc tagattcat atagattcat 1320
tgattagcct atttggggta acaaaaaaaa gctgacacgg tttcagattc caaaaataga 1380
tcatgactct gtttcttctc tgcagaggtt ttaataaaata tatgcttctt ctcatgagtt 1440
ctcgtttttt ttgtcacctt cgcagttgaa aacacaccca aattcatctt cgaatcaata 1500
```

| SEQ ID NO: 176 | moltype = DNA   length = 2871 |
|---|---|
| FEATURE | Location/Qualifiers |
| misc_feature | 1..2871 |
| | note = Nucleotide sequence of the complement of the pSSU-Oleosin gene inthe T-DNA of pJP3502.In order (complementary sequences):Glycine max Lectin terminator 348nt, 3' exon 255nt, UBQ10 intron304nt, 5' exon 213nt, SSU promoter |
| source | 1..2871 |
| | mol_type = other DNA |
| | organism = synthetic construct |

SEQUENCE: 176

```
ggcccctaga atctaattat tctattcaga ctaaattagt ataagtattt ttttaatcaa   60
taaataataa ttaataattt attagtagga gtgattgaat ttataatata ttttttttaa  120
tcatttaaag aatcttatat ctttaaattg acaagagttt taaatgggga gagtgttatc  180
atatcacaag taggattaat gtgttatagt ttcatgcca ttacgataag ttgtgaaaga  240
taacattatt atatataaca atgacaatca ctagcgatac agtagtgaga gtcgtctat   300
tacactttct tccttcgatc tgtcacatgg cggcggcccg cggccgcttc attactcgag  360
ccaggaggat ggatcgatgc tggtctgaga ccctgctacc ggttgctgac tgaactgctc  420
ggcacggtcc ttcatttcac gggccttgct cgccaacttt gtcttggccg actccaactg  480
atccgctccg ggtggatgtt tccccgtcag gtaacggtag atccaggaca gcacagacag  540
agcggcaaca ccaaatcccc cgcttgccag aaaacccgct cccaacagga agatggtagt  600
gactgcagat cagaaaaact cagattaatc gacaaattcg atcgcacaaa ctagaaacta  660
acaccagatc tagatagaaa tcacaaatcg aagagtaatt attcgacaaa actcaaatta  720
tttgaacaaa tcgatgata tctatgaaac cctaatcgag aattaagatg atatctaacg  780
atcaaaccca gaaaatcgtc ttcgatctaa gattaacaga atctaaacca aagaacatat  840
acgaaattgg gatcgaacga aaacaaaatc gaagattttg agagaataag gaacacagaa  900
atttacctgc agggaccagt acaggcgaga agatcaccag gagaggtgtg gcgattgtca  960
gcgcaatgac cgtccagcc agggtcaacc cggataacac caacaggcta cctccggcag 1020
taaccgcggt cgctgccttt acaacacgct gagcacgcgg ttgcagttgc aagtggggg  1080
cacgtgtttg ttgctgctgc ccgtagtgct ctgccatggt tttttaac ggagcaagcg  1140
gccgctgttc tcttactc tttgtgtgac tgaggtttgg tctagtgctt tggtcatcta 1200
```

```
tatataatga taacaacaat gagaacaagc tttggagtga tcggagggtc taggatacat 1260
gagattcaag tggactagga tctacaccgt tggattttga gtgtggatat gtgtgaggtt 1320
aattttactt ggtaacggcc acaaaggcct aaggagaggt gttgagaccc ttatcggctt 1380
gaaccgctgg aataatgcca cgtggaagat aattccatga atcttatcgt tatctatgag 1440
tgaaattgtg tgatggtgga gtggtgcttg ctcattttac ttgcctgctg gacttggcci 1500
tttccttatg gggaatttat attttactta ctatagagct ttcataccct ttttttacct 1560
tggatttagt taatatataa tggtatgatt catgaataaa aatgggaaat ttttgaattt 1620
gtactgctaa atgcataaga ttaggtgaaa ctgtggaata tatattttt tcatttaaaa 1680
gcaaaatttg cctttactaa gaattataaa tatagaaaat tatataacat tcaaataaaa 1740
atgaaaataa gaactttcaa aaaacagaac tatgtttaat gtgtaaagat tagtcgcaca 1800
tcaagtcatc tgttacaata tgttacaaca agtcataagc ccaacaaagt tagcacgtct 1860
aaatataaact aagagtccac gaaaatatta caaatcataa gcccaacaaa gttattgatc 1920
aaaaaaaaaa aacgcccaac aaagctaaac aaagtcaaaa aaaacttct caagtctcca 1980
tcttccttta tgaacattga aaactataca caaaacaagt cagataaatc tcttttctggg 2040
cctgtcttcc caacctccta catcacttcc ctatcggatt gaatgtttta cttgtacctt 2100
ttccgttgca atgatattga tagtatgttt gtgaaaacta ataggttaa caatcgaagt 2160
catggaatat ggatttggtc caagattttc cgagagcttt ctagtagaaa gcccatcacc 2220
agaaatttac tagtaaaata aatcaccaat taggtttctt attatgtgcc aaattcaata 2280
taattataga ggatatttca aatgaaaacg tatgaatgtt attagtaaat ggtcaggtaa 2340
gacattaaaa aaatcctacg tcagatattc aactttaaaa attcgatcag tgtggaattg 2400
tacaaaaatt tgggatctac tatatatata taatgctttc caacacttgg attttttttt 2460
ggaggctgga attttaatc tacatatttg ttttggccat gcaccaactc attgtttagt 2520
gtaatacttt gattttgtca aatatatgtg ttcgtgtata tttgtataag aatttctttg 2580
accatataca cacacacata tatatatata tatatatatt atatatcatg cacttttaat 2640
tgaaaaaata atatatatat atatagtgca ttttttctaa caaccatata tgttgcgatt 2700
gatctgcaaa aatactgcta gagtaatgaa aaatataatc tattgctgaa attatctcag 2760
atgttaagat tttcttaaag taaattcttt caaattttag ctaaaagtct tgtaataact 2820
aaagaataat acacaatctc gaccacgaaa aaaaacaca taataaattt g           2871

SEQ ID NO: 177       moltype = DNA  length = 1578
FEATURE              Location/Qualifiers
source               1..1578
                     mol_type = other DNA
                     organism = Arabidopsis thaliana
SEQUENCE: 177
gtcacacaca cataaacact ccacacgctc tgcttcgtcc aatcaccaaa cacgctttaa  60
tgactctcac gttttcctcc tccgccgcaa ccgttgccgt tgctgctgca accgtaacct 120
cctccgctag gggtccggtt tatccactcg cttcgtcgac tcttcgtgga ttagtatcti 180
tcagattaac cgcgaagaag ctgttctgc cgcctcttcg ttctcgcggc ggcgttagtg 240
tgagagccat gtctgagctt gttcaggata agaatcgtcc cgtcgcggcg agcattgctt 300
tcaatgaagc cgccggtgag acgccgagtg agcttagtca tttcccgtact ttcttggatg 360
cgcgaagtga acaagatctt ttatctggta tcaagaagga agctgaagct ggaaggttgc 420
cagcaaatgt tgcagcagga atggaagaat tgtattgaa ctacaaaaat gcagttttaa 480
gtagtggagc ttccagggca gatgaaactg ttgtatcaaa catgtctgtt gcttttgatc 540
gcatgcttct tggtgtggag gatccttata cttttaatcc atatcataaa gcagtcagag 600
aaccattga ctactacatg tttgtccata catacatccg tcctcttatt gatttcaaaa 660
attcgtacgt tggaaatgct tctatattct ctgagctgga agacaagatt cgacagggac 720
acaatatcgt gttgatatca aaccatcaaa gtgaagctga tccggctgtc atttctctat 780
tgcttgaagc acaatctcct ttcataggag agaacattaa atgtgtggct ggtgatcgag 840
tcatcactga tcctctttgt aagccgttca gtatgggaag gaacctcata tgtgtttact 900
cgaaaaagca catgaatgat gatcctgagc ttgttgaaat gaaaagaaaa gcaaacaac 960
gaagcttaaa ggagatggct acaatgctaa ggtctggcgg tcaacttata tggattgcac 1020
caagcggtgg aagggaccgc ccgaatcctt ctactgggga atggtttcct gcacccttg  1080
atgcttcttc ggtagacaac atgagaagac tggttgaaca ttctggcgct cctggacata 1140
tatatccaat gtcttttgctt tgctatgaca tcatgccccc tccacccag gttgagaaag 1200
aaatcggaga gaaagattta gttgggtttc acggtactgg actatcaatt gctcctgaaa 1260
tcaacttctc agacgtcaca gcagactgcg agagccctaa tgaggcgaaa gaagcataca 1320
gccaagcttt gtacaagtcg gtgaatgaac aatacgagat cttaaactct gcgattaaac 1380
acagaagagg agtagaagca tcaacttcaa gggtctcttt gtcacaacct tggaattagt 1440
ctctcgtttt agggtaacac tttcaaaact cataaatctt ctgtctcaga agttttgttg 1500
caactgtata tatattgaga gagagcat tgttcttca tttgcaggat acacaaacac 1560
aatcaatgga aaatactc                                              1578

SEQ ID NO: 178       moltype = AA   length = 459
FEATURE              Location/Qualifiers
source               1..459
                     mol_type = protein
                     organism = Arabidopsis thaliana
SEQUENCE: 178
MTLTFSSSAA TVAVAAATVT SSARVPVYPL ASSTLRGLVS FRLTAKKLFL PPLRSRGGVS  60
VRAMSELVQD KESSVAASIA FNEAAGETPS ELSHSRTFLD ARSEQDLLSG IKKEAEAGRL 120
PANVAAGMEE LYWNYKNAVL SSGASRADET VVSNMSVAFD RMLLGVEDPY TFNPYHKAVR 180
EPFDYYMFVH TYIRPLIDFK NSYVGNASIF SELEDKIRQG HNIVLISNHQ SEADPAVISL 240
LLEAQSPFIG ENIKCVAGDR VITDPLCKPF SMGRNLICVY SKKHMNDDPE LVDMKRKANT 300
RSLKEMATML RSGGQLIWIA PSGGRDRPNP STGEWFPAPF DASSVDNMRR LVEHSGAPGH 360
IYPMSLLCYD IMPPPQVEK EIGEKRLVGF HGTGLSIAPE INFSDVTADC ESPNEAKEAY 420
SQALYKSVNE QYEILNSAIK HRRGVEASTS RVSLSQPWN                       459

SEQ ID NO: 179       moltype = DNA  length = 2455
```

| FEATURE | Location/Qualifiers |
|---|---|
| misc_feature | 1..2455 |
| | note = Populus trichocarpa |
| source | 1..2455 |
| | mol_type = other DNA |
| | organism = synthetic construct |

SEQUENCE: 179

```
agtgcgggtg attgggtgag gagtgaagac gctgatttta gaggttttga gagagtggca    60
gtctgcagag aataggaatc cgaccatatc ctccaaaacc cgcgctggac tcagtcaccg   120
ccaatcatca atcagccacc catcaacacc aaaaatcccc gtccttttga tttccaccac   180
ataaaaatag cacactgctc ctccttcact ccattcctat cttaataata ataataataa   240
taaagctcaa ctcttctctt ctaagtcaag acatgatcct ttccattcct gctccttcgt   300
cggcattctt cacaactact aaaccgtctc caccttttcc tagggtttct aaactctgct   360
tcttaacccc ctcatattct ctttcccttc gttttagatc cactgctcga cgctccactt   420
cttttccttg tgtcctctct tctctcaacc ttcacgcaat ggctgaactc gttcaggata   480
aagaagtctt cgcttctgct gaagttgatt acagcaagaa gaaaaacagg actcgttctc   540
gctcgttttct tgatgcaaca actgaacaag agttactgtc gggaatcagg aaggaatcag   600
aagcaggaaa acttccttca aatgtgctg caggaatgaa agatctgtat cagaactaca   660
aaaccgcagt tttgcaaagt ggaattccca acgcacatga gattgtattg gaaaatatgg   720
ctgctgcatt ggatcttata ttctttgatg ttgaggaccc gtttatcttc tcaccttatc   780
acaaagcttt gagaaagcca tatgactact ttgaatttgg tcaaaagtat atccgtccat   840
tgattgattt tagaaattca tatgtaggca atgtttccat tttcaatgaa attcaagaga   900
agcttcggca gggtcacaat attgtcttga tatcaaacca ccaaactgaa gcagatccag   960
ctgtcattgc actgttgctt gaaacatcaa gccctcacat tgctgaaaac ttgatctatg  1020
ttgctgggga tagagttgtc acagatcctc tttgcaagcc attcagcatg gaaggaatc   1080
ttatatgtgt atactcaaaa aagcacatga atgatgaatc tgaacattca gaggagaaga  1140
gaaaagcaaa tatccgaagt ttgaaagaga tggctttgct tttaaggggg ggctcacaaa  1200
tagtctggat tgcaccaagt ggtggcaggg accgtccaga tcccttgtca ggagagtggt  1260
atccggcaca ctttgatgct tcttcagtag acaacatgag aaggcttgct gaacattctg  1320
gagctccagg acatgtttat cctctggcac tattatgcca tgacatcatg ccccctccgc  1380
ctcaggtgga aaaggaaatt ggagagagaa gagttatttc atttcatgga gttggattat  1440
cagttgcacc agaaatcagc ttctctgaag ttacagcggc atatgaaaat cctgaagagg  1500
ctaaggaggt atatacagag gctctgtata agtctgtgac tgagcaatac aatgtgctta  1560
aatctgctgt acatggaaaa caagggctag gggcgtccat tccaactgtt tctttgtcta  1620
agccatgaa ttagtcaacc ttttctatac ttgattaggc caatagtttt gttatatagt  1680
tctgcaactc ctggaccaca attctagcgg tccttctagt caagtatgtg ccaggagaag  1740
cttctctctc catgatgata tggatggctt tttctggaga tgcaatctaa gctacaagtt  1800
tttgctgtgc ttacattcta tcaaagccaa atctcacaca atatcttgaa gccaaattca  1860
tctgaaacgc gagctgttcc agaggttcaa tttcaggtgt gcagataaca gttcctagta  1920
aacacaagag ctagtcgtct gaggcgatat acatgtatat tttctcaatt ttttggtggc  1980
cgatcatatt cttttttacac caattgctca attgctactc attttctcc ctcgttcacc   2040
ttcaataact agaagttttc atgctataac acttgcacac agaagtacta tgaacagagt  2100
tggagcacat tttgcctctt gactaaacaa gacttgtttt tagctgccac accaaacttt  2160
ttatatgatg caattatggt agtcgttttc tcttgttttg gtcaaaaccc aaaccagcta  2220
tagttgctac agccaatcga gagtggtgca tgtttgtttg tttttttttt ttttttttgtc  2280
ctcagttata gtaaccatgt tcaactgaac tatgcatctc ttaggacacc acctcttaag  2340
ccccgtgatc taaccgtgtt ttcgaatttt tttttttttt ttgggctttt ggtttattta  2400
aacgcagcag ctttgaccca agttaaaaca aaaaaatcta ttaaaaaaat tgtag         2455
```

| SEQ ID NO: 180 | moltype = DNA length = 1389 |
|---|---|
| FEATURE | Location/Qualifiers |
| misc_feature | 1..1389 |
| | note = Jatropha curcas |
| source | 1..1389 |
| | mol_type = other DNA |
| | organism = synthetic construct |

SEQUENCE: 180

```
atgacacttt ctgcttttcc ttccacattc ctctttagaa tacaatcgcc atcaacgcct    60
agggtttcca tttccctccc ttccttatct tcaaagctct gtttggttcc tccctctttt   120
tctcctcctt cgcttgctct taaatcgagt gcgcgaagga ccattgtcc ttgcttgctc   180
tcttctctca acgccaacgt ggctcacctt ctcaaggagg aaaagaagt tgtggcttcg   240
gcttccggct gcgagaagga ggaggaaaag aagatggaac agcctagtca ctcccgcact   300
ttcctgcatg ccagaacgga acaagatttg ctgtctggaa ttagaaaaga agcagaagca   360
gggaggttgc cttcaaatgt tgcagcaggg atggaaaat tgtatcagaa ttataagaat   420
gcagtgatac aaagtggaac ccccaatgca gaagagatca tactgtcaaa tatgccgtt   480
gcttggatc gtaaagcctt ggatgttgag gacccttttg tcttctcaca ttatcacaga   540
gcattgagag agccgtttga ctactataac ttcgtcaaa attatattcg tccttttgtt   600
gattttagaa attcttatgt tggcaatatt tccttttcc atgaagtgga agagaagctt   660
cagcagggtc ataatattgt cttgatgtca aatcaccaaa ctgaagcaga cccgctattca   720
attgcattgc tgcttgagaa aacaaagccc tatattgctg agaatttgat ctatatagca   780
ggtggtagag tcataacaga tcctctttgc aagccattca gcatgggaag gaatcttata   840
tgcgtgtact caaaaaaaca catgaatgat gttcctgagc ttactgagat gaagaaaaga   900
gcaaacatac ggagtttgaa ggagatggcc attccattaa ggggtgggtc acgaatagtg   960
tggattgccc caagtggtgg taggaccgc ccagatcatc tgagtggaga atggtatcca  1020
gcacctttg atgcttcttc agtggataac atgagaaggc ttgctgaaca ttctggtgct  1080
cctgggcata tttatccatt ggcattatta tgccatgaca taatgccccc tcccttcag  1140
gtgcaaaagg aaattggaga gaacgagtg atctcctttc atggggttgg attatcaatt  1200
gcaccggaa tcagcttctc tgaaattcg ggtagttgtg aaaatcctga gaggcaaag  1260
aacatttatt cacaacttct gtatgattca gtgactcgc aatacaacgt gcttaaatct  1320
```

```
gccataaatg gcaaacgagg gctagaggct tcaattccaa ctgtctcttt gtcacaacca  1380
tggaattaa                                                          1389
```

| SEQ ID NO: 181 | moltype = DNA  length = 1368 |
|---|---|
| FEATURE | Location/Qualifiers |
| source | 1..1368 |
| | mol_type = other DNA |
| | organism = Ricinus communis |

SEQUENCE: 181

```
atgattcttt ccattctttc ccctacacta ccatcgccta gggtttgtat ttccatttct   60
tctgtatctt caaagctctc tctagtccct gtccttcttt tttctcttcc tcctcctttg  120
gccatagtaa gatggtcatc aaggtcctcc atttgtcctt gtttcttctc ttcttctctc  180
aacgccaatc cagtccccga actcctcaac gatgataaga agaagaacaa caacaacaac  240
aagagcaaga agggaaagtg tactcctcac tcccgcactt ttcttgatgc aagaactgaa  300
caagagttgc tgtatggaat taggaaggaa gcagatgcag ggaggttgcc tttaaacatt  360
gcagcaggga tggaagaagt ttatcggaat tatagaaatg cagttttgca aagtggaatt  420
ccaaatgcaa aagaaatcat actgtcaaat atggctgttg cgttagatcg tatgtgcttg  480
gatgttgagg acccttttgt cttctcacct tatcataaag cactaagaga accattcgat  540
tactataatt ttggtcaaaa ttatatccgt cctctgattg attttaggaa ttcatatgtt  600
ggcaacattt cgcttttcca tgaagttgag cagaagcttc agcagggtca caatattatt  660
ttgatgtcaa accaccagac tgaagcagat ccagctgtca ttgcattgtt gcttgaaaaa  720
acaaatccct acattgctga gaatttgatc tacgttcgag tgatagagt tgtaacagat  780
actctatgca agccattcag catgggaagg aatcttatat gtgtgtactc gaaaaaaac  840
atggctgatg ttcctgagct tactgagatg aagaaaaaag caaacattcg cagttttaag  900
gagatggtca tgatttaag ggatgggtct caaattgttt ggattgctcc aagtggtggc  960
agggaccgcc cagattcttt gactggagaa tggtgtccga cacccttga tgcttcttca 1020
gtggataaca tgagaaggat tactgaacat tctggcgctc caggacatat ttttccatta 1080
gcgttgttat gccacgatat catgcccct ccacctgagg tacaaaagga aattggagaa 1140
agaagaatga tctcctttca tggagctgga ttatctattg caccgaaat cagcttctct 1200
gaaattgctg ttgcttgcga agatcatgaa gaggctagaa acgcatatgc acaggttta 1260
tatgattctg tgactgagca atacaatgtg cttaaatctg ccatacatgg aaaacaagga 1320
ctagaggcat caacttctac cgtctcattg tcgcaaccat gggattag              1368
```

| SEQ ID NO: 182 | moltype = DNA  length = 1344 |
|---|---|
| FEATURE | Location/Qualifiers |
| source | 1..1344 |
| | mol_type = other DNA |
| | organism = Helianthus annuus |

SEQUENCE: 182

```
atgtcgattc tcccgtcttc ttctcctact ctcttcttct ccaccgcaaa ccctagggtt   60
tctgtttctc tttcacttac ttctacagtt tctacatctt catccgtgcg cagtcgctcg  120
attttccggc attttccgta cctagcgttt tctagggcag cgaatgccgc cgcggagacg  180
tttgaaggca agaagtggtc gtcgtcctcc gctacacaac cgatctccgg atccgagctc  240
ggttactcgc atacattcat cgatgctctg tctgaacaag atcttctttc tgtaattcaa  300
agagaggtag aagctggagc actgccaaaa catatcgctc actcaatgga ggaactctat  360
cagaactaca aaaatgcggt tttccaaagt ggtaatccct gtgcagaaga tactgtattg  420
tcaaacatgc gtgtagcatt tgatcgaatg ttcttggatg tgaaggagcc tttcgaattt  480
tcaccgtatc atgaagctat tcgagagcct tttaattact atatgtttgg tcaaaattat  540
attcgtcctc tgatcaattt cagggaatca tatgttggca acgtctctct tttcagtgaa  600
atggaagaac aactgaagca gggtgaaaat gtaatttga tctcaaacca ccaatccgaa  660
gcagatccag ctgtcattgc cttgttgctt gaaacaacaa atccttatat ttccgagaac  720
ataatctatg tggcagggga cagagttata acggatcctc tttgtaagcc tttcagcatg  780
ggaaggaact tgctgtgcgt atattcaaaa aaacatatga acgatgttcc tgagcttgct  840
gatatgaaaa ggagagcaaa tacaagaagt ttaaaagaga tggcttgct tttgaggggt  900
ggatcaaaaa taatggat tgcaccaagt ggtggaaggg acaggcctga tcccgtcaca  960
aatcaatggt ttccagcacc attcgatgcc agttctctgg acaacatgag aaggcttgtg 1020
gaccatgctg gtgtggtggg tcatatatat cctttagcca tactatgcca tgacatcatg 1080
ccccctcctc tcaggttga aaagaaatt ggagagaaaa ggttgatatc ttttcatggc 1140
actgaatat cagttgcacc tgaagttgat ttccaaaacg ccatgcttc ttgtggatcc 1200
cccgaggagg ccaaggcagt ttattcacag gcactttag attcagtgtg cgagcaatac 1260
aacgtgctac aatccgccat aaatggagca aaaggcttag aagcatcaac atcaagtgtc 1320
tcattgtcgc aacctgttga ctag                                        1344
```

| SEQ ID NO: 183 | moltype = DNA  length = 1374 |
|---|---|
| FEATURE | Location/Qualifiers |
| source | 1..1374 |
| | mol_type = other DNA |
| | organism = Medicago truncatula |

SEQUENCE: 183

```
atgttacaa caccattttc ttctccttca accgcatttt tctctccacc taaagcctca   60
tattcttctt cttcttcttc ttcttcttct tcttcttcgt tacctcttcg tagttctttc  120
acttttatc atcttcgatt taatgcaaca acttcttctt cttctgtaac aacttctgga  180
acttcttctt cttcatattg ttctcctctt gctttcaatt ctaataataa aaaacctaaa  240
gaaatttctg ctaatatggc ggcttcttct gtttcttctc gcactttcct caatgccaga  300
aatgaacaag atgttctttc tggaattaag aaggaagtag aagccggaac tttgcccccc  360
actattgctg aagggatgga agaattgtac cttaactata aagtgcagt tgttaaaagt  420
ggagatccca aagcagatga gattgtattg tcaaatatga ctgctttatt agatcgcata  480
ttttggatg tgaggagcc tttgtctttt gaagcacacc ataaagcaaa gagagagcct  540
tttgactact acatgtttgg ccaaaattat attcgtccct tagttgattt caacacttct  600
```

```
tacgttggca acatgcccct tttcatacaa atggaagagc aacttaagca gggacacaat  660
attatcttga tgtcaaacca ccaaagtgaa gctgatccag ctattattgc attgctgctt  720
gaaatgcgac ttccacatat tgctgaaaac ttgatttatg tggcaggaga tagagttata  780
accgatcctc tatgcaagcc cttcagtatt ggcaggaatc tgatctgtgt ttattcaaaa  840
aagcacatgc ttgatgatcc agcacttgta gagacgaaaa gaaaagcaaa tacacgaagt  900
ctgaaggaaa tggccacgct tttaaggagt ggatcacaaa taatttggat tgccccaagc  960
ggtggtaggg atcgaccagt tgccaactct ggggaatggg caccggcacc ctttgattct 1020
tcttcagtgg acaatatgcg aaggcttgtc gatcattcag gtccaccagg tcatatctat 1080
cctatggcaa tactgtgcca tgacataatg ccccctcctg ctaaaggttga aaaagaaatt 1140
ggggagaaaa gaattatatc atatcatggg actggcatat cacttgctcc agaaataagc 1200
ttttccgaca tcactgcttc ttgtgaaaat cctgaaaagg ctaaagaagc atactcgaaa 1260
gccttgtatg attctgtgac tagtcaatat gatgtgctgg agtctgccat acacggcaaa 1320
aaaggattag aagcatcaac tcccgcagtt tccttgtcgc agccatggaa gtag         1374

SEQ ID NO: 184          moltype = DNA  length = 1967
FEATURE                 Location/Qualifiers
source                  1..1967
                        mol_type = other DNA
                        organism = Glycine max
SEQUENCE: 184
ggctgagact gaggagcgga tcctatctct ctttcacaca ctctccttct ctttcgtatg   60
aagaatgagc acgaccggtt cttcggctta ccactgtgtg gcacacctcc caaataataa  120
gactatgttt atgctctcta cgccgccaac aaccacattc ttcgctacgc ctagggttct  180
tccgtttctc tcttcaaaac tttcttcttc ttcttcttct tctactgcgt cgtcctcgcc  240
ttgttgctcc tccatcactc ccaaggttaa atccaaagat aacaacaatt gctacctcgt  300
ctccgctaaa cattctcccg ctaacatgtc cgcttccggt tcgtcacgca ccttcctcaa  360
cgctcggaac gaacaagagc ttctagctgg aatcaggaaa gaagtagaag ctggatctct  420
gcctgctaat gttgctgcag gaatggaaga agtgtacaat aactataaaa gtgcagttat  480
ccaaagtgga gatcccaagt caaggagat tgtattgtcg aatatgattg ctttattgga  540
tcgcatattc ttggatgtga cggatccttt tgtctttcaa ccacaccaca aagcaaagag  600
agagcctttt gactactacg tgtttggtca gaattatatc cgtcctttag ttgatttcaa  660
aaattcttat gttggcaaca tgcccctttt cattgaaatg gaagagaaac ttaagcaggg  720
acacaacatc atcttgatgt caaatcacca aactgaagct gatccagcca tcattgcttt  780
gctgctcgaa acacgactcc catatattgc tgaaaacatg acctatgtag caggagatag  840
agttataact gatcctctgt ccaaaccatt cagtattggc aggaatctca tttgtgttta  900
ctctaaaaag cacatgcttg atgatccagc tcttgtagag atgaaaagaa atgcaaatat  960
acgagctctg aaggaaatgg ctatgctttt aaggagtgga tcacaaatag tctggattgc 1020
cccaagtggt ggaagggatc gcccagatcc ccacaccgga gaatgggcac cggcacccttt 1080
tgatacttct tcggtagata atatgagaag acttgttgaa cattctggtc caccgggcca 1140
tgtatatcct ttggcgatat tgtgccatga tataatgccc cctccactaa aggttgagaa 1200
agaaattggg gagaaaagaa ttatatcctt tcatgggact ggcatatcag tggctccagc 1260
attaagcttt tctgaaacta ctgctactag tgaaaatcct gaaaaggcta aggaggtatt 1320
cacaaaagcc ctgtatgatt ctgtgacgga gcaatataat gtgctgaaat ctgcaataca 1380
tggcaaaaaa ggatttgaag catcaactcc agtagtttct ttgtcacagt catggaagta 1440
gatgaaatct gcatttcttc attgcaattt gctctgatgc agaagcaagt tacaagactt 1500
cagtcaaaca atttcaactg attcacttct gagggactgc ctattactac accggtcacc 1560
gaatgattta gcttgttgga agtttgcagt caaatacata tttttcattt cattttttcct 1620
tttgctcttg gttgccgtta tcagcattca attcatctgg aatctgtttc agttcagaag 1680
gttcaaattc tgctgcttac tgtacaggtc tctcttagtt cggtgtcaga tttggttcgt 1740
tgactgataa aatactaaat ttttttaccta caattttgtg atcaggctta gctagctgaa 1800
tagataaaat ataattggtt ccatttgtat tttaagtcaa ctttgttcca ttatagatga 1860
atagatgtta gtattacatg ttcagacggg gtcagtgaat aaaactggtcc aaatgctaat 1920
gcaaaattat tcatattggt aaaataaaag ctctacagtt accgtta              1967

SEQ ID NO: 185          moltype = DNA  length = 1674
FEATURE                 Location/Qualifiers
source                  1..1674
                        mol_type = other DNA
                        organism = Carthamus tinctorius
SEQUENCE: 185
tctctctctc tcacacacaa cacacaaaac acacactact gctactttct ctctctacta   60
cactctcctc tcgctatgtc gatcttcttc tctccttcct ccctactctc ttcttctcc  120
accacaaacg caaatcctag ggtttctcct tcatcttcac cttcttctgc cttcactcct  180
cctctgtctt cttctcgcct ccgcccgatt ctccgggggt ttccgtgcct cgcgttctct  240
gcgccggcga atgccgccca tggcacggcg gagaccgtcc acggcaataa gtggccgtca  300
ccgtcgtcct cctcctctgc tgctacgcaa ccgtccgctg gatccgacca cggtcactct  360
cgtacattca tcgatgctcg ttccgaacaa gatcttcttt ctggaattca agagagttg  420
gaagctggaa cactgccaaa acatattgct caagcaatgg aggagctata tcagaactac  480
aaaaaatgcag ttctccaaag tgcggctcct catgcagaag atattgtgtt gtcaaacatg  540
cgtgtagcgt ttgatcgtat gttcttggat gtgaaggagc cgtttgaatt ttcaccatat  600
catgaagcta tttttggaacc ttttaactac tatatgtttg gtcaaaatta tattcggcct  660
ttggtcaatt tcagggaatc atacgttggc aatgtctccg ttttcggtgt aatggaagag  720
cagcttaagc agggtgacaa ggtggttttg atctcaaacc atcaaacaga agcagatcca  780
gctgttattg ccttgatgct tgaaacaaca aaccccacta tttctgagaa cataatctac  840
gtggcagggg atagagtaat aacagatcct ctttgcaagc ctttcagcat gggaaggaat  900
ctgttgtgcg tgtattcaaa aaagcatatg aatgatgttc ctgagcttgc tgagatgaaa  960
aaagatcaa atacaagaag tttaaaaggg aggatggctt tgcttttgag gggcggatct 1020
aaaataatat ggattgcgcc aagtggtggc agggacaggc cagatcctat cacaaatcag 1080
tggtttccgg caccgtttga tgccacttcg cttgacaaca tgaaaggct cgtggaccat 1140
```

```
gctggtttgg tggtcacat atatccttta gccatattgt gccatgacat catgcccct  1200
cctcttcagg ttgagaaaga aattggagag aagagttgga tctcttttca tggcaccgga  1260
atatcagtgg caccggaaat taatttccaa gaagttactg cctcttgtgg gtccccgag   1320
gaggcgaagg cagcttattc acaggcactc tatgattccg tgtgtgaaca atacaaggtg  1380
ctacattctg cggtacatgg aggaaaaggg ttagaagcat caacaccaag tgtctcgttg  1440
tcacaaccct tgcagtttct cgattagtct cttggtttag aggaggtgaa agcatattct  1500
tttgtttaga tgcataggt gtatagatga taccgaagaa tagatgtaca aacaagtgat   1560
agaaagatgt atgtctaatc aaaaaatgtt ttctgcatct tgtaaaggga tcttcaaaac  1620
agacctttta ttttagctgc agcaaccaat atatcaaaac aggttttctc tttt         1674

SEQ ID NO: 186         moltype = DNA   length = 1893
FEATURE                Location/Qualifiers
source                 1..1893
                       mol_type = other DNA
                       organism = Solanum tuberosum
SEQUENCE: 186
cgcacatatt catttcactc actttctttc ccgaccctt ctctctctaa agctctccag  60
tctgtggtga tgttgatcct ctcagcggct tcgtcttctt cttcctcctt catgctttct  120
tccgcttcgt cttcttctgc acgcattccg aggcagttat cttcattttc aacttgtgtt  180
ccagtagtag taacaactgt ttcttctgca gcaacttcga ctctatttcc gatttcctgc  240
ttcggtgtga aatcgaggac tgttgggatt cggaagctgc ggtgtgccgt ttttgtgct   300
tcgaaggtac gtgaatggc agaaatgatt gaagatgcca tgacggtttc tgcttctgag  360
agccatgagc ttccgcagtc ccgagacttc cttgacgcac gcactggaga agacttgcta  420
tctgctgttc aaaaagctgt ggaagatgaa aaactgccgc ttaatgttgc tgaaggaatg  480
gaggatttgt atcagaacta tcggaatgca gttttacaaa gtggagtccc caaagcagat  540
gaggccactt tgtataacat ggctcttgta tttgatcgtg ttttgtgga tgtgaaggat   600
cctttttgaat tctcgccata tcataaggcc attcgtgaac cttttgacta ttacaagttt  660
ggtcaaaatt atatccgcca gctagttgat ttcaggagtt cttatgttgg gaatatctca  720
gttttcggtg aaatggcaga gaagcttaaa caggtgata tgttgtctt gatgtcaaac    780
catcaaagtg aagccgatcc tgcgattatt gcactcttga ttgaatcaaa gctcccagat  840
attgctgaga acattattta tgttgctgga gatagagtta ttactgatcc tctttgcaag  900
ccattcagca tgggaaggaa tctcctgtgt gtttattcga aaaacatat gaatgatgac   960
cccgaacttg ctgagatgaa aaagagagca acacaagaa gcttgaagga gatggctttg  1020
ctattgaggg gtggatcaaa aataatatgg attgctccta gtgtgtggaag agataggcca  1080
gaccctgtta caaacgaatg gtatccagca ccatttgatg cttccgcgca agacaacatg  1140
aggaggcttg taacatgc tggtgtccct ggtcacattt atcctctagc aattttgtgc    1200
catgatatta tgcccctcc cgcccaggtt gagaaaaata tcggggagaa aagagttgta   1260
tcttttcatg gagctggcat atctgtggca cccaaaattg attttcatga ggttgctggt  1320
gctttggagg accctgaggc taagatggta tatacaaagg cactttatga ctctgtaagc  1380
cagcagtaca atgtgctaaa ttctgctata catggcaaac aaggactgaa ggcatcaata  1440
cctagtgttt cattatcaca accatggcag tagcttctct tccaacttta ttttcatat   1500
cttgttgctg tagtcagttt tgcagatgtt tgtttggcag ttacaatcaa atcacaagga  1560
ttacactcac aatctttcca cataccacg ttgcatgtgg ttagtctatg cagaaagttg   1620
atacaaacaa agtaattctc gaagttacag caaacataac ctgaaggaat ttttttggca  1680
gggttagata attctttga cacgaatgta cagttgcttt acattgtatt tataccaaat   1740
gttagatcca aatttgttag taatgatagc tttcaagtac tcaattctga cttttaagg   1800
tcaagtgtta gtagctatcc tagattgctg ctcatcttgc ctttgaagtg gtaatccaat  1860
ttgttgagaa atataataaa tgatgctctg cta                                1893

SEQ ID NO: 187         moltype = DNA   length = 2016
FEATURE                Location/Qualifiers
source                 1..2016
                       mol_type = other DNA
                       organism = Oryza sativa
SEQUENCE: 187
gggctggaga tggagatgga gatggagatg gagggtgggt ttggcacaaa tcccgaagcg  60
ctccggcgac cactcccaac ccagtcccca ctagggtaac aaccccttt cggattaggt   120
ttctagaagc ttcttctatg caggcgccgc cgctcgcctc ctcgccgtcg ccggcgtgga  180
ccgccatcct gcccgcgccg gcgaggggcc gctgctccg ccgcggcgcc ctccgcctcg  240
aagccaaggc cgcctggagg ccggccgcgc cagggccgcg ggtgccggcc aagggcgccg  300
tcctcgcctc cgaggtggtg ggcccctctc ccctcctcga cgcgcgcaac gagcaagagc  360
tcattttgca tatcagaaag gaagtggaga aggggaagct gcctgcagat gtcgctgcca  420
atctagaaga gctatactac aactacaagg acgcggttat gcagagcagg gatccaaatg  480
cacacgacat cgtgctttca aacatggtgg ccctgttcga ttgttctctg ctcgtgtag   540
agaatccgtt tacctttccg ccttatcaca agctgtcag ggaaccattc gactattaca  600
tgtttggtca gaactacatt aggccccttg tagactatag aaattcatat gttggtaata  660
tatccatttt ccaagacatg gaacagaagc tccaacaggg ccataatgtt gttctgatgt  720
ctaaccatca acagaagca gatccagcaa tcattgcttt gctgcttgaa agaagcaacc  780
catggatcag cgaaaacata gtttatgttg ctggtgatga ggttgttaca gatcctctca  840
gcaagccatt tagtatggga agaaacctca tttgtgtgta ctcaaaaaag catatgaatg  900
attttcctga gctagttgat atgaagagga ggcaaatac tcgtagtctg aaggaaatgg   960
ctttacttttt acgtggcggt tcacagataa tttggatagc accaagtggt ggtagagatc  1020
gtccggatcc tttgacagga gaatggcatc cggcaccatt tgatgcatct gcagtggaca  1080
acatgaggag gcttctggag catttctggtt ttcctggggca catatatcca ctctcactgc  1140
tctgctatga ggttatgcct ccaccacaga aggttgagaa agagattggt gagcaaagggg  1200
ttatatccct tccatggtgta ggcttgtcag taactgaaga gataaagtac agcgacatta  1260
cggttcatac ccaaaatgtc gacgagtgca gagagaaatt ctcagagtca ttgtacaact  1320
cagtcgttga tcagtataat gcgctcaaat ctgctatctt tagaggtcga ggagcagatt  1380
catcggacag tgccatctca ctctcacaac catggcgatg aaactccgct ttctcagttt  1440
```

```
tgttctgtct ggatttctca atgaagttac cttcatttct tttcgacaca gcagatgaac   1500
tgctgccgac attgcaattt ttcctggcag aacctttaa acttcggtat cctaacccat   1560
actaatcatg aagggaggc tgttactgtc atgcaaatct tgcctagtat gatgatttta   1620
cccagctgaa tcccagccac acatgatgcg ttcgttcatt gtttgcacac aaatattatt   1680
gcgtcatatg agtattcttt gggtcagaac tgcacagcaa cgcggcctgg gcactcaatc   1740
tggcatgttg tctatgggt gcatgcttgt taacagaaga agcccaacat gtgggatttt   1800
gtttttgcg gttaattttt ttcctgtttt ccttttgttc catgtatata tattcgattt   1860
tgatctccag gtttggagat acaatggtca aagtgttatg atagtctctt agtttgttgc   1920
ctcgaagtta tactcgggcg caacatgtct gactgatatt ctgatgatgt tactcgtttc   1980
tgaacttcct gacgccaata tggtgcttgg atgttg                            2016

SEQ ID NO: 188           moltype = DNA   length = 1888
FEATURE                  Location/Qualifiers
source                   1..1888
                         mol_type = other DNA
                         organism = Sorghum bicolor
SEQUENCE: 188
atgcacgcgc cgccgctggt cgcgttcgca gggggcgcct gccccgccac gccgcctcg    60
tcctcgccgt cgccctggct ggcctcgccg cgggccgcca tcctcgccgc gccggcgagg   120
ctcctacggt cccgccgcgg ggcacttcgg ctggaagcca aggccgcgtg gagggctgcc   180
ggaggggac ggggcccgag ggtcccggcc aagggcgctg tgctcgcctc ctatatgggc   240
gccgaggagg tggtgggacc ttcgtcgctg ctcgacgagg aagagctcat ttcacatatc   300
agaaaggaac tggataatgg aaaactccct gcagatgttg ccagtaatct ggaggagttg   360
tattataatt acaggaatgc tgttctgcaa aatggagatc ctaatgcata tgagatcatg   420
cttttcaaata tgacgctt gtttgatcgt gttctactgg atgtacagaa tccatttacc   480
tttccacctt atcacaaagc tgtgcgagaa ccgttcgact attacatgtt tggtcagaac   540
tacattaggc ctctggtaga tttcaggaac tcctatgttg gcaacattc acttttcat    600
gacatggaag agaagctgca ccagggccaa atgttgttt tgatgtctaa ccatcagaca   660
gaagcagatc cagcaattat ctccttgctt cttgaaaaaa ccaatccatg gattagtgaa   720
aacatagttt atgttgctgg agataggtt gttatgaatc cactttgcaa gccatttagc   780
atgggaagaa atctcatttg cgtgtactcg aaaaagcata tgaatgattt tcctgagcta   840
gttgagatga gaggagatc aaatacccga agtctcaagg aaatggcctt gcttttacgt   900
ggtggctcac agttaatttg gattgcacca agtggtggta gagaccgccc aaatccttca   960
acaggagaat ggtacccggc gccattcgat tcatctgcca tggacaatat gaggaggctt  1020
ctggagcatg ctggcgttcc tgggcacata tatccactat cattgctgtg ctatgaggtt  1080
atgcctccac cacaacaggt tgagaaagag attggtgagc agaggtgat atccttccat  1140
ggagtaggct tgtcagtaac tgaagaaata aaatatgggg atattactgc tcataccaag  1200
aatgctgatg agggaaggga gctattcaca aatactttgt acaactcagt tgttaatcag  1260
tacgatgtgc tcaaatctgc tatctttaga gatcgtggag cagctgtatc aaacaatgtc  1320
atctcattgt cacaaccatg gagatgaatg ttagctttct cagtttgggt ccagatttat  1380
tactgaagtt accttttcag aagagcaggt gaactgccat tgtgcaattt cactggagaa  1440
actcttgaac tttaatcttt ttgataccac tcgactttat cagtcatggt ggagcctgtc  1500
attgtcatgc agatccttgc taagaagtct gtggacaact gttggttggt caagggtgac  1560
tggtgattct gcacataggg atcctcgtaa ctgttgcatg cggtcgtccg caaattactg  1620
gttgctcagc aacgtgctgg ttgggcactg aggaatccgt caggttgcat ccttttttgcc  1680
ttgacgtcaa tttgtgtagt tgaaggttga agtgataaat tgttttatct tgtcttgtca  1740
tcatgtatat aggctcgagt cttttttggc tccacatttt tttggagata taaaagcagc  1800
aggagttatg acatgccctc agtcggccct ccttgttgaa accctttgga tgtaacctgt  1860
ctatttctta tatatactca ctgaaagt                                     1888

SEQ ID NO: 189           moltype = DNA   length = 2046
FEATURE                  Location/Qualifiers
source                   1..2046
                         mol_type = other DNA
                         organism = Zea mays
SEQUENCE: 189
gaggattcat ctcgtgtcga cgacgccttc gccctctccg agtctccgtc cgtcttccgc    60
gtcctccgca gctggactcg tgcgctattc cccaggacgc tactcccact agggttttcg   120
gattaggttt ctagaaacctt ccaccgccgc ctctccatgc acgcgccgcc gctggtcacg   180
ttcgcagggg gcgcctgccc caccaccgcc tccgcttcgc cgtcgccctg gttggcctcg   240
ccgcgggacg ccatctttgc cgcgccggcc aggcccctac ggtccccgccg cgggacactc   300
cggctggaag ctaaggccgc gtggagggct gccggagggg gacggggccc gcgggtcccg   360
gccaaggggcg ctgtgctcgc ctcctatatg ggcgccgagg aggtggtggg accatcgtcg   420
ctgcttgacg aggaagagtt catttctcac atcagaaagg aactggataa tggaaaactt   480
cctgcagatg ttgccagtaa cctggaggag ctgtattata attacaggaa tgcggttctg   540
caaaatggag atccaaatgc atatgaggtc atgctttcaa atatgatgac cttgtttgat   600
cgtgttctac tggatgtaca gaatccattt aactttccac cttatcataa agctttgcga   660
gaaccgttcg actattacat gtttggtcag aactacatta ggcctctggt agatttcagg   720
aactcctatg ttggcaacat ttcccttttc catgatatcg aagagaatct ccaccagggc   780
cacaatgttg ttttgatgtc taaccatcag tcagaagcag atccagcaat tattgccttg   840
cttcttgaaa aaaccaatcc ttggattagt gaaaacatag tttatgttgc tggcgatagg   900
gttgttaccg atccgctttg caagccattt agcatgggaa gaaatctcat ttgcgtgtac   960
tcgaaaaagc atatgaatga tttccctgag ctaattgaga tgaagaggag atcaaatact  1020
cgaagtctca aggaaatggc attgctttta cagttaatt ggattgaca cacagttaat  1080
ccgagtggtg gtagagaccg cccaaatccc tcatcaggag aatggtaccc ggcaccattc  1140
gattcatctg cagtggacaa tatgaggagg cttctggagc atgctggtgt tcctgggcac  1200
atatatccac tatcattgct gtgctatgag gttatgcctc caccacaaca ggttgagaag  1260
gagattggtg agcagagggt gatatccttc atggagcag gcttgtcagt aactgaagaa  1320
ataaactatg gagacattac tgctcatacc aagaatgctg atgaggaag ggagctattc  1380
```

```
acaaatacct tgtacaactc agttgttaac cagtcacaatg tgctcaaatc tgctatcttt   1440
agagatcgtg gagcagctgt atcaaacaat gtcatctcac tgtcacaacc atggcgatga   1500
atgtccagtt tcgttactga agttacccttt tcaaaagagc aggtgaacta tcattgtgca   1560
attttgctgg gagaaactct tgaacttaaa tcttttttgat atcactagac ttcatcaatc   1620
atggtgggagc ctgttattgt catgcagatg ctcgctaaga agtctgcaac tgttggttgg   1680
tcaaggggtga ttggcgattt tgcacatacg gatccgcagt tactgctgcc tcaggttgct   1740
cagcaatgtg ctgctggttg ggcaccgagg aatccatcag gttgcatcct tttttgcccgg   1800
acgtcgattt gtgcagttga agtggtaaac gttttttttat cttgtttcgt catcatgtat   1860
atacgtaggc ttgagtcatt gttggctcca catttttggg agatataaat gcggtaggag   1920
ttatgagatg tccacagtcg gccctccctt gttgaattcc tttggatgta tcctctctct   1980
ttcgtacatg cactcactga aagtcaatgc aaatatctcg tgtttctagt aaaaaaaaaa   2040
aaaaaa                                                              2046

SEQ ID NO: 190          moltype = DNA   length = 1994
FEATURE                 Location/Qualifiers
source                  1..1994
                        mol_type = other DNA
                        organism = Hordeum vulgare
SEQUENCE: 190
gagaaaccaa gaagcgagaa tcggcaccgt tcccgtcgcc gcctcgtcgc ctccgtcgcc   60
cgtcttcctt ttccgccgat tcgtgcccac caccaccact ctccttccca ctggctaggg   120
ttttcggttt ctagaacctc acgcccgccc gctccatgca agccccgccg ctcgccgcgc   180
tcgccggagg cgcctgggcc tctcaccgac ctgccatact agcggcgccg gcgggcctcc   240
gccgtcccag gcgctgcgcc ctccggctgc ccgtggagg ggcggccgga ggcggccggg   300
ccccgcggct accggtcaag ggcgccgtgc tcgcctccga cacggggggcg gacgaggagg   360
tgcggggcc atcgccctg ctcgacgtgc gcagcgagca agagttcgtt ctacgcgtca   420
ggaaggaagt ggagagaggg aagttgcgtc cagatgttgc tgacaacttt gaaaacctgt   480
actgcaattta caagaatgcg gtgctacaaa atggggatcc aaatgcatat cagatcatgc   540
tttccaacat gatggattta tttgaccgcg ttctgctaga tgcagagaat ccatttacgt   600
ttcagcctta tcacaaggcc atcagagaac cgtttgacta ttacactttc ggtcagaact   660
acattaggcc actggtagat tttaggaact cttatgtcgg taacatttct gtattcagtg   720
atatggagaa gcagctccgg cagggtcata atgttgttct gatgtctaat catcagacag   780
aagcggatcc agcagttatt gccttgtcac ttgaaagaag caatccgtgg attagcgaga   840
acatagttca tgttgctggg gatagggttc ttacagatcc tctttgcaag tccatttagca   900
tgggaagaaa cctcctttgt gtgtactcaa aaaagcatat gaatgatttt cctgagctaa   960
ttgagatgaa gaggagggca aacactcgaa gtctcaagga atggctttg cttttacgtg   1020
ggggttcaca tataatttgg atagctccga gtggcggtag agaccgtcct gacccccttga   1080
ctggagaatg gcacccggcg ccatttgatg catctgcagt ggataatatg aggaggcttc   1140
tggagcattc tggcgttcct gggcacatat atccattatc attgctatgc tatgagatta   1200
tgcctccacc acaacagatt gagaaagaga ttggtgagca aagggtgata tccttccatg   1260
gtgtaggctt gtcagtagct gaagaaataa agtatgggga tgttactgct caatctcaga   1320
atgctgatga ggcaagggg aacttctcag aggctctgta cagttcagtt gttgatcaat   1380
ataatgtcct caagtctgct atctttagag accgtggagc agtttcgtcg aaccctgcca   1440
tctcactctc gcaaccatgg cggtgaaact aagcttctc aggcctggat ttctcatttc   1500
ttttcgacag agcagatgaa ctgctatagt gcaacgttgt ggtttttgc tgggatggcc   1560
ttaaactttg atgtcgtcac agttaggatg aggccctgca gatcctgtaa gttgttgaag   1620
tcgcgggaag gaaaaaccgt gtgatatgct gctacaccgt gttcatgtag tgacaggaag   1680
tctgcggctg ttgtcaggtc taaatcctaa atagcacggc ggaacccagc agcagatgat   1740
gcatgtgttc atctttttgtg aacagctact gctgtatcag atggctatca tctgggccag   1800
attggtccga caaatacaga ttggcccctg gatcctggca gtcgtctgga tcaaaatgct   1860
gatattttctt tttgtgctcg tcttattttt ttgattagtt ttgtgtacat attaattctt   1920
ttgctccaaa atttggagac acatgacatg atatatacag agcagagccc aatatgtgtc   1980
gccttcctgt taac                                                      1994

SEQ ID NO: 191          moltype = DNA   length = 1936
FEATURE                 Location/Qualifiers
source                  1..1936
                        mol_type = other DNA
                        organism = Physcomitrella patens
SEQUENCE: 191
ggacgagcgg agtggagagc tatgcggca gcagctggtt ccgctggcgt ggtatgttgg   60
tctagggcag agaagcagca tgccccggtc agggggggtg gaactagtgt taccagtagt   120
accagtggca gcggccatgc gtcgttgaaa gggagcttcg atcggctcca aggtaaccgc   180
cttctgccgc aagccttgac tatgccgtcg ctgtttcggg cgaaacgcaa tggcagaagg   240
acgccgggga atgccgtgac caatttcggg aaatctgaat tccatcgtga aattagtggg   300
agtacgcggg cgaccacgca ggtggctgaa gccaccacag ctggtcttag ggagaccatt   360
gaggaccgcg ctattatcga cggtcattct cacagttttg aaggaattca atcggaagaa   420
gagttgatgc aggtaattga aaaggaggtg gaatccggtc ggctgccgaa gcgtgctggc   480
gcgggaatgg tagagttgta tcgcaattat cgagatgcta tagtgagcag tggcgtagaa   540
aatgcgatga atattgttgt gaaagtcatg tcaactgtgt tggaccggat tcttctgcag   600
ttcgaggagc cattcacatt tggatcgcac cacaagagaa tggtggagcc gtatgattac   660
tacacatttg gtcagaacta tgtgcgtcct ctcctagatt tcaggaactc ttaccttggg   720
aacttaaaga tctttgacca gatagagaag aacctgaaag aggggcacaa cgtcattttt   780
ctatccaatc accagatga gccagatcct gctgttatgg cgctgtttgct tgagcactct   840
cacccctatt tggcagagaa cttgacctat gtggctggag acagggtgt gctgatcca   900
ttctgcaaac cttttagtat gggcaggaat ctcttgtgcg tgtattcaaa aaagcacatt   960
cacgatgtac cggaccttgc tgaaatgaaa atcaaagcta atgcgaagac tttgagacag   1020
atgacgatcc tgctgaggca gggaggtcaa ttattatggg tagcacccag tggtggacgc   1080
gatcgccctg atcctgagac caacgaatgg gttcctgcac attttgactc gtctgctgtg   1140
```

```
gagaatatga agcgactatc tgacattgtc cgagtacctg ctcatttaca tgccctatca  1200
ttactatgtt ttgagattat gccacctcct gtccaggtac aaaaggagct aggagagcga  1260
agagcagtag gatttagcgg agttggtcta gccgtttccg agcaactaga ttatgattcc  1320
attgcgaagt tagtcgacga ttccaaaaat gcgaaggatg ccttttcgga tgcggcatgg  1380
agcgaagtca atgatatgta taacgtgtta aaagaagcaa tttatggtga ccaaggttgt  1440
gctgttagca cagattcctt gagactggaa cagccctggt ttgatggaag caggcgaact  1500
gattgaaaat aggtcatttg aagttttatg taaaagtatg aagcatcctt attgcttttt  1560
acgctgtcta agtccaagg atgtaagaat tcagcagcgt gtataatggc tacattgtca  1620
tgtgatattc tttctgattc gtgcgacacg atggccatgc ctgctcaatc cttgtcacca  1680
ggcgtctcag taggaaacgg tggtactgat tgctgtctgt ccgacttgat ttagtagctc  1740
ggattctgcg tactgataa cttggtctgg taataggac cgatcctatc ggtgaggagt  1800
ttgtgatata gatcaaatact gcactttgtt acaatcggaa tagatgcatt cattattcat  1860
ccaagccaac acatcctgag ttggagcata agttgaagca ctcctcaact tcattgaaag  1920
gagatttctc actacg                                                  1936

SEQ ID NO: 192           moltype = DNA   length = 2260
FEATURE                  Location/Qualifiers
source                   1..2260
                         mol_type = other DNA
                         organism = Chlamydomonas reinhardtii
SEQUENCE: 192
gaagaatgct gcacgcgact cagcagcgcg cggtcgctgg ccgtcgcccg ttctcgggtg   60
cgcgcgcgtc gaaccgcgtt gttgctcacg cggctgcgac cgtcgccacc agtctgccga  120
ccgttgacgt ccagttccac cagcctaagc tggcgggcgt gaccaacgag cagcagttca  180
aggcggtaat caagggctg gtcgctcagg gcaagttccc tccgcagctg gagcccgctt  240
gggattactt ctatgacaac tacaagaagg ctgtcaccag gtgctgcgtc gctggggccg  300
atgagaagct tgtcacccag gtgcaagcca gcattctgga caatgtcctg aaccaggcgg  360
tgaaccccta caccttcccc tctttccaca cccgccctaat tgagcccta aactactatg  420
acttcggtca gcgctacgtc gcgaccctca tcgacttcca gaactccgtg ctgggtttcc  480
gcgagcgttt cgaccgcgtt caggagctgc tggaccagaa gcaaacgtt gttatcctcg  540
cgaaccacca gacggaggcc gaccccggtg tgtttgccca tatgctggcg aagacgcacc  600
ctaagctggc gacggatgtg atctacgtcg ctggcgaccg cgttgtcacc gatccgatgt  660
gcaagccctt ctccatgggc cgcaacctct ctgcgtgca ctccaagaag cacatggacg  720
acgctccgga gctgaaggcc gcaaagatgg agaccaacgg caagacgcgg gtcgccatgc  780
aacgcaagct gaacgagggc ggcacgctca tgtggatcgc ccccagcggc ggccgcgacc  840
gccccaacgc caacgacgag tgggtgcccg taactttga tcccgccgcc gtggagctga  900
tgcgcaacct ggtgcagcgc gccaagcagc cgggccacct gatgcccatg tccatgttca  960
gctaccccat gatgccgccg cccaagaccg tggacaagtc cattggcgag cgccgcctca 1020
cggccttcac gggcgtgggc atctccctgt gcgaggagcg gcagctggcg gccatcatcg 1080
cggccagcgg ctcggaggag aaggagcaga aggctcggc caaggccgcg cacgacgcgg 1140
tgaaggagtc gtacgcggtg ctgtccaagg ccatccagga tccgccttc cgcgccaccc 1200
gcaaggagtt cacacagcc tggatggcgt aaggaggcgg gagcagcagc ggcagtggcg 1260
gcagcgacag cagtggcgga tcttgggggc acgaggcagc agctagcaca cgcggggccg 1320
gtggcggcag cggacgggag aggtgctggt gcggatgctg gtgccaggag cagtgcgtct 1380
atgcctggcg gcgcgccga ccggtgctga agctgttgtc ggcagcagca gcgggaactt 1440
gcgctggcga tggctgaagg tgatgtggct ggccgtacag caaatgctgc tgtcacgcat 1500
tgtcagcggc ggcgctgggg tccgctggga tgtgaggagt gcgagatcag catagccag 1560
gcgggtgggt tgcggtgccg ctgccgacac gtcgcacagg aaggagcagg aagggtgcgg 1620
ctgagcacca gggtcacttg gggcctgtgt tagcgtgacc gggcctgaaa gggggtattg 1680
tctggggagc agctcgacgc acattcgtgg gattgcttag gaaggagcgt tgggatggct 1740
gtgccgcgcg gtgtgcccag cacgttgact ggctctgacc cgggtcaacc aatgcgttgt 1800
ggccgttgca acgatgcttc taatcagcgt gagatggagt gtacgaatgc aggtatgacg 1860
atgaccatag acgagtgtga gcgtgtgtat ctgtggattg acacggttc attcaatcca 1920
ttcgtaccgg acatatgact atacaagacc gtgtggagtg tgtttgtgcg ctcaagactg 1980
gacgaagtgg gcgctcccga tgtggaggcg ggtgctcgcg ggttgtgtgt cttgccgcaa 2040
cgcaagcagc gtggcgtggt gtggatgatt cttgcattat gactgggtt ttaccggcgg 2100
cccagagcgt gtgtgagca aaagcaaaaa caggaacaag gagccgtgtg cacaattcgc 2160
gcggatggtg gtgctggg atctgacagg agagtgccaa cggcggccgg gtgctagtgc 2220
ttgaacatca tgtgatattg tgattgtaca aatggactgc                       2260

SEQ ID NO: 193           moltype = AA   length = 362
FEATURE                  Location/Qualifiers
source                   1..362
                         mol_type = protein
                         organism = Arabidopsis thaliana
SEQUENCE: 193
MLKLSCNVTD SKLQRSLLFF SHSYRSDPVN FIRRRIVSCS QTKKTGLVPL RAVVSADQGS   60
VVQGLATLAD QLRLGSLTED GLSYKEKFVV RSYEVGSNKT ATVETIANLL QEVGCNHAQS  120
VGFSTDGFAT TTTMRKLHLI WVTARMHIEI YKYPAWGDVV EIETWCQSEG RIGTRRDWIL  180
KDSVTGEVTG RATSKWVMMN QDTRRLQKVS DDVRDEYLVF CPQEPRLAFP EENNRSLKKI  240
PKLEDPAQYS MIGLKPRRAD LDMNQHVNNV TYIGWVLESI PQEIVDTHEL QVITLDYRRE  300
CQQDDVVDSL TTTTSEIGGT NGSATSGTQG HNDSQFLHLL RLSGDGQEIN RGTTLWRKKP  360
SS                                                                 362

SEQ ID NO: 194           moltype = AA   length = 367
FEATURE                  Location/Qualifiers
source                   1..367
                         mol_type = protein
                         organism = Arabidopsis thaliana
```

```
SEQUENCE: 194
MLKLSCNVTD HIHNLFSNSR RIFVPVHRQT RPISCFQLKK EPLRAILSAD HGNSSVRVAD    60
TVSGTSPADR LRFGRLMEDG FSYKEKFIVR SYEVGINKTA TIETIANLLQ EVACNHVQNV   120
GFSTDGFATT LTMRKLHLIW VTARMHIEIY KYPAWSDVVE IETWCQSEGR IGTRRDWILK   180
DCATGEVIGR ATSKWVMMNQ DTRRLQRVTD EVRDEYLVFC PPEPRLAFPE ENNSSLKKIP   240
KLEDPAQYSM LGLKPRRADL DMNQHVNNVT YIGWVLESIP QEIIDTHELK VITLDYRREC   300
QQDDIVDSLT TSETPNEVVS KLTGTNGSTT SSKREHNESH FLHILRLSEN GQEINRGRTQ   360
WRKKSSR                                                             367

SEQ ID NO: 195          moltype = AA  length = 412
FEATURE                 Location/Qualifiers
source                  1..412
                        mol_type = protein
                        organism = Arabidopsis thaliana
SEQUENCE: 195
MVATSATSSF FPVPSSSLDP NGKGNKIGST NLAGLNSAPN SGRMKVKPNA QAPPKINGKK    60
VGLPGSVDIV RTDTETSSHP APRTFINQLP DWSMLLAAIT TIFLAAEKQW MMLDWKPRRS   120
DMLVDPFGIG RIVQDGLVFR QNFSIRSYEI GADRSASIET VMNHLQETAL NHVKTAGLLG   180
DGFGSTPEMF KKNLIWVVTR MQVVVDKYPT WGDVVEVDTW VSQSGKNGMR RDWLVRDCNT   240
GETLTRASSV WVMMNKLTRR LSKIPEEVRG EIEPYFVNSD PVLAEDSRKL TKIDDKTADY   300
VRSGLTPRWS DLDVNQHVNN VKYIGWILES APVGIMERQK LKSMTLEYRR ECGRDSVLQS   360
LTAVTGCDIG NLATAGDVEC QHLLRLQDGA EVVRGRTEWS SKTPTTTWGT AP           412

SEQ ID NO: 196          moltype = AA  length = 345
FEATURE                 Location/Qualifiers
source                  1..345
                        mol_type = protein
                        organism = Arabidopsis thaliana
SEQUENCE: 196
MFIAVEVSPV MEDITRQSKK TSVENETGDD QSATSVVLKA KRKRRSQPRD APPQRSSVHR    60
GVTRHRWTGR YEAHLWDKNS WNETQTKKGR QVYLGAYDEE DAAARAYDLA ALKYWGRDTI   120
LNFPLCNYEE DIKEMESQSK EEYIGSLRRK SSGFSRGVSK YRGVAKHHHN GRWEARIGRV   180
FGNKYLYLGT YATQEEAAIA YDIAAIEYRG LNAVTNFDIS RYLKLPVPEN PIDTANNLLE   240
SPHSDLSPFI KPNHESDLSQ SQSSSEDNDD RKTKLLKSSP LVAEEVIGPS TPPEIAPPRR   300
SFPEDIQTYF GCQNSGKLTA EEDDVIFGDL DSFLTPDFYS ELNDC                   345

SEQ ID NO: 197          moltype = AA  length = 303
FEATURE                 Location/Qualifiers
source                  1..303
                        mol_type = protein
                        organism = Arabidopsis thaliana
SEQUENCE: 197
MAKVSGRSKK TIVDDEISDK TASASESASI ALTSKRKRKS PPRNAPLQRS SPYRGVTRHR    60
WTGRYEAHLW DKNSWNDTQT KKGRQVYLGA YDEEEAAARA YDLAALKYWG RDTLLNFPLP   120
SYDEDVKEME GQSKEEYIGS LRRKSSGFSR GVSKYRGVAR HHHNGRWEAR IGRVFATQEE   180
AAIAYDIAAI EYRGLNAVTN FDVSRYLNPN AAADKADSDS KPIRSPSREP ESSDDNKSPK   240
SEEVIEPSTS PEVIPTRRSF PDDIQTYFGC QDSGKLATEE DVIFDCFNSY INPGFYNEFD   300
YGP                                                                 303

SEQ ID NO: 198          moltype = AA  length = 445
FEATURE                 Location/Qualifiers
source                  1..445
                        mol_type = protein
                        organism = Avena sativa
SEQUENCE: 198
MKRSPPPAPP AAPPPPQPSP SSSSPACSPS PSSSSCPSSS DSSSIVIPRK RARTQKAASG    60
KPPKAKASAKR PKKDASRSSK ETDANGAAAA AGKRSSIYRG VTRHRWTGRF EAHLWDKNCF   120
TSVQNKKKGR QVYLGAYDTE DAAARAYDLA ALKYWGSETI LNFSVEDYAK EMPEMEAVSR   180
EEYLAALRRR SSGFSRGVSK YRGVARHHHN GRWEARIGRV FDTQEEAAKA               
YDLAAIEYRG ANAVTNFDIS CYLDQPQLLA QLQQGPQVVP ALQEELQHDV QHDLQNDNAV   300
QELNSGEVQM PGAMDEPIAL DDSTECINTP FEFDFSVEEN LWSPCMDYEL DAILGNNTSN   360
SANMNEWFND STFESNIGCL FEGCSNIDDC SSSKHCADLA AFDFFKEGDD NDFSNMEMEI   420
TPQANDVSCP PNDVSCPPKM ITVCN                                         445

SEQ ID NO: 199          moltype = AA  length = 420
FEATURE                 Location/Qualifiers
source                  1..420
                        mol_type = protein
                        organism = Sorghum bicolor
SEQUENCE: 199
MDMERSQQQK SPTESPPPPS PSSSSSSVSA DTVLPPPGKR RRAATTAKAK AGAKPKRARK    60
DAAAAADPPP PPAAAAAGKR SSVYRGVTRH RWTGRFEAHL WDKHCLAALH NKKKGRQVYL   120
GAYDSEEAAA RAYDLAALKY WGPETLLNFP VEDYSSEMPE MEGVSREEYL ASLRRRSSGF   180
SRGVSKYRGV ARHHHNGRWE ARIGRVFGNK YLYLGTFDTQ EEAAKAYDLA AIEYRGVNAV   240
TNFDISCYLD HPLFLAQLQQ EPQVVPALNQ EAQPDQSETE TIAQESVSSE AKTPDDNAEP   300
DDNAEPDDIA EPLITVDDSI EESLWSPCMD YELDTMSRSN FGSSINLSEW FNDADFDSNI   360
GCLFDGCSAV DEGGKDGVGL ADFSLLEDFS LFEAGDGQLK DVLSDMEEGI QPPTMISVCN   420

SEQ ID NO: 200          moltype = AA  length = 395
```

```
FEATURE                  Location/Qualifiers
source                   1..395
                         mol_type = protein
                         organism = Zea mays
SEQUENCE: 200
MERSQRQSPP PPSPSSSSSS VSADTVLVPP GKRRRAATAK AGAEPNKRIR KDPAAAAAGK    60
RSSVYRGVTR HRWTGRFEAH LWDKHCLAAL HNKKKGRQVY LGAYDSEEAA ARAYDLAALK   120
YWGPETLLNF PVEDYSSEMP EMEAVSREEY LASLRRRSSG FSRGVSKYRG VARHHHNGRW   180
EARIGRVFGN KYLYLGTFDT QEEAAKAYDL AAIEYRGVNA VTNFDISCYL DHPLFLAQLQ   240
QEPQVVPALN QEPQPDQSET GTTEQEPESS EAKTPDGSAE PDENAVPDDT AEPLTTVDDS   300
IEEGLWSPCM DYELDTMSRP NFGSSINLSE WFADADFDCN IGCLFDGCSA ADEGSKDGVG   360
LADFSLFEAG DVQLKDVLSD MEEGIQPPAM ISVCN                              395

SEQ ID NO: 201           moltype = AA   length = 430
FEATURE                  Location/Qualifiers
source                   1..430
                         mol_type = protein
                         organism = Triadica sebifera
SEQUENCE: 201
MASSSSDPVL KAELGSSGGG CSSGGGGESS EAVIANDQLL LYRGLKKPKK ERGCTAKERI    60
SKMPPCTAGK RSSIYRGVTR HRWTGRYEAH LWDKSTWNQN QNKKGKQVYL GAYDEEAAA    120
RAYDLAALKY WGPGTLINFP VTDYTRDLEE MQNMSREEYL ASLRRKSSGF SRGISKYRGL   180
SSRWESSVGR MPGSEYFSSI NYVDDPAAES EYVGSLCFER KIDLTSYIKW WGLNKTRQAE   240
SISKSAEETK PGCAEDIGGE LKTTEWAIQP TEPYQMPRLG MPVHVKKHKG SKISALSVLS   300
QSAAFKSLQE KASKKQENST DNDENENKNT NTNKIDYGKA VETSASHDSS NERPVTALGM   360
SGGLSLKRNV YQLTPFLSAP LLTNYGTIDQ LVDPILWASL VPVLPTGLSR NPEVTKTETS   420
STYTFFRPEE                                                          430

SEQ ID NO: 202           moltype = DNA   length = 1531
FEATURE                  Location/Qualifiers
source                   1..1531
                         mol_type = other DNA
                         organism = Solanum tuberosum
SEQUENCE: 202
ttttaaatca ttgttttatt ttctctttct tttacaggt ataaaaggtg aaaattgaag     60
caagattgat tgcaagctat gtgtcaccac gttattgata ctttggaaga aattttact   120
tatatgtctt tgtttaggag taatatttga tatgttttag ttagattttc ttgtcattta   180
tgctttagta taatttagt tattttatt atatgatcat gggtgaattt tgatacaaat    240
attttgtca ttaaataaat taattttatca caacttgatt actttcagtg acaaaaaatg   300
tattgtcgta gtaccctttt tgttgaata tgaataattt tttttattt gtgacaattg    360
taattgtcac tacttatgat aatatttagt gacatatatg tcgtcggtaa aagcaaacac   420
tttcagtgac aaaataatag atttaatcac aaaattatta accttttta taataataaa    480
tttatcccta atttatacat ttaaggacaa agtatttttt ttatatataa aaaatagtct   540
ttagtgacga tcgtagtgtt gagtctagaa atcataatgt tgaatctaga aaaatctcat   600
gcagtgtaaa ataaacctca aaaaggacgt tcagtccata gagggggtgt atgtgacacc   660
ccaacctcag caaaagaaaa cctcccttca acaaggacat ttgcggtgct aaacaatttc   720
aagtctcatc acacatatat ttattatata atactaatta agaatagaaa aggaaaggta   780
aacatcatta atcgtctttt gtatatttt agtgacaact gattgacgaa atctttttcg    840
tcacacaaaa ttttttagtga cgaaacatga tttatagatg atgaaattat ttgtccctca   900
taatctaatt tgttgtagtg atcattactc ctttgtttgt tttatttgtc atgttagtcc    960
attaaaaaaa aatatctctc ttcttatgta cgtgaatggt tggaacggat ctattatata   1020
atactaataa agaatagaaa aggaaagtga agtgaggttc gagggagaga atctgtttaa   1080
tatcagagtc gatcatgtgt caatttttatc gatatgaccc taacttcaac tgagtttaac   1140
caattccgat aaggcgagaa atatcatagt attgagtcta gaaaaatctc atgtagtgtg    1200
gggtaaacct cagcaaggac gttgagtcca tagaggggg tgtatgtgac accccaacct    1260
cagcaaaaga aaacctcccc tcaagaagga catttgcggt gctaaacaat ttcaagtctc   1320
atcacacata tatatatatt atataatact aataaataat agaaaaagga aagtaaaca    1380
tcactaacga cagttgcggt gcaaactgag tgaggtaata aacagcacta acttttattg   1440
gttatgtcaa actcaaagta aaatttctca acttgtttac gtgcctatat ataccatgct   1500
tgttatatgc tcaaagcacc aacaaaattt a                                   1531

SEQ ID NO: 203           moltype = DNA   length = 20
FEATURE                  Location/Qualifiers
misc_feature             1..20
                         note = Oligonucleotide primer
source                   1..20
                         mol_type = other DNA
                         organism = synthetic construct
SEQUENCE: 203
cactcgtgct ttccatcatc                                                20

SEQ ID NO: 204           moltype = DNA   length = 20
FEATURE                  Location/Qualifiers
misc_feature             1..20
                         note = Oligonucleotide primer
source                   1..20
                         mol_type = other DNA
                         organism = synthetic construct
SEQUENCE: 204
```

```
gaaggctgag caacaagagg                                                    20

SEQ ID NO: 205            moltype = DNA  length = 18
FEATURE                   Location/Qualifiers
misc_feature              1..18
                          note = Oligonucleotide primer
source                    1..18
                          mol_type = other DNA
                          organism = synthetic construct
SEQUENCE: 205
ggcgattttg gattctgc                                                      18

SEQ ID NO: 206            moltype = DNA  length = 20
FEATURE                   Location/Qualifiers
misc_feature              1..20
                          note = Oligonucleotide primer
source                    1..20
                          mol_type = other DNA
                          organism = synthetic construct
SEQUENCE: 206
cccaacccctt ccgtatacat                                                   20

SEQ ID NO: 207            moltype = DNA  length = 1970
FEATURE                   Location/Qualifiers
source                    1..1970
                          mol_type = other DNA
                          organism = Zea mays
SEQUENCE: 207
ggtaccttt tcccagaga taaatgtgga atagctctac aaacaaacgg catgatgctg           60
acacttggat ggcgaccttg caatcccaag aactattgca tacggttgcc agtcgacaaa        120
tatctacgcc atgcatggct acggtcggaa tacaccgtag cggcgggtaa ctcgccgata        180
ccgtccacgt gtccttggat gccggtcgc tgatacttct ggtcttctgg acatgcacca        240
agacaatcaa gtgattcaac cttaatttaa cataatataa ataatacgta acatccaact        300
gacgtgttca cctatagaga atattccttc tgattctact ttcagaatga tgccgttgtcc       360
gtgtatcgag caagtactct cactcgaagt atcttatctc ccacatccag cacaaaaatc        420
ttctgttcgt ggcaaatctt gtggcggttg aacgaaagaa tgctatataa gtagctatag        480
agaacgtatt atgtgtaaac caaccgttca gtgtaaatcg tgtgtaaata gtcatgttaa        540
tttttttggcg gcagatcaag tacaaactgt atgcctcgga taaacatgta caaaccacaa       600
cactggccac tagatctata tccaacgttc ataaccatcc atccctctct gctgcactct        660
gcaaacaagc accccatct cgtagcaaca tcttgtctcc gacaagctct cgatgtagtg        720
gaggccctcc accgcaatat cctagtgtat gatgttggag aagcgactcc taaataatgg        780
tggcaagatg ttgctaggtt tgtagccata gcctcaatct aagatcatcc caagccatgg        840
gacctgattc tacgaggcct acaaccaggc atgacacgtc gtctacccac tcttgtgcat        900
catcggtcac ttgatctgac ttggttccta accacttacc ctaggttcca aagccctaag        960
tttctcgtat attgttagtc attcttagtg ggagttttat gtgtatttca ttcctgttaa       1020
atagcatgcc aactaagcaa acatgatgat ataaatatgca atctaataaa aagatatatg       1080
agtgggtttc ataaaaaagg gagagagttt catgaggagt gaaactctga atacagatac       1140
tgatatgaca gctttaaaag tagtgttatg aaatcatcat tgagaaatgg tattagcact       1200
caatcgattt ctacgctgtc aattgtcatg agcacaattt tcacccaaag aggcacacca       1260
gcaatgtccg cttgtagtgt ccgagacgtt gctccatcgc cgtcgtcttg tttctgtgcg       1320
ctccattcaa tgcggcaagt ggctcaatcc caagcgggtc tgcctccca gccccagcag       1380
caaaatatct tcccatgcgg ccatgccttg aaaattggaa tagattctct agattcaccg       1440
ccgcgtcatc ttcactactt tctcactggc ccaatcagca tctccttctc cgagctcaat       1500
catgctcagt caagcgtcac caatggcgtc acggttggtt ttgtcactgt ctgcatgcaa       1560
gggtattttg cttcgcaagt gtaaatgaaa aatggatcta aacaactgca ctgcaccaat       1620
tttggaacgc ggaaccgaga gtctgtttgg gttcgtttga aacgcgctga tgtttctcat       1680
tttttaatag atgtagttac ctgatactat ttaagttgga cgatcaaacg actgtgtcaa       1740
gtgtgattaa gaaaagcatc gaaaataaaa tttatcgcca taaaaagtta aaaacagtgg       1800
ataatagtag gacctcataa tagaaaaaat tatcaaacgg aatggagggg cccaacgcag       1860
tatatagcag ccgggtggtg ccggacatcc gacgctcgtg ccagcaggcc attcttctcg       1920
ccttactccc tcacagaacc cagtaaaata tcgccagtcc cgccgtcgag                  1970

SEQ ID NO: 208            moltype = DNA  length = 584
FEATURE                   Location/Qualifiers
source                    1..584
                          mol_type = other DNA
                          organism = Aeluropus littoralis
SEQUENCE: 208
cccaagcttg accgatgcac acgctacctg ccaaggctcc ctccatccgc actctgcatc         60
gtcgcttcgg cgtaaaacttc cacgtagtac ttgtacgatt ctagctagac ccagtgcgcc       120
cacccctaccg ccggcgagcg ggcccccatc tcgcgccagg cttccatgcg ggtccaccgt       180
ggaccagccc tacgccgaac cgagcccatc cctccaccct ttcaccgcca agcgggaccc       240
gcgttggacc tttccgcttg gctggccccc accagcgtcc acgcgggcca acggcctcgc       300
gaaatgcatc tccacacgac aaaccaaaac gagaagaaaa taaatggaaa ggaaagaaac       360
ggatcgccac gcgttccaga ggcgtccgct aaccacccga ttatgcttgc gcagcgtgcg       420
taacctcgtc gtggggttaa tccgggtggc cggatcggga aagccacggc ctttataacc       480
catccctgcc ggatcgaacc ggtaccggaa acaaaaacag ggggagaaaa aaagttcttc       540
gcgaggaagg aaaaggaaaa gtcgcgtgcc gtcctcgccc acag                         584
```

| SEQ ID NO: 209 | moltype = DNA length = 928 |
| --- | --- |
| FEATURE | Location/Qualifiers |
| source | 1..928 |
| | mol_type = other DNA |
| | organism = Agrobacterium rhizogenes |

SEQUENCE: 209

```
ttagcgaaag gatgtcaaaa aaggatgccc ataattggga ggagtggggt aaagcttaaa    60
gttggcccgc tattggattt cgcgaaagcg gcattggcaa acgtggagat tgctgcattc   120
aagatacttt ttctattttc tggttaagat gtaaagtatt gccacaatca tattaattac   180
taacattgta tatgtaatat agtgcggaaa ttatctatgc caaaatgatg tattaataat   240
agcaataata atatgtgtta atcttttttca atcgggaata cgtttaagcg attatcgtgt   300
tgaataaatt attccaaaag gaaatacatg gttttggaga acctgctata gatatatgcc   360
aaatttacac tagtttagtg ggtgcaaaac tattatctct gtttctgagt ttaataaaaa   420
ataaataagc agggcgaata gcagttagcc taagaaggaa tggtggccat gtacgtagtt   480
ttaagagacc ctaataaaa ttgccagctg tgttgctttg gtgccgacag gcctaacgtg   540
gggtttagct tgacaaagta gcgcctttcc gcagcataaa taaggtagg cgggtgcgtc   600
ccattattaa aggaaaaagc aaaagctgag attccataga ccacaaacca ccattattgg   660
aggacagaac ctattccctc acgtgggtcg ctagctttaa acctaataag taaaaacaat   720
taaaagcagg caggtgtccc ttctatattc gcacaacgag gcgacgtgga gcatcgacag   780
ccgcatccat taattaataa atttgtggac ctatacctaa ctcaaatatt tttattattt   840
gctccaaatac gctaagagct ctggattata aatagtttgg atgcttcgag ttatgggtac   900
aagcaacctg tttcctactt tgttacca                                       928
```

| SEQ ID NO: 210 | moltype = DNA length = 732 |
| --- | --- |
| FEATURE | Location/Qualifiers |
| misc_feature | 1..732 |
| | note = hpRNAi construct containing a 732bp fragment |
| source | 1..732 |
| | mol_type = other DNA |
| | organism = synthetic construct |

SEQUENCE: 210

```
aatgcagttt tacaaagtgg agtacccaaa gcagatgaga tcattttgta taacatggct    60
cttgtgttgg atcgtatttt tgtggatgtg aaggatgctt tgagttctc accacatcat   120
aaggccattc gtgaacctttt tgactattac aagtttggcc aaaattatat ccgcccttta   180
cttgatttca ggagttctta tgttggcaat atatcgtttt ttggtgaaat agaagagaag   240
ctcaagcagg gcgttaatgt tgttttgatg tcaaaccacc aaaagtgaagc agatccagcg   300
gttattgctc tgttgcttga atcgaggcac ccatacattg ctgagaacat aatttatgtt   360
gcaggagata gagttattac tgatcctctt tgcaagccat tcagcatggg aaggaatctc   420
ctgtgtgttt attcgaaaaa acatatgggt gatgacccca aacttgtcga gaagaaaagg   480
agagcaaaca caagaagctt gaaggagatg gctgtgctat tgaggggtgg atcaaaacta   540
atatggattc tcctagtgg tggaagagat aggccaaacc ctgttacaaa gaatgggtat   600
ccagcgccat ttgatgcttc ttcaacagac aacatgagaa ggcttgtaga acatgctggt   660
gtccctggtc acatttatcc tctagcaata tttatgctatg atattatgcc ccctccgccc   720
caggttgaga aa                                                        732
```

| SEQ ID NO: 211 | moltype = AA length = 512 |
| --- | --- |
| FEATURE | Location/Qualifiers |
| source | 1..512 |
| | mol_type = protein |
| | organism = Elaeis guineensis |

SEQUENCE: 211

```
MAVSKNPETL APDQEPSKES DLRRRPASSP SSTAASPAVP DSSSRTSSSI TGSWTTALDG    60
DSGAGAVRIG DPKDRIGEAN DIGEKKKACS GEVPVGFVDR PSAPVHVRVV ESPLSSDTIF   120
QQSHAGLLNL CVVVLIAVNS RLIIENLMKY GLLIGSGFFF SSRLLRDWPL LICSLTLPVF   180
PLGSYMVEKL AYKKFISEPV VVSLHVILII ATIMYPVFVI LRCDSPILSG INLMLFVSSI   240
CLKLVSYAHA NYDLRSSSNS IDKGIHKSQG VSFKSLVYFI MAPTLCYQPS YPRTTCIRKG   300
WVICQLVKLV IFTGVMGFII EQYIDPIIKN SQHPLKGNVL NAMERVLKLS IPTLYVWLCV   360
FYCTFHLWLN ILAELLCFGD REFYKDWWNA KTIEEYWRMW NMPVHKWMLR HVYLPCIRNG   420
IPKGVAMVIS FFISAIFHEL CIGIPCHIFK FWAFIGIMFQ VPLVILTKYL QNKFKSAMVG   480
NMIFWFFFSI YGQPMCVLLY YHDVMNRKVG TE                                  512
```

| SEQ ID NO: 212 | moltype = AA length = 74 |
| --- | --- |
| FEATURE | Location/Qualifiers |
| source | 1..74 |
| | mol_type = protein |
| | organism = Glycine max |

SEQUENCE: 212

```
MADIDRSFDN NVSAVSTEKS SQVSDVEFSE AEEILIAMVY NLVGERWSLI AGRIPGRTAE    60
EIEKYWTSRF STSQ                                                      74
```

| SEQ ID NO: 213 | moltype = AA length = 146 |
| --- | --- |
| FEATURE | Location/Qualifiers |
| source | 1..146 |
| | mol_type = protein |
| | organism = Arabidopsis thaliana |

SEQUENCE: 213

```
MGSLQMQTSP ESDNDPRYAT VTDERKRKRM ISNRESARRS RMRKQKQLGD LINEVTLLKN    60
DNAKITEQVD EASKKYIEME SKNNVLRAQA SELTDRLRSL NSVLEMVEEI SGQALDIPEI   120
PESMQNPWQM PCPMQPIRAS ADMFDC                                        146
```

```
SEQ ID NO: 214           moltype = AA  length = 268
FEATURE                  Location/Qualifiers
source                   1..268
                         mol_type = protein
                         organism = Arabidopsis thaliana
SEQUENCE: 214
MGRGKIEIKR IENANSRQVT FSKRRSGLLK KARELSVLCD AEVAVIVFSK SGKLFEYSST    60
GMKQTLSRYG NHQSSSASKA EEDCAEVDIL KDQLSKLQEK HLQLQGKGLN PLTFKELQSL   120
EQQLYHALIT VRERKERLLT NQLEESRLKE QRAELENETL RRQVQELRSF LPSFTHYVPS   180
YIKCFAIDPK NALINHDSKC SLQNTDSDTT LQLGLPGEAH DRRTNEGERE SPSSDSVTTN   240
TSSETAERGD QSSLANSPPE AKRQRFSV                                      268

SEQ ID NO: 215           moltype = AA  length = 437
FEATURE                  Location/Qualifiers
source                   1..437
                         mol_type = protein
                         organism = Arabidopsis thaliana
SEQUENCE: 215
MEFESVFKMH YPYLAAVIYD DSSTLKDFHP SLTDDFSCVH NVHHKPSMPH TYEIPSKETI    60
RGITPSPCTE AFGACFHGTS NDHVFFGMAY TTPPTIEPNV SHVSHDNTMW ENDQNQGFIF   120
GTESTLNQAM ADSNQFNMPK PLLSANEDTI MNRRQNNQVM IKTEQIKKKN KRFQMRRICK   180
PTKKASIIKG QWTPEEDKLL VQLVDLHGTK KWSQIAKMLQ GRVGKQCRER WHNHLRPDIK   240
KDGWTEEEDI ILIKAHKEIG NRWAEIARKL PGRTENTIKN HWNATKRRQH SRRTKGKDEI   300
SLSLGSNTLQ NYIRSVTYND DPFMTANANA NIGPRNMRGK GKNVMVAVSE YDEGECKYIV   360
DGVNNLGLED GRIKMPSLAA MSASGSASTS GSASGSGSGV TMEIDEPMTD SWMVMHGCDE   420
VMMNEIALLE MIAHGRL                                                  437

SEQ ID NO: 216           moltype = AA  length = 359
FEATURE                  Location/Qualifiers
source                   1..359
                         mol_type = protein
                         organism = Arabidopsis thaliana
SEQUENCE: 216
MYHQNLISST PNQNSNPHDW DIQNPLFSIH PSAEIPSKYP FMGITSCPNT NVFEEFQYKI    60
TNDQNFPTTY NTPFPVISEG ISYNMHDVQE NTMCGYTAHN QGLIIGCHEP VLVHAVVESQ   120
QFNVPQSEDI NLVSQSERVT EDKVMFKTDH KKKDIIGKGQ WTPTEDELLV RMVKSKGTKN   180
WTSIAKMFQG RVGKQCRERW RNHLRPNIKK NDWSEEEDQI LIEVHKIVGN KWTEIAKRLP   240
GRSENIVKNH WNATKRRLHS VRTKRSDAFS PRNNALENYI RSITINNNAL MNREVDSITA   300
NSEIDSTRCE NIVDEVMNLN LHATTSVYVP EQAVLTWGYD FTKCYEPMDD TWMLMNGWN    359

SEQ ID NO: 217           moltype = AA  length = 386
FEATURE                  Location/Qualifiers
source                   1..386
                         mol_type = protein
                         organism = Arabidopsis thaliana
SEQUENCE: 217
MSKRPPPDPV AVLRGHRHSV MDVSFHPSKS LLFTGSADGE LRIWDTIQHR AVSSAWAHSR    60
ANGVLAVAAS PWLGEDKIIS QGRDGTVKCW DIEDGGLSRD PLLILETCAY HFCKFSLVKK   120
PKNSLQEAES HSRGCDEQDG GDTCNVQIAD DSERSEEDSG LLQDKDHAEG TTFVAVVGEQ   180
PTEVEIWDLN TGDKIIQLPQ SSPDESPNAS TKGRGMCMAV QLFCPPESQG FLHVLAGYED   240
GSILLWDIRN AKIPLTSVKF HSEPVLSLSV ASSCDGGISG GADDKIVMYN LNHSTGSCTI   300
RKEITLERPG VSGTSIRVDG KIAATAGWDH RIRVYNYRKG NALAILKYHR ATCNAVSYSP   360
DCELMASASE DATVALWKLY PPHKSL                                        386

SEQ ID NO: 218           moltype = AA  length = 292
FEATURE                  Location/Qualifiers
source                   1..292
                         mol_type = protein
                         organism = Arabidopsis thaliana
SEQUENCE: 218
MEPPQHQHHH HQADQESGNN NNNKSGSGGY TCRQTSTRWT PTTEQIKILK ELYYNNAIRS    60
PTADQIQKIT ARLRQFGKIE GKNVFYWFQN HKARERQKRF IGTNMTTPS SSPNSVMMAA    120
NDHYHPLLHH HHGVPMQRPA SVNVKLNQD HHLYHHNKPY PSFNNGNLNH ASSGTECGVV    180
NASNGYMSSH VYGSMEQDCS MNYNNVGGGW ANMDHHYSSA PYNFFDRAKP LFGLEGHQEE   240
EECGGDAYLE HRRTLPLFPM HGEDHINGGS GAIWKYGQSE VRPCASLELR LN           292

SEQ ID NO: 219           moltype = AA  length = 453
FEATURE                  Location/Qualifiers
source                   1..453
                         mol_type = protein
                         organism = Brassica napus
SEQUENCE: 219
MDLGSVTGNV NGSPSLKELR ESKQDRSEFD GEDCLQQSSK LARTIAEDKH LPSSYAAAYS    60
RPMSFHQGIP LARSASLLSS DSRRQEHMLS FSDKPEAFDF SKYVGLDNNK NSLSPFLHQL   120
PPPYCRTPGG GYGSGGMMMS MQGKGPFTLT QWAELEQQAL IYKYITANVP VPSSLLISIQ   180
KSFYPYRSFP PSSFGWGTFH LGFAGGKMDP EPGRCRRTDG KKWRCSKDAV PDQKYCERHI   240
NRGRHRSRKP VEVQPGQTAA SKAAAVASRN TASQIPNNRV QNVIYPSTVN LPPKEQRNNN   300
NSSFGFGHVT SPSLLTSSYL DFSSNQNKPE ELKSDWTQLS MSIPVASSSP SSTAQDKTTL   360
```

```
SPLRLDLPIQ SQQETLEAVR KVNTWIPISW GNSLGGPLGE VLNSTTSSPT LGSSPTGVLQ    420
KSTFCSLSNS SSVTSPVADN NRNNNVDYFH YTT                                453

SEQ ID NO: 220           moltype = AA  length = 461
FEATURE                  Location/Qualifiers
source                   1..461
                         mol_type = protein
                         organism = Brassica napus
SEQUENCE: 220
MDLGSVTGNV NGSPGLKELR GSKQDRSGFD GEDCLQQSSK LARTIAEDKH LPSSYAAYSR     60
PMSFHQGIPL TRSASLLSSD SRRQEHMLSF SDKPEAFDFS KYVGLDNNKN SLSPFLHQLP    120
PPYCRSSGGG YGSGGMMMSM QGKGPFTLTQ WAELEQQALI YKYITANVPV PSSLLISIQK    180
SFYPYRSFPP SSFGWGTFHL GFAGGKMDPE PGRCRRTDGK KWRCSKDAVP EQKYCERHIN    240
RGRHRSRKPV EVQPGQTAAS KAVASRDTAS QIPSNRVQNV IYPSNVNLQP KEQRNNDNSP    300
FGFGHVTSSS LLTSSYLDFS SNQEKPSGNH HNQSSWPEEL KSDWTQLSMS IPVASSSPSS    360
TAQDKTALSP LRLDLPIQSQ QETLESARKV NTWIPISWGN SLGGPLGEVL NSTTSSPTLG    420
SSPTGVLQKS TFCSLSNSSS VTSPIADNNR NNNVDYFHYT T                       461

SEQ ID NO: 221           moltype = AA  length = 409
FEATURE                  Location/Qualifiers
source                   1..409
                         mol_type = protein
                         organism = Arabidopsis thaliana
SEQUENCE: 221
MEARPVHRSG SRDLTRTSSI PSTQKPSPVE DSFMRSDNNS QLMSRPLGQT YHLLSSSNGG     60
AVGHICSSSS SGFATNLHYS TMVSHEKQQH YTGSSSNNAV QTPSSNNDSAW CHDSLPGGFL   120
DFHETNPAIQ NNCQIEDGGI AAAFDDIQKR SDWHEWADHL ITDDDPLMST NWNDLLLETN    180
SNSDSKDQKT LQIPQPQIVQ QQPSPSVELR PVSTTSSNSN NGTGKARMRW TPELHEAFVE    240
AVNSLGGSER ATPKGVLKIM KVEGLTIYHV KSHLQKYRTA RYRPEPSETG SPERKLTPLE    300
HITSLDLKGG IGITEALRLQ MEVQKQLHEQ LEIQRNLQLR IEEQGKYLQM MFEKQNSGLT    360
KGTASTSDSA AKSEQEDKKT ADSKEVPEEE TRKCEELESP QPKRPKIDN               409

SEQ ID NO: 222           moltype = DNA  length = 685
FEATURE                  Location/Qualifiers
source                   1..685
                         mol_type = other DNA
                         organism = Nicotiana benthamiana
SEQUENCE: 222
aaagtccact ggaagaatac tcttcaacag ttggaaagag ttggacctaa gtcggttggt     60
gtctgtctgt taacagcagc ttttgttggc atggccttca ctatccaatt tgttagagaa    120
ttcactagat tagggttaaa tagatctgtt ggtggggtgt tggcccttgc cttttcaaga    180
gagctaagtc cagttgtcac atcaattgta gttgctgggc gtatcggtag tgcatttgct    240
gcggaactgg gcactatgca ggtatctgag cagactgaca cgttggagat tcttggtgca    300
aatcctgttg attatttggt gacaccaaga gtgattgctt cttgcgttgc attaccattt    360
ttaaccctaa tgtgctttac agttggaatg gcatccagcg cccttttggc agatggtgtt    420
tatgaaatta gcataaacat aatcttagat tctgctctga gagctcttag atcatgggac    480
cttattagtg caatgattaa atcaggggtg tttggtgcta ttatatccat cataagctgt    540
gcttgggggg tcaccacgct gggaggtgcc aaagggttg gagagtcgac tacttcagca    600
gtagttttat ctcttgttgg catattcata gctgactttg ctctctcttg ctgtttcttc    660
cagggtgctg gcgattccct gaaga                                         685

SEQ ID NO: 223           moltype = AA  length = 824
FEATURE                  Location/Qualifiers
source                   1..824
                         mol_type = protein
                         organism = Solanum tuberosum
SEQUENCE: 223
MDISNEAKVE FISIGPSSIV GRTIAFRVLF CKSISRLRHN IFHFLIYYLY KIKNCLSYYL     60
TPLIKWFHPR NPQGILALVT LLAFLLRRYT NVKIRADMVY KRKFWRNMMK SALTYEEWAH    120
AAKMLEKETP KMNEAEFYDE ELVVNKLQEL QHRRNEGSLR DIMFFMRADL VRNLGNMCNP    180
QLHKGRLHVP KLIKEYIDEV STQLKMVCDY DSDEILLEEK LAFMHETRHA FGRTALLLSG    240
GASLGAFHVG VVKTLVEHKL MPRIIAGSSV GSIMCSVVAT RSWPELQSFF ENFWHVLQPF    300
EQMGGILTVF RRIMRQGAVH EIRQLQVMLR HLTNNLTFQG AYDMTGRVLG ITVCSPRKHE    360
PPRCLNYLTS PHVVIWSAVT ASCAFPGLFE AQELMAKDRS GNLVPYHPPF HLEPDQAAAS    420
GSSARRWRDG SLEIDLPMMQ LKELFNVNHF IVSQANPHIA PLLRIKEFVR AYGGNFAAKL    480
AHLTEMEVKH RCNQVLELGF PLRGLAKLFA QDWEGDVTVV MPATLAQYLK IIQNPSTLEV    540
QKAANQGRRC TWEKLSAIKA NCGIELALDE CVAILNHMRR LKRSAERAAA ASQGMSSSTV    600
KLNASRRIPS WNCIARENST GSLEEDFHAD ASSSLHHHHA GRNWRCNNKN AAHDHHGSDS    660
ESENADNNSW TRSGGPLMRT TSADKFIDYV QNLEMHPSQR SSRGLSIDLN NVVVREPLSP    720
SPRVTTPARR SDTEFDQRDI RIIVAEGDLL QTERTNNGIV FNVVRRGDLT PSNRSLDSEN    780
NSCFHDPVAE CVQLENPEKD MDISSASEDG ENAVLDEVTK NQII                    824

SEQ ID NO: 224           moltype = DNA  length = 2475
FEATURE                  Location/Qualifiers
source                   1..2475
                         mol_type = other DNA
                         organism = Solanum tuberosum
SEQUENCE: 224
atggatataa gtaatgaggc taaagtagag ttcatttcca taggaccttc ttcaattgta     60
```

```
ggtcgaacaa tagcctttcg agttttgttt tgcaaatcaa tatcgcggtt gaggcacaac    120
attttctatt tcttgatata ttacttgtac aagatcaaga attgtctgtc atactacttg    180
acacctttga tcaaatggtt tcacccgcgt aatccacagg ggatattagc attagtaaca    240
cttctagcct tcttgttgag gcgatatacg aatgtaaaaa tcagggctga tatggtttat    300
aagaggaaat tttggaggaa tatgatgaaa tctgcattaa cttatgagga atgggctcat    360
gctgcgaaaa tgttggagaa agagacacct aaaatgaatg aagcagagtt ttatgatgaa    420
gagttagttg taaataaact tcaagaactt caacatcgtc gtaatgaagg atctttaaga    480
gatattatgt tctttatgag agctgatctt gtgagaaatc tgggtaatat gtgtaatcca    540
cagcttcata agggtaggct tcatgtgcct aaacttatta aggagtatat tgatgaggtt    600
tcaactcagt tgaaaatggt atgtgattat gattcagatg agattttgtt ggaggagaag    660
cttgcttta tgcatgaaac aagacatgct tttggtagga cagcattgct tttaagcggg    720
ggcgcgtctt tgggagcttt tcatgttggt gtggttaaga cattggttga gcacaagctt    780
atgccaagga taattgctgg ttcgagtgtt ggatcgatta tgtgttctgt agttgcaact    840
cggtcttggc ctgagctgca gagtttttt gagaattttt ggcatgtgtt gcagccgttt    900
gaacagatgg gtggaattct aactgttttc aggaggatca tgagacaagg ggctgtacat    960
gagattaggc agttgcaggt gatgttacgc catctcacga ataatcttac tttccaagaa   1020
gcttacgata tgactggtcg agttctaggg attactgttt gctcccctag aaaacatgaa   1080
cctcctagat gtttgaacta cttgacttca cctcatgttg ttatatggag tgctgtgact   1140
gcttcttgcg cgtttcctgg tctgtttgaa gctcaagaac tgatggcaaa ggatagaagt   1200
ggtaatcttg ttcctatca tccaccattt catttggaac ctgatcaggc tgcagcttct   1260
ggttcatctg ctcgtcgatg gagggatggt agcttggaga tcgatctacc tatgatgcag   1320
ctaaaagagc tattcaacgt aaaccacttt atcgtgagcc aggcgaatcc acatattgct   1380
cctttactca ggatcaaaga gtttgtaaga gcttatggag gcaactttgc tgccaagctt   1440
gctcatctta ctgagatgga agtgaagcac agatgcaatc aggtactgga acttggtttt   1500
cccttgaggg gattagccaa gctatttgct caagattggg aaggcgatgt caccgttgta   1560
atgccagcca ctcttgctca gtacttgaag atcatacaga atccctctac tttggaggtt   1620
caaaaagcag caaatcaagg gaggagatgc acttgggaga aactatcagc cattaaggca   1680
aattgtggaa ttgagcttgc tcttgatgag tgtgtagcaa tactcaacca tatgcgtaga   1740
ctaaaaagga gcgcggagag agcagctgct gcttcacaag gcatgtcaag cagcacagtc   1800
aaactcaatg cttctagacg tattccttct tggaattgca ttgcaagaga gaactcaaca   1860
ggctcccttg aagaagactt tcacgcggat gcttcttcct ctcttcatca tcacaatgct   1920
ggtcgaaact ggcgttgtaa taacaagaat gctgcacatg atcatcatgg tagtgacagt   1980
gagtctgaaa acgcggataa taattcttgg acaagatcag gtggtccatt gatgaggaca   2040
acatcagctg ataagtttat tgactatgta caaaacttgg aaatgcatcc ttcacaacga   2100
tcgagcagag gactgagtat tgacctcaac aatgttgtag tcagggagcc tctttctccg   2160
agtccacgag tgacaacacc tgctaggaga tcagatacag aatttgatca agagacatc    2220
agaattatcg tcgctgaagg tgatttacta cagactgaaa ggactaacaa tgggattgta   2280
ttcaatgtgg taaggagagg agacttaact ccatcaaaca ggagtcttga ttcagaaaac   2340
aacagttgct ttcatgatcc agtggccgaa tgcgtgcaac tcgaaaatcc tgagaaggat   2400
atggatataa gttcagcatc agaagatgga gaaaatgcag tactagatga agtaacaaaa   2460
aatcagatca tataa                                                    2475

SEQ ID NO: 225          moltype = AA  length = 521
FEATURE                 Location/Qualifiers
source                  1..521
                        mol_type = protein
                        organism = Solanum tuberosum
SEQUENCE: 225
MAASIGALKS SPSSNNCINE RRNDSTRAVS SRNLSFSSSH LAGDKLMPIS SLRSQGVRFN     60
VRRSSLIVPP KAVSDSQNSQ TCLDPDASRS VLGIILGGGA GTRLYPLTKK RAKPAVPLGA    120
NYRLIDIPVS NCLNSNISKI YVLTQFNSAS LNRHLSRAYA SNMGGYKNEG FVEVLAAQQS    180
PENPDWFQGT ADAVRQYLWL FEEHTVLEYL ILAGDHLYRM DYEKFIQAHR ETDADITVAA    240
LPMDEKRATA FGLMKIDEEG RIIEFAEKPQ GEQLQAMKVD TTILGLDDKR AKEMPFIASM    300
GIYVISKDVM LSLLRDKFPG ANDFGSEVIP GATSLGMRVQ AYLYDGYWED IGTIEAFYNA    360
NLGITKKPVP DFSFYDRSAP IYTQPRYLPP SKMLDADVTD SVIGEGCVIK SCKIHHSVVG    420
LRSCISEGAI IEDSLLMGAD YYETDADRKL LAAKGSVPIG IGKNCHIKRA IIDKNARIGD    480
NVKIINKDNV QEAARETDGY FIKSGIVTVI KDALIPSGII I                       521

SEQ ID NO: 226          moltype = DNA  length = 1819
FEATURE                 Location/Qualifiers
source                  1..1819
                        mol_type = other DNA
                        organism = Solanum tuberosum
SEQUENCE: 226
ctagtgattg caatcacact ctaccacaca ctctctagta gagagatcag ttgataacaa     60
gctttgttaa caatggcggc ttccattgga gcctaaaaat cttcaccttc ttctaacaat    120
tgcatcaatg agagaagaaa tgattctaca cgtgcagtat ccagcagaaa tctctcattt    180
tcgtcttctc atctcgccgg agacaagttg atgcctatat cgtccttacg ttcccaagga    240
gtccgattca atgtgagaag aagttcattg attgtgccgc ctaaggctgt ttctgattcg    300
cagaattcac agacatgtct agacccagat gctagccgga gtgttttggg aattattctt    360
ggaggtggag ctgggacccg actttatcct ctaactaaaa aaagagcaaa gccagctgtt    420
ccacttggag caaattatcg tctgattgac attcctgtaa gcaactgctt gaacagtaac    480
atatccaaga tctatgttct cacacaattc aactctgcct ctctgaatcg ccacctttca    540
cgagcatatg ctagcaacat gggaggatac aaaaacgagg gcttttgtga agttcttgct    600
gctcaacaaa gtccagagaa ccccgattgg ttccagggca cggctgatgc tgtcagacaa    660
tatctgtggt tgtttgagga gcatactgtt cttgaatacc ttatacttgc tggagatcat    720
ctgtatcgaa tggattatga aagtttatt caagcccaca gagaacaga tgctgatatt    780
accgttgccg cactgccaat ggacgagaag cgtgccactg cattcggtct catgaagatt    840
gacgaagaag gacgcattat tgaatttgca gagaaaccgc aaggagagca attgcaagca    900
```

```
atgaaagtgg atactaccat tttaggtctt gatgacaaga gagctaaaga aatgcctttc    960
attgccagta tgggtatata tgtcattagc aaagacgtga tgttaagcct acttcgtgac   1020
aagttccctg gggccaatga tttggtagt gaagttattc ctggtgcaac ttcacttggg    1080
atgagagtgc aagcttattt atatgatggg tactgggaag atattggtac cattgaagct   1140
ttctacaatg ccaatttggg cattacaaaa aagccggtgc cagattttag cttttacgac   1200
cgatcagccc caatctacac ccaacctcga tatctaccac catcaaaaat gcttgatgct   1260
gatgtcacag atagtgtcat tggtgaaggt tgtgtgatca agagctgtaa gattcatcat   1320
tccgtggttg gactcagatc atgcatatca gagggagcaa ttatagaaga ctcacttttg   1380
atgggggcag attactatga gactgatgct gacaggaagt tgctggctgc aaagggcagt   1440
gtcccaattg gcatcggcaa gaattgtcac attaaaagag ccattatcga caagaatgcc   1500
cgtataggg acaatgtgaa gatcattaac aaagacaacg ttcaagaagc ggctagggaa    1560
acagatggat acttcatcaa gagtgggatt gtcaccgtca tcaaggatgc tttgattcca   1620
agtggaatca tcatctgaag aatgcgtttt aacttggtt gtcctccaag attttggcta    1680
aacagccatg aggtagaaac tgtgctgaact tttattttcc tgagctgtag aaatctagtg   1740
tacatctttc tgttatgata cttctcatta ccctacaag agaagactgg atgctgtaaa   1800
aattattcgt ctagaataa                                                1819

SEQ ID NO: 227          moltype = DNA   length = 1173
FEATURE                 Location/Qualifiers
source                  1..1173
                        mol_type = other DNA
                        organism = Sapium sebiferum L.
SEQUENCE: 227
tgccaatagc cagccaataa aacatctaca cgttttcaca cggcttttca tcacagccgt     60
tgtttttctc atctcactcc gtgccttcat cttcatcctc ttctcctctc tctctgtctc    120
tatatgtata gaagcgttag atgtcttgcg ttgttaacca attcattttt cgcttttctgc   180
ttcttctaat attataagaa agtttgattc ttcttcttgt caatctttgt tcgcggcttt    240
taacgatatc cgctaaagga aatttgaaat ttcaattatg gccgatggaa acgtcaattc    300
gcaagaacag atggctaagc aggaggaaca gaggctgaag tatttggagt ttgtacaagt    360
ggctgcaata catgctgtgg tgaccttcac aaacctctat gtttatgcca aaaacaagtc    420
gggtccattg aagcccggtg ttgagactgt tgaaggtacg gtcaagagtg tggttggacc    480
tgtttatggc aagttccatg atgttccat tgaggttctc aagtttgtcg atcgcaagat     540
tgatcaatct gtaagcagcc tagacagccg tgtgcctcca gttgtgaagc agttatcggc    600
ccaagcattt tcagtggctc gcgaagcccc agtggctgct cgtgctgtgg cttctgaagt    660
gcagactgct ggagtgaagg aaactcgatc tgggttggca agaactctgt acttcaaata    720
tgaacccaag gccaaggagc tatacaccaa gtatgaacca aaagcggaac agtgtgctgc    780
ctctgcctgg cgtaagctca atcaactccc agtcttccct catgtagctc aggttgttat    840
gccaacagca gcttattgtt ctgaaaagta caaccaggca gtacttacca ccgctgagaa    900
aggatacaga gtgtcctctt atttgccttt tgtgcccact gagagaattg ctaagttgtt    960
taggaatgag gcacctgaat ctaccccttt cctttccaat tgagcaagat gctgataaat   1020
gattcacaat ggacatgtgg acagaataaa aatctttgga tattatatgg tactgtgtat   1080
ttcaaggttc aagattactc tctacaatgt gtgaattttt gttcagatg acttaattct    1140
tgttcattca ttatatatat atatatat ata                                   1173

SEQ ID NO: 228          moltype = AA   length = 241
FEATURE                 Location/Qualifiers
source                  1..241
                        mol_type = protein
                        organism = Sapium sebiferum L.
SEQUENCE: 228
MADGNVNSQE QMAKQEEQRL KYLEFVQVAA IHAVVTFTNL YVYAKNKSGP LKPGVETVEG     60
TVKSVVGPVY GKFHDVPIEV LKFVDRKIDQ SVSSLDSRVP PVVKQLSAQA FSVAREAPVA    120
ARAVASEVQT AGVKETASGL ARTLYFKYEP KAKELYTKYE PKAEQCAASA WRKLNQLPVF    180
PHVAQVVMPT AAYCSEKYNQ AVLTTAEKGY RVSSYLPFVP TERIAKLFRN EAPESTPFLS    240
N                                                                    241

SEQ ID NO: 229          moltype = DNA   length = 1252
FEATURE                 Location/Qualifiers
source                  1..1252
                        mol_type = other DNA
                        organism = Sapium sebiferum L.
SEQUENCE: 229
ctactttttcc ctagcattag tattctaggc cccactctgt agattcctcc agctgcctga    60
tctaattttt tatcaactct tgaccgttcg atcatcccaa cggctcagat tgctactagtac  120
tttttctcaca ccgtatctcc gattctccat gactccatcg atataaatcg cagtgctcat   180
caactgaatt ctcgaaattg cggttacaag ctgctataag aagcgaaaag aaacgctgag    240
aaacaggatc cgttcctcct ccctcgtttt ttactcctta caagatggag accgagaaga    300
agattcctga attgaagcac ttaggggttcg tgaggatggc tgctattcag tcactgattt    360
gcgtctcgaa tctctacgat tacgcgaagc ataactcagg acctttgaga tccactgttg    420
gaaccgtgga gggtgccgta accaccgtag taggtccagt ttaccagaaa ttcaaagacc    480
ttcctgatga tcttcttgta tatgttgata agaaggtgga tgaaggaaca cacaagtttg    540
ataagcatgc tccacctatt gctaagaagg ctgcagccca gcccatagt ttgtttcata     600
tagccttgga gaaggtcgaa aaactcgtgc aggaggctcg tgcaggagga cctcgtgctg    660
ctctgcattt tgtggctaca gagtcgaagc acttggcgtt gacccaatct gtgaagctgt    720
atagtaaact taatcagttc cctgtcattc acactgttac agatgtaacc cttcccacag    780
ctactcactg gtcagataag tataaccata ccctttatgga cctgacccgg aagggttata    840
cgatctttgg ttattgcct ttggttccta ttgatgacat atctaagaca tttaaacaaa     900
gtaaagcaga ggagaaagaa aatgcaacta cgcataaatc tgattcatcg gattccgact    960
aaacggttgc catcatgtct aatgggtgtg gtttgttaag tatagtggtt tgcgaaaatg   1020
```

```
ttctagggtt tatgagcctg ctcgaaagat gctgagaaat ggaaatctgt actatttagg   1080
agtttttccg tactataata atgagtatga atggtttgta aattctgcct tgtgcttcct   1140
cgacaagtat atcatgcttc tatttttttac tactacttac tggactactg aattgtctca   1200
taattgtccc tagtgtctaa ttaaatatca cctccaaaat attattgaaa aa            1252

SEQ ID NO: 230           moltype = AA   length = 225
FEATURE                  Location/Qualifiers
source                   1..225
                         mol_type = protein
                         organism = Sapium sebiferum L.
SEQUENCE: 230
METEKKIPEL KHLGFVRMAA IQSLICVSNL YDYAKHNSGP LRSTVGTVEG AVTTVVGPVY    60
QKFKDLPDDL LVYVDKKVDE GTHKFDKHAP PIAKKAASQA HSLFHIALEK VEKLVQEARA   120
GGPRAALHFV ATESKHLALT QSVKLYSKLN QFPVIHTVTD VTLPTATHWS DKYNHTLMDL   180
TRKGYTIFGY LPLVPIDDIS KTFKQSKAEE KENATTHKSD SSDSD                   225

SEQ ID NO: 231           moltype = DNA   length = 938
FEATURE                  Location/Qualifiers
source                   1..938
                         mol_type = other DNA
                         organism = Sapium sebiferum L.
SEQUENCE: 231
gagtattcac actctggcct gattgggttt gctataaagg gcgatcgttg caacgctcca    60
tattgtctac ttggttttgt ttcaaatctc atcattttgt aaatttgcga cagtgtagcg   120
ttttctagga aaaaggttgc taaaggaaag tagttatcaa accgcagaaa tggcggaatc   180
cgaacttaat caacacacag atatggttca agatgatgat aaaaaactca agtatctaga   240
ttttgtacaa gtggccgcga tctatgttgt ggtttgtttc tctagtatct atgaatatgc   300
taaggaaaac tccggtccac taaaccaggg gtccaagcc gttgagtgta ccgtcaaaac   360
tgtaataagt ccggtttacg agaagtttcg cgacgtacct tttgaactcc ttaaattcgt   420
cgatcgtaaa gttgacaact ctctaggcga gttggacagg cacgtgccgt cgctggtgaa   480
gcaggcatca agccaagctc gagctgtggc tagtgaaatt caacatgctg gattggtaga   540
cgcaactaag aacattgcga agacgatgta tacaaagtat gaactgacgg cttggcagct   600
ctactgcaaa tacaagccgg tggctaagcg ttacgcggtg tcgacctggc gctcattgaa   660
ccagcttcct ctgtttcctc aagcggctca gattgcaatc ccaactgctg cttcgtggtc   720
tgagaaatac aataagatgg ttcgttacac gaaagataga ggatatccag cggcggtgta   780
tctgccattg atctcggttg agaggattgc caaggtgttc aatgaagact taaacgggcc   840
caccgtccct accaatggat catccgccgc agcacaatag ttttcatttt atgtattta   900
gtcagattga agacgctccg gagattttga aaacctga                           938

SEQ ID NO: 232           moltype = AA   length = 194
FEATURE                  Location/Qualifiers
source                   1..194
                         mol_type = protein
                         organism = Sapium sebiferum L.
SEQUENCE: 232
MAESELNQHT DMVQDDDKKL KYLDFVQVAA IYVVVCFSSI YEYAKENSGP LKPGVQAVEC    60
TVKTVISPVY EKFRDVPFEL LKFVDRKVDN SLGELDRHVP SLVKQASSQA RAVASEIQHA   120
GLVDATKNIA KTMYTKYELT AWQLYCKYKP VAKRYAVSTW RSLNQLPLFP QAAQIAIPTA   180
ASWSEKYNKM VRYT                                                    194

SEQ ID NO: 233           moltype = DNA   length = 2526
FEATURE                  Location/Qualifiers
source                   1..2526
                         mol_type = other DNA
                         organism = Sorghum bicolor
SEQUENCE: 233
atggacgagt ccggggaagc gagcgtcggc tccttcagga tcggcccgtc gacgctgctg    60
ggccgcgggg tggcgctccg cgtgcttctc ttcagctcgc tgtggcgcct gcgggcgcgc   120
gcgtacgccg ccatctcgcg cgtgcctcag cgggtgctgc cggtggcggc gtcctggctt   180
cacctcagga acaccccacgg cgtcctcctc atggtcgtgc tcttcgccct ctccctgagg   240
aagctctccg gcgcgcggtc gcgggcggc ctcgcgcgcc ggcgcaggca gtacgagaag   300
gccatgctgc atgccgggac gtacgaggtc tgggcccgcg ccgccaatgt gctcgacaag   360
atgtctgatc aggtccatga ggcggatttc tatgacgagg agctgatcag gaacaggctt   420
gaggacctcc ggaggcggga ggaggacggg tcgctgacgg acgtggtgtt ctgtatgcgt   480
ggcgatcttg ttaggaactt ggggaacatg tgcaatcctg aacttcacaa gggcaggcta   540
gaggttccta agcttataaa ggaatacatt aagaggtttt ctattcaact aagaatggtg   600
tgcgaatctg acactgatga gttgctattg ggagagaagc ttgcctttgt tcaggagacc   660
aggcatgcct ttgggaggac agccctactc ttaagtggg gtgcttcact ggggtcttc   720
catgtaggtg tagtgaaaac attggttgag cataagctc tgcctcggat tatagcagga   780
tcaagcgttg gttccattat atgttcgatt gttgctaccc ggacatggcc tgagattgag   840
agcttcttca cagactcatt tacagacctt g cagttctttg ataggatggg tggaattttt   900
gcagtgatga ggcgagtcac cactcatggt gcactgcatg acattagcca gatgcaaagg   960
cttctgaggg atctcacaag taacttaaca tttcaagagg cttatgacat gactggccgt  1020
gtccttggga tcaccgtttg ctctcctaga aaaaatgaca cacccccgctg cctcaactag  1080
ctgacgtcgc cgcacgttgt tatttggagt gctgtaactg cctcttgtgc atttcctggg  1140
ctctttgaag ctcaggaact gatggcgaag gatagatcg gcaacatagt tccccttccat  1200
gcaccctttg ccacagatcc tgaacaaggt cctggagcat caaagcgccg gtggagagat  1260
gggagcctgg aaatgggattt gcccatgatg agactcaagg agttgtttaa tgtaaaccat  1320
ttcattgtga gccaaactaa tcctcacatt tcctccctcc tccgaatgaa agagcttgtt  1380
```

```
agagtctatg gagggcgctt tgctggaaag cttgctcgtc ttgctgagat ggaggttaag   1440
tatcgatgta accaaatcct agagattggt cttccaatgg gaggacttgc aaaattgttt   1500
gctcaggact ggggagggtga tgtcaccatg gttatgccgg caacagtagc tcagtatttg   1560
aagattattc agaatccaac atatgcgag ctccaaatgg ctgccaacca aggccgcagg   1620
tgtacatggg agaagctctc tgcaatcaga gcaaactgtc ccatcgaact tgcattggat   1680
gaatctatag cagtttttaaa ccacaaacgg aggctaaaaa gaagcatgga gaggacagag   1740
gctgctttgc agggtcattc taactatgtt cgactcaaaa ctccaaggag ggtaccatca   1800
tggagctgca tcagtcgaga gaattcttca gaatctctct cggaagagat ttcagcagtt   1860
gctacttcaa ccgcgcagca aggtgctgct cttgttgtcg gcacagccac tcttttccac   1920
catgttcgac gcaattctca tgactgaagt gagagtgaat cagaaaccat tgaccttaat   1980
tcctggacca ggagtggtgg gcctctaatg aggacagcat ctgctgacat gttcatcagt   2040
ttcatcccata accttgagat tgacacggaa ttaagtaggc cctgtactgt ggagggtggt   2100
actgcaggta tttcgtcaga atctaccttc ccaaatgatc cacaaccgaa caatggctca   2160
agtgttacta ctccaggtag atgcacagaa aattctgaga ccgaggcata cgacactgtc   2220
aacaccagag ccagtcaggc ttctactccc acaagcatcg ctgtttctga aggagatttg   2280
ctgcagcctg aaagcattgc tgacggtatc ctgcttaaca ttgtgaaaag atgccttg    2340
caggctcaaa atgacagcgt aactgaattg gccgaaagct cctgcactga acatatgcg    2400
gaaacttgtg acaccatctc agggtctggc actgctgaag ataacaagga tactgctgac   2460
tcaagcaatc actcacttga tattgatgct tttgtagttt cgcatcaacc ttcagctgat   2520
gattag                                                              2526

SEQ ID NO: 234           moltype = DNA  length = 3099
FEATURE                  Location/Qualifiers
source                   1..3099
                         mol_type = other DNA
                         organism = Triticum aestivum
SEQUENCE: 234
atgcccgcgc ctgcaggtgc gtgcagccaa gccccaccgc tcgccttcta ttccgcgtcc   60
cctagcttgg cccggccctg ctccgatcca aggccgcggc ggtggcccag tgccctctcc   120
ctcctgccac gccgtccgcc gcccatggac gtcatcacca acgaggcgcg cgtggggggcg   180
ttcgcgatcg gcccgtccac ggcggcgggg cgcgcgctcg cgctgcgcgt gctcctctgc   240
ggctcgctgg cgcggctgcg gcaccgcctc gccgccgcgc tgcgcgcgcg ggcgccgctg   300
gcggcggcct ggctgcaccc gcgccacaac acgcggggga tcctgctcgc cgtctgcgcc   360
gtcgcgctgc tgctgcgcgg ccgcggggc cgcgccgggg tgcgcgcgcg ggtgcagtcc   420
gcctaccgcc gcaagttctg gcggaacatg atgcgccgcg ccgctcaccta cgaggagtgg   480
gcgcacgccg cgcggatgct cgagcgggag acgccgcgcc gcgtcaccga cgccgacctc   540
tacgacgagg agctcgtgtg caacaagctc cgtgagctca ggcaccgccg tcaggagggc   600
tcgctcaggg acatcgtctt ctgcatgcgc gccgatctgc tcaggaacct tggtaacatg   660
tgcaaccccg agctccacaa gttgagctg caggtgccta aaaccatcaa ggagtacatt   720
gaggaggtat ctactcaact gaaaatggtt tgcaattctg attcggacga gttacccctt   780
gaagagaaac tggcatttat gcatgagaca agacatgcct ttggtagatc ggccctactg   840
ctaagtggag gtgcttcatt tggctctttc catgtgggtg ttgtgaaaac cttggtagag   900
cataagcttc tacctaggat tatttcagga tcaagcgttg gcgcaataat gtgtgctatt   960
gtagccacac ggtcatggcc agaactagag agttttttg aggagtggca ttccttgaaa   1020
ttctttgacc agatgggtgg gatctttcct gtatttaaaa gaattttgac gcatggagcg   1080
gttcatgaca ttaggcactt gcagacgcag ttgagaaatc ttacaagcaa tttgacattt   1140
caagaggcat atgacatgac tggccgggtt ctcgttgtta ctgtgtgttc tccaagaaaa   1200
catgagccac cacgatgcct gaactatttg acatcacctc atgttctcat ttggagtgca   1260
gtaactgctt cctgtgcttt tcctggactt tttgaggccc aggagttgat ggccaaagat   1320
agattcggag aaacagttcc tttttcatgct ccattcttgt tgggtgtgga ggaacgagct   1380
gacgctgtca cacggcgctg gagagatggc agcttagaaa gtgatttacc catgaagcaa   1440
ttgaaggaat tattcaacgt aaatcacttc atagtaagcc aagccaatcc tcacattgct   1500
ccattactga gactaaagga gatcatcagg gcttacggag gcagctttgc tgcaaagctt   1560
gctgaacttg ctgagatgga agttaagcat aggttcaatc aagttctgga acttggatttt   1620
ccattaggag gaatagctaa gttgtttgct caacattggg aaggtgatgt gacaatcgtt   1680
atgccagcca cacttgctca gtattcgaag atcatacaga atccttcgta ttctgagctt   1740
cagaaagccg caagtcaggg taggcgatgc acttgggaaa agctctctgc tatcagggca   1800
aactgcgcta ttgagcttgc attagatgaa tgtgttgccc tcctgaacca catgcgtagg   1860
ctgaagagaa gtgcagaaag agcagctgct tcacaaggat atggtgctac aattagactc   1920
tgtccatcta gaaggattcc atcatgaat ctcatagcag agaaaattc aactggttct   1980
ctcgatgagg aaatgctcac atgtcccact gttacgagcc atcaagcagt tggagggact   2040
gctgggccat ctaacagaaa tcaccatctc aacatagta tgcatgatag cagtgacagt   2100
gaatctgaga gtatagactt gaactcatgg acgagaagtg gtggcccctct catgagaaca   2160
gcctcagcta ataaattcat cagctttgtt cagaaccttg agattgacac agaattcaga   2220
acaatttcac caaggggggag cgaaggtgat attgttacac gaatagtaa cttatttgct   2280
ggtcacccaa ttggtagaga gccagttgat aaccatccag gcctgctac tcctggtagg   2340
acctcaggca attcaggttg cgatcctcat gatactcctg ttcctaggtc tccatttggt   2400
ctttccacaa gtatcatggt ccctgaaggt gacttgctgc agccgaaaa gattgagaat   2460
ggtattttat tcaatgttgt gagaagggat gctcttgtag cgactactga cggagttgaa   2520
cctcatggat cttcacagga agcagatgtg gaaactgtac cgaccgagtg cctttatggt   2580
gcttcggatg acgacgacga caacgtgaaa ctgaatgctg atcatgaagc attatctgac   2640
cctgagatc agagatcctc agttgcagga aacctagatc cgtccacttc catggattgt   2700
caagctgatg aaacaagtac tactcgatca gaagctccat ctctctttaa tatctgtgtg   2760
gagattcctc cagcaaccat gatcagagaa aatagtcggc ccgacgagcc ttcttcagac   2820
ataagactgg agattgtaaa gacagaatgc cctgatgaga attcagctgc tgggaacgat   2880
gaagttggct cagttcctgc caataaagaa tcttccctatt gttctcagac agctgaaaat   2940
agacagcagc atcaagttga tatgggatct gtgaactcct gtagtgtttc agtttcgaaa   3000
gatgataggc atgtcagcct catttcgaac gagaaaccag ttactactc cagtggcgga   3060
gcggagagta tgacatctgg aagaaatgaa gctgactag                          3099
```

| SEQ ID NO: 235 | moltype = DNA length = 2198 |
| --- | --- |
| FEATURE | Location/Qualifiers |
| misc_feature | 1..2198 |
| | note = S. bicolor SDP1 hpRNAi fragment |
| source | 1..2198 |
| | mol_type = other DNA |
| | organism = synthetic construct |

SEQUENCE: 235

```
gcggcggcgt ggctgcaccc gcgcgacaac acgcgcggga tcctgctcgc cgtctgcgcc    60
gtcgcgctgg gtgcagtccg cctaccgccg caagttctgg cggaacatga tgcgcgccgc   120
gctcacctac gaggagtggg cgcacgcggc cggatgctt ggagtgcagt aacagcttcc   180
tgtgctttc ctggactttt tgaggccac catctaggag gattccatcc tggaatctca   240
tagcaagaga aaattcaact ggttctctat gtgcaatcct gaacttcaca agggcaggct   300
agaggttcct aagcttataa aggaatacat tgaagaggtt tctattcaac taagaatggt   360
gtgcgaatct gacactgatg agttgctatt gggagagaag cttgcctttg ttcaggagac   420
caggcatgcc tttgggagga cagccctact cttaagtggg ggtgcttcac tggggtcttt   480
ccatgtaggt gtagtgaaaa cattggttga gcataagctt ctgcctcgga ttatagcagg   540
atcaagaagg gtggacccag ctttcttgta caaagtggtc tcgaggaatt cggtacccca   600
gcttggtaag gaaataatta ttttcttttt tccttttagt ataaaatagt taagtgatgt   660
taattagtat gattataata atatagttgt tataattgta aaaaataat ttataaatat   720
attgtttaca taaacaacat agtaatgtaa aaaaatatga tactgatgt gtaagacgaa   780
gaagataaaa gttgagagta agtatattat ttttaatgaa tttgatcgaa catgtaagat   840
gatatactag cattaatatt tgttttaatc ataatagtaa ttctagctgg tttgatgaat   900
taaatatcaa tgataaaata ctagtaaaa aataagaata aataaattaa aataatattt   960
ttttatgatt aatagtttat tataattaa aatatcata ccattactaa atattttagt  1020
ttaaagtta ataaatattt tgttagaaat tccaatctgc ttgtaattta tcaataaaca  1080
aaatattaaa taacaagcta aagtaacaaa taatatcaaa ctaatagaaa cagtaatcta  1140
atgtaacaaa acataatcta atgctaatat aacaaagcgc aagatctatc attttatata  1200
gtattatttt caatcaacat tcttattaat ttctaaataa tacttgtagt tttattaact  1260
tctaaatgga ttgactatta attaaatgaa ttagtcgaac atgaataaac aaggtaacat  1320
gatagatcat gtcattgtgt tatcattgat cttacatttg gattgattac agttgggaag  1380
ctgggttcga aatcgataag cttgcgctgc agttatcatc atcatcatag acacacgaaa  1440
taaagtaatc agattatcag ttaaagtcat gtaatatttg cgccataacc aatcaattaa  1500
aaaatagatc agtttaaaga aagatcaaag ctcaaaaaaa taaaagaga aaagggtcct  1560
aaccaagaaa atgaaggaga aaactagaa atttacctgc acaagcttgg atcctctaga  1620
ccactttgta caagaaagct gggtccaccc ttcttgatcc tgctataatc cgaggcagaa  1680
gcttatgctc aaccaatgtt tcactacac ctacatggaa agaccccagt gaagcacccc  1740
cacttaagag tagggctgtc ctcccaaagg catgcctggt ctcctgaaca aaggcaagct  1800
tctctcccaa tagcaactca tcagtgtcag attcgcacac cattcttagt tgaatagaaa  1860
cctcttcaat gtattccttt ataagcttag gaacctctag cctgcccttg tgaagttcag  1920
gattgcacat agagaaccag ttgaattttc tcttgctatg agattccagg atggaatcct  1980
cctagatggt gggcctcaaa aagtccagga aaagcacagg aagtgttac tgcactccaa  2040
gcatccgcgc cgcgtgcgcc cactcctcgt aggtgagcgc ggcgcgcatc atgttccgcc  2100
agaacttgcg gcggtaggcg gactgcaccc agcgcgacgg cgcagacggc gagcaggatc  2160
ccgcgcgtgt tgtcgcgcgg gtgcagccac gccgccgc                          2198
```

| SEQ ID NO: 236 | moltype = DNA length = 22 |
| --- | --- |
| FEATURE | Location/Qualifiers |
| misc_feature | 1..22 |
| | note = Oligonucleotide primer |
| source | 1..22 |
| | mol_type = other DNA |
| | organism = synthetic construct |

SEQUENCE: 236

```
ttttaacgat atccgctaaa gg                                             22
```

| SEQ ID NO: 237 | moltype = DNA length = 23 |
| --- | --- |
| FEATURE | Location/Qualifiers |
| misc_feature | 1..23 |
| | note = Oligonucleotide primer |
| source | 1..23 |
| | mol_type = other DNA |
| | organism = synthetic construct |

SEQUENCE: 237

```
aatgaatgaa caagaattaa gtc                                            23
```

| SEQ ID NO: 238 | moltype = DNA length = 22 |
| --- | --- |
| FEATURE | Location/Qualifiers |
| misc_feature | 1..22 |
| | note = Oligonucleotide primer |
| source | 1..22 |
| | mol_type = other DNA |
| | organism = synthetic construct |

SEQUENCE: 238

```
cttttctcac accgtatctc cg                                             22
```

| SEQ ID NO: 239 | moltype = DNA length = 25 |
| --- | --- |
| FEATURE | Location/Qualifiers |

```
misc_feature          1..25
                      note = Oligonucleotide primer
source                1..25
                      mol_type = other DNA
                      organism = synthetic construct
SEQUENCE: 239
agcatgatat acttgtcgag aaagc                                         25

SEQ ID NO: 240        moltype = DNA  length = 18
FEATURE               Location/Qualifiers
misc_feature          1..18
                      note = Oligonucleotide primer
source                1..18
                      mol_type = other DNA
                      organism = synthetic construct
SEQUENCE: 240
gcgacagtgt agcgtttt                                                 18

SEQ ID NO: 241        moltype = DNA  length = 25
FEATURE               Location/Qualifiers
misc_feature          1..25
                      note = Oligonucleotide primer
source                1..25
                      mol_type = other DNA
                      organism = synthetic construct
SEQUENCE: 241
atacataaaa tgaaaactat tgtgc                                         25

SEQ ID NO: 242        moltype = DNA  length = 23
FEATURE               Location/Qualifiers
misc_feature          1..23
                      note = Oligonucleotide primer
source                1..23
                      mol_type = other DNA
                      organism = synthetic construct
SEQUENCE: 242
acagacatgt ctagacccag atg                                           23

SEQ ID NO: 243        moltype = DNA  length = 24
FEATURE               Location/Qualifiers
misc_feature          1..24
                      note = Oligonucleotide primer
source                1..24
                      mol_type = other DNA
                      organism = synthetic construct
SEQUENCE: 243
cactctcatc ccaagtgaag ttgc                                          24

SEQ ID NO: 244        moltype = DNA  length = 25
FEATURE               Location/Qualifiers
misc_feature          1..25
                      note = Oligonucleotide primer
source                1..25
                      mol_type = other DNA
                      organism = synthetic construct
SEQUENCE: 244
ctgagatgga agtgaagcac agatg                                         25

SEQ ID NO: 245        moltype = DNA  length = 21
FEATURE               Location/Qualifiers
misc_feature          1..21
                      note = Oligonucleotide primer
source                1..21
                      mol_type = other DNA
                      organism = synthetic construct
SEQUENCE: 245
ccattgttag tcctttcagt c                                             21

SEQ ID NO: 246        moltype = DNA  length = 2631
FEATURE               Location/Qualifiers
source                1..2631
                      mol_type = other DNA
                      organism = Saccharum hybrid
SEQUENCE: 246
ctgcgacagc tagaggcgcc accgcgtcct agcttcctcc aacttctcgt cggagatccc    60
ttcagggatg cccaatgcca ccgccctaa gtcaacctgc gggagctgga gcttcgccag   120
ggtcagagct gcggcagcac cctggtagac cgcattcctg atgacccgcg gggtgcgctc   180
catgaagaag tgcattcgcc caaccaagtc gagtgggtcg cctggagggg cggggaagc    240
aaaacgttgc atgcacctag cgccctggca gcgagctcct gtagtatcac ctgcgtcgcc   300
```

-continued

```
tccagctcat gctcgcaagc ctccagggcg gcccggcagt gctccaacac tttcgcctcc   360
tcctacagct ccttccacat gcagtcgtgc tccgcacgca ccttctccac ctttttactc   420
ttttctttct cttttcttgg cccatctttg gtattttcac aaatgtcccc ctacaaatga   480
taaatcacca aaactcatgg agcttgctag ttataaactc taattctaag tttggtgttt   540
atttgagtgg attttgtgtg aaagttggtg gttagaaata ggagttaagg accgccaaca   600
agatccccca cacttagccc tttgctcatc ctcgagtaaa gttcaaggac taaggtggaa   660
catctcctca aatggtacga tgcctgcata aagttattc caagcctcac ctatacatgt   720
gaactttgaa gtgtctacca cgccatcttg ggtggttgag aaatggaaca gatcagaatc   780
cagtcatctt tacctctctt gcttagataa ctttgggtttt tgtaaggttt tcaaatttaa   840
aacatagtct tgctcctcaa atgattctct catatagctc aatgtgtatg gtttctcacc   900
aaggcaatgt tttgcctctt ttcatcctac ttctaatatt tcttttgtgg agcttagggt   960
agggaatgaa aaggaagcat acttgcattg catatgttac taagtcaaaa accaaatctg  1020
aggagaagca agtcatacaa tctgatcaag atgtgcaagt gtgtggatat gtggattaag  1080
ataactcctg tttattcatg ctctcctcct taataaactt tagagggcat ggcaatcttt  1140
gcatgggcct tcatgagctc atcgtatgtc taagcatgga gctcatcatt tatataagca  1200
tggtgatacc aaaattactc cttttgagca tgtttatatt taggaggacg ttttacctgt  1260
tgaggtaaat ctgaacgcta ataaatcggc taagcaaaat aatttatcac ctgttgattc  1320
taacaatttg atgatggaca atattgatga ggtgactgac aatgattgaa aggcttttaaa  1380
ggagattgag aaggataaat ctacaataaa aatgtaaaga agaaagcatt caaagtgtga  1440
gatcggtgt ggaagactat tttgcctctt gggggtaaaa gacaacaagt ttagtaagtg  1500
gcctcaaaat tgggagggcc catgcaagat tgttaaagta attgttttgg attgacggag  1560
gcatttcaag gtgatcatct acctagagct ctcaatggga ggtgctcgaa gacatattac  1620
ccatgtgtat ggcaagatgt ttagctagta actgactgat agtgtaaacg atctccaatg  1680
gggcaagaca tattacctaa ggccaggctg gttttgcaa gttcgagtag gatatagaga  1740
ttctcgtgcg agttgtaaac gatctccaat ggggcaagac atcctaccct atatatagtg  1800
aaggggcagt agctgattga gaatcaatca atcaagcaca atataattta ttaatttttt  1860
attcaaaccc aattttttc cttttccaac cctaattata gttttccttt tgcctctagg  1920
acaaattgac gtgttccggg tatcctgctg aattaagaac aacccctaggt gcacctgtcc  1980
cgatagagtc ccacctgggt aggcattcat agggattcgt gtatttcctg caaaaaagcg  2040
attaagctgg cttctaaaac tggctaggcc ggattctgtg gccttcacta caggtgatt   2100
ttcatgtgat ccgtgcattc tagcacttttg ctatgtaacc caaacttaag tcgacaacta  2160
taaatatgct acttgcagga tgttatcacg acacaactcc taatctacgg aagcctaagt  2220
ttagttttgc tcggagacaa gcaattgtgg ccagtcacta tagctacgtc agagggtagt  2280
gggagcagtt gcgtcgttgg attgaaaaca ggtggatcgt atcagatatt atgcattcac  2340
atggacagta aatgtggtac agtaacttcg caaacaataa aatctgtcac aatttattag  2400
tgcactcctc tgacgtaaat gcttctacgt cagaggattt gattccgagg gccgctgcac  2460
ccatcactaa tgacggtctt tacccatcat catggaccat tgttcacatc catgctatca  2520
ctgtcgtcct gtccatgcac tgcagccctc tataaatact ggcatccctc ccccgttcac  2580
agatcacaca acacaagcaa gaaataaacg gtagctgcca taactagtac a           2631
```

SEQ ID NO: 247    moltype = DNA  length = 2907
FEATURE       Location/Qualifiers
source        1..2907
           mol_type = other DNA
           organism = Saccharum hybrid
SEQUENCE: 247

```
gcataggcat tgtaaaagcg gtatgcctct tcttcagtgc agaatttcat accaaccttta   60
ggtatcctgt cttccataga attttctacc tgagtaggtt cggtctggtt ggatttgtag  120
cgggtttcat gcaaaataag ttagaaatcg tgcaaacttg caatggaggt taaatttgaa  180
atatatttgc atagacaaaa caaatataga ttatgaatgg taatccaata tgacttgcat  240
tttctaactc tattgctact gtgccagatg aagaatgttc atctggagaa gtttttgtag  300
aatgtgacaa caacgggagg tcatatcaag attctgggta cccgcggaga atcggcctcc  360
atgtagttag cctcgtcagg catgggggga attggctgag atgcccccat gtagtcgtca  420
ggcatggaga gtactggctg agatgccatt gttgtgtaga tcgagagaaa cgagaagaat  480
gctagtctaa taatacccctt ccgtatgcta accaactatt ataattggca ccattttcta  540
catgctagcg cctttttgcct gctttattta attcaattgg gtccgataag catgtgaacg  600
tgggagacgg ttccgtcgga cggctccgtt tccttgtagc gtacggcgtg gacggagaaa  660
aggtgagggc ctatctctaa aggggaacga atggatggtg gacacgtgtg gggagacacc  720
gaagggacat gccgaggagg cacacaagct tcagcaggcg tctccagact ctcagaagaa  780
gaagaagctc acggcacggt tgcggctggt tcttgctgtc gctgtctcgt ggtgcacgtt  840
tctgtgatca cgctgaaatc gaccggccgg cggaccaaca ggaggtcagc tcggccactc  900
cgtctccgag cgcatgagtg caccgttcgt ccgcggttcc ttttctcgtg gtgccgtgca  960
cgcctctgcg ttcaccggca ccctgaaacc aatcagaacg ttcccttttac aggggaaagg 1020
gacaagtctg ataacctctc tgtttccatc gtcctctaac cgcgaagagc gcgcagccaca 1080
gacttagagt ctatttgttc gaaattttt actctcacaa aagctagctt ttatagacgg  1140
gcataaaagc tatcatgtcg accggcacgt ttaatattta acttataccta tgaatatc   1200
atgtcgaact atgaggatga tactttctg aacgtgattg cgtgagttat taaattgtac  1260
ttttagttgt ttgagcatga aggtctgaac tatgaattta tgatgtattg tggcttgtga  1320
gctactccgc tctacattta gttggtatca taaatattat tatattatca tataaaattg  1380
atcaacttga gatgctttga ctcttcaaga ttcttggaat gacttatcat ttgggggtagg  1440
gagtaggttt ctaaggccag tctcagtggg gtttcatcag agtttcatgg acattaaata  1500
agctgatgtg acaccgtatt gatgaagaga gagatgataa gagtttcatg cgagtagaga  1560
gagtttcatg gggatgaaac tcttcttcac tgtttccaaa atatagatgc attggtaaga  1620
gggccatgaa atctctagtg acactgacct aagatgagat tgactctagc actatgtttc  1680
aaaatctgca tgcatgcatg ctttgaatat tgtaacctca cattaactcc cctcacacat  1740
gcatgcaaac gggcggtgca cgcaaaagaa ttgagtgaag atgcacatga aaaataagta  1800
aaatgctttg gcttcatcac ccggcttaaa tgctcgacac aaaaacacgt cggtagtcaa  1860
ggttgtgcct aacaaactgg ggttcacatg taaaacacgt tcatgcctta gaaacggcct  1920
ggagggatta gatacaactt caattatatc ttagggcccc tccaatattg tcagctctaa  1980
```

```
actagtttta tgtgtcacgg tggaggagag ggaggctaaa aatataatct tgagctaacg   2040
tgaagagaag agctattttt ttttgctccc caatacatga tagatacaat atgagagaaa   2100
aaatatatga ataaagaaca ctttacatgc cagccataca atatgagatt tcatctaaga   2160
gccaacacct gactcgtact gttgaaggtg tcctagttgg agtggtcgat cttttagttg   2220
ttagtagtgt aagacctagt ttagtgctct tttcttgtct aggtttatgt tgtgttttgg   2280
ctgccaagtg ttgaacaact caaggtaagg tcccatctaa ttctaaaatg atgccaaata   2340
aagatagatt acaaagttaa acgacggaaa aactctaaaa taggatggaa agttttgtag   2400
agtaataatt ggtatgaagt ggcgaagtcg accacaacca aacataaaga gttaaatgca   2460
tggtaggctc ttgatcttgt ctggaggtgc cacttaggtc cacaaactct caaattgcat   2520
ttttgacacc ctaatgttat tcaagtgtgc cacttagatc tacaaactct caaaatgcat   2580
ttctgatacc ctagtgttgt tcaagtgtgt cacttaggca agaaaagtta gataattttg   2640
ataagctatg ggaccaaatt aatttatgta tgcatgctcg aactagttga tgatgatgga   2700
ccccataata gacactagtt catgggctgg tttccttgta tagtactagc tagtataact   2760
ttttcaagtt gtagctacta ctttagctta tactccgcat attacaatca aatagaattc   2820
ggaagtacta taaacgggag cctataaatg gagacgtttt gcatcatgag gctataacaa   2880
cttgagcaaa aacagaagcc gtgcgcc                                      2907

SEQ ID NO: 248          moltype = DNA  length = 1141
FEATURE                 Location/Qualifiers
source                  1..1141
                        mol_type = other DNA
                        organism = Saccharum hybrid
SEQUENCE: 248
actatagggc acgcgtggtc gacggcccgg gctggtctgg ttttggcctc ttttagttac   60
taaattgcca aaaagagtga ctaaaaagtg actaaactga tttagtcctc tagtcaaggg   120
actaaaccag ctaaaagaca tccgctgccc ctcattaatg cacagaagga gagagagagg   180
gagagggagg acattttggt ctttatatag tagctttaat ggactttagt acctagatcc   240
aaaccggtag tgactaaagt ttagtccttg aactgaactt taatccaggg acatggaacc   300
aaacatgccc ttaactttt tttattctaa tccctcttac attcacttgt ctcacaaagt   360
ggcaagtcat ttgccaccct cactaccagt ggcgactggt taaatatcct catgtttggt   420
ttttttttagt aaccaaatac tgcaagctat tgggaaaaaa ggcaaaaaat tatctccttg   480
cttatagttg tataatccat gatccggcaa ttgtttgtta cggagatcct gaatcctctg   540
acgtagagtt taatcaattt tagctcaaga ataatacact ataaagtgga tatgacaatc   600
accgtagtac ttatttatct tgtagtagta tactgtattc gacgtcgcgt tatgataaag   660
gcatcagaaa ctagagtact ttctagaatc tttagtcagt ttctgtaaga tgaacgtgac   720
taggaaactt atactgttgc aatcctctga cattctctga ttgaaactcg gtttccaaaa   780
atcatatgtt actaaacaaa acatatctaa ccaaatacta tgtggtagtg tagatttata   840
tgctgtgtac tgaaagtgac gtcaagtata gtagtggcag agactcaaaa gatacctgcg   900
gattctgaat accacaacca taaaaaacag gatgatgtta tacttgtccc cttccatgat   960
acaggactgt ttagtaattt cccaaacagc ccataataca ttctgcaccc tttattaaac   1020
ctctactagc tacaacatct tactccatct tgtctagttg gacaagttct ctctttcttg   1080
gctgactcca acttactaca ccgcaacttc ttgtgccctt gttccaacca tcacaattga   1140
g                                                                  1141

SEQ ID NO: 249          moltype = DNA  length = 4438
FEATURE                 Location/Qualifiers
source                  1..4438
                        mol_type = other DNA
                        organism = Saccharum hybrid
SEQUENCE: 249
aagtacaaac gtagactctg acatacacgc acgtagactc tgacatacac gcataaacga   60
acgaagaatg ttattattta tgttttgagt gggaatattt ggtactgcta tgattcacgt   120
gtgtaaggaa ggattcaaga agaaaggatg cgtttagttc gcgaaaattt ttgacttttta   180
ccactatagc actttcgttt gtatttgtta attagtgtcc aatcatggac taattagact   240
caaaagatcc gtctcgtggt tttaaaccaa actgtgtaat taatttttt tatctatatt   300
taatgctcca tatatgtgtc aaatattcga tataacgaag aatcttgaaa atttttagga   360
actaaacatg gccaaagtgt tgtcccgact gagaaacttt ggaagcagaa taaaggctca   420
aaggaacatt taaaagaaga ggatgatata taatcaaaag tggcgacaaa gaagtgtgta   480
cgacccactc gagattgacg aaggacagct tctttgttct tttgtgtgtt actgaatatg   540
taatcatctt gtatagattg gttttttaaaa tacggtggca aattaaagac gatatcactt   600
acaaagacat ggacaatgtg gaggggccaa aagttatata aacgacacgc cgaatcggtg   660
atgaacacca catgcctccc ataaagacgg tgtatcaatc tttgatataa tgggtatccg   720
tttgaggcgg catttatact tgatctagtg aaattacaag gagaggaaaa gaagtttaag   780
agaatgataa tgataatgaa aaaaatcgga tgaaaaagaa catgaacaag gcaagaggag   840
atagccgtgc acacaaaata gagataattt cctcttagaa ctatgaaaac ttcctcttct   900
ttctgcaaca ctgatttgag ttttttgttct ctatctagca tttcagtcca tcttgatgtc   960
aagtgacatg taaaaagacg tattgccccc attgctgttt taaattgtct ccacacttga   1020
caacaattta atgagttgtt aaaatattat gtgtgtttat ggccaattat acttttttagt   1080
tttgagtttt tcatgaagtc attaagatgc taaaaatata ataagttgt caatgcttgt   1140
cggaagcccc aatatgtgac taaaatgctg ctaaaagttt atagcatttgt tttaaaaatc   1200
taaacaaatt gaaaaagaa atccaaacta gaaattgtag atcttatcga aaactataag   1260
ttttatataa aaggcgactt tatctaacac cacacaagaa agatgtgctt tttctaagaa   1320
gacaagtctt agtatgtgat taatatgcta ctgaaaattt atatttatttt taagcatttt   1380
aataaccttca atggaaaca tacaaaacta agttgcagat cttatcaaga gctataattt   1440
ttatataaaa tgtatatttta aataaccaca tacaagaaag atatatgatt ttttctaaga   1500
cgacaaagct ttgtatgcaa tttaaatgt tgctaaaaaa tcatattatt ttttttatca   1560
tcttaacgtc ctcaaataaa aaaaaaatcag actagttggt atagacctca tcgaggctac   1620
aattttata aaaactcaac ttcatccggt gttgtataaa aatgatataa ttttttcctag   1680
atagagcgtt gccataagtg tatttggtc aagaaatata tgtatactta ttaatgaaat   1740
```

```
cctaacaaaa tatactttaa aatctgacgg aaatgttgga taggaaacaa aagcttaaat    1800
caatgctaaa tagggaagtt ttcatcatag ttataatgag tgatttctcc acaaaatatg    1860
atgtaccaca tgttaaatat tactcgcgca caaataatca gagcatatta ctttcatagc    1920
gtggtcgtgg ccatggccta gacttggttg tggacgtctc acttcaccaa ttgatagaaa    1980
aaaaacattt ataagaaaga aaagatacag aaaccatcac acgcgacaac atgacttgcc    2040
gaaacacaaa accaaaaccc aaactcgaga agatgctttc gagaaaaagc ctgaaaagaa    2100
aaaaaatttg cacgtaaaat caaattcgga cggcgaagag ggcaaacgag acagacaact    2160
gggtccactt gctgataaaa aagagagaga ggagggccca cttgccggcg ggcaccccctc   2220
agactgtctc caacaatact gacgcaaaca gaagacgact tggatgcaat gcgttgcgct    2280
gtggcaaaaa attaggtacc tattctcagt gtattccaac agagaacgca aaagaagatg    2340
ccgtactgcg ccatgcattc atgtgggacc ggggaggatg cggcaacag cagtttgcac    2400
gacccattgg ccggagcatg cgacgtatat ttgcgttgcg cctcgcttcc tacgcaaaat    2460
gtgtcgttgg tatgcctacc ctgttggagg gcgttttctt ctgctaaagt aacgtggagc    2520
acgcatttgc gtaggctgtt ggagatagtc tcaccacgcg gtgaccggac caggccaatt    2580
cccgagccca aaaagaaaaa agcacacaca cagagacaca cgctctcgct ctcgcctccc    2640
tgacgctgga tttaagcaga gcagggagca gaggtgcaac cgcccaccac gatctcccct   2700
cccgcacgcc ccgcgggcag acccagccaa ggcaaggcag ccgcgaaccg gagcacgccg   2760
gccggtgtcg cctcccgcgc cggcggcctg ctgctcgctc gccctcgctt ccgcattgga   2820
tcacgcggcg gttggcgact tggtggtgtc tgctgctggt gattgcgcct agccggccga   2880
cgcggagacg tgaggcgct gctcttcgct tctctcccca ctgctccct cagcggtttc    2940
tctctccctg ttatgcgtgg aggagccctg ccccgcgga acggaagcct ccgccggatc    3000
tctgttacgc cgcggttact gcctcgccct ggatttgaac ttgtttcgta attttccctt    3060
gctgcgcttc tcgatttcgg ggaggggttc tgccggcagc tctgccgctc cacctgactt    3120
ggggaccttt ctatgttccg cgacagcagc attgatgatc tgcttgtctc ttgagttttt    3180
ttttcgtgcg atgcatcgag cgcgtgggga cacgatcacg cctgatgggc ggtagtccgc    3240
gatccgcatt tctgaatccc ggcgcctagc cgaggtgcct ccggtgcttcc tggttgcctt   3300
gctgctattc ccttcttcgg atccgctctc gtacggctgg cacggtggtt gcggccttag    3360
aatttcgtgg cggcggtttg gttggattgg tgatgctgct ccgtccgcat ttatgaagga    3420
atgttctcca aactttttaag ctgctcgtgt actcggagta ttgaattgcc tgttccttgc    3480
cgctatagga ggccctgggc cagcctaccc cgctttggt tgtgattggt gatttccggc    3540
agctgttatt gtttcatgat tcgtgtgggg aaaaaaagtt tttttggttc acgagtggtt    3600
tctggtgcat gttttgacaa gttttctatg atgctggtac tgtctttacc cctgctagag    3660
tagtttggtg gtgcgttttc ctattaggtg ggaatttaat cacttcccca ctttatcgta    3720
tctctactat ggtaaccatc tttggcaat tttgattggt atagtcatgt ttaagataag    3780
cttttgaatt caatgatctt gccgttcatt agctagcact taattttgta gagctgcttg    3840
gatcaccaaa gtgccgctca atcttgttca agtgccatg atatatggga ttctgatgga    3900
actcttagca gtcgtgtcct taggcagtcg gcaccttgat aaggttccaa gagttcaatc    3960
ttacggaaga aatagtgagc ttgatctgag ttcagatcgg ttgtcttcac acttcacgat    4020
taattaccac gttttttaagg tgtgcattct cacttcttta cttccatcgt caatcttctt    4080
aactggttgg gttggaggtg tggtcatgca cccaaccaca taggttgagt cctcttcaac    4140
tcgaatttag gtgcctattt ttttcttaat aaaaaaggcc acctgattct ccttggttgg    4200
tcacattttt ttcttaataa aaaaaggcca cctcaatgtt tctccttta gcttgagcac    4260
tttttctgta tctcctcttt cttcttaatt ctgatccaag tgtcatcagc gttatattta    4320
tttgaacctg cttgcttttg taagcctgat cagtttgcaa aagttactag aacaatttaa    4380
ccatctgtgc ttgttatttc tgcaggcatc aagtttctaa caatttgaag tacctaaa     4438

SEQ ID NO: 250        moltype = DNA  length = 297
FEATURE               Location/Qualifiers
source                1..297
                      mol_type = other DNA
                      organism = Sorghum bicolor
SEQUENCE: 250
atggtggtca gcgcattcac tggacccggg attgggatcg ggttcggtgt cggctgcggg     60
ttcggcgtcg ggtgggggtt cggagggatg cctcttaaca tgtttggctt gggtattggt    120
gggggctgcg gagttggtct tggactagga tggggctttg gaaatgcttt tggttgtcag    180
tatcgatctt caagagtcca gttccagggc attgaatttc agaagaaggt tgaaggagat    240
gaagcaccaa aagttgtttc acaggagctt gctgaaaaat ctcgtcctta tggctag       297

SEQ ID NO: 251        moltype = AA   length = 98
FEATURE               Location/Qualifiers
source                1..98
                      mol_type = protein
                      organism = Sorghum bicolor
SEQUENCE: 251
MVVSAFTGPG IGIGFGVGCG FGVGWGFGGM PLNMFGLGIG GGCGVGLGLG WGFGNAFGCQ     60
YRSSRVQFQG IEFQKKVEGD EAPKVVSQEL AEKSRPYG                             98

SEQ ID NO: 252        moltype = DNA  length = 297
FEATURE               Location/Qualifiers
source                1..297
                      mol_type = other DNA
                      organism = Zea mays
SEQUENCE: 252
atggtagtca gcacgttcaa tggacccggg attgggatcg ggttcggtgt cggctgcggg     60
ttcggcgtcg ggtgggggtt cggaggaatg cctcttaaca tgtttcggctt gggtatcggt   120
ggggggtgtg gatttggtct tggactagga tggggctttg gaaatgcttt tggttgtcag    180
tatcgatctt caagagttca gttccaaggc attgaatttc agaagaaggc ggaaggagat    240
gatgcaccaa aagttgtttc accggagctt gctcaaaagt ctcgtcctta tggctag       297
```

```
SEQ ID NO: 253          moltype = AA   length = 98
FEATURE                 Location/Qualifiers
source                  1..98
                        mol_type = protein
                        organism = Zea mays
SEQUENCE: 253
MVVSTFNGPG IGIGFGVGCG FGVGWGFGGM PLNMFGLGIG GGCGFGLGLG WGFGNAFGCQ    60
YRSSRVQFQG IEFQKKAEGD DAPKVVSPEL AQKSRPYG                           98

SEQ ID NO: 254          moltype = DNA   length = 1533
FEATURE                 Location/Qualifiers
source                  1..1533
                        mol_type = other DNA
                        organism = Sorghum bicolor
SEQUENCE: 254
atggcgacgg cgatgggcgc gttggctgcc acctccctga ccccggtccc ggctgccgct   60
acgttccccg gtgatctcgg cctcggacgc cgccgggcgg ctgtgtcagg gtggcgcgcc   120
ggcgggagac ggctgcgtgc gtcgccgcct gcccggaggc cgttcctgtt ctcgccgagg   180
ggcgtttcgg actctcggag ctcgcaaacg tgccttgatc cggacgccag cacgagtgtt   240
cttgggatca tccttggagg tggtgctggg acaaggctgt atccactgac gaagaagagg   300
gcgaaaccag cagtgccgtt gcgcgccaac tacaggctca tagatatccc tgtcagcaac   360
tgtctgaaca gtaacgtctc caagatatat gtgctaacac agttcaactc tgcttcgctc   420
aaccgccacc tctcaagggc ctatgggaac aacattgccg ggtacaagaa tgagggattc   480
gttgaggtcc ttgcagcaca acagagtcca gagaatccca actggtttca gggtactgca   540
gatgctgtgc gtcaatatat gtggctattt gaggagcaca atatcatgga gttccttatt   600
ctggctggag atcacctgta ccgtatggac accaaaagt tcattcaagc ccatagaaga   660
acagatgctg atataactgt tgcagccctg ccaatggatg aacaacgtgc aactgcattt   720
ggtcttatga aaattgatga tgaagggaga atagttgagt ttgcagaaaa accaaaagga   780
gagaagctga gatcaatgat ggttgacacc actatattgg gccttgatcc tgagagggcc   840
aaggaactgc cttatattgc tagtatggga atctatgttt ttagcaaaga tgtgatgctt   900
cggcttctca gagaaaactt tcctgcagca aatgactttg gaagtgaggt tattcctggc   960
gcaacagaaa ttggattaag ggtgcaagct tactatatg atggttactg ggaagatatt   1020
ggtactattg aagcatttta taatgcaaac ttgggaataa ccaagaaacc tgtaccggat   1080
tttagcttct atgaccgttc tgctccaatt tatacgcaac ctagatactt gcctccttca   1140
aaggttcttg atgccgatgt gacagacagt gttattggcg aaggttgtgt tattaaacat   1200
tgcacaatca accattctgt agttggactc cgttcctgca tttctgaagg tgcagttata   1260
gaggattctt tgctgatggg tgcagactat tatgagactg aggatgataa gaaagtcctt   1320
tctgagaatg gtggcattcc cattggtatt gggaagaatg cacatatcag aaaagcaata   1380
atcgacaaaa atgctcgtat tggagaaaat gtgaagataa tcaattttga taatgtccaa   1440
gaagcagtaa gggagacgga aggatacttt atcaaaagtg gcattgtcac agtgattaaa   1500
gatgccttaa tccctagtgg aaccatcata taa                              1533

SEQ ID NO: 255          moltype = AA   length = 510
FEATURE                 Location/Qualifiers
source                  1..510
                        mol_type = protein
                        organism = Sorghum bicolor
SEQUENCE: 255
MATAMGALAA TSLTPVPAAA TFPGDLGLGR RRAAVSGWRA GGRRLRASPP ARRPFLFSPR    60
GVSDSRSSQT CLDPDASTSV LGIILGGGAG TRLYPLTKKR AKPAVPLRAN YRLIDIPVSN   120
CLNSNVSKIY VLTQFNSASL NRHLSRAYGN NIAGYKNEGF VEVLAAQQSP ENPNWFQGTA   180
DAVRQYMWLF EEHNIMEFLI LAGDHLYRMD YQKFIQAHRE TDADITVAAL PMDEQRATAF   240
GLMKIDDEGR IVEFAEKPKG EKLRSMMVDT TILGLDPERA KELPYIASMG IYVFSKDVML   300
RLLRENFPAA NDFGSEVIPG ATEIGLRVQA YLYDGYWEDI GTIEAFYNAN LGITKKPVPD   360
FSFYDRSAPI YTQPRYLPPS KVLDADVTDS VIGEGCVIKH CTINHSVVGL RSCISEGAVI   420
EDSLLMGADY YETEDDKKVL SENGGIPIGI GKNAHIRKAI IDKNARIGEN VKIINFDNVQ   480
EAVRETEGYF IKSGIVTVIK DALIPSGTII                                  510

SEQ ID NO: 256          moltype = DNA   length = 1554
FEATURE                 Location/Qualifiers
source                  1..1554
                        mol_type = other DNA
                        organism = Zea mays
SEQUENCE: 256
atggcgatgg cagccatagc ctccccgtcg tcgaggaccc tgatccctcc gcgacaccac   60
ggcgccgcgc cctccccgtc cacctccggc gactcctcgc tccgcctcct ctgcgcacac   120
ccgcgccacg gacggcgcgg ccgggcgatg tccgtctcga cgcccgcggc gcggagccgg   180
ccgttcgtct tctcccccgcg cgcggtgtcc gactctaaga gctcccagag ctgcctcgac   240
cccgacgcca gcacgagtgt tcttggaatc attctcggag gtgggctgg gactagattg   300
taccccttga caaagaagcg tgccaagcct gcagtgccat gggtgccaa ctatagactg   360
attgatatcc ccgtcagcaa ttgtctcaac agcaacatat ccaagatcta tgtgctaaca   420
caattcaact ctgcttccct caaccgtcac ctctcaagag cctacgggaa caacattgga   480
gggtacaaga atgacgggtt cgttgaagtc ttagctcac agcagagccc agataatcca   540
aactggtttc agggtactgc agatgctgta aggcaaatac gtggttatt tgaggaacat   600
aatgtgatga gtttctaat tcttgctggc gatcacctgt accggatgga ttatgaaaag   660
ttcattcagg cacacagaga aacgatgctg atattactg ttgctgccct accaatggat   720
gagaaacgtg caaccgcatt tggcctcatg aaaattgacg aagaaggag gattattgag   780
tttgctgaga aaccgaaagg agatcagttg aaagcaatga tggttgacac caccatacttt   840
ggccttgatg acgagagggc aaaggaaatg ccttatattg ctagcatggg tatatatgtt   900
```

```
tttagcaagg atgtaatgct tcagctcctc cgtgaacaat ttcctggagc caatgatttt    960
ggaagtgagg ttattccagg tgcaacaagc attggaaaga gggttcaggc ttatctatat   1020
gatggttatt gggaagatat tggtacaatt gaggcatttt ataatgcaaa cttgggaata   1080
accaagaagc caataccaga tttcagcttc tatgaccgtt ctgctccaat ctatacacaa   1140
cctcgacatc tgccaccttc aaaggttctt gatgctgatg tgacagacag tgttattggt   1200
gagggatgtg ttattaaaaa ctgcaagata caccattctg tagttggact ccgttcttgc   1260
atatctgaag gtgctatcat agaggacact ttactaatgg gtgcggacta ctatgagact   1320
gaagctgaca agaaactcct tgccgaaaat ggtggcattc ccattggtat tgggaagaat   1380
tcacacatca gaaaagcaat cattgacaag aatgctcgaa ttggagataa tgtgaagata   1440
ctcaacgctg acaatgttca agaagctgca agggagacag acgtgtactt catcaaaggt   1500
ggaattgtca cagtgatcaa ggatgcttta ctccctagtg ggacagttat atga          1554

SEQ ID NO: 257          moltype = AA   length = 517
FEATURE                 Location/Qualifiers
source                  1..517
                        mol_type = protein
                        organism = Zea mays
SEQUENCE: 257
MAMAAIASPS SRTLIPPRHH GAAPSPSTSG DSSLRLLCAH PRHGRRGRAM SVSTPAARSR     60
PVFSPRAVS DSKSSQTCLD PDASTSVLGI ILGGGAGTRL YPLTKKRAKP AVPLGANYRL    120
IDIPVSNCLN SNISKIYVLT QFNSASLNRH LSRAYGNNIG GYKNDGFVEV LAAQQSPDNP    180
NWFQGTADAV RQYLWLFEEH NVMEFLILAG DHLYRMDYEK FIQAHRETDA DITVAALPMD    240
EKRATAFGLM KIDEEGRIIE FAEKPKGDQL KAMMVDTTIL GLDDERAKEM PYIASMGIYV    300
FSKDVMLQLL REQFPGANDF GSEVIPGATS IGKRVQAYLY DGYWEDIGTI EAFYNANLGI    360
TKKPIPDFSF YDRSAPIYTQ PRHLPPSKVL DADVTDSVIG EGCVIKNCKI HHSVVGLRSC    420
ISEGAIIEDT LLMGADYYET EADKKLLAEN GGIPIGIGKN SHIRKAIIDK NARIGDNVKI    480
LNADNVQEAA RETDGYFIKG GIVTVIKDAL LPSGTVI                             517

SEQ ID NO: 258          moltype = DNA   length = 2049
FEATURE                 Location/Qualifiers
source                  1..2049
                        mol_type = other DNA
                        organism = Sorghum bicolor
SEQUENCE: 258
atgtcgctcc tgcggcggcg gaagcagccg cagccgccgc cgccgccctc ggacggcgac     60
gggtccgacc acgacgacag cgacaagggg aagaagccgt cctcgtcctc gtcctccgcg    120
ccgccgtcca aggaggccac gaggcggacc aaggccaagt ggtcgtgcgt ggacagctgc    180
tgctggctgg tcgggtgcgt gtgctccgcc tggtggctgc tgctcttcct ctacaacgcg    240
atgccggcct cgttcccgca gtatgtcacg gaggccatca cggggccgcc ccggaccct    300
cccggggtca agctgcagaa ggaggggctc cgtgttaagc accccgtcgt cttcgtcccc    360
ggcatcgtca ccggagggct cgagctatgg gaggccacc agtgcgccga ggggctcttc    420
cgcaagcggc tatgggcgg cacatttggt gacgtataca agagacctct atgctgggtt    480
gaacatatgt ctttggacaa cgaaacagga ttagacaaag gttaggccca                540
gtcacaggcc ttgttgcagc agactatttc gttcctggat attttgtttg ggctgtctta    600
attgccaatt tagctcgtat tggatatgaa gaaaagacca tgtacatggc tgcatatgat    660
tggaggttat ctttccagaa cactgaggtt cgtgatcaaa ctttgagcag aataaagagc    720
aacattgaac tcatggtagc aacaaatggt ggaaatagtc tggtagtgat cccgcactcc    780
atggggtcc tctatttct gcattttatg aaatggttg aagcacctcc tcccatggga     840
ggcggcggcg gtccaaactg gtgtgagaag catattaaag ctgtaatgaa tattggtgga    900
cctttcttag gagttcccaa ggcagttgct gggcttttct catctgaagc caaagatgtt    960
gccgttgcta gagctattgc tcctgatgtt ctggactcgg attttttcttgg gctccaaact   1020
ttgcgccatt tgatgcgtat gacccgaaca tgggattcga caatgtcaat gattcctaaa   1080
ggtggtgata caatttgggg aaatctggat tggtctccag aagatggcct gaatgtaaa   1140
gctaagaagc acaaaaccaa tgataccgag gtttctaagg atagcaatgg ggaaaatgtc   1200
gaagttcaac ctgagcctat taactatgga aggctggtat ccttggtaa agatgtagcg    1260
gaagcacctt cttcagagat tgagcagata gaatttcgtg atgctgttaa aggtaatagt   1320
attgccatt caaatacttc atgccgggag atctggacag aatatcatga attaggatgg   1380
ggtggaataa aggcagttga ggactacaaa gtttacactg ctagttctgt tataggacctc   1440
ctttcactcg ttgctccaag gatgatgcag cgtgggaaatg tccactttctc atatggaatt   1500
gctgataact tggatgatcc gaaatacaaa cattacaaat atggctcaaa cccccttggaa   1560
acaaagctac cgaatgctcc tgacatggaa atattttcga tgtacggagt aggcattcct   1620
accgaaaggg catatgtcta taaggttgcc ccgcaggcag agtgtaatat accctttccgg   1680
attgactcct cggctgaagg tggggaggaa aatagctgct tgaaaggggg tgtttactta   1740
gctgatggtg atgaaactgt tccagttctt agtgcgggct acatgtgtgc aaaaggatgg   1800
cgtggcaaaa ctcgtttcaa ccctgccggc agcaagactt acgtgagaga atacagccat   1860
tcaccaccct cgactctcct ggaagcaggg gcactcaga gcgtgcaca tgttgatata   1920
atggggaact ttgctctgat tgaggacatc atcagaatag ctgctgggc aaccggtgag   1980
gaaattggtg gcgaccaggt ttattcagat atattcaaat ggtcagagaa gatcaaattg   2040
aaaattgtaa                                                          2049

SEQ ID NO: 259          moltype = AA   length = 682
FEATURE                 Location/Qualifiers
source                  1..682
                        mol_type = protein
                        organism = Sorghum bicolor
SEQUENCE: 259
MSLLRRRKQP QPPPPPSDGD GSDHDDSDKG KKPSSSSSSA PPSKEATRRT KAKWSCVDSC     60
CWLVGCVCSA WWLLLFLYNA MPASFPQYVT EAITGPLPDP PGVKLQKEGL RVKHPVVFVP    120
GIVTGGLELW EGHQCAEGLF RKRLWGGTFG DVYKRPLCWV EHMSLDNETG LDKPGIRVRP    180
```

```
VTGLVAADYF VPGYFVWAVL IANLARIGYE EKTMYMAAYD WRLSFQNTEV RDQTLSRIKS    240
NIELMVATNG GNRVVVIPHS MGVLYFLHFM KWVEAPPPMG GGGGPNWCEK HIKAVMNIGG    300
PPLGVPKAVA GLFSSEAKDV AVARAIAPDV LDSDFLGLQT LRHLMRMTRT WDSTMSMIPK    360
GGDTIWGNLD WSPEDGLECK AKKHKTNDTE VSKDSNGENV EVQPEPINYG RLVSFGKDVA    420
EAPSSEIEQI EFRDAVKGNS IAHSNTSCRE IWTEYHELGW GGIKAVEDYK VYTASSVIDL    480
LHFVAPRMMQ RGNVHFSYGI ADNLDDPKYQ HYKYWSNPLE TKLPNAPDME IFSMYGVGIP    540
TERAYVYKVA PQAECNIPFR IDSSAEGGEE NSCLKGGVYL ADGDETVPVL SAGYMCAKGW    600
RGKTRFNPAG SKTYVREYSH SPPSTLLEGR GTQSGAHVDI MGNFALIEDI IRIAAGATGE    660
EIGGDQVYSD IFKWSEKIKL KL                                            682

SEQ ID NO: 260             moltype = DNA   length = 2037
FEATURE                    Location/Qualifiers
source                     1..2037
                           mol_type = other DNA
                           organism = Zea mays
SEQUENCE: 260
atgtcgctcc tgcggcggcg gaagcagcag cagctaccgc cctcggaggg cgacgggtcc     60
gaccacgacg acaacgacaa ggggaagaag ccgtcctcgt cctccgcgcc gccgtccaag    120
gagcccacga ggcggaccaa ggccaagtgg tcgtgcgtgg acagctgctg ctggctggtc    180
gggtgcgtgt gctccgcctg gtggttgctg ctctttctct acaacgcgat gccagcttcg    240
ttcccgcagt atgtcaccga ggccatcacg gggccgctcc cggacccgcc cggggtcaag    300
ctgcagaagg aggggctgcg agctaagcac cccgtcgtct tgtcccccgg catcgtcacc    360
gggggcctcg agctatggga gggacaccaa tgcgctgagg gtctcttccg caagcggcta    420
tggggcggca catttggtga cgtatacaag agacctctat gctgggttga acatatgtcg    480
ttggacaatg aaactggatt agacaaacct ggaataaggg tcaggtcagt cacaggcctt    540
gttgcagcag actatttcgt ccctggatat tttgtttggg ctgtcttaat tgccaattta    600
gctcgtattg gatatgaaga aaagaccatg tacatggctg catatgattg gaggttatct    660
ttccagaaca ctgaggttcg tgatcaaact ttgagcagaa taaagagcaa tattgaactc    720
atggtagcaa caaatggtgg aaatagggtg gtggtgatcc cacactccat gggggtcctc    780
tattttctgc atttttatgaa atgggtcgaa gcacctcctc ccatgggggg cggtggtggt    840
ccgaactggt gtgagaagca tattaaagct gtaatgaata ttggaggacc tttcttagga    900
gttcccaagg ctgttgctgg gcttttctca tctgaagcca aagatgttgc cgttgctaga    960
gctatcgctc ctgatgtcct ggactctgat tttcttggac ttcaaacttt gcgccatttg   1020
atgcgtatga cccgaacatg ggattcaaca atgtcaatgc ttcctaaagg tggtgataca   1080
atttggggaa atctggattg gtctccagaa gatggccttg aatgtaaagc taagcatcat   1140
aaaaccaatg ataccgaggt ttctaaggat agcaatgggg aaaatatcga agttcaacct   1200
gaacctataa actacggaag gctggtatcc ttcggtaaag atgtagcaga ggcaccttct   1260
tcagagattg aacagataga atttcgtgat gctgttaaag gtaacgatat cgtccattca   1320
aatgcatcat gccgggagat ctggacagag taccatgaat taggatgggg tggaataaag   1380
gcagtcgcag actacaaagt ttacactgcc agttctgtta tagaccttct tcactttgtt   1440
gctccaagga tgatgcagcg tggaaatgtc cactttttcat atggaattgc tgataacttg   1500
gatgatccga aatatcaaca ttacaaatat tggtcaaacc ccttgaaaac aaagctaccg   1560
aatgctcctg acatggaaat aatttccatg tacggagtag gcattcctac tgaaagggca   1620
tatgtctaca agttggctcc acaggcagag tgctatatac cattccggat tgacgcctcg   1680
gctgatggcg gggaggaaaa caatgctttg aaggggggtg tttacttagc tgacggcgac   1740
gaaactgttc cagttcttag cgcgggctac atgtgtgcaa aaggggtggcg tggcaaaact   1800
cgtttcaacc ctgccggcag caagacttac gtgagagagt acagccattc accaccctca   1860
actctcctgg aaggcagggg cactcagagc ggtgcacatg ttgatataat ggggaacttc   1920
gctttgatcg aggacatcat caggatagct gccggggcaa ccgtgaggaa aattggtggc   1980
gaccaggttt attcagatat attcaaatgg tcagagaaaa tcaaattgaa attgtaa      2037

SEQ ID NO: 261             moltype = AA   length = 678
FEATURE                    Location/Qualifiers
source                     1..678
                           mol_type = protein
                           organism = Zea mays
SEQUENCE: 261
MSLLRRRKQQ QLPPSEGDGS DHDDNDKGKK PSSSSAPPSK EPTRRTKAKW SCVDSCCWLV     60
GCVCSAWWLL LFLYNAMPAS FPQYVTEAIT GPLPDPPGVK LQKEGLRAKH PVVFVPGIVT    120
GGLELWEGHQ CAEGLFRKRL WGGTFGDVYK RPLCWVEHMS LDNETGLDKP GIRVRSVTGL    180
VAADYFVPGY FVWAVLIANL ARIGYEEKTM YMAAYDWRLS FQNTEVRDQT LSRIKSNIEL    240
MVATNGGNRV VVIPHSMGVL YFLHFMKWVE APPPMGGGGG PNWCEKHIKA VMNIGGPFLG    300
VPKAVAGLFS SEAKDVAVAR AIAPDVLDSD FLGLQTLRHL MRMTRTWDST MSMLPKGGDT    360
IWGNLDWSPE DGLECKAKKH KTNDTEVSKD SNGENIEVQP EPINYGRLVS FGKDVAEAPS    420
SEIEQIEFRD AVKGNDIVHS NASCREIWTE YHELGWGGIK AVADYKVYTA SSVIDLLHFV    480
APRMMQRGNV HFSYGIADNL DDPKYQHYKY WSNPLETKLP NAPDMEIISM YGVGIPTERA    540
YVYKLAPQAE CYIPFRIDAS ADGGEENKCL KGGVYLADGD ETVPVLSAGY MCAKGWRGKT    600
RFNPAGSKTY VREYSHSPPS TLLEGRGTQS GAHVDIMGNF ALIEDIIRIA AGATGEEIGG    660
DQVYSDIFKW SEKIKLKL                                                 678

SEQ ID NO: 262             moltype = DNA   length = 846
FEATURE                    Location/Qualifiers
source                     1..846
                           mol_type = other DNA
                           organism = Sorghum bicolor
SEQUENCE: 262
atgccgccgc ccagcctcac cgcggccgcc gccaccacca caacgcgccg ccgcaaggac     60
cacccggcgc cgggcggagg cgcggggcg aaggagatgg gcgcgcggc ggcgtccgcg    120
gcggaggggt gggcgcggcg gccggagtgg tgctcggcgg cgggcgtggc gggcgtgctg    180
```

```
cggcggcacc cggcgcccgc gctcttcggg tgcggcctcc tgctcttcat ggccgtcgag 240
tacaccatcc ccatggtcag gccggactcc ccgccgctcg acctgggatt catcgccacc 300
aggaacatgc acgccgccgt cgccgccacg ccctggctca actcgctcct cgccgcgctc 360
aacacggtca tcgtcgcgat gcaggcggcg tacatcctgt gggcgatcct ggcggagcag 420
cggccggggg cggccgtcgc ggcgctgatg atgttcacct gccggggcgt gctgggctgc 480
gccacgcagc tgccgctgcc cgaggagttc ctggggtccg gcatggactt ccccgtgggc 540
aacgtctcct tcttcctctt cttctcgggc cacgtcgcgg gcgcggtgat cgcggccgcc 600
gacatgcgcc gcgagggacg ggcggcgctc gcgcgcctct acgacgcgct caacgtgctc 660
caggcggtca ggctgctcgc gtgcaggggA cactacacca tcgacctggc tgtcggcgtc 720
ggggccgggg tcctcttcga cacgctctcc gggtggtact tcgacgccaa gaacggcgac 780
ggcaagaacg cgcccgagaa gcactgccgt agctgccagt gccacaaggc tctcctctca 840
cactag                                                            846

SEQ ID NO: 263           moltype = AA  length = 281
FEATURE                  Location/Qualifiers
source                   1..281
                         mol_type = protein
                         organism = Sorghum bicolor
SEQUENCE: 263
MPPPSLTAAA ATTTTRRRKD HPAPGGGAGA KEMGAAAASA AEGWARRPEW CSAAGVAGVL    60
RRHPAPALFG CGLLLFMAVE YTIPMVRPDS PPLDLGFIAT RNMHAAVAAT PWLNSLLAAL   120
NTVIVAMQAA YILWAILAEQ RPRAAVAALM MFTCRGVLGC ATQLPLPEEF LGSGMDFPVG   180
NVSFFLFFSG HVAGAVIAAA DMRREGRAAL ARLYDALNVL QAVRLLACRG HYTIDLAVGV   240
GAGVLFDTLS GWYFDAKNGD GKNAPEKHCR SCQCHKALLS H                      281

SEQ ID NO: 264           moltype = DNA  length = 849
FEATURE                  Location/Qualifiers
source                   1..849
                         mol_type = other DNA
                         organism = Zea mays
SEQUENCE: 264
atgccgccgc ccagcctcac cgccgccggc accaccacca ccacaacccg ccgccgcaac    60
gaccgagccg cgaaggtcca ccaggtactg gcgaaggcg cggggacgga ggagatgggc    120
gcggtggcgg acgggtggac gcggcccgag tggtgctcgg cggcgggcgt cgcgggcgtg   180
ctgcgcggca acccggcgcc cgcgctcttc gggtgcggcc tcctgctctt catgccgtc    240
gagtacacca tccccatggt caagccggac gcgccgccgc tcgacctagg cttcctcgcc   300
accgcgggca tgcacgccgc catcgccgcg aggcctggc ttaactcgct cctcgccgcg   360
ctcaacacgg tcttcgtcgc gatgcaggcg gcgtacatcc tgtgggccat cctcgccgag   420
cagcggccgg cggcggtcgc cgcgctc atgatgttca cttgccgggg cgtgctgggc   480
tgcgccaccc agctcccgct gccggaggag ttcctggggt ccgggatgga cttccccgtg   540
ggcaacgtct ccttcttcct cttcttctcg gccacgtcg cgggcgcggt gatcgcggcg   600
gccgacatgc ggcgcgaggg cgggctggcg ctggcgcgcc tcttcgactc gctcaacgtg   660
ctccaggtgg tcaggctgct cgcgtgcagg ggacactaca ccattgacct ggctgttgtc   720
gttgggsgcgg catcctcttc cgacacgctc tccggatggt acttcgacgc caagaacggc   780
gatagcagca acgcaccgga gaagcagtgc cggagctgcc agtgccacaa ggccctcctt   840
tcacactag                                                          849

SEQ ID NO: 265           moltype = AA  length = 282
FEATURE                  Location/Qualifiers
source                   1..282
                         mol_type = protein
                         organism = Zea mays
SEQUENCE: 265
MPPPSLTAAG TTTTTRRRN DRAAKVHQVL GEGAGTEEMG AVADGWTRPE WCSAAGVAGV     60
LRRHPAPALF GCGLLLFMAV EYTIPMVKPD APPLDLGFLA TAGMHAAIAA RPWLNSLLAA   120
LNTVFVAMQA AYILWAILAE QRPAAVAAL MMFTCRGVLG CATQLPLPEE FLGSGMDFPV   180
GNVSFFLFFS GHVAGAVIAA ADMRREGRLA LARLFDSLNV LQVVRLLACR GHYTIDLAVG   240
VGAGILFDTL SGWYFDAKNG DSSNAPEKQC RSCQCHKALL SH                     282

SEQ ID NO: 266           moltype = DNA  length = 2223
FEATURE                  Location/Qualifiers
source                   1..2223
                         mol_type = other DNA
                         organism = Sorghum bicolor
SEQUENCE: 266
atgggggggcg ccgtgttggt cgccatcgcg gcctctatcg caacttgct gcagggctgg    60
gacaatgcga caattgctgg agcggtcttg tacataaaga aggaattcaa cttgcagagc   120
gagcccctaa ttgagggcct catcgtggcc atgtccctcc ttggggcaac agtcatcacg   180
acgttctctg gggcagtggc cgactctgtt ggtaggaggc ccatgctgat cgcctcggct   240
atcctctact tgttagtggg ctggtgatg tctcgggcgc caaatgtgta tgtcttgctc   300
cttgcaaggc ttatcgatgg gtttggtatt ggttggccg tcacacttgt tcctttgtac   360
atttctgaga ctgcgccgac ggatattcga ggctgttga acacactacc gcagttcagt   420
ggttcaggag ggatgttcct ttcctactgt atggtgttg aatgtccct catgccaca    480
cctgattgga ggctccatgct tggagttctg tcgatccat cacttattta ctttggattg   540
actatcttct acttgcctga atcaccaagg tggctcgtga gtaaaggaag gatgggcgag   600
gcaaagcgca tgttgcaaag gctgcgggga agggaagatg tctcagggga aatggctctt   660
ctagttgaag gtttgggggt tgggaaagat acacgtattg aagaatacat aattggccct   720
gatgacgagc ttgctgatga agggctggct ccgatccaga gaagatcaa attatatgga   780
cctgaagaag gtctatcttg ggttgcccga cctgttcggg gacaaagtgc tcttggaagc   840
```

```
gcattaggtc tcatctctcg tcatgggagt atggctagtc agggtaagcc cctcgtggat    900
cctgtggtca ctcttttcgg aagtgttcat gaaaagatgc ctgagataat ggggagcatg    960
aggagcacat tgtttcccaa ctttggcagc atgtttagtg ttgccgaaca gcagcaggtg   1020
aaggctgact gggatgccga gagtcaaagg gagggtgacg attatgcttc agatcatggt   1080
ggcgatgca ttgaggataa cctccaaagc ccacttattt ctcgtcaagc aacaagtgtg    1140
gaaggaaagg agattgctgc acctcatggt agcataatgg gtgctgtggg aagaagcagt   1200
agcctgcagg gaggggaggc agtaagcagc atgggcattg gtggaggatg gcagttggcg   1260
tggaaatgga ctgagagaga gggcgaagat ggggaaaagg aaggtggctt ccagcgtatt   1320
tatttgcatg aggagggcgt acaaggcagg ggttctatat tgtcattacc aggaggggat   1380
gttcctcctg gtggtgagtt cgtccaggct gcagctcttg tgagtcaacc agctctttac   1440
tcaaaggaac tgctggagca acgtgctgct ggtcctgcga tgatgcatcc atctgaggca   1500
gttgctaaag tccaagatg gctgacctg tttgagcctg gagtgaagca tgcactgttt    1560
gttggcatag aatacagat cctgcaacag tttgctggca tcaatggtgt tctctactac    1620
actcctcaaa ttcttgagca agcaggtgtt ggtgttcttc tgtcgaacat tggccttagc   1680
gcatcttctg catcaattct tattagtgcc ttgacaacct tattgatgct tccaagcatt   1740
ggtattgcaa tgaggctcat ggatatgtct ggaaggaggt tcttctcct tgcgacaatc    1800
cctatcttga tagttgccct agctatcttg gtcgtggtca atattgtgga tgtgggaacc   1860
atggtgcatg ctgcactctc cacgattagt gtcatagtct atttctgctt ctttgtcatg   1920
gggtttgggc ctattcccaa cattctctgt gcagagatct ttcccaccac cgtccgcggc   1980
atctgcatag ccatctgcgc cttaaccttc tggattggtg acattatcgt gacatacaca   2040
cttcctgtga tgctgaatgc catcgggctc gctggtgtct tgggatata cgccgtcgtt    2100
tgcatcctgc tcttgtatt tgtattcatc aaggtgccag agacaaaggg catgcctctc   2160
gaggtcatca ctgagttctt ctccgttgga gcaaagcaag ccaaggaagc cagggaagat   2220
taa                                                                 2223
SEQ ID NO: 267         moltype = AA   length = 740
FEATURE                Location/Qualifiers
source                 1..740
                       mol_type = protein
                       organism = Sorghum bicolor
SEQUENCE: 267
MGGAVLVAIA ASIGNLLQGW DNATIAGAVL YIKKEFNLQS EPLIEGLIVA MSLIGATVIT    60
TFSGAVADSV GRRPMLIASA ILYFVSGLVM LWAPNVYVLL LARLIDGFGI GLAVTLVPLY   120
ISETAPTDIR GLLNTLPQFS GSGGMFLSYC MVFGMSLMPT PDWRLMLGVL SIPSLIYFGL   180
TIFYLPESPR WLVSKGRMAE AKRVLQRLRG REDVSGEMAL LVEGLGVGKD TRIEEYIIGP   240
DDELADEGLA PDPEKIKLYG PEEGLSWVAR PVRGQSALGS ALGLISRHGS MASQGKPLVD   300
PVVTLFGSVH EKMPEIMGSM RSTLFPNFGS MFSVAEQQQV KADWDAESQR EGDDYASDHG   360
GDDIEDNLQS PLISRQATSV EGKEIAAPHG SIMGAVGRSS SLQGGEAVSS MGIGGGWQLA   420
WKWTEREGED GEKEGGFQRI YLHEEGVQGR GSILSLPGGD VPPGGEFVQA AALVSQPALY   480
SKELLEQRAA GPAMMHPSEA VAKGPRWADL FEPGVKHALF VGIGIQILQQ FAGINGVLYY   540
TPQILEQAGV GVLLSNIGLS ASSASILISA LTTLLMLPSI GIAMRLMDMS GRRFLLLATI   600
PILIVALAIL VVVNIVDVGT MVHAALSTIS VIVYFCFFVM GFGPIPNILC AEIFPTTVRG   660
ICIAICALTF WIGDIIVTYT LPVMLNAIGL AGVFGIYAVV CILALVFVFI KVPETKGMPL   720
EVITEFFSVG AKQAKEARED                                               740
SEQ ID NO: 268         moltype = DNA   length = 2244
FEATURE                Location/Qualifiers
source                 1..2244
                       mol_type = other DNA
                       organism = Zea mays
SEQUENCE: 268
atgggggcg ccgtgatggt cgccatcgcg gcctctatcg gcaacttgct gcagggctgg     60
gacaatgcga caattgctgg agccgtcctg tacataaaga aggaattcaa cctgcagagc   120
gagcctctga tcgagggcct catcgtcgcc atgtccctca ttggggcaac agtcatcacg   180
acgttctccg gggcagcggc cgactgcgtt ggtaggaggc ccatgctggc cgcctcggct   240
gtcctctact tcgtcagtgg gctggtgatg ctttgggcgc caagtgtgta catcttgctc   300
ctcgcaaggc tcattgatgg gttcggtatc ggttttggcg gtcacacttgt tcctctctac   360
atctccgaga ctgcaccgac agacattcgt gggctgttga acacgttgcc gcagttcagt   420
gggtcaggag ggatgttcct ctcctactgc atggtgtttg ggatgtccct catgcccaaa   480
cctgattgga ggctcatgct tggagttctg tcgatccatt cacttattta ctttggactg   540
actgtcttct acttgcctga atcaccaagg tggcttgtga gcaaaggaag gatggcggag   600
gcgaagagag tgttgcaaag gctgcgggga agagaagatg tctcagggga gatggctctt   660
ctagttgaag gtttgggggt cggtaaagat acacgtattg aagaatacat aattggtccc   720
gatgatgaac ttgctgatga agggctggct ccagatccag aagatcaa actatatgga    780
cctgaagaag gcctacttg ggttgcccga cctgttcggg gacaaagtgc tcttggaagc    840
gcgttaggtc tcatctctcg tcatgggagt atggcggcta gtcagggtaa gcccctcgtg    900
gatcctatgg tcactctttt cggaagtgtt catgaaaaga tgcctgagat catggggagc    960
atgaggagca cattgtttcc caactttggc agcatgtttg tgttgccga ccagcagcag   1020
gtgaaagctg actgggacgc cgagagtcaa agggaaggtg aagattatgc ttcggatcat   1080
ggtggcgatg acatcgagga taacctccaa agcccactta tttctcgtca ggcaacaagt   1140
gtggaaggaa aggagatcgc tgcacctcat ggtagcatat gggtgctgt gggaaggagc    1200
agtagcttgc agggagggga ggcagtaagc agcatgggca ttggcggagg atggcagttg   1260
gcgtggaaat ggaccgagag agagggcgaa gatgggcaaa aggaaggtgg cttccagcgt   1320
atttacttgc atgaggaggg cgtacaaggc attacaggc                         1380
gggatgttc tcctggtgg tgagttcatc caggctgcag ctcttgtgag ccaaccagct    1440
ctttactcta aggaactgct ggagcaacgt gctgctggtc ctgcgatgat gcatccatct   1500
gaagcagtta ctaaaggtcc aagatgggcc gacctatttg agcctggggt gaagcatgca   1560
ctgtttgttg gcataggaat acagatcctg caacagtttg ctggcatcaa cggcgttctc   1620
tactacactc tcaaattct tgagcaagca ggcgttggtg ttcttctgtc gaacctcggc    1680
```

-continued

```
cttaacgctt cttcggcatc aatcctcatt agcgccctga cgaccttact gatgctccca 1740
agcatcggca ttgcgatgag gctcatggat atgtccggaa ggaggtttct cctcctcgcg 1800
acgatcccag tcctaatagt cgcgctactc gtcctggtgg tgtccaacat cgtggacgtg 1860
ggggacgtgg cgcacgcggc gctctccacg gccagcgtca tagtctactt ctgcttcttc 1920
gtcatggggt tcgggcccgt ccccaacatc tctgcgacaa agatcttccc caccacggtc 1980
cgcggtgtct gcatcgccat ctgcgccctg gccttctggc tcggtgacat catcgtgacg 2040
tacactctcc ccgtgatgct gaacgtcgtc gggctcgccg gcgtctttgg ggtgtacgcc 2100
gtcgtgtgcg tcctagccct cgcgttcgtg ttcgtcaagg tgcccgagac gaagggcatg 2160
cctctcgagg tcatcaccga gttcttctcc gttggggcaa agcaagccaa ggaagaggag 2220
gaggaggagg ccagggaagg ttga                                        2244
```

```
SEQ ID NO: 269          moltype = AA  length = 747
FEATURE                 Location/Qualifiers
source                  1..747
                        mol_type = protein
                        organism = Zea mays
SEQUENCE: 269
MGGAVMVAIA ASIGNLLQGW DNATIAGAVL YIKKEFNLQS EPLIEGLIVA MSLIGATVIT   60
TFSGAAADCV GRRPMLVASA VLYFVSGLVM LWAPSVYILL LARLIDGFGI GLAVTLVPLY  120
ISETAPTDIR GLLNTLPQFS GSGGMFLSYC MVFGMSLMPK PDWRLMLGVL SIPSLIYFGL  180
TVFYLPESPR WLVSKGRMAE AKRVLQRLRG REDVSGEMAL LVEGLGVGKD TRIEEYIIGP  240
DDELADEGLA PDPEKIKLYG PEEGLSWVAR PVRGQSALGS ALGLISRHGS MAASQGKPLV  300
DPMVTLFGSV HEKMPEIMGS MRSTLFPNFG SMFSVADQQQ VKADWDAESQ REGEDYASDH  360
GGDDIEDNLQ SPLISRQATS VEGKEIAAPH GSILGAVGRS SSLQGGEAVS SMGIGGGWQL  420
AWKWTEREGE DGQKEGGFQR IYLHEEGVQG NRGSILSLPG GDVPPGGEFI QAAALVSQPA  480
LYSKELLEQR AAGPAMMHPS EAVTKGPRWA DLFEPGVKHA LFVGIGIQIL QQFAGINGVL  540
YYTPQILEQA GVGVLLSNLG LNASSASILI SALTTLLMLP SIGIAMRLMD MSGRRFLLLA  600
TIPVLIAVLL VLVVSNIVDV GDVAHAALST ASVIVYFCFF VMGFGPVPNI LCAEIFPTTV  660
RGVCIAICAL AFWLGDIIVT YTLPVMLNVV GLAGVFGVYA VVCVLALAFV FVKVPETKGM  720
PLEVITEFFS VGAKQAKEEE EEEAREG                                     747
```

```
SEQ ID NO: 270          moltype = DNA  length = 2238
FEATURE                 Location/Qualifiers
source                  1..2238
                        mol_type = other DNA
                        organism = Sorghum bicolor
SEQUENCE: 270
atgtcggggg ctgttcttgt cgccatcgcc gcctccatcg gcaatctgtt gcagggggtgg   60
gacaatgcca ccatcgcagg tgctgttctg tacataaaga aggaattcca attacaaaat  120
gagcccactg tggaggggct gattgtggcc atgtcactta ttggtgccac catcatcact  180
acattctctg gccagtatc agactggatc ggccgccgcc ctatgctcat cctctcgtca  240
attctgtact ttctcagcag cctcatcatg ctatggtccc ctaatgtcta tgtcctgctg  300
ctggcacgcc tcgtagacgg attcggtatt ggcttggtgc tcacgcttgt ggcctttgta  360
atttcagaaa cagcccctcc agagattaga ggtttgctga atacactgcc acagttcagt  420
ggatcaggag ggatgttctt gtcatactgc atggtgtttg ggatgtcact gttgccatca  480
cctgattgga gaattatgct tggggtgctc gcgataccatt cattgttctt ctttggattg  540
acaatattt acctttcctga atccccaaga tggcttgtta gcaaaggtcg gatgcagag  600
gcaaagaagg tgttgcaaaa attacgcagc aaagaagatg tctcaggtga attgtcccctt  660
cttgttgaag ggttggaggt tggaggagaca acttcgattg aagagtacat cattggcct  720
gccactgacg cagccgatga tcatgttact gatggtgata aggaacaaat cacactttat  780
gggcctgaag aaggccagtc atggattgct cgaccttcca aggacccag catgcttgga  840
agtgtacttt ctctcgcatc tcgtcatggc agcttggtga accagagtgt accccttatg  900
gatccgattg tgacactttt tgggagtgtc catgagaata tgcctcaagc tggaggaagt  960
atgaggagca cattgtttcc aaactttgga agtatgttca gtgtcacaga tcagcatgcc 1020
aaaaatgagc agtgggacga agagaattct cacagggacg ttggagagta tgcatctgat 1080
ggtgcaggag gtgattatga ggacaatctc cacagtccat tgctgtccag gcagacaaca 1140
agtgcggaag gaaggacat tgtgcaccat ggtcaccgtg gaagttcttt gagcatgaga 1200
aggcaaagcc tcttggggga ggctggagag ggtgtgagca gcactgatat tggtggggga 1260
tggcagcttg catggaaatg gtcagagaag gaaggtgagg atggtaagaa ggaaggtggt 1320
ttcaaaagag tctacttgca ccaaggggga gttcctggct caagaatggg ctcaattgtt 1380
tcacttcctg gtggtggcga tgttcatgag ggtggcgagt ttgtacatgc tgctgcttta 1440
gtaagccagt cagcactttt ctcgaaggat cttaccgaac cacgcatgtc tggtgctgcc 1500
atgattaacg catccgaggt agccgccaaa ggttcaagct ggaagagattt gtttgaacct 1560
ggtgtgaggc gtgccctgtt agtcggtgtt ggaattcaga tccttcaaca gtttcgtgga 1620
atcaatggtg ttctgtacta taccccacaa attctcgagc aagctggcgt ggcagttctt 1680
ctttccaatc ttggtctcag ctcagcatca gcatctatct tgatcagttc tcactacc 1740
ttactgatgc ttcctagcat tggcttagcc atgagactta tggatctttc tggaagaagg 1800
tttttgctgc taggcacaat tccaatcttg atagcatctt tagttatcct ggtcgtgtct 1860
aatgtgattg acctgggtac agtggccat gctgcgctct ccacagtcag tgtcatcatc 1920
tacttctgct gctttgtcat gggatttggt cccatcccca acattctatg tgcagagatc 1980
tttccaacca gggttcgcgg tctctgcatt gccatctgtg ccttgacgtt ttggattgga 2040
gacatcattg tcacctacag ccttcctgta atgctgaatg ctattggact agcaggtgtt 2100
tttggcatat atgcagtcgt atgcttgatt gcctttgtgt ttgtcttcct taaggttcct 2160
gagacaaagg gaatgcccct tgaagtcatc actgagttct ttgcagttgg tgcgaagcaa 2220
gcggctgcaa aagcctaa                                              2238
```

```
SEQ ID NO: 271          moltype = AA  length = 745
FEATURE                 Location/Qualifiers
source                  1..745
```

```
                        mol_type = protein
                        organism = Sorghum bicolor
SEQUENCE: 271
MSGAVLVAIA ASIGNLLQGW DNATIAGAVL YIKKEFQLQN EPTVEGLIVA MSLIGATIIT      60
TFSGPVSDWI GRRPMLILSS ILYFLSSLIM LWSPNVYVLL LARLVDGFGI GLAVTLVPLY     120
ISETAPPEIR GLLNTLPQFS GSGGMFLSYC MVFGMSLLPS PDWRIMLGVL AIPSLFFFGL     180
TIFYLPESPR WLVSKGRMAE AKKVLQKLRS KEDVSGELSL LVEGLEVGGD TSIEEYIIGP     240
ATDAADDHVT DGDKEQITLY GPEEGQSWIA RPSKGPSMLG SVLSLASRHG SLVNQSVPLM     300
DPIVTLFGSV HENMPQAGGS MRSTLFPNFG SMFSVTDQHA KNEQWDEENL HRDDEEYASD     360
GAGGDYEDNL HSPLLSRQTT SAEGKDIVHH GHRGSSLSMR RQSLLGEAGE GVSSTDIGGG     420
WQLAWKWSEK EGEDGKKEGG FKRVYLHQEG VPGSRMGSIV SLPGGGDVHE GGEFVHAAAL     480
VSQSALFSKD LTEPRMSGAA MINASEVAAK GSSWKDLFEP GVRRALLVGV GIQILQQFAG     540
INGVLYYTPQ ILEQAGVAVL LSNLGLSSAS ASILISSLTT LLMLPSIGLA MRLMDLSGRR     600
FLLLGTIPIL IASLVILVVS NVIDLGTVAH AALSTVSVII YFCCFVMGFG PIPNILCAEI     660
FPTRVRGLCI AICALTFWIG DIIVTYSLPV MLNAIGLAGV FGIYAVVCLI AFVFVFLKVP     720
ETKGMPLEVI TEFFAVGAKQ AAAKA                                          745

SEQ ID NO: 272          moltype = DNA   length = 2238
FEATURE                 Location/Qualifiers
source                  1..2238
                        mol_type = other DNA
                        organism = Zea mays
SEQUENCE: 272
atgtcggggg ctgttcttgt cgccatagtc gcctccatcg gcaatctatt gcaggggtgg      60
gacaatgcca ccatcgcagc tgctgttctg tatataaaga aggaatttca attgcaaaat     120
gagcccactg tggagggact aattgtgtca atgtcactta tcggcgccac catcgttact     180
acattctccg ggccattatc agactcgatt ggccgacgcc ctatgcttat tctctcttca     240
attctgtact tcttcagcgg cctcatcatg ctatggtctc ctaatgtcta tgtcctgctg     300
ttggcacgct tcgtagatgg atttggtatt ggcttggctg tcacgcttgt gcctttgtac     360
atttcagaaa tagcccttc ggagattaga ggtttgctga atacactacc acaattcagt     420
ggatcaggag gaatgttctt gtcatactgc atggtgtttg gatgtccct gtcgccatca     480
cccgattgga gaattatgct tggtgtgctc gcgataccct cattgttctt ctttggtttg     540
acaatatttt atcttcctga atctccaaga tggctcgtta gcaaaggtcg gatggcagag     600
gcaaaaaagg tgttgcaaaa gttacggggg aaagacgatg tctcaggtga attgtccctt     660
cttctcgaag ggttggaggt tggaggagac acttccattg aagagtacat cattggacct     720
gccaccgagg cagccgatga tcttgttact gacggtgata aggaacaaat cacactttat     780
gggcctgaag aaggccagtc atggattgct cgaccttcca agggacccag catgcttgga     840
agtgtgcttt ctcttgcatc tcgtcatggg agcatggtga accagagtgt accccttatg     900
gatccgattg tgacacttt tggtagtgtc catgagaata tgcctcaagc tggaggaagt     960
atgaggagca cattgtttcc aaactttgga agtatgttca gtgtcacaga tcagcatgcc    1020
aaaaatgagc agtgggatga agagaatctt cataggatg acgaggagta cgcatctgat    1080
ggtgcaggag gtgactatga ggacaatctc catagcccat tgctgtccag gcaggcaaca    1140
ggtgcggaag ggaaggacat tgtgcaccat ggtcaccgtg gaagtgcttt gagcatgaga    1200
aggcaaagcc tcttagggga gggtggagat ggtgtgagca gcactgatat cggtgggga    1260
tggcagcttg cttggaaatg gtcagagaag gaaggtgaga atggtagaaa ggaaggtggt    1320
ttcaaaagag tctacttgca ccaagagga gttcctggct caagaagggg ctcaattgtt    1380
tcactcccg gtggtggcga tgttcttgag ggtagtgati ttgtacatgc tgctgcttta    1440
gtaagtcagt cagcactttt ctcaaagggt cttgctgaac acgcatgtc agatgctgcc    1500
atggttcacc catctgaggt agctgccaaa ggttcacgtt ggaaagattt gtttgaacct    1560
ggagtgaggc gtgccctgtt agtcggtgtt ggaattcaga tccttcaaca gtttgctgga    1620
ataaacggtg ttctgtacta tacccacaa attcttgagc aagctggtgt ggcagttatt    1680
ctttccaaat ttggtctcag ctcggcatca gcatccatct tgatcagttc tctcactacc    1740
ttactaatgc ttccttgcat tgggcttgcc atgctgctta tggatctttc cggaagaagg    1800
ttttgctgc taggcacaat tccaatcttg atagcatctc tagttatcct ggttgtgtcc    1860
aatctaattg atttgggtac actagcccat gctttgtcc ccaccgtcag tgttatcgtc    1920
tacttctgct gcttcgttat gggatttggt cccatcccca catttttatg tgcagagatc    1980
tttccaacca gggttcgtgg cctctgtatt gccatttgtg cctttacatt ctggatcgga    2040
gatatcatcg tcacctacag ccttcctgtg atgctgaatg ctattggact ggcgggtgtt    2100
ttcagcatat atgcagtcgt atgcttgatt cctttgtgt tcgtcttcct taaggtccct    2160
gagacaaagg ggatgcccct tgaggttatt accgaattct ttgcagttgg tgcgaagcaa    2220
gcggctgcaa aagcctaa                                                  2238

SEQ ID NO: 273          moltype = AA    length = 745
FEATURE                 Location/Qualifiers
source                  1..745
                        mol_type = protein
                        organism = Zea mays
SEQUENCE: 273
MSGAVLVAIV ASIGNLLQGW DNATIAAAVL YIKKEFQLQN EPTVEGLIVS MSLIGATIVT      60
TFSGPLSDSI GRRPMLILSS ILYFFSGLIM LWSPNVYVLL LARFVDGFGI GLAVTLVPLY     120
ISEIAPSEIR GLLNTLPQFS GSGGMFLSYC MVFGMSLSPS PDWRIMLGVL AIPSLFFFGL     180
TIFYLPESPR WLVSKGRMAE AKKVLQKLRG KDDVSGELSL LLEGLEVGGD TSIEEYIIGP     240
ATEAADDLVT DGDKEQITLY GPEEGQSWIA RPSKGPSMLG SVLSLASRHG SMVNQSVPLM     300
DPIVTLFGSV HENMPQAGGS MRSTLFPNFG SMFSVTDQHA KNEQWDEENL HRDDEEYASD     360
GAGGDYEDNL HSPLLSRQAT GAEGKDIVHH GHRGSALSMR RQSLLGEGGD GVSSTDIGGG     420
WQLAWKWSEK EGENGRKEGG FKRVYLHQEG VPGSRRGSIV SLPGGGDVLE GSEFVHAAAL     480
VSQSALFSKG LAEPRMSDAA MVHPSEVAAK GSRWKDLFEP GVRRALLVGV GIQILQQFAG     540
INGVLYYTPQ ILEQAGVAVI LSKFGLSSAS ASILISSLTT LLMLPCIGFA MLLMDLSGRR     600
FLLLGTIPIL IASLVILVVS NLIDLGTLAH ALLSTVSVIV YFCCFVMGFG PIPNILCAEI     660
```

```
FPTRVRGLCI AICAFTFWIG DIIVTYSLPV MLNAIGLAGV FSIYAVVCLI SFVFVFLKVP    720
ETKGMPLEVI TEFFAVGAKQ AAAKA                                         745

SEQ ID NO: 274           moltype = DNA  length = 1464
FEATURE                  Location/Qualifiers
source                   1..1464
                         mol_type = other DNA
                         organism = Sorghum bicolor
SEQUENCE: 274
atggtgccgg accagtggta cgacaccaac ggcgtctgga caggctccgc caccacgctc    60
cccgacggcc gcctcgccat gctctacacc ggctccacca cgcctccgt gcaggtgcag    120
tgcctcgccg tccccgccga cgacgccgac ccgctgctca ccaactggac caagtacgag    180
ggcaacccgg tcctgtaccc gccgccgggg atcgggccca aggacttccg tgaccccacc    240
acggctggt tcgacccgtc ggacaacacc tggcgcatcg tcatcgggtc caaggacgag    300
gccgagggcg accacgccgg catcgccgtc gtctacaccg ccaaggactt cgtcagcttc    360
gagctcctcc ccggcctcct ccaccgcgtc gcgaggacgg ggatgtggga gtgcatcgac    420
ttctaccccg tcgccacccg cggcaaggcg tccgggaacg gcgtcgacat gtccgacgcc    480
ttcggcaaga acggcgccat tgttgggcaa gtcgtgcagc ttatgaaggc cagcatggac    540
gacgaccgcc atgactacta cgcgctcggg aggtacgatg cggccaccaa cgagtggacg    600
ccgctcgacg ccgagaagga cgtcggcatc gggctccggt atgactgggg caagttttac    660
gcgtccaaga ccttctatga ccccgccaag cgccgccgtg tgctctgggg atgggtcggc    720
gagaccgact cggagcgcgc tgacgtctcc aagggatggg catcgttgca gggtatcccc    780
cggacggtgc tgctggacac caagacgggg agcaacctgc tgcagtggcc cgtggaggaa    840
gcggagacgc tgcgcaccaa ctccacggac ctcagcggca tcaccatcga ctacggctcg    900
gcgttccgc tcaacctccg gcgcgccacg cagctggaca tcgaggcgga gttccagctc    960
gaccgccgcg ccgtcatgtc gctcaacgag gccgacgtgg ggtacaactg cagcacgagc    1020
ggtggcgccg cggccgcggg tgccctcggc ccttcggcc tgctcgtcct cgccgaccag    1080
cacctgcgcg agcagacggc cgtctacttc tacgtggcca agggcctgga cggctccctc    1140
accacgcact tgccagga cgagtcccgg tcctccagcg ccaacgacat cgtcaagcgc    1200
gtcgtcggca gctccgtccc cgtgctggac gacgagacca cgctctcgct ccgcgtgctc    1260
gtcgaccact ccatcgtcga gagcttcgcg cagggcggaa ggtcgacggc aacctcgcgc    1320
gtctacccca ccgaggccat ctacgccaac gccggcgtgt tcctcttcaa caacgccacc    1380
gccgcgcgcg tcaccgccaa gaagctcgtc gtccacgaga tggactcatc ctacaaccac    1440
gactacatgg tcacggacat ctga                                         1464

SEQ ID NO: 275           moltype = AA  length = 487
FEATURE                  Location/Qualifiers
source                   1..487
                         mol_type = protein
                         organism = Sorghum bicolor
SEQUENCE: 275
MVPDQWYDTN GVWTGSATTL PDGRLAMLYT GSTNASVQVQ CLAVPADDAD PLLTNWTKYE    60
GNPVLYPPPG IGPKDFRDPT TAWFDPSDNT WRIVIGSKDD AEGDHAGIAV VYRTKDFVSF    120
ELLPGLLHRV ARTGMWECID FYPVATRGKA SGNGVDMSDA FGKNGAIVGD VVHVMKASMD    180
DDRHDYYALG RYDAATNEWT PLDAEKDVGI GLRYDWGKFY ASKTFYDPAK RRRVLWGWVG    240
ETDSERADVS KGWASLQGIP RTVLLDTKTG SNLLQWPVEE AETLRTNSTD LSGITIDYGS    300
APFPLNLRRAT QLDIEAEFQL DRRAVMSLNE ADVGYNCSTS GGAAARGALG PPGLLVLADQ    360
HLREQTAVYF YVAKGLDGSL TTHFCQDESR SSSANDIVKR VVGSSVPVLD DETTLSLRVL    420
VDHSIVESFA QGGRSTATSR VYPTEAIYAN AGVFLFNNAT AARVTAKKLV VHEMDSSYNH    480
DYMVTDI                                                            487

SEQ ID NO: 276           moltype = AA  length = 638
FEATURE                  Location/Qualifiers
source                   1..638
                         mol_type = protein
                         organism = Sorghum bicolor
SEQUENCE: 276
METRDTTAPL PYSYTPLPAA DAASAEVTGT GHRGGRSRRR SLCAAALVLS AALLLAVAAL    60
TGVGRRVDVV PGGAGSPRST SSISRGPDAG VSEKTSGAWS GGGRLRSPVY YKGWYHLFYQ    120
YNPDGAIWGN KIAWGHAVSR DLIHWRHLPL AMVPDQWYDT NGVWTGSATT LPDGRLAMLY    180
TGSTNASVQV QCLAVPADDA DPLLTNWTKY EGNPVLYPPP GIGPKDFRDP TTAWFDPSDN    240
TWRIVIGSKD DAEGDHAGIA VVYRTKDFVS FELLPGLLHR VARTGMWECI DFYPVATRGK    300
ASGNGVDMSD AFGKNGAIVG DVVHVMKASM DDDRHDYYAL GRYDAATNEW TPLDAEKDVG    360
IGLRYDWGKF YASKTFYDPA KRRRVLWGWV GETDSERADV SKGWASLQGI PRTVLLDTKT    420
GSNLLQWPVE EAETLRTNST DLSGITIDYG SAFFPLNLRRA TQLDIEAEFQ LDRRAVMSLN    480
EADVGYNCST SGGAAARGAL GPPGFGLLVLAD QHLREQTAVY FYVAKGLDGS LTTHFCQDES    540
RSSSANDIVK RVVGSSVPVL DDETTLSLRV LVDHSIVESF AQGGRSTATS RVYPTEAIYA    600
NAGVFLFNNA TAARVTAKKL VVHEMDSSYN HDYMVTDI                          638

SEQ ID NO: 277           moltype = DNA  length = 2022
FEATURE                  Location/Qualifiers
source                   1..2022
                         mol_type = other DNA
                         organism = Zea mays
SEQUENCE: 277
atggagaccc gggacacgga tgcgacgccc ctcccctact cgtacacgcc gctgccggcc    60
gccgacgccg cgtcggccga ggtctccggc accggcagga cgcggagcag gcggcggccc    120
ctctgcgcgc ggcgctcgt gctctccgcc gcgctgctcc tagccgtggc cgcgctcgtc    180
ggcgtcggta gccggcccgg cgcggtgggg atgacagagt cggcggcctc gtcgccgacg    240
```

```
ccgagcagga gcaggggccc cgaggccggc gtgtccgaga agacgtccgg cgcgtctgac   300
gacggcggca ggctccgtgg agccggcggg aacgccttcc cgtggagcaa tgcgatgctg   360
cagtggcagc gcacgggatt ccacttccag ccgcagaaga actggatgaa cgaccccaat   420
ggccccgtgt actacaaggg ctggtaccac ctcttctacc agtacaaccc tgacggcgcc   480
atctggggca acaagatcgc gtggggccac gccgtgtgcg gcgacctgat ccactggcgc   540
cacctcccgc tggccatggt gcccgaccag tggtacgaca ccaacggcgt gtggacgggg   600
tccgccacca cgctccccga cggccgcctc gccatgctct acacgggctc caccaacgcc   660
tccgtccagg tgcagtgcct ggccgtgccc gccgacgacg ccgacccgct gctcaccaac   720
tggaccaagt acgagggcaa cccggtgctg tacccgcccc cgggcatcgg gcccaaggac   780
ttccgcgacc ccaccacggc ctggatcgac ccctcggacg gcgcatggcc cgtcgtcatc   840
ggctccaagg acgacgacgg ccacgcgggc atcgccgtcg tctaccgcac cacggacctg   900
gtgcacttcg agctcctccc gggcctgctc accgcgtcg acggcaccgg catgtgggag   960
tgcatcgact tctaccccgt cgccacgcga ggcaggcgt cggccaacgg cgtcgacatg  1020
tccgacgcca tcgccagcaa cggcgccgtc ggcgacgtgg tcctgcacgt catgaaggcc  1080
agcatggacg acgaccgcca cgactactac gcgctgggga ggtacgacgc ggccgccaac  1140
gcctggacgc cgatcgacgc cggcagggac gtcggcatcg gcctgcgcta cgactggggc  1200
aagttctacg cgtccaagac cgttctacgac ccggccaagc cgccgccgt gctgtgggga  1260
tgggttggcg agacagactc ggagcgcgcg gacgtgtcca agggatgggc gtcgctgcag  1320
ggtatccccc ggacggtgct cctggacacc aagacgggta gcaacctgct gcagtggccc  1380
gtggaggagg tggagacgct gcgcaccaac tccaccgacc tcagcggcat caccatcgac  1440
tacggctccg tgttcccgct caacctccgc cgcgccaccc agctggacat cgaggcggag  1500
ttccagctgg accgccgcgc tgtcatgtcg ctcaacgagg cggacgtggg ctacaactgc  1560
agcaccagcg gggcgccgc cggccgcggc gcgctgggcc ccttcggcct gctcgtcctc  1620
gccgaccgcc gcctccgccg cgagcagacg gccgtctact tctacgtggc caagggcctg  1680
gacggctccc tcgccacgca cttctgccag gacgagtccc gctcctccag cgccaccgac  1740
atcgtcaagc gcgtcgtcgg cagcgccgtc ccgtgcctgg aggacgaggc cacgctctcg  1800
ctccgggtgc tcgtcgacca ctccatcgtc gagagcttcg cgcagggcgg gaggtccacc  1860
gccacatcgc gcgtctaccc caccgaggcc atctacgcca acgccggcgt cttcctcttc  1920
aacaacgcca ccgccgcgcg ggtcacggcc acgaagctcg tcgtccacga gatggactcg  1980
tcatacaacc acgactacat ggcgccggtg cagacatct ga                      2022

SEQ ID NO: 278         moltype = AA  length = 673
FEATURE                Location/Qualifiers
source                 1..673
                       mol_type = protein
                       organism = Zea mays
SEQUENCE: 278
METRDTDATP LPYSYTPLPA ADAASAEVSG TGRTRSRRRP LCAAALVLSA ALLLAVAALV    60
GVGSRPGAVG MTESAASSPT PSRSRGPEAG VSEKTSGASD DGGRLRGAGG NAFPWSNAML   120
QWQRTGFHFQ PQKNWMNDPN GPVYYKGWYH LFYQYNPDGA IWGNKIAWGH AVSRDLIHWR   180
HLPLAMVPDQ WYDTNGVWTG SATTLPDGRL AMLYTGSTNA SVQVQCLAVP ADDADPLLTN   240
WTKYEGNPVL YPPPGIGPKD FRDPTTAWID PSDGAWRVVI GSKDDDGHAG IAVVYRTTDL   300
VHFELLPGLL HRVDGTGMWE CIDFYPVATR GRASANGVDM SDAIASNGAV AGDVLHVMKA   360
SMDDDRHDYY ALGRYDAAAN AWTPIDAGRD VGIGLRYDWG KFYASKTFYD PAKRRRVLWG   420
WVGETDSERA DVSKGWASLQ GIPRTVLLDT KTGSNLLQWP VEEVETLRTN STDLSGITID   480
YGSVFPLNLR RATQLDIEAE FQLDRRAVMS LNEADVGYNC STSGGAAGRG ALGPFGLLVL   540
ADRRLRREQT AVYFYVAKGL DGSLATHFCQ DESRSSSATD IVKRVVGSAV PVLEDEATLS   600
LRVLVDHSIV ESFAQGGRST ATSRVYPTEA IYANAGVFLF NNATAARVTA TKLVVHEMDS   660
SYNHDYMAPV ADI                                                     673

SEQ ID NO: 279         moltype = DNA  length = 2451
FEATURE                Location/Qualifiers
source                 1..2451
                       mol_type = other DNA
                       organism = Sorghum bicolor
SEQUENCE: 279
atgggggaag ctgccggtga ccgtgttctg agccgcctcc acagcgtcag ggagcgcatt    60
ggcgattcac tctctgccca ccccaatgag cttgtcgccg tcttcaccag gctgaaaaac   120
cttggaaagg gtatgctgca gccccaccag atcattgccg agtacaacag tgctatccct   180
gaggctgaac gtgagaagct gaaggatggt gcctttgagg atgtcctgag ggcagctcag   240
gaagcaattg ttatccccc atgggttgca cttgccatcc gccctaggcc tggtgtctgg   300
gagtatgtga gggtcaacgt cagcgagctc gctgttgagg agctgagagt ccctgagtac   360
ctgcagttca aggaacagct tgtggaagaa ggccccaaca caactttgt tcttgagctg   420
gactttggac cattcaatgc gtccttcccc cgtccttctc tgtcaaagtc cattggcaat   480
ggtgtgcagt tcctcaacag gcacctgtca tcaaagctct ccatgacaa ggagagcatg   540
tacccccttgc tcaacttcct tcgtgcccac aactacaagg gatgaccat gatgttgaac   600
gacagaatcc gcagtctcag tgctctgcaa ggcgctctga ggaagctga ggagcacctg   660
tccaccctcc aagctgatac cccatactct gaatttcacc acaggttcca ggaacttggt   720
ctgagagaag gttggggtga ctgcgctaag cgcgcacagg agactattca cctcctcttg   780
gaccttcttg aggccccaga tccgtccacc ctggagaagt ccttggaac gatcccatg   840
gtgttcaatg ttgttatcct ctcccctcat ggttactttg ctcaagctaa tgtcttgggt   900
taccctgaca ccgagggcca ggttgtgtac attttggacc aagtccgtgc tatggagaat   960
gaaatgctgc tgaggatcaa gcagtgtggt cttgacatca caccaaagat ccttattgtt  1020
accaggttgc ttcctgatgc aactggcacc acctgttggt gaggtcttga gaaggtcctt  1080
ggcactgagc actgccatat ccttcgtgtg ccattcaaga cagaaaatgg aattgttcgc  1140
aagtggatct cgcgttttga gtctggcctt acctgagaa cttacactga tgatgtggca  1200
catgagattg ctgagagcct tcaggccaat cctgacctga tcatcggaaa ctacagtgat  1260
ggaaaccttg tcgcatgttt gctcgcgcac aagatgggtg ttactcactg taccattgcc  1320
cacgcccttg agaaaactaa gtaccctaac tctgacctca ctggaagaa gtttgaggac  1380
```

```
cactaccact tctcgtgcca gttcaccact gacttgattg ctatgaacca tgctgacttc  1440
attatcacca gtaccttcca agagattgct ggaaacaagg acaccgtcgg tcagtacgag  1500
tcacacatgg cattcacaat gcctggtctg taccgcgttg tccacggtat tgatgtgttt  1560
gacccctaag tcaacatcgt gtctcctggt gcggacttgt ccatctactt cccatacacc  1620
gagtcacaca agaggttgac ctccctccac ccggagattg aggagctcct gtacagccaa  1680
accgagaaca ccgagcacaa gtttgtgctg aacgacagga acaagccaat catcttctcc  1740
atggctcgtc ttgaccgcgt caagaactta actggtctgg tggagcttta tggccggaac  1800
aagcgcctgc aggagctggt gaacctcgtg ttgtgtgcg gtgaccacgg caacccgtcc  1860
aaggacaagg aggagcaggc cgagttcaag aagatgtttg acctcatcga gcagtacaac  1920
ctgaacgggc acatccgctg gatctccgcc cagatgaacc gtgtccgcaa cggtgagctg  1980
taccgctaca tttgcgacac caagggtgcc ttcgtcagc ctgctttcta cgaggcgttc  2040
gggctgacgg tggttgaggc catgacctgt ggcctgccca cgttcgccac cgcctatggt  2100
ggtccggctg agatcatcgt gcacggcgtg tctggcttcc acattgaccc gtaccagggc  2160
gacaaggcgt cggcgctgct cgtggacttc tttgagaagt gccagacgga ttcgagccac  2220
tggaacaaaa tctcccaggg cgggctccag cgtatcgagg agaaatacac ctggaagctg  2280
tactcggaga ggctgatgac cctgacgggc gtgtatggtt tctggaagta cgtgtccaac  2340
ctggagaggc gcgagacccg cgggtacctg gagatgctgt acgcgctcaa gtaccgcacc  2400
atggccagca ccgtgccgtt ggccgtggag ggagagcccc cagcaagtg a             2451

SEQ ID NO: 280         moltype = AA   length = 816
FEATURE                Location/Qualifiers
source                 1..816
                       mol_type = protein
                       organism = Sorghum bicolor
SEQUENCE: 280
MGEAAGDRVL SRLHSVRERI GDSLSAHPNE LVAVFTRLKN LGKGMLQPHQ IIAEYNSAIP    60
EAEREKLKDG AFEDVLRAAQ EAIVIPPWVA LAIRPRPGVW EYVRVNVSEL AVEELRVPEY   120
LQFKEQLVEE GPNNNFVLEL DFEPPNASFP RPSLSKSIGN GVQFLNRHLS SKLFHDKESM   180
YPLLNFLRAH NYKGMTMMLN DRIRSLSALQ GALRKAEEHL STLQADTPYS EFHHRFQELG   240
LEKGWGDCAK RAQETIHLLL DLLEAPDPST LEKFLGTIPM VFNVVILSPH GYFAQANVLG   300
YPDTGGQVVY ILDQVRAMEN EMLLRIKQCG LDITPKILIV TRLLPDATGT TCGQRLEKVL   360
GTEHCHILRV PFRTENGIVR KWISRFEVWP YLETYTDDVA HEIAGELQAN PDLIIGNYSD   420
GNLVACLLAH KMGVTHCTIA HALEKTKYPN SDLYWKKFED HYHFSCQFTT DLIAMNHADF   480
IITSTFQEIA GNKDTVGQYE SHMAFTMPGL YRVVHGIDVF DPKFNIVSPG ADLSIYFPYT   540
ESHKRLTSLH PEIEELLYSQ TENTEHKFVL NDRNKPIIFS MARLDRVKNL TGLVELYGRN   600
KRLQELVNLV VVCGDHGNPS KDKEEQAEFK KMFDLIEQYN LNGHIRWISA QMNRVRNGEL   660
YRYICDTKGA FVQPAFYEAF GLTVVEAMTC GLPTFATAYG GPAEIIVHGV SGFHIDPYQG   720
DKASALLVDF FEKCQTDSSH WNKISQGGLQ RIEEKYTWKL YSERLMTLTG VYGFWKYVSN   780
LERRERTRRYL EMLYALKYRT MASTVPLAVE GEPSSK                            816

SEQ ID NO: 281         moltype = DNA   length = 2451
FEATURE                Location/Qualifiers
source                 1..2451
                       mol_type = other DNA
                       organism = Zea mays
SEQUENCE: 281
atgggggaag gtgcaggtga ccgtgtcctg agccgcctcc acagcgtcag ggagcgcatt    60
ggcgactcac tctctgccca ccccaatgag cttgtcgccg tcttcaccag gctgaaaaac   120
cttgaaaagg gtatgctgca gccccaccag atcattgccg agtacaacaa tgcgatccct   180
gaggctgagc gcgagaagct caaggatggt gcttttgagg atgtcctgag ggcagctcag   240
gaggcgattg tcatcccccc atgggttgca cttgccatcc gccctaggcc tggtgtctga   300
gagtatgtga gggtcaacgt cagtgagctc gctgttgagg agctgagagt tcctgagtac   360
ctgcagttca aggaacagct tgtggaagaa ggccccaaca acaactttgt tcttgagctg   420
gactttgagc cattcaatgc ctccttcccc cgtccttctc tgtcaaagtc cattggcaat   480
ggcgtgcagt tcctcaacag gcacctgtca tcaaagctct tccatgacaa ggagagcatg   540
tacccttgc tcaacttcct tcgcgcccac aactacaagg ggatgaccat gatgttgaac   600
gacagaatcc gcagtctcag tgctctgcaa ggtgcgctga ggaaggctga ggagcacctg   660
tccaccctac aagctgatac cccatactct gaatttcacc acaggttcca ggaacttggt   720
ctggagaagg gttgggggtga ttgcgctaag cgtgcacaga agactatcca cctcctcttg   780
gacctcctgg aggcccagga tccgtccacc ctggagaagt tccttggaac gatcccatg   840
gtgttcaatg tcgttatcct ctcccctcat ggttacttcg ctcaagctaa tgtcttgggt   900
taccctgaca ccggaggcca ggttgtctac atcttggatc aagtgcgcgc tatggagaac   960
gaaatgctgc tgaggatcaa gcagtgtggt cttgacatca cgccgaagat ccttattgtc  1020
accaggttgc tccctgatgc aactggcacc acctgtgcc agcgccttga gaagttcctt  1080
ggcaccgagc actgccatat ccttcgcgtg ccattcagaa cagaaaacgg aatcgttcgc  1140
aagtggatct cgcgatttga agtctggccg tacctggaga cttacactga tgacgtggcg  1200
catgagattg ctggagagct tcaggccaat cctgacctga tcatcggaaa ctacagtgac  1260
ggaaaccttg ttgcgtgttt gctcgcccac aagatggggt tactcactg taccattgcc  1320
catgcgcttg agaaaactaa ttaccctaac tccgacctct actggaagaa gtttgaggat  1380
cactaccact tctcgtgcca gttcaccact gacttgattg caatgaacca tgccgacttc  1440
atcatcacca gtaccttcca agagatcgct ggaaacaagg acaccgtcgg ccagtacgag  1500
tcacacatgg cgttcacaat gcctggcctg taccgcgttg tccacggcat tgatgtgttc  1560
gaccccaagt caacatcgt gtctcctggc gcggacctgt ccatctactt cccgtacacc  1620
gagtcgcaca gaggctgac ctcccttcac ccggagattg aggagctcct gtacagccaa  1680
accgagaaca cggagcacaa gttcgttctg aacgacagga acaagccaat catcttctcc  1740
atggctcgtc tcgaccgtgt gaagaactta ctgggctgg tggagctgta cggccggaac  1800
aagcggctgc aggagctggt gaacctcgtg gtcgtctgcg cgaccatgg caacccttcc  1860
aaggacaagg aggagcaggc cgagttcaag aagatgtttg acctcatcga gcagtacaac  1920
ctgaacgggc acatccgctg gatctccgcc cagatgaacc gcgtccgcaa cggcgagctg  1980
```

```
taccgctaca tctgcgacac caagggcgcc ttcgtgcagc ctgctttcta cgaggctttc    2040
gggctgacgg tggttgaggc catgacctgc ggcctgccca cgttcgccac cgcctacggc    2100
ggtccggccg agatcatcgt gcacggcgtg tctggctacc acatcgaccc ttaccagggc    2160
gacaaggcgt cggccctgct cgtggacttc ttcgacaagt gccaggcgga gccgagccac    2220
tggagcaaga tctcccaggg cgggctccaa cgtatcgacg agaagtacac ctggaagctg    2280
tactcggaga ggctgatgac cctcaccggc gtgtacgggt tctggaagta cgtgtccaac    2340
ctggagaggc gcgagacccg gcggtacctg gagatgctgt acgcgctcaa gtaccgcacc    2400
atggcgagca ccgtgccgct ggccgtggag ggagagccct ccagcaagtg a             2451

SEQ ID NO: 282          moltype = AA  length = 816
FEATURE                 Location/Qualifiers
source                  1..816
                        mol_type = protein
                        organism = Zea mays
SEQUENCE: 282
MGEGAGDRVL SRLHSVRERI GDSLSAHPNE LVAVFTRLKN LGKGMLQPHQ IIAEYNNAIP     60
EAEREKLKDG AFEDVLRAAQ EAIVIPPWVA LAIRPRPGVW EYVRVNVSEL AVEELRVPEY    120
LQFKEQLVEE GPNNNFVLEL DFEPFNASFP RPSLSKSIGN GVQFLNRHLS SKLFHDKESM    180
YPLLNFLRAH NYKGMTMMLN DRIRSLSALQ GALRKAEEHL STLQDADTPYS EFHHRFQELG    240
LEKGWGDCAK RAQETIHLLL DLLEAPDPST LEKFLGTIPM VFNVVILSPH GYFAQANVLG    300
YPDTGGQVVY ILDQVRAMEN EMLLRIKQCG LDITPKILIV TRLLPDATGT TCGQRLEKVL    360
GTEHCHILRV PFRTENGIVR KWISRFEVWP YLETYTDDVA HEIAGELQAN PDLIIGNYSD    420
GNLVACLLAH KMGVTHCTIA HALEKTKYPN SDLYWKKFED HYHFSCQFTT DLIAMNHADF    480
IITSTFQEIA GNKDTVGQYE SHMAFTMPGL YRVVHGIDVF DPKFNIVSPG ADLSIYFPYT    540
ESHKRLTSLH PEIEELLYSQ TENTEHKFVL NDRNKPIIFS MARLDRVKNL TGLVELYGRN    600
KRLQELVNLV VVCGDHGNPS KDKEEQAEFK KMFDLIEQYN LNGHIRWISA QMNRVRNGEL    660
YRYICDTKGA FVQPAFYEAF GLTVVEAMTC GLPTFATAYG GPAEIIVHGV SGYHIDPYQG    720
DKASALLVDF FDKCQAEPSH WSKISQGGLQ RIEEKYTWKL YSERLMTLTG VYGFWKYVSN    780
LERRETRRYL EMLYALKYRT MASTVPLAVE GEPSSK                              816

SEQ ID NO: 283          moltype = DNA  length = 1680
FEATURE                 Location/Qualifiers
source                  1..1680
                        mol_type = other DNA
                        organism = Sorghum bicolor
SEQUENCE: 283
atggagctgg ctgtcggcgg cgggatgcgg cggtcggcgt cgcacacctc gctgtcggag     60
tcggacgact tcgagctcac gcggctgctc agcaagccgc ggatcaacgt cgagcgccag    120
cgctccttcg acgaccgctc gctcagcgac gtctcgcact cggcgggcta cggcagggga    180
ggcttcgacg gcatgtactc gcctgggggc ggcctgcgct ccctcgtcgg cacgccggca    240
tcctccgcgc tgcactcctt cgagccccac cccatcgtcg gcgacgcatg ggaggcgctc    300
cgccgctcac tcgtcttctt cgcggccag cccttggca ccgtcgccgc cgtcgaccac     360
gcttccgagg aagtcctcaa ctacgaccaa gtgtttgtga gggatttcgt gccgagcgcg    420
ctggcgtttc tgatgaatgg cgagccggat atcgtcaaga acttccttct gaagaccctg    480
ctgctgcagg gctgggagaa gaaagtcgac cggttcaagc ttggggaggg agccatgccg    540
gctagccttca aggtgatgca tgacgccaag aaggggtcg agaccctaca tgctgatttt    600
ggagagagcg ccattgggag ggttgcgcct gtggattctg gtttctggtg gatcatactc    660
ctccgggcgt acacaaaaac caccggtgat atgaccctgg cagagacacc ggagtgccaa    720
aaagggatga ggctcatact cagcctgtgc ttatctgagg gtttgatac cttcccgaca     780
ttgttatgtg ctgatggttg ctgtatgata atcgcagaa tgggtgtata tggataccct     840
attgagattc aagcccttt cttttatgca ctaaggtgtg ctcttcaaat gcttaagcat     900
gataatgaag ggaaggaatt tgtagaaaag attgctaccc gccttcatgc tttaagttat    960
cacatgcgaa gttattttg gctcgatttc caacagctaa atgacattta tcgttacaag   1020
acagaagaat attcccacac agccgtcaac aaattcaatg ttattcctga ttcaattccg   1080
gactggctat ttgactttat gccttgtcag ggtgggtttt tcattggtaa tgttagtcct   1140
gccaggatga cttccgatg gtttgcactt gaaacatga ttgctatact ttcttctctt    1200
gcaacacctg agcaatctgt tgctataatg gatcttattg aggagcgttg ggaagagctt   1260
atcggtgata tgcctctgaa gatatgttat cctgctattg agaaccatga atggcgaatt   1320
gtgacaggct gtgatccaaa aaatactaga tggagctatc acaatggagg atcgtggcca   1380
gtacttctgt ggctgctgac tgcagcctgc atcaaaactg gacggccgca aattgcaaga   1440
agagcaattg acctagcaga gaggaggctg ttgaaggatg gctggcctga gtactatgac   1500
gggaagcttg tcggtatgt tggcaagcag gcaaggaaat tccagacttg gtccatcgcg   1560
gggtatttgg tcgccaagat gatgttggaa gatccttcac atcttggcat gatctccta    1620
gaagaggata aggcgatgtt gaagcctgtt tgaagcggg ccgcatcatg gacaaactaa    1680

SEQ ID NO: 284          moltype = AA  length = 559
FEATURE                 Location/Qualifiers
source                  1..559
                        mol_type = protein
                        organism = Sorghum bicolor
SEQUENCE: 284
MELAVGGGMR RSASHTSLSE SDDFELTRLL SKPRINVERQ RSFDDRSLSD VSHSGGYGRG     60
GFDGMYSPGG GLRSLVGTPA SSALHSFEPH PIVGDAWEAL RRSLVFFRGQ PLGTVAAVDH    120
ASEEVLNYDQ VFVRDFVPSA LAFLMNGEPD IVKNFLLKTL LLQGWEKKVD RFKLGEGAMP    180
ASFKVMHDAK KGVETLHADF GESAIGRVAP VDSGFWWIIL LRAYTKTTGD MTLAETPECQ    240
KGMRLILSLC LSEGFDTFPT LLCADGCCMI DRRMGVYGYP IEIQALFFMA LRCALQMLKH    300
DNEGKEFVEK IATRLHALSY HMRSYFWLDF QQLNDIYRYK TEEYSHTAVN KFNVIPDSIP    360
DWLFDFMPCQ GGFFIGNVSP ARMDFRWFAL GNMIAILSSL ATPEQSVAIM DLIEERWEEL    420
IGDMPLKICY PAIENHEWRI VTGCDPKNTR WSYHNGGSWP VLLWLLTAAC IKTGRPQIAR    480
```

```
RAIDLAERRL LKDGWPEYYD GKLGRYVGKQ ARKFQTWSIA GYLVAKMMLE DPSHLGMISL  540
EEDKAMLKPV LKRSASWTN                                              559

SEQ ID NO: 285          moltype = DNA  length = 1680
FEATURE                 Location/Qualifiers
source                  1..1680
                        mol_type = other DNA
                        organism = Zea mays
SEQUENCE: 285
atggagctgg ctgtcggcgg cgggatgcgg cggtcggcgt cgcacacctc gctgtcggag   60
tcggatgact cgagctcac gcggctgctc agcaagccgc ggatcaacgt cgagcgccag  120
cgctccttcg acgaccgctc gcttagcgac gtctcgcact cgggcgggta cggcagggga  180
ggcttcgacg gcatgtactc gcctggggc ggcctgcgct ccctcgtcgg cacgccggcc  240
tcctccgggc tgcactcctt cgagccccac cccatcgtcg gcgacgcctg ggaggcgctc  300
cgccgctccc tcgtcttgtt ccgcggccag ccccttggca ccgttgccgc cgtcgaccac  360
gcgtccgagg aagtcctcaa ctacgaccaa gtgtttgtga gggatttcgt gccgagcgcg  420
ctggcgtttc tgatgaatgg cgagccagat atcgtcaaga acttccttct gaagaccctg  480
ctgctgcagg gctgggagaa gaaagtcgac cggttcaagc tcgggtgaggg tgccatgccg  540
gctagcttca aggttatgca tgacgccaag aaggggtcg agaccctaca tgctgatttt  600
ggggagagcg ccattgggag ggttgcgcct gtggattcgg ggttctggtg gatcatactc  660
ctccggggcct acacaaaaac caccggtgat ttgacgctgg cagagacgcc ggagtgccag  720
aaagggagga ggctcatact cagccgtgc ttatccgagg ggtcgatac ttcccgaca  780
ttgttatgtg ctgatggttg ctgtatgata gatcgcagaa tgggtgtata tggctaccct  840
attgagattc aggccctttt ctttatggca ctaaggtgtg ctcttcaaat gcttaagcat  900
gataatgaag ggaaggagtt tgtagagaag attgctactc gccttcacgc tttaagttat  960
cacatcggga gttattttttg gctcgatttc caacagctaa atgacatcta tcgttacaag 1020
acagaagaat attcccacac tgctgtcaac aaattcaatg tcattcctga ttcaattccg 1080
gattggctat ttgactttat gccttgtcag ggtgggtttt tcattggtaa tgtcagtcct 1140
gccaggatga acttccgatg gttcgcactt ggaaacatga ttgctatact ttcttcccctt 1200
gcaacacctg agcaatctgt tgctataatg gatcttatca aggagcgttg ggaagagctc 1260
attggtgaaa tgcctctgaa gatatgttat cctgctattg agaaccatga atggcgaatt 1320
gtgacgggct gtgatccaaa aaacactaga tggagttatc ataatggagg tcgtggcca 1380
gtacttctgt ggctgctgac tgcagcctgc atcaaaactg gacggccaca aatcgcaaga 1440
aggcaattg acctagcaga aaggaggctg ttgaaggatg atggcctga gtactatgat 1500
gggaagcttg gtcggtatgt tggcaagcag gcgaggaaat tccagacctg gtccatccga 1560
gggtatttgg tcgccaagat gatgttgaa gatccttcac atctcggcat gatctccctg 1620
gaagaggata gggcaatgtt gaagcctgtt tgaagcggt ctgcgtcatg gacaaactga 1680

SEQ ID NO: 286          moltype = AA  length = 559
FEATURE                 Location/Qualifiers
source                  1..559
                        mol_type = protein
                        organism = Zea mays
SEQUENCE: 286
MELAVGGGMR RSASHTSLSE SDDFELTRLL SKPRINVERQ RSFDDRSLSD VSHSGGYGRG   60
GFDGMYSPGG GLRSLVGTPA SSGLHSFEPH PIVGDAWEAL RRSLVLFRGQ PLGTVAAVDH  120
ASEEVLNYDQ VFVRDFVPSA LAFLMNGEPD IVKNFLLKTL LLQGWEKKVD RFKLGEGAMP  180
ASFKVMHDAK KGVETLHADF GESAIGRVAP VDSGFWWIIL LRAYTKTTGD LTLAETPECQ  240
KGMRLILSLC LSEGFDTFPT LLCADGCCMI DRRMGVYGYP IEIQALFFMA LRCALQMLKH  300
DNEGKEFVEK IATRLHALSY HMRSYFWLDF QQLNDIYRYK TEEYSHTAVN KFNVIPDSIP  360
DWLFDFMPCQ GGFFIGNVSP ARMDFRWFAL GNMIAILSSL ATPEQSVAIM DLIEERWEEL  420
IGEMPLKICY PAIENHEWRI VTGCDPKNTR WSYHNGGSWP VLLWLLTAAC IKTGRPQIAR  480
RAIDLAERRL LKDGWPEYYD GKLGRYVGKQ ARKFQTWSIA GYLVAKMMLE DPSHLGMISL  540
EEDRAMLKPV LKRSASWTN                                              559

SEQ ID NO: 287          moltype = DNA  length = 1785
FEATURE                 Location/Qualifiers
source                  1..1785
                        mol_type = other DNA
                        organism = Sorghum bicolor
SEQUENCE: 287
atggacgccg gcaccggggg cggcgggcca acgccatcc gcgtgcccta ccgccacctc   60
cgcgacgccg agatggagct cgtcagcctc aacgagcgg acgcgggccc gacgccgcac  120
aaggacgcg accagccgcg gagccgcggc gccaacgccg acaggaccaa gctcgtgctt  180
gcctgcatgg tcgccgcggg cgtccagttc gggtgggcac tgcagctctc cctcctcacg  240
ccatacatcc agaccctagg aatagaccat gccatggcat catttatttg gctctgtggg  300
ccaataactg gttttgtggt tcaacctttgt gttggtgttt ggagtgataa gtgccgatca  360
aagtatggga ggagaaggcc attattttg gctggatgca taatgatatg tgctgctgta  420
actttaatcg ggttttctgc agacctcggt tacatctgga tgacctaccac cgacactgc  480
agaacatata aaggttcaag atttcgagct gctatggttt tcattctagg attctgatg  540
ttggacctgg caaacaatac agtgcaaggt cctgctcgtg ctcttctagc tgatctttca  600
ggtcctgatc agtgtaattc tgcaaatgca atattctgct catggatggc tgttggaaat  660
attcttggtt ttttcagctgg tgcaagcggg gattggcaca agtggtttcc ttttctaatg  720
actagagcct gggtcgaagc tttcgttaat ttgaaagcac ctttcttagt tgcagtcgta  780
tttctttttgt tctgtatgtc tgttacgctg tacttcgctg aagagatccc actagagcca  840
aaagatgcac aaggactgtc agattctgct cctctactga acggttctag agaggatgca  900
catgcattga atgaaccaaa taatgaaaga tttcctaatg gccatgtaga tggaaacaac  960
gtgtcggcta acaacaacac tgaggaattt ccaaatgcga attccaacac agacaatgga 1020
ggagtcttca atgatggacc tggagcagtt ttggttaaca ttttgaccag catgaggcat 1080
```

```
ctacctcctg ggatgcattc agtgcttgta gttatggccc taacatggtt gtcatggttt   1140
cccttttttc ttttgacac tgactggatg gggcgtgaag tttaccatgg ggatccaaat    1200
ggagatctga gtgagaggaa agcttatgac aatggtgtcc gagaaggtgc atttggtttg   1260
ctattgaatt cagttgtcct tggcgttggt tccttccttg ttgatccact atgccggatg   1320
attggtgcaa gattggtttg ggccattagc aacttcactg tgtttatttg catgatggct   1380
acaacaatac taagttggat ctcttctgat ctgtactcaa gcaaactcca tcacatcatt   1440
ggggcaaata aaacagtcaa gactacagca ttggttgttt tctctcttct cggactgcca   1500
ctctcgatca cttatagcgt tccatttcct gtgactgctg agctgactgc tggtacagga   1560
ggtggacaag gtctggccac aggagtccta aatctcgcta ttgttgttcc ccagatagta   1620
gtgtcactcg gagcaggtcc atgggatgct ctatatgggg gaggaaacat cccagcgttc   1680
gccttggctt cggtcttctc cctggcggca ggtgtgctcg cagttctcaa gctaccaaag   1740
ctgtcgaact cgtaccaatc tgccggtttc catggatttg ctga                    1785

SEQ ID NO: 288            moltype = AA   length = 594
FEATURE                   Location/Qualifiers
source                    1..594
                          mol_type = protein
                          organism = Sorghum bicolor
SEQUENCE: 288
MDAGTGGGGP TAIRVPYRHL RDAEMELVSL NGADAGPTPH KDADQPRSRG ANADRTKLVL   60
ACMVAAGVQF GWALQLSLLT PYIQTLGIDH AMASFIWLCG PITGFVVQPC VGVWSDKCRS   120
KYGRRRPFIL AGCIMICAAV TLIGFSADLG YILGDTTEHC RTYKGSRFRA AMVFILGFWM   180
LDLANNTVQG PARALLADLS GPDQCNSANA IFCSWMAVGN ILGFSAGASG DWHKWFPFLM   240
TRACCEACGN LKAAFLVAVV FLLFCMSVTL YFAEEIPLEP KDAQGLSDSA PLLNGSREDA   300
HALNEPNNER FPNGHVDGNN VSANNNTEEF PNASNTDNG GVFNDGPGAV LVNILTSMRH    360
LPPGMHSVLV VMALTWLSWF PFFLFDTDWM GREVYHGDPN GDLSERKAYD NGVREGAFGL   420
LLNSVVLGVG SFLVDPLCRM IGARLVWAIS NFTVFICMMA TTILSWISSD LYSSKLHHII   480
GANKTVKTTA LVVFSLLGLP LSITYSVPFS VTAELTAGTG GGQGLATGVL NLAIVVPQIV   540
VSLGAPWDA LYGGGNIPAF ALASVFSLAA GVLAVLKLPK LSNSYQSAGF HGFG          594

SEQ ID NO: 289            moltype = DNA   length = 1779
FEATURE                   Location/Qualifiers
source                    1..1779
                          mol_type = other DNA
                          organism = Zea mays
SEQUENCE: 289
atggacgccg gcgccggggc cacggccatc cgagtgccct accgccacct ccgcgacgcc   60
gagatggagc tcgtcagcct caacggcggc gctcccggag gggacacggg cccgcccccg   120
ccaccgccca aggaccagcc gcggagccgc gccgacaggg ccaagctcgt gctcgcctgc   180
atggtcgccg cgggcgtcca gttcggatgg gcgctgcagc tctccctcct tacgccatac   240
atccagaccc taggaataga ccatgccatg gcatcattta tttggttgtg tgggcctata   300
actggttttg tggttcaacc ttgtgttggt gtttggagtg ataagtgccg ttcaaagtat   360
gggaggagaa gaccatttat ttttgggtgga tgcataatga tatgtgctgc tgtaactcta   420
atcgggtttt ctgcagacct cggttacatc ttagggcaca ccactgagca ctgcagaaca   480
tataaaggtt caaggtttcg agctgctatt gttttcattc taggattctg gatgttggac   540
ctggcaaaca atacagtgca aggtcctgcg cgtgctcttc agctgatct  ttcaggtcct   600
gatcagtgca attctgcaaa tgcaatattc tgctcatgga tgcgtgttgg gaatattctt   660
ggttttcag ctggagcgag tggggaatgg cacaagtggt ttccatttct aacgacaaga    720
gcatgctgtg aagcttgcgg taatttgaaa gcagcttttct tagttgcagt tgtatttctt   780
ttgttatgta tgtctgttac cctgtacttc gctgaagaga gcccactaga tccaaaagat   840
acacaaggac tatcagattc tgctcctctg ctgaacgatct ctagagatgc tgcccatgca   900
tcaaatgaac caaataatga aagatttcct aatggccatg tgggtttaaa caatgtgtcg   960
gctaacaaca cactgaggga atttacaaat gtgaattcca acacagagaa aggaggagtc   1020
tcaatgatg ggccaggagc agttttggtt aacatttga ccagaatgag gcatctacct     1080
cctggatgc attcagtgct tctagttatg gccctaacat ggttgtcatg gtttccttt    1140
ttcctttttg acactgactg gatgggacgc gaagtttacc atggggatcc aaatggagat   1200
ttgagtgaga ggaaagctta tgacaatggt gtccgagaag gtgcatttgg tttgctattg   1260
aattcagttg tccttggcgt tggttcattc cttgttgatc cactatgccg gatgattggt   1320
gcaagattag tttgggccat tagcaacttc acggtgttta tttgcatgat ggctacaacg   1380
atattaagtt ggatctcttc tgatctgtac tcaagcaaac ttcatcacat catcgggca    1440
aataaaacag tcaagatcac ggcattggtt gttttctctc ttctcggatt gccactctcc   1500
atcacttaca gcgttccgtt ttctgtgact gctgagctga ctgccggtac aggaggtgga   1560
caaggtttgg ccacaggagt cctaaatctt gctatcgtgg ttccccagat agtagtgtcg   1620
cttggagcag gtccatggga cgctctgtat ggaggaggga acccggc gttcgtcttg       1680
gcttcggtct tctccctggc agcaggtgtg ctcgcagttc tcaagctgcc aaagctgtcc   1740
aactcgtacc aatctgccgg gttccatgga tttggctga                          1779

SEQ ID NO: 290            moltype = AA   length = 592
FEATURE                   Location/Qualifiers
source                    1..592
                          mol_type = protein
                          organism = Zea mays
SEQUENCE: 290
MDAGAGATAI RVPYRHLRDA EMELVSLNGG APGGDTGPPP PPPKDQPRSR ADRTKLVLAC   60
MVAAGVQFGW ALQLSLLTPY IQTLGIDHAM ASFIWLCGPI TGFVVQPCVG VWSDKCRSKY   120
GRRRPFILAG CIMICAAVTL IGFSADLGYI LGDTTEHCRT YKGSRFRAAI VPILGFWMLD   180
LANNTVQGPA RALLADLSGP DQCNSANAIF CSWMAVGNIL GFSAGASGEW HKWFPFLTTR   240
ACCEEACGNLK AAFLVAVVFL LLCMSVTLYF AEESPLDPKD TQGLSDSAPL LNGSRDAAHA   300
SNEPNNERFP NGHVGLNNVS ANNNTEEFTN VNSNTEKGGV FNDGPGAVLV NILTRMRHLP   360
```

```
PGMHSVLLVM ALTWLSWFPF FLFDTDWMGR EVYHGDPNGD LSERKAYDNG VREGAFGLLL    420
NSVVLGVGSF LVDPLCRMIG ARLVWAISNF TVFICMMATT ILSWISSDLY SSKLHHIIGA    480
NKTVKITALV VFSLLGLPLS ITYSVPFSVT AELTAGTGGG QGLATGVLNL AIVVPQIVVS    540
LGAGPWDALY GGGNTPAFVL ASVFSLAAGV LAVLKLPKLS NSYQSAGFHG FG            592

SEQ ID NO: 291            moltype = DNA  length = 693
FEATURE                   Location/Qualifiers
source                    1..693
                          mol_type = other DNA
                          organism = Arabidopsis thaliana
SEQUENCE: 291
atggcagact tgagttttta tgtcggagtc atagggaatg ttatatcggt gcttgtcttc    60
ctctcccctg tggagacgtt tttggaggata gtgcagcgga gatcgacgga ggaatacag    120
tgttttccgt acatttgcac gttaatgagc tcgtcgttat ggacatatta cggaatagtg   180
acacctggtg aatacttggt ttctactgtc aatggctttg gtgctcttgc tgaatccatc   240
tacgttctca ttttcctctt ctttgtcccc aaatccagat tcttgaaaac agttgttgtg   300
gttctagctt tgaacgtgtg tttcccagtt atcgcgattg cgggaacaag aactctgttt   360
ggagatgcaa actcgcgttc tagttcaatg gtttcatat gtgctactct caacattatc    420
atgtatggtt ctcctctttc agctattaaa acggttgtga cgacgagaag tgtgcagttt   480
atgccatttt ggttgtcatt ttcctctttt ctgaacggcg cgatttgggg tgtctacgct   540
ttactcctac acgatatgtt tctactagtg ccaaatggaa tgggattctt cttgggata    600
atgcaactcc taatttatgc ctattacaga aatgccgaac caattgtaga agatgaagaa   660
ggcctcatac caaatcaacc tctcctcgct taa                                693

SEQ ID NO: 292            moltype = AA  length = 230
FEATURE                   Location/Qualifiers
source                    1..230
                          mol_type = protein
                          organism = Arabidopsis thaliana
SEQUENCE: 292
MADLSFYVGV IGNVISVLVF LSPVETFWRI VQRRSTEEYE CFPYICTLMS SSLWTYYGIV    60
TPGEYLVSTV NGFGALAESI YVLIPLFFVP KSRFLKTVVV VLALNCPFV IAIAGTRTLF    120
GDANSRSSSM GFICATLNII MYGSPLSAIK TVVTTRSVQF MPFWLSFFLF LNGAIWGVYA    180
LLLHDMFLLV PNGMGFFLGI MQLLIYAYYR NAEPIVEDEE GLIPNQPLLA               230

SEQ ID NO: 293            moltype = DNA  length = 4008
FEATURE                   Location/Qualifiers
source                    1..4008
                          mol_type = other DNA
                          organism = Arabidopsis thaliana
SEQUENCE: 293
atggataata acaattggag gccttctctt ccaaacggag agcctgccat ggatacaggt    60
gactggagaa cgcaattgcc acctgattcg cgtcagaaga tcgtcaacaa gataatggaa   120
acactaaaga agcaccttcc attttccgga ccagagggaa ttaacgagct caggagaatt   180
gcagctagat cgaggagaa attttcagc ggtgctctta ccagactga ttaccttcgg      240
aaaatatcaa tgaagatgct gacaatggag actaaatcac aaaatgcagc tggttcttcc   300
gcagctatcc ctgccgctaa taatggcaca tccatagatt cgatacccac caatcaaggc   360
caacttcttc caggatcgtt atcaaccaat caatctcaag cacctcagcc gttgctgtcc   420
caaaccatgc agaataatac tgcctctgga atgacgggtt ctactgcttt accatcttcc   480
atgccaccctg tttcttccat aaccaataat aacaccacaca gcgttgtgaa ccagaatgcc    540
aatatgcaaa atgtagctgg aatgttgcaa gattcatctg ggcagcatgg cctttcctcg   600
aacatgtttt caggacccca aaggcagatg ctgggtaggc acatgctat gtcttcacag     660
caacaacagc agccatatct ttaccagcag cagctacagc agcaacttct caagcagaac   720
ttccagtcag gaatgttcc caatcccaat tcgcttttgc catcacacat tcaacaacag    780
cagcaaaatg tgctgcagcc taatcaactg cattcatctc aacaacctgg tgttccaaca   840
tctgcgactc agccctccac tgtgaactca gctcctctcc aaggtctcca caccaatcag   900
caatcaagtc gcaattgtc ttctcagcag acgacacaat ctatgcttcg tcagcatcaa    960
tcgtcgatgc taaggcaaca tccgcaatca caacaagcct ctggtatcca tcagcagcaa   1020
tcttcattgc cgcaacaatc aatttctcct ctacagcagc agcctacaca attaatgcgg   1080
caacaagctg caaatagctc aggcatccaa cagaagcaga tgatggggca gcatgttgtt   1140
ggggatatgc agcagcaaca tcagcaaagg ttactgaacc aacaaaataa tgttatgaac   1200
atacaacagc agcagtcgca gcagcaacca ctgcagcagc cacagcaaca gcagaaacag   1260
cagccaccgg cccagcagca gttgatgtct caacaaaaca gcctccaggc aacgcatcag   1320
aacccactgg gcactcaaag caatgttgca ggattgcaga aaccacaaca acagttccag   1380
aattcccagg ttggcaattc gagtttgcag aataaccagc actcggtgca catgttatca   1440
caaccaacgg ttgggctgca acgaacacat caggctggcc atgcttgta ttcttctcag     1500
ggacaacagt cacaaaatca gccatcacaa cagcagatga tgccacagct tcaatcgcat   1560
catcagcagc tgggttttgca acaacaacct aatctgctac aacaggatgt gcaacaaagg   1620
ctacaagctt caggccaagt cactggttcc ctgcttccac ctcaaaatgt tgtggaccaa   1680
cagagacaac tatatcaatc ccaagaacc cttccggaga tgccatcatc atcgctggat    1740
tcgacagcac agacggaaag tgcaatggaa ggtgattggc aagaggaggt taccaaaag     1800
atcaaatcta tgaagagac ttacttacca gatctgaatg aaatctacca gagagttgca    1860
gcaaagttgc agcaagattc tatgccacag caacaaagat cagatcagct tgagaaactg   1920
agacaattca aaacaatgtt ggagcgaatg atacatttc tatctgtttc aaagagcaac    1980
atcatgcccg cattaaaaga taaggtggct tattatgaga agcagattat aggttttctta   2040
aatatgcaca ggccgaggaa gccagtacga caagggcagc ttccgcaatc tcagatgcag   2100
cctatgcagc aaccacaatc tcagacagtt caagatcaat cccatgataa ccaaacaaat    2160
ccgcagatgc aatcaatgag catgcagggt gctgggccaa gggcacaaca gagtagtatg   2220
acaaaatgc agagcaatgt tctatcatct cgtcctggag tttcagctcc acagcagaac   2280
```

-continued

```
attcccagtt ccataccggc ttctagttta gaatcaggcc aaggaaatac cttgaacaat   2340
ggacagcagg ttgccatggg atctatgcaa caaaatactt ctcaactagt aaataacagt   2400
tctgcctctg ctcaaagtgg gttgagcaca ctgcagtcga atgtgaatca acccagtta    2460
agttccagtt tgcttcagca tcagcacctc aagcaacagc aagatcaaca aatgcagctc   2520
aaacagcaat ttcaacagcg ccagatgcaa cagcaacgt tgcaagcaag acagcaacag   2580
caacagcaac agttgcaagc aagacagcaa gcggcacaat tacagcagat gaatgatatg   2640
aatgatttaa catcgaggca ggggatgaat gtcagtcgtg ggatgttca gcaacattct    2700
atgcagggtc agcgtgcgaa ttatcctctt caacagttaa aaccaggagc tgtttcgtcg   2760
cctcaacttc tgcaaggtgc atctcctcag atgtcacaac atttgtctcc tcaggttgac   2820
cagaaaaata ctgtcaacaa gatgggaact ccattgcaac ctgcaaattc cccttttgtt   2880
gtcccatctc cttcttcaac cccttggcc ccgtcccta tgcaagttga ctctgagaaa    2940
cctggttctt cttcgttgtc aatgggaaat attgcacgcc aacaagcaac cggcatgcaa   3000
ggtgtagttc agtcccctagc aattggcact ccagggatct ctgcctctcc tctccttcag   3060
gagtttacta gtcctgatgg gaatattta aattcttcga caattacatc tggaaaaccg   3120
agtgctactg agctgcctat tgaacgcctt attagagccg tgaagtccat ctcaccacaa   3180
gcccttttctt ctgcagtaag tgacatcgga tctgttgtaa gcatggttga tcggatagct   3240
ggttcagcac caggaaacgg ttcaagagct tccgttggtg aagacttggt tgcaatgact   3300
aagtgccgtc tccaagcaag aaacttcatg acccaagagg gaatgatgc gactaagaaa   3360
atgaagcgtc acacaaccgc aatgccacta agcgttgctt cactgggagg aagtgttggt   3420
gataactaca gcagtttgc tggttcagaa acatccgatc tagaatctac tgcgacttcg   3480
gatggcaaga aggcaagaac tgagaccgag catgcccttt tggaggaaat aaaggaaata   3540
aaccagcgc tgatagatac agttgttgag ataagtgatg atgaagatgc tgctgatcct   3600
agtgaggttg caatatcaag cataggtgt gaaggaacaa cagttagatt ctcgtttata    3660
gctgtttctc tcagcccagc cttgaaggct catctctcat caacacaaat gtctcctatt   3720
caaccattgc gtctgctggt tccttgtagc taccccaatg gctctccatc tcttctagat   3780
aaactccggg tcgaaaccag caaagaaaac gaggacctgt cgtccaaagc tatgcaagg   3840
ttcaacatat tgctaagaag tttgtcacag ccgatgtcgc tcaaagacat agccaagaca   3900
tgggacgcct gtgctcgggc agtgatctgt gagtacgcac agcaatttgg cggtggaact   3960
ttcagctcaa aatacggcac ttgggagaaa tatgtagcag cttcctga               4008
```

SEQ ID NO: 294         moltype = AA    length = 1335
FEATURE                Location/Qualifiers
source                 1..1335
                       mol_type = protein
                       organism = Arabidopsis thaliana
SEQUENCE: 294

```
MDNNNWRPSL PNGEPAMDTG DWRTQLPPDS RQKIVNKIME TLKKHLPFSG PEGINELRRI     60
AARFEEKIFS GALNQTDYLR KISMKMLTME TKSQNAAGSS AAIPAANNGT SIDSIPTNQG   120
QLLPGSLSTN QSQAPQPLLS QTMQNNTASG MTGSTALPSS MPPVSSITNN NTTSVVNQNA   180
NMQNVAGMLQ DSSGQHGLSS NMFSGPQRQM LGRPHAMSSQ QQQQPYLYQQ QLQQQLLKQN   240
FQSGNVPNPN SLLPSHIQQQ QQNVLQPNQL HSSQQPGVPT SATQPSTVNS APLQGLHTNQ   300
QSSPQLSSQQ TTQSMLRQHQ SSMLRQHPQS QQASGIHQQQ SSLPQQSISP LQQQPTQLMR   360
QQAANSSGIQ QKQMMGQHVV GDMQQQHQQR LLNQQNNVMN IQQQQSQQQP LQQPQQQQKQ   420
QPPAQQQLMS QQNSLQATHQ NPLGTQSNVA GLQQPQQQML NSQVGNSSLQ NNQHSVHMLS   480
QPTVGLQRTH QAGHGLYSSQ GQQSQNQPSQ QQMMPQLQSH HQQLGLQQQP NLLQQDVQQR   540
LQASGQVTGS LLPPQNVVDQ QRQLYQSQRT LPEMPSSSLD STAQTESANG GDWQEEVYQK   600
IKSMKETYLP DLNEIYQRVA AKLQQDSMPQ QQRSDQLEKL RQFKTMLERM IQFLSVSKSN   660
IMPALKDKVA YYEKQIIGFL NMHRPRKPVQ QGQLPQSQMQ PMQQPQSQTV QDQSHDNQTN   720
PQMQSMSMQG AGPRAQQSSM TNMQSNVLSS RPGVSAPQQN IPSSIPASSL ESGQGNTLNN   780
GQQVAMGSMQ QNTSQLVNNS SASAQSGLST LQSNVNQPQL SSSLLQHQHL KQQQDQQMQL   840
KQQPQQPQMQ QQQLQARQQQ QQQQLQARQQ AAQLQQMNDM NDLTSRQGMN VSRGMFQQHS   900
MQGQRANYPL QQLKPGAVSS PQLLQGASPQ MSQHLSPQVD QKNTVNKMGT PLQPANSPFV   960
VPSPSSTPLA PSPMQVDSEK PGSSSLSMGN IARQQATGMQ GVVQSLAIGT PGISASPLLQ  1020
EFTSPDGNIL NSSTITSGKP SATELPIERL IRAVKSISPQ ALSSAVSDIG SVVSMVDRIA  1080
GSAPGNGSRA SVGEDLVAMT KCRLQARNFM TQEGMMATKK MKRHTTAMPL SVASLGGSVG  1140
DNYKQFAGSE TSDLESTATS DGKKARTETE HALLEEIKEI NQRLIDTVVE ISDDEDAADP  1200
SEVAISSIGC EGTTVRFSFI AVSLSPALKA HLSSTQMSPI QPLRLLVPCS YPNGSPSLLD  1260
KLPVETSKEN EDLSSKAMAR FNILLRSLSQ PMSLKDIAKT WDACARAVIC EYAQQFGGGT  1320
FSSKYGTWEK YVAAS                                                  1335
```

SEQ ID NO: 295         moltype = DNA    length = 3927
FEATURE                Location/Qualifiers
source                 1..3927
                       mol_type = other DNA
                       organism = Zea mays
SEQUENCE: 295

```
atggacagcg ccgccaactg gcggtcaacg cagggcaccg accctgccgc cggcggcgtc    60
gatccaaacg cggctgcccc cgccggaagc gactggcgca cccagcttca gccagaggcg   120
cgccacagga tcgtgaataa gataatggag actctgagga agcacctgcc agtatcagta   180
ccagaggggc tgactgagct tcacaaaatt gctgtgcgtt ttgaagagaa aatctatact   240
gcagccacca gccagtctga ttatttgcgg aagatttgc tgaaaatgct gtccatggaa   300
agtcagacaa agacacaaca gaaccctgga atgttcaag tgattccaaa tcaaaaccct   360
cctggtccag cacctggcct tcctccacaa gttagtaatc cagcacagtc atcagctatc   420
ccattgattt ctcagcaaca gacacggcaa tcaaatgcct ctacatctgt tcaaggtctt   480
cttcctagtc ttggtcagaa ctcgtcgagt gtcagccagg catcgacgct gcataatatg   540
tctgtcatgc cacaaaatac catgaacaat ggtttagcac aagtactcc acaagatatg   600
tatgctgcac aaaaggcaaat ggctggtagg cagcagcaac aacaacaaca acaagcacat   660
aatcagttaa tttatcaaca acagaaatac ttgaaccaga aattgcagca gaattcactt   720
atgccatcgc acattcagca gcagcaacct ttattgcagt caacacagat gcaatcttca   780
```

```
cagcagccca tgatgcaaat gtcatctggt cttcagcctg ggcagactgc cattccacaa  840
actcagtcca tgacgatgca ttcagctaca caaagtggta ttcaacaaaa cccattgaat  900
tcagtacaac aatctgtgca accattactc catcagccta cacaatcgt agtgaggcag   960
cagcaacatc cacagtccat gcaccagcag tcttctctgc agcaaactca gccaactcaa 1020
cagcccaaca ttcctttgca acaacaacaa ccacaattaa tgaaccagca gtcaaattta 1080
cagcaaaatc agttaatgaa tcaacagagt ggtgttgtgg agacgcaaca gcaacaaagg 1140
ctgccagttc agtcaaataa tcttttgaat atgcagcaaa cacagcagat gatgaaccag 1200
caatctatgt ccttgcacca gccacaacaa ttggcaaacc aaggaaatat gtcaagtcta 1260
catcagcagc agcatcagca aaatcagcag cagcagcagc ttctcggaac tgggccaaat 1320
gcccgtatgc atatgttaca gcagcaaaag gtaattcagc aaccacagca gcaacagcat 1380
gctcagcaga catcaatggg tttgataaca cctcagctc agcagaacca acttcagcaa  1440
cctcagcaac atatgatgtc gcagttccag tctcagccta tcaaatgca gcaacaattg  1500
ggaatgcaac aaaggctcca aacttcagct ggcatgctct acaacaaaa taacattgat  1560
caaaagcaat atgttcaggc acagaggggc cttcaagag cacccagtac atctgtggat  1620
tccactgctc aaactggtca tccaggcata ggtgatttgc aagaggagtt atatcaaatg 1680
attaagagtt taaggacca atactttgtg gaattgaatg aattgtacaa taggtatct   1740
atcaagatac aacagattga caaccaaatg cctgctcaaa agtcagcaga gcagtatgaa  1800
aagatgaagg gcttttaaagg aatgctggag cgcacttgg atttcctgca agttaacaag  1860
agcaacattc atccaggtt gagggaaaaa atccccatt acgagaggca aattctcagt    1920
atcctaagtt cacaaagaag gaaacctgtg caggcacctg ggcagcaaac gtttcagcaa  1980
tctagtgggg aagctcctag ctctaacatt tcacagcaac ttcagacttc ccaaggttg   2040
cagcagcatg atagtcatac tagtcagatg cctcaagcaa gtttaccaag tatgaacaca 2100
ggagtacaaa cctctggagc acctgcgcct caaggaacaa actttggtgt tccaacaaca 2160
cagcaaaatg tcacaaatgc accacaggct ggctctaatt tggagaatgc tcagggaaat 2220
aatttaatc atgtgcagca tggttcaatg ggtgctgctt tgcaacagga aaggactggt  2280
cccatgcagg gtgcattgaa tgcacgcag cagtccagta gcaacatgat attcaacaat  2340
gcaatgagta caatgcagac taataacaat gcaaatgcga attcattgca gcagttaaag 2400
cagcaacgtc aggagcatca aatgatgcaa agtcagcaaa tgaagcagcg ccagcagatg 2460
atgcaacaga taacaaaaaa gcaaacgctt caaccgcagc tcccaataca gcaactaaag 2520
aaacaacagc agcaagggca gatgcagtttt ccacagcttc attctggaaaa tgatgtgaat 2580
gagctaaagg ttaggcaagg agctgcaatc aaatctggaa tgtatcaaca gctgagccaa 2640
cgtaactatt atcagcagat aaaacaggt ggtgtctttc caatttcttc tccgcaaacc 2700
ctccaaacat cgtccccaca aatttcacac cattctcctc aggttgatca gcacagtctg 2760
ttgcaatctc aagtcaaaac cgggacacca ttgcattcag ctaactcacc atttgtccca 2820
tctccatccc ctcctgtggc cccatcaccg atgccaatga attcggataa accactatcc 2880
aacttatctt cagttactag tgctgggcag gctggacatc agcaaacatc tcttgcacct 2940
caaacacaat ctatagccgt taacacacca ggtatatcag cgtcacccct gcttgcagaa 3000
ttcacaagtg ctgatggaag tccggccaat gtaccaactc aagttccagc caaatcaagc 3060
gcagcagaaa ggccctctga ccgtttgctt aaagcattgc gaacaacaca gcgtgagtcc 3120
ctaagtgctg cagtcagcga tattggatct gtcgtgagta tgattgacag gattgctgga 3180
tcagcgcctg gtaatggttc tagagctgct gtaggagaag atcttgtcgc tatgacaaag 3240
tgccgcttgc aagccaggaa cttcataact catgacggga gtggtgcatc aaagaaaatg 3300
aagcgggaca cgagtgctat gcctcttaat gtgtcatcag ctggaagcgt gaatgatagc 3360
ttgaagcaat catatggtgt tggtactcca gagctacaat caactgcaac ctcacgtgtc 3420
aagtggcaaa gggctgaggt aaaccatgct ctgatggagg agattcagga gataaaccaa 3480
cagcttatag atacagagct ccatgtctct gaggatgatg ctgagtcctt cactacatct 3540
gagggggca aagggacggt cattagatgc acattcactg ctgttgctgt ttgccccagc  3600
ttgaaatccg tgtttgcgtc agcgcagatg agtccaattt tgccgttgag gttgcttgtt 3660
cctgctagct acccgaaatg ctccccggtg ctttctagaca agtttcctga tgaacaatgc 3720
aggaactcag acgacctgtc taccaaggcc aagacaaagt tcagcgtatt gctccgggtt 3780
ctagctgagc ccatgtcact gcgagaaatc gcaaggacat gggatgcttg cgctcgcaaa 3840
gtgatcacag agtatgccca gcaaaccgga ggaggcagtt tcagctcgag ctatggttgc 3900
tgggaaagct gcgtaggcgc ttgttaa                                     3927
SEQ ID NO: 296           moltype = AA    length = 1308
FEATURE                  Location/Qualifiers
source                   1..1308
                         mol_type = protein
                         organism = Zea mays
SEQUENCE: 296
MDSAANWRST QGTDPAAGGV DPNAAAPAGS DWRTQLQPEA RHRIVNKIME TLKKHLPVSV   60
PEGLTELHKI AVRFEEKIYT AATSQSDYLR KISLKMLSME SQTKTQQNPG NVQVIPNQNP  120
PGPAPGLPPQ VSNPAQSSAI PLISQQQTRQ SNASTSVQGS LPSLGQNSSS VSQASTLHNM  180
SVMPQNTMNN GLAQGTPQDM YAAQRQMAGR QQQQQQQQAH NQLIYQQQKY LNQKLQQNSL  240
MPSHIQQQQP LLQSTQMQSS QQPMMQMSSG LQPGQTAIPQ TQSMTHSAT QSGIQQNPLN   300
SVQQSVQPLL HQPTQSVVRQ QQHPSMHQQ SSLQQTQPTQ QPNIPLQQQQ PQLMNQQSNL  360
QQNQLMNQQS GVVETQQQQR LPVQSNNLLN MQQTQQMMNQ QSMSLHQPQQ LANQGNMSSL   420
HQQQHQQNQQ QQQLLGTGPN ARMHMLQQQK VIQQPQQQAH AQQTSMGLIQ PQSQQNQLQQ  480
PQQHMMSQFQ SQPNQMQQQL GMQQRLQTSA GMLLQQNNID QKQYVQARG LQEAPSTSVD   540
STAQTGHPGI GDLQEELYQM IKSLKDQYFV ELNELYNKVS IKIQQIDNQM PAQKSAEQYE  600
KMKGFKGMLE RTLHFLQVNK SNIHPGLREK IPIYERQILS ILSSQRRKPV QAPGQQTFQQ  660
SSGQAPSSNI SQQLQTSQGL QQHDSHTSQM PQASLPSMNT GVQTSGAPAP QGTNFGVPTT  720
QQNVTNAPQA GSNLENAQGN NFNHVQHGSM GAALQQERTG PMQGALNAQQ QSSSNMISNN  780
AMSTMQTNNN ANANSLQQLK QQRQEHQMMQ SQQMKQRQQM MQQIQQKQTL QPQLPIQQLK  840
KQQQQGQMQF PQLHSGNDVN ELKVRQGAAI KSGMYQQLSQ RNYYQQIKQG GVFPISSPQT  900
LQTSSPQISH HSPQVDQHSL LQSQVKTGTP LHSANSPFVP SPSPPVAPSP MPMDSDKPLS  960
NLSSVTSAGQ AGHQQTSLAP QTQSIAVNTP GISASPLLAE FTSADGSPAN VPTQVPAKSS 1020
AAERPLDRLL KALRTTQRES LSAAVSDIGS VVSMIDRIAG SAPGNGSRAA VGEDLVAMTK 1080
CRLQARNFIT HDGSGASKKM KRDTSAMPLN VSSAGSVNDS LKQSYGVGTP ELQSTATSRV 1140
```

```
KWQRAEVNHA LMEEIQEINQ QLIDTELHVS EDDAESFTTS EGGKGTVIRC TFTAVAVCPS   1200
LKSVFASAQM SPILPLRLLV PASYPKCSPV LLDKFPDEQC RNSDDLSTKA KTKFSVLLRG   1260
LAEPMSLREI ARTWDACARK VITEYAQQTG GGSFSSSYGC WESCVGAC               1308

SEQ ID NO: 297          moltype = DNA   length = 747
FEATURE                 Location/Qualifiers
source                  1..747
                        mol_type = other DNA
                        organism = Arabidopsis thaliana
SEQUENCE: 297
atggcgacga ccttaagcag agatcaatat gtctacatgg cgaagctcgc cgagcaagcc    60
gagcgttacg aagagatggt tcaattcatg gaacagctcg taagtggagc tacaccggcc   120
ggtgagctga ccgtagaaga gaggaatctt ctctcggtcg cgtataagaa cgtgattgga   180
tctcttcgtg cggcatggag aatcgtgtct tcgattgagc aaaaggaaga gagcaggaag   240
aacgaagaac acgtgtcgct tgttaaggat tacagatcta aagttgagac tgagcttttct  300
tcgatctgtt ctgggattct caggttactt gattcgcatc taattccttc agctactgcc   360
agtgagtcta aggttttta cctgaagatg aaggagatt atcatcgtta tttggctgag    420
tttaaatctg gtgatgagag gaaaactgct gctgaagata ctatgatcgc ttacaaagct   480
gctcaggacg ttgcagttgc tgatctagca cctacacatc cgatcaggct tggtttggct   540
cttaacttct cagtgtttta ctacgagatt ctcaactctt cagagaaagc ttgtagcatg   600
gcgaaacagg cttttgaaga agccattgct gagctggaca cattgggaga ggagtcatac   660
aaggacagta ctctccatcat gcagttgcta agggacaatc taacccttg gacctccgat   720
atgcaggagc agatggatga ggcctga                                      747

SEQ ID NO: 298          moltype = AA   length = 248
FEATURE                 Location/Qualifiers
source                  1..248
                        mol_type = protein
                        organism = Arabidopsis thaliana
SEQUENCE: 298
MATTLSRDQY VYMAKLAEQA ERYEEMVQFM EQLVSGATPA GELTVEERNL LSVAYKNVIG    60
SLRAAWRIVS SIEQKEESRK NEEHVSLVKD YRSKVETELS SICSGILRLL DSHLIPSATA   120
SESKVFYLKM KGDYHRYLAE FKSGDERKTA AEDTMIAYKA AQDVAVADLA PTHPIRLGLA   180
LNFSVFYYEI LNSSEKACSM AKQAFEEAIA ELDTLGEESY KDSTLIMQLL RDNLTLWTSD   240
MQEQMDEA                                                           248

SEQ ID NO: 299          moltype = DNA   length = 762
FEATURE                 Location/Qualifiers
source                  1..762
                        mol_type = other DNA
                        organism = Sorghum bicolor
SEQUENCE: 299
atgtcgcggg aggagaatgt ctacatggcc aagctggctg agcaagcaga acggtatgag    60
gaaatggttg agtacatgga gaaggtggct aagaccgttg atgtggaaga gctcaccgtt   120
gaggagcgta acctcctatc tgttgcctac aagaatgtga ttggggcccg ccgtgcctca   180
tggcggattg tctcctccat cgagcagaag gaggagtccc gcaagaatga ggaacatgtt   240
gctcagatta aggagtaccg tggcaagatt gaggctgaat tgagcaacat ttgtgatggt   300
atcctgaagc tgcttgactc gcaccttgtg ccttcctcca ctgctgcaga gtcgaaggtg   360
ttttacctca agatgaaggg tgattatcac aggtaccttg ctgagtttaa gactggtgct   420
gagaggaagg aatctgcaga gagcacaatg gtagcttata aggcagccca ggatattgca   480
ttggctgaac tggcacctac tcatcccata aggcttggac ttgcacttaa cttctcggtg   540
ttctattatg agattctgaa ctctccggac aaagttgca accttgcaaa gcaggcatt   600
gatgaggcta tttctgagtt ggacacgctt ggtgaggaat cttacaaaga tagcaccttg   660
attatgcagc tcctaaggga caacttgacc ctctggacct tgacatcac ggaggagggc    720
actgaggagg gcaaagaagc ctcgaagggt gatgctgagt ag                     762

SEQ ID NO: 300          moltype = AA   length = 253
FEATURE                 Location/Qualifiers
source                  1..253
                        mol_type = protein
                        organism = Sorghum bicolor
SEQUENCE: 300
MSREENVYMA KLAEQAERYE EMVEYMEKVA KTVDVEELTV EERNLLSVAY KNVIGARRAS    60
WRIVSSIEQK EESRKNEEHV AQIKEYRGKI EAELSNICDG ILKLLDSHLV PSSTAAESKV   120
FYLKMKGDYH RYLAEFKTGA ERKESAESTM VAYKAAQDIA LAELAPTHPI RLGLALNFSV   180
FYYEILNSPD KACNLAKQAF DEAISELDTL GEESYKDSTL IMQLLRDNLT LWTSDITEEG   240
TEEGKEASKG DAE                                                     253

SEQ ID NO: 301          moltype = DNA   length = 777
FEATURE                 Location/Qualifiers
source                  1..777
                        mol_type = other DNA
                        organism = Arabidopsis thaliana
SEQUENCE: 301
atggcggcga cattaggcag agaccagtat gtgtacatgg cgaagctcgc cgagcaggcg    60
gagcgttacg aagagatggt tcaattcatg gaacagctcg ttacaggcgc tactccagcg   120
gaagagctca ccgttgaaga ggaatctc ctctctgttg cttacaaaaa cgtgatcgga    180
tctctacgcg ccgcctggag gatcgtgtct tcgattgagc agaaggaaga gagtaggaag   240
aacgacgagc acgtgtcgct tgtcaaggat tacagatcta aagttgagtc tgagcttttct  300
```

```
tctgtttgct ctggaatcct taagctcctt gactcgcatc tgatcccatc tgctggagcg   360
agtgagtcta aggtctttta cttgaagatg aaaggtgatt atcatcggta catggctgag   420
tttaagtctg gtgatgagag gaaaactgct gctgaagata ccatgctcgc ttacaaagca   480
gctcaggata tcgcagctgc ggatatggca cctactcatc cgataaggct tggtctggcc   540
ctgaatttct cagtgttcta ctatgagatt ctcaattcct cagacaaagc ttgtaacatg   600
gccaaacagg cttttgagga ggccatagct gagcttgaca ctctgggaga ggaatcctac   660
aaagacagca ctctcataat gcagttgctg agggacaatt taacccttg  gacctccgat   720
atgcaggtat tcacatctct ttatgccgta cctcgatatt ctacaccatt cgaataa      777
```

```
SEQ ID NO: 302          moltype = AA   length = 258
FEATURE                 Location/Qualifiers
source                  1..258
                        mol_type = protein
                        organism = Arabidopsis thaliana
SEQUENCE: 302
MAATLGRDQY VYMAKLAEQA ERYEEMVQFM EQLVTGATPA EELTVEERNL LSVAYKNVIG    60
SLRAAWRIVS SIEQKEESRK NDEHVSLVKD YRSKVESELS SVCSGILKLL DSHLIPSAGA   120
SESKVFYLKM KGDYHRYMAE FKSGDERKTA AEDTMLAYKA AQDIAAADMA PTHPIRLGLA   180
LNFSVFYYEI LNSSDKACNM AKQAFEEAIA ELDTLGEESY KDSTLIMQLL RDNLTLWTSD   240
MQVFTSLYAV PRYSTPFE                                                 258

SEQ ID NO: 303          moltype = DNA   length = 762
FEATURE                 Location/Qualifiers
source                  1..762
                        mol_type = other DNA
                        organism = Sorghum bicolor
SEQUENCE: 303
atgtcgcggg aggagaatgt ctacatggcc aagctggctg agcaagcaga acggtatgag    60
gaaatggttg agtacatgga aaggtggct aagaccgttg atgtggaaga gctcaccgtt    120
gaggagcgta acctcctatc tgttgcctac aagaatgtga ttggggcccg ccgtgcctca   180
tggcggattg tctcctccat cgagcagaag gaggagtccc gcaagaatga ggaacatgtt   240
gctcagatta aggagtaccg tggcaagatt gaggctgaat gagcaacat  ttgtgatggt   300
atcctgaagc tgcttgactc gcaccttgtg ccttcctcca ctgctgcaga gtcgaaggtg   360
ttttacctca agatgaaggg tgattatcac aggtaccttg ctgagtttaa gactggtgct   420
gagaggaagg aatctgcaga gagcacaatg gtagcttata aggcagccca ggatattgca   480
ttggctgaac tggcacctac tcatcccata aggcttggac ttgcacttaa cttctcggtg   540
ttctattatg agattctgaa ctctccggac aaagcttgca accttgcaaa gcaggcattt   600
gatgaggcta tttctgagtt ggacacgctt ggtgaggaat cttacaaaga tagcaccttg   660
attatgcagc tcctaaggga caacttgacc ctctggacct ctgacatcac ggaggagggc   720
actgaggagg gcaaagaagc ctcgaagggt gatgctgagt ag                      762

SEQ ID NO: 304          moltype = AA   length = 253
FEATURE                 Location/Qualifiers
source                  1..253
                        mol_type = protein
                        organism = Sorghum bicolor
SEQUENCE: 304
MSREENVYMA KLAEQAERYE EMVEYMEKVA KTVDVEELTV EERNLLSVAY KNVIGARRAS    60
WRIVSSIEQK EESRKNEEHV AQIKEYRGKI EAELSNICDG ILKLLDSHLV PSSTAAESKV   120
FYLKMKGDYH RYLAEFKTGA ERKESAESTM VAYKAAQDIA LAELAPTHPI RLGLALNFSV   180
FYYEILNSPD KACNLAKQAF DEAISELDTL GEESYKDSTL IMQLLRDNLT LWTSDITEEG   240
TEEGKEASKG DAE                                                      253

SEQ ID NO: 305          moltype = AA   length = 145
FEATURE                 Location/Qualifiers
source                  1..145
                        mol_type = protein
                        organism = Sesamum indicum
SEQUENCE: 305
MAEHYGQQQQ TRAPHLQLQP RAQRVVKAAT AVTAGGSLLV LSGLTLAGTV IALTIATPLL    60
VIFSPVLVPA VITIFLLGAG FLASGGFGVA ALSVLSWIYR YLTGKHPPGA DQLESAKTKL   120
ASKAREMKDR AEQFSQQPVA GSQTS                                         145

SEQ ID NO: 306          moltype = AA   length = 153
FEATURE                 Location/Qualifiers
source                  1..153
                        mol_type = protein
                        organism = Ficus pumila
SEQUENCE: 306
MAEPQSLQRG ERGEQLQLQL QQQHPRSHQ VVKAATAVTA GGSLLVLSAL ILAGTVIALT     60
IATPLFVIFS PVLVPAVITL GLIIIGFLAS GGFGVAALTV LSWIYRYVTG KHPPGADQLD   120
QARHKLASKA REMKDKAEQF GQQHLTSGQQ QSS                                153

SEQ ID NO: 307          moltype = AA   length = 142
FEATURE                 Location/Qualifiers
source                  1..142
                        mol_type = protein
                        organism = Cucumis sativus
SEQUENCE: 307
```

```
MAEHQPYQQS HQQPGSQPRY QVVKAATAAT AGGSLLVLSG LILAGTVIAL TIATPLLVIF    60
SPVLVPAVIT VSLLIMGFLA SGGFGVAGIT VFSWIYRYVT GKHPPGADQL DLARHKLASK   120
AREMKDRAEQ FGQQHTSGPQ TS                                            142

SEQ ID NO: 308          moltype = AA   length = 155
FEATURE                 Location/Qualifiers
source                  1..155
                        mol_type = protein
                        organism = Linum usitatissimum
SEQUENCE: 308
MDQSHQTYAG TMQNPSYGGG GTMHQQQQPR SYQAVKAATA ATAGGSLIVL SGLILTATVI    60
SLILATPLLV IFSPVLVPAL ITVGLLITGF LASGGFGVAA VTVLSWIYRY VTGGHPVGAD   120
SLEQARSRLA GKAREVKDRA SEFGQQHVTG GQQTS                              155

SEQ ID NO: 309          moltype = AA   length = 212
FEATURE                 Location/Qualifiers
source                  1..212
                        mol_type = protein
                        organism = Glycine max
SEQUENCE: 309
MGFACKPCMK SLPTRAKPPP QVLPPKPPLT NFSIYTLITT TLNPTTLITH SSLKTLVFHF    60
DNSHTMAELH YQQQHQYPHR YPNDPYEQQT SYSTQVVKAA TAVTAGGSLL ILASLILAGT   120
IIALTIVTPP LVIFSPVLVP AVITVALLSL GFLASGGFGV AAITVLAWIY RYVTGKYPPG   180
ADQLDSAPHK IMDKAREIKD YGQQQISGVQ AS                                 212

SEQ ID NO: 310          moltype = AA   length = 149
FEATURE                 Location/Qualifiers
source                  1..149
                        mol_type = protein
                        organism = Ananas comosus
SEQUENCE: 310
MADYQREQRG GGFMQGQQSQ QQQQQQQPMM MTAVKAATAA TAGGSMLVLS GLTLAGTVIA    60
LTVATPLLVI FSPVLVPATI AVSLLAAGFV TSGGLGLAAL SVLSWMYKYL TGKHPPGADQ   120
LEHAKARLAS KARDIKESAQ HRIDQAQGS                                     149

SEQ ID NO: 311          moltype = AA   length = 154
FEATURE                 Location/Qualifiers
source                  1..154
                        mol_type = protein
                        organism = Setaria italica
SEQUENCE: 311
MADQHRGAMG GGGGGYGDLH RGGERGETQQ RQSAMMTALK AATAATAGGS MLVLSGLILA    60
GTVIALTVAT PVLVIFSPVL VPAAITLALM AAGFVTSGGL GVAALSVFSW MYKYLTGKHP   120
PGADQLDHAK ARLASKARDI KDAAQHRIDQ AQGS                               154

SEQ ID NO: 312          moltype = AA   length = 157
FEATURE                 Location/Qualifiers
source                  1..157
                        mol_type = protein
                        organism = Fragaria vesca
SEQUENCE: 312
MAELHQQYQQ SHPFQAQQGM MQQQPKSYQV AKAATAVTAG GSLLVLSGLV LAGTVICLTV    60
ATPLLVIFSP VLVPAVITVA LIMTGFLASG GFGVAAISVL SWIYKYVTGS HPPGADKLDS   120
ARHKLAGKAR DMKDRAEQFG QQHMGTERGQ HGQHQTS                            157

SEQ ID NO: 313          moltype = AA   length = 170
FEATURE                 Location/Qualifiers
source                  1..170
                        mol_type = protein
                        organism = Brassica napus
SEQUENCE: 313
MTDTARTHHD VTNRDQYSMM GRDRDQYNMY GRDYSKSRQI AKAVTAVTAG GSLLVLSSLT    60
LVGTVIALTV ATPLLVIFSP ILVPALITVA MLITGFLSSG GFGIAAITVF SWIYKYATGE   120
HPQGSDKLDS ARMKLGSKAQ DLKDRAQYYG QQHTGGEHDR DRTRGTQHTT              170

SEQ ID NO: 314          moltype = AA   length = 147
FEATURE                 Location/Qualifiers
source                  1..147
                        mol_type = protein
                        organism = Solanum lycopersicum
SEQUENCE: 314
MADYYGQPQH TQHQFFHGGQ QPRSHQMVKA ATAVTAGGSL LLLSGLTLAA TVIALTIATP    60
VLVIFSPVIV PAVITLFLLF SGFLASGGFG VAAVSVLSWI YRYVTGKRPP GADQLEQARH   120
KLATKAGEMK DKAQEFGQQH ITGTHQT                                       147

SEQ ID NO: 315          moltype = AA   length = 163
FEATURE                 Location/Qualifiers
source                  1..163
                        mol_type = protein
```

```
                       organism = Vanilla planifolia
SEQUENCE: 315
MADSQAGPRV PVVNGNGGIG GCHALLRRIH HHSPNSSQVV GFLTLALSGA ILLLLIGITV   60
IGATLGFIAF VPLLLMTSPV WVPLVSSAFV LLAGAAAFSG TAVATAAGVT WLYRYFTGRH  120
PVGSDRVDYA RSRIADTASH VKDYAREYGG YIQSRIKDAA PGA                    163

SEQ ID NO: 316         moltype = AA  length = 241
FEATURE                Location/Qualifiers
source                 1..241
                       mol_type = protein
                       organism = Triadica sebifera
SEQUENCE: 316
MADGNVNSQE QMAKQEEQRL KYLEFVQVAA IHAVVTFTNL YVYAKNKSGP LKPGVETVEG   60
TVKSVVGPVY GKFHDVPIEV LKFVDRKIDQ SVSSLDSRVP PVVKQLSAQA FSVAREAPVA  120
ARAVASEVQT AGVKETASGL ARTLYFKYEP KAKELYTKYE PKAEQCAASA WRKLNQLPVF  180
PHVAQVVMPT AAYCSEKYNQ AVLTTAEKGY RVSSYLPFVP TERIAKLFRN EAPESTPFLS  240
N                                                                 241

SEQ ID NO: 317         moltype = AA  length = 225
FEATURE                Location/Qualifiers
source                 1..225
                       mol_type = protein
                       organism = Triadica sebifera
SEQUENCE: 317
METEKKIPEL KHLGFVRMAA IQSLICVSNL YDYAKHNSGP LRSTVGTVEG AVTTVVGPVY   60
QKFKDLPDDV LVYVDKKVDE GTHKFDKHAP PIAKKAASQA HSLFHIALEK VEKLVQEARA  120
GGPRAALHYV ATESKHLALT QSVKLYIKLN QFPVIHTVTD VTLPTATHWS DKYNHTVMDL  180
TRKGYTIFGY LPLVPIDDIS KTFKQSKAEE KEKATTHKSD SSDSD                  225

SEQ ID NO: 318         moltype = AA  length = 236
FEATURE                Location/Qualifiers
source                 1..236
                       mol_type = protein
                       organism = Triadica sebifera
SEQUENCE: 318
MAESELNQHT DMVQDDDKKL KYLDFVQVAA IYVVVCFSSI YEYAKENSGP LKPGVQAVEC   60
TVKTVISPVY EKFRDVPFEL LKFVDRKVDN SLGELDRHVP SLVKQASSQA RAVASEIQHA  120
GLVDATKNIA KTMYTKYELT AWQLYCKYKP VAKRYAVSTW RSLNQLPLFP QAAQIAIPTA  180
ASWSEKYNKM VRYTKDRGYP AAVYLPLISV ERIAKVFNED LNGPTVPTNG SSAAAQ      236

SEQ ID NO: 319         moltype = AA  length = 371
FEATURE                Location/Qualifiers
source                 1..371
                       mol_type = protein
                       organism = Cocos nucifera
SEQUENCE: 319
MVELRSSSSE MDLDRPNIEE YLTTDSIQES PKKLHLRDLL DISPTLTEAT GAIVDDSFTR   60
CFKSNPPEPW NWNVYLFPLW CLGVIIRYGI LFPLRVAILT AGWLVFFAAF IPVHFLLTAH  120
NKWRRKIERK LVEMICSVFV ASWTGVVKYH GPRPSMRPQQ VFVANHTSMI DFIILEQMTA  180
FAVIMQKHPG WVGFIQKTIL EGVGCIWFNR TESKDREVVA RKLREHIHGA DNNPLLIFPE  240
GTCVNNHYTV MFKKGAFELG CAVCPVAIKY NKIFVDAFWN SKKQSFTMHL PHLMTSWAVV  300
CDVWYLEPQY IRPGETPIEF AERVRDMISV RAGLKKVPWD GYLKYFRPSP KLTERKQQIF  360
AESVLQRLEE K                                                      371

SEQ ID NO: 320         moltype = AA  length = 389
FEATURE                Location/Qualifiers
source                 1..389
                       mol_type = protein
                       organism = Zea mays
SEQUENCE: 320
MGYIGHHGVA TLRRYKYSGV DHSLVAKYIL QPFWSRFVNI FPLWFPPNMI TLTGFMFLLT   60
SAFLGFLYSP HLDTAPPRWV HLAHGLLLFL YQTFDAVDGK QARRTNSSSP LGELFDHGCD  120
ALACAFESLA FGSTAMCGKA TFWFWFISAV PFYFATWEHF FTNTLILPIV NGPTEGLMLI  180
YLCHFFTFFT GAEWWAQDFQ KSMPLLGWVP LISEIPVYDI VLCLMIAFAV IPTIGSNIHN  240
VYKVVEARKG SMLLALAMLF PFGLLLAGVL VWSYLSPSDI MRTQPHLLII GTGFAFGFLV  300
GRMILAHLCD EPKGLKTGMC MSLAYFPFAI ANALTARLDD GNPLVDEQLV LLMYCLFTVA  360
LYMHFATSVI HEITNALGIH CFRITRKKA                                   389

SEQ ID NO: 321         moltype = AA  length = 393
FEATURE                Location/Qualifiers
source                 1..393
                       mol_type = protein
                       organism = Zea mays
SEQUENCE: 321
MGFIGAHGVE TLKRYRYSGE DRSVVAKYVL QPFWSRCVTL FPLWMPPNMI TLTGFSFLVL   60
SALLGYICSP HLDTAPPRWV HLAHGLLLFL YQTFDAVDGK QARRTSSSSP LGELFDHGCD  120
ALACAFEALA LGSTLMCGGW TLCFWVVAAV PFYLATWEHF FTNTLILPTI NGPTEGLMLI  180
YVSHLFTFFT GAEWWAQDFR KSLPFFGWIP LPFLSEIEIP LYVLVLILMI VCAVIPTVRS  240
NVSNVQEVVE ARKGSMALAL AMILPFIVLL AGVAIWCYLS PSSIMRNQPH LLVIGTGFNF  300
```

```
GYLVGRMILA HLCDEPKGLK SGMFMSLVFL CFPIANALIA KINDGSPLVD ELVLLLLYCA   360
YTVGLYLHLA VSVVHEIKDA LGIYCFRITR KEA                               393

SEQ ID NO: 322         moltype = AA  length = 389
FEATURE                Location/Qualifiers
source                 1..389
                       mol_type = protein
                       organism = Sorghum bicolor
SEQUENCE: 322
MGYIGHHGVA TLRRYKYSGV DHSLVAKYIL QPFWSRFVNI FPLWFPPNMI TLTGFMFLLT    60
SAFLGFLYSP HLDTAPPRWV HLAHGLLLFL YQTFDAVDGK QARRTNSSSP LGELFDHGCD   120
ALACAFESLA FGSTAMCGKA TFWFWFISAV PFYFATWEHF FTNTLILPIV NGPTEGLMLI   180
YLCHFFTFFT GAKWWAQDFQ KSMPLLGWVP FISEIPVYDI VLCLMIAFAV IPTIASNIHN   240
VYKVVEARKG SMVLALAMLF PFGLLLAGVL VWSYFSPSDI MRNQPHLLII GTGFAFGFLV   300
GRMILAHLCD EPKGLKTGMC MSLAYFPFAI ANALTARLDD GNPLVDEQLV LLMYCLFTVA   360
LYMHFATSVI HEITNALGIH CFRITTKKA                                    389

SEQ ID NO: 323         moltype = AA  length = 393
FEATURE                Location/Qualifiers
source                 1..393
                       mol_type = protein
                       organism = Sorghum bicolor
SEQUENCE: 323
MGFIGAHGVE TLKRYRYSGE DRSVVAKYVL QPFWSRCVTL FPLWMPPNMI TLTGFSFLVL    60
SALLGYIYSP RLDTAPPRWV HLAHGLLLFL YQTFDAVDGK QARRTSSSSP LGELFDHGCD   120
ALACAFEALA LGSTLMCGGW TFWFWVVAAV PFYLATWEHF FTNTLILPTI NGPTEGLMLI   180
YVSHLFTFLT GAEWWAQDFR KSLPFLGWIP LPFLSEIKIP LYVLVLILMI VCAVIPTVRS   240
NVSNVQEVVE TRKGSMALAL AMILPFITLL AGVAIWSYLS PSSIMRNQPH LLVIGTGFNF   300
GYLVGRMILA HLCDEPKGLK SGMFMSLVFL CFPIANALIA KINNGTPLVD ELVLLLLYCA   360
YTVGLYLHLA VSVVHEIKDA LGIYCFRITR KEA                               393
```

PLANTS WITH MODIFIED TRAITS

CROSS REFERENCE TO RELATED APPLICATIONS

This application is a divisional of U.S. application Ser. No. 16/329,939, filed Mar. 1, 2019, now allowed, which is a 371 national stage of PCT International Application No. PCT/AU2017/050948, filed Sep. 1, 2017, which claims priority of Australian Patent Application No. AU2017902756, filed Jul. 13, 2017, PCT International Application No. PCT/AU2017/050012, filed Jan. 6, 2017, Australian Patent Application No. AU2016904611, filed Nov. 11, 2016, Australian Patent Application No. AU2016903577, filed Sep. 6, 2016, and Australian Patent Application No. AU2016903541, filed Sep. 2, 2016, the contents of each of which are hereby incorporated by reference into the subject application.

REFERENCE TO SEQUENCE LISTING

This application incorporates-by-reference nucleotide and/or amino acid sequences which are present in the file named 231121_90879-Z_Sequence_Listing_EL.xml which is 885 kilobytes in size, and which was created on Nov. 21, 2023 in the IBM-PC machine format, having an operating system compatibility with MS-Windows, which is contained in the xml file filed Nov. 21, 2023 as part of this application.

FIELD OF THE INVENTION

The present invention relates, inter alia, to vegetative plant parts, such as from a *Sorghum* sp. and/or a *Zea mays* plant, which comprise a total fatty acid (TFA) content which comprises fatty acids esterified in the form of triacylglycerols (TAG) and fatty acids in the form of lipids other than TAG, wherein the vegetative plant parts comprise greatly increased levels of TFA, for example a TFA content of about 5% (w/w dry weight). The present invention also relates to the use of the vegetative plant parts as a feedstuff, and/or to produce a feedstuff, for animal consumption.

BACKGROUND OF THE INVENTION

Meeting consumer demands for livestock products, for example meat, milk and eggs is reliant on the availability of regular supplies of safe, cost-effective animal feeds, in particular feeds with high energy such as high levels of fatty acids. As consumer demands for such livestock products increase, particularly in the developing world, for example, global demand for meat products is anticipated to increase 58% between 1995 and 2020 (FAO Animal Production and Health Proceedings, 2002), an increase in feed protein supply is required.

There is a need for vegetative plant parts, particularly vegetative plant parts from important animal feed crops such as sorghum and corn, with a high total fatty acid content.

SUMMARY OF THE INVENTION

The present invention relates to plants and vegetative plant parts, preferably from *Sorghum* sp. and/or *Zea mays*, with an enhanced total fatty acid content and their uses.

Thus, in a first aspect, the present invention provides a process for producing a feedstuff for an animal, the process comprising the steps of (i) harvesting vegetative plant parts from a *Sorghum* sp. and/or a *Zea mays* plant, the vegetative plant parts comprising a total fatty acid (TFA) content which comprises fatty acids esterified in the form of triacylglycerols (TAG) and fatty acids in the form of lipids other than TAG, wherein the vegetative plant parts comprise a TFA content of about 5% (w/w dry weight), and one or more of the steps (ii) admixing the harvested plant parts with at least one other feed ingredient, (iii) baling the harvested plant parts, (iv) processing the harvested plant parts, preferably by chopping, cutting, drying, pressing or pelleting the plant parts, into a form that is suitable for consumption by the animal, and (v) storing the harvested plant parts under conditions of reduced oxygen for a period of time such that at least some of the carbohydrates in the plant parts are fermented to organic acids.

In an embodiment, the vegetative plant parts have a TAG/TFA Quotient (TTQ) of between 0.01 and 0.6. In an embodiment, the vegetative plant parts have a TTQ of between 0.01 and 0.55, or between 0.01 and 0.5, or about 0.1, or about 0.2 or about 0.3, or about 0.4 or about 0.5. Preferably, the TTQ is between 0.60 and 0.84, which corresponds to a TAG:TFA ratio of between 1.5:1 and 5:1, or between 0.84 and 0.95 which corresponds to a TAG:TFA ratio of between 5:1 and 20:1.

In an embodiment, the vegetative plant parts comprise an average TFA content of about 6%, or about 8%, or about 9% or about 10% (w/w dry weight).

In an embodiment, the TFA content of the vegetative plant parts comprises an oleic acid content which is increased by at least 2% or at least 3% relative to the oleic acid content of a corresponding wild-type vegetative plant part.

In an embodiment, the TFA content of the vegetative plant parts comprises a palmitic acid content which is increased by at least 2% or at least 3% relative to the palmitic acid content of a corresponding wild-type vegetative plant part.

In an embodiment, the TFA content of the vegetative plant parts comprises a α-linoleic acid (ALA) content which is decreased by at least 2% or at least 3% relative to the ALA content of a corresponding wild-type vegetative plant part.

In an embodiment, one or more or all of the following features apply:

(i) the vegetative plant parts are leaves and/or stems or parts thereof which comprise one or more of an increased carbon content, an increased energy content, an increased soluble protein content, a reduced starch content, a reduced total dietary fibre (TDF) content and an increased nitrogen content, each on a weight basis relative to a corresponding wild-type leaf or stem or parts thereof from a wild-type *Sorghum* sp. or *Zea mays* plant at the same stage of growth, (ii) the TFA content of the vegetative plant parts is at least about 6%, at least about 7%, at least about 8%, at least about 9%, at least about 10%, at least about 11%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, between about 6% and about 20%, between 8% and 75%, between 10% and 75%, between 11% and 75%, between about 15% and 75%, between about 20% and 75%, between about 30% and 75%, between about 40% and 75%, between about 50% and 75%, between about 60% and 75%, or between about 25% and 50% (w/w dry weight) TFA, (iii) the fatty acids esterified in the form of TAG in the vegetative plant parts is at least about 1%, at least about 2%, at least about 3%, at least about 4%, at least about 5%, at least about 6%, at least about 7%, at least about 8%, at least about 9%, at least about 10%, at least about 11%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, between about 6% and about 20%, between 8% and 75%, between 10% and 75%, between 11% and 75%, between about 15% and 75%, between about 20% and 75%, between about 30% and 75%, between about 40% and 75%, between about 50% and 75%, between about 60% and 75%, or between about 25% and 50% (w/w dry weight), (iv) the vegetative plant parts comprise an increased content of a WRI1 polypeptide, an increased content of a DGAT polypeptide, and a decreased content of a SDP1 polypeptide, each relative to a corresponding wild-type vegetative plant part, (v) the vegetative plant parts comprise an increased content of a WRI1 polypeptide, an increased content of a DGAT polypeptide, and an increased content of a LEC2 polypeptide, each relative to a corresponding wild-type vegetative plant part, (vi) the vegetative plant parts comprise an increased content of a PDAT or DGAT polypeptide, a decreased content of a TGD polypeptide, and a decreased content of a SDP1 polypeptide, each relative to a corresponding wild-type vegetative plant part, and (vii) the vegetative plant parts comprise a decreased content of a TAG lipase such as a SDP1 TAG lipase, a decreased content of a TGD polypeptide such as a TGD5 polypeptide, and optionally a decreased content of a TST polypeptide such as a TST1 polypeptide, each decrease being relative to a corresponding wild-type vegetative plant part.

In second aspect, the present invention provides a process for producing a feedstuff for an animal, the process comprising the steps of (i) harvesting vegetative plant parts from a Sorghum sp. and/or a Zea mays plant, the vegetative plant parts comprising a total fatty acid content which comprises fatty acids esterified in the form of triacylglycerols (TAG) and fatty acids in the form of lipids other than TAG, wherein the vegetative plant parts comprise a total TAG content of about 6% (w/w dry weight) and preferably have a ratio of the fatty acids esterified in the form of TAG to the fatty acids in the form of lipids other than TAG which is between 20:1 and 1.5:1 or between 5:1 and 2:1, and one or more of the steps (ii) admixing the harvested plant parts with at least one other feed ingredient, (iii) baling the harvested plant parts, (iv) processing the harvested plant parts, preferably by chopping, cutting, drying, pressing or pelleting the plant parts, into a form that is suitable for consumption by the animal, and (v) storing the harvested plant parts under conditions of reduced oxygen for a period of time such that at least some of the carbohydrates in the plant parts are fermented to organic acids.

In an embodiment of the two above aspects, one or more or all of the following features apply:

(i) the vegetative plant parts are harvested from the plant between the time of first flowering of the plant and first maturity of seed, (ii) the Sorghum sp. plant is a Sorghum bicolor plant, (iii) the vegetative plant parts include leaves and/or stems or parts thereof, (iv) the vegetative plant parts comprise an average total fatty acid content of about 8% or about 10% (w/w dry weight), (v) the total fatty acid content of the vegetative plant parts comprises an oleic acid content which is increased by at least 2% or at least 3% relative to the oleic acid content of a corresponding wild-type vegetative plant part, (vi) the total fatty acid content of the vegetative plant parts comprises a palmitic acid content which is increased by at least 2% or at least 3% relative to the palmitic acid content of a corresponding wild-type vegetative plant part, (vii) the total fatty acid content of the vegetative plant parts comprises a α-linoleic acid (ALA) content which is decreased by at least 2% or at least 3% relative to the ALA content of a corresponding wild-type vegetative plant part, (viii) the vegetative plant parts comprise an increased soluble protein content relative to a corresponding wild-type vegetative plant part, (ix) the vegetative plant parts comprise an increased nitrogen content relative to a corresponding wild-type vegetative plant part, (x) the vegetative plant parts comprise a decreased carbon:nitrogen ratio relative to a corresponding wild-type vegetative plant part, (xi) leaves of the Sorghum sp. and/or Zea mays plant comprises an increased photosynthetic capacity relative to a corresponding wild-type leaf, (xii) the vegetative plant parts comprise a decreased total dietary fibre (TDF) content relative to a corresponding wild-type vegetative plant part, (xiii) the vegetative plant parts comprise an increased carbon content relative to a corresponding wild-type vegetative plant part, (xiv) the vegetative plant parts comprise an increased transcription factor polypeptide content relative to a corresponding wild-type vegetative plant part, wherein the transcription factor polypeptide is selected from the group consisting of Wrinkled 1 (WRI1), Leafy Cotyledon 1 (LEC1), LEC1-like, Leafy Cotyledon 2 (LEC2), BABY BOOM (BBM), FUS3, ABI3, ABI4, ABI5, Dof4 and Dof11, or the group consisting of MYB73, bZIP53, AGL15, MYB115, MYB118, TAN-MEI, WUS, GFR2a1, GFR2a2 and PHR1, (xv) the vegetative plant parts comprise an increased fatty acid acyltransferase polypeptide content relative to a corresponding wild-type vegetative plant part, wherein the acyltransferase is diacylglycerol acyltransferase (DGAT) and/or phospholipid:diacylglycerol acyltransferase (PDAT), (xvi) the vegetative plant parts comprise a decreased TAG lipase polypeptide content relative to a corresponding wild-type vegetative plant part, (xvii) the vegetative plant parts comprise a decreased trigalactosyldiacylglycerol (TGD) polypeptide content relative to a corresponding wild-type vegetative plant part, (xviii) the vegetative plant parts comprise an increased content of an oil body coating (OBC) polypeptide or a lipid droplet associated polypeptide (LDAP) relative to a corresponding wild-type vegetative plant part, (xix) the vegetative plant parts comprise an increased total protein content relative to a corresponding wild-type vegetative plant part, (xx) the vegetative plant parts comprise an increased chlorophyll content relative to a corresponding wild-type vegetative plant part, (xxi) the vegetative plant parts comprise an increased energy content on a weight basis relative to a corresponding wild-type vegetative plant part, (xxii) the vegetative plant parts comprise an increased phospholipid and/or galactolipid content, preferably an increased monogalactosyl-diglyceride (MDGD) and/or increased digalactosyl-diglyceride (DGDG) content, relative to a corresponding wild-type vegetative plant part, (xxiii) the ratio of the fatty acids esterified in the form of TAG to the fatty acids in the form of lipids other than TAG is about 4, about 3.5, about 3, or about 2.5, (xxiv) the at least one other feed ingredient comprises one or more or all of: edible macronutrients, vitamins, minerals (such as calcium, phosphorus, magnesium and sulfur), hay such as alfalfa hay, brewers grain, seed meal (canola or soy), cottonseed, molasses, additional amino acids (such as lysine and methionine) non-protein nitrogen supplies (such as urea), (xxv) the period of time is between one week and 52 weeks, (xxvi) the organic acids comprise acetic acid, propionic acid or butyric acid, or any combination thereof, (xxvii) the feedstuff is silage, pellets or hay, and (xxviii) the vegetative plant parts are stored for a period of time before being mixed with the at least one other feed ingredient, (xxiv) the TTQ is about 0.1, or about 0.2 or about 0.3, or about 0.4 or about 0.5, or about 0.6, or about 0.65, or about 0.7, or about 0.75, or about 0.8, or about 0.81, or about 0.82, or about 0.83, or about 0.84, or about 0.85, or about 8.6, or about 8.7, or about 8.8, or about 8.9, or about 0.9, or about 0.91, or about 0.92, or about 0.93, or about 0.94, or about 0.95, in each case where the corresponding wild-type plant part is harvested from a wild-type Sorghum sp. or Zea mays plant at the same stage of growth.

In a further embodiment of the above aspects, one or more or all of the following features apply:

(i) the vegetative plant parts are leaves and/or stems or parts thereof which comprise one or more of an increased carbon content, an increased energy content, an increased soluble protein content and an increased nitrogen content, each on a weight basis relative to a corresponding wild-type leaf or stem or parts thereof from a wild-type Sorghum sp. or Zea mays plant at the same stage of growth, (ii) the total fatty acid content of the vegetative plant parts is at least about 8%, at least about 9%, at least about 10%, at least about 11%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, between about 6% and about 20%, between 8% and 75%, between 10% and 75%, between 11% and 75%, between about 15% and 75%, between about 20% and 75%, between about 30% and 75%, between about 40% and 75%, between about 50% and 75%, between about 60% and 75%, or between about 25% and 50% (w/w dry weight), (iii) the fatty acids esterified in the form of TAG in the vegetative plant parts is at least about 1%, at least about 2%, at least about 3%, at least about 4%, at least about 5%, at least about 6%, at least about 7%, at least about 8%, at least about 9%, at least about 10%, at least about 11%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, between about 6% and about 20%, between 8% and 75%, between 10% and 75%, between 11% and 75%, between about 15% and 75%, between about 20% and 75%, between about 30% and 75%, between about 40% and 75%, between about 50% and 75%, between about 60% and 75%, or between about 25% and 50% (w/w dry weight), (iv) the vegetative plant parts comprise an increased content of a WRI1 polypeptide, an increased content of a DGAT polypeptide, and a decreased content of a SDP1 polypeptide, each relative to a corresponding wild-type vegetative plant part, (v) the vegetative plant parts comprise an increased content of a WRI1 polypeptide, an increased content of a DGAT polypeptide, and an increased content of a LEC2 polypeptide, each relative to a corresponding wild-type vegetative plant part, (vi) the vegetative plant parts comprise an increased content of a PDAT or DGAT polypeptide, a decreased content of a TGD polypeptide, and a decreased content of a SDP1 polypeptide, each relative to a corresponding wild-type vegetative plant part, and (vii) the vegetative plant parts comprise a decreased content of a TAG lipase polypeptide such as a SDP1 polypeptide, a decreased content of a TGD polypeptide such as a TGD5 polypeptide, and optionally a decreased content of a TST polypeptide such as a TST1 polypeptide, each relative to a corresponding wild-type vegetative plant part.

In an embodiment, the vegetative plant parts comprise an increased content of one or more sucrose metabolism polypeptides selected from the group consisting of an invertase and a sucrose transport polypeptide. The invertase may be a vacuolar invertase or a cytosolic invertase, and the sucrose transport polypeptide may be, for example, a SUS4 or SUT2 that is naturally located to the vacuolar membrane.

In another aspect, the present invention provides a process for feeding an animal, the process comprising providing vegetative plant parts from a Sorghum sp. and/or a Zea mays plant to the animal, the vegetative plant parts comprising a total fatty acid (TFA) content which comprises fatty acids esterified in the form of triacylglycerols (TAG) and fatty acids in the form of lipids other than TAG, wherein the vegetative plant parts comprise a TFA content of about 5% (w/w dry weight), preferably between about 6% and about 20%.

In an embodiment of the above aspect, the vegetative plant parts have a TTQ of between 0.01 and 0.6. In an embodiment, the vegetative plant parts have a TTQ of between 0.01 and 0.55, or between 0.01 and 0.5, or about 0.1, or about 0.2 or about 0.3, or about 0.4 or about 0.5. Preferably, the TTQ is between 0.60 and 0.84 or between 0.84 and 0.95.

In another aspect, the present invention provides a process for feeding an animal, the process comprising providing vegetative plant parts from a *Sorghum* sp. and/or a *Zea mays* plant to the animal, the vegetative plant parts comprising a total fatty acid content which comprises fatty acids esterified in the form of triacylglycerols (TAG) and fatty acids in the form of lipids other than TAG, wherein the vegetative plant parts comprise a total TAG content of about 6% (w/w dry weight), preferably between about 6% and about 20%, and preferably have a ratio of the fatty acids esterified in the form of TAG to the fatty acids in the form of lipids other than TAG which is between 20:1 and 1.5:1 or between 5:1 and 2:1.

In an embodiment of the two above aspects, one or more or all of the following features apply:
  (i) the vegetative plant parts are comprised in a *Sorghum* sp. and/or *Zea mays* plant growing in a field,
  (ii) the vegetative plant parts are harvested from the *Sorghum* sp. and/or *Zea mays* plant and/or admixed with at least one other feed ingredient,
  (iii) the vegetative plant parts were processed post-harvest, preferably by chopping, cutting, drying, pressing or pelleting the plant parts, into a form that is more suitable for consumption by the animal,
  (iv) the harvested plant parts were stored under conditions of reduced oxygen for a period of time such that at least some of the carbohydrates in the plant parts are fermented to organic acids prior to being provided to the animal, and
  (v) the harvested plant parts are stored for a period of time between harvest and providing them to the animal.

In a further embodiment of the two above aspects, the animal ingests an increased amount of nitrogen, protein, carbon and/or energy potential relative to when the animal ingests the same amount on a dry weight basis of a corresponding feedstuff produced using an equivalent amount of wild-type *Sorghum* sp. and/or *Zea mays* plant or parts thereof.

In a further embodiment of the two above aspects, the process is further characterised by one or more features as described in the context of the first or second aspects of the invention.

The above two aspects are described in relation to a *Sorghum* sp. and/or *Zea mays* plant. However, it is not intended to limit the described processes to use of only a *Sorghum* sp. or *Zea mays* plant. It is intended that any suitable plant can be used in the processes.

In a further aspect, the present invention provides a feedstuff for an animal, comprising harvested vegetative plant parts from a *Sorghum* sp. and/or a *Zea mays* plant, the vegetative plant parts comprising a total fatty acid (TFA) content which comprises fatty acids esterified in the form of triacylglycerols (TAG) and fatty acids in the form of lipids other than TAG, wherein the vegetative plant parts comprise a TFA content of about 5% (w/w dry weight), preferably between about 6% and about 20%, wherein
  (i) the harvested plant parts are mixed with at least one other feed ingredient,
  (ii) the harvested plant parts were baled after harvest,
  (iii) the harvested plant parts were processed, preferably by chopping, cutting, drying, pressing or pelleting the plant parts, into a form that is suitable for consumption by the animal, and
  (iv) the harvested plant parts were stored under conditions of reduced oxygen for a period of time such that at least some of the carbohydrates in the plant parts were fermented to organic acids.

In an embodiment, the vegetative plant parts have a TTQ of between 0.01 and 0.6. In an embodiment, the vegetative plant parts have a TTQ of between 0.01 and 0.55, or between 0.01 and 0.5, or bout 0.1, or about 0.2 or about 0.3, or about 0.4 or about 0.5. Preferably, the TTQ is between 0.60 and 0.84 or between 0.84 and 0.95.

In another aspect, the present invention provides a feedstuff for an animal, comprising harvested vegetative plant parts from a *Sorghum* sp. and/or a *Zea mays* plant, the vegetative plant parts comprising a total fatty acid content which comprises fatty acids esterified in the form of triacylglycerols (TAG) and fatty acids in the form of lipids other than TAG, wherein the vegetative plant parts comprise a total TAG content of about 6% (w/w dry weight), preferably between about 6% and about 20%, and preferably have a ratio of the fatty acids esterified in the form of TAG to the fatty acids in the form of lipids other than TAG which is between 20:1 and 1.5:1 or between 5:1 and 2:1, wherein
  (i) the harvested plant parts are mixed with at least one other feed ingredient,
  (ii) the harvested plant parts were baled after harvest,
  (iii) the harvested plant parts were processed, preferably by chopping, cutting, drying, pressing or pelleting the plant parts, into a form that is suitable for consumption by the animal, and
  (iv) the harvested plant parts were stored under conditions of reduced oxygen for a period of time such that at least some of the carbohydrates in the plant parts were fermented to organic acids.

In an embodiment of the two above aspects, the feedstuff is silage, pellets or hay.

In a further embodiment of the two above aspects, the feedstuff is further characterised by one or more features as described in the context of the first or second aspects of the invention.

The above two aspects are described in relation to a *Sorghum* sp. and/or *Zea mays* plant. However, it is not intended to limit the described feedstuffs to comprising vegetative plant parts from a *Sorghum* sp. or *Zea mays* plant. It is intended that the feedstuffs relate more generally to feedstuffs comprising vegetative plant parts from any suitable plant.

In another aspect, the present invention provides a cell, preferably a *Sorghum* sp. or *Zea mays* cell, other than a seed cell, comprising a total fatty acid (TFA) content which comprises fatty acids esterified in the form of triacylglycerols (TAG) and fatty acids in the form of lipids other than TAG, wherein the cell comprises a TFA content of about 5% (w/w dry weight), preferably between about 6% and about 20%.

In an embodiment, the total fatty acid content of the cell has a TTQ of between 0.01 and 0.6. In an embodiment, the total fatty acid content of the cell has a TTQ of between 0.01 and 0.55, or between 0.01 and 0.5, or bout 0.1, or about 0.2 or about 0.3, or about 0.4 or about 0.5. Preferably, the TTQ is between 0.60 and 0.84 or between 0.84 and 0.95.

In an embodiment, the TFA content of the cell comprises an oleic acid content which is increased by at least 2% or at least 3% relative to the oleic acid content of a corresponding wild-type cell.

In an embodiment, the TFA content of the cell comprises a palmitic acid content which is increased by at least 2% or at least 3% relative to the palmitic acid content of a corresponding wild-type cell.

In an embodiment, the TFA content of the cell comprises a α-linoleic acid (ALA) content which is decreased by at least 2% or at least 3% relative to the ALA content of a corresponding wild-type cell.

In an embodiment, the cell is in a vegetative part of a plant and comprises a TAG content of at least about 1%, at least about 2%, at least about 3%, at least about 4%, at least about 5%, at least about 6%, at least about 7%, at least about 8%, at least about 10%, at least about 11%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, between about 6% and about 20%, between 8% and 75%, between 10% and 75%, between 11% and 75%, between about 15% and 75%, between about 20% and 75%, between about 30% and 75%, between about 40% and 75%, between about 50% and 75%, between about 60% and 75%, or between about 25% and 50% (w/w dry weight).

In a further embodiment, the cell is from or in a plant leaf or stem, before the plant flowers, and the cell comprises a TFA content and/or a total non-polar fatty acid content of at least about 6%, at least about 7%, at least about 8%, at least about 10%, at least about 11%, between 8% and 15%, or between 9% and 12% on a weight basis, preferably between about 6% and about 20%.

In another aspect, the present invention provides a cell, preferably a *Sorghum* sp. or *Zea mays* cell, other than a seed cell, comprising a total fatty acid content which comprises fatty acids esterified in the form of triacylglycerols (TAG) and fatty acids in the form of lipids other than TAG, wherein the cell comprises a total TAG content of about 6% (w/w dry weight), preferably between about 6% and about 20%, and has a ratio of the fatty acids esterified in the form of TAG to the fatty acids in the form of lipids other than TAG which is between 20:1 and 1.5:1 or between 5:1 and 2:1.

In another aspect, the present invention provides a cell, preferably a *Sorghum* sp. or *Zea mays* cell, comprising an increased content of a WRI1 polypeptide, an increased content of a DGAT polypeptide, and a decreased content of a SDP1 polypeptide, each relative to a corresponding wild-type cell.

In another aspect, the present invention provides a cell, preferably a *Sorghum* sp. or *Zea mays* cell, comprising an increased content of a WRI1 polypeptide, an increased content of a DGAT polypeptide, and an increased content of a LEC2 polypeptide, each relative to a corresponding wild-type cell.

In another aspect, the present invention provides a cell, preferably a *Sorghum* sp. or *Zea mays* cell, comprising an increased content of a PDAT or DGAT polypeptide, a decreased content of a TGD polypeptide, preferably a TGD5 polypeptide, and a decreased content of a SDP1 polypeptide, each relative to a corresponding wild-type cell.

In another aspect, the present invention provides a cell, preferably a *Sorghum* sp. or *Zea mays* cell, comprising a decreased content of a TAG lipase such as a SDP1 TAG lipase, a decreased content of a TGD polypeptide such as a TGD5 polypeptide, and optionally a decreased content of a TST polypeptide such as a TST1 polypeptide, each decrease being relative to a corresponding wild-type cell.

In an embodiment of the above aspects related to a cell of the invention, one or more or all of the following features apply:

(i) the cell is in a vegetative plant part which was harvested from a *Sorghum* sp. or *Zea mays* plant between the time of first flowering of the plant and first maturity of seed,
(ii) the cell is a *Sorghum bicolor* plant cell,
(iii) the cell is in a leaf or stem or a part thereof,
(iv) the cell comprises a total lipid content of about 8% or about 10% on a weight basis,
(v) the total fatty acid content of the cell comprises an oleic acid content which is increased by at least 2% or at least 3% relative to the oleic acid content of a corresponding wild-type cell,
(vi) the total fatty acid content of the cell comprises a palmitic acid content which is increased by at least 2% or at least 3% relative to the palmitic acid content of a corresponding wild-type cell,
(vii) the total fatty acid content of the cell comprises a α-linoleic acid (ALA) content which is decreased by at least 2% or at least 3% relative to the ALA content of a corresponding wild-type cell,
(viii) the cell comprises an increased soluble protein content relative to a corresponding wild-type cell,
(ix) the cell comprises an increased nitrogen content relative to a corresponding wild-type cell,
(x) the cell comprises a decreased carbon:nitrogen ratio relative to a corresponding wild-type cell,
(xi) the cell comprises an increased photosynthetic capacity relative to a corresponding wild-type cell,
(xii) the cell comprises a decreased starch and/or total dietary fibre (TDF) content relative to a corresponding wild-type cell,
(xiii) the cell comprises an increased carbon content relative to a corresponding wild-type cell,
(xiv) the cell comprises an increased transcription factor polypeptide content relative to a corresponding wild-type cell, wherein the transcription factor polypeptide is selected from the group consisting of Wrinkled 1 (WRI1), Leafy Cotyledon 1 (LEC1), LEC1-like, Leafy Cotyledon 2 (LEC2), BABY BOOM (BBM), FUS3, ABI3, ABI4, ABI5, Dof4 and Dof11, or the group consisting of MYB73, bZIP53, AGL15, MYB115, MYB118, TANMEI, WUS, GFR2a1, GFR2a2 and PHR1,
(xv) the cell comprises an increased fatty acid acyltransferase polypeptide content relative to a corresponding wild-type cell, wherein the acyltransferase is diacylglycerol acyltransferase (DGAT) and/or phospholipid:diacylglycerol acyltransferase (PDAT),
(xvi) the cell comprises a decreased TAG lipase polypeptide content relative to a corresponding wild-type cell,
(xvii) the cell comprises a decreased trigalactosyldiacylglycerol (TGD) polypeptide content relative to a corresponding wild-type cell,
(xviii) the cell comprises an increased content of an oil body coating (OBC) polypeptide or a lipid droplet associated polypeptide (LDAP) relative to a corresponding wild-type cell,
(xix) the cell comprises an increased total protein content relative to a corresponding wild-type cell,
(xx) the cell comprises an increased chlorophyll content relative to a corresponding wild-type cell,
(xxi) the cell comprises an increased energy content on a weight basis relative to a corresponding wild-type cell,
(xxii) the cell comprises an increased phospholipid and/or galactolipid content relative to a corresponding wild-type cell, preferably an increased MDGD content and/or an increased DGDG content, (xxiii) the TTQ is about 0.1, or about 0.2 or about 0.3, or about 0.4 or about 0.5, or about 0.6, or about 0.65, or about 0.7, or about 0.75, or about 0.8, or about 0.81, or about 0.82, or about 0.83, or about 0.84, or about 0.85, or about 8.6, or about 8.7, or about 8.8, or about 8.9, or about 0.9, or about 0.91, or about 0.92, or about 0.93, or about 0.94, or about 0.95, and (xxiv) the ratio of the fatty acids esterified in the form of TAG to the fatty acids in the form of lipids other than TAG is between 20:1 and 1.5:1, or between 5:1 and 2:1, or about 4, about 3.5, about 3, or about 2.5.

In an embodiment of the above aspects, the vegetative plant parts or cell of the invention comprises one or both of a) a first exogenous polynucleotide which encodes a transcription factor polypeptide that increases the expression of one or more glycolytic and/or fatty acid biosynthetic genes in the vegetative plant parts or cell, preferably a WRI1 polypeptide, and b) a second exogenous polynucleotide which encodes a polypeptide involved in the biosynthesis of one or more non-polar lipids, preferably a DGAT and/or a PDAT, and in each case any one or two or three or all four of c) a first genetic modification which down-regulates endogenous production and/or activity of a polypeptide involved in the catabolism of triacylglycerols (TAG) in the vegetative plant parts or cell, preferably an SDP1 TAG lipase, when compared to a corresponding vegetative plant part or cell lacking the genetic modification, d) a third exogenous polynucleotide which encodes a polypeptide which increases the export of fatty acids out of plastids of the vegetative plant parts or cell when compared to a corresponding vegetative plant part or cell lacking the third exogenous polynucleotide, preferably an acyl-ACP thioesterase polypeptide, e) a fourth exogenous polynucleotide which encodes a second transcription factor polypeptide that increases the expression of one or more glycolytic and/or fatty acid biosynthetic genes in the vegetative plant parts or cell, preferably a LEC2 polypeptide, and f) a second genetic modification which down-regulates endogenous production and/or activity of a polypeptide involved in importing fatty acids into plastids of the vegetative plant parts or cell when compared to a corresponding vegetative plant part or cell lacking the second genetic modification, preferably a TGD polypeptide, wherein each exogenous polynucleotide is operably linked to a promoter which is capable of directing expression of the polynucleotide in the vegetative plant parts or cell.

In an embodiment of the above aspects, the vegetative plant parts or cell further comprises one or both of a) a fifth exogenous polynucleotide which encodes an oil body coating (OBC) polypeptide or a lipid droplet associated protein (LDAP), and b) a third genetic modification which down-regulates endogenous production and/or activity of a polypeptide involved in diacylglycerol (DAG) production in the plastid when compared to a corresponding vegetative plant part or cell lacking the third genetic modification.

In an alternate embodiment of the above aspects, the vegetative plant parts or cell comprises a) a first exogenous polynucleotide which encodes a transcription factor polypeptide that increases the expression of one or more glycolytic and/or fatty acid biosynthetic genes in the vegetative plant parts or cell, preferably a WRI1 polypeptide, b) a second exogenous polynucleotide which encodes a polypeptide involved in the biosynthesis of one or more non-polar lipids, preferably a DGAT and/or a PDAT, and any one or two or all three of c) a first genetic modification which down-regulates endogenous production and/or activity of a polypeptide involved in the catabolism of triacylglycerols (TAG) in the vegetative plant parts or cell when compared to a corresponding vegetative plant part or cell lacking the genetic modification, preferably an SDP1 TAG lipase, d) a third exogenous polynucleotide which encodes a polypeptide which increases the export of fatty acids out of plastids of the vegetative plant parts or cell when compared to a corresponding vegetative plant part or cell lacking the third exogenous polynucleotide, preferably a acyl-ACP thioesterase polypeptide, and e) a fourth exogenous polynucleotide which encodes a second transcription factor polypeptide that increases the expression of one or more glycolytic and/or fatty acid biosynthetic genes in the vegetative plant parts or cell, preferably a LEC2 polypeptide, wherein each exogenous polynucleotide is operably linked to a promoter which is capable of directing expression of the polynucleotide in the vegetative plant parts or cell.

In an embodiment of the above aspect, the vegetative plant parts or cell further comprises one or more or all of a) a fifth exogenous polynucleotide which encodes an oil body coating (OBC) polypeptide or a lipid droplet associated protein (LDAP), b) a second genetic modification which down-regulates endogenous production and/or activity of a polypeptide involved in importing fatty acids into plastids of the vegetative plant parts or cell when compared to a corresponding vegetative plant part or cell lacking the second genetic modification, and c) a third genetic modification which down-regulates endogenous production and/or activity of a polypeptide involved in diacylglycerol (DAG) production in the plastid when compared to a corresponding vegetative plant part or cell lacking the third genetic modification.

In a further embodiment of the above aspects, the vegetative plant parts or cell comprises a first exogenous polynucleotide which encodes a WRI1 polypeptide, a second exogenous polynucleotide which encodes a DGAT polypeptide, and a decreased content of a TAG lipase polypeptide and/or a decreased content of a TGD polypeptide relative to a corresponding wild-type vegetative plant part or cell, wherein each exogenous polynucleotide is operably linked to a promoter which is capable of directing expression of the polynucleotide in the vegetative plant parts or cell.

In another embodiment of the above aspects, the vegetative plant parts or cell comprises an exogenous polynucleotide which encodes a PDAT or DGAT polypeptide, an increased content of the PDAT or DGAT polypeptide, a decreased content of a TGD polypeptide and a decreased content of a TAG lipase polypeptide, each relative to a corresponding wild-type vegetative plant part or cell, wherein the exogenous polynucleotide is operably linked to a promoter which is capable of directing expression of the polynucleotide in the vegetative plant parts or cell.

In another embodiment of the above aspects, the vegetative plant parts or cell comprises a decreased content of a TAG lipase such as a SDP1 TAG lipase, a decreased content of a TGD polypeptide such as a TGD5 polypeptide, and optionally a decreased content of a TST polypeptide such as a TST1 polypeptide, each decrease being relative to a corresponding wild-type vegetative plant part or cell.

In a further embodiment of the above aspects, the cell is from or in a vegetative part of a *Sorghum* sp. or *Zea mays* plant.

In a further embodiment of the above aspects, one or more or all of the following features apply:
  i) the vegetative plant parts or cell has an increased synthesis of total fatty acids relative to a corresponding vegetative plant part or cell lacking the first exogenous polynucleotide, or a decreased catabolism of total fatty acids relative to a corresponding vegetative plant part or cell lacking the first exogenous polynucleotide, or both, such that it has an increased level of total fatty acids relative to a corresponding vegetative plant part or cell lacking the first exogenous polynucleotide,
  ii) the vegetative plant parts or cell has an increased expression and/or activity of a fatty acyl acyltransferase which catalyses the synthesis of TAG, DAG or MAG, preferably TAG, relative to a corresponding vegetative plant part or cell having the first exogenous polynucleotide and lacking the exogenous polynucleotide which encodes a polypeptide involved in the biosynthesis of one or more non-polar lipids,
  iii) the vegetative plant parts or cell has a decreased production of lysophosphatidic acid (LPA) from acyl-ACP and G3P in its plastids relative to a corresponding vegetative plant part or cell having the first exogenous polynucleotide and lacking the genetic modification which down-regulates endogenous production and/or activity of a polypeptide involved in diacylglycerol (DAG) production in the plastid in the vegetative plant parts or cell,
  iv) the vegetative plant parts or cell has an altered ratio of C16:3 to C18:3 fatty acids in its total fatty acid content and/or its galactolipid content relative to a corresponding vegetative plant part or cell lacking the exogenous polynucleotide(s) and/or genetic modification(s), preferably a decreased ratio,
  v) the cell is in a vegetative part of a plant and comprises a total non-polar lipid content of at least about 8%, at least about 10%, at least about 11%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, between about 6% and about 20%, between 8% and 75%, between 10% and 75%, between 11% and 75%, between about 15% and 75%, between about 20% and 75%, between about 30% and 75%, between about 40% and 75%, between about 50% and 75%, between about 60% and 75%, or between about 25% and 50% (w/w dry weight),
  vi) the cell is in a vegetative part of a plant and comprises a TAG content of at least about 1%, at least about 2%, at least about 3%, at least about 4%, at least about 5%, at least about 6%, at least about 7%, at least about 8%, at least about 10%, at least about 11%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, between about 6% and about 20%, between 8% and 75%, between 10% and 75%, between 11% and 75%, between about 15% and 75%, between about 20% and 75%, between about 30% and 75%, between about 40% and 75%, between about 50% and 75%, between about 60% and 75%, or between about 25% and 50% (w/w dry weight),
  vii) the transcription factor polypeptide is selected from the group consisting of Wrinkled 1 (WRI1), Leafy Cotyledon 1 (LEC1), LEC1-like, Leafy Cotyledon 2 (LEC2), BABY BOOM (BBM), FUS3, ABI3, ABI4, ABI5, Dof4 and Dof11,
  viii) oleic acid comprises at least 20% (mol %), at least 22% (mol %), at least 30% (mol %), at least 40% (mol %), at least 50% (mol %), or at least 60% (mol %), preferably about 65% (mol %) or between 20% and about 65% of the total fatty acid content in the vegetative plant parts or cell,
  ix) non-polar lipid in the vegetative plant parts or cell comprises one or more polyunsaturated fatty acids selected from eicosadienoic acid (EDA), arachidonic acid (ARA), stearidonic acid (SDA), eicosatrienoic acid (ETE), eicosatetraenoic acid (ETA), eicosapentaenoic acid (EPA), docosapentaenoic acid (DPA), docosahexaenoic acid (DHA), or a combination of two of more thereof,
  x) one or more or all of the promoters are selected from a constitutive promoter such as a ubiquitin gene promoter or an actin gene promoter, a tissue-specific promoter such as a leaf and/or stem specific promoter, a developmentally regulated promoter such as a senescence-specific promoter such as a SAG12 promoter, an inducible promoter, or a circadian-rhythm regulated promoter,
  xi) the vegetative plant parts or cell comprises a total fatty acid content whose oleic acid level is increased by at least 2% or at least 3% relative to a corresponding vegetative plant part or cell lacking the exogenous polynucleotide(s) and/or genetic modification(s), and/or whose α-linolenic acid (ALA) level is decreased by at least 2% or at least 3% relative to a corresponding vegetative plant part or cell lacking the exogenous polynucleotide(s) and/or genetic modification(s),
  xii) non-polar lipid in the vegetative plant parts or cell comprises a modified level of total sterols, preferably free (non-esterified) sterols, steroyl esters, steroyl glycosides, relative to the non-polar lipid in a corresponding vegetative plant part or cell lacking the exogenous polynucleotide(s) and/or genetic modification(s),
  xiii) the level of one or more non-polar lipid(s) and/or the total non-polar lipid content of the vegetative plant parts or cell is at least 2% greater on a weight basis than in a corresponding vegetative plant parts or cell which comprises exogenous polynucleotides encoding an *Arabidposis thaliana* WRI1 (SEQ ID NO:21) and an *Arabidopsis thaliana* DGAT1 (SEQ ID NO:1).

In a further embodiment of the above aspects, one or more or all of the following features apply where relevant;
  i) the polypeptide involved in the biosynthesis of one or more non-polar lipids is a fatty acyl acyltransferase involved in the biosynthesis of TAG, DAG or monoacylglycerol (MAG) in the cell, such as a DGAT, PDAT, LPAAT, GPAT or MGAT, preferably a DGAT or a PDAT, or is a PDCT or a CPT polypeptide, or a PLC or PLD polypeptide,
  ii) the polypeptide involved in the catabolism of triacylglycerols (TAG) in the vegetative plant parts or cell is an SDP1 lipase, a Cgi58 polypeptide, an acyl-CoA oxidase such as ACX1 or ACX2, or a polypeptide involved in β-oxidation of fatty acids in the vegetative plant parts or cell such as a PXA1 peroxisomal ATP-binding cassette transporter, preferably an SDP1 lipase, iii) the oil body coating (OBC) polypeptide is oleosin, such as a polyoleosin or a caleosin, or a lipid droplet associated protein (LDAP), iv) the polypeptide which increases the export of fatty acids out of plastids of the vegetative plant parts or cell is a C16 or C18 fatty acid thioesterase such as a FATA polypeptide or a FATB polypeptide, a fatty acid transporter such as an ABCA9 polypeptide or a long-chain acyl-CoA synthetase (LACS), v) the polypeptide involved in importing fatty acids into plastids of the vegetative plant parts or cell is a fatty acid transporter, or subunit or regulatory polypeptide thereof, preferably a TGD polypeptide, more preferably a TGD5 polypeptide, and vi) the polypeptide involved in diacylglycerol (DAG) production in the plastid is a plastidial GPAT, a plastidial LPAAT or a plastidial PAP.

In an embodiment of the above aspects, the level or activity of PDCT or CPT, or both PDCT and CPT, is increased in the vegetative plant part, seed or cell of the invention relative to the wild-type. In a preferred embodiment, the vegetative plant part, seed or cell of the invention comprises one or more exogenous polynucleotides which encode a PDCT and/or CPT polypeptide. The PDCT and/or CPT polypeptide may be endogenous to the vegetative plant part, seed or cell i.e. of the same species but at an increased level or activity relative to the wild-type, or heterologous to the plant species. Each exogenous polynucleotide is operably linked to a promoter which is expressed in the vegetative plant part, seed or cell, to provide the increased level or activity of PDCT and/or CPT. In a preferred embodiment, the increased level or activity of PDCT and/or CPT provides for an increased rate of conversion of DAG to phosphatidylcholine (PC), or from PC to DAG, or more preferably of both of these. The vegetative plant part, seed or cell thereby has an increased production of DAG produced from PC, which DAG is available for production of TAG by the activity of DGAT. In a more preferred embodiment, the level of TAG in the vegetative plant part, seed or cell is increased relative to a corresponding part or cell which lacks the exogenous polynucleotides.

Alternatively, the level or activity of PDCT or CPT is decreased, or of both PDCT and CPT are decreased, in the vegetative plant part, seed or cell of the invention relative to the wild-type, for example by mutation in the endogenous gene encoding the enzyme(s) or by downregulation of the gene(s) encoding the enzyme(s) by an RNA molecule which reduces its expression. In this embodiment, there is a reduced conversion of DAG produced via the Kennedy pathway (de novo DAG) to PC, resulting in an increased level of de novo DAG available for synthesis of TAG in the vegetative plant part, seed or cell.

In an embodiment of the above aspects, the level or activity of phospholipase-C (PLC) or phospholipase-D (PLD), or both PLC and PLD, is increased in the vegetative plant part, seed or cell of the invention relative to the wild-type. In a preferred embodiment, the vegetative plant part, seed or cell of the invention comprises one or more exogenous polynucleotides which encode a PLC and/or PLD polypeptide. The PLC and/or PLD polypeptide may be endogenous to the vegetative plant part or cell but at an increased level or activity relative to the wild-type, or heterologous to the plant species. The exogenous polynucleotide is operably linked to a promoter which is expressed in the vegetative plant part or cell, to provide the increased level or activity of PLC and/or PLD. In a preferred embodiment, the increased level or activity of PLC and/or PLD provides for an increased rate of conversion of PC to DAG and phosphocholine in the case of PLC, or phosphatidic acid (PA) and choline in the case of PLD. PA is subsequently converted to DAG by the action of PAP. The vegetative plant part or cell thereby has an increased amount of DAG available for production of TAG by the activity of DGAT. In a more preferred embodiment, the level or activity of TAG in the vegetative plant part or cell is increased relative to a corresponding part or cell which lacks the exogenous polynucleotides encoding the PLC and/or PLD. In a preferred embodiment, the increased level or activity of PLC and/or PLD is in combination with an increased level or activity of PDCT and/or CPT, as described above.

In an embodiment of the above aspects, the level or activity of PDAT is increased in the vegetative plant part or cell of the invention, relative to the wild-type. In a preferred embodiment, the vegetative plant part or cell comprises one or more exogenous polynucleotides which encode a PDAT polypeptide. The PDAT polypeptide may be endogenous to the vegetative plant part or cell but at an increased level or activity relative to the wild-type, or heterologous to the plant species. The exogenous polynucleotide is operably linked to a promoter which is expressed in the vegetative plant part or cell, to provide the increased level or activity of PDAT. It is desired that the increased level or activity of PDAT provides for an increased production of TAG from DAG and PC. In a preferred embodiment, the increased level or activity of PDAT is in combination with an increased level or activity of PDCT and/or CPT, or with an increased level or activity of PLC and/or PLD, as described above.

In an embodiment of the above aspects, the level or activity of two different DGATs is increased in the vegetative plant part or cell of the invention relative to the wild-type. In a preferred embodiment, the vegetative plant part or cell of the invention comprises two exogenous polynucleotides which each encode a DGAT polypeptide, the polypeptides being different. One of the DGAT polypeptides may be endogenous to the vegetative plant part or cell but at an increased level or activity relative to the wild-type, while the other is heterologous, or both DGATs are heterologous to the plant species. The exogenous polynucleotides are each operably linked to a promoter which is expressed in the vegetative plant part or cell, to provide for increased expression of both DGATs. It is desired that the increased level or activity of two DGATs provides for an increased production of TAG produced from de novo DAG and from PC-derived DAG. In a preferred embodiment, one of the DGATs (a first DGAT) is more active on de novo DAG than PC-derived DAG, whereas the other DGAT (a second DGAT) is more active on PC-derived DAG than de novo DAG. Such differences in the DGAT activities may occur by different compartmentalisation or localisation of the two DGATs in the endoplasmic reticulum (ER) of the cell. In an embodiment, one of the DGATs is derived from a unicellular organism, for example a bacterial DGAT or a unicellular algal DGAT such as a *Chlamydomonas* DGAT or a variant thereof. In a preferred embodiment, the first DGAT is derived from a plant species which naturally produces oil which has a low level of polyunsaturated fatty acids (PUFA), e.g. less than 20% PUFA, or a DGAT homolog thereof which is at least 95% identical in amino acid sequence, and the second DGAT is derived from an oilseed species which produces a relatively higher level of PUFA, e.g. at least 40% PUFA, or a DGAT homolog thereof which is at least 95% identical in amino acid sequence. For example, the first DGAT may be from olive, coconut, palm or mangosteen, and the second DGAT may be from *Brassica*, soybean, cotton or linseed. Typically, the first DGAT is more active on de novo DAG and the second DGAT is more active on PC-derived DAG. In a preferred embodiment, the increased activity of two DGATs is in combination with an increased level or activity of PDCT and/or CPT, or with an increased level or activity of PLC and/or PLD, or an increased level or activity of PDAT, as described above.

In the above embodiments, the extent of the increase of a level or activity is preferably by at least 10% or at least 20% to a maximum of 100% or 200% increase. The extent of the decrease of a level or activity is preferably by at least 10% or 20%, to a maximum decrease of 90% or 95%, or even 100% decrease.

In the above embodiments, the increased levels or activities result in an increased TTQ in the total lipid of the vegetative plant part or cell of the invention and/or an increased level of TAG relative to a corresponding vegetative plant part or cell lacking the respective exogenous polynucleotides. In a further embodiment of the above aspects, the cell of the invention is from or in a plant leaf or stem, before the plant flowers, and the cell comprises a TFA content and/or a total non-polar fatty acid content of at least about 6%, at least about 8%, at least about 10%, at least about 11%, between 8% and 15%, or between 9% and 12% on a weight basis, preferably between about 8% and about 20%.

In a further embodiment of the above aspects, each genetic modification is independently a mutation of an endogenous gene which partially or completely inactivates the gene, such as a point mutation, an insertion or a deletion, or the genetic modification is an exogenous polynucleotide encoding an RNA molecule which reduces expression of the endogenous gene, wherein the exogenous polynucleotide is operably linked to a promoter which is capable of directing expression of the polynucleotide in the vegetative plant parts or cell.

In a further aspect, the present invention provides a plant, preferably a Sorghum sp. or Zea mays plant or part thereof, the plant comprising a vegetative plant part whose total fatty acid (TFA) content comprises fatty acids esterified in the form of triacylglycerols (TAG) and fatty acids in the form of lipids other than TAG, wherein the vegetative plant part comprises a TFA content of about 5% (w/w dry weight), preferably between about 6% and about 20%. In an embodiment, the plant part is a seed or seeds obtained from the plant, or a seed or seeds which when sown give rise to such a plant.

In another aspect, the present invention provides a plant, preferably a Sorghum sp. or Zea mays plant or part thereof, the plant comprising a vegetative plant part whose total fatty acid content comprises fatty acids esterified in the form of triacylglycerols (TAG) and fatty acids in the form of lipids other than TAG, wherein the vegetative plant part comprises a total TAG content of about 6% (w/w dry weight), preferably between about 6% and about 20%, and preferably has a ratio of the fatty acids esterified in the form of TAG to the fatty acids in the form of lipids other than TAG which is between 20:1 and 1.5:1 or between 5:1 and 2:1.

In another aspect, the present invention provides a plant, preferably, a Sorghum sp. or Zea mays plant or part thereof, the plant comprising a vegetative plant part comprising an increased content of a WRI1 polypeptide, an increased content of a DGAT polypeptide, and a decreased content of a SDP1 polypeptide, each relative to a corresponding wild-type vegetative plant part.

In another aspect, the present invention provides a plant, preferably, a Sorghum sp. or Zea mays plant or part thereof, the plant comprising a vegetative plant part comprising an increased content of a WRI1 polypeptide, an increased content of a DGAT polypeptide, and an increased content of a LEC2 polypeptide, each relative to a corresponding wild-type vegetative plant part.

In another aspect, the present invention provides a plant, preferably, a Sorghum sp. or Zea mays plant or part thereof, the plant comprising a vegetative plant part comprising an increased content of a PDAT or DGAT polypeptide, a decreased content of a TGD polypeptide, preferably a TGD5 polypeptide, and a decreased content of a SDP1 polypeptide, each relative to a corresponding wild-type vegetative plant part.

In another aspect, the present invention provides a plant, preferably a Sorghum sp. or Zea mays plant or part thereof, the plant comprising a vegetative plant part comprising a decreased content of a TAG lipase such as a SDP1 TAG lipase, a decreased content of a TGD polypeptide such as a TGD5 polypeptide, and optionally a decreased content of a TST polypeptide such as a TST1 polypeptide, each decrease being relative to a corresponding wild-type vegetative plant part.

In another aspect, the present invention provides a plant, preferably a Sorghum sp. or Zea mays plant, or part thereof, the plant comprising a vegetative part comprising an increased level or activity of PDCT and/or CPT relative to the wild-type. In an embodiment, the plant or part comprises one or more exogenous polynucleotides which encode a PDCT and/or CPT polypeptide. The PDCT and/or CPT polypeptide may be endogenous to the plant or part but present at an increased level relative to the wild-type, or heterologous to the plant species. Each exogenous polynucleotide is operably linked to a promoter which is expressed in the vegetative plant part, to provide the increased level or activity of PDCT and/or CPT. In a preferred embodiment, the increased level or activity of PDCT and/or CPT provides for an increased rate of conversion of DAG to PC, or from PC to DAG, or more preferably of both of these. The vegetative plant part thereby has an increased amount of DAG available for production of TAG by the activity of DGAT. In a more preferred embodiment, the level of TAG in the vegetative plant part is increased relative to a corresponding part which lacks the exogenous polynucleotides.

In another aspect, the present invention provides a plant, preferably a Sorghum sp. or Zea mays plant, or part thereof, the plant comprising a vegetative plant part comprising a decreased level or activity of PDCT and/or CPT relative to the wild-type. In an embodiment, the plant or part comprises a mutation in an endogenous gene(s) encoding the enzyme(s) or one or more exogenous polynucleotides which each encode an RNA molecule which reduces expression of one or both of the endogenous genes encoding the enzymes.

In another aspect, the present invention provides a plant, preferably a Sorghum sp. or Zea mays plant, or part thereof, the plant comprising a vegetative part comprising an increased level or activity of PLC or PLD, or both. In a preferred embodiment, the plant or part comprises one or more exogenous polynucleotides which encode a PLC and/or a PLD polypeptide. The PLC and/or PLD polypeptide may be endogenous to the plant or part but at an increased level or activity relative to the wild-type, or heterologous to the plant species. Each exogenous polynucleotide is operably linked to a promoter which is expressed in the vegetative plant part, to provide the increased level or activity of PLC and/or PLD. In a preferred embodiment, the increased level or activity of PLC and/or PLD provides for an increased rate of conversion of PC to DAG and phosphocholine in the case of PLC, or PA and choline in the case of PLD. The vegetative part thereby has an increased amount of DAG available for production of TAG by the activity of DGAT. In a more preferred embodiment, the level of TAG in the vegetative plant part is increased relative to a corresponding part which lacks the exogenous polynucleotides encoding the PLC and/or PLD.

In another aspect, the present invention provides a plant, preferably a *Sorghum* sp. or *Zea mays* plant, or part thereof, the plant comprising an increased level or activity of PDAT in a vegetative part relative to the wild-type. In a preferred embodiment, the vegetative part comprises one or more exogenous polynucleotides which encode a PDAT polypeptide. The PDAT polypeptide may be endogenous to the vegetative part but at an increased level or activity relative to the wild-type, or heterologous to the plant species. The exogenous polynucleotide is operably linked to a promoter which is expressed in the vegetative plant part, to provide an increased level or activity of PDAT. It is desired that the increased level or activity of PDAT provides for an increased production of TAG from DAG and PC. In a preferred embodiment, the increased level or activity of PDAT is in combination with an increased level or activity of PDCT and/or CPT, or with an increased level or activity of PLC and/or PLD, as described above.

In another aspect, the present invention provides a plant, preferably a *Sorghum* sp. or *Zea mays* plant, or part thereof, the plant comprising an increased level or activity of two different DGATs in a vegetative part relative to the wild-type. In a preferred embodiment, the plant or part thereof comprises two exogenous polynucleotides which each encode a DGAT polypeptide, the polypeptides being different. One of the DGAT polypeptides may be endogenous to the plant or part but at an increased level or activity relative to the wild-type, while the other is heterologous, or both DGATs are heterologous to the plant species. The exogenous polynucleotides are each operably linked to a promoter which is expressed in the vegetative part, to provide for increased expression of each of the DGATs. It is desired that the increased level or activity of the two DGATs provides for (i) an increased production of TAG produced from de novo DAG and (ii) an increased production of TAG produced from DAG which is produced from PC (PC-derived DAG). In an embodiment, a first DGAT is more active on de novo DAG than PC-derived DAG, whereas a second DGAT is more active on PC-derived DAG than de novo DAG. Such differences in the DGAT activities may occur by different compartmentalisation or localisation of the two DGATs in the endoplasmic reticulum (ER) of the cell. In an embodiment, one of the DGATs is derived from a unicellular organism, for example a bacterial DGAT or a unicellular algal DGAT such as a *Chlamydomonas* DGAT or a variant thereof. In a preferred embodiment, the first DGAT is derived from a plant part which produces oil which has a low level of polyunsaturated fatty acids (PUFA), e.g. less than 20% PUFA, whereas the second DGAT is derived from an oilseed which produces a relatively higher level of PUFA, e.g. at least 40% PUFA. Typically the first DGAT is more active on de novo DAG and the second DGAT is more active on PC-derived DAG. In a preferred embodiment, the increased activity of two DGATs is in combination with an increased activity of PDCT and/or CPT, or with an increased activity of PLC and/or PLD, or an increased activity of PDAT, as described above.

Combinations of the features of the above aspects are clearly contemplated for the plant, plant part and cell of the invention, and in the processes of producing and using them.

In an embodiment of the above aspects, the plant of the invention is phenotypically normal. In an embodiment, the plant of the invention has an above-ground biomass which is at least 80% relative to a corresponding wild-type plant. Preferably, the plant has a plant height which is at least 80% relative to the corresponding wild-type plant, and is male and female fertile. In an embodiment, the plant is a hybrid *Zea mays* plant.

In an embodiment of the above aspects, the vegetative plant part of the plant of the invention has a total fatty acid content characterised by a TTQ of between 0.01 and 0.6. In an embodiment, the vegetative plant part has a TTQ of between 0.01 and 0.55, or between 0.01 and 0.5, or bout 0.1, or about 0.2 or about 0.3, or about 0.4 or about 0.5. Preferably, the TTQ is between 0.60 and 0.84 or between 0.84 and 0.95.

In a preferred embodiment of the above aspects, the cell or vegetative plant part of the invention comprises one or more exogenous polynucleotides or genetic modifications which each, or in combination, increase the TTQ of the total fatty acid content of the cell or vegetative plant part relative to a corresponding cell or vegetative plant part which lacks the exogenous polynucleotide or genetic modification, wherein the exogenous polynucleotide or genetic modification provides for (i) a decreased TAG lipase polypeptide content, preferably a decreased SDP1 polypeptide content, (ii) a decreased TGD polypeptide content, preferably a decreased TGD5 polypeptide content, (iii) an increased content of an OBC polypeptide or a LDAP, (iv) an increased content of a polypeptide which increases the export of fatty acids out of plastids, preferably an acyl-ACP thioesterase, (v) a decreased TST polypeptide content, preferably a decreased TST1 polypeptide content, (vi) a modified level of a PDCT polypeptide, (vii) a modified level of a CPT polypeptide, (viii) an increased level or activity of a PLC polypeptide, (ix) an increased level or activity of a PLD polypeptide, (x) an increased level or activity of a PDAT polypeptide, and (xi) an increased level or activity of two DGAT polypeptides. More preferably, the TTQ is between 0.60 and 0.84 or between 0.84 and 0.95, and/or the cell or vegetative plant part comprises a TAG content of about 6% (w/w dry weight), preferably between about 6% and about 20%.

In an embodiment of the above aspects, the plant or part thereof comprises one or both of
  a) a first exogenous polynucleotide which encodes a transcription factor polypeptide that increases the expression of one or more glycolytic and/or fatty acid biosynthetic genes in the plant or part thereof, preferably a WRI1 polypeptide, and
  b) a second exogenous polynucleotide which encodes a polypeptide involved in the biosynthesis of one or more non-polar lipids, preferably a DGAT and/or a PDAT, and in each case any one or two or three or all four of
  c) a genetic modification which down-regulates endogenous production and/or activity of a polypeptide involved in the catabolism of triacylglycerols (TAG) in the plant or part thereof when compared to a corresponding plant or part thereof lacking the genetic modification, preferably an SDP1 TAG lipase,
  d) a third exogenous polynucleotide which encodes a polypeptide which increases the export of fatty acids out of plastids of a cell in the plant or part thereof when compared to a corresponding cell lacking the third exogenous polynucleotide, preferably an acyl-ACP thioesterase,
e) a fourth exogenous polynucleotide which encodes a second transcription factor polypeptide that increases the expression of one or more glycolytic and/or fatty acid biosynthetic genes in a cell in the plant or part thereof, preferably a LEC2 polypeptide, and
f) a second genetic modification which down-regulates endogenous production and/or activity of a polypeptide involved in importing fatty acids into plastids of the cell when compared to a corresponding cell lacking the second genetic modification, wherein each exogenous polynucleotide is operably linked to a promoter which is capable of directing expression of the polynucleotide in the plant or part thereof.

In an embodiment of the above aspects, the plant or part thereof further comprises one or both of
a) a fifth exogenous polynucleotide which encodes an oil body coating (OBC) polypeptide or a lipid droplet associated protein (LDAP), and
b) a third genetic modification which down-regulates endogenous production and/or activity of a polypeptide involved in diacylglycerol (DAG) production in plastids when compared to a corresponding plant or part thereof lacking the third genetic modification.

Alternately, in a further embodiment, the plant or part thereof comprises
a) a first exogenous polynucleotide which encodes a transcription factor polypeptide that increases the expression of one or more glycolytic and/or fatty acid biosynthetic genes in the plant or part thereof, preferably a WRI1 polypeptide,
b) a second exogenous polynucleotide which encodes a polypeptide involved in the biosynthesis of one or more non-polar lipids, preferably a DGAT polypeptide and/or a PDAT polypeptide, and any one or two or all three of
c) a genetic modification which down-regulates endogenous production and/or activity of a polypeptide involved in the catabolism of triacylglycerols (TAG) in the plant or part thereof, preferably an SDP1 TAG lipase, when compared to a corresponding plant or part thereof lacking the genetic modification,
d) a third exogenous polynucleotide which encodes a polypeptide which increases the export of fatty acids out of plastids of a cell in the plant when compared to a corresponding cell lacking the third exogenous polynucleotide, preferably an acyl-ACP thioesterase, and
e) a fourth exogenous polynucleotide which encodes a second transcription factor polypeptide that increases the expression of one or more glycolytic and/or fatty acid biosynthetic genes in a cell in the plant or part thereof, preferably a LEC2 polypeptide,
wherein each exogenous polynucleotide is operably linked to a promoter which is capable of directing expression of the polynucleotide in the plant or part thereof.

In an embodiment of the above aspect, the plant or part thereof further comprises one or more or all of
a) a fifth exogenous polynucleotide which encodes an oil body coating (OBC) polypeptide,
b) a second genetic modification which down-regulates endogenous production and/or activity of a polypeptide involved in importing fatty acids into plastids of the plant when compared to a corresponding plant lacking the second genetic modification, and
c) a third genetic modification which down-regulates endogenous production and/or activity of a polypeptide involved in diacylglycerol (DAG) production in the plastid when compared to a corresponding plant lacking the third genetic modification.

In a further embodiment of the above aspects, the plant part is a vegetative plant part and one or more or all of the promoters are expressed at a higher level in the vegetative plant part relative to seed of the plant. For example, a preferred promoter is a ubiquitin gene promoter or an SSU promoter. Alternatively, one or more or all of the promoters are other than an SSU promoter.

In a further embodiment, the plant or part thereof is further characterised by one or more features as described in the context of the cell of the invention, or of the processes of the above aspects.

In an embodiment of the above aspects, a *Sorghum* sp. or *Zea mays* plant of the invention, or a plant or part thereof used in a method of the invention or otherwise described herein, has been grown under a photoperiod of at least 13 hours per day for a period of at least 1 week, or at least 2 weeks or at least 3 weeks or at least 4 weeks, preferably up to when the plant is harvested to obtain vegetative parts from the plant. Under such conditions, the above-ground biomass of the plant is preferable at least 80% relative to a corresponding wild-type plant. Seed of the plant may be harvested from the plant after growth under such conditions.

In another embodiment of the above aspects, a *Sorghum* sp. or *Zea mays* plant of the invention, or a plant or part thereof used in a method of the invention or otherwise defined herein, was/is grown in a $CO_2$ concentration of at least 400 ppm.

In a further embodiment, a *Sorghum* sp. or *Zea mays* plant of the invention, or a plant or part thereof used in a method of the invention or otherwise described herein comprises one or more exogenous polynucleotides encoding one or more proteins which increase the total protein content in the vegetative plant part.

In another aspect, the present invention provides a population of at least about 1000 plants, each being a plant according to the invention, growing in a field, or a collection of at least about 1000 vegetative plant parts, each being a vegetative plant part according to the invention, wherein the vegetative plant parts have been harvested from plants growing in a field. Preferably the plants were grown under the photoperiod and/or $CO_2$ conditions described above.

In another aspect, the present invention provides seed of, or obtained from, a plant according to the invention, or which when sown give rise to plants of the invention. Alternatively, the seed may have been treated so it is no longer able to germinate, and/or be ground, milled, polished, cracked or heat treated.

In a further aspect, the present invention provides a process for identifying, selecting and/or obtaining a plant or part thereof of the invention, preferably a *Sorghum* sp. or *Zea mays* plant or a part thereof, with a desired phenotype, the process comprising
i) obtaining a plurality of candidate plants, or parts thereof, which each comprise one or both of
a) a first exogenous polynucleotide which encodes a transcription factor polypeptide that increases the expression of one or more glycolytic and/or fatty acid biosynthetic genes in the plant or part thereof, preferably a WRI1 polypeptide, and
b) a second exogenous polynucleotide which encodes a polypeptide involved in the biosynthesis of one or more non-polar lipids, preferably a DGAT polypeptide and/or a PDAT polypeptide, and in each case any one or two or three or all four of c) a genetic modification which down-regulates endogenous production and/or activity of a polypeptide involved in the catabolism of triacylglycerols (TAG) in the plant or part thereof when compared to a corresponding plant or part thereof lacking the genetic modification, preferably a SDP1 TAG lipase, d) a third exogenous polynucleotide which encodes a polypeptide which increases the export of fatty acids out of plastids of a cell in the plant or part thereof when compared to a corresponding cell lacking the third exogenous polynucleotide, preferably an acyl-ACP thioesterase, e) a fourth exogenous polynucleotide which encodes a second transcription factor polypeptide that increases the expression of one or more glycolytic and/or fatty acid biosynthetic genes in a cell in the plant or part thereof, preferably a LEC2 polypeptide, and f) a second genetic modification which down-regulates endogenous production and/or activity of a polypeptide involved in importing fatty acids into plastids of the cell when compared to a corresponding cell lacking the second genetic modification, wherein each exogenous polynucleotide is operably linked to a promoter which is capable of directing expression of the polynucleotide in the plant;

ii) analysing lipid in the plurality of parts, or at least a part of each plant in the plurality of candidate plants, from step i), and iii) identifying, selecting and/or obtaining a plant, or part thereof, which comprises a vegetative plant part whose total fatty acid (TFA) content comprises fatty acids esterified in the form of triacylglycerols (TAG) and fatty acids in the form of lipids other than TAG, and which has a vegetative plant part which comprises a TFA content of about 5% (w/w dry weight), preferably between about 6% and about 20%.

In an embodiment, a plant is selected, or a part thereof, which comprises a vegetative plant part whose total fatty acid content is characterised by having a TTQ of between 0.01 and 0.6. In an embodiment, a plant is selected, or part thereof, wherein the plant comprises a vegetative plant part having a TTQ of between 0.01 and 0.55, or between 0.01 and 0.5, or bout 0.1, or about 0.2 or about 0.3, or about 0.4 or about 0.5.

In a preferred embodiment, the TTQ is between 0.60 and 0.84 or between 0.84 and 0.95.

In another aspect, the present invention provides a process for identifying, selecting and/or obtaining a plant, preferably a *Sorghum* sp. or *Zea mays* plant, or a part thereof with a desired phenotype, the process comprising i) obtaining a plurality of candidate plants, or parts thereof, which each comprise one or both of a) a first exogenous polynucleotide which encodes a transcription factor polypeptide that increases the expression of one or more glycolytic and/or fatty acid biosynthetic genes in the plant or part thereof, preferably a WRI1 polypeptide, b) a second exogenous polynucleotide which encodes a polypeptide involved in the biosynthesis of one or more non-polar lipids, preferably a DGAT polypeptide and/or a PDAT polypeptide, and any one or two or all three of c) a genetic modification which down-regulates endogenous production and/or activity of a polypeptide involved in the catabolism of triacylglycerols (TAG) in the plant or part thereof, preferably an SDP1 TAG lipase, when compared to a corresponding plant or part thereof lacking the genetic modification, d) a third exogenous polynucleotide which encodes a polypeptide which increases the export of fatty acids out of plastids of a cell in the plant or part thereof when compared to a corresponding cell lacking the third exogenous polynucleotide, preferably an acyl-ACP thioesterase, and e) a fourth exogenous polynucleotide which encodes a second transcription factor polypeptide that increases the expression of one or more glycolytic and/or fatty acid biosynthetic genes in a cell in the plant or part thereof, preferably a LEC2 polypeptide, wherein each exogenous polynucleotide is operably linked to a promoter which is capable of directing expression of the polynucleotide in the plant or part thereof;

ii) analysing lipid in the plurality of parts, or at least a part of each plant in the plurality of candidate plants, from step i), iii) identifying, selecting and/or obtaining a plant or part thereof wherein the plant comprises a vegetative plant part whose total fatty acid content comprises fatty acids esterified in the form of triacylglycerols (TAG) and fatty acids in the form of lipids other than TAG, and which has a vegetative plant part which comprises a total TAG content of about 6% (w/w dry weight), preferably between about 6% and about 20%, and preferably has a ratio of the fatty acids esterified in the form of TAG to the fatty acids in the form of lipids other than TAG which is between 20:1 and 1.5:1 or between 5:1 and 2:1.

In another aspect, the present invention provides a process for identifying selecting and/or obtaining a plant, preferably a *Sorghum* sp. or *Zea mays* plant, or a part thereof, having an increased TTQ in its total fatty acid content, the process comprising i) obtaining a plurality of candidate plants, or parts thereof, which each comprise one or more genetic modifications which provides for (a) a decreased TAG lipase polypeptide content or activity, preferably a decreased SDP1 TAG lipase content or activity, (b) a decreased TGD polypeptide content or activity, preferably a decreased TGD5 polypeptide content or activity, (c) an increased content of an OBC polypeptide or a LDAP, (d) an increased content or activity of a polypeptide which increases the export of fatty acids out of plastids, preferably an acyl-ACP thioesterase, (e) a decreased TST polypeptide content or activity, preferably a decreased TST1 polypeptide content or activity, (f) a modified level or activity of a PDCT polypeptide, (g) a modified level or activity of a CPT polypeptide, (h) an increased content or activity of a PLC polypeptide, (i) an increased content or activity of PLD polypeptide, (j) an increased content or activity of a PDAT polypeptide, and (k) an increased content or activity of two DGAT polypeptides, ii) analysing lipid in the plurality of plants, or at least a part of each plant in the plurality of candidate plants, from step i), iii) identifying, selecting and/or obtaining a plant or part thereof which comprises an increased TTQ in its total fatty acid content relative to a corresponding plant or plant part which lacks the genetic modifications or relative to another plant or plant part from the plurality of candidate plants or parts thereof.

In an embodiment of the above aspect, the increased TTQ is increased by at least 0.05, preferably between 0.5 and 0.80. Each of the one or more genetic modifications, when expressed in the candidate plants or part thereof, results in a decreased polypeptide content or activity according to (a), (b) or (e), an increased content or activity according to (c), (d), (h), (i), (j) or (k), and either an increased or decreased content and or activity for (f) or (g). In the case of a decreased polypeptide content or activity, each genetic modification is, independently, a mutation of an endogenous gene encoding the polypeptide which partially or completely inactivates the gene, such as a point mutation, an insertion, or preferably a deletion, or the genetic modification comprises the integration into the genome of an exogenous polynucleotide which encodes an RNA molecule which inhibits expression of the endogenous gene, wherein the exogenous polynucleotide is operably linked to a promoter which is capable of directing expression of the polynucleotide in the plant or part thereof.

In an embodiment, step (ii) of the process of the above aspects comprises extracting lipid from the candidate plants or parts thereof, and one or more of (a) separating TAG from non-TAG lipid in the plants or parts thereof, (b) determining the relative amounts of TAG and non-TAG lipid in the extracted lipid. In an embodiment, the process comprises a step of calculating the TTQ for the candidate plants or parts, after step ii). The identified or selected plant may be identified or selected on the basis of the TTQ and/or of its TAG or TFA content. In a preferred embodiment, the identified selected plant comprises a vegetative plant part which has a TTQ which is between 0.60 and 0.84 or between 0.84 and 0.95, and/or the vegetative plant part comprises a TAG content of about 6% (w/w dry weight), preferably between about 6% and about 20%.

In an embodiment of the process of the above aspects, the process further comprises a step of propagating the plant or part thereof of the invention to obtain progeny plants or parts thereof, for example from seed or vegetative parts from the plant, or of crossing the plant with a plant of different genetic composition to introduce the genetic modification(s) into a different genetic background. The invention clearly includes the progeny plants and parts thereof which comprise the genetic modification(s) and an increased TTQ in their total fatty acid content.

In a more preferred embodiment of the process of the above aspects, the plurality of candidate plants, or parts thereof, each comprise a first exogenous polynucleotide which encodes a transcription factor polypeptide that increases the expression of one or more glycolytic and/or fatty acid biosynthetic genes in the plant or part thereof, preferably a WRI1 polypeptide, and a second exogenous polynucleotide which encodes a polypeptide involved in the biosynthesis of one or more non-polar lipids, preferably a DGAT polypeptide and/or a PDAT polypeptide. In this preferred embodiment, the genetic modification(s) which results in the decreased, increased or modified polypeptide content or activity according to (a) to (k) is additional to the first and second exogenous polynucleotides, and increases the TTQ relative to a corresponding plant or vegetative part which has the first and second exogenous polynucleotides but lacks the genetic modification(s).

In an embodiment of the process of the above aspects, the plant, or part thereof which is identified, selected and/or obtained is further characterised by one or more features as defined in the context of a plant of the invention, the *Sorghum* sp. or *Zea mays* plant of the invention, or of the processes of the above aspects.

The process for identifying, selecting and/or obtaining a plant of the invention can also be used to identify, select and/or obtain a plant which has an increased TTQ or TAG content in a stem of the plant, which preferably is accompanied by an increased TTQ or TAG content in leaves of the plant, although the TTQ and TAG content in leaves of the plant may not be increased at all or as much as in the stem.

In another aspect, the present invention provides a process for obtaining a cell or plant according to the invention, preferably a *Sorghum* sp. or *Zea mays* cell or plant, the process comprising the steps of introducing into a cell or plant, preferably a *Sorghum* sp. or *Zea mays* cell or plant, at least one exogenous polynucleotide and/or at least one genetic modification as defined above.

In an embodiment, the process comprises one or more or all steps of
  i) expressing the exogenous polynucleotide(s) and/or genetic modifications in the cell or plant or a progeny cell or plant therefrom,
  ii) analysing the lipid content of the cell or plant or progeny cell or plant, and
  iii) selecting or identifying a cell or plant according to the invention.

The obtained cell may be in a *Sorghum* or *Zea mays* plant or preferably in a vegetative part thereof.

In an embodiment, the exogenous polynucleotide(s) and/or genetic modifications provide for a modified feature which comprises a decreased, increased, or modified polypeptide content according to (a) to (k) above. In an embodiment, the process comprises a step of calculating the TTQ for the candidate plants or parts, after step ii). In a preferred embodiment, the cell or plant is selected or identified on the basis of its TTQ and/or its TAG content, more preferably a TTQ which is between 0.60 and 0.84 or between 0.84 and 0.95, and/or the vegetative plant part comprises a TAG content of about 6% (w/w dry weight), preferably between about 6% and about 20%.

In another aspect, the present invention provides a method of producing a plant, preferably a *Sorghum* sp. or *Zea mays* plant, which has integrated into its genome a set of exogenous polynucleotides and/or genetic modifications as defined herein, the method comprising the steps of
  i) crossing two parental plants, wherein one plant comprises at least one of the exogenous polynucleotides and/or at least one genetic modification as defined above, and the other plant comprises at least one of the exogenous polynucleotides and/or at least one genetic modification as defined above, and wherein between them the two parental plants comprise a set of exogenous polynucleotides and/or genetic modifications as defined above,
  ii) screening one or more progeny plants from the cross for the presence or absence of the set of exogenous polynucleotides and/or genetic modifications as defined above, and
  iii) selecting a progeny plant which comprise the set of exogenous polynucleotides and/or genetic modifications as defined above, thereby producing the plant.

In an embodiment, the plant, or part thereof which is produced is further characterised by one or more features as described in the context of a cell or plant of the invention, preferably a *Sorghum* sp. or *Zea mays* cell or plant, or of the processes of the above aspects.

In another aspect, the present invention provides a process for producing an oil product, the process comprising the steps of (i) treating, in a reactor, a composition comprising
  (a) vegetative plant parts, preferably *Sorghum* sp. or *Zea mays* vegetative plant parts whose total fatty acid (TFA) content comprises fatty acids esterified in the form of triacylglycerols (TAG) and fatty acids in the form of lipids other than TAG, wherein the vegetative plant part comprises a TFA content of about 5% (w/w dry weight), preferably at least 10%,
  (b) a solvent which comprises water, an alcohol, or both, and
  (c) optionally a catalyst,
wherein the treatment comprises heating the composition at a temperature between about 50° C. and about 450° C. and at a pressure between 5 and 350 bar for between 1 and 120 minutes in an oxidative, reductive or inert environment,
  (ii) recovering oil product from the reactor at a yield of at least 35% by weight relative to the dry weight of the vegetative plant parts, thereby producing the oil product.

In an embodiment, the vegetative plant parts have a TTQ of between 0.01 and 0.6. In an embodiment, the vegetative plant parts have a TTQ of between 0.01 and 0.55, or between 0.01 and 0.5, or bout 0.1, or about 0.2 or about 0.3, or about 0.4 or about 0.5. Preferably, the TTQ is between 0.60 and 0.84 or between 0.84 and 0.95.

In another aspect, the present invention provides a process for producing an oil product, the process comprising the steps of
  (i) treating, in a reactor, a composition comprising
    (a) vegetative plant parts, preferably *Sorghum* sp. or *Zea mays* vegetative plant parts whose total fatty acid content comprises fatty acids esterified in the form of triacylglycerols (TAG) and fatty acids in the form of lipids other than TAG, wherein the vegetative plant part comprises a total TAG content of about 6% (w/w dry weight) and preferably has a ratio of the fatty acids esterified in the form of TAG to the fatty acids in the form of lipids other than TAG which is between 20:1 and 1.5:1 or between 5:1 and 2:1,
    (b) a solvent which comprises water, an alcohol, or both, and
    (c) optionally a catalyst,
wherein the treatment comprises heating the composition at a temperature between about 50° C. and about 450° C. and at a pressure between 5 and 350 bar for between 1 and 120 minutes in an oxidative, reductive or inert environment,
  (ii) recovering oil product from the reactor at a yield of at least 35% by weight relative to the dry weight of the vegetative plant parts,
thereby producing the oil product.

In an embodiment of the two above aspects, one or more or all of the following apply:
  (i) the vegetative plant parts have a dry weight of at least 1 kg,
  (ii) the vegetative plant parts have a TFA content and/or a total non-polar lipid content of at least 10%, at least 15%, at least 20%, about 25%, about 30%, about 35%, or between 30% and 75% on a dry weight basis,
  (iii) the composition has a solids concentration between 5% and 90%,
  (iv) the catalysts comprises NaOH or KOH or both, preferably at a concentration of 0.1M to 2M,
  (v) the treatment time is between 1 and 60 minutes, preferably between 10 and 60 minutes, more preferably between 15 and 30 minutes,
  (vi) if the solvent is water the process produces a yield of the oil product between a minimum of 36%, 37%, 38%, 39% or 40% and a maximum of 55% or 60% by weight relative to the dry weight of the vegetative plant parts,
  (vii) if the solvent comprises an alcohol the process produces a yield of the oil product between a minimum of 36%, 37%, 38%, 39% or 40% and a maximum of 65% or 70% by weight relative to the dry weight of the vegetative plant parts,
  (viii) if the solvent comprises about 80% water, the oil product comprises about 30% of C13-C22 hydrocarbon compounds,
  (ix) if the solvent comprises about 50% methanol, the oil product comprises about 50% fatty acid methyl esters (FAME),
  (x) the recovered oil product has a water content of less than about 15% by weight,
  (xi) the yield of oil product is at least 2% greater by weight relative to a corresponding process using corresponding vegetative plant parts whose non-polar lipid content is less than 2% on a dry weight basis, and
  (xii) the vegetative plant parts in step (i)(a) have been physically processed by one or more of drying, chopping, shredding, milling, rolling, pressing, crushing or grinding.

In a further embodiment of the two above aspects, the process further comprises one or more of:
  (i) hydrodeoxygenation of the recovered oil product,
  (ii) treatment of the recovered oil product with hydrogen to reduce the levels of ketones or sugars in the oil product,
  (iii) production of syngas from the recovered oil product, and
  (iv) fractionating the recovered oil product to produce one or more of fuel oil, diesel oil, kerosene or gasoline.

In a further embodiment of the two above aspects, the vegetative plant parts comprise plant leaves, stems or both.

In an embodiment of the two above aspects, the vegetative plant parts which are treated are further characterised by one or more features as defined in the context of the *Sorghum* sp. or *Zea mays* plant parts or cells of the invention.

In another aspect, the present invention provides a process for producing an industrial product, the process comprising the steps of:
  i) obtaining a cell according to the invention, preferably a *Sorghum* sp. or *Zea mays* cell, a plant or part thereof of the invention, preferably a *Sorghum* sp. or *Zea mays* plant or part thereof, or a seed of the invention, and
  ii) either
    a) converting at least some of the lipid in the cell, plant or part thereof, or seed of step i) to the industrial product by applying heat, chemical, or enzymatic means, or any combination thereof, to the lipid in situ in the cell, plant or part thereof, or seed, or
    b) physically processing the cell, plant or part thereof, or seed of step i), and subsequently or simultaneously converting at least some of the lipid in the processed cell, plant or part thereof, or seed to the industrial product by applying heat, chemical, or enzymatic means, or any combination thereof, to the lipid in the processed cell, plant or part thereof, or seed, and
  iii) recovering the industrial product,
thereby producing the industrial product.

In an embodiment, the plant part is a vegetative plant part of the invention.

In an embodiment, the step of physically processing the cell, plant or part thereof, or seed comprises one or more of rolling, pressing, crushing or grinding the cell, plant or part thereof, or seed. The industrial product is as described herein.

In a further embodiment, the process further comprises the steps of:
(a) extracting at least some of the non-polar lipid content of the cell, plant or part thereof, or seed as non-polar lipid, and
(b) recovering the extracted non-polar lipid,
wherein steps (a) and (b) are performed prior to the step of converting at least some of the lipid in the cell, plant or part thereof, or seed to the industrial product.

The extracted non-polar lipid preferably comprises triacylglycerols, wherein the triacylglycerols comprise at least 90%, more preferably at least 95%, of the extracted lipid.

In another aspect, the present invention provides a process for producing extracted lipid, the process comprising the steps of:
i) obtaining a cell according to the invention, preferably a *Sorghum* sp. or *Zea mays* cell, a plant or part thereof of the invention, preferably a *Sorghum* sp. or *Zea mays* plant or part thereof, or a seed of the invention,
ii) extracting lipid from the cell, plant or part thereof, or seed, and
iii) recovering the extracted lipid,
thereby producing the extracted lipid.

In an embodiment, the step of extraction comprises one or more of drying, rolling, pressing, crushing or grinding the plant or part thereof, or seed, and/or purifying the extracted lipid or seedoil. In an embodiment, the process uses an organic solvent in the extraction process to extract the oil.

In an embodiment, the process comprises recovering the extracted lipid by collecting it in a container and/or one or more of degumming, deodorising, decolourising, drying, fractionating the extracted lipid, removing at least some waxes and/or wax esters from the extracted lipid, or analysing the fatty acid composition of the extracted lipid.

In an embodiment, the volume of the extracted lipid or oil is at least 1 litre.

In a further embodiment, one or more or all of the following features apply:
(i) the extracted lipid or oil comprises triacylglycerols, wherein the triacylglycerols comprise at least 90%, preferably at least 95% or at least 96%, of the extracted lipid or oil,
(ii) the extracted lipid or oil comprises free sterols, steroyl esters, steroyl glycosides, waxes or wax esters, or any combination thereof, and
(iii) the total sterol content and/or composition in the extracted lipid or oil is significantly different to the sterol content and/or composition in the extracted lipid or oil produced from a corresponding plant or part thereof, or seed.

In a further embodiment, the process further comprises converting the extracted lipid to an industrial product.

In a further embodiment, the industrial product is a hydrocarbon product such as fatty acid esters, preferably fatty acid methyl esters and/or a fatty acid ethyl esters, an alkane such as methane, ethane or a longer-chain alkane, a mixture of longer chain alkanes, an alkene, a biofuel, carbon monoxide and/or hydrogen gas, a bioalcohol such as ethanol, propanol, or butanol, biochar, or a combination of carbon monoxide, hydrogen and biochar.

In a further embodiment, the plant part is an aerial plant part or a green plant part, preferably a vegetative plant part such as a plant leaf or stem.

In yet a further embodiment, the step of obtaining the plant or part thereof comprises a step of harvesting the plant or part thereof with a mechanical harvester.

In another embodiment, the level of a lipid in the plant or part thereof, or seed and/or in the extracted lipid or oil is determinable by analysis by using gas chromatography of fatty acid methyl esters prepared from the extracted lipid or oil.

In another embodiment, the plant part is a vegetative plant part which comprises a total TAG content of at least about 11%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, between 8% and 75%, between 10% and 75%, between 11% and 75%, between about 15% and 75%, between about 20% and 75%, between about 30% and 75%, between about 40% and 75%, between about 50% and 75%, between about 60% and 75%, or between about 25% and 50% (w/w dry weight).

In an embodiment of the above aspects, the cells, plants or parts thereof or seeds which are used are further characterised by one or more features as defined in the context of the plant parts or cells of the invention, preferably the *Sorghum* sp. or *Zea mays* plant parts or cells.

In another aspect, the present invention provides a process for producing seed, the process comprising:
i) growing a plant according to the invention, and
ii) harvesting seed from the plant.

In an embodiment, the process comprises growing a population of at least about 1,500, at least about 3,000 or at least about 5,000 plants, each being a plant of the invention, and harvesting seed from the population of plants.

In another aspect, the present invention provides recovered or extracted lipid or soluble protein obtainable from a cell according to the invention, preferably a *Sorghum* sp. or *Zea mays* cell, a plant or part thereof of the invention, preferably a *Sorghum* sp. or *Zea mays* plant or part thereof, a seed of the invention, or obtainable by a process of the invention.

In another aspect, the present invention provides an industrial product produced by the process according to the invention, which is a hydrocarbon product such as fatty acid esters, preferably fatty acid methyl esters and/or a fatty acid ethyl esters, an alkane such as methane, ethane or a longer-chain alkane, a mixture of longer chain alkanes, an alkene, a biofuel, carbon monoxide and/or hydrogen gas, a bioalcohol such as ethanol, propanol, or butanol, biochar, or a combination of carbon monoxide, hydrogen and biochar.

In another aspect, the present invention provides use of a cell according to the invention, preferably a *Sorghum* sp. or *Zea mays* cell, a plant or part thereof of the invention, preferably a *Sorghum* sp. or *Zea mays* plant or part thereof, a seed of the invention, or the recovered or extracted lipid of the invention for the manufacture of an industrial product. Examples of industrial products of the invention include those described in the previous aspect.

In another aspect, the present invention provides a process for producing fuel, the process comprising:
i) reacting the lipid of the invention with an alcohol, optionally, in the presence of a catalyst, to produce alkyl esters, and
ii) optionally, blending the alkyl esters with petroleum based fuel.

In another aspect, the present invention provides a process for producing a synthetic diesel fuel, the process comprising:
  i) converting the lipid in a cell according to the invention, preferably a *Sorghum* sp. or *Zea mays* cell, a plant or part thereof of the invention, preferably a *Sorghum* sp. or *Zea mays* plant or part thereof, or a seed of the invention to a bio-oil by a process comprising pyrolysis or hydrothermal processing or to a syngas by gasification, and
  ii) converting the bio-oil to synthetic diesel fuel by a process comprising fractionation, preferably selecting hydrocarbon compounds which condense between about 150° C. to about 200° C. or between about 200° C. to about 300° C., or converting the syngas to a biofuel using a metal catalyst or a microbial catalyst.

In another aspect, the present invention provides a process for producing a biofuel, the process comprising converting the lipid in a cell according to the invention, preferably a *Sorghum* sp. or *Zea mays* cell, a plant or part thereof of the invention, preferably a *Sorghum* sp. or *Zea mays* plant or part thereof, or a seed of the invention to bio-oil by pyrolysis, a bioalcohol by fermentation, or a biogas by gasification or anaerobic digestion.

In an embodiment, the part is a vegetative plant part.

The present inventors have also demonstrated significant modifications in traits of transgenic plants, or parts thereof such as vegetative parts, by manipulation of lipid pathways.

Thus, in another aspect, the present invention provides a transgenic plant, or part thereof, preferably a *Sorghum* sp. or *Zea mays* plant or part thereof, comprising
  a) a first exogenous polynucleotide which encodes a transcription factor polypeptide that increases the expression of one or more glycolytic and/or fatty acid biosynthetic genes in the plant or part thereof, preferably a WRI1 polypeptide,
  b) a second exogenous polynucleotide which encodes a polypeptide involved in the biosynthesis of one or more non-polar lipids, preferably a DGAT polypeptide and/or a PDAT polypeptide,
  c) an increased triacylglycerol (TAG) content in the part or at least a part of the transgenic plant relative to a corresponding wild-type plant or part thereof, and one or more or all of the following phenotypes;
  d) an increased soluble protein content in the part or at least a part of the transgenic plant relative to a corresponding wild-type plant or part thereof,
  e) an increased nitrogen content in the part or at least a part of the transgenic plant relative to a corresponding wild-type plant or part thereof,
  f) decreased carbon:nitrogen ratio in the part or at least a part of the transgenic plant relative to a corresponding wild-type plant or part thereof,
  g) increased photosynthetic gene expression in the part or at least a part of the transgenic plant relative to a corresponding wild-type plant or part thereof,
  h) increased photosynthetic capacity in the part or at least a part of the transgenic plant relative to a corresponding wild-type plant or part thereof,
  i) decreased total dietary fibre (TDF) content in the part or at least a part of the transgenic plant relative to a corresponding wild-type plant or part thereof, j) increased carbon content in the part or at least a part of the transgenic plant relative to a corresponding wild-type plant or part thereof,
  k) increased energy content in the part or at least a part of the transgenic plant relative to a corresponding wild-type plant or part thereof, and
  l) an increased TTQ relative to a corresponding wild-type plant or part thereof,
wherein each exogenous polynucleotide is operably linked to a promoter which is capable of directing expression of the polynucleotide in the plant, or part thereof.

In an embodiment, the plant or part thereof is derived from an ancestor transgenic plant which comprises the first and second exogenous polynucleotides, wherein the ancestor transgenic plant was selected from a plurality of candidate transgenic plants each comprising the first and second exogenous polynucleotides on the basis that the ancestor transgenic plant comprised one or more or all of the following phenotypes;
  a) an increased soluble protein content in at least a part of the transgenic plant relative to a corresponding wild-type plant or part thereof,
  b) an increased nitrogen content in at least a part of the transgenic plant relative to a corresponding wild-type plant or part thereof,
  c) decreased carbon:nitrogen ratio in at least a part of the transgenic plant relative to a corresponding wild-type plant or part thereof,
  d) increased photosynthetic gene expression in at least a part of the transgenic plant relative to a corresponding wild-type plant or part thereof,
  e) increased photosynthetic capacity in at least a part of the transgenic plant relative to a corresponding wild-type plant or part thereof,
  f) decreased total dietary fibre (TDF) content in at least a part of the transgenic plant relative to a corresponding wild-type plant or part thereof,
  g) increased carbon content in at least a part of the transgenic plant relative to a corresponding wild-type plant or part thereof, and
  h) increased energy content in at least a part of the transgenic plant relative to a corresponding wild-type plant or part thereof.

In another aspect, the present invention provides a transgenic plant, or part thereof, preferably a *Sorghum* sp. or *Zea mays* plant or part thereof, comprising
  a) a first exogenous polynucleotide which encodes a transcription factor polypeptide that increases the expression of one or more glycolytic and/or fatty acid biosynthetic genes in the plant or a part thereof, preferably a WRI polypeptide,
  b) a second exogenous polynucleotide which encodes a polypeptide involved in the biosynthesis of one or more non-polar lipids, preferably a DGAT polypeptide and/or a PDAT polypeptide,
  c) an increased triacylglycerol (TAG) content in the part or at least a part of the transgenic plant relative to a corresponding wild-type plant or part thereof,
wherein each exogenous polynucleotide is operably linked to a promoter which is capable of directing expression of the polynucleotide in the plant, or part thereof, and wherein the transgenic plant is derived from an ancestor transgenic plant which comprises the first and second exogenous polynucleotides, wherein the ancestor transgenic plant was selected from a plurality of candidate transgenic plants each comprising the first and second exogenous polynucleotides on the basis that the ancestor transgenic plant comprised one or more or all of the following phenotypes;

i) an increased soluble protein content in at least a part of the transgenic plant relative to a corresponding wild-type plant or part thereof,
ii) an increased nitrogen content in at least a part of the transgenic plant relative to a corresponding wild-type plant or part thereof,
iii) decreased carbon:nitrogen ratio in at least a part of the transgenic plant relative to a corresponding wild-type plant or part thereof,
iv) increased photosynthetic gene expression in at least a part of the transgenic plant relative to a corresponding wild-type plant or part thereof,
v) increased photosynthetic capacity in at least a part of the transgenic plant relative to a corresponding wild-type plant or part thereof,
vi) decreased total dietary fibre (TDF) content in at least a part of the transgenic plant relative to a corresponding wild-type plant or part thereof,
vii) increased carbon content in at least a part of the transgenic plant relative to a corresponding wild-type plant or part thereof,
viii) increased energy content in at least a part of the transgenic plant relative to a corresponding wild-type plant or part thereof, and
ix) an increased TTQ and/or increased TAG content relative to a corresponding wild-type plant or part thereof.

In an embodiment of the above two aspects, the plant or part thereof has one or more or all of;
i) an increased soluble protein content in at least a part of the transgenic plant relative to a corresponding wild-type plant or part thereof,
ii) an increased nitrogen content in at least a part of the transgenic plant relative to a corresponding wild-type plant or part thereof,
iii) decreased carbon:nitrogen ratio in at least a part of the transgenic plant relative to a corresponding wild-type plant or part thereof.

In an embodiment, the plant or part thereof has one or more or all of,
i) the plant or part thereof has an increased soluble protein content in the part or at least a part of the transgenic plant relative to the corresponding wild-type plant or part thereof of at least about 10%, at least about 25%, at least about 50%, at least about 75%, at least about 100%, between about 10% and about 200%, between about 50% and about 150%, or between about 50% and about 125%,
ii) the plant or part thereof has an increased nitrogen content in the part or at least a part of the transgenic plant relative to the corresponding wild-type plant or part thereof of at least about 10%, at least about 25%, at least about 50%, at least about 75%, at least about 100%, between about 10% and about 200%, between about 50% and about 150% or between about 50% and about 125%,
iii) the part is a leaf which has an increased soluble protein content relative to a corresponding wild-type leaf of at least about 10%, at least about 25%, at least about 50%, at least about 75%, at least about 100%, between about 10% and about 200%, between about 50% and about 150%, or between about 50% and about 125%,
iv) the part is a leaf which has an increased nitrogen content relative to a corresponding wild-type leaf of at least about 10%, at least about 25%, at least about 50%, at least about 75%, at least about 100%, between about 10% and about 200%, between about 50% and about 150%, or between about 50% and about 125%,
v) the plant or part thereof has a decreased carbon:nitrogen content in the part or at least a part of the transgenic plant relative to the corresponding wild-type plant or part thereof of at least about 10%, at least about 25%, at least about 40%, between about 10% and about 50%, or between about 25% and about 50%,
vi) expression of one or more genes involved in photosynthesis is increased in the plant or part thereof relative to the corresponding wild-type plant or part thereof,
vii) the plant or part thereof has an increased carbon content in the part or at least a part of the transgenic plant relative to the corresponding wild-type plant or part thereof of at least about 10%, at least about 25%, at least about 50%, at least about 75%, at least about 100%, at least about 125%, at least about 150%, between about 10% and about 300%, between about 50% and about 250%, or between about 100% and about 200%,
viii) the plant or part thereof has an increased energy content in the part or at least a part of the transgenic plant relative to the corresponding wild-type plant or part thereof of at least about 10%, at least about 25%, at least about 50%, at least about 75%, at least about 100%, at least about 125%, at least about 150%, at least about 200%, at least about 250%, between about 10% and about 400%, between about 50% and about 300%, or between about 200% and about 300%,
ix) the plant or part thereof has an decreased starch content in the part or at least a part of the transgenic plant relative to the corresponding wild-type plant or part thereof of at least about 2 fold, at least about 5 fold, at least about 10 fold, at least about 15 fold, at least about 20 fold, at least about 25 fold, between about 5 fold and about 35 fold, between about 10 fold and about 30 fold, or between about 20 fold and about 30 fold,
x) the plant or part thereof has an decreased TDF content in the part or at least a part of the transgenic plant relative to the corresponding wild-type plant or part thereof of at least about 10%, at least about 30%, at least about 50%, between about 10% and about 70%, or between about 30% and about 65%, and
xi) the plant or part thereof has a soluble sugar content in the part or at least a part of the transgenic plant relative to the corresponding wild-type plant or part thereof which is about 0.5 fold to 2 fold.

In another embodiment, the plant or part thereof further comprises one or more or all of;
a) a first genetic modification which down-regulates endogenous production and/or activity of a polypeptide involved in the catabolism of triacylglycerols (TAG) in the plant, or part thereof, preferably a SDP1 TAG lipase, when compared to a corresponding plant, or part thereof, lacking the genetic modification,
b) a third exogenous polynucleotide which encodes a polypeptide which increases the export of fatty acids out of plastids of the plant when compared to a corresponding plant lacking the third exogenous polynucleotide, preferably an acyl-ACP thioesterase,
c) a fourth exogenous polynucleotide which encodes a second transcription factor polypeptide that increases the expression of one or more glycolytic and/or fatty acid biosynthetic genes in the plant, or part thereof, preferably a LEC2 polypeptide, d) a fifth exogenous polynucleotide which encodes an oil body coating (OBC) polypeptide,
e) a second genetic modification which down-regulates endogenous production and/or activity of a polypeptide involved in importing fatty acids into plastids of the plant when compared to a corresponding plant lacking the second genetic modification, and
f) a third genetic modification which down-regulates endogenous production and/or activity of a polypeptide involved in diacylglycerol (DAG) production in the plastid when compared to a corresponding plant lacking the third genetic modification, wherein each exogenous polynucleotide is operably linked to a promoter which is capable of directing expression of the polynucleotide in the plant, or part thereof.

In a preferred embodiment, the presence of the first genetic modification, the third exogenous polynucleotide or the fourth exogenous polynucleotide, together with the first and second exogenous polynucleotides increases the total non-polar lipid content of the plant or part thereof, preferably a vegetative plant part such as a leaf or stem, relative to a corresponding plant or part thereof which comprises the first and second exogenous polynucleotides but lacking each of first genetic modification, the third exogenous polynucleotide and the fourth exogenous polynucleotide. More preferably, the increase is synergistic. Most preferably, at least the promoter that directs expression of the first exogenous polynucleotide is a promoter other than a constitutive promoter. Alternatively for *Sorghum* or *Zea mays*, the promoter is preferably a constitutive promoter such as, for example a ubiquitin gene promoter.

In an embodiment, the addition of one or more of the exogenous polynucleotides or genetic modifications, preferably the exogenous polynucleotide encoding an OBC or a fatty acyl thioesterase or the genetic modification which down-regulates endogenous production and/or activity of a polypeptide involved in the catabolism of triacylglycerols (TAG) in the plant or part thereof, more preferably the exogenous polynucleotide which encodes a FATA thioesterase or an LDAP or which decreases expression of an endogenous TAG lipase such as a SDP1 TAG lipase in the plant or part thereof, results in a synergistic increase in the total non-polar lipid content of the plant or part thereof when added to the pair of transgenes WRI1 and DGAT, particularly before the plant flowers and even more particularly in the stems and/or roots of the plant. For example, see Examples 8, 11 and 15. In a preferred embodiment, the increase in the TAG content of a stem or root of the plant is at least 2-fold, more preferably at least 3-fold, relative to a corresponding plant or part thereof transformed with genes encoding WRI1 and DGAT1 but lacking the FATA thioesterase, LDAP and the genetic modification which down-regulates endogenous production and/or activity of a polypeptide involved in the catabolism of triacylglycerols (TAG) in the plant or part thereof. Most preferably, at least the promoter that directs expression of the first exogenous polynucleotide is a promoter other than a constitutive promoter. Alternatively for *Sorghum* or *Zea mays*, the promoter is preferably a constitutive promoter such as, for example a ubiquitin gene promoter.

In an embodiment, each genetic modification is, independently, a mutation of an endogenous gene which partially or completely inactivates the gene, such as a point mutation, an insertion, or a deletion, or an exogenous polynucleotide encoding an RNA molecule which inhibits expression of the endogenous gene, wherein the exogenous polynucleotide is operably linked to a promoter which is capable of directing expression of the polynucleotide in the plant, or part thereof. The point mutation may be a premature stop codon, a splice-site mutation, a frame-shift mutation or an amino acid substitution mutation that reduces activity of the gene or the encoded polypeptide. The deletion may be of one or more nucleotides within a transcribed exon or promoter of the gene, or extend across or into more than one exon, or extend to deletion of the entire gene. Preferably the deletion is introduced by use of ZF, TALEN or CRISPR technologies. In an alternate embodiment, one or more or all of the genetic modifications is an exogenous polynucleotide encoding an RNA molecule which reduces expression of the endogenous gene, wherein the exogenous polynucleotide is operably linked to a promoter which is capable of directing expression of the polynucleotide in the plant, or part thereof. Examples of exogenous polynucleotides which reduce expression of an endogenous gene are selected from the group consisting of an antisense polynucleotide, a sense polynucleotide, a microRNA, a polynucleotide which encodes a polypeptide which binds the endogenous enzyme, a double stranded RNA molecule and a processed RNA molecule derived therefrom. In an embodiment, the plant or part thereof comprises genetic modifications which are an introduced mutation in an endogenous gene and an exogenous polynucleotide encoding an RNA molecule which reduces expression of another endogenous gene. Alternatively, all of the genetic modifications that provide for the increased TTQ and or TAG levels are mutations of endogenous genes.

In an embodiment, the plant or part thereof has one or more or all of,
i) the transcription factor polypeptide is selected from the group consisting of Wrinkled 1 (WRI1), Leafy Cotyledon 1 (LEC1), LEC1-like, Leafy Cotyledon 2 (LEC2), BABY BOOM (BBM), FUS3, ABI3, ABI4, ABI5, Dof4 and Dof11, or the group consisting of MYB73, bZIP53, AGL15, MYB115, MYB118, TANMEI, WUS, GFR2a1, GFR2a2 and PHR1,
ii) the polypeptide involved in the biosynthesis of one or more non-polar lipids is a fatty acyl acyltransferase which is involved in the biosynthesis of TAG, DAG or monoacylglycerol (MAG) in the plant or part thereof, such as a DGAT, PDAT, LPAAT, GPAT or MGAT, preferably a DGAT or a PDAT, or a PDCT or a CPT polypeptide, or a PLC or PLD polypeptide,
iii) the polypeptide involved in the catabolism of triacylglycerols (TAG) in the plant, or part thereof, is an SDP1 lipase, a Cgi58 polypeptide, an acyl-CoA oxidase such as ACX1 or ACX2, or a polypeptide involved in β-oxidation of fatty acids in the plant or part thereof such as a PXA1 peroxisomal ATP-binding cassette transporter, preferably an SDP1 lipase,
iv) the oil body coating (OBC) polypeptide is oleosin, such as a polyoleosin or a caleosin, or a lipid droplet associated protein (LDAP), preferably a non-allergenic OBC,
v) the polypeptide which increases the export of fatty acids out of plastids of the plant or part thereof is a C16 or C18 fatty acid thioesterase such as a FATA polypeptide or a FATB polypeptide, a fatty acid transporter such as an ABCA9 polypeptide or a long-chain acyl-CoA synthetase (LACS),
vi) the polypeptide involved in importing fatty acids into plastids of the plant or part thereof is a fatty acid transporter, or subunit thereof, preferably a TGD polypeptide, and vii) the polypeptide involved in diacylglycerol (DAG) production in the plastid is a plastidial GPAT, a plastidial LPAAT or a plastidial PAP.

In an embodiment, the activity of PDCT or CPT in the cell or vegetative plant part is increased relative to a wild-type cell or vegetative plant part. Alternatively, the activity of PDCT or CPT is decreased, for example by mutation in the endogenous gene encoding the enzyme or by downregulation of the gene through an RNA molecule which reduces its expression.

In an embodiment, the polypeptide involved in the biosynthesis of one or more non-polar lipids is a DGAT or a PDAT and the polypeptide involved in the catabolism of TAG in the plant or part thereof is an SDP1 lipase.

In an embodiment, the transcription factor polypeptide that increases the expression of one or more glycolytic and/or fatty acid biosynthetic genes in the plant or part thereof is a WRI1 polypeptide and the polypeptide involved in the biosynthesis of one or more non-polar lipids is a DGAT or a PDAT.

In an embodiment, the transcription factor polypeptide that increases the expression of one or more glycolytic and/or fatty acid biosynthetic genes in the plant or part thereof is a WRI1 polypeptide, a LEC2 polypeptide, a LEC1 polypeptide or a LEC1-like polypeptide and the polypeptide involved in the biosynthesis of one or more non-polar lipids is a DGAT.

In an embodiment, the transcription factor polypeptide that increases the expression of one or more glycolytic and/or fatty acid biosynthetic genes in the plant or part thereof is a WRI1 polypeptide, a LEC2 polypeptide, a LEC1 polypeptide or a LEC1-like polypeptide and the polypeptide involved in the catabolism of triacylglycerols (TAG) in the plant or part thereof is an SDP1 lipase.

In an embodiment, the transcription factor polypeptide that increases the expression of one or more glycolytic and/or fatty acid biosynthetic genes in the plant or part thereof is a WRI1 polypeptide, a LEC2 polypeptide, a LEC1 polypeptide or a LEC1-like polypeptide, the polypeptide involved in the biosynthesis of one or more non-polar lipids is a DGAT or a PDAT and the polypeptide involved in the catabolism of triacylglycerols (TAG) in the plant or part thereof is an SDP1 lipase.

In an embodiment, the transcription factor polypeptide that increases the expression of one or more glycolytic and/or fatty acid biosynthetic genes in the plant is a WRI1 polypeptide, a LEC2 polypeptide, a LEC1 polypeptide or a LEC1-like polypeptide, and the polypeptide involved in importing fatty acids into plastids of the plant or part thereof is a TGD polypeptide.

In an embodiment, the transcription factor polypeptide that increases the expression of one or more glycolytic and/or fatty acid biosynthetic genes in the plant is a WRI1 polypeptide, a LEC2 polypeptide, a LEC1 polypeptide or a LEC1-like polypeptide, and the polypeptide involved in diacylglycerol (DAG) production is a plastidial GPAT.

In an embodiment, the transcription factor polypeptide that increases the expression of one or more glycolytic and/or fatty acid biosynthetic genes in the plant is a WRI1 polypeptide, a LEC2 polypeptide, a LEC1 polypeptide or a LEC1-like polypeptide, the polypeptide which increases the export of fatty acids out of plastids of the plant is a fatty acid thioesterase, preferably a FATA or a FATB polypeptide, and the polypeptide involved in importing fatty acids into plastids of the plant is a TGD polypeptide.

In an embodiment, the transcription factor polypeptide that increases the expression of one or more glycolytic and/or fatty acid biosynthetic genes in the plant is a WRI1 polypeptide, a LEC2 polypeptide, a LEC1 polypeptide or a LEC1-like polypeptide, the polypeptide which increases the export of fatty acids out of plastids of the plant is a fatty acid thioesterase, preferably a FATA or a FATB polypeptide, and the polypeptide involved in diacylglycerol (DAG) production is a plastidial GPAT.

In an embodiment, the transcription factor polypeptide that increases the expression of one or more glycolytic and/or fatty acid biosynthetic genes in the plant is a WRI1 polypeptide, a LEC2 polypeptide, a LEC1 polypeptide or a LEC1-like polypeptide, the polypeptide involved in importing fatty acids into plastids of the plant a TGD polypeptide, and the polypeptide involved in diacylglycerol (DAG) production is a plastidial GPAT.

In an embodiment, when present, the two transcription factors are WRI1 and LEC2, or WRI1 and LEC1.

In the above embodiments, the plant or part thereof preferably comprises an exogenous polynucleotide which encodes a DGAT and a genetic modification which down-regulates production of an endogenous SDP1 lipase. More preferably, the plant or part thereof does not comprise an exogenous polynucleotide encoding a PDAT, and/or is a plant or part thereof other than a *Nicotiana benthamiana* or part thereof, and/or the WRI1 is a WRI1 other than *Arabidopsis thaliana* WRI1 (SEQ ID NOs:21 or 22) and/or is a plant or part thereof other than a *Brassica napus* or part thereof. In an embodiment, at least one of the exogenous polynucleotides in the plant or part thereof is expressed from a promoter which is not a constitutive promoter such as, for example, a promoter which is expressed preferentially in green tissues or stems of the plant or that is up-regulated after commencement of flowering or during senescence.

In an embodiment, the exogenous polynucleotide encoding WRI1 comprises one or more of the following:
i) nucleotides encoding a polypeptide comprising amino acids whose sequence is set forth as any one of SEQ ID NOs:21 to 75 or 196 to 201, or a biologically active fragment thereof, or a polypeptide whose amino acid sequence is at least 30% identical to any one or more of SEQ ID NOs: 21 to 75 or 196 to 201,
ii) nucleotides whose sequence is at least 30% identical to i), and
iii) nucleotides which hybridize to i) and/or ii) under stringent conditions. Preferably, the WRI1 polypeptide is a WRI1 polypeptide other than *Arabidopsis thaliana* WRI1 (SEQ ID NOs:21 or 22). More preferably, the WRI1 polypeptide comprises amino acids whose sequence is set forth as SEQ ID NO:199, or a biologically active fragment thereof, or a polypeptide whose amino acid sequence is at least 30% identical thereto.

In an embodiment, the part is a vegetative part and one or more or all of the promoters are expressed at a higher level in the vegetative part relative to seed of the plant.

In a further embodiment, the plant or part thereof has one or more or all of;
i) the plant, or a part thereof, comprises a total non-polar lipid content of at least about 8%, at least about 10%, at least about 11%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, between 8% and 75%, between 10% and 75%, between 11% and 75%, between about 15% and 75%, between about 20% and 75%, between about 30% and 75%, between about 40% and 75%, between about 50% and 75%, between about 60% and 75%, or between about 25% and 50% (w/w dry weight), preferably before flowering,
ii) a vegetative part of a plant comprises a TAG content of at least about 8%, at least about 10%, at least about 11%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, between 8% and 75%, between 10% and 75%, between 11% and 75%, between about 15% and 75%, between about 20% and 75%, between about 30% and 75%, between about 40% and 75%, between about 50% and 75%, between about 60% and 75%, or between about 25% and 50% (w/w dry weight), preferably before flowering,
iii) one or more or all of the promoters are selected from a tissue-specific promoter such as a leaf and/or stem specific promoter, a developmentally regulated promoter such as a senescence-specific promoter such as a SAG12 promoter, an inducible promoter, or a circadian-rhythm regulated promoter,
iv) the plant, or part thereof, is one member of a population or collection of at least about 1,500, at least about 3,000 or at least about 5,000 such plants, or parts thereof, preferably vegetative plant parts, wherein the first and second exogenous polynucleotides are inserted at the same chromosomal location in the genome of each of the plants,
v) the plant is a member of the family Fabaceae (or Leguminosae) such as alfalfa, clover, peas, lucerne, beans, lentils, lupins, mesquite, carob, soybeans, and peanuts, or a member of the family Poaceae such as corn or sorghum, and
vi) the part is a leaf or leaves which are mature.

In an embodiment, before the plant flowers, a vegetative part of the plant comprises a total non-polar lipid content of at least about 8%, at least about 10%, about 11%, between 8% and 15%, or between 9% and 12% (w/w dry weight).

In a further embodiment, the plant or part thereof is;
i) a 16:3 plant or a vegetative part or seed thereof, and which comprises one or more or all of the following:
  a) an exogenous polynucleotide which encodes a polypeptide which increases the export of fatty acids out of plastids of the plant when compared to a corresponding plant lacking the exogenous polynucleotide,
  b) a first genetic modification which down-regulates endogenous production and/or activity of a polypeptide involved in importing fatty acids into plastids of the plant when compared to a corresponding plant lacking the first genetic modification, and
  c) a second genetic modification which down-regulates endogenous production and/or activity of a polypeptide involved in diacylglycerol (DAG) production in the plastid when compared to a corresponding plant lacking the second genetic modification,
wherein the exogenous polynucleotide is operably linked to a promoter which is capable of directing expression of the polynucleotide in the plant, or part thereof, or
ii) a 18:3 plant or a vegetative part or seed thereof.

In an embodiment, the plant or part thereof has one or more or all of,
i) the plant comprises a part, preferably a vegetative part, which has an increased synthesis of total fatty acids relative to a corresponding part lacking the first exogenous polynucleotide, or a decreased catabolism of total fatty acids relative to a corresponding part lacking the first exogenous polynucleotide, or both, such that it has an increased level of total fatty acids relative to a corresponding part lacking the first exogenous polynucleotide,
ii) the plant comprises a part, preferably a vegetative part, which has an increased expression and/or activity of a fatty acyl acyltransferase which catalyses the synthesis of TAG, DAG or MAG, preferably TAG, relative to a corresponding part having the first exogenous polynucleotide and lacking the exogenous polynucleotide which encodes a polypeptide involved in the biosynthesis of one or more non-polar lipids,
iii) the plant comprises a part, preferably a vegetative part, which has a decreased production of lysophosphatidic acid (LPA) from acyl-ACP and G3P in its plastids relative to a corresponding part having the first exogenous polynucleotide and lacking the genetic modification which down-regulates endogenous production and/or activity of a polypeptide involved in diacylglycerol (DAG) production in plastids in the plant part,
iv) the plant comprises a part, preferably a vegetative part, which has an altered ratio of C16:3 to C18:3 fatty acids in its total fatty acid content and/or its galactolipid content relative to a corresponding part lacking the exogenous polynucleotide(s) and/or genetic modification(s), preferably a decreased ratio,
v) oleic acid comprises at least 20% (mol %), at least 22% (mol %), at least 30% (mol %), at least 40% (mol %), at least 50% (mol %), or at least 60% (mol %), preferably about 65% (mol %) or between 20% and about 65% of the total fatty acid content in the plant, or part thereof,
vi) non-polar lipid in the plant, or part thereof preferably a vegetative part, comprises an increased level of one or more fatty acids which comprise a hydroxyl group, an epoxy group, a cyclopropane group, a double carbon-carbon bond, a triple carbon-carbon bond, conjugated double bonds, a branched chain such as a methylated or hydroxylated branched chain, or a combination of two or more thereof, or any of two, three, four, five or six of the aforementioned groups, bonds or branched chains,
vii) non-polar lipid in the plant, or part thereof preferably a vegetative part, comprises one or more polyunsaturated fatty acids selected from eicosadienoic acid (EDA), arachidonic acid (ARA), stearidonic acid (SDA), eicosatrienoic acid (ETE), eicosatetraenoic acid (ETA), eicosapentaenoic acid (EPA), docosapentaenoic acid (DPA), docosahexaenoic acid (DHA), or a combination of two of more thereof,
viii) the part is a vegetative plant part, such as a leaf or a stem, or part thereof,
ix) one or more or all of the promoters are selected from promoter other than a constitutive promoter, preferably a tissue-specific promoter such as a leaf and/or stem specific promoter, a developmentally regulated promoter such as a senescense-specific promoter such as a SAG12 promoter, an inducible promoter, or a circadian-rhythm regulated promoter, preferably wherein at least one of the promoters operably linked to an exogenous polynucleotide which encodes a transcription factor polypeptide is a promoter other than a constitutive promoter,
x) the plant, or part thereof preferably a vegetative part, comprises a total fatty acid content whose oleic acid level and/or palmitic acid level is increased by at least 2% relative to a corresponding plant, or part thereof, lacking the exogenous polynucleotide(s) and/or genetic modification(s), and/or whose α-linolenic acid (ALA) level and/or linoleic acid level is decreased by at least 2% relative to a corresponding plant, or part thereof, lacking the exogenous polynucleotide(s) and/or genetic modification(s), xi) non-polar lipid in the plant, or part thereof preferably a vegetative part, comprises a modified level of total sterols, preferably free (non-esterified) sterols, steroyl esters, steroyl glycosides, relative to the non-polar lipid in a corresponding plant, or part thereof, lacking the exogenous polynucleotide(s) and/or genetic modification(s), xii) non-polar lipid in the plant, or part thereof, comprises waxes and/or wax esters, xiii) the plant comprises an exogenous polynucleotide encoding a silencing suppressor, wherein the exogenous polynucleotide is operably linked to a promoter which is capable of directing expression of the polynucleotide in the plant, xiv) the level of one or more non-polar lipid(s) and/or the total non-polar lipid content of the plant or part thereof, preferably a vegetative plant part, is at least 2% greater on a weight basis than in a corresponding plant or part, respectively, which comprises exogenous polynucleotides encoding an *Arabidposis thaliana* WRI1 (SEQ ID NO:21) and an *Arabidopsis thaliana* DGAT 1 (SEQ ID NO:1), xv) a total polyunsaturated fatty acid (PUFA) content which is decreased relative to the total PUFA content of a corresponding plant lacking the exogenous polynucleotide(s) and/or genetic modification(s), xvi) the plant part is a potato (*Solanum tuberosum*) tuber, a sugarbeet (*Beta vulgaris*) beet, a sugarcane (*Saccharum* sp.) or sorghum (*Sorghum bicolor*) stem, a monocotyledonous plant seed having an increased total fatty acid content in its endosperm such as, for example, a wheat (*Triticum aestivum*) grain or a corn (*Zea mays*) kernel, a *Nicotiana* spp. leaf, or a legume seed having an increased total fatty acid content such as, for example, a *Brassica* sp. seed or a soybean (*Glycine max*) seed, xvii) if the plant part is a seed, the seed germinates at a rate substantially the same as for a corresponding wild-type seed or when sown in soil produces a plant whose seed germinate at a rate substantially the same as for corresponding wild-type seed, and xviii) the plant is an algal plant such as from diatoms (bacillariophytes), green algae (chlorophytes), blue-green algae (cyanophytes), golden-brown algae (chrysophytes), haptophytes, brown algae or heterokont algae.

In an embodiment, the plant or part thereof, comprises a first exogenous polynucleotide encoding a WRI1, a second exogenous polynucleotide encoding a DGAT or a PDAT, preferably a DGAT1, a third exogenous polynucleotide encoding an RNA which reduces expression of a gene encoding an SDP1 polypeptide, and a fourth exogenous polynucleotide encoding an oleosin. In preferred embodiments, the plant or part thereof has one or more or all of the following features:

i) a total lipid content of at least 8%, at least 10%, at least 12%, at least 14%, or at least 15.5% (% dry weight), ii) at least a 3 fold, at least a 5 fold, at least a 7 fold, at least an 8 fold, or at least a 10 fold, higher total lipid content in the plant or part thereof relative to a corresponding the plant or part thereof lacking the exogenous polynucleotides and genetic modifications, iii) a total TAG content of at least 5%, at least 6%, at least 6.5% or at least 7% (% weight of dry weight or seed weight), iv) at least a 40 fold, at least a 50 fold, at least a 60 fold, or at least 70 fold, at least 100 fold, or at least a 120-fold higher total TAG content relative to a corresponding the plant or part thereof lacking the exogenous polynucleotides and genetic modifications, v) oleic acid comprises at least 15%, at least 19% or at least 22% (% weight of dry weight or seed weight) of the fatty acids in TAG, vi) at least a 10 fold, at least a 15 fold or at least a 17 fold higher level of oleic acid in TAG relative to a corresponding the plant or part thereof lacking the exogenous polynucleotides and genetic modifications, vii) palmitic acid comprises at least 20%, at least 25%, at least 30% or at least 33% (% weight) of the fatty acids in TAG, viii) at least a 1.5 fold higher level of palmitic acid in TAG relative to a corresponding the plant or part thereof lacking the exogenous polynucleotides and genetic modifications, ix) linoleic acid comprises at least 22%, at least 25%, at least 30% or at least 34% (% weight) of the fatty acids in TAG, x) α-linolenic acid comprises less than 20%, less than 15%, less than 11% or less than 8% (% weight) of the fatty acids in TAG, xi) at least a 5 fold, or at least an 8 fold, lower level of α-linolenic acid in TAG relative to a corresponding plant or part thereof lacking the exogenous polynucleotides and genetic modifications, and xii) when the part is a potato tuber, a TAG content of at least 0.5% on a dry weight basis and/or a total fatty acid content of at least 1%, preferably at least 1.5% or at least 2.0%, on a dry weight basis.

In the above embodiments, a preferred plant part is a leaf piece having a surface area of at least 1 cm$^2$ or a stem piece having a length of at least 1 cm.

In an embodiment of the above aspects, the plant or plant part of the invention has been treated so it is no longer able to be propagated or give rise to a living plant, i.e. it is dead, for example a brown leaf or stem. For example, the plant or plant part has been dried and/or ground. In another embodiment, the plant part is alive, for example, a green leaf or stem.

In an embodiment, the part is a seed, fruit, or a vegetative part such as an aerial plant part or a green part such as a leaf or stem.

In the above embodiments, it is preferred that the part is a vegetative part from a plant which is growing in soil or which was grown in soil and the plant part was subsequently harvested, and wherein the vegetative part comprises at least 8% TAG on a weight basis (% dry weight) such as for example between 8% and 75% or between 8% and 30%. More preferably, the TAG content is at least 10%, such as for example between 10% and 75% or between 10% and 30%. Preferably, these TAG levels are present in the vegetative parts prior to or at flowering of the plant or prior to seed setting stage of plant development. In these embodiments, it is preferred that the ratio of the TAG content in the leaves to the TAG content in the stems of the plant is between 1:1 and 10:1, and/or the ratio is increased relative to a corresponding vegetative part comprising the first and second exogenous polynucleotides and lacking the first genetic modification.

Preferably, the vegetative plant part has an increased soluble protein content relative to the corresponding wild-type vegetative part of at least about 100%, or between about 50% and about 125%. Preferably, the vegetative plant part has an increased nitrogen content relative to the corresponding wild-type vegetative part of at least about 100%, or between about 50% and about 125%. Preferably, the vegetative plant part has an decreased carbon:nitrogen content relative to the corresponding wild-type vegetative plant part of at least about 40%, or between about 25% and about 50%. Preferably, the vegetative plant part has a decreased TDF content relative to the corresponding wild-type vegetative plant part of at least about 30%, or between about 30% and about 65%.

In an embodiment, the plant of the invention is a monocotyledonous plant, or part thereof preferably a leaf, a grain, a stem, a root or an endosperm, which has a total fatty acid content or TAG content which is increased at least 5-fold on a weight basis when compared to a corresponding wild-type monocotyledonous plant, or part thereof. Alternatively, the monocotyledonous plant has endosperm comprising a TAG content which is at least 2.0%, preferably at least 3%. more preferably at least 4% or at least 5%, on a weight basis, or part of the plant, preferably a leaf, a stem, a root, a grain or an endosperm. In an embodiment, the endosperm has a TAG content of at least 2% which is increased at least 5-fold relative to a corresponding wild-type endosperm. Preferably, the plant is fully male and female fertile, its pollen is essentially 100% viable, and its grain has a germination rate which is between 70% and 100% relative to corresponding wild-type grain. In an embodiment, the transgenic plant of the invention is a progeny plant at least two generations derived from an initial transgenic plant, and is preferably homozygous for the transgenes. In embodiments, the monocotyledonous plant, or part thereof preferably a leaf, stem, grain or endosperm, is further characterised by one or more features as described in the context of a plant or part thereof of the invention. In embodiments, the monocotyledonous plant, or part thereof preferably a leaf, a grain, stem or an endosperm of the invention preferably has an increased level of monounsaturated fatty acids (MUFA) and/or a lower level of polyunsaturated fatty acids (PUFA) in both the total fatty acid content and in the TAG fraction of the total fatty acid content, such as for example an increased level of oleic acid and a decreased level of LA (18:2), when compared to a corresponding plant or part thereof lacking the genetic modifications and/or exogenous polynucleotide(s). Preferably, the linoleic acid (LA, 18:2) level in the total fatty acid content of the grain or endosperm of the monocotyledonous plant is decreased by at least 5% and/or the level of oleic acid in the total fatty acid content is increased by at least 5% relative to a corresponding wild-type plant or part thereof, preferably at least 10% or more preferably at least 15%, when compared to a corresponding plant or part thereof lacking the genetic modifications and/or exogenous polynucleotide(s).

In an embodiment, the plant or part thereof is *Acrocomia aculeata* (macauba palm), *Arabidopsis thaliana, Aracinis hypogaea* (peanut), *Astrocaryum murumuru* (murumuru), *Astrocaryum vulgare* (tucumã), *Attalea geraensis* (Indaiirateiro), *Attalea humilis* (American oil palm), *Attalea oleifera* (andaií), *Attalea phalerata* (uricuri), *Attalea speciosa* (babassu), *Avena sativa* (oats), *Beta vulgaris* (sugar beet), *Brassica* sp. such as, for example, *Brassica carinata, Brassica juncea, Brassica napobrassica, Brassica napus* (canola), *Camelina sativa* (false flax), *Cannabis sativa* (hemp), *Carthamus tinctorius* (safflower), *Caryocar brasiliense* (pequi), *Cocos nucifera* (Coconut), *Crambe abyssinica* (Abyssinian kale), *Cucumis melo* (melon), *Elaeis guineensis* (African palm), *Glycine max* (soybean), *Gossypium hirsutum* (cotton), *Helianthus* sp. such as *Helianthus annuus* (sunflower), *Hordeum vulgare* (barley), *Jatropha curcas* (physic nut), *Joannesia princeps* (arara nut-tree), *Lemna* sp. (duckweed) such as *Lemna aequinoctialis, Lemna disperma, Lemna ecuadoriensis, Lemna gibba* (swollen duckweed), *Lemna japonica, Lemna minor, Lemna minuta, Lemna obscura, Lemna paucicostata, Lemna perpusilla, Lemna tenera, Lemna trisulca, Lemna turionifera, Lemna valdiviana, Lemna yungensis, Licania rigida* (oiticica), *Linum usitatissimum* (flax), *Lupinus angustifolius* (lupin), *Mauritia flexuosa* (buriti palm), *Maximiliana maripa* (inaja palm), *Miscanthus* sp. such as *Miscanthus×giganteus* and *Miscanthus sinensis, Nicotiana* sp. (tabacco) such as *Nicotiana tabacum* or *Nicotiana benthamiana, Oenocarpus bacaba* (bacaba-do-azeite), *Oenocarpus bataua* (pataua), *Oenocarpus distichus* (bacaba-de-leque), *Oryza* sp. (rice) such as *Oryza sativa* and *Oryza glaberrima, Panicum virgatum* (switchgrass), *Paraqueiba paraensis* (mari), *Persea amencana* (avocado), *Pongamia pinnata* (Indian beech), *Populus trichocarpa, Ricinus communis* (castor), *Saccharum* sp. (sugarcane), *Sesamum indicum* (sesame), *Solanum tuberosum* (potato), *Sorghum* sp. such as *Sorghum bicolor, Sorghum vulgare, Theobroma grandiforum* (cupuassu), *Trifolium* sp., *Trithrinax brasiliensis* (Brazilian needle palm), *Triticum* sp. (wheat) such as *Triticum aestivum* and *Zea mays* (corn).

In an embodiment, the plant, or part thereof, is a member of a population or collection of at least about 1,500, at least about 3,000 or at least about 5,000 such plants or parts.

In an embodiment, the TFA content, the TAG content, the total non-polar lipid content, or the one or more non-polar lipids, and/or the level of the oleic acid or a PUFA in the plant or part thereof is determinable by analysis by using gas chromatography of fatty acid methyl esters obtained from the plant or vegetative part thereof.

In a further embodiment, the plant part is a leaf and the total non-polar lipid content of the leaf is determinable by analysis using Nuclear Magnetic Resonance (NMR).

In each of the above embodiments, it is preferred that the plant is a transgenic progeny plant at least two generations derived from an initial transgenic plant, and is preferably homozygous for the transgenes.

In an embodiment, the plant or the part thereof of the invention is phenotypically normal, in that it is not significantly reduced in its ability to grow and reproduce when compared to an unmodified plant or part thereof. In an embodiment, the biomass, growth rate, germination rate, storage organ size, seed size and/or the number of viable seeds produced is not less than 70%, not less than 80% or not less than 90% of that of a corresponding wild-type plant when grown under identical conditions. In an embodiment, the plant is male and female fertile to the same extent as a corresponding wild-type plant and its pollen (if produced) is as viable as the pollen of the corresponding wild-type plant, preferably at least about 75%, or at least about 90%, or close to 100% viable. In an embodiment, the plant produces seed which has a germination rate of at least about 75% or at least about 90% relative to the germination rate of corresponding seed of a wild-type plant, where the plant species produces seed.

In an embodiment, the plant of the invention has a plant height which is at least about 75%, or at least about 80% or at least about 90% relative to the height of the corresponding wild-type plant grown under the same conditions. A combination of each of these features is envisaged. In an alternative embodiment, the plant of the invention has a plant height which is between 60% and 90% relative to the height of the corresponding wild-type plant grown under the same conditions. In an embodiment, the plant or part thereof of the invention, preferably a plant leaf, does not exhibit increased necrosis, i.e. the extent of necrosis, if present, is the same as that exhibited by a corresponding wild-type plant or part thereof grown under the same conditions and at the same stage of plant development. This feature applies in particular to the plant or part thereof comprising an exogenous polynucleotide which encodes a fatty acid thioesterase such as a FATB thioesterase.

In a further aspect, the present invention provides a collection of at least about 1,500, at least about 3,000 or at least about 5,000 vegetative plant parts, each being a vegetative plant part of the invention, wherein the vegetative plant parts have been harvested from plants growing in a field.

In an embodiment, the first and second exogenous polynucleotides are inserted at the same chromosomal location in the genome of each of the vegetative plant parts, preferably in the nuclear genome of each of the vegetative plant parts.

Also provided is a storage bin comprising a collection of vegetative plant parts of the invention.

Further provided is seed of, or obtained from, a plant of the invention, preferably a collection of at least about 1,500, at least about 3,000 at least about 5,000, or at least about 10,000 seeds of the invention, comprising the exogenous polynucleotides.

In another aspect, the present invention provides an extract of a plant or a part thereof of the invention. The extract preferably has a different fatty acid composition relative to a corresponding wild-type extract.

In an embodiment, the extract comprises the first and second exogenous polynucleotides.

In an embodiment, the extract is lacking at least 50% or at least 90% of the non-polar lipids of the plant or part thereof.

In an embodiment, the extract comprises the soluble protein content of the plant or part thereof.

In an embodiment, the extract comprises the nitrogen content of the plant or part thereof.

In an embodiment, the extract is lacking at least 50% or at least 90% of the chlorophyll and/or soluble sugars of the plant or part thereof.

In an embodiment, the extract comprises the carbon content of the plant or part thereof.

In an embodiment, the extract comprises a dye which binds protein in the extract.

Extracts of the invention can readily be produced using standard techniques in the art.

Combinations of the features of the above aspects are clearly contemplated for the plant, plant part and cell of the invention, and in the processes of producing and using them.

In another aspect, the present invention provides a method of producing a plant extract, the method comprising
  i) obtaining a plant or part thereof of the invention, or seed of the invention, and
  ii) processing the plant or part thereof, or seed, to produce the extract.

In an embodiment, the plant or part thereof of the invention, or seed of the invention, is transgenic.

In an embodiment, step ii) comprising producing two or more fractions from the plant or part thereof, or seed, and selecting at least one, but not all of the fractions.

In an embodiment, the selected fraction(s) has one or more of the following features;
  i) comprises the first and second exogenous polynucleotides,
  ii) is lacking at least 50% or at least 90% of the non-polar lipids of the plant or part thereof,
  iii) comprises the soluble protein content of the plant or part thereof,
  iv) comprises the nitrogen content of the plant or part thereof,
  v) is lacking at least 50% or at least 90% of the chlorophyll and/or soluble sugars of the plant or part thereof, and
  vi) comprises the carbon content of the plant or part thereof.

In a further aspect, the present invention provides a process for selecting a plant or a part thereof with a desired phenotype, the process comprising
  i) obtaining a plurality of candidate plants, or parts thereof, which each comprise
    a) a first exogenous polynucleotide which encodes a transcription factor polypeptide that increases the expression of one or more glycolytic and/or fatty acid biosynthetic genes in a plant or part thereof, and
    b) a second exogenous polynucleotide which encodes a polypeptide involved in the biosynthesis of one or more non-polar lipids, wherein each exogenous polynucleotide is operably linked to a promoter which is capable of directing expression of the polynucleotide in the plant, or part thereof,
  ii) analysing lipid in the plurality of parts, or at least a part of each plant in the plurality of candidate plants, from step i),
  iii) analysing the plurality of parts, or at least a part of each plant in the plurality of candidate plants, from step i) for one or more or all of;
    a) soluble protein content,
    b) nitrogen content,
    c) carbon:nitrogen ratio,
    d) photosynthetic gene expression,
    e) photosynthetic capacity,
    f) total dietary fibre (TDF) content,
    g) carbon content,
    h) energy content,
    i) TAG content, and
    j) TTQ, and
  iv) selecting a plant or part thereof which comprises an increased TTQ and/or an increased triacylglycerol (TAG) content in the part or at least a part of the plant relative to a corresponding wild-type plant or part thereof and a desired phenotype selected from one or more or all of the following;
    A) an increased soluble protein content in the part or at least a part of the plant relative to a corresponding wild-type plant or part thereof,
    B) an increased nitrogen content in the part or at least a part of the plant relative to a corresponding wild-type plant or part thereof,
    C) decreased carbon:nitrogen ratio in the part or at least a part of the plant relative to a corresponding wild-type plant or part thereof,
    D) increased photosynthetic gene expression in the part or at least a part of the plant relative to a corresponding wild-type plant or part thereof,
    E) increased photosynthetic capacity in the part or at least a part of the plant relative to a corresponding wild-type plant or part thereof, F) decreased total dietary fibre (TDF) content in the part or at least a part of the plant relative to a corresponding wild-type plant or part thereof, G) increased carbon content in the part or at least a part of the plant relative to a corresponding wild-type plant or part thereof, and H) increased energy content in the part or at least a part of the plant relative to a corresponding wild-type plant or part thereof.

In an embodiment, the increased triacylglycerol (TAG) content is determined by analysing one or more of the total fatty acid content, TAG content, fatty acid composition, by any means, which might or might not involve first extracting the lipid.

In yet another embodiment, the selected plant or part thereof has one or more of the features as described herein.

In another aspect, the present invention provides a process for producing a feedstuff, the process comprising admixing a plant or part thereof of any one of the invention, seed of the invention, or an extract of the invention, with at least one other food ingredient.

In another aspect, the present invention provides a feedstuff comprising a cell of the invention, plant or part thereof of the invention, seed of the invention, extracted oil or an extract of the invention.

In an embodiment, the feedstuff is silage, pellets or hay.

In yet a further aspect, the present invention provides a process for feeding an animal, the process comprising providing to the animal a cell of the invention, plant or part thereof of the invention, seed of the invention, extracted lipid or other extract of the invention, or a feedstuff of the invention. In an embodiment, the material provided to the animal is the residue plant material remaining after at least some of the oil has been extracted, such as seedmeal or leaf/stem meal.

In an embodiment, the animal ingests an increased amount of nitrogen, protein, carbon and/or energy potential relative to when the animal ingests the same amount on a dry weight basis of a corresponding wild-type cell, plant or part thereof, seed or extract or feedstuff produced from the corresponding wild-type plant or part thereof.

The present inventors have identified a sub-class of OBC that are non-allergenic, or not known to be allergenic, such as to humans.

Thus, in a further aspect, the present invention provides a recombinant eukaryotic cell, preferably a *Sorghum* sp. or *Zea mays* cell, comprising at least a first exogenous polynucleotide which encodes a non-allergenic OBC, wherein the exogenous polynucleotide is operably linked to a promoter which is capable of directing expression of the polynucleotide in the cell.

In an embodiment, the first exogenous polynucleotide comprises one or more of the following:

i) nucleotides encoding an OBC polypeptide comprising amino acids whose sequence is set forth as any one of SEQ ID NOs: 306 to 314, or a biologically active fragment thereof, or an OBC polypeptide whose amino acid sequence is at least 30% identical to any one or more of SEQ ID NOs: 306 to 314, wherein the OBC polypeptide is non-allergenic, ii) nucleotides whose sequence is at least 30% identical to i), and iii) a polynucleotide which hybridizes to one or both of i) or ii) under stringent conditions. In an embodiment, the oleosinL is not sesame oleosinL (SEQ ID NO:305).

In an embodiment, the recombinant cell comprises one or more of the following:

a) a second exogenous polynucleotide which encodes a transcription factor polypeptide that increases the expression of one or more glycolytic and/or fatty acid biosynthetic genes in the cell, preferably a WRI1 polypeptide, b) a third exogenous polynucleotide which encodes a polypeptide involved in the biosynthesis of one or more non-polar lipids, preferably a DGAT and/or a PDAT, c) a first genetic modification which down-regulates endogenous production and/or activity of a polypeptide involved in the catabolism of triacylglycerols (TAG) in the cell, preferably an SDP1 TAG lipase, when compared to a corresponding cell lacking the genetic modification, d) a fourth exogenous polynucleotide which encodes a polypeptide which increases the export of fatty acids out of plastids of the cell when compared to a corresponding cell lacking the exogenous polynucleotide, preferably an acyl-ACP thioesterase polypeptide, e) a fifth exogenous polynucleotide which encodes a second transcription factor polypeptide that increases the expression of one or more glycolytic and/or fatty acid biosynthetic genes in the cell, preferably a LEC2 polypeptide, f) a second genetic modification which down-regulates endogenous production and/or activity of a polypeptide involved in importing fatty acids into plastids of the cell, preferably a TGD polypeptide, when compared to a corresponding cell lacking the genetic modification, g) a sixth exogenous polynucleotide which encodes a lipid droplet associated protein (LDAP), h) a third genetic modification which down-regulates endogenous production and/or activity of a polypeptide involved in diacylglycerol (DAG) production in the plastid when compared to a corresponding cell lacking the genetic modification, and i) a fourth genetic modification which down-regulates endogenous production and/or activity of a polypeptide involved in importing fatty acids into plastids of the cell when compared to a corresponding cell lacking the genetic modification, wherein each exogenous polynucleotide is operably linked to a promoter which is capable of directing expression of the polynucleotide in the cell.

In an embodiment, the cell is a plant cell from or in a vegetative part of a plant and one or more or all of the promoters are expressed at a higher level in the vegetative part relative to seed of the plant.

In an embodiment, the first exogenous polynucleotide is codon optimised for expression in a plant cell such as a *Sorghum* sp. or *Zea mays* cell.

In an embodiment, one or more or all of the following features apply to the above aspects:

i) the cell has an increased synthesis of total fatty acids relative to a corresponding cell lacking the second exogenous polynucleotide, or a decreased catabolism of total fatty acids relative to a corresponding cell lacking the second exogenous polynucleotide, or both, such that it has an increased level of total fatty acids relative to a corresponding cell lacking the second exogenous polynucleotide, ii) the cell has an increased expression and/or activity of a fatty acyl acyltransferase which catalyses the synthesis of TAG, DAG or MAG, preferably TAG, relative to a corresponding cell having the second exogenous polynucleotide and lacking the third exogenous polynucleotide which encodes a polypeptide involved in the biosynthesis of one or more non-polar lipids,
iii) the cell has a decreased production of lysophosphatidic acid (LPA) from acyl-ACP and G3P in its plastids relative to a corresponding cell having the second exogenous polynucleotide and lacking the third genetic modification which down-regulates endogenous production and/or activity of a polypeptide involved in diacylglycerol (DAG) production in the plastid in the cell,
iv) the cell has an altered ratio of C16:3 to C18:3 fatty acids in its total fatty acid content and/or its galactolipid content relative to a corresponding cell lacking the exogenous polynucleotide(s) and/or genetic modification(s), preferably a decreased ratio,
v) the cell is in a vegetative part of a plant and comprises a total non-polar lipid content of at least about 8%, at least about 10%, at least about 11%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, between about 8% and 75%, between 10% and 75%, between 11% and 75%, between about 15% and 75%, between about 20% and 75%, between about 30% and 75%, between about 40% and 75%, between about 50% and 75%, between about 60% and 75%, or between about 25% and 50% (w/w dry weight),
vi) the cell is in a vegetative part of a plant and comprises a TAG content of at least about 8%, at least about 10%, at least about 11%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, between 8% and 75%, between 10% and 75%, between 11% and 75%, between about 15% and 75%, between about 20% and 75%, between about 30% and 75%, between about 40% and 75%, between about 50% and 75%, between about 60% and 75%, or between about 25% and 50% (w/w dry weight),
vii) the transcription factor polypeptide is selected from the group consisting of Wrinkled 1 (WRI1), Leafy Cotyledon 1 (LEC1), LEC1-like, Leafy Cotyledon 2 (LEC2), BABY BOOM (BBM), FUS3, ABI3, ABI4, ABI5, Dof4 and Dof11,
viii) oleic acid comprises at least 20% (mol %), at least 22% (mol %), at least 30% (mol %), at least 40% (mol %), at least 50% (mol %), or at least 60% (mol %), preferably about 65% (mol %) or between 20% and about 65% of the total fatty acid content in the cell,
ix) non-polar lipid in the cell comprises a fatty acid which comprises a hydroxyl group, an epoxy group, a cyclopropane group, a double carbon-carbon bond, a triple carbon-carbon bond, conjugated double bonds, a branched chain such as a methylated or hydroxylated branched chain, or a combination of two or more thereof, or any of two, three, four, five or six of the aforementioned groups, bonds or branched chains,
x) non-polar lipid in the cell comprises one or more polyunsaturated fatty acids selected from eicosadienoic acid (EDA), arachidonic acid (ARA), stearidonic acid (SDA), eicosatrienoic acid (ETE), eicosatetraenoic acid (ETA), eicosapentaenoic acid (EPA), docosapentaenoic acid (DPA), docosahexaenoic acid (DHA), or a combination of two of more thereof,
xi) the cell is in a plant or part thereof, preferably a vegetative plant part, or the cell is an algal cell such as a diatom (bacillariophytes), green algae (chlorophytes), blue-green algae (cyanophytes), golden-brown algae (chrysophytes), haptophytes, brown algae or heterokont algae, or the cell is from or is an organism suitable for fermentation such as a fungus,
xii) one or more or all of the promoters are selected from a tissue-specific promoter such as a leaf and/or stem specific promoter, a developmentally regulated promoter such as a senescense-specific promoter such as a SAG12 promoter, an inducible promoter, or a circadian-rhythm regulated promoter,
xiii) the cell comprises a total fatty acid content which comprises medium chain fatty acids, preferably C12:0, C14:0 or both, at a level of at least 5% of the total fatty acid content and optionally an exogenous polynucleotide which encodes an LPAAT which has preferential activity for fatty acids with a medium chain length (C8 to C14), preferably C12:0 or C14:0,
xiv) the cell comprises a total fatty acid content whose oleic acid level is increased by at least 2% relative to a corresponding cell lacking the exogenous polynucleotide(s) and/or genetic modification(s), and/or whose α-linolenic acid (ALA) level is decreased by at least 2% relative to a corresponding cell lacking the exogenous polynucleotide(s) and/or genetic modification(s),
xv) non-polar lipid in the cell comprises a modified level of total sterols, preferably free (non-esterified) sterols, steroyl esters, steroyl glycosides, relative to the non-polar lipid in a corresponding cell lacking the exogenous polynucleotide(s) and/or genetic modification(s),
xvi) non-polar lipid in the cell comprises waxes and/or wax esters,
xvii) the cell is one member of a population or collection of at least about 1000 such cells, preferably in a vegetative plant part or a seed,
xviii) the cell comprises an exogenous polynucleotide encoding a silencing suppressor, wherein the exogenous polynucleotide is operably linked to a promoter which is capable of directing expression of the polynucleotide in the cell,
xix) the level of one or more non-polar lipid(s) and/or the total non-polar lipid content of the cell is at least 2% greater on a weight basis than in a corresponding cell which comprises exogenous polynucleotides encoding an *Arabidposis thaliana* WRI1 (SEQ ID NO:21) and an *Arabidopsis thaliana* DGAT1 (SEQ ID NO:1), and
xx) a total polyunsaturated fatty acid (PUFA) content which is decreased relative to the total PUFA content of a corresponding cell lacking the exogenous polynucleotide(s) and/or genetic modification(s).

Any embodiment herein shall be taken to apply mutatis mutandis to any other embodiment unless specifically stated otherwise.

Combinations of the features of the above aspects are clearly contemplated for the plant, plant part and cell of the invention, and in the processes of producing and using them.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1. A representation of lipid synthesis in eukaryotic cells, showing export of some of the fatty acids synthesized in the plastids to the Endoplasmic Reticulum (ER) via the Plastid Associated Membrane (PLAM), and import of some of the fatty acids into the plastid from the ER for eukaryotic galactolipid synthesis. Abbreviations:

Acetyl-CoA and Malonyl-CoA: acetyl-coenzyme A and malonyl-coenzymeA;
ACCase: Acetyl-CoA carboxylase;
FAS: fatty acid synthase complex;
16:0-ACP, 18:0-ACP and 18:1-ACP: C16:0-acyl carrier protein (ACP), C18:0acyl carrier protein, C18:1-acyl carrier protein;
KAS II: ketoacyl-ACP synthase II (EC 2.3.1.41);
PLPAAT: plastidial LPAAT;
PGPAT: plastidial GPAT;
PAP: PA phosphorylase (EC 3.1.3.4);
G3P: glycerol-3-phosphate;
LPA: lysophosphatidic acid;
PA: phosphatidic acid;
DAG: diacylglycerol;
TAG: triacylglycerol;
Acyl-CoA and Acyl-PC: acyl-coenzyme A and acyl-phosphatidylcholine;
PC: phosphatidylcholine;
GPAT: glycerol-3-phosphate acyltransferase;
LPAAT: lysophosphatidic acid acyltransferase (EC 2.3.1.51);
LPCAT: acyl-CoA:lysophosphatidylcholine acyltransferase; or synonyms 1-acylglycerophosphocholine O-acyltransferase; acyl-CoA:1-acyl-sn-glycero-3-phosphocholine O-acyltransferase (EC 2.3.1.23);
CPT: CDP-choline:diacylglycerol cholinephosphotransferase; or synonyms 1-alkyl-2-acetylglycerol cholinephosphotransferase; alkylacylglycerol cholinephosphotransferase; cholinephosphotransferase; phosphorylcholine-glyceride transferase (EC 2.7.8.2);
PDCT: phosphatidylcholine:diacylglycerol cholinephosphotransferase;
PLC: phospholipase C (EC 3.1.4.3);
PLD: Phospholipase D; choline phosphatase; lecithinase D;
lipophosphodiesterase II (EC 3.1.4.4);
PDAT: phospholipid:diacylglycerol acyltransferase; or synonym
phospholipid:1,2-diacyl-sn-glycerol O-acyltransferase (EC 2.3.1.158);
FAD2: fatty acid Δ12-desaturase; FAD3, fatty acid Δ15-desaturase;
UDP-Gal: Uridine diphosphate galactose;
MGDS: monogalactosyldiacylglycerol synthase;
MGDG: monogalactosyldiacylglycerol; DGDG: digalactosyldiacylglycerol
FAD6, 7, 8: plastidial fatty acid Δ12-desaturase, plastidial ω3-desaturase, plastidial ω3-desaturase induced at low temperature, respectively.

Figure 2:
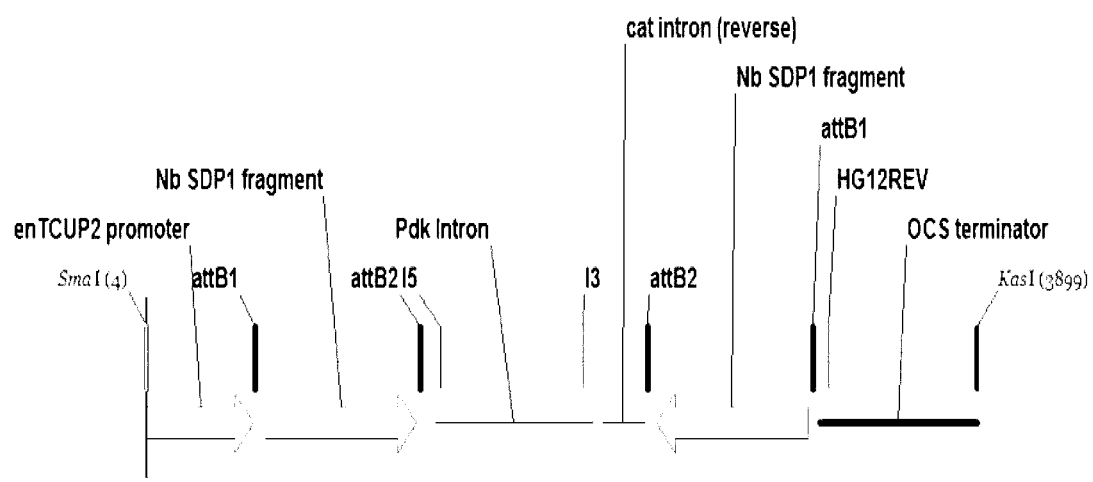

FIG. 2. Schematic representation of the *N. benthamiana* SDP1 hairpin construct. The genetic segments shown are as described in Example 2. Abbreviations are as for FIG. 12. attB sites represent recombination sites from the pHELLSGATE12 vector.

Figure 3:
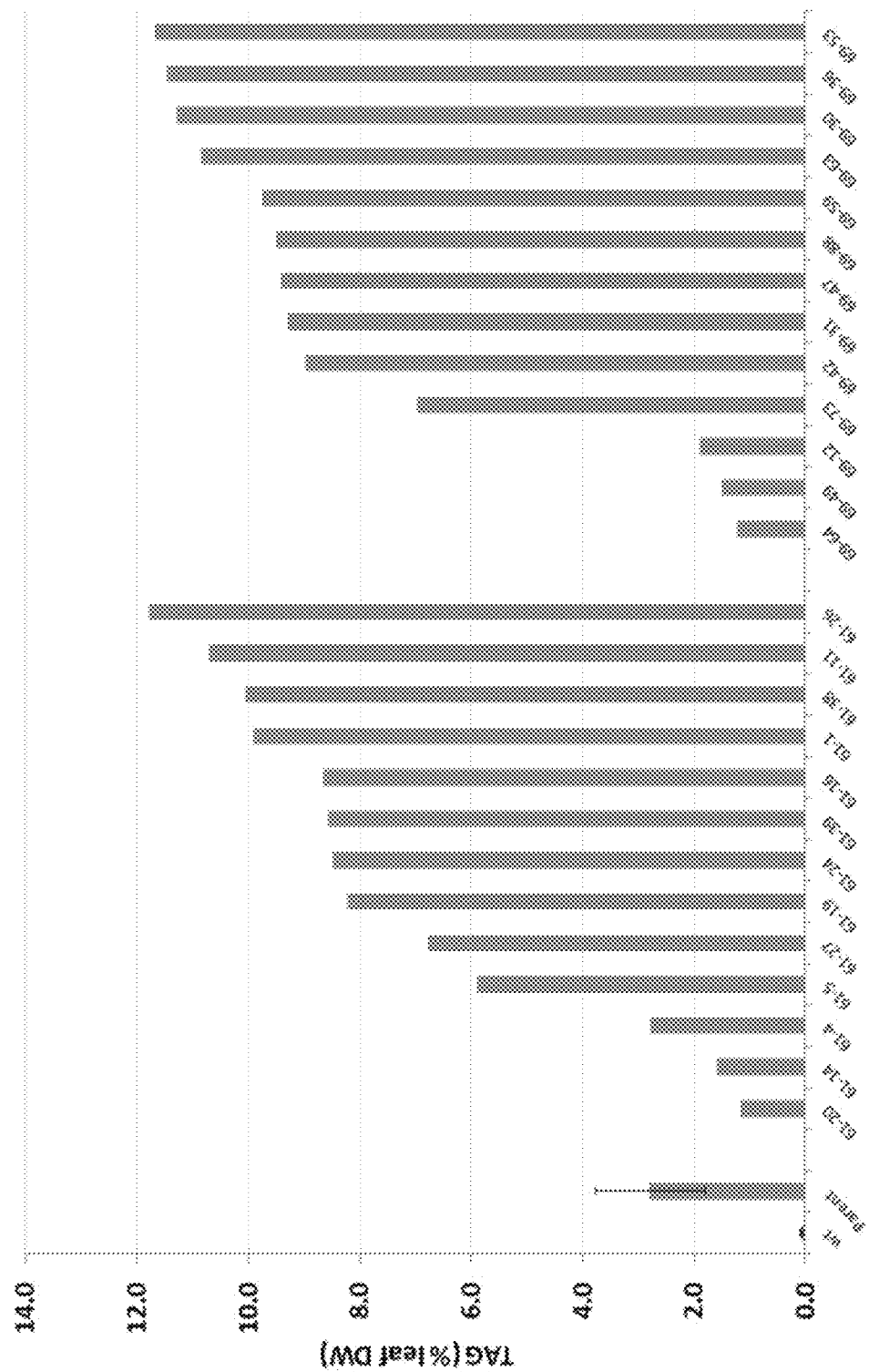

FIG. 3. TAG content in green leaf samples of tobacco plants transformed with the T-DNA from pOIL51, lines #61 and #69, harvested before flowering. The controls (parent) samples were from plants transformed with the T-DNA from pJP3502.

Figure 4:
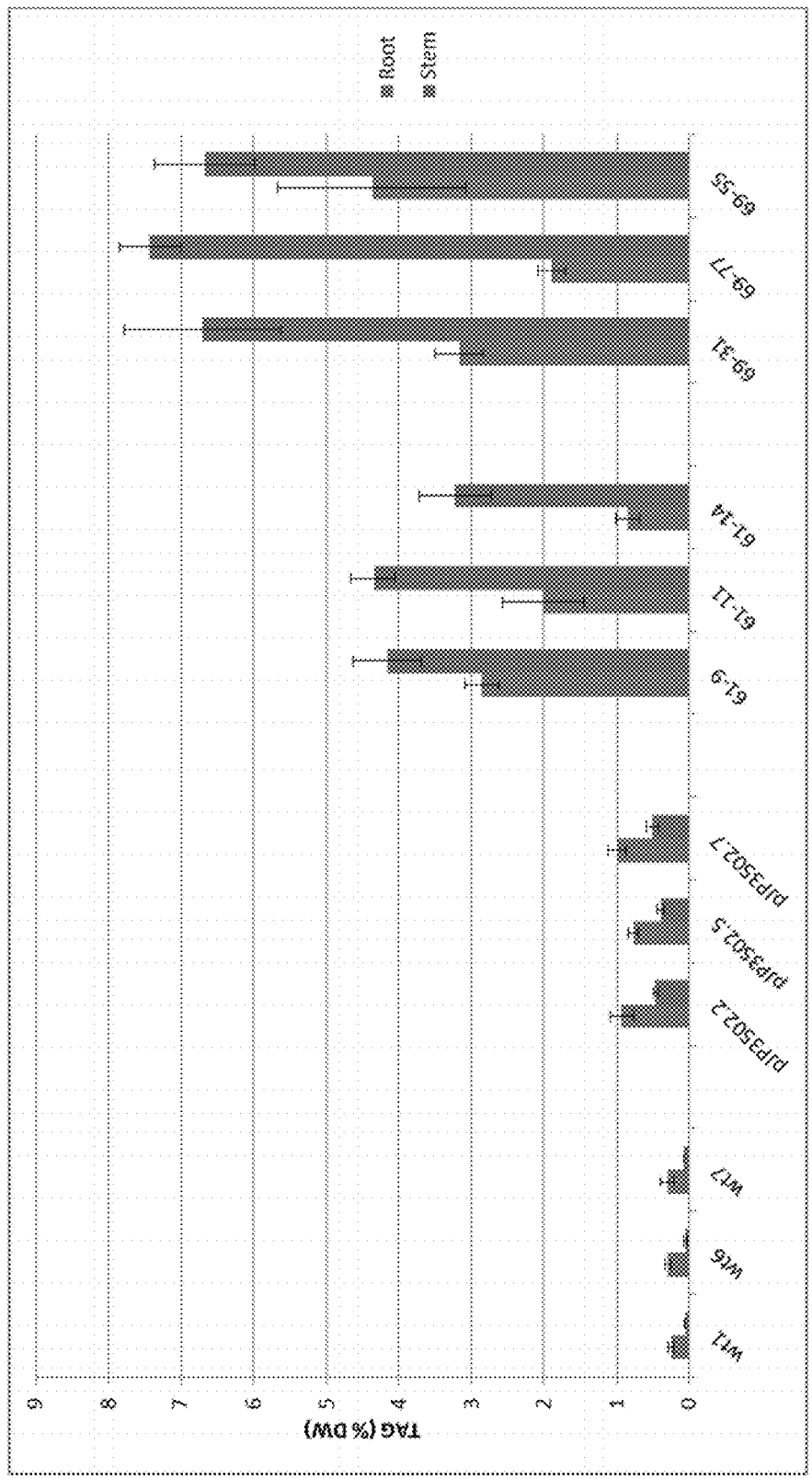

FIG. 4. TAG levels (% dry weight) in root and stem tissue of wild-type (wt) and transgenic *N. tabacum* plants containing the T-DNA from pJP3502 alone or additionally with the T-DNA from pOIL051.

Figure 5:
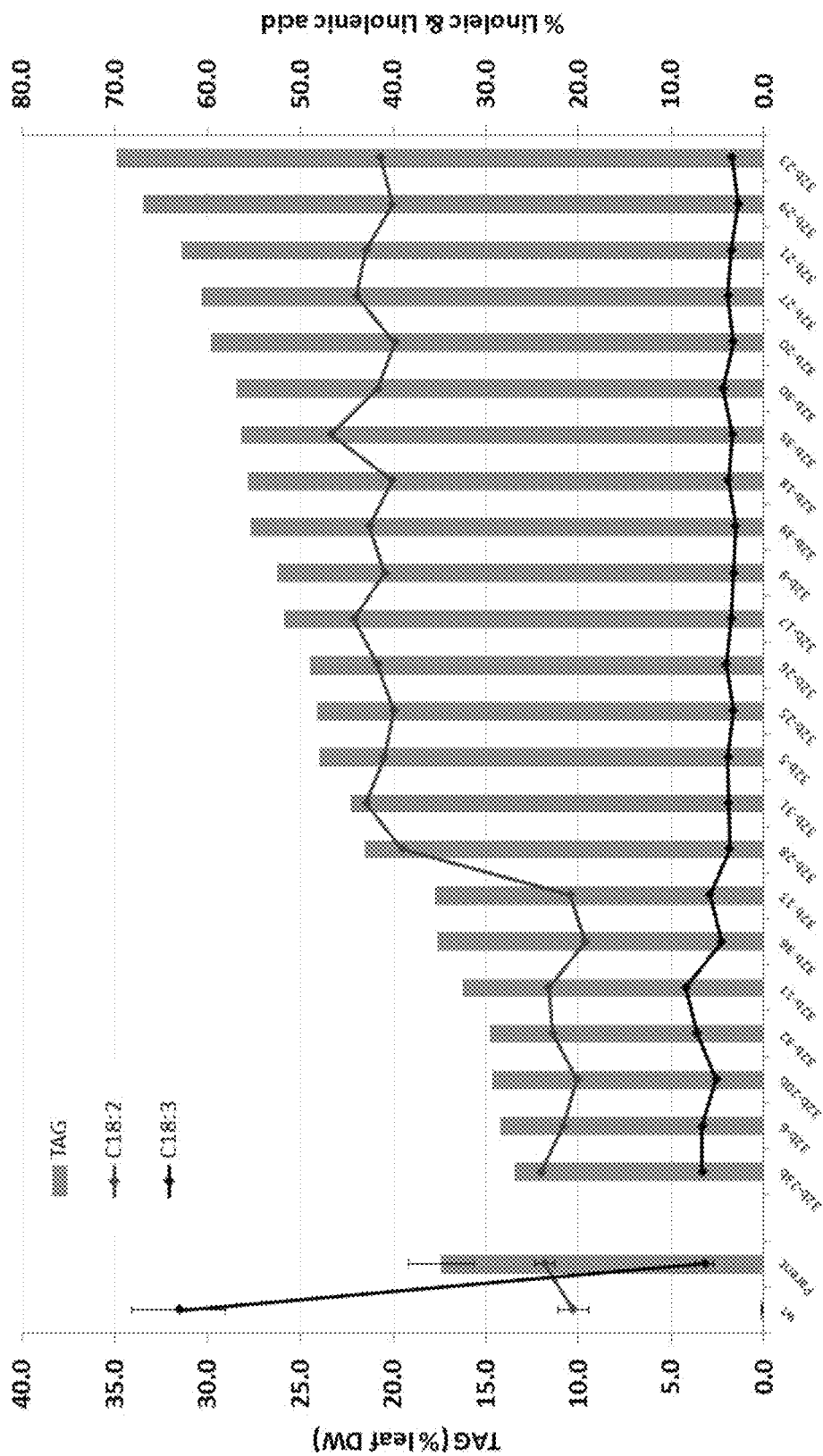

FIG. 5. TAG content in leaf samples of transformed tobacco plants at seed-setting stage of growth, transformed with the T-DNA from pOIL049, lines #23c and #32b. The controls (parent) samples were from plants transformed with the T-DNA from pJP3502. The upper line shows 18:2 percentage in the TAG and the lower line shows the 18:3 (ALA) percentage in the fatty acid content.

Figure 6:
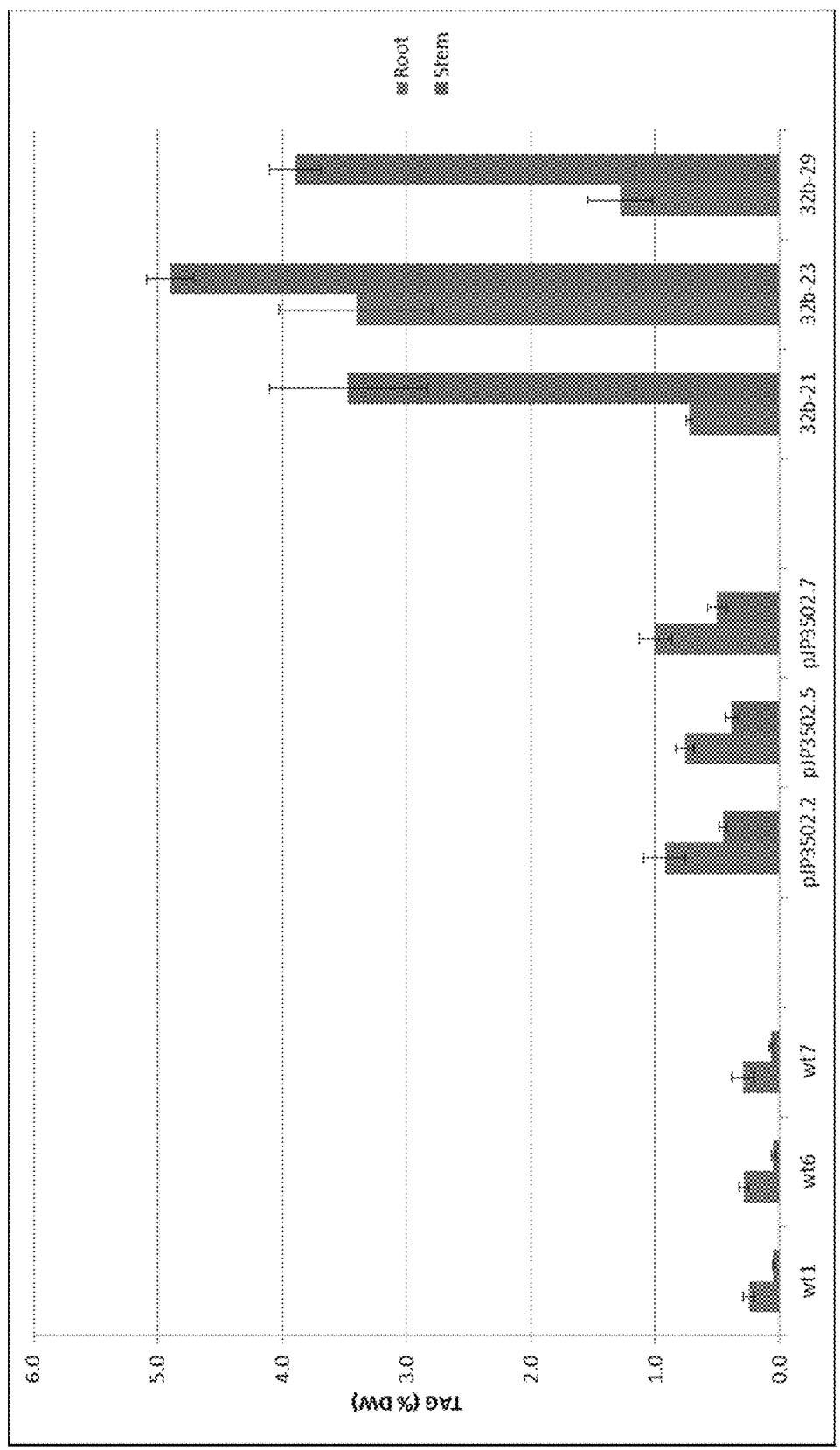

FIG. 6. TAG levels (% dry weight) in root and stem tissue of wild-type (wt) and transgenic *N. tabacum* plants containing the T-DNA from pJP3502 alone or additionally with the T-DNA from pOIL049.

Figure 7:
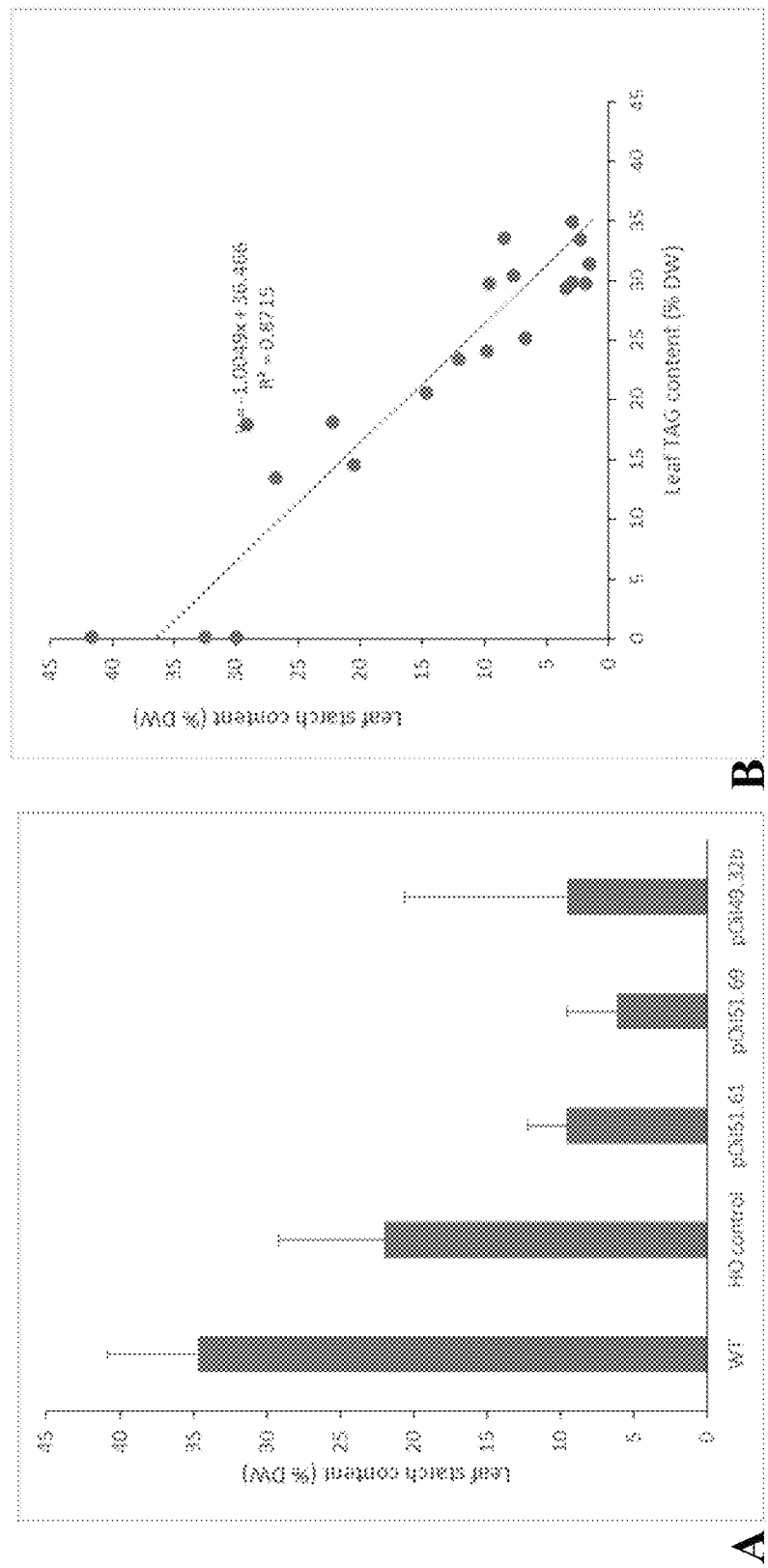

FIG. 7. A. Starch content in leaf tissue from wild-type plants (WT) and transgenic plants containing the T-DNA from pJP3502 (HO control) or the T-DNAs from both pJP3502 and pOIL051 (pOIL51.61 and pOIL51.69) or both pJP3502 and pOIL049 (pOIL49.32b). Data represent combined results from at least three individual plants. B. Correlation between starch and TAG content in leaf tissue of wild-type plants (WT) and transgenic plants containing the T-DNA from pJP3502 (HO control) or T-DNAs from both pJP3502 and pOIL051 (pOIL51.61 and pOIL51.69) or both pJP3502 and pOIL049 (pOIL49.32b). Data represent combined results from at least three individual plants.

Figure 8:
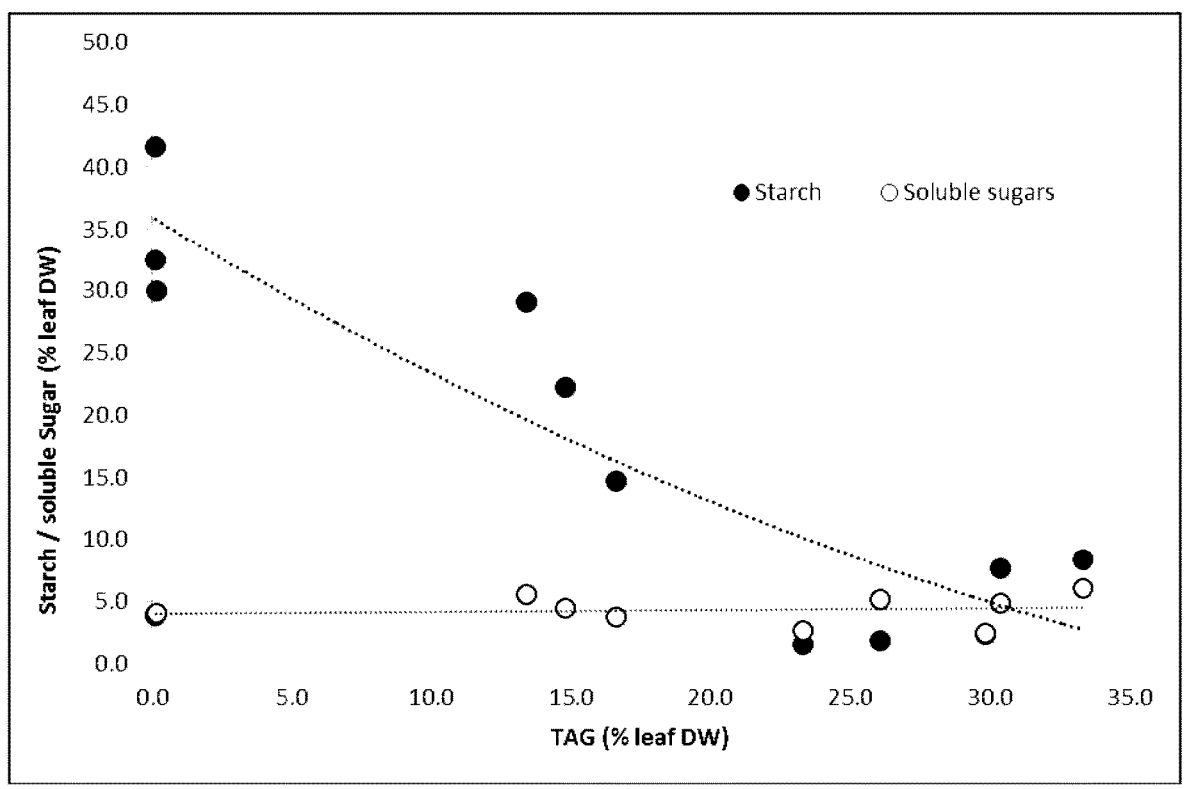

FIG. 8. Starch and soluble sugar contents on a dry weight (DW) basis in senescing leaves of wild-type plants (open circles) and transgenic plants (filled circles) (T1) sampled at seed setting stage. The transgenic *N. tabacum* plants included those designated HO, SDP1 and LEC2. In each case three plants were included in the analysis. Data points are based on triplicate analyses.

Figure 9:
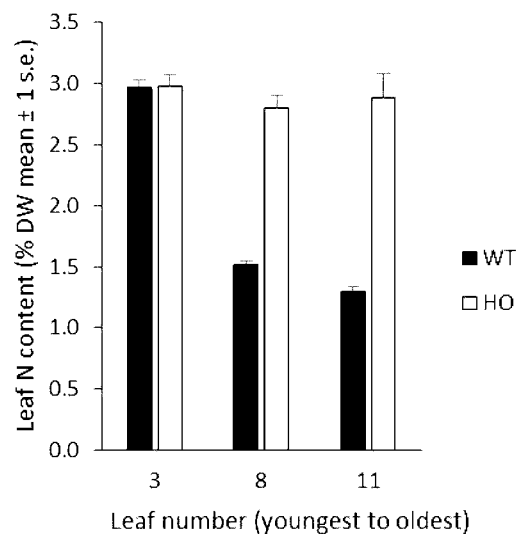
Figure 9:
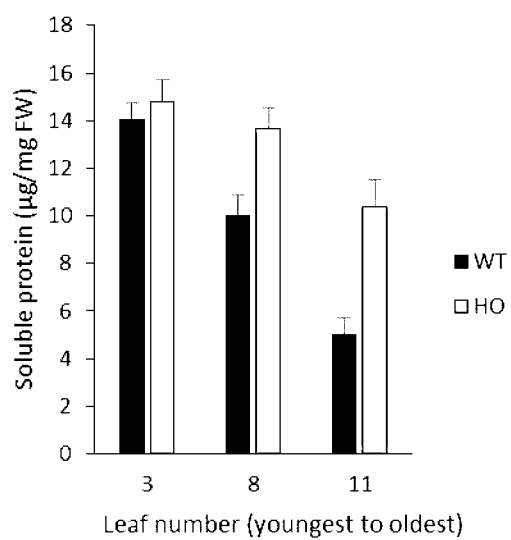

FIG. 9. Leaf N (A) and soluble protein (B) of WT and HO leaves of different ages harvested from plants 69 DAS.

Figure 10:
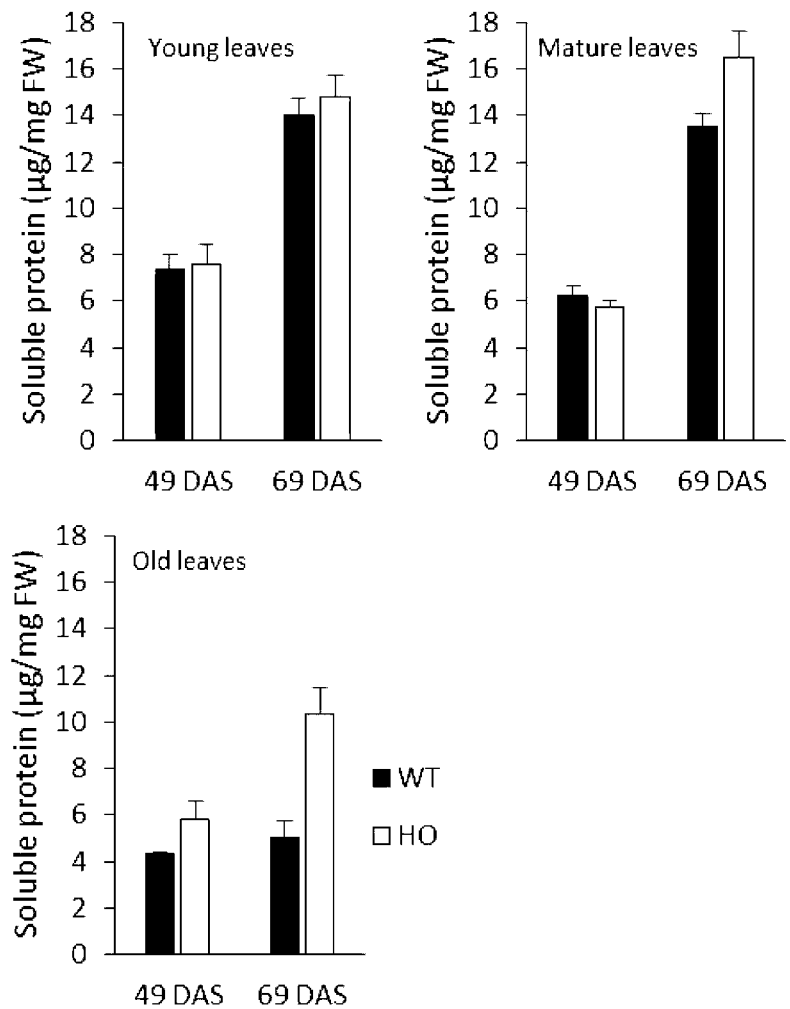

FIG. 10. Leaf soluble protein content in WT and HO tobacco as a function of leaf and plant age.

Figure 11:
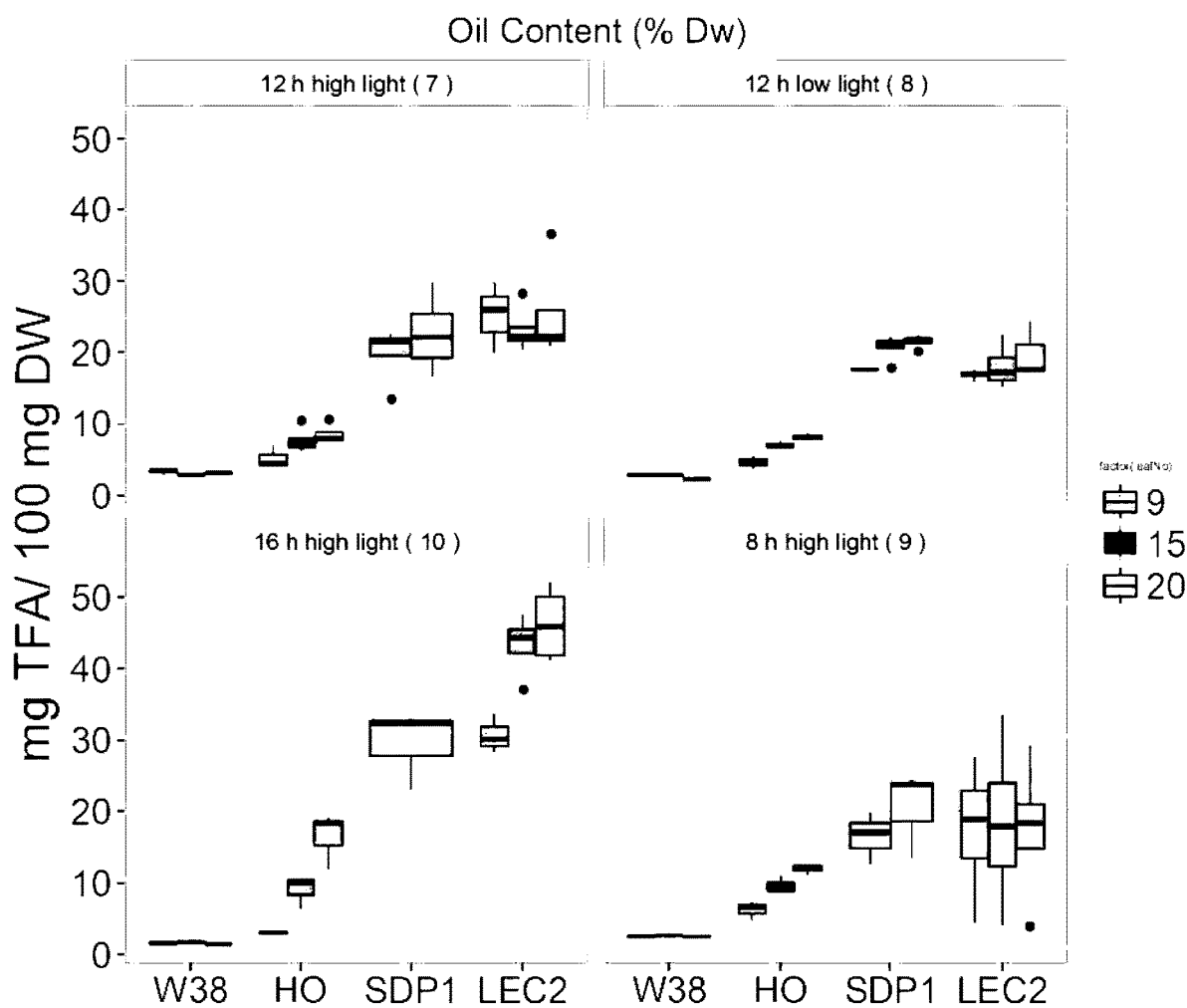

FIG. 11. Mean total fatty acid (TFA) content in mg/100 mg dry weight of leaves 9, 15 and 20 in tobacco plants grown under modified conditions: increased light intensity (top left panel); control (top right panel); increased photoperiod, increased light intensity and increased CO2 concentration (lower left panel); reduced photoperiod at high light intensity (lower right panel).

Figure 12:
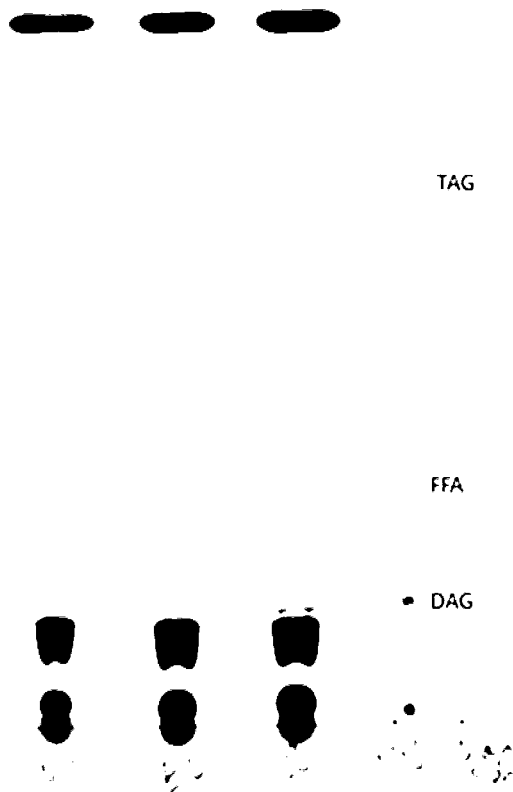

FIG. 12. TLC separation of total leaf lipids extracted from wildtype and transgenic *S. bicolor*. Wt, wildtype; EV, empty vector control; 2, *S. bicolor* transformed with pOIL136 (event 2); TAG, triacylglycerol; FFA, free fatty acids; DAG, diacylglycerol. Leaf tissue was harvested from young, vegetative plants following transfer to soil.

Figure 13:
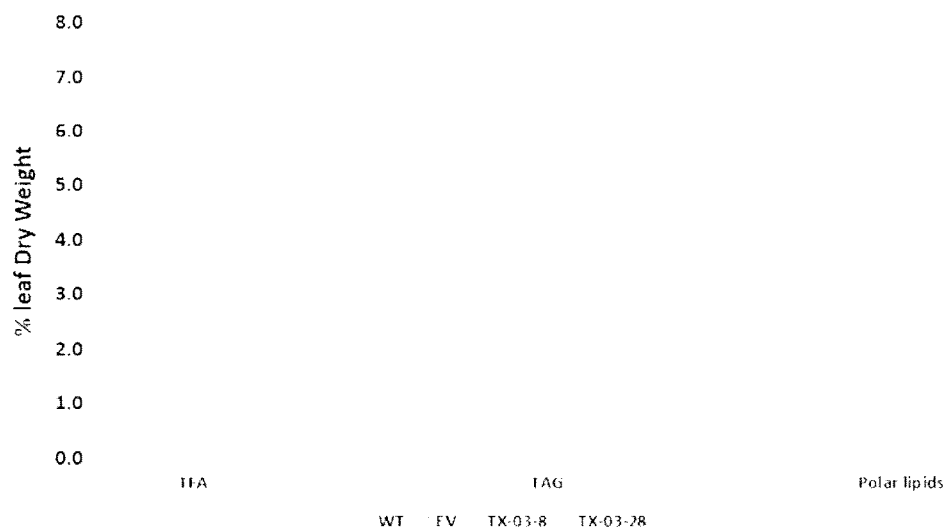
Figure 13:
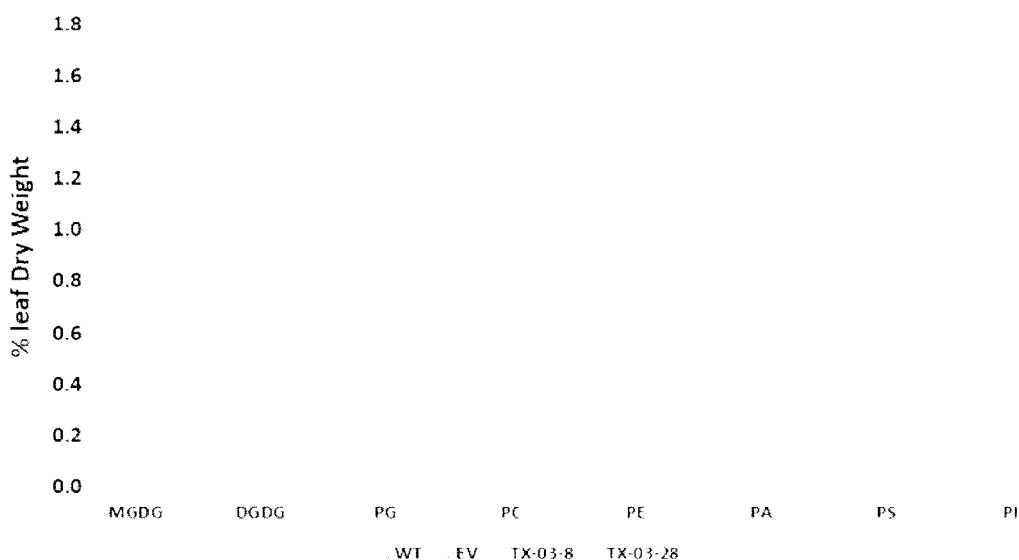

FIG. 13. A. Lipid levels in sorghum leaves transformed with a combination of the genetic constructs pOIL103 and pOIL197, at the vegetative stage of growth. The levels (weight % of dry weight) of TFA, TAG and polar lipids are shown. Each set of 4 bars show, in order, the levels in leaves from wild-type plants (WT, blue), empty vector control plants (EV, orange) and transgenic plants TX-03-8 (grey) and TX-03-38 (yellow). B. Levels of the galactolipids MGDG and DGDG and of the phospholipids PG, PC, PE, PA, PS and PI in the leaves as for A.

Figure 14:
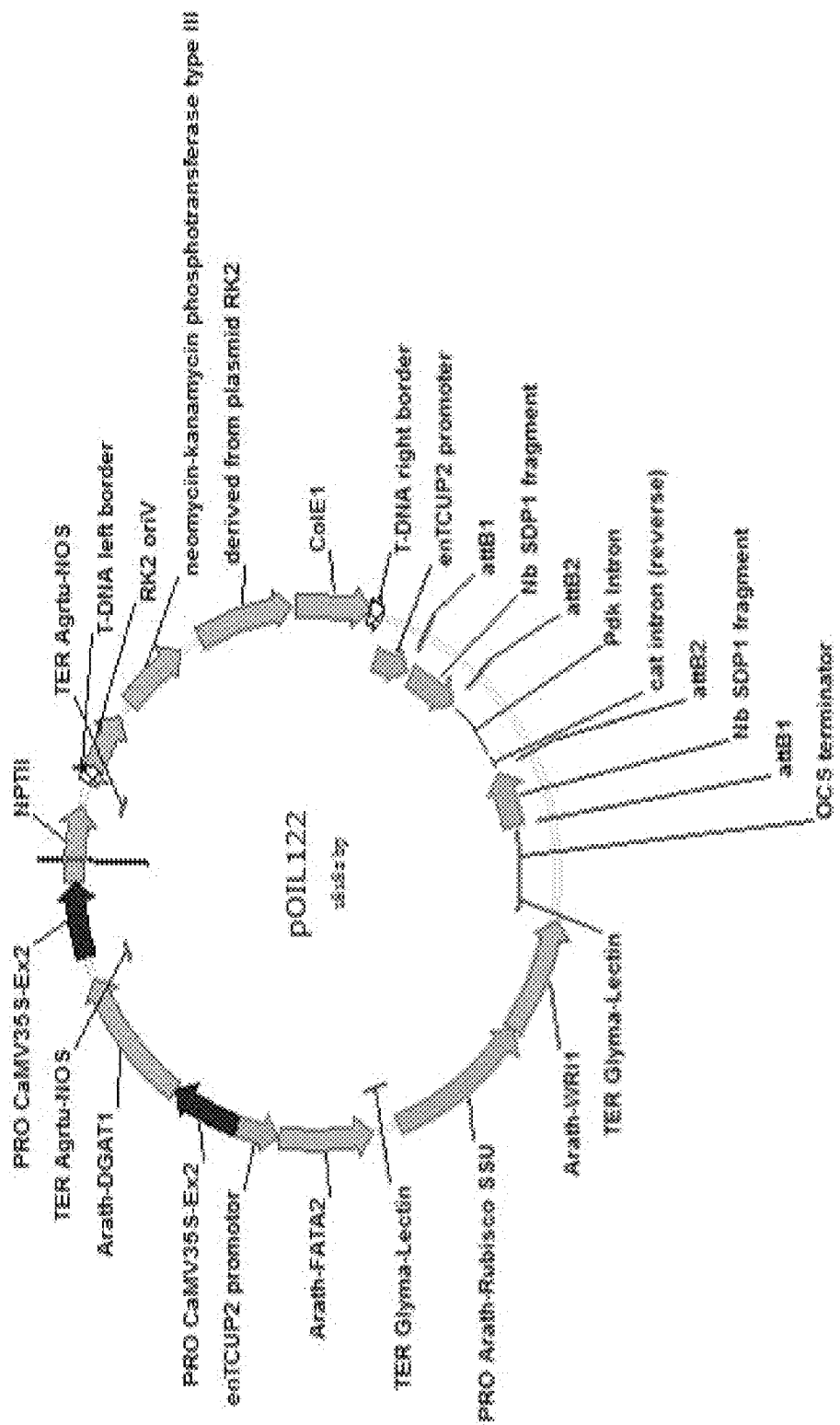

FIG. 14. Schematic diagram of vector pOIL122. Abbreviations: TER Agrtu-Nos, *Agrobacterium tumefaciens* nopaline synthase terminator; NPTII, neomycin phosphotransferase protein coding region; PRO CaMV35S-Ex2, Cauliflower Mosaic Virus 35S promoter with double enhancer region; Arath-DGAT1, *Arabidopsis thaliana* DGAT1 acyltransferase protein coding region; PRO Arath-Rubisco SSU, *A. thaliana* Rubisco small subunit promoter; Arath-FATA2, *A. thaliana* FATA2 thioesterase protein coding region; Arath-WRI, *A. thaliana* WRI1 transcription factor protein coding region; TER Glyma-Lectin, *Glycine max* lectin terminator; enTCUP2 promoter, *Nicotiana tabacum* cryptic constitutive promoter; attB1 and attB2, Gateway recombination sites; NB SDP1 fragment, *Nicotiana benthamiana* SDP1 region targeted for hpRNAi silencing; OCS terminator, *A. tumefaciens* octopine synthase terminator. Backbone features outside the T-DNA region are derived from pORE04 (Coutu et al., 2007).

Figure 15:
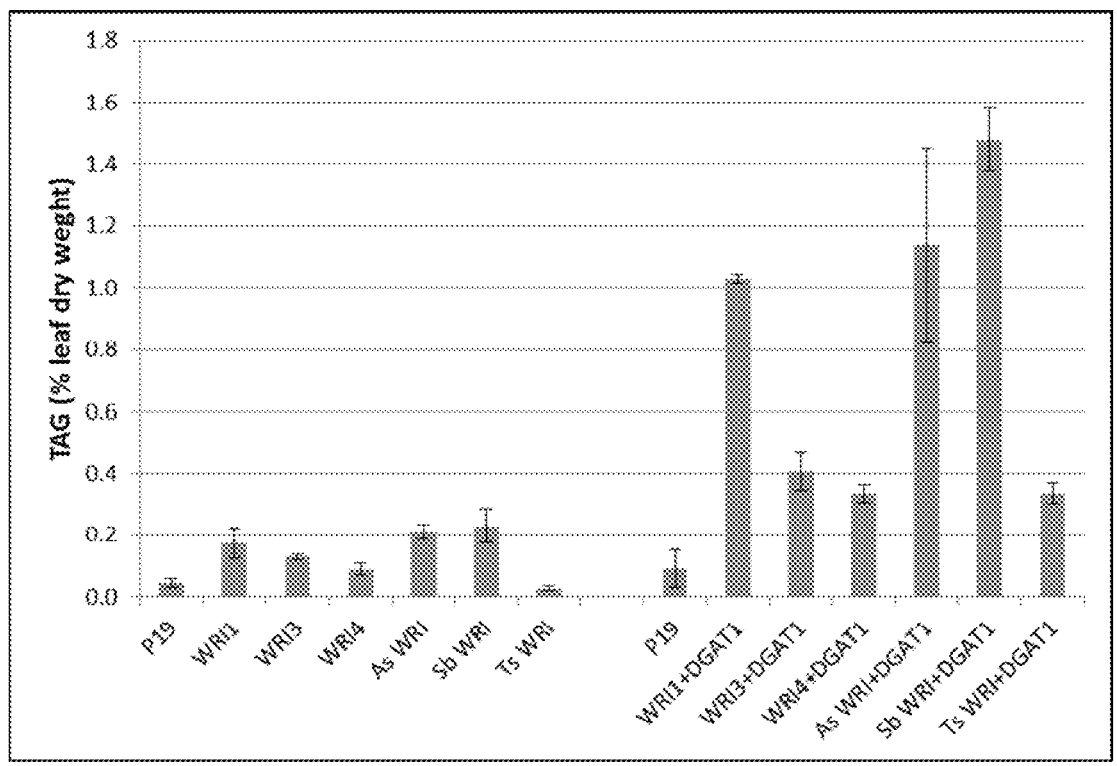

FIG. 15. TAG levels (% leaf dry weight) in *N. benthamiana* leaf tissue, infiltrated with genes encoding different WRI1 polypeptides either with (right hand bars) or without (left hand bars) co-expression of DGAT1 (n=3). All samples were infiltrated with the P19 construct as well.

Figure 16:
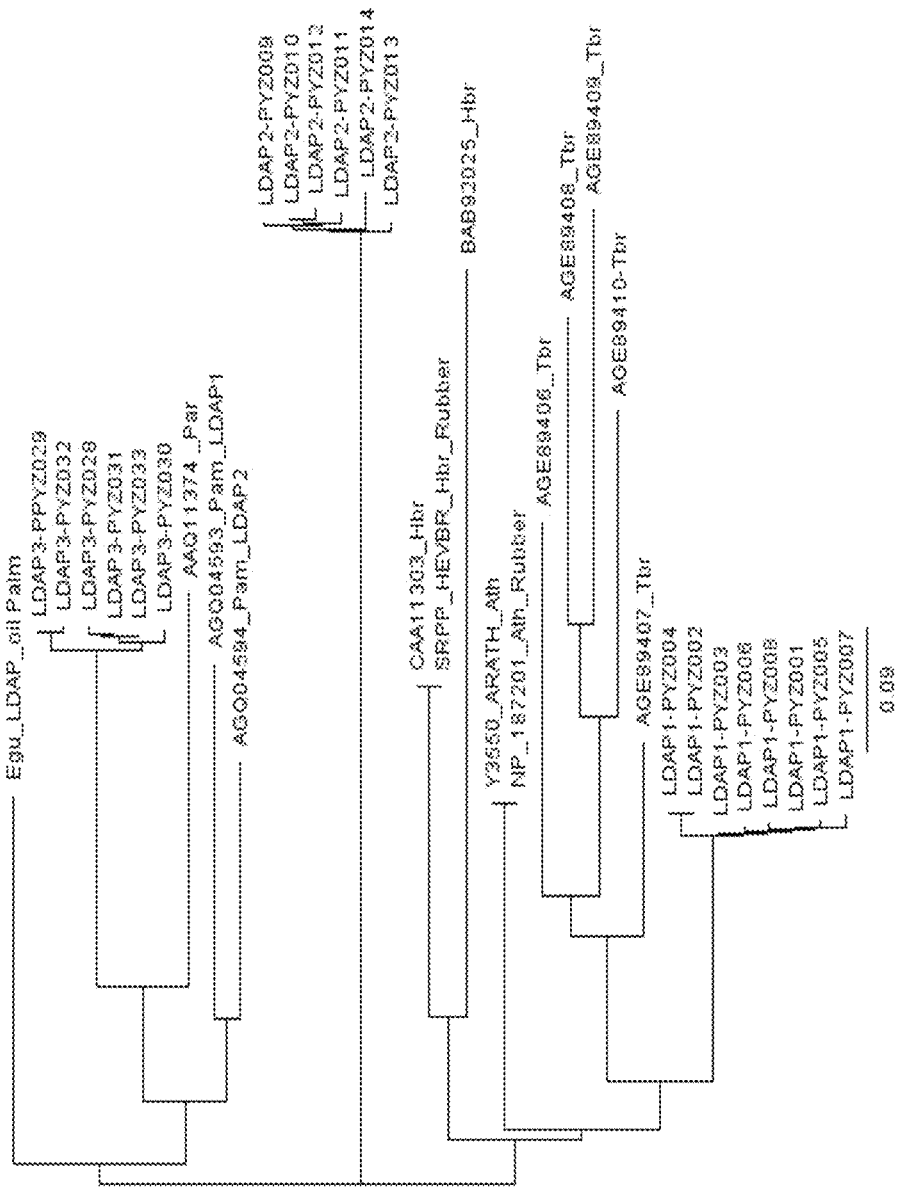

FIG. 16. Phylogenetic tree of LDAP polypeptides (Example 11).

Figure 17:
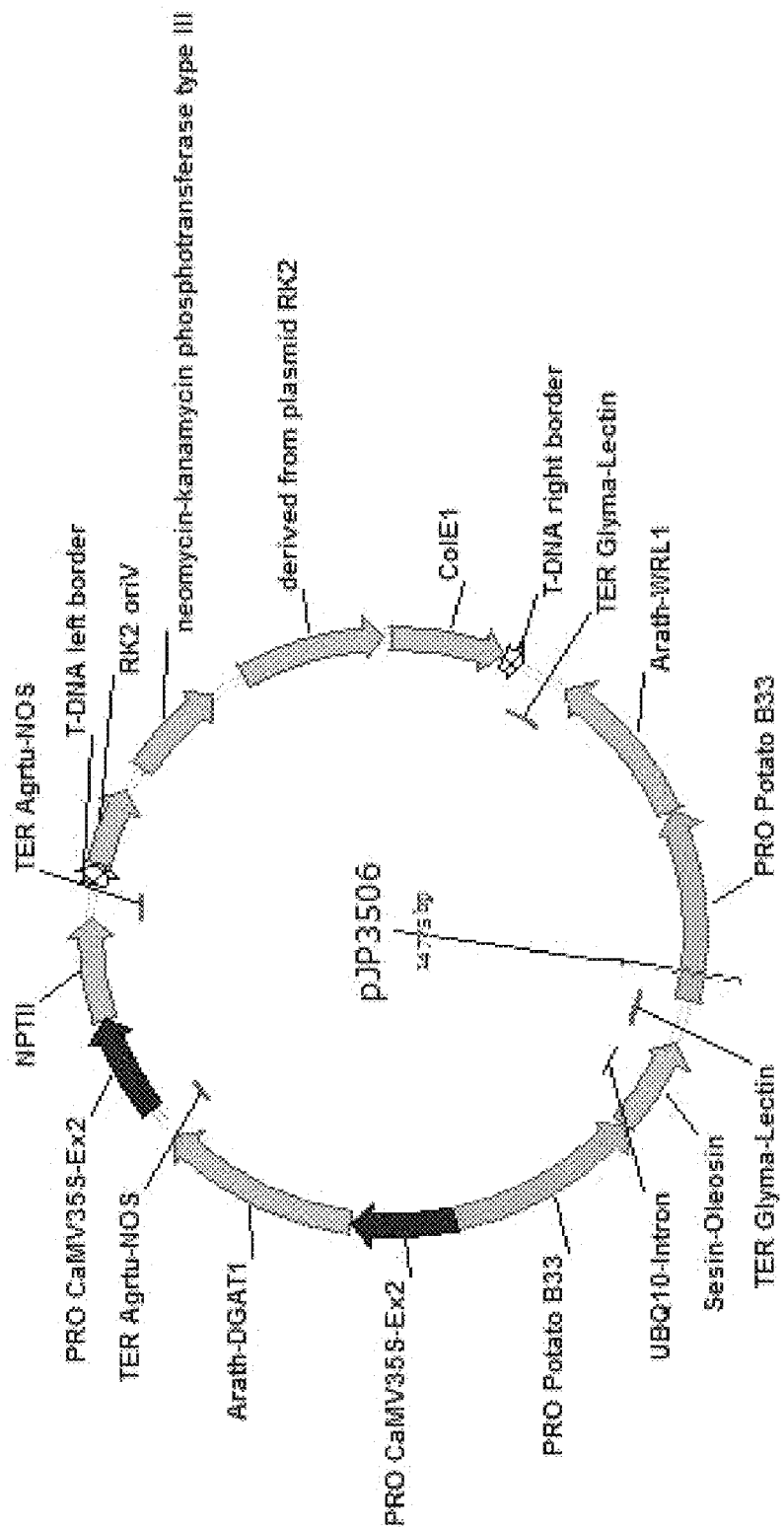

FIG. 17. Schematic representation of the genetic construct pJP3506 including the T-DNA region between the left and right borders. Abbreviations are as for FIG. 12 and: Sesin-Oleosin, *Sesame indicum* oleosin protein coding region.

Figure 18:
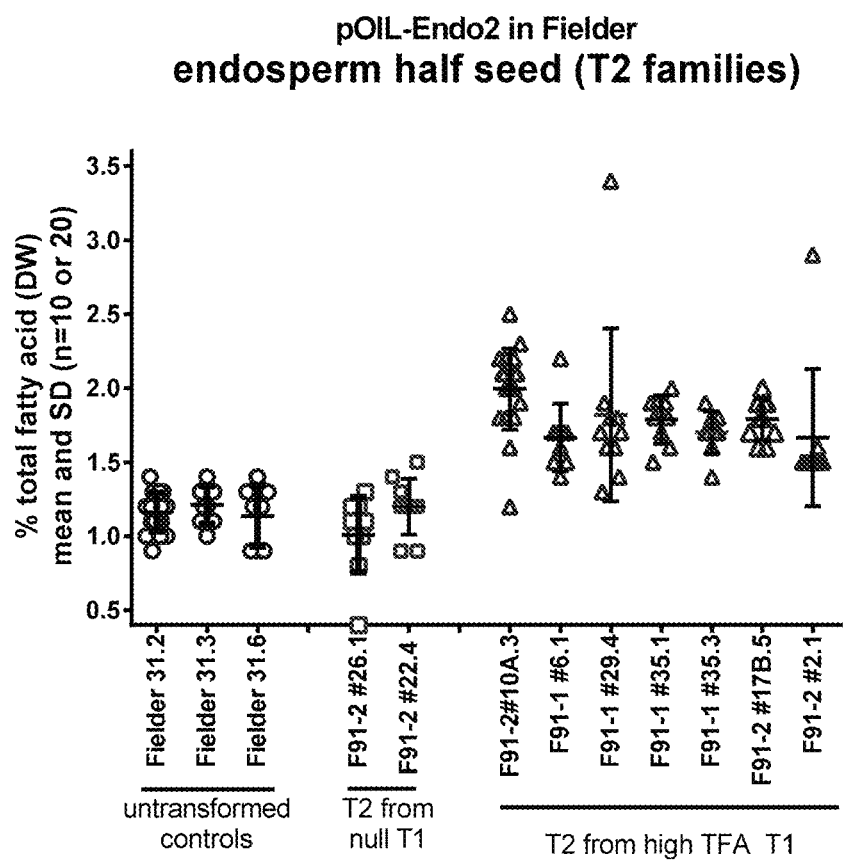

FIG. 18. Fatty acid content of transgenic wheat seed.

Figure 19:
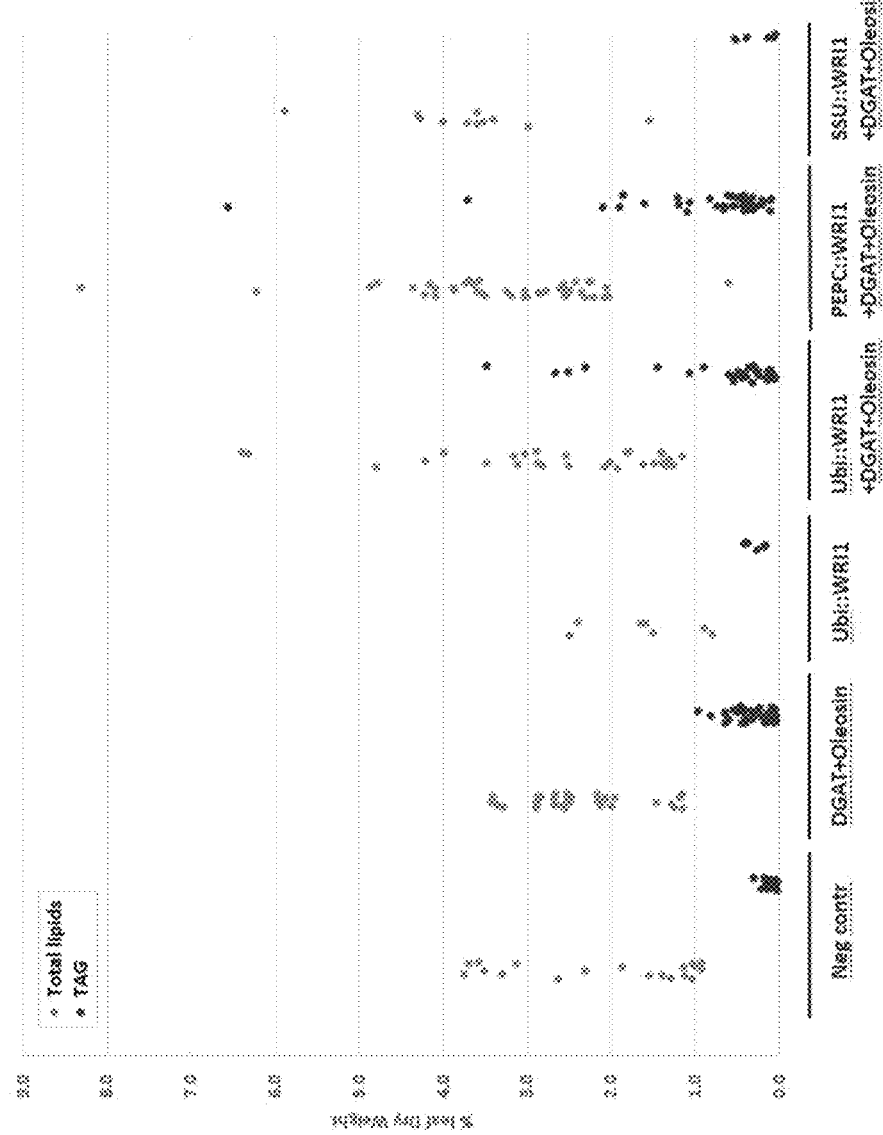

FIG. 19. Levels of TFA and TAG (weight % of leaf dry weight) in leaves of sorghum plants at the boot leaf stage of growth, for wild-type plants (Neg contr), plants transformed with a genetic construct to express DGAT and Oleosin (DGAT+Oleosin), plants transformed with a genetic construct to express WRI expressed from a Ubi promoter (Ubi::WRI1), plants transformed with genetic constructs to express DGAT, Oleosin and WRI expressed from a Ubi promoter (Ubi::WRI1+DGAT+Oleosin), plants transformed with genetic constructs to express DGAT, Oleosin and WRI expressed from a PEPC promoter (PEPC::WRI1+DGAT+Oleosin), plants transformed with genetic constructs to express DGAT, Oleosin and WRI expressed from a SSU promoter (SSU::WRI1+DGAT+Oleosin). Each dot represents the levels seen for an independent transgenic plant. For each plant type, the column of dots on the left (blue) shows TFA levels, and the column of dots on the right (red) shows TAG levels in the same set of plants.

Figure 20:
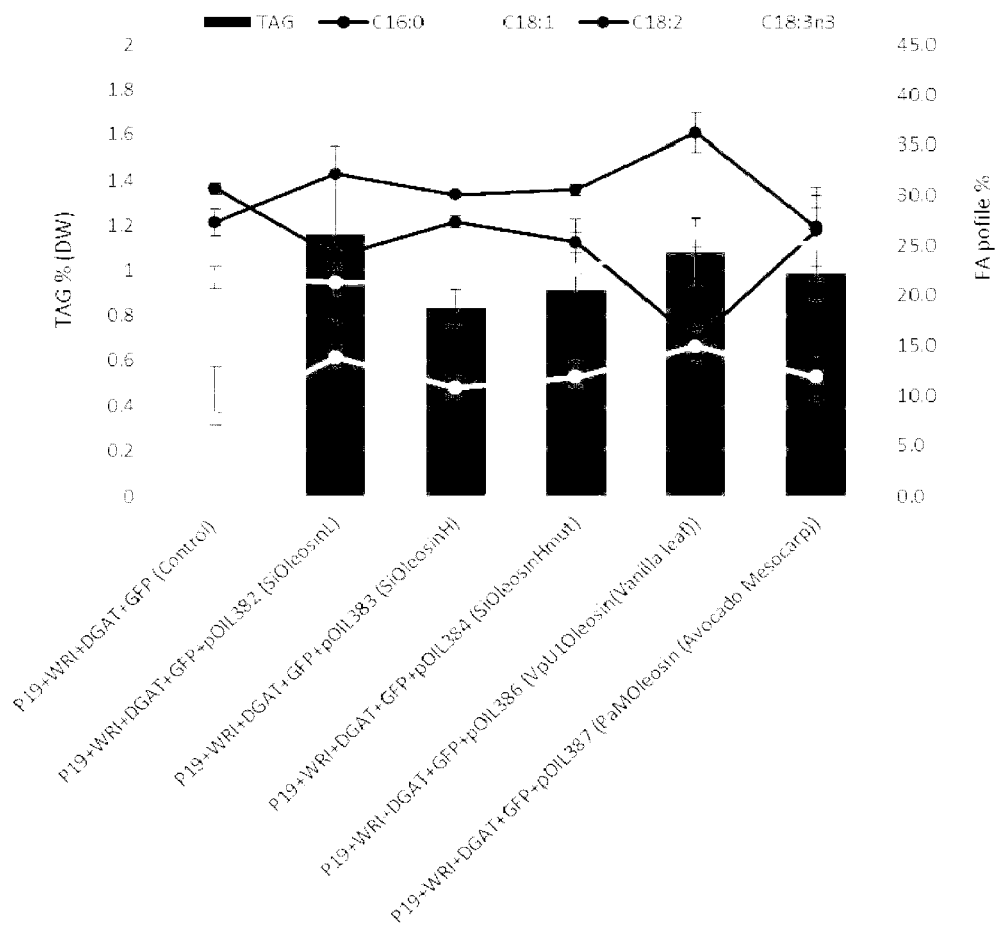

FIG. 20. TAG content and fatty acid composition for selected fatty acids in *N. benthamiana* leaf tissues after introduction of genes encoding WRI1, DGAT1 and an oil body polypeptide (pOIL382-387).

| KEY TO THE SEQUENCE LISTING | |
|---|---|
| SEQ ID NO: 1 | *Arabidopsis thaliana* DGAT1 polypeptide (CAB44774.1) |
| SEQ ID NO: 2 | *Arabidopsis thaliana* DGAT2 polypeptide (NP_566952.1) |
| SEQ ID NO: 3 | *Ricinus communis* DGAT2 polypeptide (AAY16324.1) |
| SEQ ID NO: 4 | *Vernicia fordii* DGAT2 polypeptide (ABC94474.1) |
| SEQ ID NO: 5 | *Mortierella ramanniana* DGAT2 polypeptide (AAK84179.1) |
| SEQ ID NO: 6 | *Homo sapiens* DGAT2 polypeptide (Q96PD7.2) |
| SEQ ID NO: 7 | *Homo sapiens* DGAT2 polypeptide (Q58HT5.1) |
| SEQ ID NO: 8 | *Bos taurus* DGAT2 polypeptide (Q70VZ8.1) |
| SEQ ID NO: 9 | *Mus musculus* DGAT2 polypeptide (AAK84175.1) |
| SEQ ID NO: 10 | YFP tripeptide—conserved DGAT2 and/or MGAT1/2 sequence motif |
| SEQ ID NO: 11 | HPHG tetrapeptide—conserved DGAT2 and/or MGAT1/2 sequence motif |
| SEQ ID NO: 12 | EPHS tetrapeptide—conserved plant DGAT2 sequence motif |
| SEQ ID NO: 13 | RXGFX(K/R)XAXXXGXXX(L/V)VPXXXFG(E/Q)—long conserved sequence motif of DGAT2 which is part of the putative glycerol phospholipid domain |
| SEQ ID NO: 14 | FLXLXXXN—conserved sequence motif of mouse DGAT2 and MGAT1/2 which is a putative neutral lipid binding domain |
| SEQ ID NO: 15 | plsC acyltransferase domain (PF01553) of GPAT |
| SEQ ID NO: 16 | HAD-like hydrolase (PF12710) superfamily domain of GPAT |
| SEQ ID NO: 17 | Phosphoserine phosphatase domain (PF00702). GPAT4-8 contain a N-terminal region homologous to this domain |
| SEQ ID NO: 18 | Conserved GPAT amino acid sequence GDLVICPEGTTCREP |
| SEQ ID NO: 19 | Conserved GPAT/phosphatase amino acid sequence (Motif I) |
| SEQ ID NO: 20 | Conserved GPAT/phosphatase amino acid sequence (Motif III) |

-continued

| KEY TO THE SEQUENCE LISTING | |
|---|---|
| SEQ ID NO: 21 | *Arabidopsis thaliana* WRI1 polypeptide (A8MS57) |
| SEQ ID NO: 22 | *Arabidopsis thaliana* WRI1 polypeptide (Q6X5Y6) |
| SEQ ID NO: 23 | *Arabidopsis lyrata* subsp. *lyrata* WRI1 polypeptide (XP_002876251.1) |
| SEQ ID NO: 24 | *Brassica napus* WRI1 polypepetide (ABD16282.1) |
| SEQ ID NO: 25 | *Brassica napus* WRI1 polyppetide (ADO16346.1) |
| SEQ ID NO: 26 | *Glycine max* WRI1 polypeptide (XP_003530370.1) |
| SEQ ID NO: 27 | *Jatropha curcas* WRI1 polypeptide (AEO22131.1) |
| SEQ ID NO: 28 | *Ricinus communis* WRI1 polypeptide (XP_002525305.1) |
| SEQ ID NO: 29 | *Populus trichocarpa* WRI1 polypeptide (XP_002316459.1) |
| SEQ ID NO: 30 | *Vitis vinifera* WRI1 polypeptide (CBI29147.3) |
| SEQ ID NO: 31 | *Brachypodium distachyon* WRI1 polypeptide (XP_003578997.1) |
| SEQ ID NO: 32 | *Hordeum vulgare* subsp. *vulgare* WRI1 polypeptide (BAJ86627.1) |
| SEQ ID NO: 33 | *Oryza sativa* WRI1 polypeptide (EAY79792.1) |
| SEQ ID NO: 34 | *Sorghum bicolor* WRI1 polypeptide (XP_002450194.1) |
| SEQ ID NO: 35 | *Zea mays* WRI1 polypeptide (ACG32367.1) |
| SEQ ID NO: 36 | *Brachypodium distachyon* WRI1 polypeptide (XP_003561189.1) |
| SEQ ID NO: 37 | *Brachypodium sylvaticum* WRI1 polypeptide (ABL85061.1) |
| SEQ ID NO: 38 | *Oryza sativa* WRI1 polypeptide (BAD68417.1) |
| SEQ ID NO: 39 | *Sorghum bicolor* WRI1 polypeptide (XP_002437819.1) |
| SEQ ID NO: 40 | *Sorghum bicolor* WRI1 polypeptide (XP_002441444.1) |
| SEQ ID NO: 41 | *Glycine max* WRI1 polypeptide (XP_003530686.1) |
| SEQ ID NO: 42 | *Glycine max* WRI1 polypeptide (XP_003553203.1) |
| SEQ ID NO: 43 | *Populus trichocarpa* WRI1 polypeptide (XP_002315794.1) |
| SEQ ID NO: 44 | *Vitis vinifera* WRI1 polypeptide (XP_002270149.1) |
| SEQ ID NO: 45 | *Glycine max* WRI1 polypeptide (XP_003533548.1) |
| SEQ ID NO: 46 | *Glycine max* WRI1 polypeptide (XP_003551723.1) |
| SEQ ID NO: 47 | *Medicago truncatula* WRI1 polypeptide (XP_003621117.1) |
| SEQ ID NO: 48 | *Populus trichocarpa* WRI1 polypeptide (XP_002323836.1) |
| SEQ ID NO: 49 | *Ricinus communis* WRI1 polypeptide (XP_002517474.1) |
| SEQ ID NO: 50 | *Vitis vinifera* WRI1 polypeptide (CAN79925.1) |
| SEQ ID NO: 51 | *Brachypodium distachyon* WRI1 polypeptide (XP_003572236.1) |
| SEQ ID NO: 52 | *Oryza sativa* WRI1 polypeptide (BAD10030.1) |
| SEQ ID NO: 53 | *Sorghum bicolor* WRI1 polypeptide (XP_002444429.1) |
| SEQ ID NO: 54 | *Zea mays* WRI1 polypeptide (NP_001170359.1) |
| SEQ ID NO: 55 | *Arabidopsis lyrata* subsp. *lyrata* WRI1 polypeptide (XP_002889265.1) |
| SEQ ID NO: 56 | *Arabidopsis thaliana* WRI1 polypeptide (AAF68121.1) |
| SEQ ID NO: 57 | *Arabidopsis thaliana* WRI1 polypeptide (NP_178088.2) |
| SEQ ID NO: 58 | *Arabidopsis lyrata* subsp. *lyrata* WRI1 polypeptide (XP_002890145.1) |
| SEQ ID NO: 59 | *Thellungiella halophila* WRI1 polypeptide (BAJ33872.1) |

-continued

| KEY TO THE SEQUENCE LISTING | |
|---|---|
| SEQ ID NO: 60 | *Arabidopsis thaliana* WRI1 polypeptide (NP_563990.1) |
| SEQ ID NO: 61 | *Glycine max* WRI1 polypeptide (XP_003530350.1) |
| SEQ ID NO: 62 | *Brachypodium distachyon* WRI1 polypeptide (XP_003578142.1) |
| SEQ ID NO: 63 | *Oryza sativa* WRI1 polypeptide (EAZ09147.1) |
| SEQ ID NO: 64 | *Sorghum bicolor* WRI1 polypeptide (XP_002460236.1) |
| SEQ ID NO: 65 | *Zea mays* WRI1 polypeptide (NP_001146338.1) |
| SEQ ID NO: 66 | *Glycine max* WRI1 polypeptide (XP_003519167.1) |
| SEQ ID NO: 67 | *Glycine max* WRI1 polypeptide (XP_003550676.1) |
| SEQ ID NO: 68 | *Medicago truncatula* WRI1 polypeptide (XP_003610261.1) |
| SEQ ID NO: 69 | *Glycine max* WRI1 polypeptide (XP_003524030.1) |
| SEQ ID NO: 70 | *Glycine max* WRI1 polypeptide (XP_003525949.1) |
| SEQ ID NO: 71 | *Populus trichocarpa* WRI1 polypeptide (XP_002325111.1) |
| SEQ ID NO: 72 | *Vitis vinifera* WRI1 polypeptide (CBI36586.3) |
| SEQ ID NO: 73 | *Vitis vinifera* WRI1 polypeptide (XP_002273046.2) |
| SEQ ID NO: 74 | *Populus trichocarpa* WRI1 polypeptide (XP_002303866.1) |
| SEQ ID NO: 75 | *Vitis vinifera* WRI1 polypeptide (CBI25261.3) |
| SEQ ID NO: 76 | Sorbi-WRL1 |
| SEQ ID NO: 77 | Lupan-WRL1 |
| SEQ ID NO: 78 | Ricco-WRL1 |
| SEQ ID NO: 79 | *Lupin angustifolius* WRI1 polypeptide |
| SEQ ID NO: 80 | *Aspergillus fumigatus* DGAT1 polypeptide (XP_755172.1) |
| SEQ ID NO: 81 | *Ricinus communis* DGAT1 polypeptide (AAR11479.1) |
| SEQ ID NO: 82 | *Vernicia fordii* DGAT1 polypeptide (ABC94472.1) |
| SEQ ID NO: 83 | *Vernonia galamensis* DGAT1 polypeptide (ABV21945.1) |
| SEQ ID NO: 84 | *Vernonia galamensis* DGAT1 polypeptide (ABV21946.1) |
| SEQ ID NO: 85 | *Euonymus alatus* DGAT1 polypeptide (AAV31083.1) |
| SEQ ID NO: 86 | *Caenorhabditis elegans* DGAT1 polypeptide (AAF82410.1) |
| SEQ ID NO: 87 | *Rattus norvegicus* DGAT1 polypeptide (NP_445889.1) |
| SEQ ID NO: 88 | *Homo sapiens* DGAT1 polypeptide (NP_036211.2) |
| SEQ ID NO: 89 | WRI1 motif (R G V T/S R H R W T G R) |
| SEQ ID NO: 90 | WRI1 motif (F/Y E A H L W D K) |
| SEQ ID NO: 91 | WRI1 motif (D L A A L K Y W G) |
| SEQ ID NO: 92 | WRI1 motif (S X G F S/A R G X) |
| SEQ ID NO: 93 | WRI1 motif (H H H/Q N G R/K W E A R I G R/K V) |
| SEQ ID NO: 94 | WRI1 motif (Q E E A A A X Y D) |
| SEQ ID NO: 95 | *Brassica napus* oleosin polypeptide (CAA57545.1) |
| SEQ ID NO: 96 | *Brassica napus* oleosin S1-1 polypeptide (ACG69504.1) |
| SEQ ID NO: 97 | *Brassica napus* oleosin S2-1 polypeptide (ACG69503.1) |

| KEY TO THE SEQUENCE LISTING | |
|---|---|
| SEQ ID NO: 98 | *Brassica napus* oleosin S3-1 polypeptide (ACG69513.1) |
| SEQ ID NO: 99 | *Brassica napus* oleosin S4-1 polypeptide (ACG69507.1) |
| SEQ ID NO: 100 | *Brassica napus* oleosin S5-1 polypeptide (ACG69511.1) |
| SEQ ID NO: 101 | *Arachis hypogaea* oleosin 1 polypeptide (AAZ20276.1) |
| SEQ ID NO: 102 | *Arachis hypogaea* oleosin 2 polypeptide (AAU21500.1) |
| SEQ ID NO: 103 | *Arachis hypogaea* oleosin 3 polypeptide (AAU21501.1) |
| SEQ ID NO: 104 | *Arachis hypogaea* oleosin 5 polypeptide (ABC96763.1) |
| SEQ ID NO: 105 | *Ricinus communis* oleosin 1 polypeptide (EEF40948.1) |
| SEQ ID NO: 106 | *Ricinus communis* oleosin 2 polypeptide (EEF51616.1) |
| SEQ ID NO: 107 | *Glycine max* oleosin isoform a polypeptide (P29530.2) |
| SEQ ID NO: 108 | *Glycine max* oleosin isoform b polypeptide (P29531.1) |
| SEQ ID NO: 109 | *Linum usitatissimum* oleosin low molecular weight isoform polypeptide (ABB01622.1) |
| SEQ ID NO: 110 | amino acid sequence of *Linum usitatissimum* oleosin high molecular weight isoform polypeptide (ABB01624.1) |
| SEQ ID NO: 111 | *Helianthus annuus* oleosin polypeptide (CAA44224.1) |
| SEQ ID NO: 112 | *Zea mays* oleosin polypeptide (NP_001105338.1) |
| SEQ ID NO: 113 | *Brassica napus* steroleosin polypeptide (ABM30178.1) |
| SEQ ID NO: 114 | *Brassica napus* steroleosin SLO1-1 polypeptide (ACG69522.1) |
| SEQ ID NO: 115 | *Brassica napus* steroleosin SLO2-1 polypeptide (ACG69525.1) |
| SEQ ID NO: 116 | *Sesamum indicum* steroleosin polypeptide (AAL13315.1) |
| SEQ ID NO: 117 | *Zea mays* steroleosin polypeptide (NP_001152614.1) |
| SEQ ID NO: 118 | *Brassica napus* caleosin CLO-1 polypeptide (ACG69529.1) |
| SEQ ID NO: 119 | *Brassica napus* caleosin CLO-3 polypeptide (ACG69527.1) |
| SEQ ID NO: 120 | *Sesamum indicum* caleosin polypeptide (AAF13743.1) |
| SEQ ID NO: 121 | *Zea mays* caleosin polypeptide (NP_001151906.1) |
| SEQ ID NO: 122 | pJP3502 TDNA (inserted into genome) sequence |
| SEQ ID NO: 123 | pJP3507 vector sequence |
| SEQ ID NO: 124 | Linker sequence |
| SEQ ID NO: 125 | Partial *Nicotiana benthamiana* CGI-58 sequence selected for hpRNAi silencing (pTV46) |
| SEQ ID NO: 126 | Partial *N. tabacum* AGPase sequence selected for hpRNAi silencing (pTV35) |
| SEQ ID NO: 127 | GXSXG lipase motif |
| SEQ ID NO: 128 | HX(4)D acyltransferase motif |
| SEQ ID NO: 129 | VX(3)HGF probable lipid binding motif |
| SEQ ID NO: 130 | *Arabidopsis thaliana* CGi58 polynucleotide (NM_118548.1) |
| SEQ ID NO: 131 | *Brachypodium distachyon* CGi58 polynucleotide (XM_003578402.1) |
| SEQ ID NO: 132 | *Glycine max* CGi58 polynucleotide (XM_003523590.1) |
| SEQ ID NO: 133 | *Zea mays* CGi58 polynucleotide (NM_001155541.1) |
| SEQ ID NO: 134 | *Sorghum bicolor* CGi58 polynucleotide (XM_002460493.1) |

| KEY TO THE SEQUENCE LISTING |  |
|---|---|
| SEQ ID NO: 135 | *Ricinus communis* CGi58 polynucleotide (XM_002510439.1) |
| SEQ ID NO: 136 | *Medicago truncatula* CGi58 polynucleotide (XM_003603685.1) |
| SEQ ID NO: 137 | *Arabidopsis thaliana* LEC2 polynucleotide (NM_102595.2) |
| SEQ ID NO: 138 | *Medicago truncatula* LEC2 polynucelotide (X60387.1) |
| SEQ ID NO: 139 | *Brassica napus* LEC2 polynucelotide (HM370539.1) |
| SEQ ID NO: 140 | *Arabidopsis thaliana* BBM polynucleotide (NM_121749.2) |
| SEQ ID NO: 141 | *Medicago truncatula* BBM polynucleotide (AY899909.1) |
| SEQ ID NO: 142 | *Arabidopsis thaliana* LEC2 polypeptide (NP_564304.1) |
| SEQ ID NO: 143 | *Medicago truncatula* LEC2 polypeptide (CAA42938.1) |
| SEQ ID NO: 144 | *Brassica napus* LEC2 polypeptide (ADO16343.1) |
| SEQ ID NO: 145 | *Arabidopsis thaliana* BBM polypeptide (NP_197245.2) |
| SEQ ID NO: 146 | *Medicago truncatula* BBM polypeptide (AAW82334.1) |
| SEQ ID NO: 147 | Inducible *Aspergilus niger* alcA promoter |
| SEQ ID NO: 148 | AlcR inducer that activates the AlcA promotor in the presence of ethanol |
| SEQ ID NO: 149 | *Arabidopsis thaliana* LEC1; (AAC39488) |
| SEQ ID NO: 150 | *Arabidopsis lyrata* LEC1 (XP_002862657) |
| SEQ ID NO: 151 | *Brassica napus* LEC1 (ADF81045) |
| SEQ ID NO: 152 | *Ricinus communis* LEC1 (XP_002522740) |
| SEQ ID NO: 153 | *Glycine max* LEC1 (XP_006582823) |
| SEQ ID NO: 154 | *Medicago truncatula* LEC1 (AFK49653) |
| SEQ ID NO: 155 | *Zea mays* LEC1 (AAK95562) |
| SEQ ID NO: 156 | *Arachis hypogaea* LEC1 (ADC33213) |
| SEQ ID NO: 157 | *Arabidopsis thaliana* LEC1-like (AAN15924) |
| SEQ ID NO: 158 | *Brassica napus* LEC1-like (AHI94922) |
| SEQ ID NO: 159 | *Phaseolus coccineus* LEC1-like (AAN01148) |
| SEQ ID NO: 160 | *Arabidopsis thaliana* FUS3 (AAC35247) |
| SEQ ID NO: 161 | *Brassica napus* FUS3 |
| SEQ ID NO: 162 | *Medicago truncatula* FUS3 |
| SEQ ID NO: 163 | *Arabidopsis thaliana* SDP1 cDNA sequence, Accession No. NM_120486, 3275nt |
| SEQ ID NO: 164 | *Brassica napus* SDP1 cDNA; Accession No. GN078290 |
| SEQ ID NO: 165 | *Brachypodium distachyon* SDP1 cDNA, 2670nt |
| SEQ ID NO: 166 | *Populus trichocarpa* SDP1 cDNA, 3884nt |
| SEQ ID NO: 167 | *Medicago truncatula* SDP1 cDNA; XM_003591377; 2490nt |
| SEQ ID NO: 168 | *Glycine max* SDP1 cDNA XM_003521103; 2783nt |
| SEQ ID NO: 169 | *Sorghum bicolor* SDP1 cDNA XM_002458486; 2724nt |
| SEQ ID NO: 170 | *Zea mays* SDP1 cDNA, NM_001175206; 2985nt |
| SEQ ID NO: 171 | *Physcomitrella patens* SDP1 cDNA, XM_001758117; 1998nt |
| SEQ ID NO: 172 | *Hordeum vulgare* SDP1 cDNA, AK372092; 3439nt |
| SEQ ID NO: 173 | *Nicotiana benthamiana* SDP1 cDNA, Nbv5tr6404201 |

KEY TO THE SEQUENCE LISTING

| | |
|---|---|
| SEQ ID NO: 174 | *Nicotiana benthamiana* SDP1 cDNA region targeted for hpRNAi silencing |
| SEQ ID NO: 175 | Promoter of *Arabidopsis thaliana* SDP1 gene, 1.5kb |
| SEQ ID NO: 176 | Nucleotide sequence of the complement of the pSSU-Oleosin gene in the T-DNA of pJP3502. In order (complementary sequences): *Glycine max* Lectin terminator 348nt, 3' exon 255nt, UBQ10 intron 304nt, 5' exon 213nt, SSU promoter 1751nt |
| SEQ ID NO: 177 | *Arabidopsis thaliana* plastidial GPAT cDNA, NM_179407 |
| SEQ ID NO: 178 | *Arabidopsis thaliana* plastidial GPAT polypeptide, NM_179407 |
| SEQ ID NO: 179 | *Populus trichocarpa* plastidial GPAT cDNA, XP_006368351 |
| SEQ ID NO: 180 | *Jatropha curcas* plastidial GPAT cDNA, ACR61638 |
| SEQ ID NO: 181 | *Ricinus communis* plastidial GPAT cDNA, XP_002518993 |
| SEQ ID NO: 182 | *Helianthus annuus* plastidial GPAT cDNA, ADV16382 |
| SEQ ID NO: 183 | *Medicago truncatula* plastidial GPAT cDNA, XP_003612801 |
| SEQ ID NO: 184 | *Glycine max* plastidial GPAT cDNA, XP_003516958 |
| SEQ ID NO: 185 | *Carthamus tinctorius* plastidial GPAT cDNA, CAHG3PACTR |
| SEQ ID NO: 186 | *Solanum tuberosum* plastidial GPAT cDNA, XP_006352898 |
| SEQ ID NO: 187 | *Oryza sativa* Japonica plastidial GPAT cDNA, NM_001072027 |
| SEQ ID NO: 188 | *Sorghum bicolor* plastidial GPAT cDNA, XM_002467381 |
| SEQ ID NO: 189 | *Zea mays* plastidial GPAT cDNA, NM_001158637 |
| SEQ ID NO: 190 | *Hordeum vulgare* plastidial GPAT cDNA, AK371419 |
| SEQ ID NO: 191 | *Physcomitrella patens* plastidial GPAT cDNA, XM_001771247 |
| SEQ ID NO: 192 | *Chlamydomonas reinhardtii* plastidial GPAT cDNA, XM_001694925 |
| SEQ ID NO: 193 | *Arabidopsis thaliana* FATA1 |
| SEQ ID NO: 194 | *Arabidopsis thaliana* FATA2 |
| SEQ ID NO: 195 | *Arabidopsis thaliana* FATB |
| SEQ ID NO: 196 | *Arabidopsis thaliana* WRI3 |
| SEQ ID NO: 197 | *Arabidopsis thaliana* WRI4 |
| SEQ ID NO: 198 | *Avena sativa* WRI1 |
| SEQ ID NO: 199 | *Sorghum bicolor* WRI1 |
| SEQ ID NO: 200 | *Zea mays* WRI1 |
| SEQ ID NO: 201 | *Triadica sebifera* WRI1 |
| SEQ ID NO: 202 | *S. tuberosum* Patatin B33 promoter sequence |
| SEQ ID NOs 203 to 206 and 236 to 245 | Oligonucleotide primers |
| SEQ ID NO: 207 | *Z. mays* SEE1 promoter region (1970nt from Accession number AJ494982) |
| SEQ ID NO: 208 | *A. littoralis* AlSAP promoter sequence, Accession No DQ885219 |
| SEQ ID NO: 209 | *A. rhizogenes* ArRolC promoter sequence, Accession No. DQ160187 |
| SEQ ID NO: 210 | hpRNAi construct containing a 732bp fragment of *N. benthamiana* plastidial GPAT |
| SEQ ID NO: 211 | *Elaeis guineensis* (oil palm) DGAT1 |

| KEY TO THE SEQUENCE LISTING | |
|---|---|
| SEQ ID NO: 212 | *G. max* MYB73, Accession No. ABH02868 |
| SEQ ID NO: 213 | *A. thaliana* bZIP53, Accession No. AAM14360 |
| SEQ ID NO: 214 | *A. thaliana* AGL15, Accession No NP_196883 |
| SEQ ID NO: 215 | *A. thaliana* MYB118, Accession No. AAS58517 |
| SEQ ID NO: 216 | *A. thaliana* MYB115, Accession No. AAS10103 |
| SEQ ID NO: 217 | *A. thaliana* TANMEI, Accession No. BAE44475 |
| SEQ ID NO: 218 | *A. thaliana* WUS, Accession No. NP_565429 |
| SEQ ID NO: 219 | *B. napus* GFR2a1, Accession No. AFB74090 |
| SEQ ID NO: 220 | *B. napus* GFR2a2, Accession No. AFB74089 |
| SEQ ID NO: 221 | *A. thaliana* PHR1, Accession No. AAN72198 |
| SEQ ID NO: 222 | *N. benthamiana* TGD1 fragment |
| SEQ ID NO: 223 | Potato SDP1 amino acid |
| SEQ ID NO: 224 | Potato SDP1 nucleotide sequence |
| SEQ ID NO: 225 | Potato AGPase small subunit |
| SEQ ID NO: 226 | Potato AGPase small subunit nucleotide sequence: |
| SEQ ID NO: 227 | *Sapium sebiferum* LDAP-1 nucleotide sequence |
| SEQ ID NO: 228 | *Sapium sebiferum* LDAP-1 amino acid sequence |
| SEQ ID NO: 229 | *Sapium sebiferum* LDAP-2 nucleotide sequence |
| SEQ ID NO: 230 | *Sapium sebiferum* LDAP-2 amino acid sequence |
| SEQ ID NO: 231 | *Sapium sebiferum* LDAP-3 nucleotide sequence |
| SEQ ID NO: 232 | *Sapium sebiferum* LDAP-3 amino acid sequence |
| SEQ ID NO: 233 | *S. bicolor* SDP1 (accession number XM_002463620) |
| SEQ ID NO: 234 | *T. aestivum* SDP1 nucleotide sequence (Accession number AK334547) |
| SEQ ID NO: 235 | *S. bicolor* SDP1 hpRNAi fragment. |
| SEQ ID NO: 246 | *Saccharum* hybrid DIRIGENT (DIR16) promoter sequence |
| SEQ ID NO: 247 | *Saccharum* hybrid O-Methyl transferase (OMT) promoter sequence |
| SEQ ID NO: 248 | Sequence of the A1 promoter allele of the *Saccharum* hybrid R1MYB1 gene |
| SEQ ID NO: 249 | *Saccharum* hybrid Loading Stem Gene 5 (LSG5) promoter sequence |
| SEQ ID NO: 250 | Nucleotide sequence of the protein coding region of the cDNA for *Sorghum bicolor* TGD5 gene, Accession No. XM_002442154; 297nt |
| SEQ ID NO: 251 | Amino acid sequence of *Sorghum bicolor* TGD5 polypeptide, Accession No. XM_002442154; 98aa |
| SEQ ID NO: 252 | Nucleotide sequence of the protein coding region of the cDNA for *Zea mays* TGD5 gene, Accession No. EU972796.1; 297nt |
| SEQ ID NO: 253 | Amino acid sequence of *Zea mays* TGD5 polypeptide, Accession No. EU972796.1; 98aa |
| SEQ ID NO: 254 | Nucleotide sequence of the protein coding region of the cDNA for *Sorghum bicolor* gene encoding AGPase small subunit (Accession No. XM_002462095.1); 1533nt |
| SEQ ID NO: 255 | Amino acid sequence of *Sorghum bicolor* AGPase small subunit polypeptide (Accession No. XM_002462095.1); 510aa |

| KEY TO THE SEQUENCE LISTING | |
|---|---|
| SEQ ID NO: 256 | Nucleotide sequence of the protein coding region of the cDNA for *Zea mays* gene encoding AGPase small subunit polypeptide (Accession No. XM_008666513.1); 1554nt |
| SEQ ID NO: 257 | Amino acid sequence of *Zea mays* AGPase small subunit polypeptide (Accession No. XM_008666513.1); 517aa |
| SEQ ID NO: 258 | Nucleotide sequence of the protein coding region of the cDNA for *Sorghum bicolor* PDAT1 gene (Accession No. XM_002462417.1); |
| SEQ ID NO: 259 | Amino acid sequence of *Sorghum bicolor* PDAT1 polypeptide (Accession No. XM_002462417.1); 682aa |
| SEQ ID NO: 260 | Nucleotide sequence of the protein coding region of the cDNA for *Zea mays* PDAT1 gene (Accession No. NM_001147943); 2037nt |
| SEQ ID NO: 261 | Amino acid sequence of *Zea mays* PDAT1 polypeptide (Accession No. NM_001147943); 678aa |
| SEQ ID NO: 262 | Nucleotide sequence of the protein coding region of a cDNA for *Sorghum bicolor* PDCT gene (Accession No. XM_002437214); 846nt |
| SEQ ID NO: 263 | Amino acid sequence of a *Sorghum bicolor* PDCT polypeptide (Accession No. XM_002437214); 281aa |
| SEQ ID NO: 264 | Nucleotide sequence of the protein coding region of the cDNA for *Zea mays* PDCT gene (Accession No. EU973573.1); 849nt |
| SEQ ID NO: 265 | Amino acid sequence of *Zea mays* PDCT polypeptide (Accession No. EU973573.1); 282aa |
| SEQ ID NO: 266 | Nucleotide sequence of the protein coding region of the cDNA for *Sorghum bicolor* TST1 gene (Accession No. XM_002467535.1); 2223nt |
| SEQ ID NO: 267 | Amino acid sequence of *Sorghum bicolor* TST1 polypeptide (Accession No. XM_002467535.1); 740aa |
| SEQ ID NO: 268 | Nucleotide sequence of the protein coding region of the cDNA for *Zea mays* TST1 gene (Accession No. NM_001158464); 2244nt |
| SEQ ID NO: 269 | Amino acid sequence of *Zea mays* TST1 polypeptide (Accession No. NM_001158464); 747aa |
| SEQ ID NO: 270 | Nucleotide sequence of the protein coding region of the cDNA for *Sorghum bicolor* TST2 gene (Sb04G008150; Sobic.004G099300; Accession No. KXG29849.1); 2238nt |
| SEQ ID NO: 271 | Amino acid sequence of *Sorghum bicolor* TST2 polypeptide (Accession No. KXG29849.1); 745aa |
| SEQ ID NO: 272 | Nucleotide sequence of the protein coding region of the cDNA for *Zea mays* TST2 gene (Accession No. XM_008647398.1); 2238nt |
| SEQ ID NO: 273 | Amino acid sequence of *Zea mays* TST2 polypeptide (Accession No. XM_008647398.1); 745aa |
| SEQ ID NO: 274 | Nucleotide sequence of the protein coding region of the cDNA for *Sorghum bicolor* INV3 gene (Sobic.004G004800; Sb04g000620; Accession No. XM_002451312); 1464nt |
| SEQ ID NO: 275 | Amino acid sequence of *Sorghum bicolor* INV3 polypeptide (Accession No. XM_002451312); 487aa |
| SEQ ID NO: 276 | Amino acid sequence of *Sorghum bicolor* INV3 polypeptide; alternative longer splicing form (Accession No. EES04332.2); 638aa |
| SEQ ID NO: 277 | Nucleotide sequence of the protein coding region of the cDNA for *Zea mays* INV2 gene (maize homolog to Sb INV3) (Accession No. NM_001305860.1); 2022nt |
| SEQ ID NO: 278 | Amino acid sequence of *Zea mays* INV2 polypeptide (maize homolog to Sb INV3) (Accession No. NM_001305860.1); 673aa |
| SEQ ID NO: 279 | Nucleotide sequence of the protein coding region of the cDNA for *Sorghum bicolor* SUS4 gene (Sobic.001G344500; Sb01g033060; Accession No. XM_002465116.1); 2451nt |

KEY TO THE SEQUENCE LISTING (continued)

| | |
|---|---|
| SEQ ID NO: 280 | Amino acid sequence of *Sorghum bicolor* SUS4 polypeptide (Accession No. XM_002465116.1); 816aa |
| SEQ ID NO: 281 | Nucleotide sequence of the protein coding region of the cDNA for *Zea mays* SUS1 gene (maize homolog to Sb SUS4) (Accession No. NM_001111853); 2451nt |
| SEQ ID NO: 282 | Amino acid sequence of *Zea mays* SUS1 polypeptide (Accession No. NM_001111853); 816aa |
| SEQ ID NO: 283 | Nucleotide sequence of the protein coding region of the cDNA for *Sorghum bicolor* bCIN gene (Sobic.004G172700; Sb04g022350; Accession No. XM_002453920.1); |
| SEQ ID NO: 284 | Amino acid sequence of *Sorghum bicolor* bCIN polypeptide (Accession No. XM_002453920.1); 559aa |
| SEQ ID NO: 285 | Nucleotide sequence of the protein coding region of the cDNA for *Zea mays* cytosolic INV gene (homolog of Sb bCIN) (Accession No. NM_001175248.1); 1680nt |
| SEQ ID NO: 286 | Amino acid sequence of *Zea mays* INV polypeptide (Accession No. NM_001175248.1); 559aa |
| SEQ ID NO: 287 | Nucleotide sequence of the protein coding region of the cDNA for *Sorghum bicolor* SUT4 gene (Sb04g038030; Accession No. XM_002453038.1); 1785nt |
| SEQ ID NO: 288 | Amino acid sequence of *Sorghum bicolor* SUT4 polypeptide (Accession No. XM_002453038.1); 594aa |
| SEQ ID NO: 289 | Nucleotide sequence of the protein coding region of the cDNA for *Zea mays* SUT2 gene (Accession No. AY581895.1); 1779nt |
| SEQ ID NO: 290 | Amino acid sequence of *Zea mays* SUT2 polypeptide (Accession No. AY581895.1); 592aa |
| SEQ ID NO: 291 | Nucleotide sequence of the protein coding region of the cDNA for *Arabidopsis thaliana* SWEET16 gene (Accession No. NM_001338249.1); 693nt |
| SEQ ID NO: 292 | Amino acid sequence of *Arabidopsis thaliana* SWEET16 polypeptide (Accession No. NM_001338249.1); 230aa |
| SEQ ID NO: 293 | Nucleotide sequence of the protein coding region of the cDNA for *Arabidopsis thaliana* MED15-1 gene (Accession No. NM_101446.4); 4008nt |
| SEQ ID NO: 294 | Amino acid sequence of *Arabidopsis thaliana* MED15-1 polypeptide (Accession No. NM_101446.4); 1335aa |
| SEQ ID NO: 295 | Nucleotide sequence of the protein coding region of the cDNA for *Zea mays* MED15-1 gene (Accession No. NM_001321633.1); 3927nt |
| SEQ ID NO: 296 | Amino acid sequence of *Zea mays* MED15-1 polypeptide (Accession No. NM_001321633.1); 1308aa |
| SEQ ID NO: 297 | Nucleotide sequence of the protein coding region of the cDNA for *Arabidopsis thaliana* 14-3-3κ gene (Accession No. AY079350); |
| SEQ ID NO: 298 | Amino acid sequence of *Arabidopsis thaliana* 14-3-3κ polypeptide (Accession No. AY079350); 248aa |
| SEQ ID NO: 299 | Nucleotide sequence of the protein coding region of the cDNA for *Sorghum bicolor* 14-3-3κ gene (Accession No. XM_002445734.1); 762nt |
| SEQ ID NO: 300 | Amino acid sequence of *Sorghum bicolor* 14-3-3κ polypeptide (Accession No. XM_002445734.1); 253aa |
| SEQ ID NO: 301 | Nucleotide sequence of the protein coding region of the cDNA for *Arabidopsis thaliana* 14-3-3λ gene (Accession No. NM_001203346); 777nt |
| SEQ ID NO: 302 | Amino acid sequence of *Arabidopsis thaliana* 14-3-3λ polypeptide (Accession No. NM_001203346); 258aa |
| SEQ ID NO: 303 | Nucleotide sequence of the protein coding region of the cDNA for *Sorghum bicolor* 14-3-3λ gene (Accession No. XM_002445734.1); 762nt |
| SEQ ID NO: 304 | Amino acid sequence of *Sorghum bicolor* 14-3-3λ polypeptide (Accession No. XM_002445734.1); 253aa |

-continued

KEY TO THE SEQUENCE LISTING

SEQ ID NO: 305   Amino acid sequence of *Sesamum indicum* oleosinL polypeptide
                 (Accession No. AF091840)

SEQ ID NO: 306   Amino acid sequence of *Ficus pumila* var. *awkeotsang* oleosinL
                 ortholog polypeptide (Accession No. ABQ57397.1)

SEQ ID NO: 307   Amino acid sequence of *Cucumis sativus* oleosinL ortholog
                 polypeptide (Accession No. XP_004146901.1)

SEQ ID NO: 308   Amino acid sequence of *Linum usitatissimum* oleosinL ortholog
                 polypeptide (Accession No. ABB01618.1)

SEQ ID NO: 309   Amino acid sequence of *Glycine max* oleosinL ortholog polypeptide
                 (Accession No. XP_003556321.2)

SEQ ID NO: 310   Amino acid sequence of *Ananas comosus* oleosinL ortholog
                 polypeptide (Accession No. OAY72596.1)

SEQ ID NO: 311   Amino acid sequence of *Setaria italica* oleosinL ortholog polypeptide
                 (Accession No. XP_004956407.1)

SEQ ID NO: 312   Amino acid sequence of *Fragaria vesca* subsp. *vesca* oleosinL
                 ortholog polypeptide (Accession No. XP_004307777.1)

SEQ ID NO: 313   Amino acid sequence of *Brassica napus* oleosinL ortholog
                 polypeptide (Accession No. CDY03377.1)

SEQ ID NO: 314   Amino acid sequence of *Solanum lycopersicum* oleosinL ortholog
                 polypeptide (Accession No. XP_004240765.1)

SEQ ID NO: 315.  Amino acid sequence of U1 Oleosin from *Vanilla planifolia*

SEQ ID NO: 316.  Amino acid sequence of TsLDAP1 from *Triadica sebifera* (Chinese tallow)

SEQ ID NO: 317.  Amino acid sequence of TsLDAP2 from *Triadica sebifera* (Chinese tallow)

SEQ ID NO: 318.  Amino acid sequence of TsLDAP3 from *Triadica sebifera* (Chinese tallow)

SEQ ID NO: 319.  Amino acid sequence of a GPAT9 from *Cocos nucifera* (Coconut)

SEQ ID NO: 320.  Amino acid sequence of a *Zea mays* CPT1 (Accession No. NP_001151915.1)

SEQ ID NO: 321.  Amino acid sequence of a *Zea mays* CPT1 (Accession No. XP_008649199.1)

SEQ ID NO: 322.  Amino acid sequence of a *Sorghum bicolor* CPT1 (Accession No.
                 XP_002451408.1)

SEQ ID NO: 323.  Amino acid sequence of a *Sorghum bicolor* CPT1 (Accession No.
                 XP_021305900.1)

DETAILED DESCRIPTION OF THE INVENTION

General Techniques

Unless specifically defined otherwise, all technical and scientific terms used herein shall be taken to have the same meaning as commonly understood by one of ordinary skill in the art (e.g., in cell culture, molecular genetics, plant biology, cell biology, protein chemistry, lipid and fatty acid chemistry, animal nutrition, biofuel production, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

Selected Definitions

The term "exogenous" in the context of a polynucleotide or polypeptide refers to the polynucleotide or polypeptide when present in a cell or a plant or part thereof which does not naturally comprise the polynucleotide or polypeptide. Such a cell is referred to herein as a "recombinant cell" or a "transgenic cell" and a plant comprising the cell as a "transgenic plant". In an embodiment, the exogenous polynucleotide or polypeptide is from a different genus to the cell of the plant or part thereof comprising the exogenous polynucleotide or polypeptide. In another embodiment, the exogenous polynucleotide or polypeptide is from a different species. In one embodiment, the exogenous polynucleotide or polypeptide expressed in the plant cell is from a different species or genus. The exogenous polynucleotide or polypeptide may be non-naturally occurring, such as for example, a synthetic DNA molecule which has been produced by recombinant DNA methods. The DNA molecule may, preferably, include a protein coding region which has been codon-optimised for expression in the plant cell, thereby producing a polypeptide which has the same amino acid sequence as a naturally occurring polypeptide, even though the nucleotide sequence of the protein coding region is non-naturally occurring. The exogenous polynucleotide may encode, or the exogenous polypeptide may be, for example: a diacylglycerol acyltransferase (DGAT) such as a DGAT1 or a DGAT2, a Wrinkled 1 (WRI1) transcription factor, on OBC such as an Oleosin or preferably an LDAP, a fatty acid thioesterase such as a FATA or FATB polypeptide, or a silencing suppressor polypeptide. In an embodiment, a cell of the invention is a recombinant cell.

As used herein, the term "triacylglycerol (TAG) content" or variations thereof refers to the amount of TAG in the cell, plant or part thereof. TAG content can be calculated using techniques known in the art such as the sum of glycerol and fatty acyl moieties using a relation: % TAG by weight=100× ((41×total mol FAME/3)+(total g FAME−(15×total mol FAME)))/g, where 41 and 15 are molecular weights of glycerol moiety and methyl group, respectively (where FAME is fatty acid methyl esters) (see Examples such as Example 1).

As used herein, the term "total fatty acid (TFA) content" or variations thereof refers to the total amount of fatty acids in the cell, plant or part thereof on a weight basis, as a percentage of the weight of the cell, plant or part thereof. Unless otherwise specified, the weight of the cell, plant or part thereof is the dry weight of the cell, plant or part thereof. TFA content is measured as described in Example 1 herein. The method involves conversion of the fatty acids in the sample to FAME and measurement of the amount of FAME by GC, using addition of a known amount of a distinctive fatty acid standard such as C17:0 as a quantitation standard in the GC. TFA therefore represents the weight of just the fatty acids, not the weight of the fatty acids and their linked moieties in the plant lipid.

As used herein, the "TAG/TFA Quotient" or "TTQ" parameter is calculated as the level of TAG (%) divided by the level of TFA (%), each as a percentage of the dry weight of the plant material. For example, a TAG level of 6% comprised in a TFA level of 10% yields a TTQ of 0.6. The TAG and TFA levels are measured as described herein. It is understood that, in this context, the TFA level refers to the weight of the total fatty acid content and the TAG level refers to the weight of TAG, including the glycerol moiety of TAG.

As used herein, the term "soluble protein content" or variations thereof refers to the amount of soluble protein in the plant or part thereof. Soluble protein content can be calculated using techniques known in the art. For instance, fresh tissue can be ground, chlorophyll and soluble sugars extracted by heating to 80° C. in 50-80% (v/v) ethanol in 2.5 mM HEPES buffer at pH 7.5, centriguation, washing pellet in distilled water, resuspending the pellet 0.1 M NaOH and heating to 95° C. for 30 min, and then the Bradford assay (Bradford, 1976) is used determined soluble protein content. Alternatively, fresh tissue can be ground in buffer containing 100 mM Tris-HCl pH 8.0 and 10 mM $MgCl_2$.

As used herein, the term "nitrogen content" or variations thereof refers to the amount of nitrogen in the plant or part thereof. Nitrogen content can be calculated using techniques known in the art. For example, freeze-dried tissue can be analysed using a Europa 20-20 isotope ratio mass spectrometer with an ANCA preparation system, comprising a combustion and reduction tube operating at 1000° C. and 600° C., respectively, to determine nitrogen content.

As used herein, the term "carbon content" or variations thereof refers to the amount of carbon in the plant or part thereof. Carbon content can be calculated using techniques known in the art. For example, organic carbon levels can be determined using the method described by Shaw (1959), or as described in Example 1.

As used herein, the term "carbon:nitrogen ratio" or variations thereof refers to the relative amount of carbon in the cell, plant or part thereof when compared to the amount of nitrogen in the cell, plant or part thereof. Carbon and nitrogen contents can be calculated as described above and represented as a ratio.

As used herein, the term "photosynthetic gene expression" or variations thereof refers to one or more genes expressing proteins involved in photosynthetic pathways in the plant or part thereof. Examples of photosynthetic genes which may be upregulated in plants or parts thereof of the invention include, but are not limited to, one or more of the genes listed in Table 10.

As used herein, the term "photosynthetic capacity" or variations thereof refers to the ability of the plant or part thereof to photosynthesize (convert light energy to chemical energy). Photosynthetic capacity ($A_{max}$) is a measure of the maximum rate at which leaves are able to fix carbon during photosynthesis. It is typically measured as the amount of carbon dioxide that is fixed per metre squared per second, for example as mol $m^{-2}$ $sec^{-1}$. Photosynthetic capacity can be calculated using techniques known in the art.

As used herein, the term "total dietary fibre (TDF) content" or variations thereof refers to the amount of fiber (including soluble and insoluble fibre) in the cell, plant or part thereof. As the skilled person would understand, dietary fiber includes non-starch polysaccharides such as arabinoxylans, cellulose, and many other plant components such as resistant starch, resistant dextrins, inulin, lignin, chitins, pectins, β-glucans, and oligosaccharides. TDF can be calculated using techniques known in the art. For example, using the Prosky method (Prosky et al. 1985), the McCleary method (McCleary et al., 2007) or the rapid integrated total dietary fiber method (McCleary et al., 2015).

As used herein, the term "energy content" or variations thereof refers to the amount of food energy in the plant or part thereof. More specifically, the amount of chemical energy that animals (including humans) derive from their food. Energy content can be calculated using techniques known in the art. For example, energy content can be determined based on heats of combustion in a bomb calorimeter and corrections that take into consideration the efficiency of digestion and absorption and the production of urea and other substances in the urine. As another example, energy content can be calculated as described in Example 1.

As used herein, the term "extracted lipid" refers to a composition extracted from a cell, plant or part thereof of the invention, such as a transgenic cell, plant or part thereof of the invention, which comprises at least 60% (w/w) lipid.

As used herein, the term "non-polar lipid" refers to fatty acids and derivatives thereof which are soluble in organic solvents but insoluble in water. The fatty acids may be free fatty acids and/or in an esterified form. Examples of esterified forms of non-polar lipid include, but are not limited to, triacylglycerol (TAG), diacylyglycerol (DAG), monoacylglycerol (MAG). Non-polar lipids also include sterols, sterol esters and wax esters. Non-polar lipids are also known as "neutral lipids". Non-polar lipid is typically a liquid at room temperature. Preferably, the non-polar lipid predominantly (>50%) comprises fatty acids that are at least 16 carbons in length. More preferably, at least 50% of the total fatty acids in the non-polar lipid are C18 fatty acids for example, oleic acid. In an embodiment, at least 5% of the total fatty acids in the non-polar lipids are C12 or C14 fatty acids, or both. In an embodiment, at least 50%, more preferably at least 70%, more preferably at least 80%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% of the fatty acids in non-polar lipid of the invention are present as TAG. The non-polar lipid may be further purified or treated, for example by hydrolysis with a strong base to release the free fatty acid, or by fractionation, distillation, or the like. Non-polar lipid may be present in or obtained from plant parts such as seed, leaves, tubers, beets or fruit. Non-polar lipid of the invention may form part of "seedoil" if it is obtained from seed.

The free and esterified sterol (for example, sitosterol, campesterol, stigmasterol, brassicasterol, Δ5-avenasterol, sitostanol, campestanol, and cholesterol) concentrations in the extracted lipid may be as described in Phillips et al. (2002). Sterols in plant oils are present as free alcohols, esters with fatty acids (esterified sterols), glycosides and acylated glycosides of sterols. Sterol concentrations in naturally occurring vegetable oils (seedoils) ranges up to a maximum of about 1100 mg/100 g. Hydrogenated palm oil has one of the lowest concentrations of naturally occurring vegetable oils at about 60 mg/100 g. The recovered or extracted seedoils of the invention preferably have between about 100 and about 1000 mg total sterol/100 g of oil. For use as food or feed, it is preferred that sterols are present primarily as free or esterified forms rather than glycosylated forms. In the seedoils of the present invention, preferably at least 50% of the sterols in the oils are present as esterified sterols, except for soybean seedoil which has about 25% of the sterols esterified. The canola seedoil and rapeseed oil of the invention preferably have between about 500 and about 800 mg total sterol/100 g, with sitosterol the main sterol and campesterol the next most abundant. The corn seedoil of the invention preferably has between about 600 and about 800 mg total sterol/100 g, with sitosterol the main sterol. The soybean seedoil of the invention preferably has between about 150 and about 350 mg total sterol/100 g, with sitosterol the main sterol and stigmasterol the next most abundant, and with more free sterol than esterified sterol. The cottonseed oil of the invention preferably has between about 200 and about 350 mg total sterol/100 g, with sitosterol the main sterol. The coconut oil and palm oil of the invention preferably have between about 50 and about 100 mg total sterol/100 g, with sitosterol the main sterol. The safflower seedoil of the invention preferably has between about 150 and about 250 mg total sterol/100 g, with sitosterol the main sterol. The peanut seedoil of the invention preferably has between about 100 and about 200 mg total sterol/100 g, with sitosterol the main sterol. The sesame seedoil of the invention preferably has between about 400 and about 600 mg total sterol/100 g, with sitosterol the main sterol. The sunflower seedoil of the invention preferably has between about 200 and 400 mg total sterol/100 g, with sitosterol the main sterol. Oils obtained from vegetative plant parts according to the invention preferably have less than 200 mg total sterol/100 g, more preferably less than 100 mg total sterol/100 g, and most preferably less than 50 mg total sterols/100 g, with the majority of the sterols being free sterols.

As used herein, the term "vegetative oil" refers to a composition obtained from vegetative parts of a plant which comprises at least 60% (w/w) lipid, or obtainable from the vegetative parts if the oil is still present in the vegetative part. That is, vegetative oil of the invention includes oil which is present in the vegetative plant part, as well as oil which has been extracted from the vegetative part (extracted oil). The vegetative oil is preferably extracted vegetative oil. Vegetative oil is typically a liquid at room temperature. Preferably, the total fatty acid (TFA) content in the vegetative oil predominantly (>50%) comprises fatty acids that are at least 16 carbons in length. More preferably, at least 50% of the total fatty acids in the vegetative oil are C18 fatty acids for example, oleic acid. The fatty acids are typically in an esterified form such as for example, TAG, DAG, acyl-CoA, galactolipid or phospholipid. The fatty acids may be free fatty acids and/or in an esterified form. In an embodiment, at least 50%, more preferably at least 70%, more preferably at least 80%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% of the fatty acids in vegetative oil of the invention can be found as TAG. In an embodiment, vegetative oil of the invention is "substantially purified" or "purified" oil that has been separated from one or more other lipids, nucleic acids, polypeptides, or other contaminating molecules with which it is associated in the vegetative plant part or in a crude extract. It is preferred that the substantially purified vegetative oil is at least 60% free, more preferably at least 75% free, and more preferably, at least 90% free from other components with which it is associated in the vegetative plant part or extract. Vegetative oil of the invention may further comprise non-fatty acid molecules such as, but not limited to, sterols. In an embodiment, the vegetative oil is canola oil (*Brassica* sp. such as *Brassica carinata, Brassica juncea, Brassica napobrassica, Brassica napus*) mustard oil (*Brassica juncea*), other *Brassica* oil (e.g., *Brassica napobrassica, Brassica camelina*), sunflower oil (*Helianthus* sp. such as *Helianthus annuus*), linseed oil (*Linum usitatissimum*), soybean oil (*Glycine max*), safflower oil (*Carthamus tinctorius*), corn oil (*Zea mays*), tobacco oil (*Nicotiana* sp. such as *Nicotiana tabacum* or *Nicotiana benthamiana*), peanut oil (*Arachis hypogaea*), palm oil (*Elaeis guineensis*), cotton oil (*Gossypium hirsutum*), coconut oil (*Cocos nucifera*), avocado oil (*Persea americana*), olive oil (*Olea europaea*), cashew oil (*Anacardium occidentale*), macadamia oil (*Macadamia intergrifolia*), almond oil (*Prunus amygdalus*), oat oil (*Avena sativa*), rice oil (*Oryza* sp. such as *Oryza sativa* and *Oryza glaberrima*), Arabidopsis oil (*Arabidopsis thaliana*), *Aracinis hypogaea* (peanut), *Beta vulgaris* (sugar beet), *Camelina sativa* (false flax), *Crambe abyssinica* (Abyssinian kale), *Cucumis melo* (melon), *Hordeum vulgare* (barley), *Jatropha curcas* (physic nut), *Joannesia princeps* (arara nut-tree), *Licania rigida* (oiticica), *Lupinus angustifolius* (lupin), *Miscanthus* sp. such as *Miscanthus×giganteus* and *Miscanthus sinensis, Panicum virgatum* (switchgrass), *Pongamia pinnata* (Indian beech),

*Populus trichocarpa, Ricinus communis* (castor), *Saccharum* sp. (sugarcane), *Sesamum indicum* (sesame), *Solanum tuberosum* (potato), *Sorghum* sp. such as *Sorghum bicolor, Sorghum vulgare, Theobroma grandiforum* (cupuassu), *Trifolium* sp., and *Triticum* sp. (wheat) such as *Triticum aestivum*. Vegetative oil may be extracted from vegetative plant parts by any method known in the art, such as for extracting seedoils. This typically involves extraction with nonpolar solvents such as diethyl ether, petroleum ether, chloroform/methanol or butanol mixtures, generally associated with first crushing of the seeds. Lipids associated with the starch or other polysaccharides may be extracted with water-saturated butanol. The seedoil may be "de-gummed" by methods known in the art to remove polar lipids such as phospholipids or treated in other ways to remove contaminants or improve purity, stability, or colour. The TAGs and other esters in the vegetative oil may be hydrolysed to release free fatty acids, or the oil hydrogenated, treated chemically, or enzymatically as known in the art. As used herein, the term "seedoil" has an analogous meaning except that it refers to a lipid composition obtained from seeds of plants of the invention.

As used herein, the term "fatty acid" refers to a carboxylic acid with an aliphatic tail of at least 8 carbon atoms in length, either saturated or unsaturated. Preferred fatty acids have a carbon-carbon bonded chain of at least 12 carbons in length. Most naturally occurring fatty acids have an even number of carbon atoms because their biosynthesis involves acetate which has two carbon atoms. The fatty acids may be in a free state (non-esterified) or in an esterified form such as part of a TAG, DAG, MAG, acyl-CoA (thio-ester) bound, acyl-ACP bound, or other covalently bound form. When covalently bound in an esterified form, the fatty acid is referred to herein as an "acyl" group. The fatty acid may be esterified as a phospholipid such as a phosphatidylcholine (PC), phosphatidylethanolamine (PE), phosphatidylserine (PS), phosphatidylglycerol (PG), phosphatidylinositol (PI), or diphosphatidylglycerol. Saturated fatty acids do not contain any double bonds or other functional groups along the chain. The term "saturated" refers to hydrogen, in that all carbons (apart from the carboxylic acid [—COOH] group) contain as many hydrogens as possible. In other words, the omega (o) end contains 3 hydrogens ($CH_3$—) and each carbon within the chain contains 2 hydrogens ($—CH_2—$). Unsaturated fatty acids are of similar form to saturated fatty acids, except that one or more alkene functional groups exist along the chain, with each alkene substituting a singly-bonded "—$CH_2$—$CH_2$—" part of the chain with a doubly-bonded "—CH═CH—" portion (that is, a carbon double bonded to another carbon). The two next carbon atoms in the chain that are bound to either side of the double bond can occur in a cis or trans configuration.

As used herein, the terms "monounsaturated fatty acid" or "MUFA" refer to a fatty acid which comprises at least 12 carbon atoms in its carbon chain and only one alkene group (carbon-carbon double bond), which may be in an esterified or non-esterified (free) form. As used herein, the terms "polyunsaturated fatty acid" or "PUFA" refer to a fatty acid which comprises at least 12 carbon atoms in its carbon chain and at least two alkene groups (carbon-carbon double bonds), which may be in an esterified or non-esterified form.

"Monoacylglyceride" or "MAG" is glyceride in which the glycerol is esterified with one fatty acid. As used herein, MAG comprises a hydroxyl group at an sn-1/3 (also referred to herein as sn-1 MAG or 1-MAG or 1/3-MAG) or sn-2 position (also referred to herein as 2-MAG), and therefore MAG does not include phosphorylated molecules such as PA or PC. MAG is thus a component of neutral lipids in a plant or part thereof.

"Diacylglyceride" or "DAG" is glyceride in which the glycerol is esterified with two fatty acids which may be the same or, preferably, different. As used herein, DAG comprises a hydroxyl group at a sn-1,3 or sn-2 position, and therefore DAG does not include phosphorylated molecules such as PA or PC. DAG is thus a component of neutral lipids in a plant or part thereof. In the Kennedy pathway of DAG synthesis (FIG. 1), the precursor sn-glycerol-3-phosphate (G3P) is esterified to two acyl groups, each coming from a fatty acid coenzyme A ester, in a first reaction catalysed by a glycerol-3-phosphate acyltransferase (GPAT) at position sn-1 to form LysoPA, followed by a second acylation at position sn-2 catalysed by a lysophosphatidic acid acyltransferase (LPAAT) to form phosphatidic acid (PA). This intermediate is then de-phosphorylated by PAP to form DAG. DAG may also be formed from TAG by removal of an acyl group by a lipase, or from PC essentially by removal of a choline headgroup by any of the enzymes PDCT, PLC or PLD (FIG. 1).

"Triacylglyceride" or "TAG" is a glyceride in which the glycerol is esterified with three fatty acids which may be the same (e.g. as in tri-olein) or, more commonly, different. In the Kennedy pathway of TAG synthesis, DAG is formed as described above, and then a third acyl group is esterified to the glycerol backbone by the activity of DGAT. Alternative pathways for formation of TAG include one catalysed by the enzyme PDAT (FIG. 1) and the MGAT pathway described herein.

As used herein, the term "wild-type" or variations thereof refers to cell, plant or part thereof such as a cell, vegetative plant part, seed, tuber or beet, that has not been genetically modified, such as cells, plants or parts thereof that do not comprise the first and second exogenous polynucleotides, according to this invention.

The term "corresponding" refers to a cell, plant or part thereof such as a cell, vegetative plant part, seed, tuber or beet, that has the same or similar genetic background as a cell, plant or part thereof such as a vegetative plant part, seed, tuber or beet of the invention but which has not been modified as described herein (for example, a vegetative plant part or seed which lacks the first and second exogenous polynucleotides). In a preferred embodiment, the corresponding plant or part thereof such as a vegetative plant part is at the same developmental stage as the plant or part thereof such as a vegetative plant part of the invention. For example, if the plant is a flowering plant, then preferably the corresponding plant is also flowering. A corresponding cell, plant or part thereof such as a vegetative plant part, can be used as a control to compare levels of nucleic acid or protein expression, or the extent and nature of trait modification, for example TTQ and/or TAG content, with the cell, plant or part thereof such as a vegetative plant part of the invention which is modified as described herein. A person skilled in the art is readily able to determine an appropriate "corresponding" cell, plant or part thereof such as a vegetative plant part for such a comparison.

As used herein, "compared with" or "relative to" refers to comparing levels of, for example, TTQ or triacylglycerol (TAG) content, one or more or all of soluble protein content, nitrogen content, carbon:nitrogen ratio, photosynthetic gene expression, photosynthetic capacity, total dietary fibre (TDF) content, carbon content, and energy content, or non-polar lipid content or composition, total non-polar lipid content, total fatty acid content or other parameter of the cell, plant or part thereof comprising the one or more exogenous polynucleotides, genetic modifications or exogenous polypeptides with a cell, plant or part thereof such as a vegetative plant part lacking the one or more exogenous polynucleotides, genetic modifications or polypeptides.

As used herein, "synergism", "synergistic", "acting synergistically" and related terms are each a comparative term that means that the effect of a combination of elements present in a plant or part thereof of the invention, for example a combination of elements A and B, is greater than the sum of the effects of the elements separately in corresponding plants or parts thereof, for example the sum of the effect of A and the effect of B. Where more than two elements are present in the plant or part thereof, for example elements A, B and C, it means that the effect of the combination of all of the elements is greater than the sum of the effects of the individual effects of the elements. In a preferred embodiment, it means that the effect of the combination of elements A, B and C is greater than the sum of the effect of elements A and B combined and the effect of element C. In such a case, it can be said that element C acts synergistically with elements A and B. As would be understood, the effects are measured in corresponding cells, plants or parts thereof, for example grown under the same conditions and at the same stage of biological development.

As used herein, "germinate at a rate substantially the same as for a corresponding wild-type plant" or similar phrases refers to seed of a plant of the invention being relatively able to germinate when compared to seed of a wild-type plant lacking the defined exogenous polynucleotide(s) and genetic modifications. Germination may be measured in vitro on tissue culture medium or in soil as occurs in the field. In one embodiment, the number of seeds which germinate, for instance when grown under optimal greenhouse conditions for the plant species, is at least 75%, more preferably at least 90%, when compared to corresponding wild-type seed. In another embodiment, the seeds which germinate, for instance when grown under optimal glasshouse conditions for the plant species, produce seedlings which grow at a rate which, on average, is at least 75%, more preferably at least 90%, when compared to corresponding wild-type plants. This is referred to as "seedling vigour". In an embodiment, the rate of initial root growth and shoot growth of seedlings of the invention is essentially the same compared to a corresponding wild-type seedling grown under the same conditions. In an embodiment, the leaf biomass (dry weight) of the plants of the invention is at least 80%, preferably at least 90%, of the leaf biomass relative to a corresponding wild-type plant grown under the same conditions, preferably in the field. In an embodiment, the height of the plants of the invention is at least 70%, preferably at least 80%, more preferably at least 90%, of the plant height relative to a corresponding wild-type plant grown under the same conditions, preferably in the field and preferably at maturity.

As used herein, the term "an exogenous polynucleotide which down-regulates the production and/or activity of an endogenous polypeptide" or variations thereof, refers to a polynucleotide that encodes an RNA molecule, herein termed a "silencing RNA molecule" or variations thereof (for example, encoding an amiRNA or hpRNAi), that down-regulates the production and/or activity, or itself down-regulates the production and/or activity (for example, is an amiRNA or hpRNA which can be delivered directly to, for example, the plant or part thereof) of an endogenous polypeptide. This includes where the initial RNA transcript produced by expression of the exogenous polynucleotide is processed in the cell to form the actual silencing RNA molecule. The endogenous polypeptides whose production or activity are downregulated include, for example, SDP1 TAG lipase, plastidial GPAT, plastidial LPAAT, TGD polypeptide such as TGD5, TST such as TST1 or TST2, AGPase, PDCT, CPT or Δ12 fatty acid desaturase (FAD2), or a combination of two or more thereof. Typically, the RNA molecule decreases the expression of an endogenous gene encoding the polypeptide. The extent of down-regulation is typically less than 100%, for example the production or activity is reduced by between 25% and 95% relative to the wild-type. The optimal level of remaining production or activity can be routinely determined.

As used herein, the term "on a weight basis" refers to the weight of a substance (for example, TAG, DAG, fatty acid, protein, nitrogen, carbon) as a percentage of the weight of the composition comprising the substance (for example, seed, leaf dry weight). For example, if a transgenic seed has 25 μg total fatty acid per 120 μg seed weight; the percentage of total fatty acid on a weight basis is 20.8%.

As used herein, the term "on a relative basis" refers to a parameter such as the amount of a substance in a composition comprising the substance in comparison with the parameter for a corresponding composition, as a percentage. For example, a reduction from 3 units to 2 units is a reduction of 33% on a relative basis.

As used herein, "plastids" are organelles in plants, including algae, which are the site of manufacture of carbon-based compounds from photosynthesis including sugars, starch and fatty acids. Plastids include chloroplasts which contain chlorophyll and carry out photosynthesis, etioplasts which are the predecessors of chloroplasts, as well as specialised plastids such as chromoplasts which are coloured plastids for synthesis and storage of pigments, gerontoplasts which control the dismantling of the photosynthetic apparatus during senescence, amyloplasts for starch synthesis and storage, elaioplasts for storage of lipids, and proteinoplasts for storing and modifying proteins.

As used herein, the term "biofuel" refers to any type of fuel, typically as used to power machinery such as automobiles, planes, boats, trucks or petroleum powered motors, whose energy is derived from biological carbon fixation. Biofuels include fuels derived from biomass conversion, as well as solid biomass, liquid fuels and biogases. Examples of biofuels include bioalcohols, biodiesel, synthetic diesel, vegetable oil, bioethers, biogas, syngas, solid biofuels, algae-derived fuel, biohydrogen, biomethanol, 2,5-Dimethylfuran (DMF), biodimethyl ether (bioDME), Fischer-Tropsch diesel, biohydrogen diesel, mixed alcohols and wood diesel.

As used herein, the term "bioalcohol" refers to biologically produced alcohols, for example, ethanol, propanol and butanol. Bioalcohols are produced by the action of microorganisms and/or enzymes through the fermentation of sugars, hemicellulose or cellulose.

As used herein, the term "biodiesel" refers to a composition comprising fatty acid methyl- or ethyl-esters derived from lipids by transesterification, the lipids being from living cells not fossil fuels.

As used herein, the term "synthetic diesel" refers to a form of diesel fuel which is derived from renewable feedstock rather than the fossil feedstock used in most diesel fuels.

As used herein, the term "vegetable oil" includes a pure plant oil (or straight vegetable oil) or a waste vegetable oil (by product of other industries), including oil produced in either a vegetative plant part or in seed. Vegetable oil includes vegetative oil and seedoil, as defined herein.

As used herein, the term "biogas" refers to methane or a flammable mixture of methane and other gases produced by anaerobic digestion of organic material by anaerobes.

As used herein, the term "syngas" refers to a gas mixture that contains varying amounts of carbon monoxide and hydrogen and possibly other hydrocarbons, produced by partial combustion of biomass. Syngas may be converted into methanol in the presence of catalyst (usually copper-based), with subsequent methanol dehydration in the presence of a different catalyst (for example, silica-alumina).

As used herein, the term "biochar" refers to charcoal made from biomass, for example, by pyrolysis of the biomass.

As used herein, the term "feedstock" refers to a material, for example, biomass or a conversion product thereof (for example, syngas) when used to produce a product, for example, a biofuel such as biodiesel or a synthetic diesel.

As used herein, the term "industrial product" refers to a hydrocarbon product which is predominantly made of carbon and hydrogen such as, for example, fatty acid methyl- and/or ethyl-esters or alkanes such as methane, mixtures of longer chain alkanes which are typically liquids at ambient temperatures, a biofuel, carbon monoxide and/or hydrogen, or a bioalcohol such as ethanol, propanol, or butanol, or biochar. The term "industrial product" is intended to include intermediary products that can be converted to other industrial products, for example, syngas is itself considered to be an industrial product which can be used to synthesize a hydrocarbon product which is also considered to be an industrial product. The term industrial product as used herein includes both pure forms of the above compounds, or more commonly a mixture of various compounds and components, for example the hydrocarbon product may contain a range of carbon chain lengths, as well understood in the art.

As used herein, "progeny" means the immediate and all subsequent generations of offspring produced from a parent, for example a second, third or later generation offspring.

As used herein, the term "ancestor" refers to any earlier generation of the plant comprising the first and second exogenous polynucleotides. The ancestor may be the parent plant, grandparent plant, great grandparent plant and so on.

As used herein, the term "selecting a plant" means actively selecting the plant on the basis that it has the desired phenotype, such as increased TTQ, increased TAG and protein content when compared to the corresponding wild-type plant.

As used herein, phrases such as "comprise a TFA content of about 5% (w/w dry weight)", or "comprise a total TAG content of about 6% (w/w dry weight)", or similarly structured phrases, mean that more than the defined level may be present. For instance, the phrase "comprise a TFA content of about 5% (w/w dry weight)" can be used interchangeably with "comprises at least about 5% TFA (w/w dry weight)". Extending this example further, a vegetative plant part which comprise a TFA content of about 5% (w/w dry weight) may have a 6%, or 7.5% or higher TFA content.

As used herein, unless the context indicates otherwise, the term "increased content" when used in reference to a polypeptide, or similar phrases including reference to specific polypeptide, refers to either an exogenous polypeptide or an endogenous polypeptide. For example, a vegetative plant part of the invention may comprise an increased content of a WRI1 polypeptide, an increased content of a DGAT polypeptide, and a decreased content of a SDP1 polypeptide, each relative to a corresponding wild-type vegetative plant part, wherein each of the WRI1 and DGAT polypeptides is independently either an exogenous polypeptide or an endogenous polypeptide. As another example, a vegetative plant part of the invention may comprise an increased content of a WRI1 polypeptide, an increased content of a DGAT polypeptide, and an increased content of a LEC2 polypeptide, each relative to a corresponding wild-type vegetative plant part, wherein each of the WRI1, DGAT and LEC2 polypeptides is independently either an exogenous polypeptide or an endogenous polypeptide. As a further example, a vegetative plant part of the invention may comprise an increased content of a PDAT or DGAT polypeptide, a decreased content of a TGD polypeptide, and a decreased content of a SDP1 polypeptide, each relative to a corresponding wild-type vegetative plant part wherein the PDAT or DGAT is either an exogenous polypeptide or an endogenous polypeptide, and so on. An exogenous polypeptide may be the result of expression of a transgene encoding the polypeptide in the cell or plant or part thereof of the invention. The endogenous polypeptide may be the result of increased expression of an endogenous gene, such as inducing overexpression and/or providing increased levels of a transcription factor(s) for the gene.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−10%, more preferably +/−5%, more preferably +/−2%, more preferably +/−1%, even more preferably +/−0.5%, of the designated value.

Production of Plants with Modified Traits

The present invention is based on the finding that plant traits, such two or more of non-polar lipid content, protein content, TTQ, TAG content, nitrogen content, carbon content, in plants or parts thereof can be increased by a combination of modifications selected from those designated herein as: (A). Push, (B). Pull, (C). Protect, (D). Package, (E). Plastidial Export, (F). Plastidial Import and (G). Prokaryotic Pathway.

Plants or parts thereof such as a vegetative plant parts of the invention therefore have a number of combinations of exogenous polynucleotides and/or genetic modifications each of which provide for one of the modifications. These exogenous polynucleotides and/or genetic modifications include:

(A) an exogenous polynucleotide which encodes a transcription factor polypeptide that increases the expression of one or more glycolytic and/or fatty acid biosynthetic genes in the plant or part thereof such as a vegetative plant part, providing the "Push" modification, (B) an exogenous polynucleotide which encodes a polypeptide involved in the biosynthesis of one or more non-polar lipids in the plant or part thereof such as a vegetative plant part, providing the "Pull" modification, (C) a genetic modification which down-regulates endogenous production and/or activity of a polypeptide involved in the catabolism of triacylglycerols (TAG) in the plant or part thereof such as a vegetative plant part when compared to a corresponding plant or part thereof such as a vegetative plant part lacking the genetic modification, providing the "Protect" modification, (D) an exogenous polynucleotide which encodes an oil body coating (OBC) polypeptide such as a lipid droplet associated polypeptide (LDAP), providing the "Package" modification, (E) an exogenous polynucleotide which encodes a polypeptide which increases the export of fatty acids out of plastids of the plant or part thereof such as a vegetative plant part, when compared to a corresponding plant or part thereof such as a vegetative plant part lacking the exogenous polynucleotide, providing the "Plastidial Export" modification, (F) a genetic modification which down-regulates endogenous production and/or activity of a polypeptide involved in importing fatty acids into plastids of the plant or part thereof such as a vegetative plant part when compared to a corresponding plant or part thereof such as a vegetative plant part lacking the genetic modification, providing the "Plastidial Import" modification, and G) a genetic modification which down-regulates endogenous production and/or activity of a polypeptide involved in diacylglycerol (DAG) production in the plastid of the plant or part thereof such as a vegetative plant part when compared to a corresponding plant or part thereof such as a vegetative plant part lacking the genetic modification, providing the "prokaryotic Pathway" modification.

Preferred combinations (also referred to herein as sets) of exogenous polynucleotides and/or genetic modifications of the invention are;

1) A, B and optionally one of C, D, E, F or G;
2) A, C and optionally one of D, E, F or G;
3) A, D and optionally one of E, F or G;
4) A, E and optionally F or G;
5) A, F and optionally G;
6) A and G;
7) A, B, C and optionally one of D, E, F or G;
8) A, B, D and optionally one of E, F or G;
9) A, B, E and optionally F or G;
10) A, B, F and optionally G;
11) A, B, C, D and optionally one of E, F or G;
12) A, B, C, E and optionally F or G;
13) A, B, C, F and optionally G;
14) A, B, D, E and optionally F or G;
15) A, B, D, F and optionally G;
16) A, B, E, F and optionally G;
17) A, C, D and optionally one of E, F or G;
18) A, C, E and optionally F or G;
19) A, C, F and optionally G;
20) A, C, D, E and optionally F or G;
21) A, C, D, F and optionally G;
22) A, C, E, F and optionally a fifth modification G;
23) A, D, E and optionally F or G;
24) A, D, F and optionally G;
25) A, D, E, F and optionally G;
26) A, E, F and optionally G;
27) Six of A, B, C, D, E, F and G omitting one of A, B, C, D, E, F or G, and
28) Any one of 1-26 above where there are two or more exogenous polynucleotides encoding two or more different transcription factor polypeptides that increases the expression of one or more glycolytic and/or fatty acid biosynthetic genes in the plant or part thereof, for example one exogenous polynucleotide encoding WRI1 and another exogenous polynucleotide encoding LEC2.

In each of the above preferred combinations there may be at least two different exogenous polynucleotides which encode at least two different transcription factor polypeptides that increases the expression of one or more glycolytic and/or fatty acid biosynthetic genes in the plant or part thereof such as a vegetative plant part.

These modifications are described more fully as follows:

A. The "Push" modification is characterised by an increased synthesis of total fatty acids in the plastids of the plant or part thereof. In an embodiment, this occurs by the increased expression and/or activity of a transcription factor which regulates fatty acid synthesis in the plastids. In one embodiment, this can be achieved by expressing in a transgenic plant or part thereof an exogenous polynucleotide which encodes a transcription factor polypeptide that increases the expression of one or more glycolytic and/or fatty acid biosynthetic genes in the plant or part thereof. In an embodiment, the increased fatty acid synthesis is not caused by the provision to the plant or part thereof of an altered ACCase whose activity is less inhibited by fatty acids, relative to the endogenous ACCase in the plant or part thereof. In an embodiment, the plant or part thereof comprises an exogenous polynucleotide which encodes the transcription factor, preferably under the control of a promoter other than a constitutive promoter. The transcription factor may be selected from the group consisting of WRI1, LEC1, LEC1-like, LEC2, BBM, FUS3, ABI3, ABI4, ABI5, Dof4, Dof11 or the group consisting of MYB73, bZIP53, AGL15, MYB115, MYB118, TANMEI, WUS, GFR2a1, GFR2a2 and PHR1, and is preferably WRI1, LEC1 or LEC2. In a further embodiment, the increased synthesis of total fatty acids is relative to a corresponding wild-type plant or part thereof. In an embodiment, there are two or more exogenous polynucleotides encoding two or more different transcription factor polypeptides. The "Push" modification may also be achieved by increased expression of polypeptides which modulate activity of WRI1, such as MED15 or 14-3-3 polypeptides.

B. The "Pull" modification is characterised by increased expression and/or activity in the plant or part thereof of a fatty acyl acyltransferase which catalyses the synthesis of TAG, DAG or MAG in the plant or part thereof, such as a DGAT, PDAT, LPAAT, GPAT or MGAT, preferably a DGAT or a PDAT. In one embodiment, this can be achieved by expressing in a transgenic plant or part thereof an exogenous polynucleotide which encodes a polypeptide involved in the biosynthesis of one or more non-polar lipids. In an embodiment, the acyltransferase is a membrane-bound acyltransferase that uses an acyl-CoA substrate as the acyl donor in the case of DGAT, LPAAT, GPAT or MGAT, or an acyl group from PC as the acyl donor in the case of PDAT. The Pull modification can be relative to a corresponding wild-type plant or part thereof or, preferably, relative to a corresponding plant or part thereof which has the Push modification. In an embodiment, the plant or part thereof comprises an exogenous polynucleotide which encodes the fatty acyl acyltransferase. The "Pull" modification can also be achieved by increased expression of a PDCT, CPT or phospholipase C or D polypeptide which increases the production of DAG from PC.

C. The "Protect" modification is characterised by a reduction in the catabolism of triacylglycerols (TAG) in the plant or part thereof. In an embodiment, this can be achieved through a genetic modification in the plant or part thereof which down-regulates endogenous production and/or activity of a polypeptide involved in the catabolism of triacylglycerols (TAG) in the plant or part thereof when compared to a corresponding plant or part thereof lacking the genetic modification. In an embodiment, the plant or part thereof has a reduced expression and/or activity of an endogenous TAG lipase in the plant or part thereof, preferably an SDP1 lipase, a Cgi58 polypeptide, an acyl-CoA oxidase such as the ACX1 or ACX2, or a polypeptide involved in β-oxidation of fatty acids in the plant or part thereof such as a PXA1 peroxisomal ATP-binding cassette transporter. This may occur by expression in the plant or part thereof of an exogenous polynucleotide which encodes an RNA molecule which reduces the expression of, for example, an endogenous gene encoding the TAG lipase such as the SDP1 lipase, acyl-CoA oxidase or the polypeptide involved in β-oxidation of fatty acids in the plant or part thereof, or by a mutation in an endogenous gene encoding, for example, the TAG lipase, acyl-CoA oxidase or polypeptide involved in β-oxidation of fatty acids. In an embodiment, the reduced expression and/or activity is relative to a corresponding wild-type plant or part thereof or relative to a corresponding plant or part thereof which has the Push modification.

D. The "Package" modification is characterised by an increased expression and/or accumulation of an oil body coating (OBC) polypeptide. In an embodiment, this can be achieved by expressing in a transgenic plant or part thereof an exogenous polynucleotide which encodes an oil body coating (OBC) polypeptide. The OBC polypeptide may be an oleosin, such as for example a polyoleosin, a caoleosin or a steroleosin, or preferably an LDAP. In an embodiment, the level of oleosin that is accumulated in the plant or part thereof is at least 2-fold higher relative to the corresponding plant or part thereof comprising the oleosin gene from the T-DNA of pJP3502. In an embodiment, the increased expression or accumulation of the OBC polypeptide is not caused solely by the Push modification. In an embodiment, the expression and/or accumulation is relative to a corresponding wild-type plant or part thereof or, preferably, relative to a corresponding plant or part thereof which has the Push modification.

E. The "Plastidial Export" modification is characterised by an increased rate of export of total fatty acids out of the plastids of the plant or part thereof. In one embodiment, this can be achieved by expressing in a plant or part thereof an exogenous polynucleotide which encodes a polypeptide which increases the export of fatty acids out of plastids of the plant or part thereof when compared to a corresponding plant or part thereof lacking the exogenous polynucleotide. In an embodiment, this occurs by the increased expression and/or activity of a fatty acid thioesterase (TE), a fatty acid transporter polypeptide such as an ABCA9 polypeptide, or a long-chain acyl-CoA synthetase (LACS). In an embodiment, the plant or part thereof comprises an exogenous polynucleotide which encodes the TE, fatty acid transporter polypeptide or LACS. The TE may be a FATB polypeptide or preferably a FATA polypeptide. In an embodiment, the Plastidial Export modification is relative to a corresponding wild-type plant or part thereof or, preferably, relative to a corresponding plant or part thereof which has the Push modification.

F. The "Plastidial Import" modification is characterised by a reduced rate of import of fatty acids into the plastids of the plant or part thereof from outside of the plastids. In an embodiment, this can be achieved through a genetic modification in the plant or part thereof which down-regulates endogenous production and/or activity of a polypeptide involved in importing fatty acids into plastids of the plant or part thereof when compared to a corresponding plant or part thereof lacking the genetic modification. For example, this may occur by expression in the plant or part thereof of an exogenous polynucleotide which encodes an RNA molecule which reduces the expression of an endogenous gene encoding an transporter polypeptide such as a TGD polypeptide, for example a TGD1, TGD2, TGD3, TGD4 or preferably a TGD5 polypeptide, or by a mutation in an endogenous gene encoding the TGD polypeptide. In an embodiment, the reduced rate of import is relative to a corresponding wild-type plant or part thereof or relative to a corresponding plant or part thereof which has the Push modification.

G. The "Prokaryotic Pathway" modification is characterised by a decreased amount of DAG or rate of production of DAG in the plastids of the plant or part thereof. In an embodiment, this can be achieved through a genetic modification in the plant or part thereof which down-regulates endogenous production and/or activity of a polypeptide involved in diacylglycerol (DAG) production in the plastid when compared to a corresponding plant or part thereof lacking the genetic modification. In an embodiment, the decreased amount or rate of production of DAG occurs by a decreased production of LPA from acyl-ACP and G3P in the plastids. The decreased amount or rate of production of DAG may occur by expression in the plant or part thereof of an exogenous polynucleotide which encodes an RNA molecule which reduces the expression of an endogenous gene encoding a plastidial GPAT, plastidial LPAAT or a plastidial PAP, preferably a plastidial GPAT, or by a mutation in an endogenous gene encoding the plastidial polypeptide. In an embodiment, the decreased amount or rate of production of DAG is relative to a corresponding wild-type plant or part thereof or, preferably, relative to a corresponding plant or part thereof which has the Push modification.

The Push modification is highly desirable in the invention, and the Pull modification is preferred. The Protect and Package modifications may be complementary i.e. one of the two may be sufficient. The plant or part thereof may comprise one, two or all three of the Plastidial Export, Plastidial Import and Prokaryotic Pathway modifications. In an embodiment, at least one of the exogenous polynucleotides in the plant or part thereof, preferably at least the exogenous polynucleotide encoding the transcription factor which regulates fatty acid synthesis in the plastids, is expressed under the control of (H) a promoter other than a constitutive promoter such as, for example, a developmentally related promoter, a promoter that is preferentially active in photosynthetic cells, a tissue-specific promoter, a promoter which has been modified by reducing its expression level relative to a corresponding native promoter, or is preferably a senescence-specific promoter. More preferably, at least the exogenous polynucleotide encoding the transcription factor which regulates fatty acid synthesis in the plastids is expressed under the control of a promoter other than a constitutive promoter and the exogenous polynucleotide which encodes an RNA molecule which down-regulates endogenous production and/or activity of a polypeptide involved in the catabolism of triacylglycerols is also expressed under the control of a promoter other than a constitutive promoter, which promoters may be the same or different. Alternatively in monocotyledonous plants, the exogenous polynucleotide encoding the transcription factor which regulates fatty acid synthesis in the plastids is expressed under the control of a constitutive promoter such as, for example, a ubiquitin gene promoter or an actin gene promoter.

Plants produce some, but not all, of their membrane lipids such as MGDG in plastids by the so-called prokaryotic pathway (FIG. 1). In plants, there is also a eukaryotic pathway for synthesis of galactolipids and glycerolipids which synthesizes FA first of all in the plastid and then assembles the FA into glycerolipids in the ER. MGDG synthesised by the eukaryotic pathway contains C18:3 (ALA) fatty acid esterified at the sn-2 position of MGDG. The DAG backbone including the ALA for the MGDG synthesis by this pathway is assembled in the ER and then imported into the plastid. In contrast, the MGDG synthesized by the prokaryotic pathway contains C16:3 fatty acid esterified at the sn-2 position of MGDG. The ratio of the contribution of the prokaryotic pathway relative to the eukaryotic pathway in producing MGDG (16:3) vs MGDG (18:3) is a characteristic and distinctive feature of different plant species (Mongrand et al. 1998). This distinctive fatty acid composition of MGDG allows all higher plants (angiosperms) to be classified as either so-called 16:3 or 18:3 plants. 16:3 species, exemplified by $Arabidopsis$ and $Brassica$ $napus$, generally have both of the prokaryotic and eukaryotic pathways of MGDG synthesis operating, whereas the 18:3 species exemplified by $Sorghum$ $bicolor$, $Zea$ $mays$, $Nicotiana$ $tabacum$, $Pisum$ $sativum$ and $Glycine$ $max$ generally have only (or almost entirely) the eukaryotic pathway of MGDG synthesis, providing little or no C16:3 fatty acid accumulation in the vegetative tissues. As used herein, a "16:3 plant" or "16:3 species" is one which has more than 2% C16:3 fatty acid in the total fatty acid content of its photosynthetic tissues. As used herein, a "18:3 plant" or "18:3 species" is one which has less than 2% C16:3 fatty acid in the total fatty acid content of its photosynthetic tissues. As described herein, a plant can be converted from being a 16:3 plant to an 18:3 plant by suitable genetic modifications. The proportion of flux between the prokaryote and eukaryote pathways is not conserved across different plant species or tissues. In 16:3 species up to 40% of flux in leaves occurs via the prokaryotic pathway (Browse et al., 1986), while in 18:3 species, such as pea and soybean, about 90% of FAs which are synthesized in the plastid are exported out of the plastid to the ER to supply the source of FA for the eukaryotic pathway (Ohlrogge and Browse, 1995; Somerville et al., 2000).

Therefore different amounts of 18:3 and 16:3 fatty acids are found within the glycolipids of different plant species. This is used to distinguish between 18:3 plants whose fatty acids with 3 double bonds are almost entirely C18 fatty acids and the 16:3 plants that contain both $C_{16}$- and $C_{18}$-fatty acids having 3 double bonds. In chloroplasts of 18:3 plants, enzymic activities catalyzing the conversion of phosphatidate to diacylglycerol and of diacylglycerol to monogalactosyl diacylglycerol (MGD) are significantly less active than in 16:3 chloroplasts. In leaves of 18:3 plants, chloroplasts synthesize stearoyl-ACP2 in the stroma, introduce the first double bond into the saturated hydrocarbon chain, and then hydrolyze the thioester by thioesterases (FIG. 1). Released oleate is exported across chloroplast envelopes into membranes of the cell, probably the endoplasmic reticulum, where it is incorporated into PC. PC-linked oleoyl groups are desaturated in these membranes and subsequently move back into the chloroplast. The MGD-linked acyl groups are substrates for the introduction of the third double bond to yield MGD with two linolenoyl residues. This galactolipid is characteristic of 18:3 plants such as Asteraceae and Fabaceae, for example. In photosynthetically active cells of 16:3 plants which are represented, for example, by members of Apiaceae and Brassicaceae, two pathways operate in parallel to provide thylakoids with MGD.

In one embodiment, the plant or part thereof such as a vegetative plant part of the invention produces higher levels of non-polar lipids such as TAG, or total fatty acid (TFA) content, preferably both, than a corresponding plant or part thereof such as a vegetative plant part which lacks the genetic modifications or exogenous polynucleotides. In one example, plants of the invention produce seeds, leaves, or have leaf portions of at least 1 $cm^2$ in surface area, stems and/or tubers having an increased non-polar lipid content such as TAG or TFA content, preferably both, when compared to corresponding seeds, leaves, leaf portions of at least 1 $cm^2$ in surface area, stems or tubers.

In another embodiment, the plant or part thereof such as a vegetative plant part, produce TAGs that are enriched for one or more particular fatty acids. A wide spectrum of fatty acids can be incorporated into TAGs, including saturated and unsaturated fatty acids and short-chain and long-chain fatty acids. Some non-limiting examples of fatty acids that can be incorporated into TAGs and which may be increased in level include: capric (10:0), lauric (12:0), myristic (14:0), palmitic (16:0), palmitoleic (16:1), stearic (18:0), oleic (18:1), vaccenic (18:1), linoleic (18:2), eleostearic (18:3), γ-linolenic (18:3), α-linolenic (18:3ω3), stearidonic (18:4ω3), arachidic (20:0), eicosadienoic (20:2), dihomo-γ-linoleic (20:3), eicosatrienoic (20:3), arachidonic (20:4), eicosatetraenoic (20:4), eicosapentaenoic (20:5ω3), behenic (22:0), docosapentaenoic (22:5), docosahexaenoic (22:6ω3), lignoceric (24:0), nervonic (24:1), cerotic (26:0), and montanic (28:0) fatty acids. In one embodiment of the present invention, the plant or part thereof is enriched for TAGs comprising oleic acid, and/or is reduced in linolenic acid (ALA), preferably by at least 2% or at least 5% on an absolute basis.

Preferably, the plant or part thereof such as a vegetative plant part of the invention is transformed with one or more exogenous polynucleotides such as chimeric DNAs. In the case of multiple chimeric DNAs, these are preferably covalently linked on one DNA molecule such as, for example, a single T-DNA molecule, and preferably integrated at a single locus in the host cell genome, preferably the host nuclear genome. Alternatively, the chimeric DNAs are on two or more DNA molecules which may be unlinked in the host genome, or the DNA molecule(s) is not integrated into the host genome, such as occurs in transient expression experiments. The plant or part thereof such as a vegetative plant part is preferably homozygous for the one DNA molecule inserted into its genome.

Transcription Factors

Various transcription factors are involved in plant cells in the synthesis of fatty acids and lipids incorporating the fatty acids such as TAG, and therefore can be manipulated for the Push modification. A preferred transcription factor is WRI1. As used herein, the term "Wrinkled 1" or "WRI1" or "WRL1" refers to a transcription factor of the AP2/ER-WEBP class which regulates the expression of several enzymes involved in glycolysis and de novo fatty acid biosynthesis. WRI1 has two plant-specific (AP2/EREB) DNA-binding domains. WRI1 in at least $Arabidopsis$ also regulates the breakdown of sucrose via glycolysis thereby regulating the supply of precursors for fatty acid biosynthesis. In other words, it controls the carbon flow from the photosynthate to storage lipids. wri1 mutants in at least $Arabidopsis$ have a wrinkled seed phenotype, due to a defect in the incorporation of sucrose and glucose into TAGs.

Examples of genes which are transcribed by WRI1 include, but are not limited to, one or more, preferably all, of genes encoding pyruvate kinase (At5 g52920, At3 g22960), pyruvate dehydrogenase (PDH) E1alpha subunit (At1 g01090), acetyl-CoA carboxylase (ACCase), BCCP2 subunit (At5 g15530), enoyl-ACP reductase (At2 g05990; EAR), phosphoglycerate mutase (At1 g22170), cytosolic fructokinase, and cytosolic phosphoglycerate mutase, sucrose synthase (SuSy) (see, for example, Liu et al., 2010; Baud et al., 2007; Ruuska et al., 2002).

WRI1 contains the conserved domain AP2 (cd00018). AP2 is a DNA-binding domain found in transcription regulators in plants such as APETALA2 and EREBP (ethylene responsive element binding protein). In EREBPs the domain specifically binds to the 11 bp GCC box of the ethylene response element (ERE), a promotor element essential for ethylene responsiveness. EREBPs and the C-repeat binding factor CBF1, which is involved in stress response, contain a single copy of the AP2 domain. APETALA2-like proteins, which play a role in plant development contain two copies.

Other sequence motifs which may be found in WRI1 and its functional homologs include:

1.
(SEQ ID NO: 89)
R G V T/S R H R W T G R.

2.
(SEQ ID NO: 90)
F/Y E A H L W D K.

3.
(SEQ ID NO: 91)
D L A A L K Y W G.

4.
(SEQ ID NO: 92)
S X G F S/A R G X.

5.
(SEQ ID NO: 93)
H H H/Q N G R/K W E A R I G R/K V.

6.
(SEQ ID NO: 94)
Q E E A A A X Y D.

As used herein, the term "Wrinkled 1" or "WRI1" also includes "Wrinkled 1-like" or "WRI1-like" proteins. Examples of WRI1 proteins include Accession Nos: Q6X5Y6, (*Arabidopsis thaliana*; SEQ ID NO:22), XP_002876251.1 (*Arabidopsis lyrata* subsp. *Lyrata*; SEQ ID NO:23), ABD16282.1 (*Brassica napus*; SEQ ID NO:24), ADO16346.1 (*Brassica napus*; SEQ ID NO:25), XP_003530370.1 (*Glycine max*; SEQ ID NO:26), AEO22131.1 (*Jatropha curcas*; SEQ ID NO:27), XP_002525305.1 (*Ricinus communis*; SEQ ID NO:28), XP_002316459.1 (*Populus trichocarpa*; SEQ ID NO:29), CBI29147.3 (*Vitis vinifera*: SEQ ID NO:30), XP_003578997.1 (*Brachypodium distachyon*; SEQ ID NO:31), BAJ86627.1 (*Hordeum vulgare* subsp. *vulgare*; SEQ ID NO:32), EAY79792.1 (*Oryza sativa*; SEQ ID NO:33), XP_002450194.1 (*Sorghum bicolor*; SEQ ID NO:34), ACG32367.1 (*Zea mays*; SEQ ID NO:35), XP_003561189.1 (*Brachypodium distachyon*; SEQ ID NO:36), ABL85061.1 (*Brachypodium sylvaticum*; SEQ ID NO:37), BAD68417.1 (*Oryza sativa*; SEQ ID NO:38), XP_002437819.1 (*Sorghum bicolor*; SEQ ID NO:39), XP_002441444.1 (*Sorghum bicolor*; SEQ ID NO:40), XP_003530686.1 (*Glycine max*; SEQ ID NO:41), XP_003553203.1 (*Glycine max*; SEQ ID NO:42), XP_002315794.1 (*Populus trichocarpa*; SEQ ID NO:43), XP_002270149.1 (*Vitis vinifera*; SEQ ID NO:44), XP_003533548.1 (*Glycine max*; SEQ ID NO:45), XP_003551723.1 (*Glycine max*; SEQ ID NO:46), XP_003621117.1 (*Medicago truncatula*; SEQ ID NO:47), XP_002323836.1 (*Populus trichocarpa*; SEQ ID NO:48), XP_002517474.1 (*Ricinus communis*; SEQ ID NO:49), CAN79925.1 (*Vitis vinifera*, SEQ ID NO:50), XP_003572236.1 (*Brachypodium distachyon*; SEQ ID NO:51), BAD10030.1 (*Oryza sativa*; SEQ ID NO:52), XP_002444429.1 (*Sorghum bicolor*; SEQ ID NO:53), NP_001170359.1 (*Zea mays*; SEQ ID NO:54), XP_002889265.1 (*Arabidopsis lyrata* subsp. *lyrata*; SEQ ID NO:55), AAF68121.1 (*Arabidopsis thaliana*; SEQ ID NO:56), NP_178088.2 (*Arabidopsis thaliana*; SEQ ID NO:57), XP_002890145.1 (*Arabidopsis lyrata* subsp. *lyrata*; SEQ ID NO:58), BAJ33872.1 (*Thellungiella halophila*; SEQ ID NO:59), NP_563990.1 (*Arabidopsis thaliana*; SEQ ID NO:60), XP_003530350.1 (*Glycine max*; SEQ ID NO:61), XP_003578142.1 (*Brachypodium distachyon*; SEQ ID NO:62), EAZ09147.1 (*Oryza sativa*; SEQ ID NO:63), XP_002460236.1 (*Sorghum bicolor*; SEQ ID NO:64), NP_001146338.1 (*Zea mays*; SEQ ID NO:65), XP_003519167.1 (*Glycine max*; SEQ ID NO:66), XP_003550676.1 (*Glycine max*; SEQ ID NO:67), XP_003610261.1 (*Medicago truncatula*; SEQ ID NO:68), XP_003524030.1 (*Glycine max*; SEQ ID NO:69), XP_003525949.1 (*Glycine max*; SEQ ID NO:70), XP_002325111.1 (*Populus trichocarpa*; SEQ ID NO:71), CBI36586.3 (*Vitis vinifera*; SEQ ID NO:72), XP_002273046.2 (*Vitis vinifera*; SEQ ID NO:73), XP_002303866.1 (*Populus trichocarpa*; SEQ ID NO:74), and CBI25261.3 (*Vitis vinifera*; SEQ ID NO:75). Further examples include Sorbi-WRL1 (SEQ ID NO:76), Lupan-WRL1 (SEQ ID NO:77), Ricco-WRL1 (SEQ ID NO:78), and Lupin *angustifolius* WRI1 (SEQ ID NO:79). A preferred WRI1 is a maize WRI1 or a sorghum WRI1.

More recently, a subset of WRI1-like transcription factors have been re-classified as WRI2, WRI3 or WRI4 transcription factors, which are characterised by preferential expression in stems and/or roots of plants rather than in developing seeds (To et al., 2012). Despite their re-classification, these are included in the definition of "WRI1" herein. Preferred WRI1-like transcription factors are those which can complement the function of a wri1 mutation in a plant, particularly the function in developing seed of the plant such as in an *A. thaliana* wri1 mutant. The function of a WRI1-like polypeptide can also be assayed in the *N. benthamiana* transient assays as described herein.

The WRI1 transcription factor may be endogenous to the plant or cell, or exogenous to the plant or cell, for example expressed from an exogenous polynucleotide. The WRI1 transcription factor may be a naturally occurring WRI1 polypeptide or a variant thereof, provided it retains transcription factor activity. The level or activity of an endogenous WRI1 polypeptide may also be increased by increased expression of a MED15 polypeptide (Kim et al., 2016), for example polypeptides whose amino acid sequences are provided as SEQ ID NOs:293 or 295, or of a 14-3-3 polypeptide (Ma et al., 2016), for example SEQ ID NOs: 297-304. MED15 polypeptide is thought to assist in directing WRI1 to its target promoters and expression of WRI1 expression itself, while 14-3-3 polypeptides are thought to interact with WRI1 polypeptide to increase the WRI1 effect.

As used herein, a "LEAFY COTYLEDON" or "LEC" polypeptide means a transcription factor which is a LEC1, LEC1-like, LEC2, ABI3 or FUS3 transcription factor which exhibits broad control on seed maturation and fatty acid synthesis. LEC2, FUS3 and ABI3 are related polypeptides that each contain a B3 DNA-binding domain of 120 amino acids (Yamasaki et al., 2004) that is only found in plant proteins. They can be distinguished by phylogenetic analysis to determine relatedness in amino acid sequence to the members of the *A. thaliana* polypeptides having the Accession Nos as follows: LEC2, Accession No. AAL12004.1; FUS3 (also known as FUSCA3), Accession No. AAC35247. LEC1 belongs to a different class of polypeptides and is homologous to a HAP3 polypeptide of the CBF binding factor class (Lee et al., 2003). The LEC1, LEC2 and FUS3 genes are required in early embryogenesis to maintain embryonic cell fate and to specify cotyledon identity and in later in initiation and maintenance of embryo maturation (Santos-Mendoza et al., 2008). They also induce expression of genes encoding seed storage proteins by binding to RY motifs present in the promoters, and oleosin genes. They can also be distinguished by their expression patterns in seed development or by their ability to complement the corresponding mutation in *A. thaliana*.

As used herein, the term "Leafy Cotyledon 1" or "LEC1" refers to a NF-YB-type transcription factor which participates in zygotic development and in somatic embryogenesis. The endogenous gene is expressed specifically in seed in both the embryo and endosperm. LEC1 activates the gene encoding WRI1 as well as a large class of fatty acid synthesis genes. Ectopic expression of LEC2 also causes rapid activation of auxin-responsive genes and may cause formation of somatic embryos. Examples of LEC1 polypeptides include proteins from *Arabidopsis thaliana* (AAC39488, SEQ ID NO:149), *Medicago truncatula* (AFK49653, SEQ ID NO:154) and *Brassica napus* (ADF81045, SEQ ID NO:151), *A. lyrata* (XP_002862657, SEQ ID NO:150), *R. communis* (XP_002522740, SEQ ID NO:152), *G. max* (XP_006582823, SEQ ID NO:153), *A. hypogaea* (ADC33213, SEQ ID NO:156), *Z. mays* (AAK95562, SEQ ID NO:155).

LEC1-like (L1L) is closely related to LEC1 but has a different pattern of gene expression, being expressed earlier during embryogenesis (Kwong et al., 2003). Examples of LEC1-like polypeptides include proteins from *Arabidopsis thaliana* (AAN15924, SEQ ID NO:157), *Brassica napus* (AHI94922, SEQ ID NO:158), and *Phaseolus coccineus* LEC1-like (AAN01148, SEQ ID NO: 159).

As used herein, the term "Leafy Cotyledon 2" or "LEC2" refers to a B3 domain transcription factor which participates in zygotic development and in somatic embryogenesis and which activates expression of a gene encoding WRI1. Its ectopic expression facilitates the embryogenesis from vegetative plant tissues (Alemanno et al., 2008). Examples of LEC2 polypeptides include proteins from *Arabidopsis thaliana* (Accession No. NP_564304.1, SEQ ID NO:142), *Medicago truncatula* (Accession No. CAA42938.1, SEQ ID NO:143) and *Brassica napus* (Accession No. ADO16343.1, SEQ ID NO:144).

In an embodiment, an exogenous polynucleotide of the invention which encodes a LEC2 comprises one or more of the following:
i) nucleotides encoding a polypeptide comprising amino acids whose sequence is set forth as any one of SEQ ID NOs:142 to 144, or a biologically active fragment thereof, or a polypeptide whose amino acid sequence is at least 30% identical to any one or more of SEQ ID NOs:142 to 144,
ii) nucleotides whose sequence is at least 30% identical to i), and
iii) a polynucleotide which hybridizes to one or both of i) or ii) under stringent conditions.

As used herein, the term "FUS3" refers to a B3 domain transcription factor which participates in zygotic development and in somatic embryogenesis and is detected mainly in the protodermal tissue of the embryo (Gazzarrini et al., 2004). Examples of FUS3 polypeptides include proteins from *Arabidopsis thaliana* (AAC35247, SEQ ID NO:160), *Brassica napus* (XP_006293066.1, SEQ ID NO:161) and *Medicago truncatula* (XP_003624470, SEQ ID NO:162). Over-expression of any of LEC1, L1L, LEC2, FUS3 and ABI3 from an exogenous polynucleotide is preferably controlled by a developmentally regulated promoter such as a senescence specific promoter, an inducible promoter, or a promoter which has been engineered for providing a reduced level of expression relative to a native promoter, particularly in plants other than *Arabidopsis thaliana* and *B. napus* cv. Westar, in order to avoid developmental abnormalities in plant development that are commonly associated with over-expression of these transcription factors (Mu et al., 2008).

As used herein, the term "BABY BOOM" or "BBM" refers an AP2/ERF transcription factor that induces regeneration under culture conditions that normally do not support regeneration in wild-type plants. Ectopic expression of *Brassica napus* BBM (BnBBM) genes in *B. napus* and *Arabidopsis* induces spontaneous somatic embryogenesis and organogenesis from seedlings grown on hormone-free basal medium (Boutilier et al., 2002). In tobacco, ectopic BBM expression is sufficient to induce adventitious shoot and root regeneration on basal medium, but exogenous cytokinin is required for somatic embryo (SE) formation (Srinivasan et al., 2007). Examples of BBM polypeptides include proteins from *Arabidopsis thaliana* (Accession No. NP_197245.2, SEQ ID NO:145), maize (U.S. Pat. No. 7,579,529), *Sorghum bicolor* (Accession No. XP_002458927) and *Medicago truncatula* (Accession No. AAW82334.1, SEQ ID NO:146).

In an embodiment, an exogenous polynucleotide of the invention which encodes BBM comprises, unless specified otherwise, one or more of the following:
i) nucleotides encoding a polypeptide comprising amino acids whose sequence is set forth as one of SEQ ID NOs:145 or 146, or a biologically active fragment thereof, or a polypeptide whose amino acid sequence is at least 30% identical to one or both of SEQ ID NOs: 145 or 146,
ii) nucleotides whose sequence is at least 30% identical to i), and
iii) a polynucleotide which hybridizes to one or both of i) or ii) under stringent conditions.

An ABI3 polypeptide (*A. thaliana* Accession No. NP_189108) is related to the maize VP1 protein, is expressed at low levels in vegetative tissues and affects plastid development. An ABI4 polypeptide (*A. thaliana* Accession NP_181551) belongs to a family of transcription factors that contain a plant-specific AP2 domain (Finkelstein et al., 1998) and acts downstream of ABI3. ABI5 (*A. thaliana* Accession No. NP 565840) is a transcription factor of the bZIP family which affects ABA sensitivity and controls the expression of some LEA genes in seeds. It binds to an ABA-responsive element.

Each of the following transcription factors was selected on the basis that they functioned in embryogenesis in plants. Accession numbers are provided in Table 26. Homologs of each can be readily identified in many other plant species and tested as described in Example 9.

MYB73 is a transcription factor that has been identified in soybean, involved in stress responses.

bZIP53 is a transcription factor in the bZIP protein family, identified in *Arabidopsis*.

AGL15 (Agamous-like 15) is a MADS box transcription factor which is natively expressed during embryogenesis. AGL15 is also natively expressed in leaf primordia, shoot apical meristems and young floral buds, suggesting that AGL15 may also have a function during post-germinative development. AGL15 has a role in embryogenesis and gibberellic acid catabolism. It targets B3 domain transcription factors that are key regulators of embryogenesis.

MYB115 and MYB118 are transcription factors in the MYB family from *Arabidopsis* involved in embryogenesis.

TANMEI also known as EMB2757 encodes a WD repeat protein required for embryo development in *Arabidopsis*.

WUS, also known as Wuschel, is a homeobox gene that controls the stem cell pool in embryos. It is expressed in the stem cell organizing center of meristems and is required to keep the stem cells in an undifferentiated state. The transcription factor binds to a TAAT element core motif.

GFR2a1 and GFR2a2 are transcription factors at least from soybean.

Fatty Acyl Acyltransferases

As used herein, the term "fatty acyl acyltransferase" refers to a protein which is capable of transferring an acyl group from acyl-CoA, PC or acyl-ACP, preferably acyl-CoA or PC, onto a substrate to form TAG, DAG or MAG. These acyltransferases include DGAT, PDAT, MGAT, GPAT and LPAAT.

As used herein, the term "diacylglycerol acyltransferase" (DGAT) refers to a protein which transfers a fatty acyl group from acyl-CoA to a DAG substrate to produce TAG. Thus, the term "diacylglycerol acyltransferase activity" refers to the transfer of an acyl group from acyl-CoA to DAG to produce TAG. A DGAT may also have MGAT function but predominantly functions as a DGAT, i.e., it has greater catalytic activity as a DGAT than as a MGAT when the enzyme activity is expressed in units of nmoles product/min/mg protein (see for example, Yen et al., 2005). The activity of DGAT may be rate-limiting in TAG synthesis in seeds (Ichihara et al., 1988). DGAT uses an acyl-CoA substrate as the acyl donor and transfers it to the sn-3 position of DAG to form TAG. The enzyme functions in its native state in the endoplasmic reticulum (ER) of the cell.

There are three known types of DGAT, referred to as DGAT1, DGAT2 and DGAT3, respectively. DGAT1 polypeptides are membrane proteins that typically have 10 transmembrane domains, DGAT2 polypeptides are also membrane proteins but typically have 2 transmembrane domains, whilst DGAT3 polypeptides typically have none and are thought to be soluble in the cytoplasm, not integrated into membranes. Plant DGAT1 polypeptides typically have about 510-550 amino acid residues while DGAT2 polypeptides typically have about 310-330 residues. DGAT1 is the main enzyme responsible for producing TAG from DAG in most developing plant seeds, whereas DGAT2s from plant species such as tung tree (*Vernicia fordii*) and castor bean (*Ricinus communis*) that produce high amounts of unusual fatty acids appear to have important roles in the accumulation of the unusual fatty acids in TAG. Over-expression of AtDGAT1 in tobacco leaves resulted in a 6-7 fold increased TAG content (Bouvier-Nave et al., 2000).

Examples of DGAT1 polypeptides include DGAT1 proteins from *Aspergillus fumigatus* (XP_755172.1; SEQ ID NO:80), *Arabidopsis thaliana* (CAB44774.1; SEQ ID NO:1), *Ricinus communis* (AAR11479.1; SEQ ID NO:81), *Vernicia fordii* (ABC94472.1; SEQ ID NO:82), *Vernonia galamensis* (ABV21945.1 and ABV21946.1; SEQ ID NO:83 and SEQ ID NO:84, respectively), *Euonymus alatus* (AAV31083.1; SEQ ID NO:85), *Nannochloropsis oceanica* (Zienkiewicz et al 2017), yeast (Zulu et al 2017), *Caenorhabditis elegans* (AAF82410.1; SEQ ID NO:86), *Rattus norvegicus* (NP 445889.1; SEQ ID NO:87), *Homo sapiens* (NP_036211.2; SEQ ID NO:88), as well as variants and/or mutants thereof. Examples of DGAT2 polypeptides include proteins encoded by DGAT2 genes from *Arabidopsis thaliana* (NP_566952.1; SEQ ID NO:2), *Ricinus communis* (AAY16324.1; SEQ ID NO:3), *Vernicia fordii* (ABC94474.1; SEQ ID NO:4), *Mortierella ramanniana* (AAK84179.1; SEQ ID NO:5), *Homo sapiens* (Q96PD7.2; SEQ ID NO:6) (Q58HT5.1; SEQ ID NO:7), *Bos taurus* (Q70VZ8.1; SEQ ID NO:8), *Mus musculus* (AAK84175.1; SEQ ID NO:9), as well as variants and/or mutants thereof. DGAT1 and DGAT2 amino acid sequences show little homology. Expression in leaves of an exogenous DGAT2 was twice as effective as a DGAT1 in increasing oil content (TAG). Further, *A. thaliana* DGAT2 had a greater preference for linoleoyl-CoA and linolenoyl-CoA as acyl donors relative to oleoyl-CoA, compared to DGAT1. This substrate preference can be used to distinguish the two DGAT classes in addition to their amino acid sequences.

Examples of DGAT3 polypeptides include proteins encoded by DGAT3 genes from peanut (*Arachis hypogaea*, Saha, et al., 2006), as well as variants and/or mutants thereof. A DGAT has little or no detectable MGAT activity, for example, less than 300 pmol/min/mg protein, preferably less than 200 pmol/min/mg protein, more preferably less than 100 pmol/min/mg protein.

In an embodiment, an exogenous polynucleotide of the invention which encodes a DGAT1 comprises one or more of the following:

i) nucleotides encoding a polypeptide comprising amino acids whose sequence is set forth as any one of SEQ ID NOs:1 or 80 to 88, or a biologically active fragment thereof, or a polypeptide whose amino acid sequence is at least 30% identical to any one or more of SEQ ID NOs: 1 or 80 to 88, ii) nucleotides whose sequence is at least 30% identical to i), and iii) a polynucleotide which hybridizes to one or both of i) or ii) under stringent conditions.

In an embodiment, an exogenous polynucleotide of the invention which encodes a DGAT2 comprises one or more of the following:

i) nucleotides encoding a polypeptide comprising amino acids whose sequence is set forth as any one of SEQ ID NOs:2 to 9, or a biologically active fragment thereof, or a polypeptide whose amino acid sequence is at least 30% identical to any one or more of SEQ ID NOs: 2 to 9, ii) nucleotides whose sequence is at least 30% identical to i), and iii) a polynucleotide which hybridizes to one or both of i) or ii) under stringent conditions.

As used herein, the term "phospholipid:diacylglycerol acyltransferase" (PDAT; EC 2.3.1.158) or its synonym "phospholipid:1,2-diacyl-sn-glycerol O-acyltransferase" means an acyltransferase that transfers an acyl group from a phospholipid, typically from the sn-2 position of PC, to the sn-3 position of DAG to form TAG and lysophosphocholine (LPC). This reaction is different to DGAT and uses phospholipids as the acyl-donors. Increased expression of PDAT such as PDAT1, which may be exogenous or endogenous to the cell or plant of the invention, increases the production of TAG from PC. The enzyme LPCAT can re-acylate the LPC to form more PC, allowing for continued production of DAG by PDAT. There are several forms of PDAT in plant cells including PDAT1, PDAT2 or PDAT3 (Ghosal et al., 2007). Sequences of exemplary PDAT coding regions and polypeptides are provided herein as SEQ ID NOs:258-261 (*Sorghum* and *Zea mays* PDAT1, Accession Nos XM_002462417.1 and NM_001147943), (Dahlqvist et al., 2000; Fan et al., 2013; Fan et al., 2014) although any PDAT encoding gene can be used. Homologs and naturally occurring variants of PDATs from these or other plant, fungal or algal species can readily be identified and used in the present invention. In an embodiment, the homolog or variant is at least 95% identical, preferably at least 99% identical, to the amino acid sequence of the listed SEQ ID NO or Accession No. The PDAT may be exogenous or endogenous to the plant or part thereof.

As used herein, the term "monoacylglycerol acyltransferase" or "MGAT" refers to a protein which transfers a fatty acyl group from acyl-CoA to a MAG substrate, for example sn-2 MAG, to produce DAG. Thus, the term "monoacylglycerol acyltransferase activity" at least refers to the transfer of an acyl group from acyl-CoA to MAG to produce DAG. The term "MGAT" as used herein includes enzymes that act on sn-1/3 MAG and/or sn-2 MAG substrates to form sn-1,3 DAG and/or sn-1,2/2,3-DAG, respectively. In a preferred embodiment, the MGAT has a preference for sn-2 MAG substrate relative to sn-1 MAG, or substantially uses only sn-2 MAG as substrate. As used herein, MGAT does not include enzymes which transfer an acyl group preferentially to LysoPA relative to MAG, such enzymes are known as LPAATs. That is, a MGAT preferentially uses non-phosphorylated monoacyl substrates, even though they may also have low catalytic activity on LysoPA. A preferred MGAT does not have detectable activity in acylating LysoPA. A MGAT may also have DGAT function but predominantly functions as a MGAT, i.e., it has greater catalytic activity as a MGAT than as a DGAT when the enzyme activity is expressed in units of nmoles product/min/mg protein (also see Yen et al., 2002). There are three known classes of MGAT, referred to as, MGAT1, MGAT2 and MGAT3, respectively. Examples of MGAT1, MGAT2 and MGAT3 polypeptides are described in WO2013/096993.

As used herein, an "MGAT pathway" refers to an anabolic pathway, different to the Kennedy pathway for the formation of TAG, in which DAG is formed by the acylation of either sn-1 MAG or preferably sn-2 MAG, catalysed by MGAT. The DAG may subsequently be used to form TAG or other lipids. WO2012/000026 demonstrated firstly that plant leaf tissue can synthesise MAG from G-3-P such that the MAG is accessible to an exogenous MGAT expressed in the leaf tissue, secondly MGAT from various sources can function in plant tissues, requiring a successful interaction with other plant factors involved in lipid synthesis and thirdly the DAG produced by the exogenous MGAT activity is accessible to a plant DGAT, or an exogenous DGAT, to produce TAG. MGAT and DGAT activity can be assayed by introducing constructs encoding the enzymes (or candidate enzymes) into *Saccharomyces cerevisiae* strain H1246 and demonstrating TAG accumulation.

Some of the motifs that have been shown to be important for catalytic activity in some DGAT2s are also conserved in MGAT acyltransferases. Of particular interest is a putative neutral lipid-binding domain with the consensus sequence FLXLXXXN (SEQ ID NO:14) where each X is independently any amino acid other than proline, and N is any nonpolar amino acid, located within the N-terminal transmembrane region followed by a putative glycerol/phospholipid acyltransferase domain. The FLXLXXXN motif (SEQ ID NO:14) is found in the mouse DGAT2 (amino acids 81-88) and MGAT1/2 but not in yeast or plant DGAT2s. It is important for activity of the mouse DGAT2. Other DGAT2 and/or MGAT1/2 sequence motifs include:

1. A highly conserved YFP tripeptide (SEQ ID NO:10) in most DGAT2 polypeptides and also in MGAT1 and MGAT2, for example, present as amino acids 139-141 in mouse DGAT2. Mutating this motif within the yeast DGAT2 with non-conservative substitutions rendered the enzyme non-functional.

2. HPHG tetrapeptide (SEQ ID NO:11), highly conserved in MGATs as well as in DGAT2 sequences from animals and fungi, for example, present as amino acids 161-164 in mouse DGAT2, and important for catalytic activity at least in yeast and mouse DGAT2. Plant DGAT2 acyltransferases have a EPHS (SEQ ID NO:12) conserved sequence instead, so conservative changes to the first and fourth amino acids can be tolerated.

3. A longer conserved motif which is part of the putative glycerol phospholipid domain. An example of this motif is RXGFX(K/R)XAXXXGXXX(L/V)VPXXXFG(E/Q) (SEQ ID NO:13), which is present as amino acids 304-327 in mouse DGAT2. This motif is less conserved in amino acid sequence than the others, as would be expected from its length, but homologs can be recognised by motif searching. The spacing may vary between the more conserved amino acids, i.e., there may be additional X amino acids within the motif, or less X amino acids compared to the sequence above.

One important component in glycerolipid synthesis from fatty acids esterified to ACP or CoA is the enzyme sn-glycerol-3-phosphate acyltransferase (GPAT), which is another of the polypeptides involved in the biosynthesis of non-polar lipids. This enzyme is involved in different metabolic pathways and physiological functions. It catalyses the following reaction: G3P+fatty acyl-ACP or -CoA→LPA+free-ACP or -CoA. The GPAT-catalyzed reaction occurs in three distinct plant subcellular compartments: plastid, endoplasmic reticulum (ER) and mitochondria. These reactions are catalyzed by three different types of GPAT enzymes, a soluble form localized in plastidial stroma which uses acyl-ACP as its natural acyl substrate (PGPAT in FIG. 1), and two membrane-bound forms localized in the ER and mitochondria which use acyl-CoA and acyl-ACP as natural acyl donors, respectively (Chen et al., 2011).

As used herein, the term "glycerol-3-phosphate acyltransferase" (GPAT; EC 2.3.1.15) and its synonym "glycerol-3-phosphate O-acyltransferase" refer to a protein which acylates glycerol-3-phosphate (G-3-P) to form LysoPA and/or MAG, the latter product forming if the GPAT also has phosphatase activity on LysoPA. The acyl group that is transferred is from acyl-CoA if the GPAT is an ER-type GPAT (an "acyl-CoA:sn-glycerol-3-phosphate 1-O-acyltransferase" also referred to as "microsomal GPAT") or from acyl-ACP if the GPAT is a plastidial-type GPAT (PGPAT). Thus, the term "glycerol-3-phosphate acyltransferase activity" refers to the acylation of G-3-P to form LysoPA and/or MAG. The term "GPAT" encompasses enzymes that acylate G-3-P to form sn-1 LPA and/or sn-2 LPA, preferably sn-2 LPA. Preferably, the GPAT which may be over-expressed in the Pull modification is a membrane bound GPAT that functions in the ER of the cell, more preferably a GPAT9, and the plastidial GPAT that is down-regulated in the Prokaryotic Pathway modification is a soluble GPAT ("plastidial GPAT"). In a preferred embodiment, the GPAT has phosphatase activity. In a most preferred embodiment, the GPAT is a sn-2 GPAT having phosphatase activity which produces sn-2 MAG.

As used herein, the term "sn-1 glycerol-3-phosphate acyltransferase" (sn-1 GPAT) refers to a protein which acylates sn-glycerol-3-phosphate (G-3-P) to preferentially form 1-acyl-sn-glycerol-3-phosphate (sn-1 LPA). Thus, the term "sn-1 glycerol-3-phosphate acyltransferase activity" refers to the acylation of sn-glycerol-3-phosphate to form 1-acyl-sn-glycerol-3-phosphate (sn-1 LPA).

As used herein, the term "sn-2 glycerol-3-phosphate acyltransferase" (sn-2 GPAT) refers to a protein which acylates sn-glycerol-3-phosphate (G-3-P) to preferentially form 2-acyl-sn-glycerol-3-phosphate (sn-2 LPA). Thus, the term "sn-2 glycerol-3-phosphate acyltransferase activity" refers to the acylation of sn-glycerol-3-phosphate to form 2-acyl-sn-glycerol-3-phosphate (sn-2 LPA).

The GPAT family is large and all known members contain two conserved domains, a plsC acyltransferase domain (PF01553; SEQ ID NO:15) and a HAD-like hydrolase (PF12710; SEQ ID NO:16) superfamily domain and variants thereof. In addition to this, at least in *Arabidopsis thaliana*, GPATs in the subclasses GPAT4-GPAT8 all contain a N-terminal region homologous to a phosphoserine phosphatase domain (PF00702; SEQ ID NO:17), and GPATs which produce MAG as a product can be identified by the presence of such a homologous region. Some GPATs expressed endogenously in leaf tissue comprise the conserved amino acid sequence GDLVICPEGTTCREP (SEQ ID NO:18). GPAT4 and GPAT6 both contain conserved residues that are known to be critical to phosphatase activity, specifically conserved amino acids in Motif I (DXDX[T/V][L/V]; SEQ ID NO:19) and Motif III (K-[G/S][D/S]XXX[D/N]; SEQ ID NO:20) located at the N-terminus (Yang et al., 2010).

Homologues of *Arabidopsis* GPAT4 (Accession No. NP_171667.1) and GPAT6 (NP_181346.1) include AAF02784.1 (*Arabidopsis thaliana*), AAL32544.1 (*Arabidopsis thaliana*), AAP03413.1 (*Oryza sativa*), ABK25381.1 (*Picea sitchensis*), ACN34546.1 (*Zea Mays*), BAF00762.1 (*Arabidopsis thaliana*), BAH00933.1 (*Oryza sativa*), EAY84189.1 (*Oryza sativa*), EAY98245.1 (*Oryza sativa*), EAZ21484.1 (*Oryza sativa*), EEC71826.1 (*Oryza sativa*), EEC76137.1 (*Oryza sativa*), EEE59882.1 (*Oryza sativa*), EFJ08963.1 (*Selaginella moellendorffii*), EFJ11200.1 (*Selaginella moellendorffii*), NP_001044839.1 (*Oryza sativa*), NP_001045668.1 (*Oryza sativa*), NP_001147442.1 (*Zea mays*), NP_001149307.1 (*Zea mays*), NP_001168351.1 (*Zea mays*), AFH02724.1 (*Brassica napus*) NP_191950.2 (*Arabidopsis thaliana*), XP_001765001.1 (*Physcomitrella patens*), XP_001769671.1 (*Physcomitrella patens*), (*Vitis vinifera*), XP_002275348.1 (*Vitis vinifera*), XP_002276032.1 (*Vitis vinifera*), XP_002279091.1 (*Vitis vinifera*), XP_002309124.1 (*Populus trichocarpa*), XP_002309276.1 (*Populus trichocarpa*), XP_002322752.1 (*Populus trichocarpa*), XP_002323563.1 (*Populus trichocarpa*), XP_002439887.1 (*Sorghum bicolor*), XP_002458786.1 (*Sorghum bicolor*), XP_002463916.1 (*Sorghum bicolor*), XP_002464630.1 (*Sorghum bicolor*), XP_002511873.1 (*Ricinus communis*), XP_002517438.1 (*Ricinus communis*), XP_002520171.1 (*Ricinus communis*), ACT32032.1 (*Vernicia fordii*), NP_001051189.1 (*Oryza sativa*), AFH02725.1 (*Brassica napus*), XP_002320138.1 (*Populus trichocarpa*), XP_002451377.1 (*Sorghum bicolor*), XP_002531350.1 (*Ricinus communis*), and XP_002889361.1 (*Arabidopsis lyrata*).

The soluble plastidial GPATs (PGPAT, also known as ATS1 in *Arabidopsis thaliana*) have been purified and genes encoding them cloned from several plant species such as pea (*Pisum sativum*, Accession number: P30706.1), spinach (*Spinacia oleracea*, Accession number: Q43869.1), squash (*Cucurbita moschate*, Accession number: P10349.1), cucumber (*Cucumis sativus*, Accession number: Q39639.1) and *Arabidopsis thaliana* (Accession number: Q43307.2). The soluble plastidial GPAT is the first committed step for what is known as the prokaryotic pathway of glycerolipid synthesis and is operative only in the plastid (FIG. 1). The so-called prokaryotic pathway is located exclusively in plant plastids and assembles DAG for the synthesis of galactolipids (MGDG and DGMG) which contain C16:3 fatty acids esterified at the sn-2 position of the glycerol backbone.

Conserved motifs and/or residues can be used as a sequence-based diagnostic for the identification of GPAT enzymes. Alternatively, a more stringent function-based assay could be utilised. Such an assay involves, for example, feeding labelled glycerol-3-phosphate to cells or microsomes and quantifying the levels of labelled products by thin-layer chromatography or a similar technique. GPAT activity results in the production of labelled LPA whilst GPAT/phosphatase activity results in the production of labelled MAG.

As used herein, the term "lysophosphatidic acid acyltransferase" (LPAAT; EC 2.3.1.51) and its synonyms "1-acyl-glycerol-3-phosphate acyltransferase", "acyl-CoA:1-acyl-sn-glycerol-3-phosphate 2-O-acyltransferase" and "1-acylglycerol-3-phosphate O-acyltransferase" refer to a protein which acylates lysophosphatidic acid (LPA) to form phosphatidic acid (PA). The acyl group that is transferred is from acyl-CoA if the LPAAT is an ER-type LPAAT or from acyl-ACP if the LPAAT is a plastidial-type LPAAT (PL-PAAT). Thus, the term "lysophosphatidic acid acyltransferase activity" refers to the acylation of LPA to form PA.

Oil Body Coating Polypeptides

Plant seeds and pollen accumulate TAG in subcellular structures called oil bodies which generally range from 0.5-2.5 µm in diameter. As used herein, "lipid droplets", also referred to as "oil bodies", are lipid rich cellular organelles for storage or exchange of neutral lipids including predominantly TAG. Lipid droplets can vary greatly in size from about 20 nm to 100 m. These organelles have a TAG core surround by a phospholipid monolayer containing several embedded proteins which are involved in lipid metabolism and storage as well as lipid trafficking to other membranes, including oleosins if the oil bodies are from plant seeds or floral tissues (Jolivet et al., 2004). They generally consist of 0.5-3.5% protein while the remainder is the lipid. They are the least dense of the organelles in most cells and can therefore be isolated readily by flotation centrifugation. Oleosins represent the most abundant (at least 80%) of the protein in the membrane of oil bodies from seeds.

In an embodiment, the oil body coating polypeptide is non-allergenic, or not known to be allergenic, such as to humans. As used herein, the term "allergenic polypeptide" means a polypeptide which is characterised by the presence of two features: (i) its amino acid sequence comprises a region of at least 80 consecutive amino acids whose sequence is at least 35% identical to a sequence of at least 80 consecutive amino acids of a known allergenic protein, and (ii) its amino acid sequence comprises at least 8 consecutive amino acids which are identical in sequence to a region of at least 8 consecutive amino acids of a known allergenic protein. As used herein, a "non-allergenic polypeptide" is a polypeptide which is not an allergenic polypeptide. Preferred non-allergenic polypeptides are polypeptides which do not have each of features (i) and (ii). For clarity, non-allergenic polypeptides may have feature (i) or (ii) but not both (i) and (ii). A subset of non-allergenic polypeptides have feature (i) but not feature (ii); these are less preferred than polypeptides which have neither feature (i) nor (ii).

The features described as (i) and (ii) may be determined by carrying out a search using the AllergenOnline database and search facility, available at www.allergenonline.org. Two searches are carried out using the amino acid sequence of the polypeptide of interest, which is used as a query to search the database of known allergen sequences at AllergenOnline. The first search uses a sliding window of 80 amino acids from the polypeptide of interest (amino acids 1-80, 2-81, 3-82 etc), looking for matches of at least 35% identity by the FASTA program (Pearson and Lipman, 1988). The 35% identity for 80 amino acid segments was proposed in a scientific advisory to regulators for evaluating polypeptides in genetically modified crops, see FAO/WHO 2001 and Codex 2003. The segment matching process evaluating segments of 80 amino acids appears to be quite conservative. That is, when this first search is used on its own in classifying polypeptides as potentially allergenic, a positive match at the 35% identity level may mis-classify polypeptides as potentially allergenic when the extent of identity does not have biological significance for allergenicity. Therefore, the second search for an 8-amino acid match is also carried out, and the polypeptide of interest is classified as a potential allergen on the basis of a positive match in both searches, not just one search.

When the AllergenOnline database was searched using query sequences, polypeptides including maize WRI1, *Arabidopsis* DGAT1, palm DGAT1.1, coconut GPAT9, *Arabidopsis* FatA2, *Arabidopsis* caleosin (At2 g33380), *Nannochloropsis* LDSP, pepper fibrillin, *Rhodococcus* TadA, and all caleosins tested showed zero matches in the 80 amino acid sliding window search and are therefore classified as non-allergenic. Other sequences including the vanilla U1 oleosin, Chinese tallow LDAP2, *Arabidopsis* steroleosin (At5 g50600), peanut Oleosin3, sesame oleosinH, avocado oleosin, fig oleosin, cucumber oleosin, flax oleosin, soybean oleosin, *Brassica* oleosin and potato oleosin all produced one or more matches in the 80 amino acid sliding window search (i.e at least 35% identity to a known allergenic protein in a region of at least 80 amino acids) but did not provide any matches in the 8 amino acid search. These were therefore classified as non-allergenic according to the definition above. In contrast, sesame oleosinL was identified as an allergenic polypeptide, providing matches in both searches.

As used herein, the term "Oleosin" refers to an amphipathic protein present in the membrane of oil bodies in the storage tissues of seeds (see, for example, Huang, 1996; Tai et al., 2002, Lin et al., 2005; Capuano et al., 2007; Lui et al., 2009; Shimada and Hara-Nishimura, 2010) and artificially produced variants (see for example WO2011/053169 and WO2011/127118).

Oleosins are of low $M_r$ (15-26,000), corresponding to about 140-230 amino acid residues, which allows them to become tightly packed on the surface of oil bodies. Within each seed species, there are usually two or more oleosins of different $M_r$. Each oleosin molecule contains a relatively hydrophilic, variable N-terminal domain (for example, about 48 amino acid residues), a central totally hydrophobic domain (for example, of about 70-80 amino acid residues) which is particularly rich in aliphatic amino acids such as alanine, glycine, leucine, isoleucine and valine, and an amphipathic α-helical domain of about 30-40 amino acid residues at or near the C-terminus. The central hydrophobic domain typically contains a proline knot motif of about 12 residues at its center. Generally, the central stretch of hydrophobic residues is inserted into the lipid core and the amphiphatic N-terminal and/or amphiphatic C-terminal are located at the surface of the oil bodies, with positively charged residues embedded in a phospholipid monolayer and the negatively charged ones exposed to the exterior.

As used herein, the term "Oleosin" encompasses polyoleosins which have multiple oleosin polypeptides fused together in a head-to-tail fashion as a single polypeptide (WO2007/045019), for example 2×, 4× or 6× oleosin peptides, and caleosins which bind calcium and which are a minor protein component of the proteins that coat oil bodies in seeds (Froissard et al., 2009), and steroleosins which bind sterols (WO2011/053169). However, generally a large proportion (at least 80%) of the oleosins of oil bodies will not be caleosins and/or steroleosins. The term "oleosin" also encompasses oleosin polypeptides which have been modified artificially, such oleosins which have one or more amino acid residues of the native oleosins artificially replaced with cysteine residues, as described in WO2011/053169. Typically, 4-8 residues are substituted artificially, preferably 6 residues, but as many as between 2 and 14 residues can be substituted. Preferably, both of the amphipathic N-terminal and C-terminal domains comprise cysteine substitutions. The modification increases the cross-linking ability of the oleosins and increases the thermal stability and/or the stability of the proteins against degradation by proteases.

A substantial number of oleosin protein sequences, and nucleotide sequences encoding therefor, are known from a large number of different plant species. Examples include, but are not limited to, oleosins from sesame, *Arabidposis*, canola, corn, rice, peanut, castor, soybean, flax, grape, cabbage, cotton, sunflower, sorghum and barley. Examples of oleosins (with their Accession Nos) include *Brassica napus* oleosin (CAA57545.1; SEQ ID NO:95), *Brassica napus* oleosin S1-1 (ACG69504.1; SEQ ID NO:96), *Brassica napus* oleosin S2-1 (ACG69503.1; SEQ ID NO:97), *Brassica napus* oleosin S3-1 (ACG69513.1; SEQ ID NO:98), *Brassica napus* oleosin S4-1 (ACG69507.1; SEQ ID NO:99), *Brassica napus* oleosin S5-1 (ACG69511.1; SEQ ID NO:100), *Arachis hypogaea* oleosin 1 (AAZ20276.1; SEQ ID NO:101), *Arachis hypogaea* oleosin 2 (AAU21500.1; SEQ ID NO:102), *Arachis hypogaea* oleosin 3 (AAU21501.1; SEQ ID NO:103), *Arachis hypogaea* oleosin 5 (ABC96763.1; SEQ ID NO:104), *Ricinus communis* oleosin 1 (EEF40948.1; SEQ ID NO:105), *Ricinus communis* oleosin 2 (EEF51616.1; SEQ ID NO:106), *Glycine max* oleosin isoform a (P29530.2; SEQ ID NO:107), *Glycine max* oleosin isoform b (P29531.1; SEQ ID NO:108), *Linum usitatissimum* oleosin low molecular weight isoform (ABB01622.1; SEQ ID NO:109), *Linum usitatissimum* oleosin high molecular weight isoform (ABB01624.1; SEQ ID NO:110), *Helianthus annuus* oleosin (CAA44224.1; SEQ ID NO:111), *Zea mays* oleosin (NP_001105338.1; SEQ ID NO:112), *Brassica napus* steroleosin (ABM30178.1; SEQ ID NO:113), *Brassica napus* steroleosin SLO1-1 (ACG69522.1; SEQ ID NO:114), *Brassica napus* steroleosin SLO2-1 (ACG69525.1; SEQ ID NO:115), *Sesamum indicum* steroleosin (AAL13315.1; SEQ ID NO:116), *Sesame indicum* OleosinL (Tai et al., 2002; Accession number AF091840; SEQ ID NO:305), *Ficus pumila* var. *awkeotsang* oleosin L-isoform (Accession No. ABQ57397.1; SEQ ID NO: 306), *Cucumis sativus* oleosinL (Accession No. XP_004146901.1; SEQ ID NO: 307), *Linum usitatissimum* oleosinL (Accession No. ABB01618.1; SEQ ID NO: 308), *Glycine max* oleosinL (Accession No.

XP_003556321.2; SEQ ID NO: 309), *Ananas comosus* oleosinL (Accession No. OAY72596.1; SEQ ID NO: 310), *Setaria italica* oleosinL (Accession No. XP_004956407.1; SEQ ID NO: 311), *Fragaria vesca* subsp. *vesca* oleosinL (Accession No. XP_004307777.1; SEQ ID NO: 312), *Brassica napus* oleosinL (Accession No. CDY03377.1; SEQ ID NO: 313), *Solanum lycopersicum* oleosinL (Accession No. XP_004240765.1; SEQ ID NO: 314), *Sesame indicum* OleosinH1 (Tai et al., 2002; Accession number AF302807), *Vanilla planfolia* leaf OleosinU1 (Huang and Huang, 2016; Accession number SRX648194), *Persea americana* mesocarp OleosinM lipid droplet associated protein (Huang and Huang, 2016; Accession number SRX627420), *Arachis hypogaea* Oleosin 3 (Parthibane et al., 2012; Accession number AY722696), *A. thaliana* Caleosin3 (Shen et al., 2014; Laibach et al., 2015; Accession number AK317039), *A. thaliana* steroleosin (Accession number AT081653), *Zea mays* steroleosin (NP_001152614.1; SEQ ID NO:117), *Brassica napus* caleosin CLO-1 (ACG69529.1; SEQ ID NO:118), *Brassica napus* caleosin CLO-3 (ACG69527.1; SEQ ID NO:119), *Sesamum indicum* caleosin (AAF13743.1; SEQ ID NO:120), *Zea mays* caleosin (NP_001151906.1; SEQ ID NO:121), *Glycine max* caleosin (AAB71227). Other lipid encapsulation polypeptides that are functionally equivalent are plastoglobulins and MLDP polypeptides (WO2011/127118).

In an embodiment, an exogenous polynucleotide of the invention which encodes an oleosin comprises, unless specified otherwise, one or more of the following:
  i) nucleotides encoding a polypeptide comprising amino acids whose sequence is set forth as any one of SEQ ID NOs:95 to 112 or 305 to 314, or a biologically active fragment thereof, or a polypeptide whose amino acid sequence is at least 30% identical to any one or more of SEQ ID NOs: 95 to 112 or 305 to 314,
  ii) nucleotides whose sequence is at least 30% identical to i), and
  iii) a polynucleotide which hybridizes to one or both of i) or ii) under stringent conditions.

In an embodiment, an exogenous polynucleotide of the invention which encodes a steroleosin comprises, unless specified otherwise, one or more of the following:
  i) nucleotides encoding a polypeptide comprising amino acids whose sequence is set forth as any one of SEQ ID NOs:113 to 117, or a biologically active fragment thereof, or a polypeptide whose amino acid sequence is at least 30% identical to any one or more of SEQ ID NOs: 113 to 117,
  ii) nucleotides whose sequence is at least 30% identical to i), and
  iii) a polynucleotide which hybridizes to one or both of i) or ii) under stringent conditions.

In an embodiment, the oleosin is oleosinL or an ortholog thereof. OleosinL lacks the about 18 amino acid H-form insertion towards the C-terminus of other oleosins (see, for example, Tai et al., 2002). Thus, OleosinL's can readily be distinguished from other oleosins based on protein alignment.

In an embodiment, an exogenous polynucleotide of the invention which encodes an oleosinL comprises, unless specified otherwise, one or more of the following:
  i) nucleotides encoding a polypeptide comprising amino acids whose sequence is set forth as any one of SEQ ID NOs: 305 to 314, or a biologically active fragment thereof, or a polypeptide whose amino acid sequence is at least 30% identical to any one or more of SEQ ID NOs: 305 to 314,
  ii) nucleotides whose sequence is at least 30% identical to i), and
  iii) a polynucleotide which hybridizes to one or both of i) or ii) under stringent conditions.

In an alternate embodiment, an exogenous polynucleotide of the invention which encodes an oleosin comprises, unless specified otherwise, one or more of the following:
  i) nucleotides encoding a polypeptide comprising amino acids whose sequence is set forth as any one of SEQ ID NOs: 306 to 314, or a biologically active fragment thereof, or a polypeptide whose amino acid sequence is at least 30% identical to any one or more of SEQ ID NOs: 306 to 314,
  ii) nucleotides whose sequence is at least 30% identical to i), and
  iii) a polynucleotide which hybridizes to one or both of i) or ii) under stringent conditions, wherein the oleosin is not allergenic, or not known to be allergenic, such as to humans.

As used herein, a "lipid droplet associated protein" or "LDAP" means a polypeptide which is associated with lipid droplets in plants in tissues or organs other than seeds, anthers and pollen, such as fruit tissues including pericarp and mesocarp. LDAPs may be associated with oil bodies in seeds, anthers or pollen as well as in the tissues or organs other than seeds, anthers and pollen. They are distinct from oleosins which are polypeptides associated with the surface of lipid droplets in seed tissues, anthers and pollen. LDAPs as used herein include LDAP polypeptides that are produced naturally in plant tissues as well as amino acid sequence variants that are produced artificially. The function of such variants can be tested as exemplified in Example 11.

Horn et al. (2013) identified two LDAP genes which are expressed in avocado pericarp. The encoded avocado LDAP1 and LDAP2 polypeptides were 62% identical in amino acid sequence and had homology to polypeptide encoded by *Arabidopsis* At3 g05500 and a rubber tree SRPP-like protein. Gidda et al. (2013) identified three LDAP genes that were expressed in oil palm (*Elaeis guineensis*) mesocarp but not in kernels and concluded that LDAP genes were plant specific and conserved amongst all plant species. LDAP polypeptides may contain additional domains (Gidda et al., (2013). Genes encoding LDAPs are generally up-regulated in non-seed tissues with abundant lipid and can be identified thereby, but are thought to be expressed in all non-seed cells that produce oil including for transient storage. Horn et al. (2013) shows a phylogenetic tree of SRPP-like proteins in plants. Exemplary LDAP polypeptides are described in Example 11 and Example 17 herein, such as *Rhodococcus opacus* TadA lipid droplet associated protein (MacEachran et al., 2010; Accession number HM625859), *Nannochloropsis* oceanica LSDP oil body protein (Vieler et al., 2012; Accession number JQ268559) and *Trichoderma reesei* HFBI hydrophobin (Linder et al., 2005; Accession number Z68124). Homologs of LDAPs in other plant species can be readily identified by those skilled in the art.

In an embodiment, an exogenous polynucleotide of the invention which encodes a LDAP comprises, unless specified otherwise, one or more of the following:
  i) nucleotides encoding a polypeptide comprising amino acids whose sequence is set forth as any one of SEQ ID NOs: 228, 230 or 232, or a biologically active fragment thereof, or a polypeptide whose amino acid sequence is at least 30% identical to any one or more of SEQ ID NOs: 228, 230 or 232, ii) nucleotides whose sequence is at least 30% identical to i), and iii) a polynucleotide which hybridizes to one or both of i) or ii) under stringent conditions.

As used herein, the term a "polypeptide involved in starch biosynthesis" refers to any polypeptide, the downregulation of which in a plant cell below normal (wild-type) levels results in a reduction in the level of starch synthesis and a decrease in the levels of starch. This reduces the flow of carbon from sugars into starch. An example of such a polypeptide is AGPase.

As used herein, the term "ADP-glucose phosphorylase" or "AGPase" refers to an enzyme which regulates starch biosynthesis, catalysing conversion of glucose-1-phosphate and ATP to ADP-glucose which serves as the building block for starch polymers. The active form of the AGPase enzyme consists of 2 large and 2 small subunits.

The AGPase enzyme in plants exists primarily as a tetramer which consists of 2 large and 2 small subunits. Although these subunits differ in their catalytic and regulatory roles depending on the species (Kuhn et al., 2009), in plants the small subunit generally displays catalytic activity. The molecular weight of the small subunit is approximately 50-55 kDa. Sequences of exemplary AGPase small subunit polypeptides are provided herein as SEQ ID NOs:254-257 (*Sorghum* and *Zea mays* AGPase, Accession Nos XM_002462095.1 and XM_008666513.1) (Sanjaya et al. 2011, Zale et al. 2016). The molecular weight of the large subunit is approximately 55-60 kDa. The plant enzyme is strongly activated by 3-phosphoglycerate (PGA), a product of carbon dioxide fixation; in the absence of PGA, the enzyme exhibits only about 3% of its activity. Plant AGPase is also strongly inhibited by inorganic phosphate (Pi). In contrast, bacterial and algal AGPase exist as homotetramers of 50 kDa. The algal enzyme, like its plant counterpart, is activated by PGA and inhibited by Pi, whereas the bacterial enzyme is activated by fructose-1,6-bisphosphate (FBP) and inhibited by AMP and Pi.

TAG Lipases and Beta-Oxidation

As used herein, the term "polypeptide involved in the degradation of lipid and/or which reduces lipid content" refers to any polypeptide which catabolises lipid, the downregulation of which in a plant cell below normal (wild-type) levels results an increase in the level of oil, such as fatty acids and/or TAGs, in a cell of a transgenic plant or part thereof such as a vegetative part, tuber, beet or a seed. Examples of such polypeptides include, but are not limited to, lipases, or a lipase such as a CGi58 (Comparative Gene identifier-58-Like) polypeptide, a SUGAR-DEPENDENT1 (SDP1) triacylglycerol lipase (see, for example, Kelly et al., 2011) and a lipase described in WO 2009/027335.

As used herein, the term "TAG lipase" (EC.3.1.1.3) refers to a protein which hydrolyzes TAG into one or more fatty acids and any one of DAG, MAG or glycerol. Thus, the term "TAG lipase activity" refers to the hydrolysis of TAG into glycerol and fatty acids.

As used herein, the term "CGi58" refers to a soluble acyl-CoA-dependent lysophosphatidic acid acyltransferase encoded by the At4 g24160 gene in *Arabidopsis thaliana* and its homologs in other plants and "Ict1p" in yeast and its homologs. The plant gene such as that from *Arabidopsis* gene locus At4 g24160 is expressed as two alternative transcripts: a longer full-length isoform (At4 g24160.1) and a smaller isoform (At4 g24160.2) missing a portion of the 3' end (see James et al., 2010; Ghosh et al., 2009; US 201000221400). Both mRNAs code for a protein that is homologous to the human CGI-58 protein and other orthologous members of this c/P hydrolase family (ABHD). In an embodiment, the CGI58 (At4 g24160) protein contains three motifs that are conserved across plant species: a GXSXG lipase motif (SEQ ID NO:127), a HX(4)D acyltransferase motif (SEQ ID NO:128), and VX(3)HGF, a probable lipid binding motif (SEQ ID NO:129). The human CGI-58 protein has lysophosphatidic acid acyltransferase (LPAAT) activity but not lipase activity. In contrast, the plant and yeast proteins possess a canonical lipase sequence motif GXSXG (SEQ ID NO:127), that is absent from vertebrate (humans, mice, and zebrafish) proteins, and have lipase and phospholipase activity (Ghosh et al., 2009). Although the plant and yeast CGI58 proteins appear to possess detectable amounts of TAG lipase and phospholipase A activities in addition to LPAAT activity, the human protein does not.

Disruption of the homologous CGI-58 gene in *Arabidopsis thaliana* results in the accumulation of neutral lipid droplets in mature leaves. Mass spectroscopy of isolated lipid droplets from cgi-58 loss-of-function mutants showed they contain triacylglycerols with common leaf-specific fatty acids. Leaves of mature cgi-58 plants exhibit a marked increase in absolute triacylglycerol levels, more than 10-fold higher than in wild-type plants. Lipid levels in the oil-storing seeds of cgi-58 loss-of-function plants were unchanged, and unlike mutations in β-oxidation, the cgi-58 seeds germinated and grew normally, requiring no rescue with sucrose (James et al., 2010).

Examples of nucleotides encoding CGi58 polypeptides include those from *Arabidopsis thaliana* (NM_118548.1 encoding NP_194147.2; SEQ ID NO:130), *Brachypodium distachyon* (XP_003578450.1; SEQ ID NO:131), *Glycine max* (XM_003523590.1 encoding XP_003523638.1; SEQ ID NO:132), *Zea mays* (NM_001155541.1 encoding NP_001149013.1; SEQ ID NO:133), *Sorghum bicolor* (XM_002460493.1 encoding XP_002460538.1; SEQ ID NO:134), *Ricinus communis* (XM_002510439.1 encoding XP_002510485.1; SEQ ID NO:135), *Medicago truncatula* (XM_003603685.1 encoding XP_003603733.1; SEQ ID NO:136), and *Oryza sativa* (encoding EAZ09782.1).

In an embodiment, a genetic modification of the invention down-regulates endogenous production of CGi58, wherein CGi58 is encoded by one or more of the following:

i) nucleotides comprising a sequence set forth as any one of SEQ ID NOs:130 to 136, ii) nucleotides comprising a sequence which is at least 30% identical to any one or more of SEQ ID NOs:130 to 136, and iii) a polynucleotide which hybridizes to one or both of i) or ii) under stringent conditions.

Other lipases which have lipase activity on TAG include SUGAR-DEPENDENT1 triacylglycerol lipase (SDP1, see for example Eastmond et al., 2006; Kelly et al., 2011) and SDP1-like polypeptides found in plant species as well as yeast (TGL4 polypeptide) and animal cells, which are involved in storage TAG breakdown. The SDP1 and SDP1-like polypeptides appear to be responsible for initiating TAG breakdown in seeds following germination (Eastmond et al., 2006). Plants that are mutant in SDP1, in the absence of exogenous WRI1 and DGAT1, exhibit increased levels of PUFA in their TAG. As used herein, "SDP1 polypeptides" include SDP1 polypeptides, SDP1-like polypeptides and their homologs in plant species. SDP1 and SDP1-like polypeptides in plants are 800-910 amino acid residues in length and have a patatin-like acylhydrolase domain that can associate with oil body surfaces and hydrolyse TAG in preference to DAG or MAG. SDP1 is thought to have a preference for hydrolysing the acyl group at the sn-2 position of TAG.

*Arabidopsis* contains at least three genes encoding SDP1 lipases, namely SDP1 (Accession No. NP_196024, nucleotide sequence SEQ ID NO:163 and homologs in other species), SDP1L (Accession No. NM_202720 and homologs in other species, Kelly et al., 2011) and ATGLL (At1 g33270) (Eastmond et al, 2006). Of particular interest for reducing gene activity are SDP1 genes which are expressed in vegetative tissues in plants, such as in leaves, stems and roots. Levels of non-polar lipids in vegetative plant parts can therefore be increased by reducing the activity of SDP1 polypeptides in the plant parts, for example by either mutation of an endogenous gene encoding a SDP1 polypeptide or introduction of an exogenous gene which encodes a silencing RNA molecule which reduces the expression of an endogenous SDP1 gene. Such a reduction is of particular benefit in tuber crops such as sugarbeet and potato, and in "high sucrose" plants such as sweet sorghum, sugarcane and sugarbeet.

Genes encoding SDP1 homologues (including SDP1-like homologues) in a plant species of choice can be identified readily by homology to known SDP1 gene sequences. Known SDP1 nucleotide or amino acid sequences include Accession Nos.: in *Brassica napus*, GN078290 (SEQ ID NO:164), GN078281, GN078283; *Capsella rubella*, XP_006287072; *Theobroma cacao*, XP_007028574.1; *Populus trichocarpa*, XP_002308909 (SEQ ID NO:166); *Prunus persica*, XP_007203312; *Prunus mume*, XP_008240737; *Malus domestica*, XP_008373034; *Ricinus communis*, XP_002530081; *Medicago truncatula*, XP_003591425 (SEQ ID NO:167); *Solanum lycopersicum*, XP_004249208; *Phaseolus vulgaris*, XP_007162133; *Glycine max*, XP_003554141 (SEQ ID NO:168); *Solanum tuberosum*, XP_006351284; *Glycine max*, XP_003521151; *Cicer arietinum*, XP_004493431; *Cucumis sativus*, XP_004142709; *Cucumis melo*, XP_008457586; *Jatropha curcas*, KDP26217; *Vitis vinifera*, CBI30074; *Oryza sativa, Japonica* Group BAB61223; *Oryza sativa*, Indica Group EAY75912; *Oryza sativa, Japonica* Group NP_001044325; *Sorghum bicolor*, XP_002458531 (SEQ ID NO:169); *Brachypodium distachyon*, XP_003567139 (SEQ ID NO:165); *Zea mays*, AFW85009; *Hordeum vulgare*, BAK03290 (SEQ ID NO:172); *Aegilops tauschii*, EMT32802; *Sorghum bicolor*, XP_002463665; *Zea mays*, NP_001168677 (SEQ ID NO:170); *Hordeum vulgare*, BAK01155; *Aegilops tauschii*, EMT02623; *Triticum urartu*, EMS67257; *Physcomitrella patens*, XP_001758169 (SEQ ID NO:171). Preferred SDP1 sequences for use in genetic constructs for inhibiting expression of the endogenous genes are from cDNAs corresponding to the genes which are expressed most highly in the plant cells, vegetative plant parts or the seeds, whichever is to be modified. Nucleotide sequences which are highly conserved between cDNAs corresponding to all of the SDP1 genes in a plant species are preferred if it is desired to reduce the activity of all members of a gene family in that species.

In an embodiment, a genetic modification of the invention down-regulates endogenous production of SDP1, wherein SDP1 is encoded by one or more of the following:
  i) nucleotides whose sequence is set forth as any one of SEQ ID NOs:163 to 174,
  ii) nucleotides whose sequence is at least 30% identical to any one or more of the sequences set forth as SEQ ID NOs:163 to 174, and
  iii) a sequence of nucleotides which hybridizes to one or both of i) or ii) under stringent conditions.

As shown in the Examples, reduction of the expression and/or activity of SDP1 TAG lipase in plant leaves greatly increased the TAG content, both in terms of the amount of TAG that accumulated and the earlier timing of accumulation during plant development, in the context of co-expression of the transcription factor WRI1 and a fatty acyl acyltransferase. In particular, the increase was observed in plants prior to flowering, and was up to about 70% on a weight basis (% dry weight) at the onset of senescence. The increase was relative to the TAG levels observed in corresponding plant leaves transformed with exogenous polynucleotides encoding the WRI1 and fatty acyl acyltransferase but lacking the modification that reduced SDP1 expression and/or activity.

Reducing the expression of other TAG catabolism genes in plant parts can also increase TAG content, such as the ACX genes encoding acyl-CoA oxidases such as the Acx1 (At4 g16760 and homologs in other plant species) or Acx2 (At5 g65110 and homologs in other plant species) genes. Another polypeptide involved in lipid catabolism is PXA1 which is a peroxisomal ATP-binding cassette transporter that is requires for fatty acid import for β-oxidation (Zolman et al. 2001).

Export of Fatty Acids from Plastids

As used herein, the term "polypeptide which increases the export of fatty acids out of plastids of the cell" refers to any polypeptide which aids in fatty acids being transferred from within plastids of plant cells in a plant or part thereof to outside the plastid, which may be any other part of the cell such as for example the endoplasmic reticulum (ER). Examples of such polypeptides include, but are not limited to, a C16 or C18 fatty acid thioesterase such as a FATA polypeptide or a FATB polypeptide, a C8 to C14 fatty acid thioesterase (which is also a FATB polypeptide), a fatty acid transporter such as an ABCA9 polypeptide or a long-chain acyl-CoA synthetase (LACS).

As used herein, the term "fatty acid thioesterase" or "FAT" or "acyl-ACP thioesterase" refers to an enzyme which catalyses the hydrolysis of the thioester bond between an acyl moiety and acyl carrier protein (ACP) in acyl-ACP and the release of a free fatty acid. Such enzymes typically function in the plastids of an organism which is synthesizing de novo fatty acids. As used herein, the term "C16 or C18 fatty acid thioesterase" refers to an enzyme which catalyses the hydrolysis of the thioester bond between a C16 and/or C18 acyl moiety and ACP in acyl-ACP and the release of free C16 or C18 fatty acid in the plastid. The free fatty acid is then re-esterified to CoA in the plastid envelope as it is transported out of the plastid. The substrate specificity of the fatty acid thioesterase (FAT) enzyme in the plastid is involved in determining the spectrum of chain length and degree of saturation of the fatty acids exported from the plastid. FAT enzymes can be classified into two classes based on their substrate specificity and nucleotide sequences, FATA and FATB (EC 3.1.2.14) (Jones et al., 1995). FATA polypeptides prefer oleoyl-ACP as substrate, while FATB polypeptides show higher activity towards saturated acyl-ACPs of different chain lengths such as acting on palmitoyl-ACP to produce free palmitic acid. Examples of FATA polypeptides useful for the invention include, but are not limited to, those from *Arabidopsis thaliana* (NP_189147), *Arachis hypogaea* (GU324446), *Helianthus annuus* (AAL79361), *Carthamus tinctorius* (AAA33020), *Morus notabilis* (XP_010104178.1), *Brassica napus* (CDX77369.1), *Ricinus communis* (XP_002532744.1) and *Camelina sativa* (AFQ60946.1). Examples of FATB polypeptides useful for the invention include, but are not limited to, those from *Zea mays* (AIL28766), *Brassica napus* (ABH11710), *Helianthus annuus* (AAX19387), *Arabidopsis thaliana* (AEE28300), *Umbellularia californica*

(AAC49001), *Arachis hypogaea* (AFR54500), *Ricinus communis* (EEF47013) and *Brachypodium sylvaticum* (ABL85052.1).

As used herein, the term "fatty acid transporter" relates to a polypeptide present in the plastid membrane which is involved in actively transferring fatty acids from a plastid to outside the plastid. Examples of ABCA9 (ABC transporter A family member 9) polypeptides useful for the invention include, but are not limited to, those from *Arabidopsis thaliana* (Q9FLT5), *Capsella rubella* (XP_006279962.1), *Arabis alpine* (KFK27923.1), *Camelina sativa* (XP_010457652.1), *Brassica napus* (CDY23040.1) and *Brassica rapa* (XP_009136512.1).

As used herein, the term "acyl-CoA synthetase" or "ACS" (EC 6.2.1.3) means a polypeptide which is a member of a ligase family that catalyzes the formation of fatty acyl-CoA by a two-step process proceeding through an adenylated intermediate, using a non-esterified fatty acid, CoA and ATP as substrates to produce an acyl-CoA ester, AMP and pyrophosphate as products. As used herein, the term "long-chain acyl-CoA synthetase" (LACS) is an ACS that has activity on at least a C18 free fatty acid substrate although it may have broader activity on any of C14-C20 free fatty acids. The endogenous plastidial LACS enzymes are localised in the outer membrane of the plastid and function with fatty acid thioesterase for the export of fatty acids from the plastid (Schnurr et al., 2002). In *Arabidopsis*, there are at least nine identified LACS genes (Shockey et al., 2002). Preferred LACS polypeptides are of the LACS9 subclass, which in *Arabidopsis* is the major plastidial LACS. Examples of LACS polypeptides useful for the invention include, but are not limited to, those from *Arabidopsis thaliana* (Q9CAP8), *Camelina sativa* (XP_010416710.1), *Capsella rubella* (XP_006301059.1), *Brassica napus* (CDX79212.1), *Brassica rapa* (XP_009104618.1), *Gossypium raimondii* (XP_012450538.1) and *Vitis Vinifera* (XP_002285853.1). Homologs of the above mentioned polypeptides in other species can readily be identified by those skilled in the art.

Polypeptides Involved in Diacylglycerol (DAG) Production

Levels of non-polar lipids in, for example, vegetative plant parts can also be increased by reducing the activity of polypeptides involved in diacylglycerol (DAG) production in the plastid in the plant parts, for example by either mutation of an endogenous gene encoding such a polypeptide or introduction of an exogenous gene which encodes a silencing RNA molecule which reduces the expression of a target gene involved in diacylglycerol (DAG) production in the plastid.

As used herein, the term "polypeptide involved in diacylglycerol (DAG) production in the plastid" refers to any polypeptide in the plastid of plant cells in a plant or part thereof that is directly involved in the synthesis of diacylglycerol. Examples of such polypeptides include, but are not limited to, a plastidial GPAT, a plastidial LPAAT or a plastidial PAP.

GPATs are described elsewhere in the present document. Examples of plastidial GPAT polypeptides which can be targeted for down-regulation in the invention include, but are not limited to, those from *Arabidopsis thaliana* (BAA00575), *Capsella rubella* (XP_006306544.1), *Camelina sativa* (010499766.1), *Brassica napus* (CDY43010.1), *Brassica rapa* (XP_009145198.1), *Helianthus annuus* (ADV16382.1) and *Citrus unshiu* (BAB79529.1). Homologs in other species can readily be identified by those skilled in the art.

LPAATs are described elsewhere in the present document. As the skilled person would appreciate, plastidial LPAATs to be targeted for down-regulation for reducing DAG synthesis in the plastid are not endogenous LPAATs which function outside of the plastid such as those in the ER, for example being useful for producing TAG comprising medium chain length fatty acids. Examples of plastidial LPAAT polypeptides which can be targeted for down-regulation in the invention include, but are not limited to, those from *Brassica napus* (ABQ42862), *Brassica rapa* (XP_009137939.1), *Arabidopsis thaliana* (NP_194787.2), *Camelina sativa* (XP_010432969.1), *Glycine max* (XP_006592638.1) and *Solanum tuberosum* (XP_006343651.1). Homologs in other species of the above mentioned polypeptides can readily be identified by those skilled in the art.

As used herein, the term "phosphatidic acid phosphatase" (PAP) (EC 3.1.3.4) refers to a protein which hydrolyses the phosphate group on 3-sn-phosphatidate to produce 1,2-diacyl-sn-glycerol (DAG) and phosphate. Examples of plastidial PAP polypeptides which can be targeted for down-regulation in the invention include, but are not limited to, those from *Arabidopsis thaliana* (Q6NLA5), *Capsella rubella* (XP_006288605.1), *Camelina sativa* (XP_010452170.1), *Brassica napus* (CDY10405.1), *Brassica rapa* (XP 009122733.1), *Glycine max* (XP_003542504.1) and *Solanum tuberosum* (XP_006361792.1). Homologs in other species of the above mentioned polypeptides can readily be identified by those skilled in the art.

Levels of TAG in, for example, vegetative plant parts can also be increased by increasing the activity of polypeptides involved in diacylglycerol (DAG) production in the ER in the plant parts. DAG is also produced in the plants and plant parts of the invention by release of the DAG moiety from PC and can be used for synthesis of TAG. This DAG is termed herein "PC-derived DAG". The release can occur through one or more of the enzymes phosphatidylcholine:diacylglycerol cholinephosphotransferase (PDCT), the reverse reaction of choline:diacylglycerol cholinephospho-transferase (CPT), or phospholipase C (PLC) or phospholipase D (PLD). These enzymes result in DAG production in the ER rather than the plastid. As used herein, the term "phosphatidylcholine:diacylglycerol cholinephosphotransferase" or "PDCT" (EC 2.7.8.2) means an cholinephosphotransferase that transfers a phosphocholine headgroup from a phospholipid, typically PC, to produce DAG, or the reverse reaction to produce PC from DAG. PDCT can therefore interconvert PC and DAG (Lu et al., 2009; Hu et al., 2012). Thus, the two substrates of the forward reaction are cytidine monophosphate (CMP) and phosphatidylcholine and the two products are CDP-choline and DAG. PDCT belongs to the phosphatidic acid phosphatase-related protein family and typically possesses lipid phosphatase/phosphotransferase (LPT) domains. In *Arabidopsis thaliana*, PDCT is encoded by the ROD1 (At3 g15820) and ROD2 (At3 g15830) genes (Lu et al., 2009). Homologous genes are readily identified in other plant species (Guan et al., 2015). Sequences of exemplary PDCT coding regions and polypeptides are provided herein as SEQ ID NOs:262-265 (*Sorghum* and *Zea mays* PDCT, Accession Nos XM_002437214 and EU973573.1), although any PDCT encoding gene can be used. Exemplary PDCT polypeptides have the amino acid sequences provided by Accession Nos. NP_566527.1 (*Arabidopsis*), XP_010487422.1 (*Camelina sativa*), XP_003531718.1 (*Glycine max*), XP_013695400.1 (*Brassica napus*), XP_012073167.1 (*Jatropha curcas*), XP_002517643.1 (*Ricinus communis*) XP_013587626.1 (*Brassica oleracea*), XP_016725741.1 and XP_016725742.1 (*Gossypium hirsutum*), AQK82308.1, NP_001145186.1 (*Zea mays*), and XP_021306179.1 (*Sorghum bicolor*). Homologs and naturally occurring variants from these or other plant, fungal or algal species can readily be identified and used in the present invention. In an embodiment, the homolog or variant is at least 95% identical, preferably at least 99% identical, to the amino acid sequence of the listed Accession No. In an embodiment, the PDCT is other than *A. thaliana* PDCT (Lu et al., 2009). Increased expression of PDCT, which may be exogenous or endogenous to the cell or plant of the invention and which is preferably expressed from an exogenous polynucleotide, increases the flow of esterified acyl groups from PC to DAG and thereby increases the TTQ in the total fatty acid content and the level of TAG in vegetative plant parts or cells of the invention. Alternatively, decreasing the level of PDCT activity in the cell or plant by mutation in the gene or by a silencing RNA molecule reduces the production of PC from DAG, the reverse PDCT reaction, and allows for more of the de novo DAG to be used for TAG synthesis.

The PDCT enzyme provides for the transfer of 18:1 from DAG into PC for desaturation and also for the reverse transfer of the polyunsaturated fatty acids 18:2 and 18:3 from PC into DAG which can be used in TAG synthesis. Fatty acid labelling experiments indicate that de novo DAG and PC-derived DAG are represented by two separate pools of DAG (Bates 2016), perhaps kept spatially separated in the ER. Some reports suggest that PC-derived DAG might be the predominant form of DAG used in TAG synthesis (Bates and Browse, 2011).

As used herein, the term "CDP-choline:diacylglycerol cholinephospho-transferase" or "CPT", (EC 2.7.8.2) means an enzyme that catalyses the transfer of a choline group from CDP-choline to DAG, forming PC and CMP. This forward reaction results in the net synthesis of PC from DAG. CPT also catalyses the reverse reaction, forming DAG from PC, possibly allowing for the equilibration of DAG and PC levels in the cell. *Arabidopsis* contains two genes (AtAAPT1 and AtAAPT2, Accession Nos AAC61768.1 and AAC61769.1) that encode CPT enzymes. Mutations in either gene affect membrane homeostasis and the double mutant is lethal (Liu et al., 2015). Exemplary CPT enzymes have the amino acid sequences provided by the following Accession Nos: XP_010495346.1 and XP_019084815.1 (*Camelina sativa*); XP_013731103.1 and XP_013720632.1 (*Brassica napus*); XP_013585950.1 (*Brassica oleracea*); XP_015572083.1 (*Ricinus communis*); XP_016679754.1 (*Gossypium hirsutum*); XP_010687532.1 (*Beta vulgaris*); XP_012081980.1 (*Jatropha curcas*); XP_011070871.1 (*Sesamum indicum*); NP_001151915.1 and XP_008649199.1 (*Zea mays*); XP_002451408.1 and XP_021305900.1 (*Sorghum bicolor*). Homologs and naturally occurring variants from these or other plant, fungal or algal species can readily be identified and used in the present invention. In an embodiment, the homolog or variant is at least 95% identical, preferably at least 99% identical, to the amino acid sequence of the listed Accession No.

Phospholipases are enzymes that hydrolyze phospholipids into products such as phosphatidic acid (PA), DAG, free fatty acids (FFA) or lysophospholipids (LPL), depending on the class of phospholipase. As used herein, the term "phospholipase C" or "PLC" means an enzyme which catalyses the cleavage of a phospholipid to form DAG and a phosphorylated headgroup, where the cleavage occurs at the ester linkage between the phosphate group and the glycerol backbone of the phospholipid. The phosphorylated headgroup is phosphocholine when the phospholipid is PC. PLCs are distinct from phospholipase D enzymes which cleave the headgroup of phospholipids to form phosphatidic acid (PA) rather than DAG as product, and from phospholipase A1 and phospholipase A2 which produce FFA from the phospholipids. PLCs are membrane-associated enzymes found widely in plants, animals and prokaryoyes. PLCs can be divided into three classes, the phosphatidylinositol-specific phospholipases C (PI-PLC), the phosphatidylcholine-specific phospholipases C (PC-PLC), and the PLC which hydrolyze glycosylphosphatidylinositol (GPI)-anchored proteins (GPI-PLC), according to their substrate specificity range (Pokotylo et al., 2013, Hong et al., 2016). Multidomain animal PI-PLCs are G-protein activated enzymes regulating calcium levels and protein kinase C, and are therefore key components of the regulatory systems of cellular growth and development. The PI-PLCs are less preferred in the present invention. PC-PLCs, in plants also known as non-specific PLCs (NPC) have broader substrate ranges and are typically most active on PC, and are therefore preferred in the present invention. PC-PLCs have been identified in bacteria (Titball 1993), fungi (Morelle et al., 2005) and plants (Hong et al., 2016), the plant ones being more preferred. Six PC-PLC genes have been identified in *Arabidopsis* (Wang, 2001; Nakamura et al., 2005), nine genes in soybean (Huang et al., 2010), five genes in rice (Singh et al., 2013) and multiple copies in diverse plant species. The plant PC-PLCs are classified in several sub-groups, namely the NPC1, NPC2, NPC3-5 and NPC6 sub-groups (Pokotylo et al., 2013) based on homology to the *Arabidopsis* amino acid sequences, also having differing (but overlapping) substrate specificities and tissue distributions. For example, *Arabidopsis* NPC4 showed activity towards PC and PE, slight activity towards PS, but not PA and PIP2. NPC5 was able to cleave PC and PE, whereas NPC3 demonstrated lysophosphatidic acid (LPA) phosphatase activity resulting in MAG production as well as cleaving PC. NPC4 was expressed in mature leaves, and NPC6 was expressed in most tissues. The *Arabidopsis* PLCs have between 510 and 540 amino acid residues. In plants, PLCs are involved in lipid remodelling and the plant responses to phosphate deprivation and osmotic, salt and heat stresses, amongst other functions. Examples of PLCs include those identified, with amino acid sequences in the following Accession Nos., from *Arabidopsis*: NPC1, NP_172203.2; NPC2, NP_180255.1; NPC4, NP_566206.1; NPC5, NP_566207.1; NPC6, NP_190430.2; from *Camelina sativa*, NPC1, XP_010457889.1; NPC2, XP_010473071.1; NPC4, XP_010463802.1; NPC5, XP_010485694.1; NPC6, XP_010426358.1; from *Brassica napus* NPC1, XP_013687149.1; NPC2, XP_013744020.1; NPC4, XP_013682889.1; NPC6, XP_002511167.1; from *Ricinus communis* NPC1, XP_002525632.1; NPC4, XP_002524007.1; NPC6, XP_002511167.1; from *Gossypium hirsutum* NPC1, XP_016715492.1; NPC2, XP_016745351.1; NPC4, XP_016697678.1; NPC6, XP_016734150.1; from *Beta vulgaris* NPC1, XP_010685575.1; NPC2, XP_010673757.1; NPC4, XP_010691936.1; from *Zea mays* NPC1 homolog, NP_001170209.1; from *Oryza sativa* NPC1, XP_015631592.1; from *Glycine max* NPC1, XP_003551286.1; NPC2, XP_003556783.1; NPC4, XP_003521010.1; NPC6, XP_003523153.1; NPC6, XP_003526950.1; from *Jatropha curcas* NPC2, XP_012065897.1; NPC4, XP_012070293.1; NPC6, XP_012090681.1; from *Solanum tuberosum* NPC2, XP_006362756.1; from *Elaeis guineensis* NPC2, XP_010938556.1; NPC4, XP_010919939.1; from *Brachypodium distachyon* NPC2, XP_003565100.1; from *Trifolium subterraneum* NPC4, GAU26202.1; NPC6, GAU26767.1; from *Medicago truncatula* NPC4, XP_013444051.1; and from *Helianthus annuus* NPC6, XP_021984157.1. Homologs and naturally occurring variants from these or other plant, fungal or algal species can readily be identified and used in the present invention. In an embodiment, the homolog or variant is at least 95% identical, preferably at least 99% identical, to the amino acid sequence of the listed Accession No.

As used herein, the term "phospholipase D" or "PLD" means an enzyme which catalyses the cleavage of a the phosphodiesteric linkage of a headgroup of a membrane phospholipid to form phosphatidic acid (PA) and soluble headgroup, the cleavage occurring at the phosphodiester bond distal to the glycerol backbone of the phospholipid. The soluble headgroup product is choline when the phospholipid is PC. The PA is subsequently converted to DAG by the action of PAP. Many PLDs have been identified in plants, animals, fungi and prokaryotes. All of the plant species examined have a PLD family of at least 10 PLD genes (Wang, 2005), for example the *Arabidopsis* PLD family has 12 genes identified. PLDs are classified in subgroups $\alpha$, $\beta$, $\gamma$, $\delta$, $\delta$ and $\zeta$ based on sequence and enzymatic properties (Hong et al, 2016). PLDs have either a C2 domain of approximately 130 amino acids involved in calcium ion and phospholipid binding or a pleckstrin homology (PH) domain and a phox (PX) homology domain. All examined eukaryotic PLDs contain two duplicated catalytic HKD motifs, separated by more than 300 amino acids in *Arabidopsis* PLDs, but which interact with each other to form the active site (Hong et al, 2013). Exemplary PLDs include those from *Arabidopsis*: Accession Nos. AAL06337.1, CAJ58441.1; from *Camelina sativa*, XP_010465702.1, XP_010430169.1; from *Gossypium hirsutum*, XP_016724300.1; from *Ricinus communis*, XP_015573380.1; from *Solanum lycopersicum*, XP_004229274.1; from *Jatropha curcas*, XP_012083994.1; from *Glycine max*, XP_003534832.1, NP_001275522.1; from *Elaeis guineensis*, XP_010921600.1; from *Brassica rapa*, XP_009146059.1; from *Beta vulgaris*, XP_010693582.1 and XP_016713715.1; *Medicago truncatula* XP_003591178.2; and from *Brassica napus*, XP_013677646.1. Homologs and naturally occurring variants from these or other plant, fungal or algal species can readily be identified and used in the present invention. In an embodiment, the homolog or variant is at least 95% identical, preferably at least 99% identical, to the amino acid sequence of the listed Accession No.

Import of Fatty Acids into Plastids

Levels of non-polar lipids in vegetative plant parts can also be increased by reducing the activity of TGD polypeptides in the plant parts, for example by either mutation of an endogenous gene encoding a TGD polypeptide or introduction of an exogenous gene which encodes a silencing RNA molecule which reduces the expression of an endogenous TGD gene. As used herein, a "Trigalactosyldiacylglycerol (TGD) polypeptide" is one which is involved in the ER to chloroplast lipid trafficking (Xu et al., 2010; Fan et al., 2015) and involved in forming a protein complex which has permease function for lipids. Four such polypeptides are known to form or be associated with a TGD permease, namely TGD-1 (Accession No. At1 g19800 and homologs in other species), TGD-2 (Accession No At2 g20320 and homologs in other species), TGD-3 (Accession No. NM-105215 and homologs in other species) and TGD-4 (At3 g06960 and homologs in other species) (US 20120237949). TGD5 is also involved in ER to chloroplast lipid trafficking, and down-regulation of TGD5 is associated with increased oil production (US2015/337017; Fan et al., 2015). Sequences of exemplary TGD5 polypeptides are provided herein as SEQ ID NOs:250-253 (*Sorghum* and *Zea mays* TGD5, Accession Nos XM_002442154 and EU972796.1). TGD-1, -2 and -3 polypeptides are thought to be components of an ATP-Binding Cassette (ABC) transporter associated with the inner envelope membrane of the chloroplast. TGD-2 and TGD-4 polypeptides bind to phosphatidic acid whereas TGD-3 polypeptide functions as an ATPase in the chloroplast stroma. As used herein, an "endogenous TGD gene" is a gene which encodes a TGD polypeptide in a plant. Mutations in TGD-1 gene in *A. thaliana* caused accumulation of triacylglycerols, oligogalactolipids and phosphatidic acid (PA) (Xu et al., 2005). Mutations in TGD genes or SDP1 genes, or indeed in any desired gene in a plant, can be introduced in a site-specific manner by artificial zinc finger nuclease (ZFN), TAL effector (TALEN) or CRISPR technologies (using a Cas9 type nuclease) as known in the art. Preferred exogenous genes encoding silencing RNAs are those encoding a double-stranded RNA molecule such as a hairpin RNA or an artificial microRNA precursor.

Sucrose Metabolism

The TAG levels and/or the TTQ of the total fatty content in the cells, plants and plant parts of the invention can also be increased by modifying sucrose metabolism, particularly in the stems of plants such as sugarcane, *Sorghum* and *Zea mays*. In an embodiment, this is achieved by increasing expression of a sucrose metabolism polypeptide such as invertase or sucrose synthase, or of a sucrose transport polypeptide such as SUS1, SUS4, SUT2, SUT4, or SWEET. The effect of these polypeptides is to increase the supply of sucrose and its monosaccharide components in the cytosol of the cells and/or to decrease the transfer and/or storage of sucrose in the vacuoles of the cells, particularly in stem cells. Sequences of examples of these polypeptides are provided in SEQ ID NOs:274-292. Invertase such as bCIN, INV2 or INV3 acts to convert sucrose into hexoses which can be exported from the vacuoles into the cytoplasm (McKinley et al., 2016). Increased expression of SUS1 or SUS4 breaks down cytosolic sucrose into hexoses for glycolysis and de novo fatty acid synthesis rather than transfer of the sucrose into vacuoles, such as in stem parenchyma cells (McKinley et al., 2016). Increased expression of sugar transport polypeptides such as tonoplast sucrose exporter, for example SUT2 or SUT4, or SWEET polypeptide releases vacuolar sucrose for cytosolic glycolysis and increases de novo fatty acid biosynthesis (Bihmidine et al., 2016; Qazi et al., 2012; Schneider et al., 2012; Hedrich et al., 2015; Klemens et al., 2013).

The TAG levels and/or the TTQ of the total fatty content in the cells, plants and plant parts of the invention can also be increased by reducing the level of TST polypeptides such as TST1 or TST2, particularly in the stems of plants such as sugarcane, *Sorghum* and *Zea mays*. TST polypeptide can be decreased by mutation of the endogenous genes encoding the polypeptide, or by introduction of an exogenous polynucleotide that encodes a silencing RNA molecule. Sequences of exemplary TST cDNAs and polypeptides are provided as SEQ ID NOs:266-273.

Fatty Acid Modifying Enzymes

As used herein, the term "FAD2" refers to a membrane bound delta-12 fatty acid desaturase that desaturates oleic acid ($C18:1^{\Delta 9}$) to produce linoleic acid ($C18:2^{\Delta 9,12}$).

As used herein, the term "epoxygenase" or "fatty acid epoxygenase" refers to an enzyme that introduces an epoxy group into a fatty acid resulting in the production of an epoxy fatty acid. In preferred embodiment, the epoxy group is introduced at the 12th carbon on a fatty acid chain, in which case the epoxygenase is a Δ12-epoxygenase, especially of a C16 or C18 fatty acid chain. The epoxygenase may be a Δ9-epoxygenase, a Δ15 epoxygenase, or act at a different position in the acyl chain as known in the art. The epoxygenase may be of the P450 class. Preferred epoxygenases are of the mono-oxygenase class as described in WO98/46762. Numerous epoxygenases or presumed epoxygenases have been cloned and are known in the art. Further examples of expoxygenases include proteins comprising an amino acid sequence provided in SEQ ID NO:21 of WO 2009/129582, polypeptides encoded by genes from *Crepis paleastina* (CAA76156, Lee et al., 1998), *Stokesia laevis* (AAR23815) (monooxygenase type), *Euphorbia lagascae* (AAL62063) (P450 type), human CYP2J2 (arachidonic acid epoxygenase, U37143); human CYPIA1 (arachidonic acid epoxygenase, K03191), as well as variants and/or mutants thereof.

As used herein, the term, "hydroxylase" or "fatty acid hydroxylase" refers to an enzyme that introduces a hydroxyl group into a fatty acid resulting in the production of a hydroxylated fatty acid. In a preferred embodiment, the hydroxyl group is introduced at the 2nd, 12th and/or 17th carbon on a C18 fatty acid chain. Preferably, the hydroxyl group is introduced at the $12^{th}$ carbon, in which case the hydroxylase is a Δ12-hydroxylase. In another preferred embodiment, the hydroxyl group is introduced at the 15th carbon on a C16 fatty acid chain. Hydroxylases may also have enzyme activity as a fatty acid desaturase. Examples of genes encoding Δ12-hydroxylases include those from *Ricinus communis* (AAC9010, van de Loo 1995); *Physaria lindheimeri*, (ABQ01458, Dauk et al., 2007); *Lesquerella fendleri*, (AAC32755, Broun et al., 1998); *Daucus carota*, (AAK30206); fatty acid hydroxylases which hydroxylate the terminus of fatty acids, for example: *A. thaliana* CYP86A1 (P48422, fatty acid ω-hydroxylase); *Vicia sativa* CYP94A1 (P98188, fatty acid ω-hydroxylase); mouse CYP2E1 (X62595, lauric acid ω-1 hydroxylase); rat CYP4A1 (M57718, fatty acid ω-hydroxylase), as well as variants and/or mutants thereof.

As used herein, the term "conjugase" or "fatty acid conjugase" refers to an enzyme capable of forming a conjugated bond in the acyl chain of a fatty acid. Examples of conjugases include those encoded by genes from *Calendula officinalis* (AF343064, Qiu et al., 2001); *Vernicia fordii* (AAN87574, Dyer et al., 2002); *Punica granatum* (AY178446, Iwabuchi et al., 2003) and *Trichosanthes kirilowii* (AY178444, Iwabuchi et al., 2003); as well as variants and/or mutants thereof.

As used herein, the term "acetylenase" or "fatty acid acetylenase" refers to an enzyme that introduces a triple bond into a fatty acid resulting in the production of an acetylenic fatty acid. In a preferred embodiment, the triple bond is introduced at the 2nd, 6th, 12th and/or 17th carbon on a C18 fatty acid chain. Examples acetylenases include those from *Helianthus annuus* (AA038032, ABC59684), as well as variants and/or mutants thereof.

Examples of such fatty acid modifying genes include proteins according to the following Accession Numbers which are grouped by putative function, and homologues from other species: Δ12-acetylenases ABC00769, CAA76158, AA038036, AA038032; Δ12 conjugases AAG42259, AAG42260, AAN87574; Δ12-desaturases P46313, ABS18716, AAS57577, AAL61825, AAF04093, AAF04094; Δ12 epoxygenases XP_001840127, CAA76156, AAR23815; Δ12-hydroxylases ACF37070, AAC32755, ABQ01458, AAC49010; and Δ12 P450 enzymes such as AF406732.

Silencing Suppressors

In an embodiment, a transgenic plant or part thereof of the invention may comprise a silencing suppressor.

As used herein, a "silencing suppressor" enhances transgene expression in a plant or part thereof of the invention. For example, the presence of the silencing suppressor results in higher levels of a polypeptide(s) produced an exogenous polynucleotide(s) in a plant or part thereof of the invention when compared to a corresponding plant or part thereof lacking the silencing suppressor. In an embodiment, the silencing suppressor preferentially binds a dsRNA molecule which is 21 base pairs in length relative to a dsRNA molecule of a different length. This is a feature of at least the p19 type of silencing suppressor, namely for p19 and its functional orthologs. In another embodiment, the silencing suppressor preferentially binds to a double-stranded RNA molecule which has overhanging 5' ends relative to a corresponding double-stranded RNA molecule having blunt ends. This is a feature of the V2 type of silencing suppressor, namely for V2 and its functional orthologs. In an embodiment, the dsRNA molecule, or a processed RNA product thereof, comprises at least 19 consecutive nucleotides, preferably whose length is 19-24 nucleotides with 19-24 consecutive basepairs in the case of a double-stranded hairpin RNA molecule or processed RNA product, more preferably consisting of 20, 21, 22, 23 or 24 nucleotides in length, and preferably comprising a methylated nucleotide, which is at least 95% identical to the complement of the region of the target RNA, and wherein the region of the target RNA is i) within a 5' untranslated region of the target RNA, ii) within a 5' half of the target RNA, iii) within a protein-encoding open-reading frame of the target RNA, iv) within a 3' half of the target RNA, or v) within a 3' untranslated region of the target RNA.

Further details regarding silencing suppressors are well known in the art and described in WO 2013/096992 and WO 2013/096993.

Polynucleotides

The terms "polynucleotide", and "nucleic acid" are used interchangeably. They refer to a polymeric form of nucleotides of any length, either deoxyribonucleotides or ribonucleotides, or analogs thereof. A polynucleotide of the invention may be of genomic, cDNA, semisynthetic, or synthetic origin, double-stranded or single-stranded and by virtue of its origin or manipulation: (1) is not associated with all or a portion of a polynucleotide with which it is associated in nature, (2) is linked to a polynucleotide other than that to which it is linked in nature, or (3) does not occur in nature. The following are non-limiting examples of polynucleotides: coding or non-coding regions of a gene or gene fragment, exons, introns, messenger RNA (mRNA), transfer RNA (tRNA), ribosomal RNA (rRNA), ribozymes, cDNA, recombinant polynucleotides, plasmids, vectors, isolated DNA of any sequence, isolated RNA of any sequence, chimeric DNA of any sequence, nucleic acid probes, and primers. For in vitro use, a polynucleotide may comprise modified nucleotides such as by conjugation with a labeling component.

As used herein, an "isolated polynucleotide" refers to a polynucleotide which has been separated from the polynucleotide sequences with which it is associated or linked in its native state, or a non-naturally occurring polynucleotide.

As used herein, the term "gene" is to be taken in its broadest context and includes the deoxyribonucleotide sequences comprising the transcribed region and, if translated, the protein coding region, of a structural gene and including sequences located adjacent to the coding region on both the 5' and 3' ends for a distance of at least about 2 kb on either end and which are involved in expression of the gene. In this regard, the gene includes control signals such as promoters, enhancers, termination and/or polyadenylation signals that are naturally associated with a given gene, or heterologous control signals, in which case, the gene is referred to as a "chimeric gene". The sequences which are located 5' of the protein coding region and which are present on the mRNA are referred to as 5' non-translated sequences. The sequences which are located 3' or downstream of the protein coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns", "intervening regions", or "intervening sequences." Introns are segments of a gene which are transcribed into nuclear RNA (nRNA). Introns may contain regulatory elements such as enhancers. Introns are removed or "spliced out" from the nuclear or primary transcript; introns are therefore absent in the mRNA transcript. A gene which contains at least one intron may be subject to variable splicing, resulting in alternative mRNAs from a single transcribed gene and therefore polypeptide variants. A gene in its native state, or a chimeric gene may lack introns. The mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above.

As used herein, "chimeric DNA" refers to any DNA molecule that is not naturally found in nature; also referred to herein as a "DNA construct" or "genetic construct". Typically, a chimeric DNA comprises regulatory and transcribed or protein coding sequences that are not naturally found together in nature. Accordingly, chimeric DNA may comprise regulatory sequences and coding sequences that are derived from different sources, or regulatory sequences and coding sequences derived from the same source, but arranged in a manner different than that found in nature. The open reading frame may or may not be linked to its natural upstream and downstream regulatory elements. The open reading frame may be incorporated into, for example, the plant genome, in a non-natural location, or in a replicon or vector where it is not naturally found such as a bacterial plasmid or a viral vector. The term "chimeric DNA" is not limited to DNA molecules which are replicable in a host, but includes DNA capable of being ligated into a replicon by, for example, specific adaptor sequences.

A "transgene" is a gene that has been introduced into the genome by a transformation procedure. The term includes a gene in a progeny plant or part thereof such as a vegetative plant part which was introducing into the genome of a progenitor cell thereof. Such progeny cells etc may be at least a $3^{rd}$ or $4^{th}$ generation progeny from the progenitor cell which was the primary transformed cell, or of the progenitor transgenic plant (referred to herein as a T0 plant). Progeny may be produced by sexual reproduction or vegetatively such as, for example, from tubers in potatoes or ratoons in sugarcane. The term "genetically modified", "genetic modification" and variations thereof, is a broader term that includes introducing a gene into a cell by transformation or transduction, mutating a gene in a cell and genetically altering or modulating the regulation of a gene in a cell, or the progeny of any cell modified as described above.

A "genomic region" as used herein refers to a position within the genome where a transgene, or group of transgenes (also referred to herein as a cluster), have been inserted into a cell, or predecessor thereof. Such regions only comprise nucleotides that have been incorporated by the intervention of man such as by methods described herein.

A "recombinant polynucleotide" of the invention refers to a nucleic acid molecule which has been constructed or modified by artificial recombinant methods. The recombinant polynucleotide may be present in a cell of a plant or part thereof in an altered amount or expressed at an altered rate (e.g., in the case of mRNA) compared to its native state. In one embodiment, the polynucleotide is introduced into a cell that does not naturally comprise the polynucleotide. Typically an exogenous DNA is used as a template for transcription of mRNA which is then translated into a continuous sequence of amino acid residues coding for a polypeptide of the invention within the transformed cell. In another embodiment, the polynucleotide is endogenous to the plant or part thereof and its expression is altered by recombinant means, for example, an exogenous control sequence is introduced upstream of an endogenous gene of interest to enable the transformed plant or part thereof to express the polypeptide encoded by the gene, or a deletion is created in a gene of interest by ZFN, Talen or CRISPR methods.

A recombinant polynucleotide of the invention includes polynucleotides which have not been separated from other components of the cell-based or cell-free expression system, in which it is present, and polynucleotides produced in said cell-based or cell-free systems which are subsequently purified away from at least some other components. The polynucleotide can be a contiguous stretch of nucleotides or comprise two or more contiguous stretches of nucleotides from different sources (naturally occurring and/or synthetic) joined to form a single polynucleotide. Typically, such chimeric polynucleotides comprise at least an open reading frame encoding a polypeptide of the invention operably linked to a promoter suitable of driving transcription of the open reading frame in a cell of interest.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

A polynucleotide of, or useful for, the present invention may selectively hybridise, under stringent conditions, to a polynucleotide defined herein. As used herein, stringent conditions are those that: (1) employ during hybridisation a denaturing agent such as formamide, for example, 50% (v/v) formamide with 0.1% (w/v) bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (2) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS, and/or (3) employ low ionic strength and high temperature for washing, for example, 0.015 M NaCl/0.0015 M sodium citrate/0.1% SDS at 50° C.

Polynucleotides of the invention may possess, when compared to naturally occurring molecules, one or more mutations which are deletions, insertions, or substitutions of nucleotide residues. Polynucleotides which have mutations relative to a reference sequence can be either naturally occurring (that is to say, isolated from a natural source) or synthetic (for example, by performing site-directed mutagenesis or DNA shuffling on the nucleic acid as described above).

Polynucleotides for Reducing Expression of Genes
RNA Interference

RNA interference (RNAi) is particularly useful for specifically reducing the expression of a gene, which results in reduced production of a particular protein if the gene encodes a protein. Although not wishing to be limited by theory, Waterhouse et al. (1998) have provided a model for the mechanism by which dsRNA (duplex RNA) can be used to reduce protein production. This technology relies on the presence of dsRNA molecules that contain a sequence that is essentially identical to the mRNA of the gene of interest or part thereof. Conveniently, the dsRNA can be produced from a single promoter in a recombinant vector or host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules is well within the capacity of a person skilled in the art, particularly considering Waterhouse et al. (1998), Smith et al. (2000), WO 99/32619, WO 99/53050, WO 99/49029, and WO 01/34815.

In one example, a DNA is introduced that directs the synthesis of an at least partly double stranded RNA product(s) with homology to the target gene to be inactivated such as, for example, a SDP1, TGD, plastidial GPAT, plastidial LPAAT, plastidial PAP, AGPase gene. The DNA therefore comprises both sense and antisense sequences that, when transcribed into RNA, can hybridize to form the double stranded RNA region. In one embodiment of the invention, the sense and antisense sequences are separated by a spacer region that comprises an intron which, when transcribed into RNA, is spliced out. This arrangement has been shown to result in a higher efficiency of gene silencing (Smith et al., 2000). The double stranded region may comprise one or two RNA molecules, transcribed from either one DNA region or two. The presence of the double stranded molecule is thought to trigger a response from an endogenous system that destroys both the double stranded RNA and also the homologous RNA transcript from the target gene, efficiently reducing or eliminating the activity of the target gene.

The length of the sense and antisense sequences that hybridize should each be at least 19 contiguous nucleotides, preferably at least 50 contiguous nucleotides, more preferably at least 100 or at least 200 contiguous nucleotides. Generally, a sequence of 100-1000 nucleotides corresponding to a region of the target gene mRNA is used. The full-length sequence corresponding to the entire gene transcript may be used. The degree of identity of the sense sequence to the targeted transcript (and therefore also the identity of the antisense sequence to the complement of the target transcript) should be at least 85%, at least 90%, or 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

Preferred small interfering RNA ("siRNA") molecules comprise a nucleotide sequence that is identical to about 19-25 contiguous nucleotides of the target mRNA. Preferably, the siRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the organism in which it is to be introduced, for example, as determined by standard BLAST search.

microRNA

MicroRNAs (abbreviated miRNAs) are generally 19-25 nucleotides (commonly about 20-24 nucleotides in plants) non-coding RNA molecules that are derived from larger precursors that form imperfect stem-loop structures. miRNAs bind to complementary sequences on target messenger RNA transcripts (mRNAs), usually resulting in translational repression or target degradation and gene silencing. Artificial miRNAs (amiRNAs) can be designed based on natural miRNAs for reducing the expression of any gene of interest, as well known in the art.

In plant cells, miRNA precursor molecules are believed to be largely processed in the nucleus. The pri-miRNA (containing one or more local double-stranded or "hairpin" regions as well as the usual 5' "cap" and polyadenylated tail of an mRNA) is processed to a shorter miRNA precursor molecule that also includes a stem-loop or fold-back structure and is termed the "pre-miRNA". In plants, the pre-miRNAs are cleaved by distinct DICER-like (DCL) enzymes, yielding miRNA:miRNA* duplexes. Prior to transport out of the nucleus, these duplexes are methylated.

In the cytoplasm, the miRNA strand from the miRNA: miRNA duplex is selectively incorporated into an active RNA-induced silencing complex (RISC) for target recognition. The RISC– complexes contain a particular subset of Argonaute proteins that exert sequence-specific gene repression (see, for example, Millar and Waterhouse, 2005; Pasquinelli et al., 2005; Almeida and Allshire, 2005).

Cosuppression

Genes can suppress the expression of related endogenous genes and/or transgenes already present in the genome, a phenomenon termed homology-dependent gene silencing. Most of the instances of homologydependent gene silencing fall into two classes—those that function at the level of transcription of the transgene, and those that operate post-transcriptionally.

Post-transcriptional homology-dependent gene silencing (i.e., cosuppression) describes the loss of expression of a transgene and related endogenous or viral genes in transgenic plants. Cosuppression often, but not always, occurs when transgene transcripts are abundant, and it is generally thought to be triggered at the level of mRNA processing, localization, and/or degradation. Several models exist to explain how cosuppression works (see in Taylor, 1997).

Cosuppression involves introducing an extra copy of a gene or a fragment thereof into a plant in the sense orientation with respect to a promoter for its expression. The size of the sense fragment, its correspondence to target gene regions, and its degree of sequence identity to the target gene can be determined by those skilled in the art. In some instances, the additional copy of the gene sequence interferes with the expression of the target plant gene. Reference is made to WO 97/20936 and EP 0465572 for methods of implementing co-suppression approaches.

Antisense Polynucleotides

The term "antisense polynucletoide" shall be taken to mean a DNA or RNA molecule that is complementary to at least a portion of a specific mRNA molecule encoding an endogenous polypeptide and capable of interfering with a post-transcriptional event such as mRNA translation. The use of antisense methods is well known in the art (see for example, G. Hartmann and S. Endres, Manual of Antisense Methodology, Kluwer (1999)). The use of antisense techniques in plants has been reviewed by Bourque (1995) and Senior (1998). Bourque (1995) lists a large number of examples of how antisense sequences have been utilized in plant systems as a method of gene inactivation. Bourque also states that attaining 100% inhibition of any enzyme activity may not be necessary as partial inhibition will more than likely result in measurable change in the system. Senior (1998) states that antisense methods are now a very well established technique for manipulating gene expression.

In one embodiment, the antisense polynucleotide hybridises under physiological conditions, that is, the antisense polynucleotide (which is fully or partially single stranded) is at least capable of forming a double stranded polynucleotide with mRNA encoding an endogenous polypeptide, for example, a SDP1, TGD, plastidial GPAT, plastidial LPAAT, plastidial PAP or AGPase mRNA under normal conditions in a cell.

Antisense molecules may include sequences that correspond to the structural genes or for sequences that effect control over the gene expression or splicing event. For example, the antisense sequence may correspond to the targeted coding region of endogenous gene, or the 5'-untranslated region (UTR) or the 3'-UTR or combination of these. It may be complementary in part to intron sequences, which may be spliced out during or after transcription, preferably only to exon sequences of the target gene. In view of the generally greater divergence of the UTRs, targeting these regions provides greater specificity of gene inhibition.

The length of the antisense sequence should be at least 19 contiguous nucleotides, preferably at least 50 nucleotides, and more preferably at least 100, 200, 500 or 1000 nucleotides. The full-length sequence complementary to the entire gene transcript may be used. The length is most preferably 100-2000 nucleotides. The degree of identity of the antisense sequence to the targeted transcript should be at least 90% and more preferably 95-100%. The antisense RNA molecule may of course comprise unrelated sequences which may function to stabilize the molecule.

Recombinant Vectors

One embodiment of the present invention includes a recombinant vector, which comprises at least one polynucleotide defined herein and is capable of delivering the polynucleotide into a host cell. Recombinant vectors include expression vectors. Recombinant vectors contain heterologous polynucleotide sequences, that is, polynucleotide sequences that are not naturally found adjacent to a polynucleotide defined herein, that preferably, are derived from a different species. The vector can be either RNA or DNA, and typically is a viral vector, derived from a virus, or a plasmid. Plasmid vectors typically include additional nucleic acid sequences that provide for easy selection, amplification, and transformation of the expression cassette in prokaryotic cells, e.g., pUC-derived vectors, pGEM-derived vectors or binary vectors containing one or more T-DNA regions. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells.

"Operably linked" as used herein, refers to a functional relationship between two or more nucleic acid (e.g., DNA) segments. Typically, it refers to the functional relationship of a transcriptional regulatory element (promoter) to a transcribed sequence. For example, a promoter is operably linked to a coding sequence of a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements such as enhancers need not be physically contiguous or located in close proximity to the coding sequences whose transcription they enhance.

When there are multiple promoters present, each promoter may independently be the same or different.

Recombinant vectors may also contain one or more signal peptide sequences to enable an expressed polypeptide defined herein to be retained in the endoplasmic reticulum (ER) in the cell, or transfer into a plastid, and/or contain fusion sequences which lead to the expression of nucleic acid molecules as fusion proteins. Examples of suitable signal segments include any signal segment capable of directing the secretion or localisation of a polypeptide defined herein.

To facilitate identification of transformants, the recombinant vector desirably comprises a selectable or screenable marker gene. By "marker gene" is meant a gene that imparts a distinct phenotype to cells expressing the marker gene and thus, allows such transformed cells to be distinguished from cells that do not have the marker. A selectable marker gene confers a trait for which one can "select" based on resistance to a selective agent (e.g., a herbicide, antibiotic). A screenable marker gene (or reporter gene) confers a trait that one can identify through observation or testing, that is, by "screening" (e.g., β-glucuronidase, luciferase, GFP or other enzyme activity not present in untransformed cells). Exemplary selectable markers for selection of plant transformants include, but are not limited to, a hyg gene which encodes hygromycin B resistance; a neomycin phosphotransferase (nptII) gene conferring resistance to kanamycin, paromomycin; a glutathione-S-transferase gene from rat liver conferring resistance to glutathione derived herbicides as for example, described in EP 256223; a glutamine synthetase gene conferring, upon overexpression, resistance to glutamine synthetase inhibitors such as phosphinothricin as for example, described in WO 87/05327; an acetyltransferase gene from *Streptomyces viridochromogenes* conferring resistance to the selective agent phosphinothricin as for example, described in EP 275957; a gene encoding a 5-enol-shikimate-3-phosphate synthase (EPSPS) conferring tolerance to N-phosphonomethylglycine as for example, described by Hinchee et al. (1988); a bar gene conferring resistance against bialaphos as for example, described in WO91/02071; a nitrilase gene such as bxn from *Klebsiella ozaenae* which confers resistance to bromoxynil (Stalker et al., 1988); a dihydrofolate reductase (DHFR) gene conferring resistance to methotrexate (Thillet et al., 1988); a mutant acetolactate synthase gene (ALS) which confers resistance to imidazolinone, sulfonylurea, or other ALS-inhibiting chemicals (EP 154,204); a mutated anthranilate synthase gene that confers resistance to 5-methyl tryptophan; or a dalapon dehalogenase gene that confers resistance to the herbicide.

Preferably, the recombinant vector is stably incorporated into the genome of the cell such as the plant cell. Accordingly, the recombinant vector may comprise appropriate elements which allow the vector to be incorporated into the genome, or into a chromosome of the cell.

Expression Vector

As used herein, an "expression vector" is a DNA vector that is capable of transforming a host cell and of effecting expression of one or more specified polynucleotides. Expression vectors of the present invention contain regulatory sequences such as transcription control sequences, translation control sequences, origins of replication, and other regulatory sequences that are compatible with the host cell and that control the expression of polynucleotides of the present invention. In particular, expression vectors of the present invention include transcription control sequences. Transcription control sequences are sequences which control the initiation, elongation, and termination of transcription. Particularly important transcription control sequences are those which control transcription initiation such as promoter, enhancer, operator and repressor sequences. The choice of the regulatory sequences used depends on the target organism such as a plant and/or target organ or tissue of interest. Such regulatory sequences may be obtained from any eukaryotic organism such as plants or plant viruses, or may be chemically synthesized. A number of vectors suitable for stable transfection of plant cells or for the establishment of transgenic plants have been described in for example, Pouwels et al., Cloning Vectors: A Laboratory Manual, 1985, supp. 1987, Weissbach and Weissbach, Methods for Plant Molecular Biology, Academic Press, 1989, and Gelvin et al., Plant Molecular Biology Manual, Kluwer Academic Publishers, 1990. Typically, plant expression vectors include for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, a transcription termination site, and/or a polyadenylation signal.

A number of constitutive promoters that are active in plant cells have been described. Suitable promoters for constitutive expression in plants include, but are not limited to, the cauliflower mosaic virus (CaMV) 35S promoter, the Figwort mosaic virus (FMV) 35S, the light-inducible promoter from the small subunit (SSU) of the ribulose-1,5-bis-phosphate carboxylase, the rice cytosolic triosephosphate isomerase promoter, the adenine phosphoribosyltransferase promoter of *Arabidopsis*, the rice actin 1 gene promoter, the mannopine synthase and octopine synthase promoters, the Adh promoter, the sucrose synthase promoter, the R gene complex promoter, and the chlorophyll α/β binding protein gene promoter. These promoters have been used to create DNA vectors that have been expressed in plants, see for example, WO 84/02913. All of these promoters have been used to create various types of plant-expressible recombinant DNA vectors.

For the purpose of expression in source tissues of the plant such as the leaf, seed, root or stem, it is preferred that the promoters utilized in the present invention have relatively high expression in these specific tissues. For this purpose, one may choose from a number of promoters for genes with tissue- or cell-specific, or -enhanced expression. Examples of such promoters reported in the literature include, the chloroplast glutamine synthetase GS2 promoter from pea, the chloroplast fructose-1,6-biphosphatase promoter from wheat, the nuclear photosynthetic ST-LS1 promoter from potato, the serine/threonine kinase promoter and the glucoamylase (CHS) promoter from *Arabidopsis thaliana*. Also reported to be active in photosynthetically active tissues are the ribulose-1,5-bisphosphate carboxylase promoter from eastern larch (*Larix laricina*), the promoter for the Cab gene, Cab6, from pine, the promoter for the Cab-1 gene from wheat, the promoter for the Cab-1 gene from spinach, the promoter for the Cab 1R gene from rice, the pyruvate, orthophosphate dikinase (PPDK) promoter from *Zea mays*, the promoter for the tobacco Lhcb1*2 gene, the *Arabidopsis thaliana* Suc2 sucrose-$H^{30}$ symporter promoter, and the promoter for the thylakoid membrane protein genes from spinach (PsaD, PsaF, PsaE, PC, FNR, AtpC, AtpD, Cab, RbcS). Other promoters for the chlorophyll α/β-binding proteins may also be utilized in the present invention such as the promoters for LhcB gene and PsbP gene from white mustard (*Sinapis alba*).

A variety of plant gene promoters that are regulated in response to environmental, hormonal, chemical, and/or developmental signals, also can be used for expression of RNA-binding protein genes in plant cells, including promoters regulated by (1) heat, (2) light (e.g., pea RbcS-3A promoter, maize RbcS promoter), (3) hormones such as abscisic acid, (4) wounding (e.g., WunI), or (5) chemicals such as methyl jasmonate, salicylic acid, steroid hormones, alcohol, Safeners (WO 97/06269), or it may also be advantageous to employ (6) organ-specific promoters.

As used herein, the term "plant storage organ specific promoter" refers to a promoter that preferentially, when compared to other plant tissues, directs gene transcription in a storage organ of a plant. For the purpose of expression in sink tissues of the plant such as the tuber of the potato plant, the fruit of tomato, or the seed of soybean, canola, cotton, *Zea mays*, wheat, rice, and barley, it is preferred that the promoters utilized in the present invention have relatively high expression in these specific tissues. The promoter for β-conglycinin or other seed-specific promoters such as the napin, zein, linin and phaseolin promoters, can be used. Root specific promoters may also be used. An example of such a promoter is the promoter for the acid chitinase gene. Expression in root tissue could also be accomplished by utilizing the root specific subdomains of the CaMV 35S promoter that have been identified.

In a particularly preferred embodiment, the promoter directs expression in tissues and organs in which lipid biosynthesis takes place. Such promoters may act in seed development at a suitable time for modifying lipid composition in seeds. Preferred promoters for seed-specific expression include: 1) promoters from genes encoding enzymes involved in lipid biosynthesis and accumulation in seeds such as desaturases and elongases, 2) promoters from genes encoding seed storage proteins, and 3) promoters from genes encoding enzymes involved in carbohydrate biosynthesis and accumulation in seeds. Seed specific promoters which are suitable are, the oilseed rape napin gene promoter (U.S. Pat. No. 5,608,152), the *Vicia faba* USP promoter (Baumlein et al., 1991), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980), or the legumin B4 promoter (Baumlein et al., 1992), and promoters which lead to the seed-specific expression in monocots such as maize, barley, wheat, rye, rice and the like. Notable promoters which are suitable are the barley lpt2 or lpt1 gene promoter (WO 95/15389 and WO 95/23230), or the promoters described in WO 99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene, the rye secalin gene). Other promoters include those described by Broun et al. (1998), Potenza et al. (2004), US 20070192902 and US 20030159173. In an embodiment, the seed specific promoter is preferentially expressed in defined parts of the seed such as the cotyledon(s) or the endosperm. Examples of cotyledon specific promoters include, but are not limited to, the FP1 promoter (Ellerstrom et al., 1996), the pea legumin promoter (Perrin et al., 2000), and the bean phytohemagglutnin promoter (Perrin et al., 2000). Examples of endosperm specific promoters include, but are not limited to, the maize zein-1 promoter (Chikwamba et al., 2003), the rice glutelin-1 promoter (Yang et al., 2003), the barley D-hordein promoter (Horvath et al., 2000) and wheat HMW glutenin promoters (Alvarez et al., 2000). In a further embodiment, the seed specific promoter is not expressed, or is only expressed at a low level, in the embryo and/or after the seed germinates.

In another embodiment, the plant storage organ specific promoter is a fruit specific promoter. Examples include, but are not limited to, the tomato polygalacturonase, E8 and Pds promoters, as well as the apple ACC oxidase promoter (for review, see Potenza et al., 2004). In a preferred embodiment, the promoter preferentially directs expression in the edible parts of the fruit, for example the pith of the fruit, relative to the skin of the fruit or the seeds within the fruit.

In an embodiment, the inducible promoter is the *Aspergillus nidulans* alc system. Examples of inducible expression systems which can be used instead of the *Aspergillus nidulans* alc system are described in a review by Padidam (2003) and Corrado and Karali (2009). In another embodiment, the inducible promoter is a safener inducible promoter such as, for example, the maize ln2-1 or ln2-2 promoter (Hershey and Stoner, 1991), the safener inducible promoter is the maize GST-27 promoter (Jepson et al., 1994), or the soybean GH2/4 promoter (Ulmasov et al., 1995).

In another embodiment, the inducible promoter is a senescence inducible promoter such as, for example, senescence-inducible promoter SAG (senescence associated gene) 12 and SAG 13 from *Arabidopsis* (Gan, 1995; Gan and Amasino, 1995) and LSC54 from *Brassica napus* (Buchanan-Wollaston, 1994). Such promoters show increased expression at about the onset of senescence of plant tissues, in particular the leaves.

For expression in vegetative tissue leaf-specific promoters, such as the ribulose biphosphate carboxylase (RBCS) promoters, can be used. For example, the tomato RBCS1, RBCS2 and RBCS3A genes are expressed in leaves and light grown seedlings (Meier et al., 1997). A ribulose bisphosphate carboxylase promoters expressed almost exclusively in mesophyll cells in leaf blades and leaf sheaths at high levels, described by Matsuoka et al. (1994), can be used. Another leaf-specific promoter is the light harvesting chlorophyll a/b binding protein gene promoter (see, Shiina et al., 1997). The *Arabidopsis thaliana* myb-related gene promoter (Atmyb5) described by Li et al. (1996), is leaf-specific. The Atmyb5 promoter is expressed in developing leaf trichomes, stipules, and epidermal cells on the margins of young rosette and cauline leaves, and in immature seeds. A leaf promoter identified in maize by Busk et al. (1997), can also be used.

In some instances, for example when LEC2 or BBM is recombinantly expressed, it may be desirable that the transgene is not expressed at high levels. An example of a promoter which can be used in such circumstances is a truncated napin A promoter which retains the seed-specific expression pattern but with a reduced expression level (Tan et al., 2011).

The 5' non-translated leader sequence can be derived from the promoter selected to express the heterologous gene sequence of the polynucleotide of the present invention, or may be heterologous with respect to the coding region of the enzyme to be produced, and can be specifically modified if desired so as to increase translation of mRNA. For a review of optimizing expression of transgenes, see Koziel et al. (1996). The 5' non-translated regions can also be obtained from plant viral RNAs (Tobacco mosaic virus, Tobacco etch virus, Maize dwarf mosaic virus, Alfalfa mosaic virus, among others) from suitable eukaryotic genes, plant genes (wheat and maize chlorophyll a/b binding protein gene leader), or from a synthetic gene sequence. The present invention is not limited to constructs wherein the non-translated region is derived from the 5' non-translated sequence that accompanies the promoter sequence. The leader sequence could also be derived from an unrelated promoter or coding sequence. Leader sequences useful in context of the present invention comprise the maize Hsp70 leader (U.S. Pat. Nos. 5,362,865 and 5,859,347), and the TMV omega element.

The termination of transcription is accomplished by a 3' non-translated DNA sequence operably linked in the expression vector to the polynucleotide of interest. The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in plant cells. The nopaline synthase 3' untranslated region, the 3' untranslated region from pea small subunit Rubisco gene, the 3' untranslated region from soybean 7S seed storage protein gene are commonly used in this capacity. The 3' transcribed, non-translated regions containing the polyadenylate signal of *Agrobacterium* tumor-inducing (Ti) plasmid genes are also suitable.

Recombinant DNA technologies can be used to improve expression of a transformed polynucleotide by manipulating, for example, the efficiency with which the resultant transcripts are translated by codon optimisation according to the host cell species or the deletion of sequences that destabilize transcripts, and the efficiency of post-translational modifications.

Transfer Nucleic Acids

Transfer nucleic acids can be used to deliver an exogenous polynucleotide to a cell and comprise one, preferably two, border sequences and one or more polynucleotides of interest. The transfer nucleic acid may or may not encode a selectable marker. Preferably, the transfer nucleic acid forms part of a binary vector in a bacterium, where the binary vector further comprises elements which allow replication of the vector in the bacterium, selection, or maintenance of bacterial cells containing the binary vector. Upon transfer to a eukaryotic cell, the transfer nucleic acid component of the binary vector is capable of integration into the genome of the eukaryotic cell or, for transient expression experiments, merely of expression in the cell.

As used herein, the term "extrachromosomal transfer nucleic acid" refers to a nucleic acid molecule that is capable of being transferred from a bacterium such as *Agrobacterium* sp., to a plant cell such as a plant leaf cell. An extrachromosomal transfer nucleic acid is a genetic element that is well-known as an element capable of being transferred, with the subsequent integration of a nucleotide sequence contained within its borders into the genome of the recipient cell. In this respect, a transfer nucleic acid is flanked, typically, by two "border" sequences, although in some instances a single border at one end can be used and the second end of the transferred nucleic acid is generated randomly in the transfer process. A polynucleotide of interest is typically positioned between the left border-like sequence and the right border-like sequence of a transfer nucleic acid. The polynucleotide contained within the transfer nucleic acid may be operably linked to a variety of different promoter and terminator regulatory elements that facilitate its expression, that is, transcription and/or translation of the polynucleotide. Transfer DNAs (T-DNAs) from *Agrobacterium* sp. such as *Agrobacterium tumefaciens* or *Agrobacterium rhizogenes*, and man made variants/mutants thereof are probably the best characterized examples of transfer nucleic acids. Another example is P-DNA ("plant-DNA") which comprises T-DNA border-like sequences from plants.

As used herein, "T-DNA" refers to a T-DNA of an *Agrobacterium tumefaciens* Ti plasmid or from an *Agrobacterium rhizogenes* Ri plasmid, or variants thereof which function for transfer of DNA into plant cells. The T-DNA may comprise an entire T-DNA including both right and left border sequences, but need only comprise the minimal sequences required in cis for transfer, that is, the right T-DNA border sequence. The T-DNAs of the invention have inserted into them, anywhere between the right and left border sequences (if present), the polynucleotide of interest. The sequences encoding factors required in trans for transfer of the T-DNA into a plant cell such as vir genes, may be inserted into the T-DNA, or may be present on the same replicon as the T-DNA, or preferably are in trans on a compatible replicon in the *Agrobacterium* host. Such "binary vector systems" are well known in the art. As used herein, "P-DNA" refers to a transfer nucleic acid isolated from a plant genome, or man made variants/mutants thereof, and comprises at each end, or at only one end, a T-DNA border-like sequence.

As used herein, a "border" sequence of a transfer nucleic acid can be isolated from a selected organism such as a plant or bacterium, or be a man made variant/mutant thereof. The border sequence promotes and facilitates the transfer of the polynucleotide to which it is linked and may facilitate its integration in the recipient cell genome. In an embodiment, a border-sequence is between 10-80 bp in length. Border sequences from T-DNA from *Agrobacterium* sp. are well known in the art and include those described in Lacroix et al. (2008).

Whilst traditionally only *Agrobacterium* sp. have been used to transfer genes to plants cells, there are now a large number of systems which have been identified/developed which act in a similar manner to *Agrobacterium* sp. Several non-*Agrobacterium* species have recently been genetically modified to be competent for gene transfer (Chung et al., 2006; Broothaerts et al., 2005). These include *Rhizobium* sp. NGR234, *Sinorhizobium meliloti* and *Mezorhizobium loti*.

As used herein, the terms "transfection", "transformation" and variations thereof are generally used interchangeably. "Transfected" or "transformed" cells may have been manipulated to introduce the polynucleotide(s) of interest, or may be progeny cells derived therefrom.

Plants

The invention also provides a plant or part thereof comprising two or more exogenous polynucleotides and/or genetic modifications as described herein. The term "plant" when used as a noun refers to whole plants, whilst the term "part thereof" refers to plant organs (e.g., leaves, stems, roots, flowers, fruit), single cells (e.g., pollen), seed, seed parts such as an embryo, endosperm, scutellum or seed coat, plant tissue such as vascular tissue, plant cells and progeny of the same. As used herein, plant parts comprise plant cells.

As used herein, the terms "in a plant" and "in the plant" in the context of a modification to the plant means that the modification has occurred in at least one part of the plant, including where the modification has occurred throughout the plant, and does not exclude where the modification occurs in only one or more but not all parts of the plant. For example, a tissue-specific promoter is said to be expressed "in a plant", even though it might be expressed only in certain parts of the plant. Analogously, "a transcription factor polypeptide that increases the expression of one or more glycolytic and/or fatty acid biosynthetic genes in the plant" means that the increased expression occurs in at least a part of the plant.

As used herein, the term "plant" is used in it broadest sense, including any organism in the Kingdom Plantae. It also includes red and brown algae as well as green algae. It includes, but is not limited to, any species of flowering plant, grass, crop or cereal (e.g., oilseed, maize, soybean), fodder or forage, fruit or vegetable plant, herb plant, woody plant or tree. It is not meant to limit a plant to any particular structure. It also refers to a unicellular plant (e.g., microalga). The term "part thereof" in reference to a plant refers to a plant cell and progeny of same, a plurality of plant cells, a structure that is present at any stage of a plant's development, or a plant tissue. Such structures include, but are not limited to, leaves, stems, flowers, fruits, nuts, roots, seed, seed coat, embryos. The term "plant tissue" includes differentiated and undifferentiated tissues of plants including those present in leaves, stems, flowers, fruits, nuts, roots, seed, for example, embryonic tissue, endosperm, dermal tissue (e.g., epidermis, periderm), vascular tissue (e.g., xylem, phloem), or ground tissue (comprising parenchyma, collenchyma, and/or sclerenchyma cells), as well as cells in culture (e.g., single cells, protoplasts, callus, embryos, etc.). Plant tissue may be in planta, in organ culture, tissue culture, or cell culture.

As used herein, the term "vegetative tissue" or "vegetative plant part" is any plant tissue, organ or part other than organs for sexual reproduction of plants. The organs for sexual reproduction of plants are specifically seed bearing organs, flowers, pollen, fruits and seeds. Vegetative tissues and parts include at least plant leaves, stems (including bolts and tillers but excluding the heads), tubers and roots, but excludes flowers, pollen, seed including the seed coat, embryo and endosperm, fruit including mesocarp tissue, seed-bearing pods and seed-bearing heads. In one embodiment, the vegetative part of the plant is an aerial plant part. In another or further embodiment, the vegetative plant part is a green part such as a leaf or stem.

A "transgenic plant" or variations thereof refers to a plant that contains a transgene not found in a wild-type plant of the same species, variety or cultivar. Transgenic plants as defined in the context of the present invention include plants and their progeny which have been genetically modified using recombinant techniques to cause production of at least one polypeptide defined herein in the desired plant or part thereof. Transgenic plant parts has a corresponding meaning.

The plant and plant parts of the invention may comprise genetic modifications, for example gene mutations, and be considered as "non-transgenic" provided they lack transgenes.

The terms "seed" and "grain" are used interchangeably herein. "Grain" refers to mature grain such as harvested grain or grain which is still on a plant but ready for harvesting, but can also refer to grain after imbibition or germination, according to the context. Mature grain commonly has a moisture content of less than about 18%. In a preferred embodiment, the moisture content of the grain is at a level which is generally regarded as safe for storage, preferably between 5% and 15%, between 6% and 8%, between 8% and 10%, or between 10% and 15%. "Developing seed" as used herein refers to a seed prior to maturity, typically found in the reproductive structures of the plant after fertilisation or anthesis, but can also refer to such seeds prior to maturity which are isolated from a plant. Mature seed commonly has a moisture content of less than about 12%.

As used herein, the term "plant storage organ" refers to a part of a plant specialized to store energy in the form of for example, proteins, carbohydrates, lipid. Examples of plant storage organs are seed, fruit, tuberous roots, and tubers. A preferred plant storage organ of the invention is seed.

As used herein, the term "phenotypically normal" refers to a genetically modified plant or part thereof, for example a plant such as a transgenic plant, or a storage organ such as a seed, tuber or fruit of the invention not having a significantly reduced ability to grow and reproduce when compared to an unmodified plant or part thereof. Preferably, the biomass, growth rate, germination rate, storage organ size, seed size and/or the number of viable seeds produced is not less than 90% of that of a plant lacking said genetic modifications or exogenous polynucleotides when grown under identical conditions. This term does not encompass features of the plant which may be different to the wild-type plant but which do not effect the usefulness of the plant for commercial purposes such as, for example, a ballerina phenotype of seedling leaves. In an embodiment, the genetically modified plant or part thereof which is phenotypically normal comprises a recombinant polynucleotide encoding a silencing suppressor operably linked to a plant storage organ specific promoter and has an ability to grow or reproduce which is essentially the same as a corresponding plant or part thereof not comprising said polynucleotide.

Plants go through a series of growing stages from sowing of a seed, germination and emergence of a seedling, through to flowering, seed setting, physiological maturity and ultimately senescence. These stages are well known and readily defined, for example for *Sorghum* plants as follows. Taking the day the seedling first emerges above the soil as day 0, the vegetative stage of growth is defined herein as from 10 days to initiation of flowering at about 60-70 days, and physiological maturity is reached at about 100 days, depending on the environmental conditions. The vegetative stage includes the boot leaf stage from about 45 days until the first flowering. The boot leaf is the last leaf formed on the plant, from which the panicle (head) emerges. The "boot leaf stage" is defined as from when the boot leaf has fully emerged to initiation of flowering.

As used herein, the term "commencement of flowering" or "initiation of flowering" with respect to a plant refers to the time that the first flower on the plant opens, or the time of onset of anthesis.

As used herein, the term "seed set" with respect to a seed-bearing plant refers to the time when the first seed of the plant reaches maturity. This is typically observable by the colour of the seed or its moisture content, well known in the art.

As used herein, the term "mature" as it relates to a plant leaf means that it has reached full size but has not begun to show signs of ageing or death such as yellowing and/or sensensce. The skilled person can readily determine whether a leaf of a particular plant can be considered as mature.

As used herein, the term "senescence" with respect to a whole plant refers to the final stage of plant development which follows the completion of growth, usually after the plant reaches maximum aerial biomass or height. Senescence begins when the plant aerial biomass reaches its maximum and begins to decline in amount and generally ends with death of most of the plant tissues. It is during this stage that the plant mobilises and recycles cellular components from leaves and other parts which accumulated during growth to other parts to complete its reproductive development. Senescence is a complex, regulated process which involves new or increased gene expression of some genes. Often, some plant parts are senescing while other parts of the same plant continue to grow. Therefore, with respect to a plant leaf or other green organ, the term "senescence" as used herein refers to the time when the amount of chlorophyll in the leaf or organ begins to decrease. Senescence is typically associated with desiccation of the leaf or organ, mostly in the last stage of senescence. Senescence is usually observable by the change in colour of the leaf from green towards yellow and eventually to brown when fully desiccated. It is believed that cellular senescence underlies plant and organ senescence.

Plants provided by or contemplated for use in the practice of the present invention include both monocotyledons and dicotyledons. In preferred embodiments, the plants of the present invention are crop plants (for example, cereals and pulses, maize, wheat, potatoes, rice, sorghum, millet, cassava, barley) or legumes such as soybean, beans or peas. The plants may be grown for production of edible roots, tubers, leaves, stems, flowers or fruit. The plants may be vegetable plants whose vegetative parts are used as food. The plants of the invention may be: *Acrocomia aculeata* (macauba palm), *Arabidopsis thaliana*, *Aracinis hypogaea* (peanut), *Astrocaryum murumuru* (murumuru), *Astrocaryum vulgare* (tucumã), *Attalea geraensis* (Indaií-rateiro), *Attalea humilis* (American oil palm), *Attalea oleifera* (andaiá), *Attalea phalerata* (uricuri), *Attalea speciosa* (babassu), *Avena sativa* (oats), *Beta vulgaris* (sugar beet), *Brassica* sp. such as *Brassica carinata*, *Brassica juncea*, *Brassica napobrassica*, *Brassica napus* (canola), *Camelina sativa* (false flax), *Cannabis sativa* (hemp), *Carthamus tinctorius* (safflower), *Caryocar brasiliense* (pequi), *Cocos nucifera* (Coconut), *Crambe abyssinica* (Abyssinian kale), *Cucumis melo* (melon), *Elaeis guineensis* (African palm), *Glycine max* (soybean), *Gossypium hirsutum* (cotton), *Helianthus* sp. such as *Helianthus annuus* (sunflower), *Hordeum vulgare* (barley), *Jatropha curcas* (physic nut), *Joannesia princeps* (arara nut-tree), *Lemna* sp. (duckweed) such as *Lemna aequinoctialis*, *Lemna disperma*, *Lemna ecuadoriensis*, *Lemna gibba* (swollen duckweed), *Lemna japonica*, *Lemna minor*, *Lemna minuta*, *Lemna obscura*, *Lemna paucicostata*, *Lemna perpusilla*, *Lemna tenera*, *Lemna trisulca*, *Lemna turionifera*, *Lemna valdiviana*, *Lemna yungensis*, *Licania rigida* (oiticica), *Linum usitatissimum* (flax), *Lupinus angustifolius* (lupin), *Mauritia flexuosa* (buriti palm), *Maximiliana maripa* (inaja palm), *Miscanthus* sp. such as *Miscanthus× giganteus* and *Miscanthus sinensis*, *Nicotiana* sp. (tabacco) such as *Nicotiana tabacum* or *Nicotiana benthamiana*,

*Oenocarpus bacaba* (bacaba-do-azeite), *Oenocarpus bataua* (pataua), *Oenocarpus distichus* (bacaba-de-leque), *Oryza* sp. (rice) such as *Oryza sativa* and *Oryza glaberrima*, *Panicum virgatum* (switchgrass), *Paraqueiba paraensis* (mari), *Persea amencana* (avocado), *Pongamia pinnata* (Indian beech), *Populus trichocarpa*, *Ricinus communis* (castor), *Saccharum* sp. (sugarcane), *Sesamum indicum* (sesame), *Solanum tuberosum* (potato), *Sorghum* sp. such as *Sorghum bicolor*, *Sorghum vulgare*, *Theobroma grandiforum* (cupuassu), *Trifolium* sp., *Trithrinax brasiliensis* (Brazilian needle palm), *Triticum* sp. (wheat) such as *Triticum aestivum*, *Zea mays* (corn), alfalfa (*Medicago sativa*), rye (*Secale cerale*), sweet potato (*Lopmoea batatus*), cassava (*Manihot esculenta*), coffee (*Cofea* spp.), pineapple (*Anana comosus*), citris tree (*Citrus* spp.), cocoa (*Theobroma cacao*), tea (*Camellia senensis*), banana (*Musa* spp.), avocado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*) and almond (*Prunus amygdalus*).

In an embodiment, the plant is not a *Nicotiana* sp.

Other preferred plants include C4 grasses such as, in addition to those mentioned above, *Andropogon gerardi*, *Bouteloua curtipendula*, *B. gracilis*, *Buchloe dactyloides*, *Schizachyrium scoparium*, *Sorghastrum nutans*, *Sporobolus cryptandrus*; C3 grasses such as *Elymus canadensis*, the legumes *Lespedeza capitata* and *Petalostemum villosum*, the forb *Aster azureus*; and woody plants such as *Quercus ellipsoidalis* and *Q. macrocarpa*. Other preferred plants include C3 grasses.

In a preferred embodiment, the plant is an angiosperm.

In an embodiment, the plant is an oilseed plant, preferably an oilseed crop plant. As used herein, an "oilseed plant" is a plant species used for the commercial production of lipid from the seeds of the plant. The oilseed plant may be, for example, oil-seed rape (such as canola), maize, sunflower, safflower, soybean, sorghum, flax (linseed) or sugar beet. Furthermore, the oilseed plant may be other Brassicas, cotton, peanut, poppy, rutabaga, mustard, castor bean, sesame, safflower, *Jatropha curcas* or nut producing plants. The plant may produce high levels of lipid in its fruit such as olive, oil palm or coconut. Horticultural plants to which the present invention may be applied are lettuce, endive, or vegetable Brassicas including cabbage, broccoli, or cauliflower. The present invention may be applied in tobacco, cucurbits, carrot, strawberry, tomato, or pepper.

In a preferred embodiment, the plant is a member of the family Fabaceae (or Leguminosae) such as alfalfa, clover, peas, lucerne, beans, lentils, lupins, mesquite, carob, soybeans, and peanuts, or a member of the family Poaceae such as corn, sorghum, wheat, barley and oats. In a particularly preferred embodiment, the plant is alfalfa, clover, corn or sorghum, each of which are particularly useful for forage or fodder for animals.

In a preferred embodiment, the transgenic plant is homozygous for each and every gene that has been introduced (transgene) so that its progeny do not segregate for the desired phenotype. The transgenic plant may also be heterozygous for the introduced transgene(s), preferably uniformly heterozygous for the transgene such as for example, in F1 progeny which have been grown from hybrid seed. Such plants may provide advantages such as hybrid vigour, well known in the art.

Transformation of Plants

Transgenic plants can be produced using techniques known in the art, such as those generally described in Slater et al., Plant Biotechnology—The Genetic Manipulation of Plants, Oxford University Press (2003), and Christou and Klee, Handbook of Plant Biotechnology, John Wiley and Sons (2004).

As used herein, the terms "stably transforming", "stably transformed" and variations thereof refer to the integration of the polynucleotide into the genome of the cell such that they are transferred to progeny cells during cell division without the need for positively selecting for their presence. Stable transformants, or progeny thereof, can be identified by any means known in the art such as Southern blots on chromosomal DNA, or in situ hybridization of genomic DNA, enabling their selection.

*Agrobacterium*-mediated transfer is a widely applicable system for introducing genes into plant cells because DNA can be introduced into cells in whole plant tissues, plant organs, or explants in tissue culture, for either transient expression, or for stable integration of the DNA in the plant cell genome. For example, floral-dip (in planta) methods may be used. The use of *Agrobacterium*-mediated plant integrating vectors to introduce DNA into plant cells is well known in the art. The region of DNA to be transferred is defined by the border sequences, and the intervening DNA (T-DNA) is usually inserted into the plant genome. It is the method of choice because of the facile and defined nature of the gene transfer.

Acceleration methods that may be used include for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells, for example of immature embryos, by a propelling force. Exemplary particles include those comprised of tungsten, gold, platinum, and the like.

In another method, plastids can be stably transformed. Methods disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932,479, and WO 99/05265). Other methods of cell transformation can also be used and include but are not limited to the introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., In: Methods for Plant Molecular Biology, Academic Press, San Diego, Calif, (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polynucleotide is cultivated using methods well known to one skilled in the art.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Northern blot hybridisation, Western blot and enzyme assay. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics. Preferably, the vegetative plant parts are harvested at a time when the yield of non-polar lipids are at their highest. In one embodiment, the vegetative plant parts are harvested about at the time of flowering, or after flowering has initiated. Preferably, the plant parts are harvested at about the time senescence begins, usually indicated by yellowing and drying of leaves.

Transgenic plants formed using *Agrobacterium* or other transformation methods typically contain a single genetic locus on one chromosome. Such transgenic plants can be referred to as being hemizygous for the added gene(s). More preferred is a transgenic plant that is homozygous for the added gene(s), that is, a transgenic plant that contains two added genes, one gene at the same locus on each chromosome of a chromosome pair. A homozygous transgenic plant can be obtained by self-fertilising a hemizygous transgenic plant, germinating some of the seed produced and analyzing the resulting plants for the gene of interest.

It is also to be understood that two different transgenic plants that contain two independently segregating exogenous genes or loci can also be crossed (mated) to produce offspring that contain both sets of genes or loci. Selfing of appropriate F1 progeny can produce plants that are homozygous for both of the exogenous genes or loci. Back-crossing to a parental plant and out-crossing with a non-transgenic plant are also contemplated, as is vegetative propagation. Similarly, a transgenic plant can be crossed with a second plant comprising a genetic modification such as a mutant gene and progeny containing both of the transgene and the genetic modification identified. Descriptions of other breeding methods that are commonly used for different traits and crops can be found in Fehr, In: Breeding Methods for Cultivar Development, Wilcox J. ed., American Society of Agronomy, Madison Wis. (1987).

Tilling

In one embodiment, TILLING (Targeting Induced Local Lesions IN Genomes) can be used to produce plants in which endogenous genes comprise a mutation, for example genes encoding an SDP1 or TGD polypeptide, TST, a plastidial GPAT, plastidial LPAAT, phosphatidic acid phosphatase (PAP), or a combination of two or more thereof. In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time. For a TILLING assay, heteroduplex methods using specific endonucleases can be used to detect single nucleotide polymorphisms (SNPs). Alternatively, Next Generation Sequencing of DNA from pools of mutagenised plants can be used to identify mutants in the gene of choice. Typically, a mutation frequency of one mutant per 1000 plants in the mutagenised population is achieved. Using this approach, many thousands of plants can be screened to identify any individual with a single base change as well as small insertions or deletions (1-30 bp) in any gene or specific region of the genome. TILLING is further described in Slade and Knauf (2005), and Henikoff et al. (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004).

Genome Editing Using Site-Specific Nucleases

Genome editing uses engineered nucleases such as RNA guided DNA endonucleases or nucleases composed of sequence specific DNA binding domains fused to a non-specific DNA cleavage module. These engineered nucleases enable efficient and precise genetic modifications by inducing targeted DNA double stranded breaks that stimulate the cell's endogenous cellular DNA repair mechanisms to repair the induced break. Such mechanisms include, for example, error prone non-homologous end joining (NHEJ) and homology directed repair (HDR).

In the presence of donor plasmid with extended homology arms, HDR can lead to the introduction of single or multiple transgenes to correct or replace existing genes. In the absence of donor plasmid, NHEJ-mediated repair yields small insertion or deletion mutations of the target that cause gene disruption.

Engineered nucleases useful in the methods of the present invention include zinc finger nucleases (ZFNs), transcription activator-like (TAL) effector nucleases (TALEN) and CRISPR/Cas9 type nucleases, and related nucleases.

Typically nuclease encoded genes are delivered into cells by plasmid DNA, viral vectors or in vitro transcribed mRNA.

A zinc finger nuclease (ZFN) comprises a DNA-binding domain and a DNA-cleavage domain, wherein the DNA binding domain is comprised of at least one zinc finger and is operatively linked to a DNA-cleavage domain. The zinc finger DNA-binding domain is at the N-terminus of the protein and the DNA-cleavage domain is located at the C-terminus of said protein.

A ZFN must have at least one zinc finger. In a preferred embodiment, a ZFN would have at least three zinc fingers in order to have sufficient specificity to be useful for targeted genetic recombination in a host cell or organism. Typically, a ZFN having more than three zinc fingers would have progressively greater specificity with each additional zinc finger.

The zinc finger domain can be derived from any class or type of zinc finger. In a particular embodiment, the zinc finger domain comprises the $Cis_2His_2$ type of zinc finger that is very generally represented, for example, by the zinc finger transcription factors TFIIIA or Sp1. In a preferred embodiment, the zinc finger domain comprises three $Cis_2His_2$ type zinc fingers. The DNA recognition and/or the binding specificity of a ZFN can be altered in order to accomplish targeted genetic recombination at any chosen site in cellular DNA. Such modification can be accomplished using known molecular biology and/or chemical synthesis techniques. (see, for example, Bibikova et al., 2002).

The ZFN DNA-cleavage domain is derived from a class of non-specific DNA cleavage domains, for example the DNA-cleavage domain of a Type II restriction enzyme such as FokI (Kim et al., 1996). Other useful endonucleases may include, for example, HhaI, HindIII, Nod, BbvCI, EcoRI, BglI, and AlwI.

A transcription activator-like (TAL) effector nuclease (TALEN) comprises a TAL effector DNA binding domain and an endonuclease domain.

TAL effectors are proteins of plant pathogenic bacteria that are injected by the pathogen into the plant cell, where they travel to the nucleus and function as transcription factors to turn on specific plant genes. The primary amino acid sequence of a TAL effector dictates the nucleotide sequence to which it binds. Thus, target sites can be predicted for TAL effectors, and TAL effectors can be engineered and generated for the purpose of binding to particular nucleotide sequences.

Fused to the TAL effector-encoding nucleic acid sequences are sequences encoding a nuclease or a portion of a nuclease, typically a nonspecific cleavage domain from a type II restriction endonuclease such as FokI (Kim et al., 1996). Other useful endonucleases may include, for example, HhaI, HindIII, Nod, BbvCI, EcoRI, BglI, and AlwI. The fact that some endonucleases (e.g., FokI) only function as dimers can be capitalized upon to enhance the target specificity of the TAL effector. For example, in some cases each FokI monomer can be fused to a TAL effector sequence that recognizes a different DNA target sequence, and only when the two recognition sites are in close proximity do the inactive monomers come together to create a functional enzyme. By requiring DNA binding to activate the nuclease, a highly site-specific restriction enzyme can be created.

A sequence-specific TALEN can recognize a particular sequence within a preselected target nucleotide sequence present in a cell. Thus, in some embodiments, a target nucleotide sequence can be scanned for nuclease recognition sites, and a particular nuclease can be selected based on the target sequence. In other cases, a TALEN can be engineered to target a particular cellular sequence.

Genome Editing Using Programmable RNA-Guided DNA Endonucleases

Distinct from the site-specific nucleases described above, the clustered regulatory interspaced short palindromic repeats (CRISPR)/Cas system provides an alternative to ZFNs and TALENs for inducing targeted genetic alterations, via RNA-guided DNA cleavage.

CRISPR systems rely on CRISPR RNA (crRNA) and transactivating chimeric RNA (tracrRNA) for sequence-specific cleavage of DNA. Three types of CRISPR/Cas systems exist: in type II systems, Cas9 serves as an RNA-guided DNA endonuclease that cleaves DNA upon crRNA-tracrRNA target recognition. CRISPR RNA base pairs with tracrRNA to form a two-RNA structure that guides the Cas9 endonuclease to complementary DNA sites for cleavage.

The CRISPR system can be portable to plant cells by co-delivery of plasmids expressing the Cas endonuclease and the necessary crRNA components. The Cas endonuclease may be converted into a nickase to provide additional control over the mechanism of DNA repair (Cong et al., 2013).

CRISPRs are typically short partially palindromic sequences of 24-40 bp containing inner and terminal inverted repeats of up to 11 bp. Although isolated elements have been detected, they are generally arranged in clusters (up to about 20 or more per genome) of repeated units spaced by unique intervening 20-58 bp sequences. CRISPRs are generally homogenous within a given genome with most of them being identical. However, there are examples of heterogeneity in, for example, the Archaea (Mojica et al., 2000).

Feedstuffs

The present invention includes compositions which can be used as feedstuffs. For purposes of the present invention, "feedstuffs" include any food or preparation for animal (including human) consumption and which serves to nourish or build up tissues or supply energy, and/or to maintain, restore or support adequate nutritional status or metabolic function. Feedstuffs of the invention include nutritional compositions for babies and/or young children.

As used herein, the term "animal" refers to any eukaryotic organism capable of ingesting plant derived material. In an embodiment, the animal is a ruminant animal (cattle, sheep, goats etc). Alternatively, the animal is a non-ruminant animal. In one embodiment, the animal is a mammal. In an embodiment, the animal is a human. In an embodiment, the animal is a livestock animal such, but not limited to, as cattle, goats, sheep, pigs, horses, poultry such as chickens and the like. In an embodiment, the cattle are diary cattle or beef cattle. In another embodiment, the animal is a fish, for instance fish bred using aquaculture including, but not limited to, salmon, trout, carp, bass, bream, turbot, sole, milkfish, grey mullet, grouper, flounder, sea bass, cod, haddock, Japanese flounder, catfish, char, whitefish, sturgeon, tench, roach, pike, pike-perch, yellowtail, tilapia, eel or tropical fish (such as the fresh, brackish, and salt water tropical fish). The animal may be a crustacean such as, but not limited to, krill, clams, shrimp (including prawns), crab, and lobster.

Feedstuffs of the invention may comprise for example, a plant or part thereof such as a vegetative plant part of the invention along with a suitable carrier(s). The term "carrier" is used in its broadest sense to encompass any component which may or may not have nutritional value. As the person skilled in the art will appreciate, the carrier must be suitable for use (or used in a sufficiently low concentration) in a feedstuff, such that it does not have deleterious effect on an organism which consumes the feedstuff. Feedstuffs may comprise plant parts which have been harvested and subsequently processed or treated, for example, by chopping, cutting, drying, pressing or pelleting the plant parts, into a form that is suitable for consumption by the animal, or altered by processes such as drying or fermentation to produce hay or silage.

The feedstuff of the present invention comprises a lipid and/or protein produced directly or indirectly by use of the methods, plants or parts thereof disclosed herein. The composition may either be in a solid or liquid form. Additionally, the composition may include edible macronutrients, vitamins, and/or minerals in amounts desired for a particular use. The amounts of these ingredients will vary depending on whether the composition is intended for use with normal individuals or for use with individuals having specialized needs such as individuals suffering from metabolic disorders and the like.

Examples of suitable carriers with nutritional value include, but are not limited to, macronutrients such as edible fats, carbohydrates and proteins. Examples of such edible fats include, but are not limited to, coconut oil, borage oil, fungal oil, black current oil, soy oil, and mono- and di-glycerides. Examples of such carbohydrates include, but are not limited to, glucose, edible lactose, and hydrolyzed starch. Additionally, examples of proteins which may be utilized in the nutritional composition of the invention include, but are not limited to, soy proteins, electrodialysed whey, electrodialysed skim milk, milk whey, or the hydrolysates of these proteins.

With respect to vitamins and minerals, the following may be added to the feedstuff compositions of the present invention, calcium, phosphorus, potassium, sodium, chloride, magnesium, manganese, iron, copper, zinc, selenium, iodine, and vitamins A, E, D, C, and the B complex. Other such vitamins and minerals may also be added.

A feedstuff composition of the present invention may also be added to food even when supplementation of the diet is not required. For example, the composition may be added to food of any type, including, but not limited to, margarine, butter, cheeses, milk, yogurt, chocolate, candy, snacks, salad oils, cooking oils, cooking fats, meats, fish and beverages.

Additionally, material produced in accordance with the present invention may also be used as animal food supplements to alter an animal's tissue or milk fatty acid composition to one more desirable for human or animal consumption, or to reduce methane production in ruminant animals. Furthermore, feedstuffs of the invention can be used in aquaculture to increase the levels of fatty acids and nutrition in fish for human or animal consumption.

Preferred feedstuffs of the invention are the plants, seed and other plant parts such as leaves, fruits and stems which may be used directly as food or feed for humans or other animals. For example, animals may graze directly on such plants grown in the field, or be fed more measured amounts in controlled feeding. The invention includes the use of such plants and plant parts as feed for increasing the polyunsaturated fatty acid levels in humans and other animals.

For consumption by non-human animals the feedstuff may be in any suitable form for such as, but not limited to, silage, hay or pasture growing in a field. In an embodiment, the feedstuff for non-human consumption is a leguminous plant, or part thereof, which is a member of the family Fabaceae family (or Leguminosae) such as alfalfa, clover, peas, lucerne, beans, lentils, lupins, mesquite, carob, soybeans, and peanuts.

In embodiment, the animal is in a feedlot and/or a shed.

In an embodiment, the plant or fraction thereof comprises at least about 5%, at least about 10%, at least about 50%, at least about 75%, at least about 90% or all of the feedstuff.

Silage

As used herein, "silage" is a relatively high-moisture fodder which has been produced and stored in a process called ensilage and which is typically fed to cattle, sheep or other ruminants. During the storage time, carbohydrates, lipids and proteins in the plant material ferment, producing organic acids, or are broken down oxidatively, or both. The plant material upon harvest and the post-fermentation plant materials are both included in silage as the term is used herein. Silage is typically made from grass crops such as maize, sorghum, oats or other cereals, or from mixed pasture grasses and legumes such as alfalfa or clover, using the green, above-ground parts of the plants. Silage is made either by placing cut vegetation (usually the whole above-ground plant biomass which can include reproductive tissues) in a pit or silo or other means for storage, and compressing it down so as to leave as little air as possible with the plant material. Oxygen is excluded to some extent by covering it with a plastic sheet or by wrapping the plant material tightly within plastic film (baling) to reduce air inflow. Silage is made from plant material with a suitable moisture content, generally about 50% to 60% of the fresh weight, depending on the means of storage and the degree of compression used and the amount of water that will be lost in storage, but not exceeding 75%. For sorghum and corn, harvest begins when the whole-plant moisture is at a suitable level, ideally a few days before it is ripe. For pasture-type crops, the plants are mowed and allowed to wilt for a day or so until the moisture content drops to a suitable level. Ideally the crop is mowed when in full flower and deposited in the pit or silo on the day of its cutting. At harvesting, or after, the plant material is shredded or chopped by the harvester into pieces typically about 1-5 cm long. The plant material may be placed in large heaps on the ground and compressed to reduce the amount of air, then covered with plastic, or into a silo. Alternatively, the plant material may be baled in plastic wrapping to exclude air, which typically requires a lower moisture content of about 30-40%, but still too damp to be stored as dry hay.

The cut or chopped, stored plant material undergoes mostly anaerobic fermentation, which starts about 48 hours after the pit or silo is filled. The fermentation process converts sugars and other carbohydrates such as hemicellulose to organic acids, mostly acetic, propionic, lactic and butyric acids. Fermentation starts after the trapped oxygen is consumed and is essentially complete after about two weeks of storage, or may continue for longer periods. When the plant material is closely packed, the supply of oxygen is limited and the fermentation results in the decomposition of the carbohydrates, some lipids and proteins in the material into the organic acids. This product is named sour silage. If, on the other hand, the fodder is more loosely packed, the main reaction is oxidation which proceeds more rapidly and the temperature rises. If the mass is compressed when the temperature is 60-75 C, the reaction ceases and sweet silage results. Fermentation may be aided by inoculation with specific microorganisms such as lactic acid bacteria to speed fermentation or improve the resulting silage, e.g. with *Lactobacillus plantarum*.

Bulk silage is commonly fed to dairy cattle, while baled silage tends to be used for beef cattle, sheep and horses. The advantages of silage as animal feed are several. During fermentation, the silage bacteria act on the cellulose and other carbohydrates in the forage to produce the organic fatty acids, thereby lowering the pH. This inhibits competing bacteria that might cause spoilage and the organic acids thereby act as natural preservatives, improve digestibility and palatability. This preservative action is particularly important during winter in temperate regions, when green forage is unavailable.

Silage can be produced using techniques known in the art such as those described in CN 101940272 CN 103461658 CN 101946853, CN 101946853, CN 104381743, U.S. Pat. Nos. 3,875,304 and 6,224,916. Pellets for animal feed can be produced using techniques known in the art such as those described in U.S. Pat. Nos. 3,035,920, 3,573,924 and 5,871,802.

Plant Biomass

An increase in the total lipid content of plant biomass equates to greater energy content, making its use as a feed or forage or in the production of biofuel more economical.

The main components of naturally occurring plant biomass are carbohydrates (approximately 75%, dry weight) and lignin (approximately 25%), which can vary with plant type. The carbohydrates are mainly cellulose or hemicellulose fibers, which impart strength to the plant structure, and lignin, which holds the fibers together. Plant biomass typically has a low energy density as a result of both its physical form and moisture content. This also makes it inconvenient and inefficient for storage and transport without some kind of pre-processing. There are a range of processes available to convert it into a more convenient form including: 1) physical pre-processing (for example, grinding) or 2) conversion by thermal (for example, combustion, gasification, pyrolysis) or chemical (for example, anaerobic digestion, fermentation, composting, transesterification) processes. In this way, the biomass is converted into what can be described as a biomass fuel.

Combustion

Combustion is the process by which flammable materials are allowed to burn in the presence of air or oxygen with the release of heat. The basic process is oxidation. Combustion is the simplest method by which biomass can be used for energy, and has been used to provide heat. This heat can itself be used in a number of ways: 1) space heating, 2) water (or other fluid) heating for central or district heating or process heat, 3) steam raising for electricity generation or motive force. When the flammable fuel material is a form of biomass the oxidation is of predominantly the carbon (C) and hydrogen (H) in the cellulose, hemicellulose, lignin, and other molecules present to form carbon dioxide ($CO_2$) and water ($H_2O$). The plants of the invention provide improved fuel for combustion by virtue of the increased lipid content.

Gasification

Gasification is a partial oxidation process whereby a carbon source such as plant biomass, is broken down into carbon monoxide (CO) and hydrogen ($H_2$), plus carbon dioxide ($CO_2$) and possibly hydrocarbon molecules such as methane ($CH_4$). If the gasification takes place at a relatively low temperature, such as 700° C. to 1000° C., the product gas will have a relatively high level of hydrocarbons compared to high temperature gasification. As a result it may be used directly, to be burned for heat or electricity generation via a steam turbine or, with suitable gas clean up, to run an internal combustion engine for electricity generation. The combustion chamber for a simple boiler may be close coupled with the gasifier, or the producer gas may be cleaned of longer chain hydrocarbons (tars), transported, stored and burned remotely. A gasification system may be closely integrated with a combined cycle gas turbine for electricity generation (IGCC—integrated gasification combined cycle). Higher temperature gasification (1200° C. to 1600° C.) leads to few hydrocarbons in the product gas, and a higher proportion of CO and $H_2$. This is known as synthesis gas (syngas or biosyngas) as it can be used to synthesize longer chain hydrocarbons using techniques such as Fischer-Tropsch (FT) synthesis. If the ratio of $H_2$ to CO is correct (2:1) FT synthesis can be used to convert syngas into high quality synthetic diesel biofuel which is compatible with conventional fossil diesel and diesel engines.

Pyrolysis

As used herein, the term "pyrolysis" means a process that uses slow heating in the absence of oxygen to produce gaseous, oil and char products from biomass. Pyrolysis is a thermal or thermo-chemical conversion of lipid-based, particularly triglyceride-based, materials. The products of pyrolysis include gas, liquid and a sold char, with the proportions of each depending upon the parameters of the process. Lower temperatures (around 400° C.) tend to produce more solid char (slow pyrolysis), whereas somewhat higher temperatures (around 500° C.) produce a much higher proportion of liquid (bio-oil), provided the vapour residence time is kept down to around is or less. Temperatures of about 275° C. to about 375° C. can be used to produce liquid bio-oil having a higher proportion of longer chain hydrocarbons. Pyrolysis involves direct thermal cracking of the lipids or a combination of thermal and catalytic cracking. At temperatures of about 400-500° C., cracking occurs, producing short chain hydrocarbons such as alkanes, alkenes, alkadienes, aromatics, olefins and carboxylic acid, as well as carbon monoxide and carbon dioxide.

Four main catalyst types can be used including transition metal catalysts, molecular sieve type catalysts, activated alumina and sodium carbonate (Maher et al., 2007). Examples are given in U.S. Pat. No. 4,102,938. Alumina ($Al_2O_3$) activated by acid is an effective catalyst (U.S. Pat. No. 5,233,109). Molecular sieve catalysts are porous, highly crystalline structures that exhibit size selectivity, so that molecules of only certain sizes can pass through. These include zeolite catalysts such as ZSM-5 or HZSM-5 which are crystalline materials comprising $AlO_4$ and $SiO_4$ and other silica-alumina catalysts. The activity and selectivity of these catalysts depends on the acidity, pore size and pore shape, and typically operate at 300-500° C. Transition metal catalysts are described for example in U.S. Pat. No. 4,992,605. Sodium carbonate catalyst has been used in the pyrolysis of oils (Dandik and Aksoy, 1998).

As used herein, "hydrothermal processing", "HTP", also referred to as "thermal depolymerisation" is a form of pyrolysis which reacts the plant-derived matter, specifically the carbon-containing material in the plant-derived matter, with hydrogen to produce a bio-oil product comprised predominantly of paraffinic hydrocarbons along with other gases and solids. A significant advantage of HTP is that the vegetative plant material does not need to be dried before forming the composition for the conversion reaction, although the vegetative plant material can be dried beforehand to aid in transport or storage of the biomass. The biomass can be used directly as harvested from the field. The reactor is any vessel which can withstand the high temperature and pressure used and is resistant to corrosion. The solvent used in the HTP includes water or is entirely water, or may include some hydrocarbon compounds in the form of an oil. Generally, the solvent in HTP lacks added alcohols. The conversion reaction may occur in an oxidative, reductive or inert environment. "Oxidative" as used herein means in the presence of air, "reductive" means in the presence of a reducing agent, typically hydrogen gas or methane, for example 10-15% $H_2$ with the remainder of the gas being $N_2$, and "inert" means in the presence of an inert gas such as nitrogen or argon. The conversion reaction is preferably carried out under reductive conditions. The carbon-containing materials that are converted include cellulose, hemicellulose, lignin and proteins as well as lipids. The process uses a conversion temperature of between 270° C. and 400° C. and a pressure of between 70 and 350 bar, typically 300° C. to 350° C. and a pressure between 100-170 bar. As a result of the process, organic vapours, pyrolysis gases and charcoal are produced. The organic vapours are condensed to produce the bio-oil. Recovery of the bio-oil may be achieved by cooling the reactor and reducing the pressure to atmospheric pressure, which allows bio-oil (organic) and water phases to develop and the bio-oil to be removed from the reactor.

The yield of the recovered bio-oil is calculated as a percentage of the dry weight of the input biomass on a dry weight basis. It is calculated according to the formula: weight of bio-oil×100/dry weight of the vegetative plant parts. The weight of the bio-oil does not include the weight of any water or solids which may be present in a bio-oil mixture, which are readily removed by filtration or other known methods.

The bio-oil may then be separated into fractions by fractional distillation, with or without additional refining processes. Typically, the fractions that condense at these temperatures are termed: about 370° C., fuel oil; about 300° C., diesel oil; about 200° C., kerosene; about 150° C., gasoline (petrol). Heavier fractions may be cracked into lighter, more desirable fractions, well known in the art. Diesel fuel typically is comprised of C13-C22 hydrocarbon compounds.

Transesterification

"Transesterification" as used herein is the conversion of lipids, principally triacylglycerols, into fatty acid methyl esters or ethyl esters by reaction with short chain alcohols such as methanol or ethanol, in the presence of a catalyst such as alkali or acid. Methanol is used more commonly due to low cost and availability, but ethanol, propanol or butanol or mixtures of the alcohols can also be used. The catalysts may be homogeneous catalysts, heterogeneous catalysts or enzymatic catalysts. Homogeneous catalysts include ferric sulphate followed by KOH. Heterogeneous catalysts include CaO, $K_3PO_4$, and $WO_3/ZrO_2$. Enzymatic catalysts include Novozyme 435 produced from *Candida antarctica.*

Transesterification can be carried out on extracted oil, or preferably directly in situ in the vegetative plant material. The vegetative plant parts may be dried and milled prior to being used to prepare the composition for the conversion reaction, but does not need to be. The advantage of direct conversion to fatty acid esters, preferably FAME, is that the conversion can use lower temperatures and pressures and still provide good yields of the product, for example, comprising at least 50% FAME by weight. The yield of recovered bio-oil by transesterification is calculated as for the HTP process.

Production of Non-Polar Lipids

Techniques that are routinely practiced in the art can be used to extract, process, purify and analyze the lipids such as the TAG produced by plants or parts thereof of the instant invention. Such techniques are described and explained throughout the literature in sources such as, Fereidoon Shahidi, Current Protocols in Food Analytical Chemistry, John Wiley & Sons, Inc. (2001) D1.1.1-D1.1.11, and Perez-Vich et al. (1998).

Production of Oil from Vegetative Plant Parts or Seed

Typically, vegetative plant parts or plant seeds are cooked, pressed, and/or extracted to produce crude vegetative oil or seedoil, which is then degummed, refined, bleached, and deodorized. Generally, techniques for crushing seed are known in the art. For example, oilseeds can be tempered by spraying them with water to raise the moisture content to, for example, 8.5%, and flaked using a smooth roller with a gap setting of 0.23 to 0.27 mm. Depending on the type of seed, water may not be added prior to crushing. Application of heat deactivates enzymes, facilitates further cell rupturing, coalesces the lipid droplets, and agglomerates protein particles, all of which facilitate the extraction process. Vegetative plant parts can be similarly treated, depending on the moisture content.

In an embodiment, the majority of the vegetative oil or seedoil is released by passage through a screw press. Cakes (vegetative plant meal, seedmeal) expelled from the screw press may then be solvent extracted for example, with hexane, using a heat traced column, or not be solvent treated, in which case it may be more suitable as animal feed. Alternatively, crude vegetative oil or seedoil produced by the pressing operation can be passed through a settling tank with a slotted wire drainage top to remove the solids that are expressed with the vegetative oil or seedoil during the pressing operation. The clarified vegetative oil or seedoil can be passed through a plate and frame filter to remove any remaining fine solid particles. Once the solvent is stripped from the crude oil, the pressed and extracted portions are combined and subjected to normal lipid processing procedures (i.e., degumming, caustic refining, bleaching, and deodorization).

Extraction of the lipid from vegetative plant parts of the invention uses analogous methods to those known in the art for seedoil extraction. One way is physical extraction, which often does not use solvent extraction. Expeller pressed extraction is a common type, as are the screw press and ram press extraction methods. Mechanical extraction is typically less efficient than solvent extraction where an organic solvent (e.g., hexane) is mixed with at least the plant biomass, preferably after the biomass is dried and ground. The solvent dissolves the lipid in the biomass, which solution is then separated from the biomass by mechanical action (e.g., with the pressing processes above). This separation step can also be performed by filtration (e.g., with a filter press or similar device) or centrifugation etc. The organic solvent can then be separated from the non-polar lipid (e.g., by distillation). This second separation step yields non-polar lipid from the plant and can yield a re-usable solvent if one employs conventional vapor recovery. In an embodiment, the oil and/or protein content of the plant part or seed is analysed by near-infrared reflectance spectroscopy as described in Hom et al. (2007) prior to extraction.

If the vegetative plant parts are not to be used immediately to extract the lipid it is preferably processed to ensure the lipid content is retained as much as possible (see, for example, Christie, 1993), such as by drying the vegetative plant parts.

Degumming

Degumming is an early step in the refining of oils and its primary purpose is the removal of most of the phospholipids from the oil, which may be present as approximately 1-2% of the total extracted lipid. Addition of ~2% of water, typically containing phosphoric acid, at 70-80° C. to the crude oil results in the separation of most of the phospholipids accompanied by trace metals and pigments. The insoluble material that is removed is mainly a mixture of phospholipids and triacylglycerols and is also known as lecithin. Degumming can be performed by addition of concentrated phosphoric acid to the crude oil to convert non-hydratable phosphatides to a hydratable form, and to chelate minor metals that are present. Gum is separated from the oil by centrifugation. The oil can be refined by addition of a sufficient amount of a sodium hydroxide solution to titrate all of the fatty acids and removing the soaps thus formed.

Alkali Refining

Alkali refining is one of the refining processes for treating crude oil, sometimes also referred to as neutralization. It usually follows degumming and precedes bleaching. Following degumming, the oil can treated by the addition of a sufficient amount of an alkali solution to titrate all of the fatty acids and phosphoric acids, and removing the soaps thus formed. Suitable alkaline materials include sodium hydroxide, potassium hydroxide, sodium carbonate, lithium hydroxide, calcium hydroxide, calcium carbonate and ammonium hydroxide. This process is typically carried out at room temperature and removes the free fatty acid fraction. Soap is removed by centrifugation or by extraction into a solvent for the soap, and the neutralised oil is washed with water. If required, any excess alkali in the oil may be neutralized with a suitable acid such as hydrochloric acid or sulphuric acid.

Bleaching

Bleaching is a refining process in which oils are heated at 90-120° C. for 10-30 minutes in the presence of a bleaching earth (0.2-2.0%) and in the absence of oxygen by operating with nitrogen or steam or in a vacuum. This step in oil processing is designed to remove unwanted pigments (carotenoids, chlorophyll, gossypol etc), and the process also removes oxidation products, trace metals, sulphur compounds and traces of soap.

Deodorization

Deodorization is a treatment of oils and fats at a high temperature (200-260° C.) and low pressure (0.1-1 mm Hg). This is typically achieved by introducing steam into the oil at a rate of about 0.1 ml/minute/100 ml of oil. Deodorization can be performed by heating the oil to 260° C. under vacuum, and slowly introducing steam into the oil at a rate of about 0.1 ml/minute/100 ml of oil. After about 30 minutes of sparging, the oil is allowed to cool under vacuum. The oil is typically transferred to a glass container and flushed with argon before being stored under refrigeration. If the amount of oil is limited, the oil can be placed under vacuum for example, in a Parr reactor and heated to 260° C. for the same length of time that it would have been deodorized. This treatment improves the colour of the oil and removes a majority of the volatile substances or odorous compounds including any remaining free fatty acids, monoacylglycerols and oxidation products.

Winterisation

Winterization is a process sometimes used in commercial production of oils for the separation of oils and fats into solid (stearin) and liquid (olein) fractions by crystallization at sub-ambient temperatures. It was applied originally to cottonseed oil to produce a solid-free product. It is typically used to decrease the saturated fatty acid content of oils.

Algae

Algae can produce 10 to 100 times as much mass as terrestrial plants in a year and can be cultured in open-ponds (such as raceway-type ponds and lakes) or in photobioreactors. The most common oil-producing algae can generally include the diatoms (bacillariophytes), green algae (chlorophytes), blue-green algae (cyanophytes), and golden-brown algae (chrysophytes). In addition a fifth group known as haptophytes may be used. Groups include brown algae and heterokonts. Specific non-limiting examples algae include the Classes: Chlorophyceae, Eustigmatophyceae, Prymnesiophyceae, Bacillariophyceae. Bacillariophytes capable of oil production include the genera *Amphipleura, Amphora, Chaetoceros, Cyclotella, Cymbella, Fragilaria, Hantzschia, Navicula, Nitzschia, Phaeodactylum*, and *Thalassiosira*. Specific non-limiting examples of chlorophytes capable of oil production include *Ankistrodesmus, Botryococcus, Chlorella, Chlorococcum, Dunaliella, Monoraphidium, Oocystis, Scenedesmus*, and *Tetraselmis*. In one aspect, the chlorophytes can be *Chlorella* or *Dunaliella*. Specific non-limiting examples of cyanophytes capable of oil production include *Oscillatoria* and *Synechococcus*. A specific example of chrysophytes capable of oil production includes Boekelovia. Specific non-limiting examples of haptophytes include Isochysis and Pleurochysis.

Specific algae useful in the present invention include, for example, *Chlamydomonas* sp. such as *Chlamydomonas reinhardtii, Dunaliella* sp. such as *Dunaliella salina, Dunaliella tertiolecta, D. acidophila, D. Lateralis. D.martima. D. parva, D. polmorpha, D. primolecta, D. pseudosalina, D. quartolecta. D. viridis, Haematococcus* sp., *Chlorella* sp. such as *Chlorella vulgaris, Chlorella sorokiniana* or *Chlorella protothecoides, Thraustochytrium* sp., *Schizochytrium* sp., *Volvox* sp, *Nannochloropsis* sp., *Botryococcus braunii* which can contain over 60 wt % lipid, *Phaeodactylum tricornutum, Thalassiosira pseudonana, Isochrysis* sp., *Pavlova* sp., *Chlorococcum* sp, *Ellipsoidion* sp., *Neochloris* sp., *Scenedesmus* sp.

Algae of the invention can be harvested using microscreens, by centrifugation, by flocculation (using for example, chitosan, alum and ferric chloride) and by froth flotation. Interrupting the carbon dioxide supply can cause algae to flocculate on its own, which is called "autoflocculation". In froth flotation, the cultivator aerates the water into a froth, and then skims the algae from the top. Ultrasound and other harvesting methods are currently under development.

Lipid may be extracted from the algae by mechanical crushing. When algal mass is dried it retains its lipid content, which can then be "pressed" out with an oil press. Osmotic shock may also be used to release cellular components such as lipid from algae, and ultrasonic extraction can accelerate extraction processes. Chemical solvents (for example, hexane, benzene, petroleum ether) are often used in the extraction of lipids from algae. Enzymatic extraction using enzymes to degrade the cell walls may also be used to extract lipids from algae. Supercritical $CO_2$ can also be used as a solvent. In this method, $CO_2$ is liquefied under pressure and heated to the point that it becomes supercritical (having properties of both a liquid and a gas), allowing it to act as a solvent.

Uses of Plant Lipids

The lipids produced by the methods described have a variety of uses. In some embodiments, the lipids are used as food oils. In other embodiments, the lipids are refined and used as lubricants or for other industrial uses such as the synthesis of plastics. In some preferred embodiments, the lipids are refined to produce biodiesel. Biodiesel can be made from oils derived from the plants, algae and fungi of the invention. Use of plant triacylglycerols for the production of biofuel is reviewed in Durrett et al. (2008). The resulting fuel is commonly referred to as biodiesel and has a dynamic viscosity range from 1.9 to 6.0 $mm^2 s^{-1}$ (ASTM D6751). Bioalcohol may produced from the fermentation of sugars or the biomass other than the lipid left over after lipid extraction. General methods for the production of biofuel can be found in, for example, Maher and Bressler (2007), Greenwell et al. (2010), Karmakar et al. (2010), Alonso et al. (2010), Liu et al. (2010a). Gong and Jiang (2011), Endalew et al. (2011) and Semwal et al. (2011).

The present invention provides methods for increasing oil content in vegetative tissues. Plants of the present invention have increased energy content of leaves and/or stems such that the whole above-ground plant parts may be harvested and used to produce biofuel. Furthermore, the level of oleic acid is increased significantly while the polyunsaturated fatty acid alpha linolenic acid (ALA) was reduced. The plants, algae and fungi of the present invention thereby reduce the production costs of biofuel.

Biodiesel

The production of biodiesel, or alkyl esters, is well known. There are three basic routes to ester production from lipids: 1) Base catalysed transesterification of the lipid with alcohol; 2) Direct acid catalysed esterification of the lipid with methanol; and 3) Conversion of the lipid to fatty acids, and then to alkyl esters with acid catalysis. Any method for preparing fatty acid alkyl esters and glyceryl ethers (in which one, two or three of the hydroxy groups on glycerol are etherified) can be used. For example, fatty acids can be prepared, for example, by hydrolyzing or saponifying TAG with acid or base catalysts, respectively, or using an enzyme such as a lipase or an esterase. Fatty acid alkyl esters can be prepared by reacting a fatty acid with an alcohol in the presence of an acid catalyst. Fatty acid alkyl esters can also be prepared by reacting TAG with an alcohol in the presence of an acid or base catalyst. Glycerol ethers can be prepared, for example, by reacting glycerol with an alkyl halide in the presence of base, or with an olefin or alcohol in the presence of an acid catalyst. The alkyl esters can be directly blended with diesel fuel, or washed with water or other aqueous solutions to remove various impurities, including the catalysts, before blending.

Aviation Fuel

For improved performance of biofuels, thermal and catalytic chemical bond-breaking (cracking) technologies have been developed that enable converting bio-oils into bio-based alternatives to petroleum-derived diesel fuel and other fuels, such as jet fuel.

The use of medium chain fatty acid source, such produced by a cell of the invention, a plant or part thereof of the invention, a seed of the invention, or a transgenic version of any one thereof, precludes the need for high-energy fatty acid chain cracking to achieve the shorter molecules needed for jet fuels and other fuels with low-temperature flow requirements. This method comprises cleaving one or more medium chain fatty acid groups from the glycerides to form glycerol and one or more free fatty acids. In addition, the method comprises separating the one or more medium chain fatty acids from the glycerol, and decarboxylating the one or more medium chain fatty acids to form one or more hydrocarbons for the production of the jet fuel.

Compositions

The present invention also encompasses compositions, particularly pharmaceutical compositions, comprising one or more plants, plant parts, lipids, proteins, nitrogen containing molecules, or carbon containing molecules, produced using the methods of the invention.

A pharmaceutical composition may additionally comprise an active ingredient and a standard, well-known, non-toxic pharmaceutically-acceptable carrier, adjuvant or vehicle such as phosphate-buffered saline, water, ethanol, polyols, vegetable oils, a wetting agent, or an emulsion such as a water/oil emulsion. The composition may be in either a liquid or solid form. For example, the composition may be in the form of a tablet, capsule, ingestible liquid, powder, topical ointment or cream. Proper fluidity can be maintained for example, by the maintenance of the required particle size in the case of dispersions and by the use of surfactants. It may also be desirable to include isotonic agents for example, sugars, sodium chloride, and the like. Besides such inert diluents, the composition can also include adjuvants such as wetting agents, emulsifying and suspending agents, sweetening agents, flavoring agents and perfuming agents.

A typical dosage of a particular fatty acid is from 0.1 mg to 20 g, taken from one to five times per day (up to 100 g daily) and is preferably in the range of from about 10 mg to about 1, 2, 5, or 10 g daily (taken in one or multiple doses). As known in the art, a minimum of about 300 mg/day of fatty acid, especially polyunsaturated fatty acid, is desirable. However, it will be appreciated that any amount of fatty acid will be beneficial to the subject.

Possible routes of administration of the pharmaceutical compositions of the present invention include for example, enteral and parenteral. For example, a liquid preparation may be administered orally. Additionally, a homogenous mixture can be completely dispersed in water, admixed under sterile conditions with physiologically acceptable diluents, preservatives, buffers or propellants to form a spray or inhalant.

The dosage of the composition to be administered to the subject may be determined by one of ordinary skill in the art and depends upon various factors such as weight, age, overall health, past history, immune status, etc., of the subject.

Additionally, the compositions of the present invention may be utilized for cosmetic purposes. The compositions may be added to pre-existing cosmetic compositions, such that a mixture is formed, or a fatty acid produced according to the invention may be used as the sole "active" ingredient in a cosmetic composition.

Polypeptides

The terms "polypeptide" and "protein" are generally used interchangeably herein.

A polypeptide or class of polypeptides may be defined by the extent of identity (% identity) of its amino acid sequence to a reference amino acid sequence, or by having a greater % identity to one reference amino acid sequence than to another. The % identity of a polypeptide to a reference amino acid sequence is typically determined by GAP analysis (Needleman and Wunsch, 1970; GCG program) with parameters of a gap creation penalty=5, and a gap extension penalty=0.3. The query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns two sequences over their entire length, and the extent of identity is determined over the full length of the reference sequence. The polypeptide or class of polypeptides may have the same enzymatic activity as, or a different activity than, or lack the activity of, the reference polypeptide. Preferably, the polypeptide has an enzymatic activity of at least 10% of the activity of the reference polypeptide.

As used herein a "biologically active fragment" is a portion of a polypeptide of the invention which maintains a defined activity of a full-length reference polypeptide for example, DGAT activity. Biologically active fragments as used herein exclude the full-length polypeptide. Biologically active fragments can be any size portion as long as they maintain the defined activity. Preferably, the biologically active fragment maintains at least 10% of the activity of the full length polypeptide.

With regard to a defined polypeptide or enzyme, it will be appreciated that % identity figures higher than those provided herein will encompass preferred embodiments. Thus, where applicable, in light of the minimum % identity figures, it is preferred that the polypeptide/enzyme comprises an amino acid sequence which is at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the polypeptides defined herein can be prepared by introducing appropriate nucleotide changes into a nucleic acid defined herein, or by in vitro synthesis of the desired polypeptide. Such mutants include for example, deletions, insertions, or substitutions of residues within the amino acid sequence. A combination of deletions, insertions and substitutions can be made to arrive at the final construct, provided that the final polypeptide product possesses the desired characteristics.

Mutant (altered) polypeptides can be prepared using any technique known in the art, for example, using directed evolution or rational design strategies (see below). Products derived from mutated/altered DNA can readily be screened using techniques described herein to determine if they possess transcription factor, fatty acid acyltransferase or OBC activities.

In designing amino acid sequence mutants, the location of the mutation site and the nature of the mutation will depend on characteristic(s) to be modified. The sites for mutation can be modified individually or in series for example, by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide removed and a different residue inserted in its place. The sites of greatest interest for substitutional mutagenesis to inactivate enzymes include sites identified as the active site(s). Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 1 under the heading of "exemplary substitutions".

TABLE 1

Exemplary substitutions.

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

In a preferred embodiment a mutant/variant polypeptide has only, or not more than, one or two or three or four conservative amino acid changes when compared to a naturally occurring polypeptide. Details of conservative amino acid changes are provided in Table 1. As the skilled person would be aware, such minor changes can reasonably be predicted not to alter the activity of the polypeptide when expressed in a transgenic plant or part thereof. Mutants with desired activity may be engineered using standard procedures in the art such as by performing random mutagenesis, targeted mutagenesis, or saturation mutagenesis on known genes of interest, or by subjecting different genes to DNA shuffling.

EXAMPLES

Example 1. General Materials and Methods

Expression of Genes in Plant Cells in a Transient Expression System

Genes were expressed in plant cells using a transient expression system essentially as described by Voinnet et al. (2003) and Wood et al. (2009). Binary vectors containing the coding region to be expressed by a strong constitutive e35S promoter containing a duplicated enhancer region were introduced into *Agrobacterium tumefaciens* strain AGL1. A chimeric binary vector, 35S:p19, for expression of the p19 viral silencing suppressor was separately introduced into AGL1, as described in WO2010/057246. A chimeric binary vector, 35S:V2, for expression of the V2 viral silencing suppressor was separately introduced into AGL1. The recombinant cells were grown to stationary phase at 28° C. in LB broth supplemented with 50 mg/L kanamycin and 50 mg/L rifampicin. The bacteria were then pelleted by centrifugation at 5000 g for 5 min at room temperature before being resuspended to OD600=1.0 in an infiltration buffer containing 10 mM MES pH 5.7, 10 mM $MgCl_2$ and 100 uM acetosyringone. The cells were then incubated at 28° C. with shaking for 3 hours after which the OD600 was measured and a volume of each culture, including the viral suppressor construct 35S:p19 or 35S:V2, required to reach a final concentration of OD600=0.125 added to a fresh tube. The final volume was made up with the above buffer. Leaves were then infiltrated with the culture mixture and the plants were typically grown for a further three to five days after infiltration before leaf discs were recovered for either purified cell lysate preparation or total lipid isolation.

Transformation of *Sorghum bicolor* L.

Plant Material

*Sorghum* plants of the inbred cultivar TX-430 (Miller, 1984) were grown in a plant growth chamber (Conviron, PGC-20 flex) at 28±1° C. "day" temperature and 20±1° C. "night" temperature, with a 16 hr photoperiod at a light intensity during the "day" of 900-1000 LUX. Panicles were covered with white translucent paper bags before flowering. Immature embryos were harvested from panicles 12-15 days after anthesis. Panicles were washed several times with water and developing seeds that were uniform in size were isolated and surface-sterilized using 20% commercial bleach mixed with 0.1% Tween-20 for 15-20 min. They were then washed with sterile distilled water 3 times each for 20 min, and blotted dry in a laminar flow hood. Immature embryos (IEs) ranging from 1.4 to 2.5 mm in length were aseptically isolated in the laminar flow hood and used as the starting tissue for preparation of green regenerative tissue.

Base Cultivation Media

Media used for plant transformation were based on MS (Murashige and Skoog, 1962), supplied by PhytoTechnology Laboratories (M519). The pH of the media was adjusted to 5.8 before sterilization at 121° C. for 15 min. Heat sensitive plant growth regulators and other additives such as Geneticin (G418, Sigma) used as a selection agent, were filter sterilized (0.2 μm) and added to the media after sterilization when the media had cooled to about 55° C. The optimized culture medium composition for the different stages of plant transformation from callus induction to plant regeneration from green tissue induced from immature embryos is presented in Table 2.

Cultivation Methods and Materials

The isolated IEs ranging from 1.4 to 2.5 mm in length were placed onto callus induction media-osmotic medium (CIM-osmotic medium, Table 2) with their scutellum facing upward. The CIM base medium was modified to improve callus quality and induction frequency from immature embryos, as well as callus regeneration media, by including α-Lipoic acid (1 to 5 mg/l), Melatonin (5 to 10 mg/l) and 2-Aminoidan-2-phosphonic acid HCl (1 to 2 mg/l) unless otherwise stated. For the development of green tissue, immature embryos were incubated under fluorescent light of approximately 45-50 μmol s$^{-1}$ m$^{-2}$ (16 h/day) in a tissue culture room at 24±2° C. After three days of culture, the root and shoot poles of the immature embryos were aseptically separated and re-inoculated on to the same CIM and maintained under the same conditions as described above. They were subcultured every two weeks onto the same CIM for 6 weeks and evaluated for callus quality, callus induction efficiency and transformation efficiency.

Callus initiated from IEs in the first 3-4 weeks on CIM were mostly embryogenic and slowly differentiated into embryogenic callus with nodular structures which were coloured from pale to darker green. Embryogenic calli with green nodular structures were selected and maintained on the same medium (CIM) by subculturing every 2 weeks for up to 6 months or more, for use as explants for transformation. This type of tissue is termed herein as "differentiating embryogenic callus" tissue or "DEC" tissue, since this tissue forms nodular structures of differentiating cells which maintain embryogenic and organogenic potential, even though the tissues were really a mixture of callus cells, cells forming nodular structures and granular structures, and intermediate cells which the inventors understood were on the developmental pathway somewhere between callus (which is undifferentiated cells) and the nodular structures. Sometimes, the tissues included early stage (globular) somatic embryos.

TABLE 2

Media used in DEC tissue induction and transformation of sorghum

| Name of the medium | Composition | Culture duration |
|---|---|---|
| CIM-Osmotic Medium | MS medium powder with vitamins, 4.33 g/l; 2,4-D, 1 mg/l; BAP, 0.5 mg/l; L-proline, 0.7 g/l; L-Lipoic acid, 1 mg/l; peptone, 0.82 g/l; Myo-inositol, 150 mg/l; Copper sulfate, 0.8 mg/l; Manitol, 36.4 g/l; Sorbitol, 36.4 g/l; Agar, 8.5 g/l, pH 5.8 | 3-4 hrs before bombardment; o/n post bombardment |
| CIM-pre selection medium | MS medium powder with vitamins, 4.33 g/l; 2,4-D, 1 mg/l; BAP, 0.5 mg/l; L-proline, 0.7 g/l; L-Lipoic acid, 1 mg/l; peptone, 0.82 g/l; Myo-inositol, 150 mg/l; Copper sulfate, 0.8 mg/l; Maltose, 30 g/l; L-cysteine, 50 mg/l; Ascorbic acid, 15 mg/l; Agar, 9 g/l, pH 5.8 | 3-4 days |
| CIM-callus induction medium/ G25 | MS medium powder with vitamins, 4.33 g/l; 2,4-D, 1 mg/l; BAP, 0.5 mg/l; L-proline, 0.7 g/l; L-Lipoic acid, 1 mg/l; peptone, 0.82 g/l; Myo-inositol, 150 mg/l; Copper sulfate, 0.8 mg/l; Maltose, 30 g/l; Geneticin, 25 mg/l; Agar, 9 g/l, pH 5.8 | 4 weeks |
| SIM-shoot induction medium/ G25 | MS medium powder with vitamins, 4.33 g/l; BAP, 1.0 mg/l; 2,4-D, 0.5 mg/l; L-proline, 0.7 g/l; L-Lipoic acid, 1 mg/l; peptone, 0.82 g/l; Myo-inositol, 150 mg/l; Copper sulfate, 0.8 mg/l; Maltose, 30 g/l; Geneticin, 25 mg/l; Agar, 9 g/l, pH 5.8 | 2 weeks |
| SRM-shoot regeneration medium/ G25 | MS medium powder with vitamins, 4.33 g/l; BAP, 1.0 mg/l; TDZ, 0.5 mg/l; L-proline, 0.7 g/l; L-Lipoic acid, 1 mg/l; peptone, 0.82 g/l; Myo-inositol, 150 mg/l; Copper sulfate, 0.8 mg/l; Maltose, 30 g/l; Geneticin, 25 mg/l; Agar, 9 g/l, pH 5.8 | 2 weeks |
| SOG-shoot out growth medium/ G30 | MS medium powder with vitamins, 2.2 g/l; L-proline, 0.7 g/l; L-Lipoic acid, 1 mg/l; peptone, 0.82 g/l; Myo-inositol, 150 mg/l; Copper sulfate, 0.8 mg/l; Sucrose, 15 g/l; Geneticin, 30 mg/l; Agar, 9 g/l, pH 5.8 | 2 weeks |
| RIM-root induction medium/ G15 | MS medium powder with vitamins, 4.33 g/l; L-proline, 0.7 g/l; L-Lipoic acid, 1 mg/l; peptone, 0.82 g/l; Myo-inositol, 150 mg/l; Copper sulfate, 0.8 mg/l; sucrose, 15 g/l; IAA, 1 mg/l; IBA, 1 mg/l; NAA, 1 mg/l; PVP, 2 g/l; Geneticin, 15 mg/l; Agar 9 g/l, pH 5.8 | 4 weeks |

Particle-Bombardment of Green Regenerative DEC Tissues

Plasmids containing a selectable marker gene encoding the neomycin phosphotransferase II (NptII) providing resistance to the antibiotic Geneticin, under the control of the pUbi promoter and terminated by the nos 3' region, were made or obtained for experiments to achieve stable transformation or for co-bombardment with other plasmids. Plasmid DNAs were isolated using a Zymopure™ Maxiprep kit (USA) according to the manufacturer's instructions. As a control vector for transformation, a genetic vector was obtained which contained uidA (GUS) and bar genes designed for expression in plant cells. The uidA gene was under the regulatory control of a maize polyubiquitin promoter (pUbi) and an *Agrobacterium tumefaciens* octopine synthase polyadenylation/terminator (ocs 3') sequence. The sequence between the promoter and the protein coding region included the 5' UTR and first intron of the Ubi gene. The uidA reporter gene also contained, within its protein coding region, an intron from a castor bean catalase gene which prevented translation of functional GUS protein in *Agrobacterium*, thereby reducing the background GUS gene expression in inoculated plant tissues. Therefore, any GUS expression would be due to expression of the uidA gene in the plant cells. The bar gene was also under the regulatory control of a pUbi promoter and terminated with an *Agrobacterium* nopaline synthase 3' regulatory sequence (nos 3'). The uidA/bar vector was initially used in experiments to detect transient gene expression in the sorghum DEC tissues.

Uniform healthy, green regenerative DEC tissues (4-5 mm in size), produced using methods described above and having been cultured for 6 weeks to 6 months from initiation, were used for microprojectile-mediated transformation (bombardment) with the plasmids. Approximately 15 uniform green DEC tissues (each 4-5 mm) were placed at the centre of a petri dish (90 mm diameter) containing CIM-osmotic medium (Table 2) and incubated in the dark for about 4 hrs prior to bombardment. Bombardment was performed with a PDS-1000 He device (Biorad, Hercules, CA) as described by Liu et al. (2014). Post bombardment, the tissues were kept on the same osmotic medium overnight and transferred to pre-selection medium the next morning.

Green DEC tissues bombarded with the genetic vector plasmid having a selectable marker encoding NptII were transferred to CIM-PS medium for 3-4 days before any selection, with addition to the medium of two compounds as antioxidants, L-cysteine (50 mg/l) and ascorbic acid (15 mg/l) (Table 2). Without the addition of these antioxidants in pre-selection medium, many of the bombarded tissues turned brown, some quite dark brown in colour, and many lost any ability to grow further. After 3-4 days on pre-selection medium, some of the bombarded tissues were subjected to GUS staining and viewed under a microscope to count the distinctive blue (GUS positive) spots, to check that genes had been transferred and could be expressed. The inclusion of the two antioxidants in the pre-selection medium improved the efficiency of the transformation as shown by the transient expression of the GUS gene.

Selection and Regeneration of Transgenic Plants with Optimised Conditions

Following bombardment and 3-4 days culture on pre-selection medium without selective agent (Geneticin), the bombarded tissues had increased in size from 4-5 mm to about 6-7 mm. These tissues were transferred to selective medium CIM/G25 containing 25 mg/l Geneticin (Table 2) and cultured for a further 4 weeks. When possible, the bombarded tissues were split into 2-6 pieces each, increasing the recovery of independent transformants. All of the tissues were cultured on the media as described in Table 2 and maintained in order to regenerate putative transgenic plants.

Plants were regenerated efficiently upon growth on these media. Each bombarded tissue and the shoots obtained from it were subcultured and maintained separately for calculation of the transformation efficiency. Positive transformation was confirmed by PCR on plant genomic DNA isolated from shoot samples, showing the presence of the selectable marker gene. The number of transformants was calculated per input DEC tissue. Transformation efficiencies of about 50% were obtained, expressed as independent transformants per input bombarded tissue.

Agrobacterium-Mediated Transformation of Green Regenerative DEC Tissues

Uniform healthy, green regenerative DEC tissues (4-5 mm in size) produced using methods described in the foregoing examples and which have been cultured for 6 weeks to 6 months from initiation, are used for *Agrobacterium*-mediated transformation.

Genetic vectors having T-DNA regions containing the genes for transformation were designed and made for transformation of green regenerative DEC tissues using *Agrobacterium*-mediated transformation. A control binary vector contained uidA (GUS) and bar genes designed for expression in plant cells. The uidA gene was under the regulatory control of a maize polyubiquitin promoter (pUbi) and an *Agrobacterium tumefaciens* octopine synthase polyadenylation/terminator (ocs 3') sequence. The sequence between the promoter and the protein coding region included the 5' UTR and first intron of the Ubi gene. The uidA reporter gene also contained, within its protein coding region, an intron from a castor bean catalase gene which prevented translation of functional GUS protein in *Agrobacterium*, thereby reducing the background GUS gene expression in inoculated plant tissues. Therefore, any GUS expression was due to expression of the uidA gene in the plant cells. The bar gene was also under the regulatory control of a pUbi promoter and terminated with an *Agrobacterium* nopaline synthase 3' regulatory sequence (nos 3').

A suitable *Agrobacterium tumefaciens* strain was obtained e.g., AGL1 as described in Lazo et al. (1991) and the genetic vector is introduced into the *Agrobacterium tumefaciens* strain by heat shock method.

*Agrobacterium* cultures harboring the genetic construct are grown in suitable medium e.g., LB medium, and under appropriate conditions to produce an *Agrobacterium* inoculum, after which time the uniform healthy, green regenerative DEC tissues are infected with *Agrobacterium* inoculum. The infected DEC tissues are blotted on sterile filter paper to remove excess *Agrobacterium* and transferred to co-cultivation medium, optionally supplemented with antioxidants, and incubated in the dark at approximately 22-24° C. for 2-4 days. Following incubation, the DEC tissues are treated with an appropriate agent to kill the *Agrobacterium*, washed in sterile water, transferred to an appropriate medium and allowed to grow. After 4-6 weeks, shoots are excised and cultured on shoot elongation medium, after which time putative transgenic shoots are then detected using appropriate assays.

Brassica napus Transformation

*Brassica napus* seeds were sterilized using chlorine gas as described by Kereszt et al. (2007) and germinated on tissue culture medium. Cotyledonary petioles with 2-4 mm stalk were isolated as described by Belide et al. (2013) and used as explants. *A. tumefaciens* AGL1 (Lazo et al., 1991) cultures containing the binary vector were prepared and cotyledonary petioles inoculated with the cultures as described by Belide et al. (2013). Infected cotyledonary petioles were cultured on MS medium supplemented with 1 mg/L TDZ+0.1 mg/L NAA+3 mg/L AgNO$_3$+250 mg/L cefotaxime, 50 mg/L timentin and 25 mg/L kanamycin and cultured for 4 weeks at 24° C. with 16 hr/8 hr light-dark photoperiod with a biweekly subculture on to the same medium. Explants with green callus were transferred to shoot initiation medium (MS+1 mg/L kinetin+3 mg/L AgNO$_3$+250 mg/L cefotaxime+50 mg/L timentin+25 mg/L kanamycin) and cultured for another 2-3 weeks. Small shoots (~1 cm) were isolated from the resistant callus and transferred to shoot elongation medium (MS medium with 0.1 mg/L gibberelic acid+3 mg/L AgNO$_3$+250 mg/L cefotaxime+25 mg/L kanamycin) and cultured for another two weeks. Healthy shoots with one or two leaves were selected and transferred to rooting media (1/2 MS with 1 mg/L NAA+20 mg/L ADS+3 mg/L AgNO$_3$+250 mg/L cefotaxime) and cultured for 2-3 weeks. DNA was isolated from small leaves of resistant shoots using the plant DNA isolation kit (Bioline, Alexandria, NSW, Australia) as described by the manufacturer's protocol. The presence of T-DNA sequences was tested by PCR amplification on genomic DNA. Positive, transgenic shoots with roots were transferred to pots containing seedling raising mix and grown in a glasshouse at 24° C. daytime/16° C. night-time (standard conditions).

Purified Leaf Lysate—Enzyme Assays

*Nicotiana benthamiana* leaf tissues previously infiltrated as described above were ground in a solution containing 0.1

M potassium phosphate buffer (pH 7.2) and 0.33 M sucrose using a glass homogenizer. Leaf homogenate was centrifuged at 20,000 g for 45 minutes at 4° C. after which each supernatant was collected. Protein content in each supernatant was measured according to Bradford (1976) using a Wallac1420 multi-label counter and a Bio-Rad Protein Assay dye reagent (Bio-Rad Laboratories, Hercules, CA USA). Acyltransferase assays used 100 μg protein according to Cao et al. (2007) with some modifications. The reaction medium contained 100 mM Tris-HCl (pH 7.0), 5 mM $MgCl_2$, 1 mg/mL BSA (fatty acid-free), 200 mM sucrose, 40 mM cold oleoyl-CoA, 16.4 μM sn-2 monooleoylglycerol [$^{14}C$] (55 mCi/mmol, American Radiochemicals, Saint Louis, MO USA) or 6.0 μM [$^{14}C$]glycerol-3-phosphate (G-3-P) disodium salt (150 mCi/mmol, American Radiochemicals). The assays were carried out for 7.5, 15, or 30 minutes.

Lipid Analysis
Analysis of Oil Content in Seeds

When seed oil content or total fatty acid composition was to be determined in small seeds such as *Arabidopsis* seeds, fatty acids in the seeds were directly methylated without crushing of seeds. Seeds were dried in a desiccator for 24 hours and approximately 4 mg of seed was transferred to a 2 ml glass vial containing a Teflon-lined screw cap. 0.05 mg triheptadecanoin (TAG with three C17:0 fatty acids) dissolved in 0.1 ml toluene was added to the vial as internal standard. Seed fatty acids were methylated by adding 0.7 ml of 1N methanolic HCl (Supelco) to the vial containing seed material. Crushing of the seeds was not necessary for complete methylation with small seeds such as *Arabidopsis* seeds. The mixture was vortexed briefly and incubated at 80° C. for 2 hours. After cooling the mixtures to room temperature, 0.3 ml of 0.9% NaCl (w/v) and 0.1 ml hexane was added to the vial and mixed well for 10 minutes in a Heidolph Vibramax 110. The FAME were collected into a 0.3 ml glass insert and analysed by GC with a flame ionization detector (FID) as described below.

The peak area of individual FAME were first corrected on the basis of the peak area responses of a known amount of the same FAMEs present in a commercial standard GLC-411 (NU-CHEK PREP, INC., USA). GLC-411 contains equal amounts of 31 fatty acids (% by weight), ranging from C8:0 to C22:6. In case of fatty acids which were not present in the standard, the peak area responses of the most similar FAME was taken. For example, the peak area response of FAMEs of 16:1d9 was used for 16:1d7 and the FAME response of C22:6 was used for C22:5. The corrected areas were used to calculate the mass of each FAME in the sample by comparison to the internal standard mass. Oil is stored mainly in the form of TAG and its weight was calculated based on FAME weight. Total moles of glycerol was determined by calculating moles of each FAME and dividing total moles of FAMEs by three. TAG content was calculated as the sum of glycerol and fatty acyl moieties using a relation: % oil by weight=100×((41×total mol FAME/3)+(total g FAME− (15× total mol FAME)))/g seed, where 41 and 15 are molecular weights of glycerol moiety and methyl group, respectively.

Analysis of Fatty Acid Content in Larger Seeds

To determine fatty acid composition in single seeds that were larger, such as canola and *Camelina* seeds, or *Sorghum* or corn seeds, direct methylation of fatty acids in the seed was performed as for *Arabidopsis* seeds except with breaking of the seed coats. This method extracted sufficient oil from the seed to allow fatty acid composition analysis. To determine the fatty acid composition of total extracted lipid from seeds, seeds were crushed and lipids extracted with $CHCl_3$/MeOH. Aliquots of the extracted lipid were methylated and analysed by GC. Pooled seed-total lipid content (seed oil content) of canola was determined by two extractions of lipid using $CHCl_3$/MeOH from a known weight of desiccated seeds after crushing, followed by methylation of aliquots of the lipids together with the 17:0 fatty acids as internal standard. In the case of larger seeds such as *Camelina*, the lipid from a known amount of seeds was methylated together with known amount of 17:0 fatty acids as for the *Arabidopsis* oil analysis and FAME were analysed by GC. For TAG quantitation, TAG was fractionated from the extracted lipid using TLC and directly methylated in silica using 17:0 TAG as an internal standard. These methods are described more fully as follows.

After harvest at plant maturity, seeds were desiccated by storing the seeds for 24 hours at room temperature in a desiccator containing silica gel as desiccant. Moisture content of the seeds was typically 6-8%. Total lipids were extracted from known weights of the desiccated seeds by crushing the seeds using a mixture of chloroform and methanol (2/1 v/v) in an eppendorf tube using a Reicht tissue lyser (22 frequency/seconds for 3 minutes) and a metal ball. One volume of 0.1M KCl was added and the mixture shaken for 10 minutes. The lower non-polar phase was collected after centrifuging the mixture for 5 minutes at 3000 rpm. The remaining upper (aqueous) phase was washed with 2 volumes of chloroform by mixing for 10 minutes. The second non-polar phase was also collected and pooled with the first. The solvent was evaporated from the lipids in the extract under nitrogen flow and the total dried lipid was dissolved in a known volume of chloroform.

To measure the amount of lipid in the extracted material, a known amount of 17:0-TAG was added as internal standard and the lipids from the known amount of seeds incubated in 1 N methanolic-HCl (Supelco) for 2 hours at 80° C. FAME thus made were extracted in hexane and analysed by GC. Individual FAME were quantified on the basis of the amount of 17:0 TAG-FAME. Individual FAME weights, after subtraction of weights of the esterified methyl groups from FAME, were converted into moles by dividing by molecular weights of individual FAME. Total moles of all FAME were divided by three to calculate moles of TAG and therefore glycerol. Then, moles of TAG were converted in to weight of TAG. Finally, the percentage oil content on a seed weight basis was calculated using seed weights, assuming that all of the extracted lipid was TAG or equivalent to TAG for the purpose of calculating oil content. This method was based on Li et al. (2006). Seeds other than *Camelina* or canola seeds that are of a similar size can also be analysed by this method.

Canola and other seed oil content can be measured by nuclear magnetic resonance techniques (Rossell and Pritchard, 1991) by a pulsed wave NMS 100 Minispec (Bruker Pty Ltd Scientific Instruments, Germany). The NMR method can simultaneously measured moisture content. Seed oil content can also be measured by near infrared reflectance (NIR) spectroscopy such as using a NIRSystems Model 5000 monochromator. Moisture content can also be measured on a sample from a batch of seeds by drying the seeds in the sample for 18 hours at about 100° C., according to Li et al. (2006).

Analysis of Lipids from Leaf Lysate Assays

Lipids from the lysate assays were extracted using chloroform:methanol:0.1 M KCl (2:1:1) and recovered. The different lipid classes in the samples were separated on Silica gel 60 thin layer chromatography (TLC) plates (MERCK, Dermstadt, Germany) impregnated with 10% boric acid. The solvent system used to fractionate TAG from the lipid extract was chloroform/acetone (90/10 v/v). Individual lipid classes were visualized by exposing the plates to iodine vapour and identified by running parallel authentic standards on the same TLC plate. The plates were exposed to phosphor imaging screens overnight and analysed by a Fujifilm FLA-5000 phosphorimager before liquid scintillation counting for DPM quantification.

Total Lipid Isolation and Fractionation of Lipids from Vegetative Tissues

Fatty acid composition of total lipid in leaf and other vegetative tissue samples was determined by direct methylation of the fatty acids in freeze-dried samples. For total lipid quantitation, fatty acids in a known weight of freeze-dried samples, with 17:0 FFA, were directly methylated. To determine total TAG levels in leaf samples, TAG was fractionated by TLC from extracted total lipids, and methylated in the presence of 17:0 TAG internal standard, because of the presence of substantial amounts of polar lipids in leaves. This was done as follows. Tissues including leaf samples were freeze-dried, weighed (dry weight) and total lipids extracted as described by Bligh and Dyer (1959) or by using chloroform:methanol:0.1 M KCl (CMK; 2:1:1) as a solvent. Total lipids were extracted from $N$. $benthamiana$ leaf samples, after freeze dying, by adding 900 µL of a chloroform/methanol (2/1 v/v) mixture per 1 cm diameter leaf sample. 0.8 µg DAGE was added per 0.5 mg dry leaf weight as internal standard when TLC-FID analysis was to be performed. Samples were homogenized using an IKA ultra-turrax tissue lyser after which 500 µL 0.1 M KCl was added. Samples were vortexed, centrifuged for 5 min and the lower phase was collected. The remaining upper phase was extracted a second time by adding 600 µL chloroform, vortexing and centrifuging for 5 min. The lower phase was recovered and pooled into the previous collection. Lipids were dried under a nitrogen flow and resuspended in 2 µL chloroform per mg leaf dry weight. Total lipids of $N$. $tabacum$ leaves or leaf samples were extracted as above with some modifications. If 4 or 6 leaf discs (each approx 1 cm$^2$ surface area) were combined, 1.6 ml of CMK solvent was used, whereas if 3 or less leaf discs were combined, 1.2 ml CMK was used. Freeze dried leaf tissues were homogenized in an eppendorf tube containing a metallic ball using a Reicht tissue lyser (Qiagen) for 3 minutes at 20 frequency/sec.

Separation of Neutral Lipids Via TLC and Transmethylation

Known volumes of total leaf extracts such as, for example, 30 µL were loaded on a TLC silica gel 60 plate (1×20 cm) (Merck KGaA, Germany). The neutral lipids were fractionated into the different types and separated from polar lipids via TLC in an equilibrated development tank containing a hexane/DEE/acetic acid (70/30/1 v/v/v/) solvent system. The TAG bands were visualised by primuline spraying, marked under UV, scraped from the TLC plate, transferred to 2 mL GC vials and dried with $N_2$. 750 µL of 1N methanolic-HCl (Supelco analytical, USA) was added to each vial together with a known amount of C17:0 TAG as an internal standard, depending on the amount of TAG in each sample. Typically, 30 µg of the internal standard was added for low TAG samples whilst up to 200 µg of internal standard was used in the case of high TAG samples.

Lipid samples for fatty acid composition analysis by GC were transmethylated by incubating the mixtures at 80° C. for 2 hours in the presence of the methanolic-HCl. After cooling samples to room temperature, the reaction was stopped by adding 350 µl $H_2O$. Fatty acyl methyl esters (FAME) were extracted from the mixture by adding 350 µl hexane, vortexing and centrifugation at 1700 rpm for 5 min. The upper hexane phase was collected and transferred into GC vials with 300 µl conical inserts. After evaporation, the samples were resuspended in 30 µl hexane. One µl was injected into the GC.

The amount of individual and total fatty acids (TFA) present in the lipid fractions was quantified by GC by determining the area under each peak and calculated by comparison with the peak area for the known amount of internal standard. TAG content in leaf was calculated as the sum of glycerol and fatty acyl moieties in the TAG fraction using a relation: % TAG by weigh=100×((41×total mol FAME/3)+(total g FAME−(15×total mol FAME)))/g leaf dry weight, where 41 and 15 are molecular weights of glycerol moiety and methyl group, respectively.

Capillary Gas-Liquid Chromatography (GC)

FAME were analysed by GC using an Agilent Technologies 7890A GC (Palo Alto, California, USA) equipped with an SGE BPX70 (70% cyanopropyl polysilphenylene-siloxane) column (30 m×0.25 mm i.d., 0.25 µm film thickness), an FID, a split/splitless injector and an Agilent Technologies 7693 Series auto sampler and injector. Helium was used as the carrier gas. Samples were injected in split mode (50:1 ratio) at an oven temperature of 150° C. After injection, the oven temperature was held at 150° C. for 1 min, then raised to 210° C. at 3° C. min$^{-1}$ and finally to 240° C. at 50° C. min$^{-1}$. Peaks were quantified with Agilent Technologies ChemStation software (Rev B.04.03 (16), Palo Alto, California, USA) based on the response of the known amount of the external standard GLC-411 (Nucheck) and C17:0-Me internal standard.

Quantification of TAG via Iatroscan

One µL of lipid extract was loaded on one Chromarod-SII for TLC-FID Iatroscan™ (Mitsubishi Chemical Medience Corporation—Japan). The Chromarod rack was then transferred into an equilibrated developing tank containing 70 mL of a hexane/CHCl$_3$/2-propanol/formic acid (85/10.716/0.567/0.0567 v/v/v/v) solvent system. After 30 min of incubation, the Chromarod rack was dried for 3 min at 100° C. and immediately scanned on an Iatroscan MK-6s TLC-FID analyser (Mitsubishi Chemical Medience Corporation—Japan). Peak areas of DAGE internal standard and TAG were integrated using SIC-480II integration software (Version: 7.0-E SIC System instruments Co., LTD—Japan).

TAG quantification was carried out in two steps. First, DAGE was scanned in all samples to correct the extraction yields after which concentrated TAG samples were selected and diluted. Next, TAG was quantified in diluted samples with a second scan according to the external calibration using glyceryl trilinoleate as external standard (Sigma-Aldrich).

Quantification of TAG in Leaf Samples by GC

The peak area of individual FAME were first corrected on the basis of the peak area responses of known amounts of the same FAMEs present in a commercial standard GLC-411 (NU-CHEK PREP, Inc., USA). The corrected areas were used to calculate the mass of each FAME in the sample by comparison to the internal standard. Since oil is stored primarily in the form of TAG, the amount of oil was calculated based on the amount of FAME in each sample. Total moles of glycerol were determined by calculating the number of moles of FAMEs and dividing total moles of FAMEs by three. The amount of TAG was calculated as the sum of glycerol and fatty acyl moieties using the formula: % oil by weight=100×((41×total mol FAME/3)+(total g FAME−(15×total mol FAME)))/g leaf dry weight, where 41 and 15 were the molecular weights of glycerol moiety and methyl group, respectively.

Soluble Protein Extraction and Quantitation

Soluble protein was extracted from 10-20 mg ground fresh plant tissue. Briefly, chlorophyll and soluble sugars were extracted at 80° C. in 50-80% (v/v) ethanol in 2.5 mM HEPES buffer at pH 7.5 and the pellet was retained for soluble protein determination. The pellet was washed in distilled water, resuspended in 400 µl 0.1 M NaOH and heated at 95° C. for 30 min. The soluble protein in the supernatant was determined using a Bradford assay (Bradford, 1976). Soluble protein was also extracted from freshly ground tissue in buffer containing 100 mM Tris-HCl pH 8.0 and 10 mM $MgCl_2$. Quantitation of the soluble protein by Bradford assay gave results similar to those obtained using the extraction with NaOH.

SDS-Polyacrylamide Gel Electrophoresis (SDS-PAGE)

Total protein was extracted from frozen, ground leaf tissue by heating the samples in Laemmli buffer (1:3 w/v) at 95° C. for 10 min. Aliquots of the supernatant, normalised to fresh weight (FW), were separated on a 10% acrylamide gel according to Laemmli (1970).

Leaf Nitrogen Content

Total nitrogen content (% dry weight, DW) of 2-2.2 mg freeze-dried leaf tissue was determined using a Europa 20-20 isotope ratio mass spectrometer with an ANCA preparation system, comprising a combustion and reduction tube operating at 1000° C. and 600° C., respectively.

Carbon and Energy Contents

Carbon and energy contents were calculated based on the amount of TAG, starch and total carbohydrates in wildtype and transgenic leaf tissues (% leaf dry weight). Starch levels (% leaf dry weight) were first converted to glucose equivalents by multiplying by a factor of 180/162 to take into account the loss of water due to chain linkages. Soluble sugars were defined as the difference between the total carbohydrate and starch levels. The carbon and energy contents of TAG and soluble sugars were calculated based on the energy density, molecular weight and carbon contents of triolein (35114 kJ/mol; 885.4 g/mol; 57 mol C/mol) and glucose (28.3 kJ/mol; 180 g/mol; 6 mol C/mol), respectively. The carbon and energy contents of the starch-glucose equivalents were calculated as described above for the soluble sugar fraction. In summary, the formulas used to obtain carbon content and energy density of the different carbon metabolic pools are as follows:

Carbon content of TAG (mmol C/g leaf dry weight)
=(% TAG×57 mol C/mol TAG×1000)/(100× 885.4 g/mol TAG)

Carbon content of soluble sugars (mmol C/g leaf dry weight)=[(% total carbohydrates−(% starch× 180/162))×6 mol C/mol glucose*1000]/ (100*180 g/mol glucose)

Carbon content of starch (mmol C/g leaf dry weight) =[(% starch×180/162))×6 mol C/mol glucose*1000]/(100*180 g/mol glucose)

Energy content of TAG (kJ/g leaf dry weight)=(% TAG×39.66 kJ/g TAG)/100

Energy content of soluble sugars (kJ/g leaf dry weight)=[(% total carbohydrates−(% starch× 180/162))×15.57 kJ/mol glucose]/100 Energy content of starch (kJ/g leaf dry weight)=[(% starch×180/162))×15.57 kJ/mol glucose]/100.

Example 2. Silencing of a TAG Lipase in Plants Accumulating High Levels of TAG in Leaf Tissue The Sugar Dependent 1 (SDP1) TAG lipase has been demonstrated to play a role in TAG turnover in non-seed tissues of *A. thaliana* as well as during seed germination (Eastmond et al., 2006; Kelly et al., 2011; Kelly et al., 2013). SDP1 is expressed in developing seed and the SDP1 polypeptide is also present in mature seed in association with oil bodies. Silencing of the gene encoding SDP1 resulted in a small but significant increase in TAG levels in *A. thaliana* roots and stems (<0.4% on dry weight basis) while an even smaller increase was observed in leaf tissue (Kelly et al., 2013).

To determine whether TAG levels could be increased further in leaf and stem tissues relative to co-expression of AtWRI1 and AtDGAT1, an experiment was designed to silence an endogenous SDP1 gene in *N. tabacum* plants which were homozygous for a T-DNA having genes for transgenic expression of the WRI, DGAT1 and Oleosin polypeptides (Vanhercke et al., 2014). A BLAST search of the *N. benthamiana* transcriptome (Naim et al., 2012) using the AtSDP1 nucleotide sequence as query identified a transcript (Nbv5tr6385200, SEQ ID NO:173) with homology to the *A. thaliana* SDP1 gene. A 713 bp region (SEQ ID NO:174) was selected for hairpin mediated gene silencing. A 3.903 kb synthetic fragment was designed, based on the pHELLSGATE12 vector, which comprised, in order, the enTCUP2 constitutive promoter, the 713 bp *N. benthamiana* SDP1 fragment in sense orientation flanked by attB1 and attB2 sites, a Pdk intron, a cat intron sequence in reverse orientation, a second 713 bp *N. benthamiana* SDP1 fragment flanked by attB1 and attB2 sites in reverse (antisense) orientation, and the OCS 3' region terminator/polyadenylation site (FIG. 2). The insert was subcloned into pJP3303 using SmaI and KasI restriction sites and the resulting expression vector was designated pOIL051. This chimeric DNA contains a hygromycin resistance selectable marker gene.

pOIL051 was used to produce transformed *N. tabacum* plants by *Agrobacterium*-mediated transformation. The starting plant cells were from transgenic plants which were homozygous for the T-DNA of pJP3502 (Vanhercke et al., 2014). Transgenic plants containing the T-DNA from pOIL051 were selected by hygromycin resistance and transferred to soil in the glasshouse or in a controlled environment cabinet for continued growth. Leaf samples were harvested from confirmed double-transformants (T0 plants) before flowering, at flowering and at seed setting stages of plant development, and the TAG level in each determined. Transgenic plants containing only low levels of leaf TAG, or TAG at the same level as controls, were identified by means of lipid extraction from leaf samples and analysis by spot TLC and discarded. TAG levels in the remaining population of transformants were quantified by GC as described in Example 1. Before flowering, the majority of these plants exhibited greatly increased TAG levels (>5% of leaf dry weight) in their leaf tissue while 4 plants contained TAG levels above 10% (Table 3). The maximum TAG level observed in leaves of these plants, before flowering, was 11.3% in plant 51-13. As a comparison, the transgenic plants of the parental *N. tabacum* line expressing AtWRI1, AtDGAT1 and Oleosin displayed TAG levels of about 2% before flowering and about 6% during flowering (Vanhercke et al., 2014). The addition of the SDP1-inhibitory construct to the AtWRI1 plus AtDGAT1 combination was therefore synergistic for increasing the TAG levels in these plants. Surprisingly, the TAG content in leaves harvested from the doubly-transformed plants at flowering stage was greatly increased, observing 30.5% on a dry weight basis (Table 4), representing a 5-fold increase relative to the plants not silenced for SDP1. To the great amazement of the inventors, the TAG level reached an astonishing 70.7% (% of dry weight) in samples of senescing leaves (green and yellow) at the seed setting stage (Table 5). When NMR was used to measure the oil content of entire leaves from the tobacco plants at seed setting stage, the TAG content in some green leaves that had started senescing was about 43% and in some brown, desiccated leaves was 42%. When such leaves were pressed between two brown paper filters, the exuded oil soaked into the paper and made it translucent, whereas control tobacco leaves did not do so, providing a simple screening method for detecting plants having high oil content.

Two primary transformants (#61, #69) containing each of the T-DNAs from pJP3502 and pOIL51 and displaying high TAG levels were analyzed by digital PCR (ddPCR) using a hygromycin gene-specific primer pair to determine the number of pOIL51 T-DNA insertions. The plant designated #61 contained one T-DNA insertion from pOIL51, whereas plant #69 contained three T-DNA insertions from pOIL51. T1 progeny plants of both lines were screened again by ddPCR to identify homozygous, heterozygous and null plants. Progeny plants of plant #61 containing no insertions from pOIL51 (nulls; total of 7) or 2 T-DNA insertions (i.e. homozygous for that T-DNA; total of 12) were selected for further analysis. Similarly, progeny plants of line #69 containing zero T-DNA insertions from pOIL51 (nulls; total of 2) or 2 such insertions (total of 15) or 4 or 5 insertions (total of 5) were maintained for further analysis.

The selected T1 plants were grown in the glasshouse at the same time and under the same conditions as control plants. Green leaf tissue samples from the T1 plants before flowering were dried and total fatty acid (TFA) and TAG contents determined by GC analysis. TFA contents of the plants containing both T-DNAs ranged from 4.6% to 16.1% on a dry weight basis including TAG levels in the same leaves of 1.2% to 11.8% on a dry weight basis (FIG. 3). This was much greater compared to the plants containing only the T-DNA from pJP3502 and growing alongside under the same conditions and analysed at the same stage of growth, again showing the synergism between reducing TAG lipase activity and the WRI1 plus DGAT combination. Plants containing only the pJP3502 T-DNA contained between 4.2% and 6.8% TFA including TAG levels of 1.4% to 4.1% on a dry weight basis (FIG. 3). Wild-type plants contained, on average, about 0.8% TFA including less than 0.5% TAG on a dry weight basis. The fatty acid composition in the total fatty acid content and the TAG content of leaves from each of lines #61 and #69 were similar to the composition in leaves containing only the T-DNA from pJP3502 (parent). Compared to the wild-type control leaves, plants containing both of the T-DNAs from pOIL51 and pJP3502 exhibited increased levels of C16:0, C18:1 and C18:2 fatty acids. This significant shift in fatty acid composition came largely at the expense of C18:3 which was reduced from about 50-55% to about 20-30% as a percentage of the total fatty acid content.

TABLE 3

TAG levels (% leaf dry weight) and TAG fatty acid composition in leaf tissue from *N. tabacum* plants (T0 generation) expressing WRI1, DGAT1 and Oleosin transgenes and super-transformed with a T-DNA encoding an SDP1 hairpin construct (pOIL051), compared to wild-type (untransformed). Leaf samples were harvested during vegetative stage (before flowering). Lipid samples also contained 0.0-0.2% C16:3, 0.0-0.4% C20:1; 0.0-0.1% C20:2n-6.

| Line | C14:0 | C16:0 | C16:1 | C18:0 | C18:1 | C18:1d11 | C18:2 | C18:3n3 | C20:0 | C22:0 | C24:0 | % TAG |
|---|---|---|---|---|---|---|---|---|---|---|---|---|
| WT | 2.5 | 20.2 | 0.0 | 8.6 | 5.6 | 0.0 | 18.9 | 44.2 | 0.0 | 0.0 | 0.0 | 0.1 |
| 23-31 | 0.0 | 66.0 | 0.0 | 0.0 | 34.0 | 0.0 | 0.0 | 0.0 | 0.0 | 0.0 | 0.0 | 0.0 |
| 23-29 | 0.0 | 36.1 | 1.4 | 5.1 | 21.0 | 0.8 | 23.3 | 7.1 | 2.4 | 1.5 | 1.1 | 2.9 |
| 57 | 0.1 | 47.2 | 0.3 | 5.4 | 19.2 | 1.9 | 0.0 | 21.2 | 2.1 | 1.2 | 1.1 | 3.4 |
| 23-1 | 0.2 | 30.8 | 1.9 | 4.9 | 41.2 | 1.0 | 13.7 | 2.4 | 1.9 | 1.1 | 0.7 | 4.0 |
| 58 | 0.1 | 31.4 | 0.2 | 3.8 | 12.2 | 1.6 | 33.6 | 13.2 | 1.7 | 1.0 | 0.7 | 4.0 |
| 21 | 0.1 | 31.9 | 0.3 | 3.9 | 10.7 | 1.5 | 32.3 | 15.2 | 1.9 | 1.1 | 0.8 | 4.7 |
| 23-30 | 0.2 | 34.1 | 0.7 | 4.9 | 29.4 | 0.9 | 17.5 | 5.7 | 2.9 | 1.8 | 1.7 | 4.9 |
| 40 | 0.1 | 34.4 | 0.2 | 4.3 | 14.3 | 1.5 | 29.7 | 11.8 | 1.7 | 1.0 | 0.7 | 5.1 |
| 22 | 0.1 | 35.8 | 0.2 | 4.3 | 12.8 | 1.5 | 29.8 | 11.7 | 1.8 | 1.0 | 0.7 | 5.1 |
| 15 | 0.1 | 37.2 | 0.1 | 3.9 | 8.6 | 1.7 | 29.3 | 16.0 | 1.5 | 0.8 | 0.6 | 5.1 |
| 16 | 0.1 | 35.2 | 0.1 | 3.9 | 13.9 | 1.7 | 28.5 | 13.6 | 1.4 | 0.7 | 0.6 | 5.3 |
| 25 | 0.1 | 34.4 | 0.2 | 3.9 | 15.4 | 1.8 | 27.6 | 13.2 | 1.6 | 0.9 | 0.7 | 5.4 |
| 65 | 0.1 | 26.9 | 0.2 | 3.8 | 19.2 | 1.5 | 35.7 | 9.1 | 1.7 | 0.8 | 0.6 | 5.5 |
| 12 | 0.2 | 31.7 | 0.2 | 3.6 | 15.9 | 1.7 | 30.5 | 12.8 | 1.6 | 0.9 | 0.7 | 5.5 |
| 28 | 0.1 | 31.4 | 0.2 | 3.5 | 13.5 | 1.7 | 32.7 | 13.7 | 1.5 | 0.8 | 0.6 | 5.6 |
| 26 | 0.1 | 31.4 | 0.2 | 3.5 | 13.5 | 1.7 | 32.7 | 13.7 | 1.5 | 0.8 | 0.6 | 5.8 |
| 19 | 0.1 | 30.5 | 0.2 | 3.7 | 14.9 | 1.6 | 31.7 | 13.7 | 1.7 | 0.9 | 0.7 | 5.9 |
| 30 | 0.1 | 30.4 | 0.2 | 3.7 | 21.3 | 2.2 | 31.2 | 7.4 | 1.6 | 0.8 | 0.7 | 5.9 |
| 6 | 0.1 | 37.5 | 0.2 | 4.4 | 10.5 | 1.7 | 31.9 | 10.6 | 1.5 | 0.7 | 0.6 | 6.0 |
| 4 | 0.1 | 34.2 | 0.2 | 3.9 | 11.9 | 1.7 | 32.6 | 12.5 | 1.4 | 0.6 | 0.5 | 6.1 |
| 42 | 0.1 | 30.6 | 0.2 | 4.5 | 17.3 | 1.8 | 32.7 | 9.2 | 1.7 | 0.9 | 0.7 | 6.3 |
| 45 | 0.1 | 31.6 | 0.2 | 3.9 | 18.2 | 1.8 | 30.4 | 10.5 | 1.6 | 0.8 | 0.6 | 6.6 |
| 56 | 0.1 | 26.8 | 0.2 | 4.2 | 20.0 | 1.5 | 34.3 | 8.7 | 1.9 | 1.0 | 0.8 | 6.7 |
| 43 | 0.1 | 28.5 | 0.2 | 3.8 | 18.6 | 1.6 | 34.1 | 9.6 | 1.7 | 0.9 | 0.6 | 7.1 |
| 32 | 0.1 | 28.1 | 0.2 | 3.4 | 16.8 | 1.8 | 35.5 | 10.6 | 1.6 | 0.8 | 0.6 | 7.2 |
| 70 | 0.1 | 26.3 | 0.2 | 3.5 | 25.5 | 1.8 | 31.0 | 8.9 | 1.3 | 0.6 | 0.5 | 7.4 |
| 69 | 0.1 | 30.9 | 0.2 | 4.0 | 15.7 | 1.7 | 31.7 | 12.9 | 1.5 | 0.7 | 0.5 | 7.4 |
| 61 | 0.1 | 31.0 | 0.2 | 4.0 | 16.4 | 1.6 | 34.1 | 9.5 | 1.5 | 0.7 | 0.5 | 7.5 |
| 20 | 0.1 | 33.3 | 0.1 | 3.8 | 11.7 | 1.6 | 31.4 | 14.8 | 1.5 | 0.8 | 0.6 | 7.8 |
| 53 | 0.1 | 33.1 | 0.1 | 3.8 | 18.2 | 1.9 | 29.8 | 10.4 | 1.3 | 0.6 | 0.5 | 8.4 |
| 18 | 0.1 | 29.4 | 0.2 | 3.7 | 18.4 | 1.7 | 32.8 | 10.9 | 1.4 | 0.6 | 0.5 | 9.1 |
| 51-1 | 0.1 | 29.0 | 2.0 | 3.6 | 17.1 | 1.6 | 33.8 | 9.9 | 1.4 | 0.7 | 0.5 | 9.2 |
| 47 | 0.1 | 30.5 | 0.1 | 4.2 | 20.3 | 1.5 | 31.9 | 8.3 | 1.5 | 0.7 | 0.5 | 9.3 |

TABLE 3-continued

TAG levels (% leaf dry weight) and TAG fatty acid composition in
leaf tissue from *N. tabacum* plants (T0 generation) expressing WRI1, DGAT1 and Oleosin
transgenes and super-transformed with a T-DNA encoding an SDP1 hairpin construct (pOIL051),
compared to wild-type (untransformed). Leaf samples were harvested during vegetative stage (before
flowering). Lipid samples also contained 0.0-0.2% C16:3, 0.0-0.4% C20:1; 0.0-0.1% C20:2n-6.

| Line | C14:0 | C16:0 | C16:1 | C18:0 | C18:1 | C18:1d11 | C18:2 | C18:3n3 | C20:0 | C22:0 | C24:0 | % TAG |
|---|---|---|---|---|---|---|---|---|---|---|---|---|
| 51-60 | 0.1 | 30.7 | 2.6 | 3.4 | 15.8 | 1.9 | 31.2 | 11.6 | 1.3 | 0.7 | 0.5 | 10.2 |
| 46 | 0.1 | 24.8 | 0.1 | 3.6 | 28.8 | 1.6 | 30.3 | 7.9 | 1.3 | 0.6 | 0.5 | 10.2 |
| 48 | 0.1 | 33.1 | 0.1 | 3.8 | 16.5 | 1.7 | 30.4 | 11.4 | 1.4 | 0.7 | 0.5 | 10.7 |
| 51-13 | 0.1 | 25.4 | 2.2 | 3.3 | 23.8 | 1.6 | 32.7 | 8.3 | 1.3 | 0.6 | 0.4 | 11.3 |

TABLE 4

TAG levels (% leaf dry weight) and TAG composition in leaf tissue from *N. tabacum* plants
(T0 generation) expressing WRI1, DGAT1 and Oleosin transgenes and supertransformed with a
T-DNA encoding an SDP1 hairpin construct (pOIL051). Leaf samples were harvested during flowering.

| Line | C14:0 | C16:0 | C16:1 | C18:0 | C18:1 | C18:1d11 | C18:2 | C18:3n3 | C20:0 | C22:0 | C24:0 | % TAG |
|---|---|---|---|---|---|---|---|---|---|---|---|---|
| WT | 0.2 | 14.8 | 0.6 | 8.5 | 9.2 | 0.3 | 20.0 | 44.5 | 0.6 | 0.3 | 0.4 | 0.3 |
| 21 | 0.1 | 25.7 | 2.1 | 3.7 | 21.2 | 1.0 | 31.0 | 11.7 | 1.5 | 0.8 | 0.6 | 8.8 |
| 56 | 0.1 | 33.2 | 1.4 | 4.9 | 20.7 | 1.0 | 26.3 | 7.4 | 2.1 | 1.3 | 0.9 | 9.2 |
| 65 | 0.1 | 24.7 | 1.5 | 3.8 | 28.5 | 1.0 | 29.0 | 7.5 | 1.7 | 0.9 | 0.6 | 12.0 |
| 42 | 0.1 | 34.0 | 1.5 | 4.4 | 16.8 | 1.1 | 29.4 | 7.6 | 2.2 | 1.4 | 1.1 | 13.1 |
| 28 | 0.1 | 29.5 | 2.4 | 3.5 | 16.4 | 1.2 | 28.7 | 14.6 | 1.5 | 1.0 | 0.6 | 13.2 |
| 30 | 0.1 | 19.1 | 1.9 | 3.3 | 31.8 | 1.0 | 30.6 | 9.3 | 1.3 | 0.7 | 0.4 | 13.6 |
| 20 | 0.1 | 22.4 | 1.8 | 3.7 | 27.4 | 0.9 | 29.0 | 10.8 | 1.7 | 0.9 | 0.7 | 14.6 |
| 19 | 0.1 | 20.9 | 1.7 | 3.1 | 28.4 | 1.0 | 31.6 | 10.0 | 1.4 | 0.8 | 0.5 | 15.7 |
| 12 | 0.1 | 24.4 | 1.6 | 3.6 | 22.1 | 0.9 | 35.1 | 8.9 | 1.4 | 0.8 | 0.5 | 15.8 |
| 16 | 0.1 | 21.5 | 1.8 | 3.4 | 34.9 | 1.0 | 26.2 | 7.9 | 1.4 | 0.7 | 0.5 | 16.4 |
| 57 | 0.1 | 25.0 | 1.7 | 4.1 | 27.7 | 1.0 | 28.4 | 8.4 | 1.6 | 0.9 | 0.6 | 17.2 |
| 26 | 0.1 | 22.5 | 1.6 | 3.5 | 28.4 | 1.1 | 31.2 | 7.6 | 1.7 | 1.0 | 0.7 | 18.0 |
| 39 | 0.1 | 30.0 | 2.2 | 3.7 | 22.7 | 1.6 | 24.3 | 11.6 | 1.5 | 0.9 | 0.7 | 18.1 |
| 70 | 0.1 | 22.1 | 2.1 | 3.6 | 36.3 | 1.0 | 24.2 | 7.2 | 1.4 | 0.7 | 0.5 | 18.3 |
| 45 | 0.1 | 21.4 | 1.8 | 3.7 | 34.4 | 1.0 | 27.5 | 6.9 | 1.4 | 0.8 | 0.5 | 19.1 |
| 32 | 0.1 | 23.3 | 1.6 | 3.2 | 24.4 | 1.1 | 33.6 | 9.0 | 1.5 | 0.9 | 0.6 | 19.5 |
| 18 | 0.1 | 23.4 | 2.1 | 3.3 | 26.4 | 0.9 | 30.2 | 10.3 | 1.4 | 0.7 | 0.5 | 20.6 |
| 20Y | 0.1 | 22.3 | 1.6 | 3.6 | 30.3 | 0.9 | 28.5 | 9.1 | 1.6 | 0.9 | 0.6 | 20.8 |
| 43 | 0.1 | 28.1 | 2.0 | 3.5 | 21.5 | 1.2 | 29.9 | 10.2 | 1.5 | 0.9 | 0.6 | 21.2 |
| 4 | 0.1 | 27.9 | 1.9 | 3.7 | 26.3 | 1.2 | 26.2 | 9.3 | 1.5 | 0.8 | 0.5 | 21.8 |
| 1 | 0.1 | 23.8 | 2.0 | 3.7 | 30.2 | 1.1 | 28.1 | 8.0 | 1.4 | 0.7 | 0.5 | 22.3 |
| 61 | 0.1 | 24.2 | 2.2 | 4.0 | 32.0 | 1.1 | 25.2 | 7.8 | 1.5 | 0.8 | 0.6 | 23.9 |
| 60 | 0.1 | 24.4 | 2.2 | 3.7 | 31.0 | 1.1 | 25.4 | 8.6 | 1.5 | 0.8 | 0.6 | 25.0 |
| 46 | 0.1 | 23.3 | 2.0 | 3.7 | 32.9 | 1.0 | 24.0 | 9.2 | 1.6 | 0.9 | 0.7 | 25.7 |
| 6 | 0.1 | 31.5 | 2.6 | 3.5 | 19.5 | 1.6 | 25.5 | 12.7 | 1.3 | 0.7 | 0.5 | 26.3 |
| 13 | 0.1 | 21.8 | 1.9 | 3.6 | 35.1 | 1.0 | 25.1 | 8.1 | 1.5 | 0.8 | 0.5 | 26.8 |
| 69 | 0.1 | 21.8 | 1.6 | 4.3 | 33.4 | 0.8 | 26.9 | 7.6 | 1.7 | 0.8 | 0.5 | 26.9 |
| 53 | 0.1 | 27.1 | 2.1 | 3.5 | 24.1 | 1.2 | 29.4 | 9.2 | 1.4 | 0.8 | 0.5 | 29.2 |
| 48 | 0.1 | 29.5 | 2.5 | 3.9 | 21.1 | 1.3 | 29.0 | 9.2 | 1.6 | 0.8 | 0.6 | 29.5 |
| 47 | 0.1 | 30.9 | 2.5 | 3.4 | 19.4 | 1.5 | 28.5 | 10.6 | 1.3 | 0.8 | 0.5 | 30.5 |

TABLE 5

TAG content (% leaf dry weight) and TAG composition in leaf tissue from *N. tabacum* plants
(T0 generation) expressing WRI1, DGAT1 and Oleosin transgenes and supertransformed with a T-DNA
encoding an SDP1 hairpin construct (pOIL051). Leaf samples were harvested at seed setting stage.

| Sample | C14:0 | C16:0 | C16:1 | 16:3 | C18:0 | C18:1 | C18:1d11 | C18:2 | C18:3n3 | C20:0 | C20:1d11 | C22:0 | C24:0 | TAG content |
|---|---|---|---|---|---|---|---|---|---|---|---|---|---|---|
| wt | 0.0 | 13.0 | 0.0 | 0.0 | 8.4 | 7.0 | 0.0 | 24.7 | 46.8 | 0.0 | 0.0 | 0.0 | 0.0 | 0.3 |
| 73 | 0.0 | 26.6 | 1.7 | 0.0 | 8.5 | 9.4 | 0.0 | 27.0 | 25.6 | 1.1 | 0.0 | 0.0 | 0.0 | 0.6 |
| 18 | 0.1 | 15.0 | 1.8 | 0.0 | 4.8 | 14.4 | 0.4 | 43.9 | 16.3 | 1.7 | 0.4 | 0.7 | 0.5 | 3.3 |
| 41 | 0.1 | 22.3 | 1.2 | 0.3 | 4.4 | 24.0 | 0.6 | 32.8 | 10.8 | 1.7 | 0.3 | 0.8 | 0.5 | 5.2 |
| 19 | 0.1 | 14.5 | 1.5 | 0.3 | 3.0 | 21.6 | 0.7 | 44.8 | 10.6 | 1.4 | 0.4 | 0.7 | 0.4 | 7.2 |
| 20 | 0.1 | 26.7 | 2.4 | 0.1 | 4.3 | 24.9 | 1.0 | 25.2 | 11.3 | 1.9 | 0.3 | 1.0 | 0.8 | 9.6 |
| 30 | 0.1 | 18.6 | 1.5 | 0.3 | 3.5 | 24.8 | 0.7 | 38.9 | 8.9 | 1.4 | 0.3 | 0.7 | 0.4 | 9.9 |
| 65 | 0.1 | 22.2 | 1.4 | 0.3 | 3.5 | 30.9 | 0.7 | 29.1 | 8.1 | 1.7 | 0.3 | 1.0 | 0.6 | 11.3 |
| 42 | 0.1 | 23.6 | 1.5 | 0.2 | 4.1 | 29.0 | 0.9 | 30.3 | 5.9 | 2.0 | 0.4 | 1.3 | 0.8 | 12.0 |

TABLE 5-continued

TAG content (% leaf dry weight) and TAG composition in leaf tissue from *N. tabacum* plants (T0 generation) expressing WRI1, DGAT1 and Oleosin transgenes and supertransformed with a T-DNA encoding an SDP1 hairpin construct (pOIL051). Leaf samples were harvested at seed setting stage.

| Sample | C14:0 | C16:0 | C16:1 | 16:3 | C18:0 | C18:1 | C18:1d11 | C18:2 | C18:3n3 | C20:0 | C20:1d11 | C22:0 | C24:0 | TAG content |
|---|---|---|---|---|---|---|---|---|---|---|---|---|---|---|
| 32 | 0.1 | 21.3 | 1.3 | 0.3 | 3.3 | 21.4 | 0.9 | 40.7 | 7.1 | 1.7 | 0.3 | 1.0 | 0.6 | 13.7 |
| 39 | 0.1 | 25.8 | 1.7 | 0.3 | 3.6 | 27.2 | 1.2 | 27.2 | 8.2 | 2.0 | 0.4 | 1.4 | 0.9 | 14.0 |
| 45 | 0.1 | 23.0 | 1.5 | 0.1 | 3.8 | 28.0 | 0.9 | 32.6 | 6.3 | 1.8 | 0.3 | 1.0 | 0.6 | 14.4 |
| 13 | 0.1 | 26.9 | 2.8 | 0.1 | 3.7 | 32.6 | 1.1 | 21.6 | 7.6 | 1.6 | 0.3 | 0.8 | 0.7 | 14.6 |
| R45 | 0.1 | 23.4 | 1.5 | 0.2 | 4.1 | 27.8 | 0.9 | 32.2 | 6.1 | 1.8 | 0.3 | 1.0 | 0.6 | 14.6 |
| 21 | 0.1 | 23.1 | 1.6 | 0.2 | 3.5 | 27.4 | 0.8 | 31.2 | 8.2 | 1.8 | 0.3 | 1.1 | 0.7 | 15.0 |
| 9 | 0.1 | 23.2 | 1.4 | 0.2 | 3.5 | 23.3 | 0.8 | 35.6 | 8.5 | 1.6 | 0.3 | 0.9 | 0.5 | 15.4 |
| 12 | 0.1 | 24.5 | 1.4 | 0.2 | 3.4 | 22.3 | 0.8 | 36.2 | 7.4 | 1.7 | 0.3 | 1.1 | 0.7 | 15.9 |
| 4 | 0.1 | 21.9 | 1.8 | 0.2 | 3.6 | 22.8 | 0.9 | 35.9 | 9.5 | 1.6 | 0.3 | 0.9 | 0.6 | 16.1 |
| 49 | 0.1 | 23.5 | 1.4 | 0.2 | 4.0 | 25.3 | 0.8 | 34.3 | 6.6 | 1.8 | 0.3 | 1.1 | 0.7 | 16.8 |
| 26 | 0.1 | 22.2 | 1.3 | 0.2 | 3.8 | 25.4 | 0.8 | 35.2 | 6.5 | 2.1 | 0.3 | 1.3 | 0.8 | 17.2 |
| 16 | 0.1 | 22.2 | 1.8 | 0.3 | 3.4 | 29.9 | 0.8 | 30.1 | 8.1 | 1.5 | 0.3 | 0.9 | 0.6 | 18.2 |
| 1 | 0.1 | 27.4 | 2.7 | 0.1 | 4.0 | 32.0 | 1.2 | 22.9 | 6.3 | 1.6 | 0.3 | 0.8 | 0.7 | 18.7 |
| 70 | 0.1 | 27.1 | 2.7 | 0.2 | 3.7 | 32.6 | 1.0 | 21.5 | 7.6 | 1.6 | 0.3 | 0.8 | 0.7 | 19.0 |
| 6 | 0.1 | 30.6 | 2.6 | 0.2 | 3.3 | 13.0 | 1.4 | 32.8 | 12.9 | 1.4 | 0.2 | 0.9 | 0.6 | 21.5 |
| 47 | 0.1 | 28.0 | 2.1 | 0.2 | 3.6 | 18.5 | 1.3 | 33.2 | 9.9 | 1.5 | 0.2 | 0.9 | 0.5 | 21.6 |
| 69 | 0.1 | 25.4 | 2.3 | 0.1 | 4.3 | 32.4 | 0.9 | 23.5 | 7.4 | 1.8 | 0.3 | 0.8 | 0.6 | 22.5 |
| 53 | 0.1 | 23.9 | 2.1 | 0.2 | 3.4 | 28.2 | 1.1 | 30.2 | 7.6 | 1.5 | 0.3 | 0.9 | 0.5 | 23.2 |
| 46 | 0.1 | 25.9 | 2.7 | 0.2 | 3.7 | 32.0 | 1.1 | 22.8 | 8.2 | 1.6 | 0.3 | 0.8 | 0.7 | 24.0 |
| 43 | 0.1 | 23.7 | 1.6 | 0.2 | 3.1 | 22.6 | 0.9 | 37.6 | 7.4 | 1.4 | 0.2 | 0.8 | 0.5 | 24.0 |
| 48 | 0.1 | 27.4 | 2.2 | 0.1 | 4.1 | 23.0 | 1.1 | 31.3 | 6.9 | 1.9 | 0.3 | 1.0 | 0.7 | 24.4 |
| 28 | 0.1 | 23.0 | 1.4 | 0.2 | 3.3 | 24.8 | 1.0 | 35.6 | 7.3 | 1.6 | 0.3 | 0.9 | 0.6 | 26.6 |
| 1Y | 0.1 | 24.3 | 2.5 | 0.1 | 3.8 | 35.7 | 1.1 | 22.6 | 6.7 | 1.6 | 0.3 | 0.7 | 0.6 | 28.1 |
| 56G | 0.1 | 25.5 | 1.8 | 0.2 | 3.7 | 26.7 | 0.9 | 29.8 | 7.3 | 1.8 | 0.3 | 1.1 | 0.7 | 33.9 |
| 57 | 0.1 | 25.1 | 1.9 | 0.2 | 3.2 | 20.1 | 1.0 | 35.2 | 10.0 | 1.5 | 0.3 | 0.9 | 0.6 | 35.4 |
| 56Y | 0.2 | 24.8 | 1.4 | 0.2 | 4.1 | 27.2 | 0.8 | 31.0 | 6.0 | 2.0 | 0.4 | 1.2 | 0.8 | 39.6 |
| 69Y | 0.1 | 24.7 | 2.1 | 0.2 | 4.1 | 32.0 | 0.8 | 24.3 | 7.8 | 1.9 | 0.3 | 0.9 | 0.7 | 46.5 |
| R69Y | 0.1 | 24.7 | 2.1 | 0.2 | 4.1 | 32.0 | 0.8 | 24.4 | 7.9 | 1.9 | 0.3 | 0.9 | 0.7 | 46.8 |
| 61 | 0.1 | 26.6 | 2.7 | 0.1 | 3.6 | 31.6 | 1.1 | 23.8 | 7.4 | 1.4 | 0.3 | 0.7 | 0.5 | 49.2 |
| 61Y | 0.1 | 25.8 | 2.4 | 0.1 | 3.7 | 32.4 | 1.1 | 24.3 | 6.9 | 1.5 | 0.3 | 0.7 | 0.5 | 58.1 |
| 60 | 0.1 | 24.6 | 2.4 | 0.2 | 3.6 | 34.1 | 1.0 | 24.4 | 6.4 | 1.5 | 0.3 | 0.7 | 0.5 | 70.7 |

Y = yellow leaf,
G = green leaf.

The substantial increase in TFA levels including the TAG levels between the plants containing only the pJP3502 T-DNA and plants containing the T-DNAs from both pOIL51 and pJP3502 was maintained throughout plant development. Control plants containing only the T-DNA from pJP3502 contained 7.7% to 17.5% TAG during flowering while TAG levels ranged from 14.1% to 20.7% on a dry weight basis during seed setting. The TAG content in leaves from plants containing both pJP3502 and pOIL51 T-DNAs varied between 6.3% and 23.3% during flowering and 12.6% and 33.6% during seed setting. Similar changes in fatty acid composition of the TAG fraction at both stages were detected as described earlier for the vegetative growth stage.

TAG levels were also found to be increased further in other vegetative tissues of the transgenic plants such as roots and stem. Some root tissues of the transgenic *N. tabacum* plants transformed with the T-DNA of pOIL051 contained 4.4% TAG, and some stem tissues 7.4% TAG, on a dry weight basis (FIG. 4). Wild-type plants and *N. tabacum* containing only the T-DNA from pJP3502 exhibited much lower TAG levels in both tissues. The addition of the hairpin SDP1 construct to decrease expression of the endogenous TAG lipase was clearly synergistic with the genes encoding the transcription factor and biosynthesis of TAG (WRI1 and DGAT) for increasing TAG content in the stems and roots. Of note, TAG levels in the roots were lower compared to stem tissue within the same plant while an inverse trend was observed in wild-type plants and *N. tabacum* containing only the T-DNA from pJP3502. The TAG composition of root and stem tissues exhibited similar changes in C18:1 and C18:3 fatty acids as observed previously in transgenic leaf tissue. C18:2 levels in TAG were reduced in transgenic stem tissue while C16 fatty acids were typically reduced in transgenic root tissues when compared to the wild-type control.

Therefore, the inventors concluded that addition of an exogenous gene for silencing the endogenous SDP1 gene to the combination of WRI1 and DGAT increased the total fatty acid content, including the TAG content, at all stages of the plant growth, and acted synergistically with WRI1 and DGAT, particularly in the stems and roots.

T1 seeds from the transgenic plants were plated on tissue culture media in vitro at room temperature to test the extent and timing of germination. Germination of T1 seed from three independently transformed lines was the same compared to seed from the transgenic plants transformed only with the T-DNA from pJP3502. Furthermore, early seedling vigour appeared to be unaffected. This was surprising given the role of SDP1 in germination in *A. thaliana* seeds and the observed defects in germination in SDP1 mutants (Eastmond et al., 2006). To overcome any germination defects if such had occurred, a second construct is designed in which the SDP1 inhibitory RNA is expressed from a promoter which is essentially not expressed, or at low levels, in seed, such as for example a promoter from a photosynthetic gene such as SSU. The inventors consider that it is beneficial to reduce the risk of deleterious effects on seed germination or early seedling vigour to avoid a constitutive promoter, or at least to avoid a promoter expressed in seeds, to drive expression of the SDP1 inhibitory RNA.

It was noted that the T0 plants with the highest TAG levels had been grown under high light conditions in the controlled environment room (500 micro moles light intensity, 16 hr light/26° C.-8 hr dark/18° C. day cycle) and appeared smaller (about 70% in height relative to the plants transformed with the T-DNA from pJP3502) than the wild-type control plants. The inventors concluded that the combination of transgenes and/or genetic modifications for the "push", "pull", "protect" and "package" approaches was particularly favourable for achieving high levels of TAG in vegetative plant parts. In this example, WRI1 provided the "push", DGAT provided the "pull", silencing of SDP1 provided the "protect" and Oleosin provided the "packaging" of TAG.

Example 3. Senescence-Specific Expression of a Transcription Factor

Ectopic expression of master regulators of embryo and seed development such as LEC2 have been reported to increase TAG levels in non-seed tissues (Santos-Mendoza et al., 2005; Slocombe et al., 2009; Andrianov et al., 2010). However, constitutive over-expression of LEC2 in plants transformed with a 35S-LEC2 gene resulted in unwanted pleiotropic effects on plant development and morphology including somatic embryogenesis and abnormal leaf structures (Stone et al., 2001; Santos-Mendoza et al., 2005). To test whether limiting LEC2 expression to the leaf senescence stage of plant development, i.e. after plants had fully grown and reached their full biomass, would minimize undesirable phenotypic effects but still increase leaf lipid levels, a chimeric DNA was designed and made for expression of LEC2 under the control of a *A. thaliana* senescence specific promoter from the SAG12 gene (U37336; Gan and Amasino, 1995).

To make the genetic construct, a 3.635 kb synthetic DNA fragment was made comprising, in order, an *A. thaliana* SAG12 senescence-specific promoter, the LEC2 protein coding sequence and a *Glycine max* Lectin gene terminator/polyadenylation region. This fragment was inserted between the SacI and NotI restriction sites of pJP3303. This construct was designated pOIL049 and tested in leaves of *N. tabacum* plants which were stably transformed with genes encoding WRI1, DGAT1 and Oleosin polypeptides, containing the T-DNA from pJP3502. Using *Agrobacterium*-mediated transformation methods, the pOIL049 construct was used to transform *N. tabacum* plant cells which were homozygous for the T-DNA of pJP3502. Transgenic plants comprising the genes from pOIL049 were selected by hygromycin resistance and were grown to maturity in the glasshouse. Samples are taken from transgenic leaf tissue at different stages of growth including at leaf senescence and contain increased TAG levels compared to the *N. tabacum* pJP3502 parent line.

A total of 149 independent T0 plants (i.e. primary transformants) were obtained. Upper green leaves of all plants and the lower brown, fully senesced leaves of selected events were sampled at the seed setting stage of plant development and TAG contents were quantified by TLC-GC. The number of pOIL49 T-DNA insertions in selected plants was determined by ddPCR using a hygromycin gene-specific primer pair. A TAG level of 30.2% on a dry weight basis was observed in green leaf tissue harvested at seed setting stage. TAG levels in brown leaves were lower in most of the plants sampled. However, three plants (#32b, #8b and #23c) displayed greater TAG levels in brown senesced leaf tissue than in the green expanding leaves. These plants contained 1, 2 or 3 T-DNA insertions from pOIL49.

T1 progeny of plants #23c and #32b were screened by ddPCR to identify nulls, heterozygous and homozygous plants for the T-DNA from pOIL049. Progeny plants of plant #23c containing zero T-DNA insertions from pOIL049 (nulls; total of 7) or two T-DNA insertions of the T-DNA from pOIL049 (homozygous; total of 4) were selected for further analysis. Similarly, progeny plants of plant #32b containing zero insertions (nulls; total of 6) or two insertions (homozygous; total of 9) were maintained for further analysis. Green leaf tissue was sampled before flowering and TFA and TAG contents were determined by GC. Wild-type plants and plants transformed with the T-DNA from pJP3502 were the same as before (Example 2) and were grown alongside in the same glasshouse. TFA levels in leaves of the transformants containing the T-DNA from pOIL049 ranged from 5.2% to 19.5% on a dry weight basis before flowering (FIG. 5). TAG levels in the same tissues ranged from 0.8% to 15.4% on a dry weight basis. This was considerably greater than in plants containing only the T-DNA from pJP3502. TAG levels in plants containing the T-DNAs from pJP3502 and pOIL049 further increased to 38.5% and 34.9% during flowering and seed setting, respectively. When the fatty acid composition of the total fatty acid content was analysed for leaves homozygous for the T-DNA from pOIL049, increased levels of C18:2 and reduced levels of C18:3 were observed (FIG. 5) while the percentages of C16:0 and C18:1 remained about the same relative to leaves transformed only with the T-DNA from pJP3502. These data demonstrated that the addition of a second transcription factor gene under the control of a non-constitutive promoter to provide developmentally-regulated expression was able to further increase TAG levels in vegetative tissues of a plant. The data also indicated that the senescence-specific promoter SAG12 had some expression in the green tissue prior to senescence of the leaves.

TAG levels were much increased in stem tissue when compared to both wild-type *N. tabacum* plants and transgenic plants containing the T-DNA from pJP3502 alone. Some stem tissues of the transgenic *N. tabacum* plants transformed with the T-DNA from pOIL049 contained 4.9% TAG on a dry weight basis (FIG. 6). On the other hand, TAG levels in root tissue exhibited large variation between the three pOIL049 plants with some root tissues containing 3.4% TAG. Of note, TAG levels in roots were lower compared to stem tissue within the same plant while an inverse trend was observed in wild-type plants and *N. tabacum* containing only the T-DNA from pJP3502. The TAG composition of root and stem tissues exhibited similar changes in C18:1 and C18:3 fatty acids as observed previously in transgenic leaf tissue. C18:2 levels in TAG were reduced in transgenic stem tissue while C16 fatty acids were typically reduced in transgenic root tissues when compared to the wild-type control.

Corresponding genetic constructs are made encoding other transcription factors under the control of the SAG12 promoter, namely LEC1, LEC1like, FUS3, ABI3, ABI4 and ABI5 and others (see Example 9). For example, additional constructs were made for the expression of the monocot transcription factor *Zea mays* LEC1 (Shen et al., 2010) or *Sorghum bicolor* LEC1 (Genbank Accession No. XM_002452582.1) under the control of monocot-derived homolog of the *A. thaliana* SAG12 promoter such as the maize SEE1 promoter (Robson et al., 2004). Further constructs are made for expression of the transcription factors under developmentally controlled promoters, for example which are preferentially expressed at flowering (e.g. day length sensitive promoters), Phytochrome promoters, Chryptochrome promoters, or in plant stems during secondary growth such as a promoter from a CesA gene. These constructs are used to transform plants, and plants which produce at least 8% TAG in vegetative parts are selected.

Example 4. Analysis of Transgenic Plants

Plant Material and Growth Conditions

Plants of three TAG accumulating transgenic lines were grown in growth cabinets or in a glasshouse under controlled conditions:
1. Plants over-expressing genes encoding WRI1, DGAT and oleosin (Vanhercke et al, 2014), designated here as HO plants, being plants of the T2 generation which were homozygous for the introduced T-DNA from pJP3052.
2. T1 plants transformed with an RNAi construct to silence the SDP1 TAG lipase as well as the T-DNA from pJP3502, encoding the WRI1, DGAT and oleosin polypeptides, from two independent transformed lines. See Example 2. These plants were designated SDP1.
3. T1 plants transformed with a genetic construct for over-expressing the transcription factor LEC2 from the SAG12 promoter, as well as the T-DNA from pJP3502 encoding the WRI1, DGAT and oleosin polypeptides. See Example 3. These plants were designated LEC2, and were progeny from a single T0 plant.

Wild-type plants (WT, of cultivar Wisconsin 38) were used as control plants and grown at the same time and under the same conditions as the transgenic plants. For vegetative samples, WT and HO tobacco plants were grown in PGC20/PGC20FLEX plant growth cabinets (Conviron) at ambient $CO_2$ concentrations with 250-450 µmol $m^{-2}$ $s^{-1}$ illumination from fluorescent bulbs. Plants were grown under 12 hr light/25° C.: 12 hr dark/20° C. daily cycles. Plants from which samples were to be harvested at 49 days after sowing (DAS) were grown in 1.25 litre pots in soil with osmocote fertiliser. Plants from which samples were to be harvested at 69 DAS were grown in 4 litre pots in soil and watered every 14 days with aquasol fertiliser. For all assays, samples were taken from four plants of each genotype. For samples to be harvested at seed-setting stage of growth, WT, HO, SDP1 and LEC2 plants were grown in a glasshouse without artificial light (n=3, 3, 8, 6, respectively). For all analyses, leaf discs were harvested from leaves at the end of the growth phase with light, snap frozen and stored at −80° C. until analysis.

TAG Levels and Fatty Acid Composition

TAG levels were measured in leaves of mature WT, HO, SDP1 and LEC2 plants. The fatty acid composition in TAG of the leaves was also determined. The data are shown in Table 6 for the LEC2 and SDP1 plants.

Starch and Sugar Levels

Starch and soluble sugar levels were measured in leaf tissue sampled from the wild-type (WT) and transgenic HO, SDP1 and LEC2 plants. In general, an inverse correlation was found between TAG and starch levels in leaf tissue on a dry weight basis in the leaves having both T-DNAs (FIG. 7 and FIG. 8). In contrast, leaf soluble sugars levels were about the same in the transgenic plants as in the wild-type plants, suggesting that there was no significant bottleneck in the conversion from sugars to TAG. An effect of the leaf position in the plants was observed in wild-type plants where starch levels tended to increase from lower leaf to higher leaf position. No such effect was detected in the transgenic plants.

Carbon and Energy Contents

The amounts of carbon and energy in the TAG, starch and sugar contents in leaves of the HO, SDP1 and LEC2 plants were measured and compared to wild-type plants, on a dry weight basis. The data (Table 7) showed that each of the carbon and energy contents increased in the HO plants and increased even further in the SDP1 and LEC2 plants relative to the WT plants. The increase was seen for the sum of TAG, starch and soluble sugars, as well as for the sum of TAG and starch. It was concluded that the increase in carbon content by increasing the TAG content more than compensated for the reduced starch content. Therefore, the transgenic plants exhibited increased total carbon content and increased total energy content on a dry weight basis.

Nitrogen and Soluble Protein Contents

Nitrogen and protein contents were measured in leaf samples of the transformed and control plants as described in Example 1, for plants at 69 DAS. The third leaf from the top of each of the WT and HO tobacco plants, which leaves were not yet fully expanded and therefore still growing, had the same nitrogen content at about 3.0% by DW. Older (lower) leaves on each plant were also analysed. In the WT plants, the leaf nitrogen content decreased with leaf age, whereas the nitrogen content was relatively maintained in older HO leaves with less of a decline compared to the WT plants. For example, older leaves such as leaf 11 from the top of the HO plants had more than twice as much nitrogen (2.9%) compared to the corresponding leaves in WT plants (1.3%; FIG. 9a). A similar trend was observed for total soluble protein with twice as much soluble protein detected in older HO leaves compared to WT (10.4 and 5.0 µg/mg FW, respectively; FIG. 9B). The same trends were observed when soluble protein samples were electrophoresed by SDS-PAGE, after normalising sample loading according to leaf fresh weights.

TABLE 6

TAG levels (% leaf dry weight) and fatty acid composition in TAG of selected *N. tabacum* primary transformants over-expressing LEC2 (pOIL049) or a silencing construct targeted against the gene encoding SDP1 TAG lipase (pOIL051). Both constructs were transformed independently into a previously established *N. tabacum* transgenic line over-expressing genes encoding WRI1, DGAT1 and OLEOSIN (Vanhercke et al., 2014).

| Transgene | Line | Leaf | C16:0 | C16:1 | C18:0 | C18:1$^{\Delta 9}$ | C18:2$^{\Delta 9,12}$ | C18:3$^{\Delta 9,12,15}$ | Other | % TAG |
|---|---|---|---|---|---|---|---|---|---|---|
| LEC2 | #8 | green | 28.3 | 3.1 | 3.2 | 19.8 | 30.5 | 10.2 | 5.0 | 8.3 |
|  | #8 | brown | 31.1 | 2.4 | 3.7 | 16.5 | 32.4 | 7.7 | 6.2 | 12.6 |
| LEC2 | #23 | green | 26.6 | 5.5 | 0.1 | 5.4 | 48.0 | 7.3 | 7.2 | 14.3 |
|  | #23 | brown | 26.2 | 5.2 | 2.5 | 3.5 | 47.0 | 8.1 | 7.5 | 28.7 |
| LEC2 | #32 | green | 28.0 | 1.0 | 4.3 | 19.7 | 29.2 | 10.9 | 6.7 | 5.8 |
|  | #32 | brown | 22.3 | 3.1 | 2.4 | 19.7 | 39.0 | 7.2 | 6.3 | 14.0 |

TABLE 6-continued

TAG levels (% leaf dry weight) and fatty acid composition in TAG of selected *N. tabacum* primary transformants over-expressing LEC2 (pOIL049) or a silencing construct targeted against the gene encoding SDP1 TAG lipase (pOIL051). Both constructs were transformed independently into a previously established *N. tabacum* transgenic line over-expressing genes encoding WRI1, DGAT1 and OLEOSIN (Vanhercke et al., 2014).

| Transgene | Line | Leaf | C16:0 | C16:1 | C18:0 | C18:1$^{\Delta 9}$ | C18:2$^{\Delta 9,12}$ | C18:3$^{\Delta 9,12,15}$ | Other | % TAG |
|---|---|---|---|---|---|---|---|---|---|---|
| SDP1 | #60 | brown | 28.0 | 3.8 | 3.1 | 35.9 | 19.7 | 5.8 | 3.6 | 26.4 |
| SDP1 | #61 | brown | 27.7 | 3.7 | 3.4 | 34.0 | 20.7 | 6.5 | 4.0 | 27.9 |
| SDP1 | #69 | yellow-green | 28.1 | 3.4 | 3.6 | 29.5 | 23.3 | 8.1 | 3.9 | 32.9 |

TABLE 7

Carbon and energy contents of TAG, starch and soluble sugars in leaf tissues of wild-type and transgenic *N. tabacum* plants.

| | Carbon (mmol C/gDW) | | | Energy (kJ/g DW)* | | |
|---|---|---|---|---|---|---|
| | TAG | Starch | Soluble sugars | TAG | Starch | Soluble sugars |
| wt1 | 0.08 | 15.41 | 1.33 | 0.05 | 7.20 | 0.62 |
| wt6 | 0.08 | 12.01 | 1.29 | 0.05 | 5.61 | 0.60 |
| wt7 | 0.09 | 11.10 | 1.37 | 0.06 | 5.18 | 0.64 |
| HO #2 | 10.69 | 5.43 | 1.24 | 6.59 | 2.54 | 0.58 |
| HO #5 | 8.63 | 10.78 | 1.86 | 5.32 | 5.04 | 0.87 |
| HO #7 | 9.51 | 8.22 | 1.47 | 5.86 | 3.84 | 0.69 |
| SDP1 #69-1 | 19.56 | 2.83 | 1.61 | 12.05 | 1.32 | 0.75 |
| SDP1 #69-60 | 21.44 | 3.11 | 2.03 | 13.21 | 1.45 | 0.95 |
| SDP1 #69-91 | 16.78 | 0.68 | 1.71 | 10.33 | 0.32 | 0.80 |
| LEC2 #32-21 | 14.99 | 0.57 | 0.88 | 9.23 | 0.27 | 0.41 |
| LEC2 #32-29 | 19.19 | 0.86 | 0.82 | 11.82 | 0.40 | 0.39 |

*assuming 2803 kJ/mol for glucose and 35114 kJ/mol for triolein (Sanjaya et al., 2011)

In both WT and HO plants, leaf protein content increased with plant age (FIG. 10, Table 8). In younger plants (49 DAS), soluble protein content was slightly but not significantly higher in older leaves from HO plants compared to WT. By 69 DAS, this difference was significant with an 87% increase in old HO leaves compared to WT (p<0.05, t-test). It was concluded that the leaves of the HO plants had significantly increased nitrogen and protein contents relative to the corresponding leaves in the WT plants. In this context, a "corresponding leaf" meant a leaf of the same age of a plant grown under the same conditions.

TABLE 8

Leaf soluble protein content in WT and HO tobacco (µg/mg FW).

| | WT | | HO | |
|---|---|---|---|---|
| Plant age | 49 DAS | 69 DAS | 49 DAS | 69 DAS |
| Range | 4.3-9.9 | 3.0-15.2 | 2.5-11.3 | 7.9-19.1 |

Range includes young, mature and older leaves of younger (49 DAS) and older (69 DAS) plants.

Nitrogen Content in SDP1 and LEC2 Plants

The transgenic plants designated LEC2 and SDP1 exhibited increased TAG accumulation compared to the HO plants throughout growth (Examples 2 and 3), increasing with plant age. Leaf samples of the transgenic plants grown in growth cabinets or in the glasshouse were assayed for nitrogen, protein and carbon contents. The LEC2 and SDP1 plants exhibited each of increased leaf carbon content, leaf nitrogen content and soluble protein content relative to the WT plants (Table 9). At the seed setting stage of growth, the LEC2 and SDP1 leaves had between 50% and 100% more nitrogen than WT leaves. The leaf soluble protein content increased between 40% and 87% in LEC2 and SDP1 leaves, respectively, relative to the WT leaves. Leaf carbon content also increased. Despite moderate increases in leaf carbon content (16% to 21%) in LEC2 and SDP1 lines, the greater relative increase in leaf nitrogen content decreased the carbon to nitrogen ratio by up to 40% compared to WT leaves.

Total Dietary Fibre (TDF)

Analysis of the total dietary fibre of WT, SDP1 and LEC2 in mature leaves obtained at flowering showed that WT leaves had a TDF content of 27%, SDP1 leaves had a TDF content of 15.9% (59% reduction when compared to WT), and LEC2 leaves had a TDF content of 17.9% (34% reduction when compared to WT).

TABLE 9

TAG content (% dry weight), carbon content, nitrogen content and soluble protein content of WT, LEC2 and SDP1 tobacco leaves.

| | TAG content | Nitrogen content | Carbon content | C:N rato | Soluble protein content |
|---|---|---|---|---|---|
| WT | 0.17 | 0.50 | 43.08 | 86:1 | 1.47 |
| LEC2 | 24.57 | 0.85 | 52.08 | 51:1 | 2.06 |
| SDP1 | 28.52 | 1.07 | 49.92 | 60:1 | 2.75 |

For TAG analysis n = 3-8 and for C, N and soluble protein n = 2-5.

Upregulation of Genes Involved in Photosynthesis

The observations described above on the increase in carbon and energy contents in the transgenic plants led the inventors to consider whether the plants might exhibit an increase in photosynthetic capacity, related to the altered carbon allocation between starch and TAG. Therefore, the transcriptome of the HO plants was determined and compared to the transcriptome from WT plants grown under the same conditions. RNA was isolated from plants at the flowering stage, converted to cDNA and the full transcriptomes were determined. When the resultant sequence libraries were compared for the frequency of representation of individual genes, numerous genes involved in photosynthesis were observed to be up-regulated (over-expressed) in the HO plants. Table 10 lists representative genes which were up-regulated. From this, it was concluded that the capacity for photosynthesis was increased in the transgenic plants.

Effects of Modifying Photoperiod and Light Intensity

The growth conditions were modified compared to those described above, in order to test the effect of increasing or decreasing the photoperiod from the 12 hrs, and of increasing light intensity. In one growth chamber using high light intensity and long photoperiod, the $CO_2$ concentration was also increased above the ambient. The following conditions were tested, in each case plants were grown in PGC20/PGC20FLEX plant growth cabinets (Conviron) at 25° C. during the light period, 20° C. during the dark period and leaf samples were harvested at seed-setting stage of growth from leaf Nos. 9, 15 and 20 counting from the bottom of each plant. Leaf 9 was therefore the oldest of the sampled leaves, leaf 15 intermediate, and leaf 20 the youngest leaf sampled. Leafs were assayed for total fatty acid (TFA) content as described in Example 1.

TABLE 10

Listing of genes related to photosynthesis and whose expression was up-regulated.

| Unigene | log2FC | logCPM | LR | PValue | *Arabidopsis* Annotation | *Nicotiana* Annotation |
|---|---|---|---|---|---|---|
| c72304_g2_i2 | 1.03 | 6.31 | 14.04 | 0.000179411 | PSBP-2 photosystem II subunit P-2 chr2:13118937-13120090 | PREDICTED: Oxygen-evolving enhancer protein 2-1, chloroplastic (LOC104217148) |
| c63827_g1_i2 | 2.31 | 0.95 | 21.08 | 4.40E-06 | NA | PREDICTED: PsbQ-like protein 1, chloroplastic (LOC104213138) variant X1 |
| c72304_g2_i6 | 1.19 | 2.43 | 15.20 | 9.66E-05 | PSBP-1, OEE2, PSII-P, OE23 photosystem II subunit P-1 chr1:2047825-2049418 | PREDICTED: Oxygen-evolving enhancer protein 2-2, chloroplastic (LOC104220111) |
| c72995_g1_i1 | 3.02 | 3.42 | 101.49 | 7.18E-24 | NA | PREDICTED: Ferredoxin, root R-B1-like (LOC104250181), transcript variant X2 |
| c66865_g1_i2_1 | 1.30 | 2.69 | 12.05 | 0.000518939 | NA | PREDICTED: Photosystem II repair protein PSB27-H1, chloroplastic (LOC104235950) |
| c64448_g1_i1_1 | 1.06 | 8.91 | 13.35 | 0.000258132 | NA | PREDICTED: Ferredoxin (LOC104243179), mRNA |
| c65326_g1_i1 | 1.17 | 8.45 | 20.85 | 4.97E-06 | NA | PREDICTED: Oxygen-evolving enhancer protein 3-2, (LOC104238927) |
| c68151_g1_i1 | 0.78 | 8.00 | 9.37 | 0.002201414 | PSAF photosystem I subunit F chr1:11214824-11216037 | PREDICTED: Photosystem I reaction center subunit III, (LOC104229855) |
| c70874_g1_i3 | 0.77 | 6.00 | 11.61 | 0.000655078 | PSAF photosystem I subunit F chr1:11214824-11216037 | PREDICTED: Photosystem I reaction center subunit III, LOC104227234) |
| c72380_g2_i1 | 0.82 | 8.81 | 15.30 | 9.19E-05 | ATPC1 ATPase, F1 complex, gamma subunit protein chr4:2350498-2352018 | PREDICTED: ATP synthase gamma chain, chloroplastic (LOC104212794) |
| c84022_g2_i1 | 1.25 | 6.54 | 19.65 | 9.29E-06 | NA | PREDICTED: Plastocyanin A'/A" (LOC104226609) |
| c80197_g1_i1_1 | 0.66 | 6.27 | 9.60 | 0.00194393 | PSBO-1, OEE1, OEE33, OE33, PSBO1, MSP-1 PS II oxygen-evolving complex 1 | PREDICTED: Oxygen-evolving enhancer protein 1, chloroplastic (LOC104219516) |
| c80359_g2_i3 | 0.74 | 6.41 | 8.91 | 0.002843257 | PSBP-2 photosystem II subunit P-2 chr2:13118937-13120090 | PREDICTED: oxygen-evolving enhancer protein 2-2, (LOC104220111), variant X2 |
| c84616_g2_i1 | 0.95 | 8.53 | 13.93 | 0.000189474 | NA | PREDICTED: Oxygen-evolving enhancer protein 3-2, chloroplastic-like (LOC104238927) |
| c60857_g1_i2_1 | 2.13 | 2.76 | 61.06 | 5.54E-15 | NA | PREDICTED: Ferredoxin, root R-B2-like (LOC104216941), transcript variant X1 |
| c66431_g3_i1 | 2.04 | 1.10 | 26.67 | 2.41E-07 | NA | PREDICTED: Plastocyanin (LOC104222137), mRNA |
| c70844_g1_i1 | 0.72 | 8.77 | 10.45 | 0.001227902 | PSBO-1, OEE1, OEE33, OE33, PSBO1, MSP-1 PS II oxygen-evolving complex 1 chr5:26568653-26570278 | PREDICTED: Oxygen-evolving enhancer protein 1, chloroplastic (LOC104219516), mRNA |
| c72588_g1_i1_1 | 0.58 | 9.38 | 8.50 | 0.003545489 | NA | PREDICTED: Photosystem I reaction center subunit XI, chloroplastic (LOC104221829) |
| c63567_g3_i1 | 0.96 | 8.50 | 15.81 | 7.01E-05 | PSAO photosystem I subunit O chr1:2640813-2641828 | PREDICTED: Photosystem I subunit O-like (LOC104237017), transcript variant X1 |
| c79260_g1_i1 | 1.76 | 6.42 | 68.73 | 1.13E-16 | PSBO-1, OEE1, OEE33, OE33, PSBO1, MSP-1 PS II oxygen-evolving complex 1 chr5:26568653-26570278 | PREDICTED: Oxygen-evolving enhancer protein 1, chloroplastic-like (LOC104210963), mRNA |
| c70844_g1_i5 | 1.16 | 6.10 | 24.55 | 7.23E-07 | PSBO2, PSBO-2, OEC33 photosystem II subunit O-2 chr3:18890876-18892426 | PREDICTED: Oxygen-evolving enhancer protein 1, (LOC104210963) |
| c72502_g1_i1 | 0.86 | 4.19 | 12.14 | 0.000493881 | NA | PREDICTED: Oxygen-evolving enhancer protein 1, (LOC104210963) |
| c79863_g1_i3_1 | 1.26 | 2.23 | 13.31 | 0.000263854 | NA | PREDICTED: Plastocyanin A'/A" (LOC104226609) |
| c72380_g1_i1_2 | 0.85 | 8.57 | 20.42 | 6.23E-06 | ATPC1 ATPase, F1 complex, gamma subunit protein chr4:2350498-2352018 | PREDICTED: ATP synthase gamma chain, chloroplastic (LOC104212794) |
| c66717_g2_i2 | 0.61 | 10.76 | 10.67 | 0.001090419 | NA | PREDICTED: Photosystem II 10 kDa polypeptide, chloroplastic (LOC104224572) |
| c60043_g4_i1 | 3.40 | 1.72 | 78.26 | 9.04E-19 | NA | PREDICTED: Ferredoxin, root R-B2-like (LOC104216941), transcript variant X1 |
| c64427_g1_i1_1 | 0.70 | 9.07 | 8.59 | 0.003381803 | NA | PREDICTED: Photosystem II reaction center W protein, (LOC104244017) |

1. Control conditions: 8 plants were grown with 300 µmol m$^{-2}$ s$^{-1}$ illumination from fluorescent bulbs, with a 12-hour photoperiod;
2. Increased light intensity: 7 plants were grown with 700 µmol m$^{-2}$ s illumination from fluorescent bulbs, with a 12-hour photoperiod;
3. Reduced photoperiod: 9 plants were grown with 700 µmol m$^{-2}$ s$^{-1}$ illumination from fluorescent bulbs, with a 8-hour photoperiod;
4. Increased light intensity and photoperiod: 10 plants were grown with 700 µmol m$^{-2}$ s$^{-1}$ illumination from fluorescent bulbs, with a 12-hour photoperiod, at 700 ppm $CO_2$ concentration.

The average data for leaves 9, 15 and 20 of each genotype are plotted in FIG. 11. Increased light intensity alone did not significantly affect the TFA levels. Decreasing the photoperiod from 12 hrs to 8 hrs decreased the levels of TFA but to a surprisingly small extent. That is, even reducing the amount of light received each 24 hours by 33% had remarkably small effect. The most dramatic results observed were from the test using an increased photoperiod under increased light intensity and increased $CO_2$ concentration. The TFA levels increased dramatically, reaching 50% (w/w dry weight) and above in leaves of the LEC2 plants. Since the TFA assays measured only the fatty acid components of lipids, this meant that the total lipid level was even higher in these leaves.

Example 5. Modifying Traits in Vegetative Parts of Monocotyledonous Plants

Chimeric DNA constructs were designed to increase oil content in monocotyledonous plants, for example the C4 plant *S. bicolor* (sorghum), by expressing a combination of genes encoding WRI1, *Z. mays* LEC1 (Accession number AAK95562; SEQ ID NO:155), DGAT and Oleosin in the transgenic plants. Several pairs of constructs for biolistic co-transformation were designed and produced by restriction enzyme-ligation cloning, as follows.

The genetic construct pOIL136 was a binary vector containing three monocot expression cassettes, namely a selectable marker gene encoding phosphinothricin acetyltransferase (PAT) for plant selection, a second cassette for expressing DGAT and a third for expressing Oleosin. pJP136 was first produced by amplifying an actin gene promoter from *Oryza sativa* (McElroy et al., 1990) and inserting it as a blunt-ClaI fragment into pORE04 (Coutu et al., 2007) to produce pOIL094. pOIL095 was then produced by inserting a version of the *Sesamum indicum* Oleosin gene which had been codon optimised for monocot expression into pOIL094 at the KpnI site. pOIL093 was produced by cloning a monocot codon optimised version of the *Umbelopsis ramanniana* DGAT2a gene (Lardizabal et al., 2008) as a SmaI-KpnI fragment into a vector already containing a *Zea mays* Ubiquitin gene promoter. pOIL134 was then produced by cloning the NotI DGAT2a expression cassette from pOIL093 into pOIL095 at the NotI sites. pOIL141 was produced by inserting the selectable marker gene coding for PAT as a BamHI-SacI fragment into a vector containing the *Z. mays* Ubiquitin promoter. Finally, pOIL136 was produced by cloning the *Z. mays* Ubiquitin::PAT expression cassette as a blunt-AscI fragment into the ZraI-AscI of pOIL096. The genetic construct pOIL136 therefore contained the following expression cassettes: promoter *O. sativa* Actin::*S. indicum* Oleosin, promoter *Z. mays* Ubiquitin::*U. ramanniana* DGAT2a and promoter *Z. mays* Ubiquitin::PAT.

A similar vector pOIL197, containing NPTII instead of PAT was constructed by subcloning of the *Z. mays* Ubiquitin::NPTII cassette from pUKN as a HindIII-SmaI fragment into the AscI (blunted) and HindIII sites of pJP3343. The resulting vector, pOIL196, was then digested with HindIII (blunted) and AgeI. The resulting 3358 bp fragment was cloned into the ZraI-AgeI sites of pOIL134, yielding pOIL197.

A set of constructs containing genes encoding the *Z. mays* WRI1 (ZmWRI) or the LEC1 (ZmLEC1) transcription factors under the control of different promoters were designed and produced for biolistic co-transformation in combination with pOIL136 or pOIL197 to test the effect of promoter strength and cell specificity on the function of WRI1 or LEC1, or both if combined, when expressed in vegetative tissues of a C4 plant such as sorghum. This separate set of constructs did not contain a selectable marker gene, except for pOIL333 which contained NPTII as selectable marker. The different promoters tested were as follows. The *Z. mays* Ubiquitin gene promoter (pZmUbi) was a strong constitutive monocot promoter while the enhanced CaMV 35S promoter (e35S) having a duplicated enhancer region was reported to result in lower transgene expression levels (reviewed in Girijashankar and Swathisree, 2009). Whilst the *Z. mays* phosphoenolpyruvate carboxylase (pZmPEPC) gene promoter was active in leaf mesophyl cells (Matsuoka and Minami, 1989), the site of photosynthesis in C4 plant species, the *Z. mays* Rubisco small subunit (pZmSSU) gene promoter was specific for the bundle sheath cell layer (Nomura et al., 2000; Lebrun et al., 1987), the cells where carbon fixation takes place in C4 plants.

The expression of the *Z. mays* gene encoding the SEE1 cysteine protease (Accession number AJ494982) was identified as similar to that of the *A. thaliana* SAG12 senescence-specific promoter during plant development. Therefore a 1970 bp promoter from the SEE1 gene (SEQ ID NO:207) was also selected to drive expression of the genes encoding the *Z. mays* WRI1 and LEC1 transcription factors. Further, the promoter from the gene encoding *Aeluropus littoralis* zinc finger protein AlSAP (Ben Saad et al., 2011; Accession number DQ885219; SEQ ID NO:208), the promoter from the gene encoding the *Saccharum* hybrid DIRIGENT (DIR16) (Damaj et al., 2010; Accession number GU062718; SEQ ID NO:246), the promoter from the gene encoding the *Saccharum* hybrid O-Methyl transferase (OMT) (Damaj et al., 2010; Accession number GU062719; SEQ ID NO:247), the A1 promoter allel from the gene encoding the *Saccharum* hybrid R1MYB1 (Mudge et al., 2009; Accession number JX514703.1; SEQ ID NO:248), the promoter from the gene encoding the *Saccharum* hybrid Loading Stem Gene 5 (LSG5) (Moyle and Birch, 2013; Accession number JX514698.1; SEQ ID NO:249) and the promoter from the sucrose-responsive ArRolC gene from *A. rhizogenes* (Yokoyama et al., 1994; Accession number DQ160187; SEQ ID NO:209) were also selected for expression of ZmWRI1 expression in stem tissue. Therefore, each of these promoters was individually joined upstream of the ZmWRI1 or ZmLEC1 coding regions, as follows.

An intermediate vector, pOIL100, was first produced by cloning the *Z. mays* WRI1 coding sequence and a transcription terminator/polyadenylation region, flanked by AscI-NcoI sites, into the same sites in the binary vector pJP3343. The different versions of the constructs for WRI1 expression were based on this vector and were produced by cloning the various promoters into pOIL100. pOIL01 was produced by cloning a XhoI-SalI fragment containing the e35S promoter with duplicated enhancer region into the XhoI site of pOIL100. pOIL102 was produced by cloning a HindIII-AvrII fragment containing the Z. mays Ubiquitin gene promoter into the HindIII-XbaI sites of pOIL100. pOIL103 was produced by cloning a HindIII-NcoI fragment containing a Z. mays PEPC gene promoter into the HindIII-NcoI sites of pOIL100. pOIL104 was produced by cloning a HindIII-AvrII fragment containing a Z. mays SSU gene promoter into the HindIII-AvrII sites of pOIL100.

A synthetic fragment containing the Z. mays SEE1 promoter region flanked by HindIII-XhoI unique sites was synthesized. This fragment was cloned upstream of the Z. mays WRI1 protein coding region using the HindIII-XhoI sites in pOIL100. The resulting vector was designated pOIL329. A synthetic fragment containing the A. littoralis AlSAP promoter region flanked by XhoI-XbaI unique sites was synthesized. This fragment was cloned upstream of the Z. mays WRI1 coding region using the XbaI-XhoI sites in pOIL100. The resulting vector was designated pOIL330. A synthetic fragment containing the A. rhizogenes ArRolC promoter region flanked by PspOMI-XhoI unique sites was synthesized. This fragment was cloned upstream of the Z. mays WRI1 coding region using the PspOMI-XhoI sites in pOIL100. The resulting vector was designated pOIL335. Finally, a binary vector (pOIL333) containing the Z. mays SEE1::ZmLEC1 expression cassette was obtained in three steps. First, a 35S::GUS expression vector was constructed by amplifying the GUS coding region with flanking primers containing AvrII and KpnI sites. The resulting fragment was subsequently cloned into the SpeI-KpnI sites of pJP3343. The resulting vector was designated pTV 111. Next, the 35S promoter region of pTV 111 was replaced by the Z. mays SEE1 promoter. To this end, the Z. mays SEE1 sequence was amplified using flanking primers containing HindIII and XhoI unique sites. The resulting fragment was cut with the respective restriction enzymes and subcloned into the SalI-HindIII sites of pTV111. The resulting vector was designated pOIL332. Next the ZmLEC1 coding sequence was amplified using flanking primers containing NotI and EcoRV sites. This resulting fragment was subcloned into the respective sites of pOIL332, yielding pOIL333.

A 2673 bp synthetic fragment containing the Saccharum DIR16 promoter region flanked by HindIII-XbaI sites was synthesized. This fragment was cloned upstream of the Z. mays WRI1 protein coding region using the HindIII-XbaI sites in pOIL100. The resulting vector was designated pOIL337. A 2947 bp synthetic fragment containing the Saccharum OMT promoter region flanked by XhoI-XbaI sites was synthesized. This fragment was cloned upstream of the Z. mays WRI1 protein coding region using the XhoI-XbaI sites in pOIL100. The resulting vector was designated pOIL339. A 1181 bp synthetic fragment containing the Saccharum R1MYB1 promoter region flanked by HindIII-XhoI sites was synthesized. This fragment was cloned upstream of the Z. mays WRI1 protein coding region using the HindIII-XhoI sites in pOIL100. The resulting vector was designated pOIL341. A 4482 bp synthetic fragment containing the Saccharum LSG5 promoter region flanked by XbaIII-SmaI sites was synthesized. This fragment was cloned as an XbaIII-SmaI fragment upstream of the Z. mays WRI1 protein coding region using the StuI-NheI sites in pOIL100. The resulting vector was designated pOIL343.

Whole plasmid DNA was prepared from pOIL101, pOIL102, pOIL103, pOIL104, pOIL197 and pOIL136 for biolistic transformation. pOIL197 DNA was then mixed with either pOIL101, pOIL102, pOIL103 or pOIL104 and transformed by biolistic-mediated transformation into S. bicolor (grain sorghum TX430) differentiating embryonic calli (DEC) tissues as described in Example 1. Alternatively, constructs for expression of the same combinations of genes are transformed separately or co-transformed by Agrobacterium-mediated transformation (Gurel et al., 2009; Wu et al., 2014) into DEC tissues.

Twenty-five to fifty transgenic plants were regenerated and selected by antibiotic resistance for the pairs of constructs including pOIL197 with each of pOIL102 (pZmUbi::WRI1), pOIL103 (pZmPEPC::WRI1) and pOIL104 (pSSU::WRI1). Transformations were also carried out with pOIL197 alone and with pOIL102 or pOIL103 alone, and for an "empty vector" control. The presence of the desired transgenes in plants that were resistant to the selective agent was demonstrated by PCR. The copy number of each transgene was also determined by digital PCR.

Total leaf lipids were quantified in a first subset of transgenic S. bicolor plants prior to their transfer from MS medium to soil. This preliminary screening suggested slightly elevated total lipid levels in leaf tissue of some events at this very early stage. The line with the highest total lipid content, pOIL136 (2), was further analyzed by thin layer chromatography (TLC) to determine the effect of transgene expression on TAG accumulation. Leaf tissue of this particular line was sampled at vegetative stage following transfer to soil in the glasshouse. When compared to the wildtype and empty vector negative controls, pOIL136 (2) exhibited increased TAG levels in leaf tissue after TLC separation and iodine staining. Subsequent quantification revealed 10-fold increased TAG in the transgenic line compared to the negative controls. The TAG profile was dominated by the polyunsaturated fatty acids linoleic and α-linolenic acid.

After confirmed transgenic plants were transferred to soil in pots in the glasshouse, whole leaves were sampled from primary transformants at vegetative stage of growth (i.e. prior to the appearance of the boot leaf), at the boot leaf stage (defined as when the boot leaf has fully emerged, the boot leaf is the last leaf formed on the plant and from which the panicle (head) emerges) and at the mature seed-setting stage. Total fatty acid (TFA) and triacylglycerol (TAG) contents (% leaf dry weight) were quantified by TLC-GC as described in Example 1.

TFA levels in wildtype and empty vector negative controls decreased during plant development (Table 11) and were in the range 0.7-3.3% (weight/dry weight). The highest TFA levels were detected prior to the appearance of the boot leaf (termed the vegetative stage of growth) and were not higher than 3.3%. TAG levels in the same plants were consistently low in the range 0-0.2% during the entire plant life cycle (Table 11). Both the TFA content and the TAG content had fatty acid compositions of predominantly C16:0, C18:2$^{\Delta 9,12}$ (LA) and C18:3$^{\Delta 9,12,15}$ (ALA). In particular, ALA was present at about 50-75% of the TFA content, reflecting the use of this fatty acid in wild-type plastid membranes. ALA also was the main fatty acid in the very small amount of TAG present in the wild-type leaves.

Thirty-five confirmed transgenic plants which had been transformed with pOIL197 or pOIL136, each vectors comprising both pZmUbi:DGAT and pZmUbi:Oleosin genes in addition to the selectable marker genes, were analysed at the vegetative, boot leaf and mature seed setting stages. The data are presented in Tables 12-14. Generally, the pOIL197 and pOIL136 primary transformants displayed increased TFA and TAG accumulation compared to the negative control lines, but only to about double for the TFA level compared to the controls. The highest TFA levels were detected at the vegetative stage of growth (Table 12). Similar to the wildtype and negative control lines, TFA levels decreased with progressing plant age (Tables 13 and 14). Maximum TFA levels at vegetative, boot leaf and mature seed setting stages equalled 5%, 4.5% and 2.1%, respectively. The highest TAG levels detected varied between 0.9 and 1.9% depending on the age of the plant at the time of sampling (Table 13), so were increased up to 10-fold relative to the very low levels in the wild-type leaves (Table 11). The TFA composition remained largely unchanged at the different stages and was dominated by ALA. The TAG composition displayed a higher degree of variation between the different transgenic lines. Compared to the fatty acid composition of the TFA content, the levels of stearic acid, oleic acid and LA (18:$2^{\Delta9,12}$) consistently increased in TAG throughout all plant stages investigated.

Nine primary transgenic plants made by transformation with pOIL102 (pZmUbi:WRI1) were generated by co-bombardment of pOIL102 and pUKN, containing the NPTII selectable marker gene. Tables 15-17 show the data for TFA and TAG contents and fatty acid compositions were measured at the three growth stages. When compared to the plants transformed with the constructs encoding DGAT2 and Oleosin (pOIL197 or pOIL136), TFA and TAG levels in the pOIL102 transgenic events were generally lower. Indeed, levels of TFA and TAG were similar to the levels in the wild-type and negative control plants. Maximum TFA levels at vegetative, boot leaf and mature seed setting stages were 2.6%, 2.5% and 2.0%, respectively (Tables 15-17). Maximum TAG levels observed were 0.2%, 0.4% and 0.9% at vegetative, boot leaf and mature seed setting stages, respectively.

Thirty-six primary transgenic plants made by co-bombardment with both pOIL197 (pZmUbi:DGAT and pZmUbi:Oleosin) and pOIL102 (pZmUbi:WRI1) and confirmed to have integrated both genetic constructs were analysed for TFA and TAG contents and fatty acid composition at the three growth stages. The data are presented in Tables 18-20. Some of the plants exhibited greatly increased TFA and TAG levels compared to the transformations with single pOIL197, pOIL136 or pOIL102 vectors. Maximum TFA levels at vegetative, boot leaf and mature seed setting stages in the pOIL102+pOIL197 population equalled 7.2%, 6.4% and 6.1%, respectively (Tables 18-20). Importantly, the maximum observed TAG levels increased during plant development from 2.7% (vegetative stage) to 3.5% (boot leaf stage) and 4.3% (mature seed setting stage) (Tables 18-20). Compared with the data obtained for the separate transformations with the DGAT and WRI1 transgenes, this exemplified the synergism for co-expressing DGAT and WRI1 transgenes to increase non-polar lipid accumulation in vegetative plant tissues. High levels of TAG and TFA were in most cases associated with a substantial reduction in the $C18:3^{\Delta9,12,15}$ content, which was reduced by about 50% in the lines with the highest levels of TAG.

Thirty-six primary transformants containing both pOIL197 (pZmUbi:DGAT and pZmUbi:Oleosin) and pOIL103 (pZmPEPC:WRI1) were analysed for TFA and TAG contents and fatty acid composition during the three stages of plant development. The data are presented in Tables 21-23. Some plants with this gene combination exhibited the highest TFA and TAG levels detected in this experimental series. TFA levels were observed at vegetative, boot leaf and mature seed setting stages in the pOIL103+pOIL197 population at 8.3%, 8.3% and 4.5%, respectively (Tables 21-23). TAG levels were observed at vegetative, boot leaf and mature seed setting stages at 2.3%, 6.6% and 3.0%, respectively (Tables 21-23). Of note, the highest TAG (6.6%) and TFA (8.3%) levels amongst all transgenic lines were detected in event TX-03-31 at boot leaf stage. While $C18:3^{\Delta9,12,15}$ typically dominated the TFA fraction, TAG compositions in this population displayed a high degree of variability. Of note, some events exhibited increases in levels of palmitic acid (C16:0) and/or linoleic acid (LA, $C18:2^{\Delta9,12}$) at the expense of ALA. Indeed, the ALA level in both TFA and TAG contents was reduced below 40% in some events, less than 30% in selected events. The ALA level in TAG was less than 20% in some selected events.

Plants containing the higher levels of TFA and TAG were propagated by separating tillers and transplanting them into soil in new pots. The tillers produced new roots and continued to grow. When leaf samples of the new plants were analysed, TAG levels of 8.3% in a TFA level of 9.3% were observed.

Sixteen primary transformants containing both pOIL197 (pZmUbi:DGAT and pZmUbi:Oleosin) and pOIL104 (pSSU:WRI1) were analysed for TFA and TAG contents and fatty acid composition. Leaves of primary transformants containing both pOIL197 and pOIL104 T-DNA regions, sampled at vegetative stage of growth were observed with 4.1% and 5.9% TFA (Table 24). Surprisingly, the highest TFA levels detected in this population were accompanied by a relatively low TAG content. TAG levels in pOIL104+pOIL197 transgenic plants at vegetative and boot leaf stages reached only to 0.6% and 2.8%. Increased TAG levels were typically associated with a reduction in $C18:3^{\Delta9,12,15}$ and an increase in both palmitic acid and LA.

The TFA and TAG levels in many independent transformed plants are shown schematically in FIG. 19.

Expression levels of the WRI1 and DGAT1 genes in a number of plants were measured by a RT-PCR method. It was observed that plant TX-03-31 which had a relatively high TTQ had the highest level of expression of DGAT amongst the tested plants. It was concluded that high levels of DGAT expression were beneficial for increasing the TAG level and also the TTQ.

Perhaps the most surprising and unexpected conclusion drawn from the large amount of data in this Example was the relatively high level of TFA accompanied by the low levels of TAG, except in a few exceptional plants such as plant TX-03-31 (Table 22). That is, although substantially much increased fatty acid synthesis was occurring, much of the increased fatty acid was not appearing as TAG. This conclusion was completely the opposite of what had been observed with the WRI1+DGAT transgenic plants for *Nicotiana* including tobacco. To quantitate this in the sorghum plants, the quotient of the TAG to TFA level was calculated for all of the above mentioned transgenic sorghum populations (Tables 11-24). The TAG/TFA Quotient (TTQ) parameter was calculated as the level of TAG (%) divided by the level of TFA (%), each as a percentage of the dry weight of the plant material (leaf in this case). It was observed that for many of the sorghum lines, the TTQ was in the range of 0.01 to 0.6. Addition of one or more further genetic modifications to the plants which provide for a reduction in the level of SDP1, TGD or TST, or an increase in the levels of one or more of PDAT, PDCT or CPT polypeptides increases the TTQ to above 0.6 for a larger proportion of the plant lines. In particular, reduction in TAG lipase in the plants increases the TTQ to up to 0.95.

Due to the large difference in absolute TFA and TAG levels in many transgenic lines, the inventors selected two pOIL102+pOIL197 events for quantification of the major neutral and polar lipid classes, to determine the type of lipid in which the high level of fatty acids was present. The types of lipid were separated by TLC and quantitated. At the vegetative stage of growth, TX-02-8 and TX-02-19 contained 4.5% and 7.2% TFA, respectively (Table 18). TAG content was only slightly increased in the TX-02-8 leaves while the levels of phosphatidylcholine (PC, a phospholipid) and the galactolipid MGDG were comparable to the negative controls. TX-02-19 exhibited increased TAG, PC and MGDG levels, indicating an increase in both neutral and polar lipid classes.

A more detailed lipid analysis was performed on the TX-03-8 plant (boot leaf stage) and TX-03-28 (vegetative stage) (FIG. 13). A wildtype (flowering) and empty vector transformant (vegetative stage) served as controls for comparison. Despite differences in plant age at the time of sampling, leaves of both transgenic plants contained increased levels of TFA and total polar lipids. TX-03-28 contained up to 3.4% TAG at vegetative stage while TAG levels in TX-03-8 were only slightly increased at boot leaf stage. Both transgenic lines exhibited surprisingly large increases in the amounts of the galactolipids MGDG and DGDG. Increases in different polar lipid classes, the phospholipids PC, PG, PE, PA, PS, PI, were less pronounced but still significant (FIG. 13B). Further investigation by LC-MS revealed increased levels of C18:0, C18:2$^{\Delta9,12}$ and C18:3$^{\Delta9,12,15}$ in the free fatty acid fraction of both transgenic lines, suggesting a flux through PC via acyl editing prior to lipolysis. DAG molecular species in transgenic leaf tissues that were increased included 34:2 (likely C16:0/C18:2$^{\Delta9,12}$), 34:3 (likely C16:0/C18:3$^{\Delta9,12,15}$), 36:4 (likely C18:2$^{\Delta9,12}$/C18:2$^{\Delta9,12}$ and C18:1$^{\Delta9}$/C18:3$^{\Delta9,12,15}$) and 36:5 (likely C18:2$^{\Delta9,12}$/C18:3$^{\Delta9,2,15}$) The enrichment of poly-unsaturated fatty acids in the DAG fraction matched with the TAG composition and suggested PC-derived DAG as the precursor to TAG synthesis. Similar changes in PC and PE molecular species were observed in both transgenic plants while PI species mainly had C16:0 and C18 fatty acids. PG molecular species were highly enriched in C16:0, reflecting their plastidial synthesis via the prokaryotic pathway. Galactolipids in both transgenic lines were mainly derived from the eukaryotic lipid pathway i.e. enriched in C18 fatty acids. The major MGDG molecular species was 36:6 (likely C18:3$^{\Delta9,12,15}$/C18:3$^{\Delta9,12,15}$), serving as a substrate for DGDG 36:6 synthesis. A second major DGDG species in both transgenic lines, 34:3 (likely C16:0/C18:3$^{\Delta9,12,15}$), was also likely from extra-plastidial origin. TAG molecular species consisting of C16/C16/C18 (48:X), C16/C16/C18 (50:X) and C16/C18/C18 (52:x) were increased in transgenic leaf tissues. Interestingly, 54:8 (likely C18:2$^{\Delta9,12}$/C18:3$^{\Delta9,12,15}$/C18:3$^{\Delta9,12,15}$) and 54:9 (likely C18:3$^{\Delta9,12,15}$/C18:3$^{\Delta9,12,15}$/C18:3$^{\Delta9,12,15}$) were reduced compared to the negative controls. Taken together, these results suggest increased flux of acyl chains into TAG via PC in the transgenic lines whilst galactolipid biosynthesis mainly occurred via the eukaryotic pathway. These data also led the inventors to understand that reduction of TGD activity or increases in PDCT and/or CPT in the plants in addition to the present transgenes would likely enhance the TFA and TAG levels.

The chimeric DNA constructs for Agrobacterium-mediated transformation are used to transform Zea mays (corn) as described by Gould et al. (1991). Briefly, shoot apex explants are co-cultivated with transgenic Agrobacterium for two days before being transferred onto a MS salt media containing kanamycin and carbenicillin. After several rounds of sub-culture, transformed shoots and roots spontaneously form and are transplanted to soil. The constructs are similarly used to transform Hordeum vulgare (barley) and Avena sativa (oats) using transformation methods known for these species. Briefly, for barley, the Agrobacterium cultures are used to transform cells in immature embryos of barley (cv. Golden Promise) according to published methods (Tingay et al., 1997; Bartlett et al., 2008) with some modifications in that embryos between 1.5 and 2.5 mm in length are isolated from immature caryopses and the embryonic axes removed. The resulting explants are co-cultivated for 2-3 days with the transgenic Agrobacterium and then cultured in the dark for 4-6 weeks on media containing timentin and hygromycin to generate embryogenic callus before being moved to transition media in low light conditions for two weeks. Calli are then transferred to regeneration media to allow for the regeneration of shoots and roots before transfer of the regenerated plantlets to soil. Transformed plants are obtained and grown to maturity in the glasshouse.

TABLE 11

TFA and TAG levels, fatty acid composition and TTQ in wild-type (WT) and empty vector (EV) negative controls during different stages of plant development.

| Stage | Line | TAG or TFA | C16:0 | C18:0 | C18:1 | C18:2 | C18:3 | Other | TFA | TAG | TTQ |
|---|---|---|---|---|---|---|---|---|---|---|---|
| Veg | WT1 | TFA | 9.9 | 1.2 | 0.7 | 8.8 | 75.4 | 4.0 | 1.7 | | |
| Veg | WT1 | TAG | 22.5 | 3.6 | 3.0 | 31.8 | 37.4 | 1.6 | | 0.0 | 0.027 |
| Veg | WT2 | TFA | 12.0 | 1.7 | 0.7 | 8.5 | 73.0 | 4.2 | 2.2 | | |
| Veg | WT2 | TAG | 12.1 | 3.2 | 2.1 | 29.0 | 52.3 | 1.4 | | 0.1 | 0.028 |
| Veg | WT3 | TFA | 15.3 | 1.5 | 0.7 | 10.0 | 69.8 | 2.7 | 2.7 | | |
| Veg | WT3 | TAG | 17.4 | 6.5 | 2.6 | 27.2 | 38.0 | 8.3 | | 0.0 | 0.000 |
| Veg | WT6 | TFA | 12.2 | 1.8 | 0.5 | 7.7 | 72.8 | 5.1 | 3.3 | | |
| Veg | WT6 | TAG | 18.8 | 6.8 | 3.7 | 17.4 | 44.7 | 8.5 | | 0.1 | 0.017 |
| Veg | EV1 | TFA | 13.0 | 2.1 | 0.9 | 9.6 | 70.6 | 3.8 | 2.0 | | |
| Veg | EV1 | TAG | 6.5 | 2.8 | 1.6 | 19.2 | 51.4 | 18.5 | | 0.2 | 0.090 |
| Veg | EV3 | TFA | 12.1 | 1.9 | 0.9 | 9.4 | 72.7 | 3.0 | 2.1 | | |
| Veg | EV3 | TAG | 9.7 | 3.8 | 2.3 | 25.1 | 57.6 | 1.6 | | 0.1 | 0.056 |
| BL | EV1 | TFA | 17.6 | 1.9 | 1.5 | 14.7 | 59.0 | 5.4 | 1.5 | | |
| BL | EV1 | TAG | 17.5 | 6.5 | 3.7 | 30.7 | 35.6 | 5.9 | | 0.0 | 0.031 |
| BL | WT3 | TFA | 14.4 | 3.9 | 2.4 | 11.1 | 62.6 | 5.6 | 1.1 | | |
| BL | WT3 | TAG | 9.4 | 4.8 | 4.0 | 19.1 | 61.2 | 1.6 | | 0.2 | 0.153 |
| MSS | WT3 | TFA | 14.2 | 3.9 | 2.2 | 10.2 | 63.6 | 5.9 | 1.2 | | |
| MSS | WT3 | TAG | 15.3 | 12.5 | 3.9 | 18.2 | 43.9 | 6.2 | | 0.1 | 0.067 |
| MSS | EV3 | TFA | 16.5 | 5.0 | 1.6 | 12.7 | 50.6 | 13.6 | 0.7 | | |
| MSS | EV3 | TAG | 13.4 | 11.4 | 2.6 | 19.6 | 50.0 | 3.0 | | 0.1 | 0.192 |

Veg: Vegetative;
BL, Boot leaf stage of growth;
MSS, Mature seed setting stage

TABLE 12

TFA and TAG levels, fatty acid composition and TTQ in sorghum
leaves transformed with pOIL197 or pOIL136 (pZmUbi:DGAT; pZmUbi:Oleosin)
during the vegetative stage of growth. The lines are listed in order of increasing TFA levels.

| Line | TAG or TFA | C16:0 | C18:0 | C18:1 | C18:2 | C18:3n3 | Other | TFA | TAG | TTQ |
|---|---|---|---|---|---|---|---|---|---|---|
| TX-197-18 | TFA | 16.3 | 3.7 | 1.7 | 13.3 | 59.7 | 5.3 | 0.7 | | |
| TX-197-18 | TAG | 13.9 | 5.0 | 2.7 | 22.2 | 53.0 | 3.3 | | 0.1 | 0.188 |
| TX-197-12 | TFA | 15.4 | 2.5 | 1.6 | 13.8 | 56.7 | 10.0 | 1.0 | | |
| TX-197-12 | TAG | 12.6 | 4.0 | 3.5 | 28.6 | 47.8 | 3.4 | | 0.1 | 0.106 |
| TX-197-04 | TFA | 12.8 | 3.7 | 1.5 | 9.2 | 65.4 | 7.4 | 1.2 | | |
| TX-197-04 | TAG | 8.0 | 5.0 | 3.1 | 16.6 | 65.3 | 2.1 | | 0.2 | 0.169 |
| TX-136-03 | TFA | 13.9 | 2.2 | 2.0 | 11.7 | 65.5 | 4.8 | 1.2 | | |
| TX-136-03 | TAG | 12.1 | 3.8 | 4.2 | 27.8 | 50.5 | 1.6 | | 0.1 | 0.064 |
| TX-197-06 | TFA | 13.8 | 2.7 | 1.7 | 10.9 | 63.3 | 7.5 | 1.2 | | |
| TX-197-06 | TAG | 9.8 | 4.0 | 3.5 | 22.6 | 56.6 | 3.4 | | 0.1 | 0.107 |
| TX-197-20 | TFA | 15.3 | 2.6 | 1.5 | 12.1 | 61.4 | 7.2 | 1.2 | | |
| TX-197-20 | TAG | 13.5 | 4.2 | 3.3 | 25.5 | 50.3 | 3.1 | | 0.1 | 0.085 |
| TX-136-24 | TFA | 12.2 | 2.0 | 1.6 | 10.9 | 69.0 | 4.3 | 1.5 | | |
| TX-136-24 | TAG | 11.7 | 3.3 | 3.0 | 23.3 | 55.9 | 2.8 | | 0.4 | 0.243 |
| TX-197-16 | TFA | 14.4 | 2.2 | 1.7 | 13.5 | 61.1 | 7.2 | 1.9 | | |
| TX-197-16 | TAG | 14.8 | 3.5 | 3.2 | 25.3 | 47.9 | 5.3 | | 0.4 | 0.235 |
| TX-197-05 | TFA | 12.2 | 2.3 | 1.3 | 9.9 | 68.2 | 6.1 | 2.0 | | |
| TX-197-05 | TAG | 10.4 | 4.3 | 2.9 | 21.0 | 58.7 | 2.7 | | 0.1 | 0.070 |
| TX-197-17 | TFA | 14.0 | 2.2 | 2.4 | 19.5 | 55.4 | 6.5 | 2.1 | | |
| TX-197-17 | TAG | 13.7 | 3.3 | 4.4 | 33.8 | 40.4 | 4.4 | | 0.6 | 0.264 |
| TX-197-22 | TFA | 11.9 | 1.7 | 0.9 | 8.5 | 71.6 | 5.4 | 2.1 | | |
| TX-197-22 | TAG | 11.5 | 4.3 | 2.4 | 23.9 | 55.2 | 2.8 | | 0.1 | 0.041 |
| TX-197-21 | TFA | 10.8 | 1.6 | 0.9 | 7.9 | 73.3 | 5.5 | 2.4 | | |
| TX-197-21 | TAG | 9.9 | 3.8 | 2.6 | 24.2 | 57.0 | 2.5 | | 0.1 | 0.045 |
| TX-197-10 | TFA | 10.5 | 1.5 | 0.8 | 9.3 | 72.8 | 5.2 | 2.7 | | |
| TX-197-10 | TAG | 9.0 | 2.8 | 2.4 | 26.6 | 55.6 | 3.7 | | 0.2 | 0.078 |
| TX-197-50 | TFA | 12.9 | 1.8 | 1.0 | 10.8 | 68.1 | 5.3 | 2.8 | | |
| TX-197-50 | TAG | 14.7 | 4.4 | 2.5 | 23.1 | 48.8 | 6.6 | | 0.3 | 0.107 |
| TX-197-07 | TFA | 10.5 | 1.4 | 0.8 | 10.1 | 71.8 | 5.4 | 2.8 | | |
| TX-197-07 | TAG | 9.6 | 2.9 | 2.5 | 31.3 | 49.6 | 4.1 | | 0.2 | 0.067 |
| TX-197-48 | TFA | 13.2 | 1.8 | 1.2 | 11.4 | 67.0 | 5.4 | 2.8 | | |
| TX-197-48 | TAG | 10.1 | 3.1 | 2.5 | 25.5 | 53.1 | 5.6 | | 0.3 | 0.104 |
| TX-197-08 | TFA | 11.4 | 1.1 | 1.4 | 12.4 | 68.1 | 5.6 | 2.9 | | |
| TX-197-08 | TAG | 15.9 | 3.7 | 6.1 | 45.2 | 23.2 | 5.8 | | 0.1 | 0.027 |
| TX-197-13 | TFA | 10.8 | 1.6 | 0.7 | 8.0 | 73.5 | 5.4 | 2.9 | | |
| TX-197-13 | TAG | 10.5 | 3.6 | 2.2 | 24.1 | 51.2 | 8.4 | | 0.1 | 0.037 |
| TX-197-15 | TFA | 10.5 | 1.3 | 0.7 | 8.9 | 73.0 | 5.6 | 2.9 | | |
| TX-197-15 | TAG | 9.6 | 2.8 | 2.2 | 26.9 | 55.3 | 3.3 | | 0.2 | 0.067 |
| TX-136-02 | TFA | 12.5 | 1.5 | 1.3 | 14.3 | 66.1 | 4.3 | 2.9 | | |
| TX-136-02 | TAG | 14.0 | 2.6 | 2.7 | 27.3 | 48.4 | 5.0 | | 0.7 | 0.245 |
| TX-197-19 | TFA | 10.9 | 1.4 | 0.8 | 9.1 | 73.0 | 4.8 | 3.1 | | |
| TX-197-19 | TAG | 11.1 | 3.0 | 2.3 | 27.3 | 52.6 | 3.6 | | 0.2 | 0.063 |
| TX-197-40 | TFA | 9.9 | 1.1 | 0.5 | 8.2 | 77.4 | 3.0 | 3.1 | | |
| TX-197-40 | TAG | 15.4 | 6.3 | 2.3 | 27.1 | 46.7 | 2.2 | | 0.0 | 0.008 |
| TX-197-47 | TFA | 11.9 | 2.0 | 0.7 | 7.3 | 73.0 | 5.2 | 3.2 | | |
| TX-197-47 | TAG | 10.4 | 3.6 | 2.4 | 19.7 | 60.1 | 3.8 | | 0.1 | 0.028 |
| TX-197-49 | TFA | 12.0 | 1.7 | 2.1 | 16.0 | 63.1 | 5.1 | 3.2 | | |
| TX-197-49 | TAG | 13.5 | 3.8 | 6.6 | 36.9 | 31.9 | 7.3 | | 0.3 | 0.085 |
| TX-197-28 | TFA | 11.1 | 1.3 | 0.4 | 8.0 | 75.6 | 3.5 | 3.2 | | |
| TX-197-28 | TAG | 17.5 | 4.9 | 1.3 | 22.3 | 47.4 | 6.6 | | 0.1 | 0.024 |
| TX-197-14 | TFA | 9.8 | 1.2 | 0.8 | 10.2 | 72.8 | 5.2 | 3.3 | | |
| TX-197-14 | TAG | 9.4 | 2.7 | 3.5 | 39.4 | 39.5 | 5.5 | | 0.1 | 0.045 |
| TX-197-51 | TFA | 12.5 | 2.0 | 1.0 | 10.6 | 68.3 | 5.6 | 3.4 | | |
| TX-197-51 | TAG | 14.0 | 4.5 | 2.3 | 22.4 | 49.8 | 7.0 | | 0.4 | 0.122 |
| TX-136-01 | TFA | 12.5 | 1.5 | 1.3 | 13.3 | 69.1 | 2.3 | 3.4 | | |
| TX-136-01 | TAG | 15.0 | 3.1 | 2.8 | 27.8 | 44.9 | 6.4 | | 0.8 | 0.234 |
| TX-197-11 | TFA | 10.2 | 1.1 | 0.9 | 11.2 | 71.1 | 5.5 | 3.5 | | |
| TX-197-11 | TAG | 12.2 | 3.3 | 4.6 | 43.3 | 30.0 | 6.6 | | 0.1 | 0.034 |
| TX-197-33 | TFA | 10.9 | 1.4 | 0.4 | 8.0 | 75.7 | 3.6 | 3.5 | | |
| TX-197-33 | TAG | 14.0 | 4.7 | 1.6 | 20.4 | 53.0 | 6.3 | | 0.1 | 0.025 |
| TX-136-25 | TFA | 13.1 | 2.4 | 0.6 | 11.5 | 67.5 | 4.9 | 3.8 | | |
| TX-136-25 | TAG | 15.8 | 4.4 | 1.2 | 21.1 | 49.7 | 7.8 | | 0.8 | 0.202 |
| TX-197-09 | TFA | 10.5 | 1.3 | 0.7 | 9.4 | 73.0 | 5.1 | 3.8 | | |
| TX-197-09 | TAG | 11.5 | 3.5 | 2.4 | 30.4 | 48.4 | 3.9 | | 0.2 | 0.047 |
| TX-197-30 | TFA | 11.8 | 1.7 | 0.6 | 8.9 | 73.0 | 4.0 | 3.8 | | |
| TX-197-30 | TAG | 15.3 | 4.1 | 1.6 | 22.0 | 51.3 | 5.7 | | 0.2 | 0.051 |
| TX-197-23 | TFA | 10.5 | 1.4 | 1.4 | 14.1 | 67.5 | 5.1 | 4.3 | | |
| TX-197-23 | TAG | 13.1 | 3.0 | 3.7 | 36.3 | 38.7 | 5.3 | | 0.8 | 0.175 |
| TX-197-37 | TFA | 10.3 | 2.0 | 2.4 | 18.6 | 62.8 | 3.9 | 5.0 | | |
| TX-197-37 | TAG | 12.9 | 4.0 | 6.2 | 38.7 | 31.6 | 6.7 | | 1.2 | 0.230 |

TABLE 13

TFA and TAG levels, fatty acid composition and TTQ in sorghum leaves transformed with pOIL197 or pOIL136 (pZmUbi:DGAT; pZmUbi:Oleosin) during the boot leaf stage of growth. The lines are listed in order of increasing TFA levels.

| Line | TAG or TFA | C16:0 | C18:0 | C18:1 | C18:2 | C18:3n3 | Other | TFA | TAG | TTQ |
|---|---|---|---|---|---|---|---|---|---|---|
| TX-197-14 | TFA | 12.7 | 5.2 | 2.0 | 14.4 | 57.7 | 8.1 | 1.2 | | |
| TX-197-14 | TAG | 8.8 | 7.1 | 3.1 | 22.7 | 54.7 | 3.6 | | 0.3 | 0.266 |
| TX-197-15 | TFA | 14.5 | 5.0 | 2.3 | 14.7 | 55.8 | 7.7 | 1.2 | | |
| TX-197-15 | TAG | 12.7 | 7.1 | 3.2 | 21.0 | 51.7 | 4.3 | | 0.3 | 0.262 |
| TX-197-19 | TFA | 13.1 | 3.2 | 2.0 | 14.3 | 60.9 | 6.4 | 1.2 | | |
| TX-197-19 | TAG | 10.6 | 4.3 | 3.4 | 24.4 | 54.0 | 3.2 | | 0.2 | 0.203 |
| TX-136-03 | TFA | 14.1 | 1.8 | 1.7 | 12.6 | 65.0 | 4.8 | 1.2 | | |
| TX-136-03 | TAG | 14.5 | 4.3 | 4.5 | 32.9 | 42.2 | 1.6 | | 0.1 | 0.045 |
| TX-197-08 | TFA | 14.4 | 3.5 | 1.3 | 14.2 | 62.2 | 4.4 | 1.2 | | |
| TX-197-08 | TAG | 13.7 | 5.2 | 2.7 | 22.4 | 50.5 | 5.5 | | 0.3 | 0.211 |
| TX-197-11 | TFA | 14.1 | 3.8 | 2.0 | 15.0 | 57.0 | 8.2 | 1.3 | | |
| TX-197-11 | TAG | 10.3 | 4.8 | 3.0 | 22.8 | 55.9 | 3.1 | | 0.3 | 0.267 |
| TX-136-24 | TFA | 15.5 | 2.2 | 2.2 | 16.9 | 58.1 | 5.2 | 1.3 | | |
| TX-136-24 | TAG | 14.7 | 3.3 | 4.0 | 32.4 | 42.9 | 2.7 | | 0.2 | 0.164 |
| TX-136-02 | TFA | 12.3 | 1.5 | 1.4 | 14.7 | 65.7 | 4.4 | 1.5 | | |
| TX-136-02 | TAG | 13.9 | 2.7 | 3.0 | 28.7 | 46.6 | 5.1 | | 0.7 | 0.444 |
| TX-197-30 | TFA | 13.1 | 2.3 | 1.3 | 9.3 | 65.1 | 8.8 | 2.0 | | |
| TX-197-30 | TAG | 10.0 | 3.0 | 2.2 | 15.0 | 65.3 | 4.5 | | 0.4 | 0.223 |
| TX-197-46 | TFA | 13.2 | 2.5 | 0.8 | 7.9 | 71.2 | 4.5 | 2.0 | | |
| TX-197-46 | TAG | 17.3 | 18.6 | 3.2 | 14.7 | 42.5 | 3.7 | | 0.1 | 0.033 |
| TX-197-45 | TFA | 13.6 | 2.7 | 0.6 | 6.7 | 71.7 | 4.5 | 2.1 | | |
| TX-197-45 | TAG | 22.7 | 17.7 | 4.4 | 12.9 | 38.6 | 3.6 | | 0.1 | 0.030 |
| TX-197-39 | TFA | 12.6 | 3.6 | 1.1 | 9.0 | 66.2 | 7.4 | 2.1 | | |
| TX-197-39 | TAG | 9.5 | 4.0 | 1.6 | 12.8 | 66.7 | 5.5 | | 0.6 | 0.291 |
| TX-197-22 | TFA | 13.6 | 2.0 | 0.8 | 7.3 | 71.3 | 4.9 | 2.1 | | |
| TX-197-22 | TAG | 13.8 | 3.3 | 1.8 | 14.2 | 64.6 | 2.3 | | 0.1 | 0.056 |
| TX-197-34 | TFA | 12.0 | 3.2 | 1.2 | 9.6 | 67.9 | 5.9 | 2.2 | | |
| TX-197-34 | TAG | 9.1 | 4.6 | 2.3 | 18.4 | 63.2 | 2.3 | | 0.4 | 0.190 |
| TX-197-50 | TFA | 13.0 | 2.5 | 1.1 | 9.1 | 66.8 | 7.5 | 2.5 | | |
| TX-197-50 | TAG | 11.4 | 4.6 | 2.1 | 15.3 | 59.8 | 6.9 | | 0.5 | 0.183 |
| TX-197-43 | TFA | 12.4 | 2.3 | 0.7 | 8.0 | 71.9 | 4.7 | 2.5 | | |
| TX-197-43 | TAG | 11.0 | 4.4 | 1.8 | 15.7 | 62.3 | 4.8 | | 0.2 | 0.065 |
| TX-197-32 | TFA | 12.5 | 2.1 | 1.1 | 9.0 | 70.0 | 5.3 | 2.5 | | |
| TX-197-32 | TAG | 12.8 | 3.7 | 2.1 | 16.1 | 60.3 | 5.0 | | 0.6 | 0.220 |
| TX-197-33 | TFA | 12.1 | 2.7 | 0.7 | 7.9 | 71.0 | 5.6 | 2.5 | | |
| TX-197-33 | TAG | 11.1 | 4.8 | 1.4 | 15.4 | 62.4 | 4.9 | | 0.3 | 0.130 |
| TX-197-41 | TFA | 12.8 | 1.9 | 0.7 | 8.1 | 72.8 | 3.7 | 2.6 | | |
| TX-197-41 | TAG | 15.1 | 5.9 | 2.4 | 16.7 | 53.7 | 6.3 | | 0.2 | 0.065 |
| TX-197-36 | TFA | 12.2 | 2.0 | 0.8 | 7.7 | 71.6 | 5.6 | 2.6 | | |
| TX-197-36 | TAG | 11.4 | 3.4 | 1.6 | 13.9 | 65.6 | 4.1 | | 0.4 | 0.158 |
| TX-197-42 | TFA | 12.4 | 2.1 | 0.8 | 8.2 | 70.3 | 6.3 | 2.7 | | |
| TX-197-42 | TAG | 12.4 | 5.4 | 2.3 | 17.8 | 57.1 | 5.0 | | 0.2 | 0.060 |
| TX-197-51 | TFA | 13.6 | 2.1 | 1.0 | 9.9 | 66.8 | 6.6 | 2.7 | | |
| TX-197-51 | TAG | 13.1 | 4.6 | 3.0 | 18.8 | 53.4 | 7.0 | | 0.5 | 0.175 |
| TX-197-49 | TFA | 15.2 | 2.9 | 1.0 | 9.3 | 65.3 | 6.3 | 2.7 | | |
| TX-197-49 | TAG | 17.3 | 5.0 | 2.0 | 16.7 | 52.7 | 6.3 | | 0.5 | 0.192 |
| TX-197-48 | TFA | 13.0 | 2.3 | 1.0 | 8.8 | 68.5 | 6.4 | 2.8 | | |
| TX-197-48 | TAG | 13.0 | 4.7 | 2.2 | 16.1 | 58.0 | 6.0 | | 0.4 | 0.144 |
| TX-197-38 | TFA | 12.2 | 2.0 | 1.0 | 7.7 | 72.1 | 5.0 | 2.9 | | |
| TX-197-38 | TAG | 11.2 | 3.4 | 2.2 | 14.9 | 63.8 | 4.5 | | 0.5 | 0.160 |
| TX-197-35 | TFA | 12.8 | 1.8 | 0.9 | 8.5 | 69.4 | 6.6 | 2.9 | | |
| TX-197-35 | TAG | 12.7 | 2.9 | 1.7 | 14.5 | 63.3 | 4.9 | | 0.7 | 0.227 |
| TX-197-40 | TFA | 12.7 | 1.9 | 0.7 | 7.7 | 73.9 | 3.1 | 2.9 | | |
| TX-197-40 | TAG | 16.3 | 4.7 | 3.3 | 20.8 | 52.4 | 2.6 | | 0.1 | 0.031 |
| TX-197-47 | TFA | 13.9 | 2.4 | 0.6 | 6.9 | 72.2 | 3.9 | 2.9 | | |
| TX-197-47 | TAG | 24.6 | 19.8 | 5.2 | 10.7 | 34.8 | 4.9 | | 0.0 | 0.017 |
| TX-136-01 | TFA | 11.6 | 1.4 | 1.3 | 14.1 | 67.2 | 4.3 | 3.3 | | |
| TX-136-01 | TAG | 14.6 | 2.9 | 3.0 | 29.5 | 44.1 | 5.9 | | 0.7 | 0.199 |
| TX-197-44 | TFA | 13.5 | 2.1 | 1.4 | 14.7 | 63.1 | 5.1 | 3.4 | | |
| TX-197-44 | TAG | 14.4 | 4.3 | 3.1 | 25.0 | 45.0 | 8.2 | | 0.8 | 0.245 |
| TX-136-25 | TFA | 13.6 | 2.2 | 0.7 | 10.8 | 67.4 | 5.2 | 3.4 | | |
| TX-136-25 | TAG | 16.6 | 4.2 | 1.4 | 20.1 | 51.5 | 6.1 | | 1.0 | 0.286 |
| TX-197-28 | TFA | 11.5 | 1.3 | 0.4 | 7.8 | 75.3 | 3.6 | 3.4 | | |
| TX-197-28 | TAG | 17.4 | 4.5 | 1.6 | 19.5 | 50.2 | 6.9 | | 0.1 | 0.035 |
| TX-197-37 | TFA | 12.6 | 3.4 | 6.3 | 17.4 | 54.1 | 6.2 | 4.5 | | |
| TX-197-37 | TAG | 13.4 | 5.0 | 10.1 | 27.4 | 40.2 | 3.9 | | 1.9 | 0.426 |

TABLE 14

TFA and TAG levels, fatty acid composition and TTQ in sorghum leaves transformed with pOIL197 or pOIL136 (pZmUbi:DGAT; pZmUbi:Oleosin) during the mature seed setting stage of growth. The lines are listed in order of increasing TFA levels.

| Line | TAG or TFA | C16:0 | C18:0 | C18:1 | C18:2 | C18:3n3 | Other | TFA | TAG | TTQ |
|---|---|---|---|---|---|---|---|---|---|---|
| TX-197-13 | TFA | 15.2 | 6.6 | 2.6 | 12.0 | 44.7 | 18.8 | 1.0 | | |
| TX-197-13 | TAG | 10.2 | 7.0 | 2.7 | 20.4 | 55.6 | 4.1 | | 0.1 | 0.131 |
| TX-197-22 | TFA | 16.0 | 4.3 | 2.3 | 8.5 | 54.6 | 14.3 | 1.0 | | |
| TX-197-22 | TAG | 13.8 | 7.6 | 3.5 | 12.7 | 59.7 | 2.7 | | 0.2 | 0.153 |
| TX-197-19 | TFA | 13.6 | 5.3 | 1.1 | 12.4 | 56.4 | 11.2 | 1.1 | | |
| TX-197-19 | TAG | 10.8 | 8.3 | 1.6 | 18.6 | 55.2 | 5.5 | | 0.2 | 0.209 |
| TX-197-18 | TFA | 14.2 | 4.9 | 2.6 | 11.2 | 52.9 | 14.1 | 1.1 | | |
| TX-197-18 | TAG | 10.6 | 7.8 | 2.9 | 18.9 | 56.2 | 3.5 | | 0.2 | 0.148 |
| TX-136-24 | TFA | 15.1 | 4.6 | 1.5 | 12.7 | 57.6 | 8.5 | 1.2 | | |
| TX-136-24 | TAG | 11.3 | 5.2 | 2.1 | 18.9 | 56.5 | 6.1 | | 0.2 | 0.191 |
| TX-197-15 | TFA | 13.2 | 6.5 | 1.1 | 14.4 | 57.6 | 7.3 | 1.3 | | |
| TX-197-15 | TAG | 9.2 | 8.2 | 1.7 | 21.1 | 54.0 | 5.8 | | 0.3 | 0.239 |
| TX-197-10 | TFA | 12.8 | 7.6 | 1.6 | 15.2 | 50.0 | 12.8 | 1.3 | | |
| TX-197-10 | TAG | 8.9 | 7.7 | 1.9 | 22.6 | 53.9 | 5.0 | | 0.4 | 0.301 |
| TX-197-11 | TFA | 13.5 | 5.8 | 1.7 | 14.0 | 57.1 | 8.0 | 1.3 | | |
| TX-197-11 | TAG | 9.0 | 6.7 | 2.2 | 20.3 | 56.9 | 4.9 | | 0.3 | 0.242 |
| TX-197-33 | TFA | 14.8 | 4.9 | 1.8 | 12.6 | 54.9 | 10.9 | 1.3 | | |
| TX-197-33 | TAG | 12.3 | 6.2 | 2.6 | 21.3 | 51.3 | 6.3 | | 0.5 | 0.372 |
| TX-197-20 | TFA | 15.4 | 3.8 | 1.1 | 9.4 | 62.7 | 7.6 | 1.3 | | |
| TX-197-20 | TAG | 21.9 | 13.9 | 3.9 | 17.6 | 36.4 | 6.3 | | 0.1 | 0.043 |
| TX-197-21 | TFA | 14.8 | 3.6 | 1.3 | 13.0 | 61.0 | 6.3 | 1.4 | | |
| TX-197-21 | TAG | 24.9 | 14.9 | 4.5 | 22.7 | 27.3 | 5.7 | | 0.0 | 0.026 |
| TX-197-09 | TFA | 15.6 | 5.0 | 1.8 | 15.1 | 53.6 | 8.9 | 1.5 | | |
| TX-197-09 | TAG | 13.6 | 6.1 | 2.6 | 21.3 | 51.7 | 4.7 | | 0.4 | 0.277 |
| TX-197-38 | TFA | 13.9 | 4.2 | 1.4 | 12.0 | 59.7 | 8.7 | 1.6 | | |
| TX-197-38 | TAG | 12.3 | 6.4 | 2.7 | 21.6 | 49.7 | 7.4 | | 0.4 | 0.230 |
| TX-197-32 | TFA | 14.2 | 3.6 | 1.5 | 13.3 | 58.5 | 8.9 | 1.7 | | |
| TX-197-32 | TAG | 12.3 | 5.2 | 2.7 | 22.1 | 50.5 | 7.3 | | 0.5 | 0.279 |
| TX-197-17 | TFA | 14.4 | 3.5 | 1.5 | 12.4 | 57.0 | 11.3 | 2.0 | | |
| TX-197-17 | TAG | 14.0 | 4.9 | 1.5 | 17.0 | 52.1 | 10.4 | | 0.7 | 0.333 |
| TX-197-40 | TFA | 13.3 | 3.5 | 1.2 | 8.6 | 63.9 | 9.5 | 2.1 | | |
| TX-197-40 | TAG | 13.5 | 7.9 | 2.2 | 16.2 | 56.0 | 4.2 | | 0.1 | 0.042 |
| TX-197-16 | TFA | 13.9 | 4.7 | 1.2 | 13.8 | 54.1 | 12.3 | 2.1 | | |
| TX-197-16 | TAG | 10.9 | 5.9 | 1.7 | 18.6 | 51.8 | 11.1 | | 0.9 | 0.444 |

TABLE 15

TFA and TAG levels, fatty acid composition and TTQ in sorghum leaves transformed with pOIL102 (pZmUbi:WRI1) during the vegetative stage of growth.

| Line | TAG or TFA | C16:0 | C18:0 | C18:1 | C18:2 | C18:3n3 | Other | TFA | TAG | TTQ |
|---|---|---|---|---|---|---|---|---|---|---|
| TX-102-1 | TFA | 17.3 | 2.4 | 3.1 | 15.6 | 55.8 | 5.9 | 1.2 | | |
| TX-102-1 | TAG | 13.5 | 2.6 | 5.6 | 28.7 | 43.5 | 6.1 | | 0.2 | 0.182 |
| TX-102-6 | TFA | 12.4 | 1.4 | 1.1 | 9.6 | 71.7 | 3.8 | 2.0 | | |
| TX-102-6 | TAG | 21.2 | 13.4 | 4.6 | 27.3 | 32.3 | 1.3 | | 0.0 | 0.015 |
| TX-102-4 | TFA | 11.2 | 1.0 | 0.7 | 7.7 | 76.4 | 3.0 | 2.2 | | |
| TX-102-4 | TAG | 11.3 | 3.3 | 2.0 | 23.7 | 59.6 | 0.0 | | 0.0 | 0.019 |
| TX-102-8 | TFA | 10.2 | 1.2 | 0.5 | 7.2 | 77.9 | 3.0 | 2.3 | | |
| TX-102-8 | TAG | 11.6 | 3.4 | 0.0 | 23.2 | 61.8 | 0.0 | | 0.0 | 0.013 |
| TX-102-5 | TFA | 11.1 | 1.6 | 0.9 | 8.8 | 74.3 | 3.3 | 2.4 | | |
| TX-102-5 | TAG | 17.1 | 12.2 | 0.0 | 27.5 | 43.2 | 0.0 | | 0.0 | 0.015 |
| TX-102-2 | TFA | 11.4 | 1.5 | 1.0 | 9.4 | 73.5 | 3.2 | 2.4 | | |
| TX-102-2 | TAG | 13.7 | 2.9 | 3.6 | 31.2 | 48.6 | 0.0 | | 0.0 | 0.018 |
| TX-102-3 | TFA | 11.8 | 1.5 | 1.0 | 8.8 | 73.3 | 3.7 | 2.6 | | |
| TX-102-3 | TAG | 17.1 | 3.7 | 4.4 | 29.9 | 44.0 | 0.9 | | 0.0 | 0.016 |
| TX-102-7 | TFA | 12.1 | 1.4 | 1.0 | 9.3 | 72.4 | 3.8 | 2.6 | | |
| TX-102-7 | TAG | 20.9 | 15.0 | 4.8 | 26.4 | 31.6 | 1.3 | | 0.0 | 0.013 |

TABLE 16

TFA and TAG levels, fatty acid composition and TTQ in sorghum leaves transformed with pOIL102 (pZmUbi:WRI1) during the boot leaf stage of growth.

| Line | TAG or TFA | C16:0 | C18:0 | C18:1 | C18:2 | C18:3n3 | Other | TFA | TAG | TTQ |
|---|---|---|---|---|---|---|---|---|---|---|
| TX-102-8 | TFA | 16.9 | 4.2 | 2.3 | 12.3 | 57.7 | 6.5 | 0.9 | | |
| TX-102-8 | TAG | 14.5 | 6.2 | 13.5 | 25.7 | 36.8 | 3.4 | | 0.2 | 0.243 |
| TX-102-4 | TFA | 17.1 | 4.2 | 2.0 | 12.5 | 57.5 | 6.7 | 0.9 | | |
| TX-102-4 | TAG | 10.5 | 4.4 | 3.0 | 20.0 | 59.6 | 2.6 | | 0.2 | 0.182 |
| TX-102-1 | TFA | 16.6 | 4.3 | 3.9 | 15.4 | 50.7 | 9.1 | 1.1 | | |
| TX-102-1 | TAG | 10.7 | 4.4 | 5.3 | 21.9 | 54.1 | 3.6 | | 0.3 | 0.273 |
| TX-102-5 | TFA | 16.7 | 4.1 | 1.7 | 11.6 | 60.2 | 5.8 | 1.1 | | |
| TX-102-5 | TAG | 11.7 | 5.5 | 2.8 | 21.4 | 56.1 | 2.5 | | 0.1 | 0.118 |
| TX-102-6 | TFA | 17.8 | 3.8 | 15.9 | 17.0 | 38.8 | 6.6 | 1.5 | | |
| TX-102-6 | TAG | 19.6 | 7.0 | 29.4 | 25.4 | 13.9 | 4.7 | | 0.4 | 0.267 |
| TX-102-2 | TFA | 15.0 | 1.9 | 1.7 | 19.1 | 56.5 | 5.9 | 1.7 | | |
| TX-102-2 | TAG | 10.6 | 1.9 | 2.7 | 30.2 | 51.2 | 3.4 | | 0.4 | 0.258 |
| TX-102-7 | TFA | 15.0 | 3.1 | 7.0 | 13.9 | 56.1 | 4.9 | 2.4 | | |
| TX-102-7 | TAG | 16.1 | 6.5 | 20.5 | 28.0 | 24.4 | 4.5 | | 0.3 | 0.111 |
| TX-102-3 | TFA | 14.4 | 3.5 | 9.5 | 13.4 | 50.9 | 8.2 | 2.5 | | |
| TX-102-3 | TAG | 16.9 | 6.7 | 23.9 | 24.7 | 22.5 | 5.2 | | 0.4 | 0.150 |

TABLE 17

TFA and TAG levels, fatty acid composition and TTQ in sorghum leaves transformed with pOIL102 (pZmUbi:WRI1) during the mature seed setting stage of growth.

| Line | TAG or TFA | C16:0 | C18:0 | C18:1 | C18:2 | C18:3n3 | Other | TFA | TAG | TTQ |
|---|---|---|---|---|---|---|---|---|---|---|
| TX-102-5 | TFA | 17.0 | 5.2 | 1.8 | 11.2 | 53.2 | 11.5 | 1.0 | | |
| TX-102-5 | TAG | 15.7 | 7.6 | 3.5 | 19.8 | 49.7 | 3.8 | | 0.1 | 0.090 |
| TX-102-8 | TFA | 17.1 | 5.0 | 2.6 | 12.5 | 50.0 | 12.8 | 1.0 | | |
| TX-102-8 | TAG | 18.0 | 9.4 | 4.6 | 21.5 | 41.5 | 4.9 | | 0.1 | 0.096 |
| TX-102-1 | TFA | 17.2 | 5.2 | 2.6 | 17.7 | 45.5 | 11.9 | 1.0 | | |
| TX-102-1 | TAG | 13.3 | 6.8 | 4.0 | 26.5 | 43.8 | 5.6 | | 0.2 | 0.203 |
| TX-102-9 | TFA | 15.9 | 5.1 | 1.6 | 12.9 | 53.8 | 10.8 | 1.1 | | |
| TX-102-9 | TAG | 14.0 | 7.2 | 3.2 | 24.1 | 48.3 | 3.2 | | 0.1 | 0.089 |
| TX-102-4 | TFA | 17.4 | 5.3 | 3.1 | 12.0 | 48.4 | 13.7 | 1.1 | | |
| TX-102-4 | TAG | 15.4 | 6.2 | 4.1 | 22.0 | 48.1 | 4.2 | | 0.1 | 0.092 |
| TX-102-6 | TFA | 18.2 | 4.7 | 6.3 | 18.6 | 40.9 | 11.3 | 1.5 | | |
| TX-102-6 | TAG | 18.4 | 7.6 | 14.5 | 31.7 | 21.0 | 6.8 | | 0.2 | 0.147 |
| TX-102-2 | TFA | 14.4 | 6.8 | 29.7 | 18.8 | 18.8 | 11.4 | 2.0 | | |
| TX-102-2 | TAG | 12.3 | 9.1 | 40.3 | 21.8 | 7.4 | 9.0 | | 0.9 | 0.456 |

TABLE 18

TFA and TAG levels, fatty acid composition and TTQ in sorghum leaves transformed with pOIL102 (pZmUbi:WRI1) and pOIL197 (pZmUbi:DGAT and pZmUbi:Oleosin) during the vegetative stage of growth. The lines are listed in order of increasing TFA levels.

| Line | TAG or TFA | C16:0 | C18:0 | C18:1 | C18:2 | C18:3n3 | Other | TFA | TAG | TTQ |
|---|---|---|---|---|---|---|---|---|---|---|
| TX-02-28 | TFA | 12.0 | 2.4 | 0.6 | 9.5 | 71.2 | 4.4 | 2.2 | | |
| TX-02-28 | TAG | 11.6 | 5.0 | 1.4 | 16.1 | 61.1 | 4.8 | | 0.2 | 0.081 |
| TX-02-18 | TFA | 12.9 | 2.3 | 0.8 | 10.0 | 69.6 | 4.4 | 2.2 | | |
| TX-02-18 | TAG | 11.1 | 4.9 | 1.9 | 21.7 | 58.2 | 2.2 | | 0.1 | 0.059 |
| TX-02-37 | TFA | 8.7 | 1.2 | 0.4 | 7.0 | 79.1 | 3.7 | 2.3 | | |
| TX-02-37 | TAG | 18.3 | 6.5 | 0.0 | 24.0 | 45.7 | 5.5 | | 0.0 | 0.013 |
| TX-02-29 | TFA | 12.0 | 2.6 | 0.5 | 7.5 | 72.3 | 5.1 | 2.4 | | |
| TX-02-29 | TAG | 10.0 | 3.8 | 1.3 | 14.5 | 66.1 | 4.3 | | 0.1 | 0.041 |
| TX-02-126 | TFA | 13.2 | 1.5 | 0.6 | 10.0 | 70.5 | 4.1 | 2.6 | | |
| TX-02-126 | TAG | 17.4 | 3.3 | 1.6 | 22.3 | 49.8 | 5.6 | | 0.2 | 0.085 |
| TX-02-23 | TFA | 11.0 | 2.9 | 0.4 | 5.9 | 73.1 | 6.8 | 2.6 | | |
| TX-02-23 | TAG | 11.1 | 3.9 | 1.6 | 12.9 | 66.7 | 3.9 | | 0.1 | 0.048 |
| TX-02-38 | TFA | 19.6 | 2.0 | 3.1 | 20.5 | 47.8 | 6.9 | 2.7 | | |
| TX-02-38 | TAG | 28.4 | 3.4 | 5.8 | 31.7 | 21.5 | 9.3 | | 2.2 | 0.832 |
| TX-02-24 | TFA | 10.9 | 2.5 | 0.4 | 6.3 | 74.5 | 5.3 | 2.8 | | |
| TX-02-24 | TAG | 16.1 | 5.2 | 2.4 | 11.6 | 58.3 | 6.4 | | 0.1 | 0.033 |

TABLE 18-continued

TFA and TAG levels, fatty acid composition and TTQ in sorghum leaves transformed with pOIL102 (pZmUbi:WRI1) and pOIL197 (pZmUbi:DGAT and pZmUbi:Oleosin) during the vegetative stage of growth. The lines are listed in order of increasing TFA levels.

| Line | TAG or TFA | C16:0 | C18:0 | C18:1 | C18:2 | C18:3n3 | Other | TFA | TAG | TTQ |
|---|---|---|---|---|---|---|---|---|---|---|
| TX-02-25 | TFA | 10.9 | 2.1 | 0.6 | 8.9 | 72.2 | 5.3 | 2.9 | | |
| TX-02-25 | TAG | 9.5 | 4.3 | 1.5 | 15.7 | 61.7 | 7.3 | | 0.3 | 0.099 |
| TX-02-31 | TFA | 9.3 | 1.2 | 0.6 | 8.7 | 76.4 | 3.7 | 3.1 | | |
| TX-02-31 | TAG | 24.5 | 7.2 | 4.5 | 33.7 | 30.2 | 0.0 | | 0.0 | 0.007 |
| TX-02-129 | TFA | 11.3 | 1.4 | 0.6 | 9.0 | 74.0 | 3.8 | 3.2 | | |
| TX-02-129 | TAG | 18.7 | 5.0 | 2.2 | 28.1 | 38.7 | 7.2 | | 0.1 | 0.026 |
| TX-02-34 | TFA | 10.1 | 1.3 | 0.8 | 10.2 | 73.4 | 4.2 | 3.3 | | |
| TX-02-34 | TAG | 14.0 | 3.4 | 2.5 | 28.2 | 46.3 | 5.6 | | 0.3 | 0.098 |
| TX-02-127 | TFA | 11.3 | 1.6 | 0.4 | 6.6 | 77.3 | 2.7 | 3.4 | | |
| TX-02-127 | TAG | 14.6 | 5.6 | 1.9 | 16.6 | 52.9 | 8.5 | | 0.0 | 0.012 |
| TX-02-09 | TFA | 11.9 | 2.1 | 0.6 | 8.7 | 73.5 | 3.3 | 3.5 | | |
| TX-02-09 | TAG | 12.4 | 5.0 | 1.8 | 21.9 | 56.0 | 3.0 | | 0.1 | 0.024 |
| TX-02-131 | TFA | 11.0 | 1.4 | 0.3 | 8.1 | 75.9 | 3.2 | 3.5 | | |
| TX-02-131 | TAG | 16.9 | 4.9 | 1.1 | 21.3 | 48.8 | 6.9 | | 0.1 | 0.023 |
| TX-02-33 | TFA | 8.6 | 1.1 | 0.5 | 8.4 | 78.1 | 3.4 | 3.5 | | |
| TX-02-33 | TAG | 19.9 | 5.9 | 3.0 | 28.7 | 34.9 | 7.5 | | 0.0 | 0.010 |
| TX-02-36 | TFA | 9.5 | 1.3 | 0.8 | 11.0 | 73.5 | 4.0 | 3.6 | | |
| TX-02-36 | TAG | 13.7 | 3.8 | 2.6 | 33.7 | 41.7 | 4.6 | | 0.3 | 0.071 |
| TX-02-35 | TFA | 9.2 | 1.3 | 0.4 | 6.8 | 77.9 | 4.3 | 3.6 | | |
| TX-02-35 | TAG | 21.6 | 7.7 | 2.0 | 20.5 | 39.3 | 9.0 | | 0.0 | 0.012 |
| TX-02-10 | TFA | 12.3 | 2.0 | 3.4 | 20.8 | 56.6 | 4.7 | 4.0 | | |
| TX-02-10 | TAG | 18.5 | 4.0 | 7.8 | 38.5 | 23.6 | 7.5 | | 1.0 | 0.250 |
| TX-02-30 | TFA | 14.9 | 3.8 | 1.9 | 14.3 | 59.0 | 6.1 | 4.1 | | |
| TX-02-30 | TAG | 18.6 | 7.6 | 4.1 | 24.8 | 33.7 | 11.2 | | 0.9 | 0.223 |
| TX-02-12 | TFA | 13.7 | 1.6 | 0.8 | 10.1 | 69.0 | 4.7 | 4.5 | | |
| TX-02-12 | TAG | 10.5 | 4.2 | 1.7 | 26.2 | 55.5 | 1.9 | | 0.1 | 0.024 |
| TX-02-08 | TFA | 16.6 | 2.2 | 1.9 | 11.0 | 63.9 | 4.5 | 4.5 | | |
| TX-02-08 | TAG | 22.6 | 5.6 | 6.4 | 24.2 | 34.2 | 7.0 | | 0.2 | 0.039 |
| TX-02-27 | TFA | 10.9 | 1.2 | 0.5 | 8.9 | 75.8 | 2.7 | 4.6 | | |
| TX-02-27 | TAG | 19.0 | 6.0 | 2.7 | 27.8 | 39.2 | 5.3 | | 0.0 | 0.011 |
| TX-02-13 | TFA | 14.6 | 1.5 | 1.1 | 12.9 | 65.4 | 4.4 | 4.6 | | |
| TX-02-13 | TAG | 11.9 | 5.1 | 3.8 | 34.0 | 39.5 | 5.7 | | 0.3 | 0.062 |
| TX-02-05 | TFA | 14.3 | 1.4 | 0.9 | 12.1 | 66.6 | 4.7 | 5.2 | | |
| TX-02-05 | TAG | 10.4 | 3.0 | 4.0 | 42.7 | 35.8 | 4.1 | | 0.2 | 0.031 |
| TX-02-21 | TFA | 13.8 | 1.0 | 0.6 | 10.9 | 67.9 | 5.7 | 5.3 | | |
| TX-02-21 | TAG | 9.0 | 3.2 | 1.2 | 23.1 | 59.3 | 4.2 | | 0.6 | 0.121 |
| TX-02-07 | TFA | 15.6 | 1.7 | 0.6 | 8.6 | 68.9 | 4.6 | 5.5 | | |
| TX-02-07 | TAG | 21.8 | 6.4 | 3.6 | 24.6 | 34.8 | 8.8 | | 0.1 | 0.019 |
| TX-02-11 | TFA | 21.0 | 1.9 | 0.6 | 8.9 | 62.3 | 5.2 | 5.6 | | |
| TX-02-11 | TAG | 28.4 | 10.5 | 3.8 | 22.8 | 27.1 | 7.4 | | 0.2 | 0.027 |
| TX-02-14 | TFA | 15.4 | 2.4 | 1.8 | 11.5 | 64.6 | 4.2 | 5.7 | | |
| TX-02-14 | TAG | 17.0 | 6.0 | 6.1 | 32.1 | 32.6 | 6.1 | | 0.2 | 0.029 |
| TX-02-16 | TFA | 19.8 | 1.6 | 4.2 | 25.8 | 43.5 | 5.0 | 5.7 | | |
| TX-02-16 | TAG | 25.7 | 2.5 | 7.5 | 38.8 | 18.6 | 6.9 | | 2.7 | 0.481 |
| TX-02-01 | TFA | 13.9 | 1.4 | 0.6 | 10.5 | 69.1 | 4.6 | 5.8 | | |
| TX-02-01 | TAG | 9.4 | 3.3 | 2.4 | 29.9 | 51.9 | 3.1 | | 0.1 | 0.012 |
| TX-02-02 | TFA | 15.2 | 1.8 | 0.8 | 10.5 | 67.3 | 4.4 | 5.8 | | |
| TX-02-02 | TAG | 12.7 | 3.7 | 3.3 | 35.6 | 39.1 | 5.6 | | 0.2 | 0.036 |
| TX-02-06 | TFA | 17.7 | 1.5 | 0.7 | 9.4 | 66.3 | 4.2 | 6.1 | | |
| TX-02-06 | TAG | 25.6 | 3.9 | 3.0 | 23.9 | 35.2 | 8.4 | | 0.2 | 0.033 |
| TX-02-04 | TFA | 12.8 | 1.3 | 1.0 | 11.8 | 68.7 | 4.5 | 6.3 | | |
| TX-02-04 | TAG | 17.9 | 4.0 | 3.7 | 32.7 | 35.9 | 5.8 | | 0.1 | 0.013 |
| TX-02-19 | TFA | 11.9 | 1.8 | 1.5 | 15.6 | 64.5 | 4.7 | 7.2 | | |
| TX-02-19 | TAG | 10.9 | 3.9 | 5.2 | 41.9 | 30.6 | 7.5 | | 0.7 | 0.097 |

TABLE 19

TFA and TAG levels, fatty acid composition and TTQ in sorghum leaves transformed with pOIL102 (pZmUbi:WRI1) and pOIL197 (pZmUbi:DGAT and pZmUbi:Oleosin) during the boot leaf stage of growth. The lines are listed in order of increasing TFA levels.

| Line | TAG or TFA | C16:0 | C18:0 | C18:1 | C18:2 | C18:3n3 | Other | TFA | TAG | TTQ |
|---|---|---|---|---|---|---|---|---|---|---|
| TX-02-27 | TFA | 17.3 | 3.8 | 1.4 | 10.1 | 60.1 | 7.2 | 1.0 | | |
| TX-02-27 | TAG | 11.9 | 4.4 | 2.1 | 19.4 | 61.2 | 0.8 | | 0.2 | 0.164 |
| TX-02-21 | TFA | 15.9 | 2.3 | 2.0 | 19.3 | 53.3 | 7.3 | 1.2 | | |
| TX-02-21 | TAG | 12.6 | 3.7 | 2.7 | 27.0 | 51.0 | 3.0 | | 0.4 | 0.318 |

TABLE 19-continued

TFA and TAG levels, fatty acid composition and TTQ in sorghum leaves transformed with pOIL102 (pZmUbi:WRI1) and pOIL197 (pZmUbi:DGAT and pZmUbi:Oleosin) during the boot leaf stage of growth. The lines are listed in order of increasing TFA levels.

| Line | TAG or TFA | C16:0 | C18:0 | C18:1 | C18:2 | C18:3n3 | Other | TFA | TAG | TTQ |
|---|---|---|---|---|---|---|---|---|---|---|
| TX-02-01 | TFA | 15.2 | 4.2 | 5.1 | 14.7 | 53.2 | 7.5 | 1.3 | | |
| TX-02-01 | TAG | 11.7 | 5.6 | 9.3 | 26.1 | 42.9 | 4.5 | | 0.3 | 0.199 |
| TX-02-12 | TFA | 15.3 | 3.2 | 2.0 | 13.6 | 58.9 | 6.9 | 1.3 | | |
| TX-02-12 | TAG | 13.7 | 4.2 | 3.6 | 25.1 | 50.4 | 2.9 | | 0.1 | 0.111 |
| TX-02-33 | TFA | 15.9 | 4.3 | 1.0 | 10.1 | 59.7 | 9.1 | 1.4 | | |
| TX-02-33 | TAG | 14.3 | 5.4 | 2.7 | 18.9 | 54.7 | 4.0 | | 0.1 | 0.107 |
| TX-02-13 | TFA | 15.4 | 5.1 | 11.4 | 19.4 | 39.1 | 9.5 | 1.4 | | |
| TX-02-13 | TAG | 12.9 | 6.5 | 20.3 | 25.2 | 28.6 | 6.4 | | 0.5 | 0.389 |
| TX-02-36 | TFA | 16.2 | 3.4 | 1.8 | 12.3 | 58.5 | 7.8 | 1.4 | | |
| TX-02-36 | TAG | 15.4 | 5.8 | 3.3 | 21.5 | 48.9 | 5.1 | | 0.3 | 0.209 |
| TX-02-37 | TFA | 13.3 | 3.5 | 1.3 | 9.9 | 65.3 | 6.7 | 1.4 | | |
| TX-02-37 | TAG | 9.6 | 3.6 | 3.8 | 20.4 | 60.6 | 2.1 | | 0.2 | 0.137 |
| TX-02-18 | TFA | 14.6 | 3.0 | 1.4 | 9.8 | 65.5 | 5.7 | 1.4 | | |
| TX-02-18 | TAG | 12.5 | 5.6 | 4.3 | 20.6 | 54.8 | 2.3 | | 0.1 | 0.077 |
| TX-02-34 | TFA | 16.6 | 2.2 | 2.2 | 17.6 | 54.7 | 6.7 | 1.4 | | |
| TX-02-34 | TAG | 14.1 | 2.8 | 4.1 | 30.3 | 44.7 | 4.1 | | 0.3 | 0.231 |
| TX-02-31 | TFA | 13.3 | 3.1 | 1.8 | 10.1 | 64.7 | 7.0 | 1.5 | | |
| TX-02-31 | TAG | 5.4 | 1.8 | 3.2 | 17.8 | 71.1 | 0.7 | | 0.3 | 0.171 |
| TX-02-29 | TFA | 13.2 | 3.2 | 1.1 | 8.2 | 68.6 | 5.6 | 1.6 | | |
| TX-02-29 | TAG | 10.5 | 4.7 | 2.9 | 18.1 | 62.0 | 1.8 | | 0.1 | 0.082 |
| TX-02-35 | TFA | 17.8 | 3.4 | 6.5 | 14.0 | 50.3 | 8.0 | 1.6 | | |
| TX-02-35 | TAG | 18.8 | 5.3 | 19.1 | 28.4 | 22.4 | 6.1 | | 0.2 | 0.108 |
| TX-02-09 | TFA | 14.0 | 3.3 | 0.9 | 9.9 | 66.0 | 6.0 | 1.6 | | |
| TX-02-09 | TAG | 11.2 | 4.7 | 1.9 | 19.6 | 58.7 | 3.9 | | 0.1 | 0.036 |
| TX-02-24 | TFA | 12.9 | 3.5 | 0.6 | 7.9 | 67.3 | 7.7 | 1.8 | | |
| TX-02-24 | TAG | 10.7 | 3.5 | 1.6 | 11.8 | 69.0 | 3.4 | | 0.1 | 0.044 |
| TX-02-126 | TFA | 13.8 | 2.7 | 1.1 | 9.9 | 66.4 | 6.0 | 1.8 | | |
| TX-02-126 | TAG | 12.8 | 4.3 | 2.1 | 17.0 | 58.6 | 5.2 | | 0.5 | 0.247 |
| TX-02-23 | TFA | 13.6 | 2.7 | 0.7 | 8.9 | 68.3 | 5.8 | 1.9 | | |
| TX-02-23 | TAG | 10.0 | 3.3 | 2.2 | 18.2 | 63.9 | 2.4 | | 0.1 | 0.047 |
| TX-02-07 | TFA | 17.5 | 2.3 | 10.9 | 17.5 | 44.5 | 7.3 | 1.9 | | |
| TX-02-07 | TAG | 21.0 | 3.9 | 24.5 | 27.4 | 15.2 | 8.0 | | 0.4 | 0.225 |
| TX-02-28 | TFA | 12.8 | 2.9 | 0.5 | 7.7 | 68.4 | 7.8 | 2.0 | | |
| TX-02-28 | TAG | 13.0 | 5.5 | 1.2 | 11.1 | 64.3 | 4.8 | | 0.1 | 0.063 |
| TX-02-04 | TFA | 13.6 | 2.9 | 1.2 | 12.1 | 65.3 | 4.9 | 2.1 | | |
| TX-02-04 | TAG | 12.0 | 4.4 | 2.4 | 21.6 | 55.9 | 3.6 | | 0.4 | 0.206 |
| TX-02-25 | TFA | 12.2 | 2.8 | 0.5 | 9.4 | 68.8 | 6.3 | 2.5 | | |
| TX-02-25 | TAG | 10.3 | 4.2 | 1.0 | 15.4 | 62.5 | 6.6 | | 0.4 | 0.159 |
| TX-02-05 | TFA | 13.6 | 3.6 | 3.2 | 14.7 | 59.8 | 5.1 | 2.5 | | |
| TX-02-05 | TAG | 12.2 | 5.5 | 7.0 | 26.8 | 43.4 | 5.1 | | 0.6 | 0.220 |
| TX-02-14 | TFA | 15.9 | 5.7 | 30.9 | 12.7 | 26.0 | 8.9 | 2.8 | | |
| TX-02-14 | TAG | 17.9 | 8.5 | 42.6 | 14.9 | 7.8 | 8.4 | | 1.4 | 0.514 |
| TX-02-131 | TFA | 12.6 | 1.4 | 0.6 | 8.3 | 73.1 | 3.9 | 2.9 | | |
| TX-02-131 | TAG | 16.0 | 3.9 | 1.9 | 18.0 | 53.9 | 6.3 | | 0.2 | 0.061 |
| TX-02-129 | TFA | 12.1 | 1.6 | 1.0 | 10.4 | 70.5 | 4.3 | 2.9 | | |
| TX-02-129 | TAG | 12.8 | 3.6 | 2.5 | 22.0 | 53.6 | 5.5 | | 0.3 | 0.106 |
| TX-02-08 | TFA | 17.6 | 2.6 | 5.6 | 17.2 | 51.2 | 5.8 | 3.0 | | |
| TX-02-08 | TAG | 24.4 | 5.9 | 15.8 | 29.3 | 15.8 | 8.8 | | 0.6 | 0.183 |
| TX-02-02 | TFA | 17.9 | 3.1 | 7.2 | 15.5 | 49.6 | 6.7 | 3.1 | | |
| TX-02-02 | TAG | 23.7 | 6.5 | 17.7 | 22.8 | 19.6 | 9.7 | | 0.6 | 0.194 |
| TX-02-11 | TFA | 25.1 | 4.1 | 9.0 | 16.3 | 36.3 | 9.1 | 3.2 | | |
| TX-02-11 | TAG | 33.3 | 6.6 | 13.9 | 20.9 | 16.0 | 9.3 | | 1.1 | 0.341 |
| TX-02-127 | TFA | 11.4 | 1.6 | 0.3 | 8.9 | 75.4 | 2.4 | 3.5 | | |
| TX-02-127 | TAG | 21.0 | 5.8 | 1.4 | 20.6 | 47.4 | 3.9 | | 0.1 | 0.016 |
| TX-02-30 | TFA | 16.4 | 3.1 | 3.7 | 17.1 | 53.8 | 5.9 | 4.0 | | |
| TX-02-30 | TAG | 21.3 | 5.0 | 7.6 | 27.1 | 30.5 | 8.5 | | 0.9 | 0.236 |
| TX-02-19 | TFA | 13.5 | 2.7 | 25.4 | 22.6 | 30.8 | 5.0 | 4.2 | | |
| TX-02-19 | TAG | 14.0 | 3.3 | 34.3 | 27.0 | 16.6 | 4.8 | | 2.3 | 0.548 |
| TX-02-06 | TFA | 24.0 | 4.8 | 14.3 | 19.6 | 29.7 | 7.7 | 4.8 | | |
| TX-02-06 | TAG | 29.7 | 6.9 | 19.2 | 23.0 | 13.4 | 7.7 | | 2.7 | 0.555 |
| TX-02-10 | TFA | 22.0 | 3.3 | 10.3 | 22.7 | 33.7 | 7.9 | 6.3 | | |
| TX-02-10 | TAG | 24.8 | 4.1 | 12.9 | 27.0 | 22.4 | 8.8 | | 3.5 | 0.551 |
| TX-02-38 | TFA | 24.8 | 4.4 | 13.9 | 24.5 | 23.7 | 8.7 | 6.4 | | |
| TX-02-38 | TAG | 21.5 | 5.3 | 8.6 | 25.2 | 39.3 | 0.0 | | 2.5 | 0.392 |

TABLE 20

TFA and TAG levels, fatty acid composition and TTQ in sorghum leaves transformed with pOIL102 (pZmUbi:WRI1) and pOIL197 (pZmUbi:DGAT and pZmUbi:Oleosin) during the mature seed setting stage of growth.

| Line | TAG or TFA | C16:0 | C18:0 | C18:1 | C18:2 | C18:3n3 | Other | TFA | TAG | TTQ |
|---|---|---|---|---|---|---|---|---|---|---|
| TX-02-18 | TFA | 15.6 | 5.5 | 1.1 | 13.2 | 54.3 | 10.3 | 0.8 | | |
| TX-02-18 | TAG | 14.2 | 7.7 | 2.5 | 22.7 | 49.2 | 3.7 | | 0.1 | 0.133 |
| TX-02-31 | TFA | 15.6 | 4.4 | 1.6 | 11.1 | 55.9 | 11.4 | 0.9 | | |
| TX-02-31 | TAG | 12.3 | 6.3 | 3.2 | 19.8 | 56.2 | 2.2 | | 0.2 | 0.163 |
| TX-02-37 | TFA | 14.8 | 4.7 | 1.8 | 10.3 | 57.5 | 10.8 | 1.0 | | |
| TX-02-37 | TAG | 9.6 | 5.8 | 3.2 | 20.6 | 58.6 | 2.1 | | 0.1 | 0.147 |
| TX-02-12 | TFA | 16.4 | 3.8 | 1.7 | 13.0 | 54.8 | 10.2 | 1.0 | | |
| TX-02-12 | TAG | 15.1 | 6.2 | 3.3 | 21.0 | 50.0 | 4.4 | | 0.3 | 0.258 |
| TX-02-29 | TFA | 14.9 | 4.7 | 1.1 | 9.8 | 60.0 | 9.5 | 1.1 | | |
| TX-02-29 | TAG | 14.4 | 12.7 | 2.4 | 17.5 | 50.6 | 2.4 | | 0.1 | 0.125 |
| TX-02-01 | TFA | 14.9 | 4.6 | 1.4 | 10.5 | 59.0 | 9.5 | 1.3 | | |
| TX-02-01 | TAG | 15.8 | 6.4 | 3.1 | 17.3 | 54.3 | 3.1 | | 0.1 | 0.083 |
| TX-02-23 | TFA | 14.3 | 4.6 | 1.4 | 8.2 | 63.5 | 8.0 | 1.3 | | |
| TX-02-23 | TAG | 9.9 | 6.1 | 2.6 | 13.2 | 48.5 | 19.8 | | 0.1 | 0.104 |
| TX-02-09 | TFA | 14.1 | 4.5 | 0.9 | 8.4 | 65.0 | 7.0 | 1.4 | | |
| TX-02-09 | TAG | 16.4 | 11.7 | 2.4 | 14.0 | 51.6 | 3.8 | | 0.1 | 0.052 |
| TX-02-24 | TFA | 15.1 | 4.3 | 0.9 | 11.6 | 59.3 | 8.8 | 1.5 | | |
| TX-02-24 | TAG | 14.5 | 7.4 | 2.3 | 23.8 | 48.0 | 4.1 | | 0.1 | 0.094 |
| TX-02-28 | TFA | 14.3 | 3.5 | 0.7 | 8.6 | 65.9 | 7.0 | 1.5 | | |
| TX-02-28 | TAG | 16.3 | 13.2 | 1.9 | 12.4 | 52.0 | 4.2 | | 0.1 | 0.074 |
| TX-02-34 | TFA | 15.2 | 3.8 | 1.4 | 15.3 | 54.2 | 10.1 | 1.5 | | |
| TX-02-34 | TAG | 13.3 | 5.8 | 2.2 | 22.3 | 47.0 | 9.5 | | 0.5 | 0.347 |
| TX-02-27 | TFA | 14.8 | 2.8 | 0.9 | 8.9 | 67.5 | 5.1 | 1.5 | | |
| TX-02-27 | TAG | 15.9 | 11.9 | 3.5 | 20.2 | 46.5 | 1.9 | | 0.1 | 0.049 |
| TX-02-33 | TFA | 14.6 | 4.1 | 2.4 | 13.3 | 57.2 | 8.4 | 1.5 | | |
| TX-02-33 | TAG | 12.5 | 7.3 | 4.1 | 21.9 | 49.1 | 5.2 | | 0.3 | 0.200 |
| TX-02-07 | TFA | 12.3 | 4.2 | 0.8 | 8.4 | 69.9 | 4.4 | 1.5 | | |
| TX-02-07 | TAG | 10.6 | 5.5 | 2.3 | 17.8 | 60.8 | 2.9 | | 0.1 | 0.042 |
| TX-02-05 | TFA | 15.4 | 6.5 | 7.0 | 21.7 | 39.3 | 10.2 | 1.6 | | |
| TX-02-05 | TAG | 13.1 | 8.3 | 11.4 | 30.1 | 28.9 | 8.3 | | 0.6 | 0.376 |
| TX-02-08 | TFA | 18.4 | 2.8 | 2.5 | 14.4 | 52.5 | 9.5 | 1.9 | | |
| TX-02-08 | TAG | 25.0 | 6.2 | 7.6 | 23.7 | 27.3 | 10.2 | | 0.2 | 0.128 |
| TX-02-127 | TFA | 12.6 | 2.8 | 0.6 | 7.5 | 71.9 | 4.5 | 2.4 | | |
| TX-02-127 | TAG | 11.9 | 5.0 | 2.1 | 14.6 | 63.4 | 2.9 | | 0.1 | 0.026 |
| TX-02-38 | TFA | 41.9 | 14.1 | 19.6 | 8.7 | 1.5 | 14.2 | 3.0 | | |
| TX-02-38 | TAG | 25.3 | 9.9 | 32.5 | 16.1 | 2.7 | 13.4 | | 1.1 | 0.365 |
| TX-02-02 | TFA | 16.5 | 6.8 | 28.2 | 15.1 | 21.2 | 12.2 | 3.5 | | |
| TX-02-02 | TAG | 16.5 | 9.8 | 39.1 | 16.5 | 7.1 | 10.9 | | 1.7 | 0.496 |
| TX-02-06 | TFA | 25.3 | 4.8 | 12.0 | 24.3 | 19.3 | 14.3 | 4.0 | | |
| TX-02-06 | TAG | 27.1 | 6.2 | 14.7 | 27.8 | 12.4 | 11.8 | | 2.6 | 0.658 |
| TX-02-30 | TFA | 17.0 | 4.1 | 6.7 | 20.2 | 43.3 | 8.7 | 4.3 | | |
| TX-02-30 | TAG | 19.6 | 5.8 | 11.4 | 27.4 | 26.1 | 9.7 | | 2.2 | 0.509 |
| TX-02-14 | TFA | 13.3 | 7.3 | 56.1 | 6.2 | 8.8 | 8.3 | 6.1 | | |
| TX-02-14 | TAG | 13.7 | 8.7 | 60.1 | 6.1 | 4.3 | 7.1 | | 4.3 | 0.706 |

TABLE 21

TFA and TAG levels, fatty acid composition and TTQ in pOIL103 + pOIL197 primary transformants at vegetative setting stage.

| Line | TFA or TAG | C16:0 | C18:0 | C18:1 | C18:2 | C18:3n3 | Other | TFA | TAG | TTQ |
|---|---|---|---|---|---|---|---|---|---|---|
| TX-03-07 | TFA | 22.6 | 3.3 | 1.3 | 12.7 | 51.8 | 8.4 | 2.4 | | |
| TX-03-07 | TAG | 29.4 | 5.6 | 3.3 | 20.9 | 31.3 | 9.4 | | 0.1 | 0.056 |
| TX-03-02 | TFA | 17.7 | 2.6 | 1.1 | 9.1 | 64.0 | 5.4 | 2.4 | | |
| TX-03-02 | TAG | 20.2 | 5.1 | 2.8 | 16.4 | 47.7 | 7.7 | | 0.2 | 0.079 |
| TX-03-01 | TFA | 16.9 | 2.5 | 1.2 | 8.7 | 65.7 | 4.9 | 2.8 | | |
| TX-03-01 | TAG | 18.8 | 5.4 | 3.3 | 17.3 | 47.7 | 7.5 | | 0.3 | 0.096 |
| TX-03-52 | TFA | 13.8 | 1.4 | 0.8 | 8.9 | 70.6 | 4.5 | 2.9 | | |
| TX-03-52 | TAG | 23.2 | 4.3 | 2.3 | 19.6 | 42.8 | 7.8 | | 0.2 | 0.082 |
| TX-03-47 | TFA | 14.1 | 1.6 | 0.6 | 6.5 | 73.5 | 3.7 | 3.0 | | |
| TX-03-47 | TAG | 20.6 | 3.9 | 3.8 | 18.0 | 48.6 | 5.2 | | 0.1 | 0.023 |
| TX-03-17 | TFA | 15.3 | 1.4 | 0.5 | 7.1 | 72.1 | 3.6 | 3.0 | | |
| TX-03-17 | TAG | 29.4 | 4.0 | 2.0 | 16.8 | 41.6 | 6.3 | | 0.1 | 0.039 |
| TX-03-05 | TFA | 23.2 | 2.0 | 0.6 | 8.1 | 61.2 | 4.9 | 3.0 | | |
| TX-03-05 | TAG | 43.9 | 4.4 | 1.6 | 14.4 | 28.9 | 6.8 | | 0.2 | 0.053 |
| TX-03-53 | TFA | 19.6 | 1.9 | 1.1 | 10.9 | 61.0 | 5.6 | 3.1 | | |

TABLE 21-continued

TFA and TAG levels, fatty acid composition and TTQ in
pOIL103 + pOIL197 primary transformants at vegetative setting stage.

| Line | TFA or TAG | C16:0 | C18:0 | C18:1 | C18:2 | C18:3n3 | Other | TFA | TAG | TTQ |
|---|---|---|---|---|---|---|---|---|---|---|
| TX-03-53 | TAG | 35.3 | 3.9 | 3.1 | 20.5 | 30.7 | 6.5 | | 0.3 | 0.082 |
| TX-03-19 | TFA | 20.8 | 1.8 | 0.6 | 9.1 | 63.9 | 3.9 | 3.1 | | |
| TX-03-19 | TAG | 39.9 | 4.4 | 1.8 | 17.2 | 26.9 | 9.8 | | 0.2 | 0.056 |
| TX-03-10 | TFA | 27.8 | 4.3 | 1.1 | 21.0 | 38.0 | 7.8 | 3.1 | | |
| TX-03-10 | TAG | 35.2 | 7.3 | 1.7 | 26.3 | 19.8 | 9.7 | | 1.4 | 0.442 |
| TX-03-48 | TFA | 21.4 | 2.1 | 0.8 | 9.0 | 62.0 | 4.8 | 3.2 | | |
| TX-03-48 | TAG | 39.1 | 4.5 | 2.3 | 15.6 | 31.7 | 6.8 | | 0.2 | 0.062 |
| TX-03-61 | TFA | 16.7 | 1.3 | 1.8 | 17.6 | 57.4 | 5.3 | 3.2 | | |
| TX-03-61 | TAG | 19.0 | 4.6 | 2.9 | 33.9 | 28.9 | 10.7 | | 0.2 | 0.047 |
| TX-03-32 | TFA | 15.6 | 1.5 | 0.7 | 10.7 | 67.3 | 4.1 | 3.2 | | |
| TX-03-32 | TAG | 28.8 | 4.0 | 3.4 | 26.5 | 29.2 | 8.1 | | 0.1 | 0.032 |
| TX-03-40 | TFA | 15.0 | 1.3 | 0.6 | 9.1 | 69.8 | 4.2 | 3.3 | | |
| TX-03-40 | TAG | 27.6 | 3.7 | 2.2 | 25.2 | 32.1 | 9.2 | | 0.2 | 0.057 |
| TX-03-49 | TFA | 17.3 | 1.5 | 0.5 | 8.0 | 68.0 | 4.8 | 3.3 | | |
| TX-03-49 | TAG | 35.0 | 6.9 | 1.9 | 18.4 | 26.4 | 11.3 | | 0.1 | 0.015 |
| TX-03-21 | TFA | 13.1 | 1.3 | 0.6 | 7.8 | 73.7 | 3.5 | 3.3 | | |
| TX-03-21 | TAG | 20.3 | 4.1 | 3.3 | 23.1 | 43.0 | 6.3 | | 0.1 | 0.029 |
| TX-03-62 | TFA | 18.0 | 1.1 | 1.9 | 13.6 | 59.8 | 5.5 | 3.3 | | |
| TX-03-62 | TAG | 26.2 | 4.8 | 5.7 | 30.2 | 24.9 | 8.3 | | 0.2 | 0.051 |
| TX-03-26 | TFA | 14.0 | 1.5 | 0.5 | 7.9 | 72.3 | 3.8 | 3.4 | | |
| TX-03-26 | TAG | 22.8 | 3.8 | 3.2 | 22.8 | 40.5 | 6.9 | | 0.1 | 0.023 |
| TX-03-36 | TFA | 19.7 | 1.6 | 0.8 | 8.9 | 63.7 | 5.2 | 3.5 | | |
| TX-03-36 | TAG | 37.1 | 3.9 | 2.3 | 17.1 | 30.5 | 9.0 | | 0.3 | 0.075 |
| TX-03-50 | TFA | 16.7 | 1.3 | 0.8 | 9.3 | 66.7 | 5.2 | 3.5 | | |
| TX-03-50 | TAG | 35.9 | 3.9 | 4.0 | 21.9 | 25.2 | 9.2 | | 0.1 | 0.026 |
| TX-03-23 | TFA | 19.5 | 1.6 | 0.3 | 6.1 | 67.1 | 5.4 | 3.5 | | |
| TX-03-23 | TAG | 39.0 | 4.3 | 1.2 | 13.9 | 32.7 | 9.0 | | 0.2 | 0.044 |
| TX-03-45 | TFA | 15.0 | 1.6 | 0.3 | 6.2 | 71.9 | 5.0 | 3.5 | | |
| TX-03-45 | TAG | 27.1 | 4.7 | 0.8 | 14.1 | 41.7 | 11.6 | | 0.3 | 0.087 |
| TX-03-34 | TFA | 20.6 | 1.7 | 0.8 | 11.0 | 60.3 | 5.6 | 3.5 | | |
| TX-03-34 | TAG | 36.1 | 3.9 | 2.1 | 21.6 | 27.5 | 8.9 | | 0.2 | 0.068 |
| TX-03-51 | TFA | 12.3 | 1.3 | 0.7 | 9.3 | 72.9 | 3.6 | 3.6 | | |
| TX-03-51 | TAG | 23.8 | 4.8 | 2.6 | 26.7 | 32.2 | 9.9 | | 0.1 | 0.034 |
| TX-03-63 | TFA | 15.7 | 1.3 | 1.8 | 16.9 | 59.7 | 4.7 | 3.7 | | |
| TX-03-63 | TAG | 23.9 | 3.8 | 2.9 | 31.7 | 26.6 | 11.1 | | 0.2 | 0.049 |
| TX-03-41 | TFA | 21.0 | 1.7 | 0.6 | 8.0 | 63.7 | 4.9 | 3.7 | | |
| TX-03-41 | TAG | 44.7 | 3.8 | 1.7 | 15.2 | 27.4 | 7.1 | | 0.2 | 0.067 |
| TX-03-20 | TFA | 10.7 | 1.5 | 0.7 | 9.0 | 74.7 | 3.3 | 3.7 | | |
| TX-03-20 | TAG | 14.1 | 4.0 | 2.3 | 24.1 | 47.3 | 8.2 | | 0.2 | 0.061 |
| TX-03-29 | TFA | 20.3 | 1.9 | 0.9 | 11.0 | 61.2 | 4.7 | 3.7 | | |
| TX-03-29 | TAG | 37.1 | 4.4 | 3.1 | 21.2 | 27.5 | 6.7 | | 0.2 | 0.054 |
| TX-03-25 | TFA | 12.1 | 1.5 | 0.5 | 6.5 | 75.9 | 3.5 | 3.8 | | |
| TX-03-25 | TAG | 17.6 | 7.2 | 2.7 | 16.6 | 48.5 | 7.3 | | 0.1 | 0.030 |
| TX-03-33 | TFA | 24.1 | 2.2 | 0.9 | 13.0 | 53.2 | 6.6 | 3.8 | | |
| TX-03-33 | TAG | 40.6 | 4.3 | 1.7 | 20.9 | 23.3 | 9.1 | | 0.6 | 0.168 |
| TX-03-22 | TFA | 22.3 | 1.7 | 1.2 | 13.8 | 54.5 | 6.5 | 3.9 | | |
| TX-03-22 | TAG | 37.9 | 3.3 | 2.2 | 23.4 | 23.5 | 9.8 | | 1.0 | 0.245 |
| TX-03-46 | TFA | 24.4 | 1.7 | 0.7 | 9.9 | 57.3 | 6.0 | 4.0 | | |
| TX-03-46 | TAG | 45.2 | 3.2 | 1.4 | 17.6 | 24.6 | 8.0 | | 0.6 | 0.148 |
| TX-03-11 | TFA | 25.4 | 2.8 | 1.0 | 20.8 | 42.9 | 7.2 | 4.0 | | |
| TX-03-11 | TAG | 33.4 | 4.8 | 1.5 | 28.8 | 21.6 | 9.9 | | 1.4 | 0.337 |
| TX-03-18 | TFA | 20.8 | 2.7 | 0.9 | 13.9 | 56.2 | 5.5 | 4.1 | | |
| TX-03-18 | TAG | 33.6 | 7.1 | 2.7 | 24.8 | 21.5 | 10.3 | | 0.3 | 0.078 |
| TX-03-57 | TFA | 12.9 | 1.4 | 1.8 | 15.8 | 63.4 | 4.6 | 4.2 | | |
| TX-03-57 | TAG | 14.5 | 2.5 | 7.6 | 41.5 | 24.9 | 9.0 | | 0.5 | 0.127 |
| TX-03-58 | TFA | 13.0 | 1.5 | 1.8 | 15.7 | 63.3 | 4.8 | 4.2 | | |
| TX-03-58 | TAG | 16.4 | 3.4 | 4.9 | 35.3 | 31.2 | 8.8 | | 0.6 | 0.148 |
| TX-03-54 | TFA | 22.8 | 1.9 | 1.0 | 16.4 | 51.2 | 6.8 | 5.0 | | |
| TX-03-54 | TAG | 36.0 | 3.5 | 1.7 | 26.1 | 21.6 | 11.1 | | 1.2 | 0.245 |
| TX-03-28 | TFA | 28.3 | 2.2 | 1.0 | 16.8 | 44.1 | 7.6 | 5.4 | | |
| TX-03-28 | TAG | 40.9 | 3.3 | 1.4 | 23.4 | 22.4 | 8.6 | | 2.3 | 0.434 |
| TX-03-31 | TFA | 22.2 | 2.2 | 2.0 | 25.2 | 41.6 | 6.8 | 5.6 | | |
| TX-03-31 | TAG | 30.9 | 3.6 | 3.0 | 34.7 | 18.5 | 9.3 | | 2.3 | 0.410 |
| TX-03-04 | TFA | 24.3 | 3.4 | 0.6 | 10.5 | 55.4 | 5.8 | 7.0 | | |
| TX-03-04 | TAG | 36.1 | 6.5 | 2.2 | 15.9 | 31.3 | 8.0 | | 0.1 | 0.016 |
| TX-03-08 | TFA | 22.6 | 1.9 | 0.6 | 6.8 | 63.8 | 4.3 | 8.3 | | |
| TX-03-08 | TAG | 46.4 | 4.6 | 4.2 | 11.1 | 26.7 | 7.0 | | 0.1 | 0.017 |

TABLE 22

TFA and TAG levels, fatty acid composition and TTQ in
pOIL103 + pOIL197 primary transformants at boot leaf stage.

| Line | TFA or TAG | C16:0 | C18:0 | C18:1 | C18:2 | C18:3n3 | Other | TFA | TAG | TTQ |
|---|---|---|---|---|---|---|---|---|---|---|
| TX-03-20 | TFA | 12.2 | 2.6 | 1.7 | 10.3 | 67.5 | 5.7 | 2.1 | | |
| TX-03-20 | TAG | 9.4 | 3.6 | 3.3 | 18.1 | 63.0 | 2.5 | | 0.4 | 0.217 |
| TX-03-54 | TFA | 13.6 | 3.5 | 3.0 | 12.1 | 61.5 | 6.4 | 2.1 | | |
| TX-03-54 | TAG | 14.1 | 6.9 | 7.0 | 22.5 | 43.5 | 6.0 | | 0.4 | 0.207 |
| TX-03-61 | TFA | 23.9 | 3.1 | 1.7 | 19.0 | 43.9 | 8.3 | 2.2 | | |
| TX-03-61 | TAG | 31.4 | 6.6 | 3.4 | 28.3 | 19.6 | 10.8 | | 0.4 | 0.159 |
| TX-03-02 | TFA | 14.9 | 3.0 | 2.8 | 12.1 | 60.6 | 6.6 | 2.2 | | |
| TX-03-02 | TAG | 14.8 | 5.5 | 5.6 | 20.6 | 46.7 | 6.8 | | 0.5 | 0.222 |
| TX-03-53 | TFA | 18.5 | 3.7 | 8.9 | 15.4 | 43.1 | 10.4 | 2.3 | | |
| TX-03-53 | TAG | 20.1 | 6.8 | 16.7 | 24.5 | 23.3 | 8.6 | | 0.6 | 0.275 |
| TX-03-01 | TFA | 13.4 | 3.0 | 3.0 | 12.5 | 61.8 | 6.4 | 2.3 | | |
| TX-03-01 | TAG | 13.9 | 5.5 | 7.5 | 23.0 | 42.6 | 7.4 | | 0.4 | 0.164 |
| TX-03-47 | TFA | 12.8 | 2.1 | 1.6 | 7.5 | 70.7 | 5.3 | 2.4 | | |
| TX-03-47 | TAG | 14.8 | 5.1 | 5.0 | 19.3 | 52.1 | 3.7 | | 0.1 | 0.050 |
| TX-03-07 | TFA | 18.4 | 2.8 | 7.6 | 15.6 | 47.1 | 8.5 | 2.5 | | |
| TX-03-07 | TAG | 25.8 | 6.4 | 18.7 | 25.5 | 15.2 | 8.5 | | 0.3 | 0.127 |
| TX-03-05 | TFA | 21.4 | 2.3 | 1.4 | 9.7 | 59.1 | 6.1 | 2.6 | | |
| TX-03-05 | TAG | 36.4 | 5.6 | 3.9 | 17.1 | 28.4 | 8.6 | | 0.4 | 0.168 |
| TX-03-49 | TFA | 18.1 | 3.7 | 8.2 | 13.2 | 52.0 | 4.9 | 2.6 | | |
| TX-03-49 | TAG | 24.1 | 8.2 | 18.3 | 20.9 | 18.8 | 9.7 | | 0.5 | 0.212 |
| TX-03-34 | TFA | 19.0 | 2.7 | 6.0 | 15.4 | 50.6 | 6.4 | 2.6 | | |
| TX-03-34 | TAG | 24.8 | 10.5 | 10.9 | 23.9 | 20.6 | 9.3 | | 0.8 | 0.287 |
| TX-03-32 | TFA | 18.2 | 2.2 | 1.6 | 12.4 | 60.2 | 5.4 | 2.8 | | |
| TX-03-32 | TAG | 20.8 | 14.6 | 3.2 | 21.4 | 31.5 | 8.5 | | 0.6 | 0.204 |
| TX-03-04 | TFA | 18.8 | 3.1 | 5.8 | 13.4 | 50.3 | 8.6 | 2.9 | | |
| TX-03-04 | TAG | 26.7 | 7.5 | 14.6 | 23.1 | 19.0 | 9.1 | | 0.3 | 0.118 |
| TX-03-23 | TFA | 18.9 | 1.7 | 1.0 | 7.9 | 63.2 | 7.3 | 2.9 | | |
| TX-03-23 | TAG | 25.0 | 4.6 | 2.5 | 18.1 | 39.6 | 10.2 | | 0.2 | 0.070 |
| TX-03-25 | TFA | 14.5 | 1.8 | 0.4 | 6.4 | 73.5 | 3.4 | 3.0 | | |
| TX-03-25 | TAG | 20.3 | 5.1 | 1.0 | 12.3 | 53.6 | 7.7 | | 0.3 | 0.110 |
| TX-03-18 | TFA | 21.1 | 2.9 | 1.2 | 17.8 | 46.3 | 10.7 | 3.0 | | |
| TX-03-18 | TAG | 22.6 | 5.9 | 4.5 | 31.1 | 22.6 | 13.3 | | 0.4 | 0.143 |
| TX-03-50 | TFA | 16.5 | 2.6 | 6.1 | 12.9 | 53.9 | 8.0 | 3.0 | | |
| TX-03-50 | TAG | 20.2 | 19.9 | 12.9 | 19.6 | 20.6 | 6.8 | | 0.7 | 0.217 |
| TX-03-60 | TFA | 20.2 | 2.9 | 0.8 | 14.1 | 55.7 | 6.2 | 3.1 | | |
| TX-03-60 | TAG | 30.5 | 6.2 | 1.6 | 21.6 | 30.2 | 9.9 | | 0.6 | 0.202 |
| TX-03-21 | TFA | 12.3 | 1.7 | 0.5 | 6.8 | 74.4 | 4.4 | 3.2 | | |
| TX-03-21 | TAG | 16.1 | 4.7 | 1.6 | 13.1 | 57.0 | 7.5 | | 0.2 | 0.067 |
| TX-03-40 | TFA | 17.1 | 1.4 | 0.4 | 8.0 | 68.2 | 4.9 | 3.2 | | |
| TX-03-40 | TAG | 34.5 | 4.4 | 0.9 | 14.5 | 39.8 | 5.9 | | 0.4 | 0.112 |
| TX-03-62 | TFA | 25.3 | 2.9 | 1.7 | 14.7 | 47.9 | 7.6 | 3.3 | | |
| TX-03-62 | TAG | 40.3 | 5.6 | 3.5 | 22.3 | 18.7 | 9.5 | | 0.6 | 0.171 |
| TX-03-36 | TFA | 19.5 | 2.0 | 2.0 | 11.4 | 58.3 | 6.8 | 3.5 | | |
| TX-03-36 | TAG | 31.2 | 4.0 | 4.4 | 20.0 | 29.4 | 11.0 | | 0.6 | 0.160 |
| TX-03-63 | TFA | 25.4 | 3.6 | 2.6 | 18.2 | 42.0 | 8.2 | 3.5 | | |
| TX-03-63 | TAG | 33.1 | 6.1 | 3.8 | 24.9 | 21.6 | 10.4 | | 1.4 | 0.383 |
| TX-03-45 | TFA | 16.4 | 1.4 | 0.5 | 8.1 | 69.1 | 4.5 | 3.5 | | |
| TX-03-45 | TAG | 30.8 | 4.6 | 1.4 | 16.2 | 40.7 | 6.3 | | 0.2 | 0.058 |
| TX-03-17 | TFA | 14.2 | 1.8 | 0.8 | 6.9 | 71.2 | 5.2 | 3.6 | | |
| TX-03-17 | TAG | 18.7 | 4.5 | 2.2 | 13.5 | 52.8 | 8.3 | | 0.4 | 0.120 |
| TX-03-57 | TFA | 18.7 | 3.4 | 1.5 | 13.8 | 55.8 | 6.8 | 3.6 | | |
| TX-03-57 | TAG | 23.4 | 6.3 | 3.0 | 21.0 | 36.2 | 10.1 | | 1.2 | 0.330 |
| TX-03-11 | TFA | 29.1 | 6.4 | 2.1 | 22.4 | 33.0 | 7.1 | 3.6 | | |
| TX-03-11 | TAG | 30.6 | 8.5 | 2.8 | 27.0 | 19.7 | 11.4 | | 1.9 | 0.510 |
| TX-03-48 | TFA | 27.1 | 3.7 | 3.7 | 20.6 | 37.2 | 7.6 | 3.7 | | |
| TX-03-48 | TAG | 31.2 | 5.0 | 5.5 | 27.1 | 23.0 | 8.1 | | 2.1 | 0.569 |
| TX-03-29 | TFA | 20.1 | 2.3 | 1.7 | 13.4 | 55.5 | 7.1 | 3.7 | | |
| TX-03-29 | TAG | 33.0 | 5.0 | 4.1 | 24.3 | 26.4 | 7.2 | | 0.4 | 0.104 |
| TX-03-26 | TFA | 15.3 | 1.6 | 0.4 | 5.9 | 71.3 | 5.5 | 3.9 | | |
| TX-03-26 | TAG | 25.2 | 4.6 | 1.7 | 13.3 | 49.7 | 5.5 | | 0.3 | 0.074 |
| TX-03-10 | TFA | 28.6 | 6.8 | 2.1 | 21.8 | 33.0 | 7.7 | 3.9 | | |
| TX-03-10 | TAG | 31.0 | 8.5 | 2.9 | 26.7 | 18.6 | 12.2 | | 1.9 | 0.491 |
| TX-03-58 | TFA | 16.3 | 2.6 | 1.3 | 14.5 | 60.3 | 5.0 | 4.1 | | |
| TX-03-58 | TAG | 20.4 | 5.2 | 2.8 | 24.3 | 39.2 | 8.2 | | 1.1 | 0.278 |
| TX-03-08 | TFA | 19.8 | 2.0 | 0.7 | 6.6 | 64.9 | 5.9 | 4.1 | | |
| TX-03-08 | TAG | 34.8 | 5.2 | 2.7 | 14.3 | 34.5 | 8.5 | | 0.2 | 0.051 |
| TX-03-33 | TFA | 27.4 | 2.4 | 1.5 | 16.3 | 46.0 | 6.4 | 4.2 | | |
| TX-03-33 | TAG | 39.2 | 5.4 | 2.3 | 21.9 | 20.8 | 10.5 | | 1.6 | 0.386 |
| TX-03-22 | TFA | 19.8 | 2.8 | 3.1 | 11.8 | 53.4 | 9.1 | 4.2 | | |
| TX-03-22 | TAG | 28.4 | 5.3 | 5.4 | 19.4 | 38.3 | 3.2 | | 1.2 | 0.287 |
| TX-03-41 | TFA | 18.1 | 2.6 | 3.1 | 11.1 | 58.0 | 7.1 | 4.8 | | |
| TX-03-41 | TAG | 27.8 | 6.0 | 6.8 | 19.3 | 34.9 | 5.3 | | 0.7 | 0.139 |
| TX-03-46 | TFA | 24.6 | 2.0 | 0.6 | 7.9 | 57.4 | 7.4 | 4.9 | | |

TABLE 22-continued

TFA and TAG levels, fatty acid composition and TTQ in
pOIL103 + pOIL197 primary transformants at boot leaf stage.

| Line | TFA or TAG | C16:0 | C18:0 | C18:1 | C18:2 | C18:3n3 | Other | TFA | TAG | TTQ |
|---|---|---|---|---|---|---|---|---|---|---|
| TX-03-46 | TAG | 44.7 | 4.2 | 1.3 | 13.4 | 31.4 | 5.0 |  | 1.1 | 0.220 |
| TX-03-28 | TFA | 28.5 | 2.1 | 1.3 | 23.4 | 33.7 | 11.0 | 6.2 |  |  |
| TX-03-28 | TAG | 36.0 | 2.9 | 3.1 | 29.6 | 18.5 | 10.0 |  | 3.7 | 0.596 |
| TX-03-31 | TFA | 33.4 | 2.9 | 4.3 | 28.6 | 25.5 | 5.5 | 8.3 |  |  |
| TX-03-31 | TAG | 38.0 | 3.6 | 4.9 | 30.6 | 14.8 | 8.1 |  | 6.6 | 0.789 |

TABLE 23

TFA and TAG levels, fatty acid composition and TTQ in
pOIL103 + pOIL197 primary transformants at mature seed setting stage.

| Line | TFA or TAG | C16:0 | C18:0 | C18:1 | C18:2 | C18:3n3 | Other | TFA | TAG | TTQ |
|---|---|---|---|---|---|---|---|---|---|---|
| TX-03-52 | TFA | 15.5 | 6.7 | 4.3 | 14.3 | 48.7 | 10.6 | 1.2 |  |  |
| TX-03-52 | TAG | 12.7 | 7.9 | 8.3 | 21.4 | 41.1 | 8.7 |  | 0.4 | 0.315 |
| TX-03-51 | TFA | 15.6 | 6.4 | 4.3 | 13.6 | 52.0 | 8.0 | 1.5 |  |  |
| TX-03-51 | TAG | 13.7 | 8.9 | 8.2 | 18.6 | 41.2 | 9.5 |  | 0.4 | 0.296 |
| TX-03-07 | TFA | 20.6 | 4.2 | 13.1 | 18.1 | 32.1 | 11.9 | 1.6 |  |  |
| TX-03-07 | TAG | 25.5 | 7.8 | 23.7 | 24.5 | 9.3 | 9.1 |  | 0.4 | 0.227 |
| TX-03-04 | TFA | 23.9 | 3.7 | 4.0 | 16.5 | 38.8 | 13.1 | 1.7 |  |  |
| TX-03-04 | TAG | 35.3 | 6.1 | 9.5 | 24.6 | 14.7 | 9.8 |  | 0.2 | 0.110 |
| TX-03-54 | TFA | 16.6 | 5.0 | 6.7 | 16.1 | 45.8 | 9.9 | 1.7 |  |  |
| TX-03-54 | TAG | 16.6 | 7.2 | 12.4 | 22.7 | 34.2 | 6.9 |  | 0.4 | 0.245 |
| TX-03-21 | TFA | 14.4 | 4.2 | 1.0 | 10.0 | 62.7 | 7.7 | 1.8 |  |  |
| TX-03-21 | TAG | 12.8 | 6.6 | 1.9 | 16.5 | 55.4 | 6.7 |  | 0.2 | 0.133 |
| TX-03-08 | TFA | 19.3 | 3.6 | 7.1 | 16.4 | 45.3 | 8.3 | 1.9 |  |  |
| TX-03-08 | TAG | 23.5 | 7.3 | 16.2 | 24.6 | 19.6 | 8.7 |  | 0.4 | 0.213 |
| TX-03-02 | TFA | 16.4 | 4.8 | 7.5 | 22.0 | 39.7 | 9.5 | 1.9 |  |  |
| TX-03-02 | TAG | 15.1 | 6.4 | 14.0 | 30.3 | 25.6 | 8.7 |  | 0.6 | 0.334 |
| TX-03-34 | TFA | 24.2 | 4.9 | 5.2 | 18.2 | 32.4 | 15.2 | 2.0 |  |  |
| TX-03-34 | TAG | 27.1 | 7.3 | 8.6 | 26.6 | 18.1 | 12.3 |  | 0.6 | 0.298 |
| TX-03-17 | TFA | 16.9 | 4.2 | 2.0 | 10.6 | 55.2 | 11.1 | 2.2 |  |  |
| TX-03-17 | TAG | 19.7 | 6.7 | 3.7 | 18.4 | 41.4 | 10.0 |  | 0.2 | 0.107 |
| TX-03-26 | TFA | 19.3 | 3.4 | 0.8 | 9.9 | 57.6 | 9.1 | 2.2 |  |  |
| TX-03-26 | TAG | 23.9 | 6.7 | 2.0 | 18.2 | 39.3 | 9.9 |  | 0.3 | 0.129 |
| TX-03-32 | TFA | 23.2 | 3.9 | 1.7 | 15.5 | 44.5 | 11.2 | 2.3 |  |  |
| TX-03-32 | TAG | 29.0 | 6.3 | 3.8 | 24.8 | 25.6 | 10.6 |  | 0.5 | 0.206 |
| TX-03-41 | TFA | 19.7 | 4.9 | 6.3 | 21.7 | 36.5 | 10.9 | 2.3 |  |  |
| TX-03-41 | TAG | 20.9 | 7.6 | 11.6 | 29.3 | 20.3 | 10.5 |  | 0.8 | 0.331 |
| TX-03-49 | TFA | 21.1 | 5.7 | 14.9 | 19.3 | 27.5 | 11.4 | 2.3 |  |  |
| TX-03-49 | TAG | 22.6 | 8.3 | 23.7 | 24.7 | 12.0 | 8.8 |  | 0.9 | 0.375 |
| TX-03-25 | TFA | 17.9 | 3.2 | 0.6 | 8.7 | 62.6 | 7.1 | 2.6 |  |  |
| TX-03-25 | TAG | 21.9 | 6.3 | 1.5 | 14.2 | 47.7 | 8.3 |  | 0.4 | 0.149 |
| TX-03-40 | TFA | 20.8 | 3.4 | 0.8 | 5.8 | 59.7 | 9.6 | 2.7 |  |  |
| TX-03-40 | TAG | 27.6 | 6.3 | 0.4 | 8.6 | 46.3 | 10.8 |  | 0.7 | 0.238 |
| TX-03-36 | TFA | 22.8 | 4.2 | 2.6 | 15.7 | 45.2 | 9.5 | 2.9 |  |  |
| TX-03-36 | TAG | 27.1 | 7.1 | 5.0 | 22.9 | 25.1 | 12.9 |  | 0.8 | 0.282 |
| TX-03-10 | TFA | 28.4 | 5.3 | 1.7 | 21.5 | 30.3 | 12.7 | 3.3 |  |  |
| TX-03-10 | TAG | 32.7 | 7.8 | 2.3 | 25.2 | 18.6 | 13.3 |  | 1.9 | 0.570 |
| TX-03-46 | TFA | 27.5 | 3.7 | 1.7 | 12.2 | 41.4 | 13.4 | 3.7 |  |  |
| TX-03-46 | TAG | 36.4 | 5.1 | 1.8 | 15.1 | 29.1 | 12.4 |  | 1.6 | 0.420 |
| TX-03-48 | TFA | 26.7 | 5.0 | 6.5 | 24.7 | 24.7 | 12.3 | 4.5 |  |  |
| TX-03-48 | TAG | 28.6 | 6.1 | 7.6 | 28.2 | 17.6 | 12.0 |  | 3.0 | 0.679 |

TABLE 24

TFA and TAG levels, fatty acid composition and TTQ in pOIL104 (pSSU:WRI1) + pOIL197
(pZmUbi:DGAT and pZmUbi:Oleosin) primary transformants at vegetative setting stage.

| Line | TFA or TAG | C16:0 | C18:0 | C18:1 | C18:2 | C18:3n3 | Other | TFA | TAG | TTQ |
|---|---|---|---|---|---|---|---|---|---|---|
| TX-04-02 | TFA | 12.6 | 1.7 | 1.2 | 11.3 | 68.4 | 4.7 | 2.7 |  |  |
| TX-04-02 | TAG | 19.2 | 8.2 | 3.9 | 29.4 | 35.1 | 4.2 |  | 0.0 | 0.008 |
| TX-04-25 | TFA | 12.4 | 1.5 | 0.7 | 8.1 | 72.7 | 4.7 | 3.1 |  |  |

TABLE 24-continued

TFA and TAG levels, fatty acid composition and TTQ in pOIL104 (pSSU:WRI1) + pOIL197
(pZmUbi:DGAT and pZmUbi:Oleosin) primary transformants at vegetative setting stage.

| Line | TFA or TFA | C16:0 | C18:0 | C18:1 | C18:2 | C18:3n3 | Other | TFA | TAG | TTQ |
|---|---|---|---|---|---|---|---|---|---|---|
| TX-04-25 | TAG | 21.9 | 11.7 | 5.3 | 19.8 | 38.3 | 3.0 |  | 0.1 | 0.020 |
| TX-04-11 | TFA | 13.5 | 2.0 | 0.5 | 7.2 | 70.8 | 6.0 | 3.2 |  |  |
| TX-04-11 | TAG | 17.4 | 3.9 | 3.3 | 13.6 | 55.2 | 6.5 |  | 0.1 | 0.019 |
| TX-04-27 | TFA | 13.1 | 1.7 | 1.5 | 9.8 | 67.8 | 6.0 | 3.2 |  |  |
| TX-04-27 | TAG | 18.2 | 3.6 | 2.6 | 24.1 | 44.6 | 6.8 |  | 0.4 | 0.134 |
| TX-04-24 | TFA | 12.9 | 1.9 | 0.6 | 7.6 | 72.2 | 4.8 | 3.3 |  |  |
| TX-04-24 | TAG | 24.2 | 11.4 | 3.7 | 17.3 | 40.5 | 3.1 |  | 0.1 | 0.017 |
| TX-04-16 | TFA | 13.0 | 2.9 | 0.8 | 8.9 | 70.0 | 4.5 | 3.4 |  |  |
| TX-04-16 | TAG | 22.5 | 8.1 | 4.9 | 22.3 | 37.5 | 4.6 |  | 0.1 | 0.023 |
| TX-04-30 | TFA | 13.0 | 1.6 | 1.3 | 8.7 | 70.2 | 5.2 | 3.5 |  |  |
| TX-04-30 | TAG | 18.5 | 3.8 | 2.6 | 22.5 | 46.9 | 5.8 |  | 0.3 | 0.072 |
| TX-04-10 | TFA | 18.9 | 2.7 | 1.0 | 8.3 | 60.8 | 8.3 | 3.5 |  |  |
| TX-04-10 | TAG | 34.0 | 5.5 | 3.2 | 17.7 | 30.0 | 9.5 |  | 0.1 | 0.034 |
| TX-04-13 | TFA | 13.0 | 2.0 | 0.7 | 6.4 | 72.7 | 5.1 | 3.5 |  |  |
| TX-04-13 | TAG | 16.2 | 5.0 | 3.6 | 14.8 | 55.9 | 4.5 |  | 0.1 | 0.017 |
| TX-04-19 | TFA | 19.4 | 2.2 | 0.6 | 9.9 | 62.7 | 5.2 | 3.5 |  |  |
| TX-04-19 | TAG | 30.2 | 4.3 | 3.1 | 24.8 | 33.2 | 4.4 |  | 0.1 | 0.025 |
| TX-04-06 | TFA | 11.6 | 1.6 | 1.0 | 11.2 | 69.6 | 5.1 | 3.6 |  |  |
| TX-04-06 | TAG | 14.1 | 4.5 | 3.4 | 27.9 | 40.6 | 9.4 |  | 0.1 | 0.036 |
| TX-04-14 | TFA | 12.9 | 3.3 | 3.3 | 8.6 | 65.7 | 6.1 | 3.6 |  |  |
| TX-04-14 | TAG | 20.3 | 8.9 | 4.0 | 21.4 | 40.2 | 5.3 |  | 0.1 | 0.024 |
| TX-04-04 | TFA | 10.7 | 1.8 | 0.6 | 8.0 | 74.3 | 4.6 | 3.9 |  |  |
| TX-04-04 | TAG | 11.0 | 10.1 | 3.8 | 17.2 | 56.3 | 1.7 |  | 0.2 | 0.044 |
| TX-04-15 | TFA | 17.4 | 2.4 | 1.1 | 12.2 | 60.2 | 6.5 | 4.0 |  |  |
| TX-04-15 | TAG | 28.5 | 5.6 | 2.2 | 23.3 | 31.6 | 8.9 |  | 0.6 | 0.160 |
| TX-04-08 | TFA | 17.5 | 1.9 | 1.9 | 15.1 | 57.5 | 6.1 | 4.0 |  |  |
| TX-04-08 | TAG | 28.0 | 4.5 | 4.8 | 29.5 | 23.5 | 9.7 |  | 0.5 | 0.130 |
| TX-04-22 | TFA | 13.1 | 3.5 | 1.4 | 12.9 | 63.9 | 5.3 | 4.1 |  |  |
| TX-04-22 | TAG | 17.1 | 7.8 | 4.3 | 29.5 | 33.3 | 8.0 |  | 0.6 | 0.150 |
| TX-04-09 | TFA | 13.7 | 2.4 | 4.1 | 20.4 | 53.8 | 5.5 | 4.1 |  |  |
| TX-04-09 | TAG | 17.4 | 5.3 | 9.5 | 38.1 | 20.6 | 9.1 |  | 0.6 | 0.158 |

The chimeric DNA constructs for *Agrobacterium*-mediated transformation are used to transform *Zea mays* (corn) as described by Gould et al. (1991). Briefly, shoot apex explants are co-cultivated with transgenic *Agrobacterium* for two days before being transferred onto a MS salt media containing kanamycin and carbenicillin. After several rounds of sub-culture, transformed shoots and roots spontaneously form and are transplanted to soil. The constructs are similarly used to transform *Hordeum vulgare* (barley) and *Avena sativa* (oats) using transformation methods known for these species. Briefly, for barley, the *Agrobacterium* cultures are used to transform cells in immature embryos of barley (cv. Golden Promise) according to published methods (Tingay et al., 1997; Bartlett et al., 2008) with some modifications in that embryos between 1.5 and 2.5 mm in length are isolated from immature caryopses and the embryonic axes removed. The resulting explants are co-cultivated for 2-3 days with the transgenic *Agrobacterium* and then cultured in the dark for 4-6 weeks on media containing timentin and hygromycin to generate embryogenic callus before being moved to transition media in low light conditions for two weeks. Calli are then transferred to regeneration media to allow for the regeneration of shoots and roots before transfer of the regenerated plantlets to soil. Transformed plants are obtained and grown to maturity in the glasshouse.

Example 6. Modifying Traits in Dicotyledonous Plants

Oil content in the dicotyledonous plant species *Trifolium repens* (clover), a legume commonly used as a pasture species, was increased by expressing the combination of WRI1, DGAT and Oleosin genes in vegetative parts. The construct pJP3502 was used to transform *T. repens* by *Agrobacterium*-mediated transformation (Larkin et al., 1996). Briefly, the genetic construct pJP3502 was introduced into *A. tumefaciens* via a standard electroporation procedure. The binary vector also contained a 35S:NptII selectable marker gene within the T-DNA. The transformed *Agrobacterium* cells were grown on solid LB media supplemented with kanamycin (50 mg/L) and rifampicin (25 mg/L) and incubated at 28° C. for two days. A single colony was used to initiate a fresh culture. Following 48 hours vigorous culture, the *Agrobacterium* cells was used to treat *T. repens* (cv. Haifa) cotyledons that had been dissected from imbibed seed as described by Larkin et al. (1996). Following co-cultivation for three days the explants were exposed to 25 mg/L kanamycin to select transformed shoots and then transferred to rooting medium to form roots, before transfer to soil.

Six transformed plants containing the T-DNA from pJP3502 were obtained and transferred to soil in the glasshouse. Increased oil content was observed in the non-seed tissue of some of the plants, with one plant showing greater than 4-fold increase in TAG levels in the leaves. Such plants are useful as animal feed, for example by growing the plants in pastures, providing feed with an increased energy content per unit weight (energy density) and resulting in increased growth rates in the animals.

The construct pJP3502 is also used to transform other leguminous plants such as alfalfa (*Medicago sativa*) and barrel medic (*Medicago truncatula*) by the method of Wright et al. (2006) to obtain transgenic plants which have increased TAG content in vegetative parts. The transgenic plants are useful as pasture species or as hay or silage as a source of feed for animals such as, for example, cattle, sheep and horses, providing an increased energy density in the feed.

Example 7. Modification of Plastidial GPAT Expression

Over-Expression of Plastidial GPAT in Plant Cells

A number of experiments were performed to test the hypothesis that the presence of a highly active 16:3 prokaryotic pathway in a plant (i.e. a so-called 16:3 plant) would provide much lower TAG levels in vegetative tissues upon introduction of the gene combination on pJP3502, relative to 18:3 plants. These experiments are described in the following Examples. Initially, the inventors tested whether the high level TAG accumulation observed in transgenic N. benthamiana could be disrupted by over-expression of a plastidial GPAT, increasing the flux in the prokaryotic pathway.

A coding region for expression of the Arabidopsis thaliana plastidial GPAT, ATS1 (Nishida et al., 1993), was amplified by RT-PCR from A. thaliana total RNA and cloned as an EcoRI-PstI fragment into the binary expression vector pJP3343 under the control of the 35S promoter to produce the constitutive expression vector pOIL098. The effect of over-expressing a plastidial GPAT in a high oil leaf background is determined by infiltration of the chimeric vector pOIL098 into high oil leaf tissue. The high oil leaf tissue is generated either by co-infiltration of WRI1 and DGAT binary expression vectors (Example 1) or by infiltrating pOIL098 into leaves of a Nicotiana plant stably transformed with the T-DNA from pJP3502 or another high oil vector. Oil content is expected to be reduced in the infiltrated leaf spots co-expressing the ATS1-encoding gene. This is determined by analysing TFA and TAG as proportions of sample dry mass. This is also determined by observing incorporation of labelled acetate into fatty acids produced by microsomes or leaf lysates made from infiltrated leaf spots.

Oil Accumulation in a Plastidial GPAT Mutant of Arabidopsis thaliana

The ats1 mutant of A. thaliana has a disruptive mutation in the gene encoding plastidial GPAT which reduced plastidial GPAT activity to a level of only 3.8% of the wild-type (Kunst et al., 1988). Non-seed TAG accumulation levels, at least in leaves, stems and roots, in both parental and ats1 mutant A. thaliana is tested and compared. The T-DNA of the pJP3502 construct for over-expression of the combination of genes encoding WRI1, DGAT and Oleosin is introduced by transformation into plants of both genotypes. The gene combination in the T-DNA of pJP3502 increases fatty acid synthesis in both plant backgrounds. However, the accumulation of TAG in the ats1 mutant is expected to be significantly higher on average than in the transgenic plants derived from the wild-type (parental) genotype due to the reduction in plastidial GPAT activity and therefore the reduced flux of fatty acids into the plastidial prokaryotic pathway. The ratio of the fatty acids C16:3 to C18:3 is significantly reduced in leaves of the ats1 mutant, both transformed and untransformed.

Silencing the Gene Encoding Plastidial GPAT in Plant Cells

In addition to genetically modifying a plant by introducing a mutation in a gene encoding a plastidial GPAT, the flux of fatty acids through the prokaryotic 16:3 pathway can be reduced and thereby increase oil content in vegetative parts by silencing the plastidial GPAT. This is demonstrated by producing a transgenic cassette having a constitutive or leaf-specific promoter expressing an RNA hairpin corresponding to a region of the gene encoding the plastidial GPAT from the selected species. As an example, an RNAi hairpin expression cassette is produced using the 581 bp SalI-EcoRV fragment of the A. thaliana plastidial GPAT cDNA sequence (NM_179407, SEQ ID NO:177). A region of any gene encoding a plastidial GPAT which has a high degree of sequence identity to the nucleotide sequence of NM_179407 can also be used to construct a gene for expression of a hairpin RNA for silencing an endogenous plastidial GPAT gene. A hpRNAi construct containing a 732 bp fragment (SEQ ID NO:210) of the N. benthamiana plastidial GPAT flanked by SmaI and KasI unique sites was designed for stable transformation into N. tabacum. The synthesized N. benthamiana plastidial GPAT fragment was subcloned into the SmaI-KasI sites of pJP3303, resulting in pOIL113. It is expected that reducing plastidial fatty acid retention will result in an increase in TAG accumulation, particularly when combined with a "Push" component such as over-expression of a transcription factor such as WRI1, or by a "Pull" component such as a DGAT or PDAT, and/or reduced SDP1 or TGD activity.

Inactivation of the gene encoding a plastidial GPAT or indeed any gene can be achieved using CRISPR/Cas9 methods. For example, inactivation of the gene encoding A. thaliana plastidial GPAT (Accession No. NM_179407) can be carried out by CRISPR/Cas9/sgRNA-mediated gene disruption and subsequent mutagenesis by non homologous end joining (NHEJ) DNA repair. Before targeted DNA cleavage, Cas9 stimulates DNA strand separation and allows a sgRNA to hybridize with a specific 20 nt sequence in the targeted gene. This positions the target DNA into the active site of Cas9 in proper orientation in relation to a PAM (tandem guanosine nucleotides) binding site. This positioning allows separate nuclease domains of Cas9 to independently cleave each strand of the target DNA sequence at a point 3-nt upstream of the PAM site. The double-strand break then undergoes error-prone NHEJ DNA repair during which deletions or insertions of a few nucleotides occur and result in inactivation of the plastidial GPAT gene. SgRNA sequences targeting the A. thaliana GPAT gene are identified and selected through the use of the CRISPR web tool (Xie et al., 2014). The 20nt target sequence can be any 20nt sequence within the target gene, including within non-coding regions of the gene such as a promoter or intron, provided that it is a specific sequence within the genome. The sequence can be inserted into a binary vector containing the CRISPR/Cas9/sgRNA expression cassette and kanamycin plant selectable marker (Jiang et al., 2013) and transformed into the plant cells by Agrobacterium-mediated transformation. Transgenic T1 plants can be screened for mutations in the plastidial GPAT gene by PCR amplification and DNA sequencing.

Example 8. Increasing Expression of Thioesterase in Plant Cells

De novo fatty acid synthesis takes place in the plastids of eukaryotic cells where the fatty acids are synthesized while bound to acyl carrier protein as acyl-ACP conjugates. Following chain elongation to C16:0 and C18:0 acyl groups and then desaturation to C18:1 while linked to ACP, the fatty acids are cleaved from the ACP by thioesterases and enter the eukaryotic pathway by export from the plastids and transport to the ER where they participate in membrane and storage lipid biogenesis. In chloroplasts, the export process has two steps: firstly, acyl chains are released as free fatty acids by the enzymatic activity of acyl-ACP thioesterases (fatty acyl thioesterase; FAT), secondly by reaction with CoA to form acyl-CoA esters which is catalysed by long chain acyl-CoA synthetases (LACS). *A. thaliana* contains 3 fatty acyl thioesterases which can be distinguished based on their acyl chain specificity. FATA1 and FATA2 preferentially hydrolyze unsaturated acyl-ACPs while saturated acyl-ACP chains are typically cleaved by FATB.

To explore the effect upon total fatty acid content, TAG content, and fatty acid composition of the co-expression of a thioesterase and genes encoding the WRI1 and/or DGAT polypeptides, chimeric genes were made for each of the three *A. thaliana* thioesterases by insertion of the coding regions into the pJP3343 binary expression vector for transient expression in *N. benthamiana* leaf cells from the 35S promoter. Protein coding regions for the *A. thaliana* FATA1 (Accession No. NP_189147.1, SEQ ID NO:193) and FATA2 (Accession No. NP_193041.1, SEQ ID NO:194) thioesterases were amplified from silique cDNA using primers containing EcoRI and PstI sites and subsequently cloned into pJP3343 using the same restriction sites. The resulting expression vectors were designated pOIL079 and pOIL080, respectively. The protein coding region of the *A. thaliana* FATB gene (Accession No. NP_172327.1, SEQ ID NO:195) was amplified using primers containing NotI and SacI flanking sites and cloned into the corresponding restriction sites of pJP3343, resulting in pOIL081. Constructs pOIL079, pOIL080 and pOIL081 are infiltrated into *N. benthamiana* leaf tissue, either individually or in combination with constructs containing the genes for the *A. thaliana* WRI1 transcription factor (AtWRI1) (pJP3414) and/or DGAT1 acyltransferase (AtDGAT1) (pJP3352). For comparison, chimeric genes encoding the *Cocos nucifera* FatB1 (CnFATB1) (pJP3630), *C. nucifera* FatB2 (CnFATB2) (pJP3629) were introduced into *N. benthamiana* leaf tissue in parallel with the *Arabidopsis* thioesterases, to compare the effect of the FatB polypeptides having MCFA specificity to the *Arabidopsis* thioesterases which do not have MCFA specificity. All of the infiltrations included a chimeric gene for expression of the p19 silencing suppressor as described in Example 1. The negative control infiltrated only the p19 T-DNA.

A synergistic effect was observed between thioesterase expression and WRI1 and/or DGAT over-expression on TAG levels in *N. benthamiana* leaves. Expression of the thioesterase genes without the WRI1 or DGAT genes significantly increased TAG levels above the low level in the negative control (p19 alone). For example, expression of the coconut FATB2 thioesterase resulted in an 8.2-fold increase in TAG levels in the leaves compared to the negative control. Co-expression of the *A. thaliana* WRI1 transcription factor with each of the thioesterases further increased TAG levels compared to the AtWRI1 control. Co-expression of each of the coconut thioesterases CnFATB1 and CnFATB2 with WRI1 resulted in higher TAG levels than each of the three *A. thaliana* thioesterases with WRI1. Interestingly, the converse was observed when the *A. thaliana* DGAT1 acyltransferase was co-expressed in combination with a thioesterase and WRI1. This suggested a better match in acyl-chain specificity of the *A. thaliana* thioesterases and the *A. thaliana* DGAT1 acyltransferase, resulting in a greater flux of acyl-chains from the acyl-ACP into TAG. The non-MCFA thioesterases were also considerably more effective in elevating the percentage of oleic acid in the total fatty acid content in the leaves. Co-expression of the AtWRI1, AtD-GAT1 and AtFATA2 resulted in the greatest level of TAG in the leaves, providing a level which was 1.6-fold greater than when AtWRI1 and AtDGAT1 were co-expressed without the thioesterase. These experiments confirmed the synergistic increase in oil synthesis and accumulation when both WRI1 and DGAT were co-expressed as well as showing the further synergistic increase obtained by adding a thioesterase to the combination.

Three different binary expression vectors were constructed to test the effect of co-expression of genes encoding WRI1, DGAT1 and FATA on TAG levels and fatty acid composition in stably transformed *N. tabacum* leaves. The vector pOIL121 contained an SSU::AtWRI1 gene for expression of AtWRI1 from the SSU promoter, a 35S::AtDGAT1 gene for expression of AtDGAT from the 35S promoter, and an enTCUP2::AtFATA2 gene for expression of AtFATA2 from the enTCUP2 promoter which is a constitutive promoter. These genetic constructs were derived from pOIL38 by first digesting the DNA with NotI to remove the gene coding for the *S. indicum* oleosin. The protein coding region of the *A. thaliana* FATA2 gene was amplified and flanked with NotI sites using pOIL80 DNA as template. This fragment was then inserted into the NotI site of pOIL38. pOIL121 then served as a parent vector for pOIL122 which contained an additional enTCUP2::SDP1 hairpin RNA cassette for RNAi-mediated silencing of the endogenous SDP1 gene in the transgenic plants. To do this, the entire *N. benthamiana* SDP1 hairpin cassette was isolated from pOIL51 (Example 2) as an SfoI-SmaI fragment and cloned into the SfoI site of pOIL121, producing pOIL122 (FIG. 14). A third vector, pOIL123, containing the SSU::WRI1 and 35S::DGAT1 genes and the enTCUP2::SDP1 hairpin RNA gene was obtained in a similar way by cloning the enTCUP2::SDP1 hairpin RNA cassette as a SfoI-SmaI fragment into the SfoI site of pOIL36.

In summary, the vectors contained the gene combinations:
pOIL121: SSU::AtWRI1, 35S::AtDGAT1, enTCUP2::AtFATA2.
pOIL122: SSU::AtWRI1, 35S::AtDGAT1, enTCUP2::AtFATA2, enTCUP2::SDP1 hairpin.
pOIL123: SSU::AtWRI1, 35S::AtDGAT1, enTCUP2::SDP1 hairpin.

The three constructs were each used to produce transformed *N. tabacum* plants (cultivar Wi38) by *Agrobacterium*-mediated transformation. Co-expression of the *A. thaliana* FATA2 thioesterase or silencing of the endogenous SDP1 TAG lipase in combination with AtWRI1 and AtDGAT1 expression each resulted in further elevated TAG levels compared to expression of AtWRI1 and AtDGAT1 in the absence of both of the thioesterase gene and the SDP1-silencing gene. The greatest TAG yields were obtained using pOIL122 by the combined action of all four chimeric genes.

It is noted that *N. benthamiana* is an 18:3 plant. The same constructs pOIL079, pOIL080 and pOIL081 are used to transform *A. thaliana*, a 16:3 plant.

The inventors conceived of the model that increasing plastidial fatty acid export such as by increased fatty acyl thioesterase activity reduces acyl-ACP accumulation in the plastids, thereby increasing fatty acid biosynthesis as a result of reduced feedback inhibition on the acetyl-CoA carboxylase (ACCase) (Andre et al., 2012; Moreno-Perez et al., 2012). Thioesterase over-expression increases export of acyl chains from the plastids into the ER, thereby providing an efficient link between so-called 'Push' and 'Pull' metabolic engineering strategies.

Example 9. The Effect of Different Transcription Factor Polypeptides on Plant Traits Previously reported experiments with WRI1 and DGAT (Vanhercke et al., 2013) used a synthetic gene encoding *A. thaliana* AtWRI1 (Accession No. AAP80382.1) and a synthetic gene encoding AtDGAT1, also from *A. thaliana* (Accession No. AAF19262; SEQ ID NO: 1). To compare other WRI polypeptides with AtWRI1 for their ability to combine with DGAT to increase oil content, other WRI coding sequences were identified and used to generate constructs for expression in *N. benthamiana* leaves. Nucleotide sequences encoding the *A. thaliana* WRI3 (Accession No. AAM91814.1, SEQ ID NO:196) and WRI4 (Accession No. NP_178088.2, SEQ ID NO:197) transcription factors (To et al., 2012) were synthesized and inserted as EcoRI fragments into pJP3343 under the control of the 35S promoter. The resulting binary expression vectors were designated pOIL027 and pOIL028, respectively. The coding sequence for the oat (*Avena sativa*) WRI1 (AsWRI1, SEQ ID NO:198) was PCR amplified from a vector provided by Prof. Sten Stymne (Swedish University of Agricultural Sciences) using flanking primers containing additional EcoRI sites. The amplified fragment was inserted into pJP3343 resulting in pOIL055. A WRI1 candidate sequence from *S. bicolor* (Accession No. XP_002450194.1, SEQ ID NO:199) was identified by a BLASTp search on the NCBI server using the *Zea mays* WRI1 amino acid sequence (Accession No. NP_001137064.1, SEQ ID NO:200) as query. The protein coding region of the *S. bicolor* WRI1 gene (SbWRIJ) was synthesized and inserted as an EcoRI fragment into pJP3343, yielding pOIL056. A gene candidate encoding a WRI1 was identified from the Chinese tallow (*Triadica sebifera*; TsWRI1, SEQ ID NO:201) transcriptome (Uday et al., submitted). The protein coding region was synthesized and inserted as an EcoRI fragment into pJP3343 resulting in pOIL070. The pJP3414 and pJP3352 binary vectors containing the coding sequences for expression of the *A. thaliana* WRI1 and DGAT1 polypeptides were as described by Vanhercke et al. (2013).

Plasmids containing the various WRI coding sequences were introduced into *N. benthamiana* leaf tissue for transient expression using a gene encoding the p19 viral suppressor protein in all inoculations as described in Example 1. The genes encoding the WRI polypeptides were either tested alone or in combination with the DGAT1 acyltransferase gene, the latter to provide greater TAG biosynthesis and accumulation. The positive control in this experiment was the combination of the genes encoding *A. thaliana* WRI1 transcription factor and AtDGAT1. All infiltrations were done in triplicate using three different plants and TAG levels were analyzed as described in Example 1. Expression of most of the individual WRI polypeptides in the absence of exogenously added DGAT1 resulted in increased, yet still low, TAG levels (<0.23% on dry weight basis) in infiltrated leaf spots, compared to the control which had only the p19 construct (FIG. 15). The exception was TsWRI1 which, by itself, did not appear to increase TAG levels significantly. In addition, differences in TAG levels produced by expression of the different WRI transcription factors on their own were not great. Both AsWRI1 and SbWRI1 yielded TAG levels similar to AtWRI1 on its own. Analysis of the TAG fatty acid composition revealed only minor changes except for increased C18:1Δ9 levels from expression of AtWRI3 in the infiltrated leaf tissues (Table 25).

TABLE 25

TAG fatty acid composition in *N. benthamiana* leaf samples infiltrated with different chimeric genes for expression of WRI (n = 3). All samples were also infiltrated with the P19 construct. The TAG samples also contained 0.1-0.4% C14:0; 0.5-1.2% C16:3 and; 0.1-0.7% C18:1Δ11.

| | Infiltrated genes | | | | | | | | | |
|---|---|---|---|---|---|---|---|---|---|---|
| | C16:0 | C16:1 | C18:0 | C18:1 | C18:2 | C18:3n3 | C20:0 | C20:1 | C22:0 | C24:0 |
| Control (P19) | 33.6 ± 4.7 | 0.5 ± 0.4 | 8.9 ± 2.2 | 4.7 ± 0.6 | 16.9 ± 1.0 | 32.2 ± 7.8 | 1.1 ± 0.2 | 0.8 ± 1.5 | 0.0 | 0.0 |
| WRI1 | 35.5 ± 3.4 | 0.7 ± 0.2 | 5.2 ± 0.8 | 5.4 ± 1.3 | 17.1 ± 1.0 | 33.1 ± 2.7 | 0.8 ± 0.1 | 0.5 ± 0.6 | 0.3 ± 0.0 | 0.0 |
| WRI3 | 27.3 ± 1.6 | 0.9 ± 0.2 | 4.8 ± 0.3 | 10.2 ± 1.5 | 16.1 ± 1.0 | 37.8 ± 1.2 | 0.8 ± 0.1 | 0.6 ± 0.7 | 0.1 ± 0.2 | 0.0 |
| WRI4 | 30.1 ± 0.4 | 1.0 ± 0.4 | 5.2 ± 0.8 | 4.6 ± 0.6 | 17.2 ± 0.4 | 38.1 ± 1.6 | 0.8 ± 0.1 | 1.3 ± 1.3 | 0.0 | 0.0 |
| AsWRI | 35.7 ± 3.0 | 1.7 ± 0.4 | 5.3 ± 0.7 | 6.5 ± 0.3 | 15.4 ± 0.4 | 31.6 ± 1.6 | 0.8 ± 0.1 | 0.4 ± 0.7 | 0.3 ± 0.1 | 0.0 |
| SbWRI | 37.4 ± 0.8 | 1.9 ± 0.3 | 4.8 ± 0.3 | 7.0 ± 1.2 | 15.2 ± 0.3 | 30.8 ± 0.3 | 0.8 ± 0.1 | 0.4 ± 0.6 | 0.3 ± 0.0 | 0.0 |
| TsWRI | 34.5 ± 4.8 | 0.0 | 9.4 ± 8.2 | 5.9 ± 1.7 | 16.0 ± 0.7 | 29.3 ± 12.4 | 0.0 | n.d. | 0.0 | 0.0 |
| Control (P19) | 31.0 ± 2.1 | 0.9 ± 0.1 | 8.7 ± 1.3 | 8.0 ± 2.3 | 24.9 ± 1.5 | 22.1 ± 4.7 | 2.0 ± 0.1 | 0.0 | 0.6 ± 0.6 | 0.2 ± 0.4 |
| WRI1 + DGAT | 27.7 ± 0.1 | 0.3 ± 0.0 | 7.0 ± 0.1 | 17.2 ± 0.7 | 27.9 ± 0.9 | 14.7 ± 0.3 | 2.4 ± 0.2 | 0.3 ± 0.0 | 1.1 ± 0.1 | 0.8 ± 0.2 |
| WRI3 + DGAT | 30.0 ± 0.8 | 0.6 ± 0.1 | 5.9 ± 0.4 | 13.9 ± 2.9 | 21.5 ± 1.1 | 21.3 ± 0.8 | 2.8 ± 0.1 | 0.2 ± 0.0 | 1.8 ± 0.1 | 1.0 ± 0.2 |
| WRI4 + DGAT | 27.0 ± 0.5 | 0.2 ± 0.1 | 8.5 ± 0.2 | 5.8 ± 0.7 | 23.9 ± 0.8 | 25.2 ± 1.3 | 3.5 ± 0.1 | 0.2 ± 0.0 | 2.1 ± 0.2 | 1.7 ± 0.2 |
| AsWRI + DGAT | 33.8 ± 0.5 | 1.1 ± 0.1 | 5.5 ± 0.9 | 12.2 ± 1.6 | 26.0 ± 1.9 | 16.3 ± 1.3 | 2.2 ± 0.2 | 0.2 ± 0.0 | 1.2 ± 0.1 | 0.8 ± 0.1 |
| SbWRI + DGAT | 34.6 ± 0.5 | 1.3 ± 0.1 | 5.6 ± 0.4 | 13.9 ± 1.6 | 23.6 ± 1.3 | 15.8 ± 0.6 | 2.2 ± 0.1 | 0.2 ± 0.0 | 1.2 ± 0.1 | 0.9 ± 0.1 |
| TsWRI + DGAT | 25.4 ± 0.5 | 0.2 ± 0.0 | 9.4 ± 0.1 | 7.7 ± 1.0 | 27.0 ± 1.3 | 22.1 ± 2.4 | 3.6 ± 0.2 | 0.2 ± 0.0 | 1.8 ± 0.2 | 1.3 ± 0.2 |

In contrast, differences in TAG yields from expression of the different WRI polypeptides were more pronounced upon co-expression with the AtDGAT1 acyltransferase. This again demonstrated the synergistic effect of WRI1 and DGAT co-expression on TAG biosynthesis in infiltrated *N. benthamiana* leaf tissue, as reported by Vanhercke et al. (2013). Intermediate TAG levels were observed upon co-expression of DGAT1 with AtWRI3, AtWRI4 and TsWRI1 expressing vectors while levels obtained with the AsWRI1 and AtWRI1 were significantly lower. In a result that could not have been predicted beforehand, the highest TAG yields were obtained with co-expression of DGAT with SbWRI1, even though the assay was done in dicotyledonous cells. TAG fatty acid composition analysis revealed increased levels of C18:19 and decreased levels of C18:3$^{\Delta 9,12,15}$ (ALA) in the case of SbWRI1, AsWRI1 and the AtWRI1 positive control. Unlike AtWRI1, however, expression of AsWRI1 and SbWRI1 both displayed increased C16:0 levels compared to the p19 negative control. Interestingly, AtWRI3 infiltrated leaf samples exhibited a distinct TAG profile with C18:10$^{\Delta 9}$ being enriched while C16:0 and ALA were only slightly affected.

This experiment showed that the *S. bicolor* WRI1 transcription factor, SbWRI1, was superior to AtWRI1 when co-expressed with DGAT to increase TAG levels in vegetative plant parts. The inventors also concluded that a transcription factor, for example a WRI1, from a monocotyledonous plant could function well in a dicotyledonous plant cell, indeed might even have superior activity compared to a corresponding transcription factor from a dicotyledonous plant. Likewise, a transcription factor from a dicotyledonous plant could function well in a monocotyledonous plant cell.

Use of Other Transcription Factors

Genetic constructs were prepared for expression of each of 14 different transcription factors in plant cells to test their ability to function for increasing TAG levels in combination with other genes involved in TAG biosynthesis and accumulation. These transcription factors were candidates as alternatives for WRI1 or for addition to combinations including one or more of WRI1, LEC1 and LEC2 transcription factors for use in plant cells, particularly in vegetative plant parts. Their selection was largely based on their reported involvement in embryogenesis (reviewed in Baud and Lepiniec (2010), and Ikeda et al. (2006)), similar to LEC2. Experiments were therefore carried out to assay their function, using the N. benthamiana expression system (Example 1), as follows.

Nucleotide sequences of the protein coding regions of the following transcription factors were codon optimized for expression in N. benthamiana and N. tabacum, synthesized and subcloned as NotI-SacI fragments into the respective sites of pJP3343: A. thaliana FUS3 (pOIL164) (Luerssen et al., 1998; Accession number AAC35247; SEQ ID NO:160), A. thaliana LEC1L (pOIL165) (Kwong et al. 2003; Accession number AAN15924; SEQ ID NO:157), A. thaliana LEC1 (pOIL166) (Lotan et al., 1998; Accession number AAC39488; SEQ ID NO:149), G. max MYB73 (pOIL167) (Liu et al., 2014; Accession number ABH02868; SEQ ID NO:212), A. thaliana bZIP53 (pOIL168) (Alonso et al., 2009; Accession number AAM14360; SEQ ID NO:213), A. thaliana AGL15 (pOIL169) (Zheng et al., 2009; Accession number NP_196883; SEQ ID NO:214), A. thaliana MYB118 (Accession number AAS58517; pOIL170; SEQ ID NO:215), MYB115 (Wang et al., 2002; Accession number AAS10103; pOIL171; SEQ ID NO:216), A. thaliana TANMEI (pOIL172) (Yamagishi et al., 2005; Accession number BAE44475; SEQ ID NO:217), A. thaliana WUS (pOIL173) (Laux et al., 1996; Accession number NP_565429; SEQ ID NO:218), A. thaliana BBM (pOIL174) (Boutilier et al., 2002; Accession number AAM33893, SEQ ID NO:145), B. napus GFR2a1 (Accession number AFB74090; pOIL177; SEQ ID NO:219) and GFR2a2 (Accession number AFB74089; pOIL178; SEQ ID NO:220) (Liu et al. (2012)). In addition, a codon optimized version of the A. thaliana PHR1 transcription factor involved in adaptation to high light phosphate starvation conditions was similarly subcloned into pJP3343 (pOIL189) (Nilsson et al (2012); Accession number AAN72198; SEQ ID NO:221). These transcription factors are summarised in Table 26.

As a screening assay to determine the function of these transcription factors, the genetic constructs and a gene encoding DGAT1 were co-infiltrated into N. benthamiana leaf cells as described in Example 1, either with or without a gene encoding WRI1. Total lipid content and fatty acid composition of the leaf cells were analysed 5 days post-infiltration. Among the various embryogenic transcription factors tested, only overexpression of FUS3 resulted in significantly increased TAG levels in N. benthamiana leaf tissue when compared to DGAT and DGAT1+WRI1 control infiltrations (Table 27).

TABLE 26

Additional transcription factors and the genetic constructs for their expression

| Plasmid | Transcription factor | Species | Length (amino acid) | Accession number |
|---|---|---|---|---|
| pOIL164 | FUS3 | A. thaliana | 312 | AAC35247 |
| pOIL165 | LEC1L | A. thaliana | 234 | AAN15924 |
| pOIL166 | LEC1 | A. thaliana | 208 | AAC39488 |
| pOIL167 | MYB73 | G. max | 74 | ABH02868 |
| pOIL168 | bZIP53 | A. thaliana | 146 | AAM14360 |
| pOIL169 | AGL15 | A. thaliana | 268 | NP_196883 |
| pOIL170 | MYB118 | A. thaliana | 437 | AAS58517 |
| pOIL171 | MYB115 | A. thaliana | 359 | AAS10103 |
| pOIL172 | TANMEI | A. thaliana | 386 | BAE44475 |
| pOIL173 | WUS | A. thaliana | 292 | NP_565429 |
| pOIL174 | BBM | A. thaliana | 584 | AAM33803 |
| pOIL177 | GFR2a1 | B. napus | 453 | AFB74090 |
| pOIL178 | GFR2a2 | B. napus | 461 | AFB74089 |
| pOIL189 | PHR1 | A. thaliana | 409 | AAN72198 |

TABLE 27

TAG level (% leaf dry weight) and fatty acid profile of infiltrated N. benthamiana leaves.

| | C16:0 | C16:1 | C18:0 | C18:1 | C18:2 | C18:3 | TAG |
|---|---|---|---|---|---|---|---|
| P19 | 27.1 ± 1.5 | 0.3 ± 0.1 | 9.6 ± 1.7 | 4.4 ± 1.2 | 22.4 ± 4.0 | 30.5 ± 0.9 | 0.0 |
| P19 + DGAT1 | 26.3 ± 1.0 | 0.1 ± 0.0 | 10.7 ± 0.6 | 3.7 ± 0.7 | 26.1 ± 1.6 | 26.4 ± 1.4 | 0.2 ± 0.0 |
| P19 + DGAT1 + FUS3 | 24.1 ± 1.0 | 0.1 ± 0.0 | 6.3 ± 0.4 | 5.2 ± 1.6 | 27.9 ± 1.8 | 30.0 ± 1.8 | 0.6 ± 0.1 |
| P19 + DGAT1 + LEC1L | 26.0 ± 1.4 | 0.1 ± 0.0 | 10.3 ± 0.8 | 3.9 ± 1.0 | 26.6 ± 2.1 | 26.4 ± 0.7 | 0.2 ± 0.0 |
| P19 | 30.3 ± 0.7 | 0.0 | 12.4 ± 0.7 | 6.8 ± 0.9 | 22.9 ± 0.2 | 26.0 ± 0.9 | 0.0 |
| P19 + DGAT1 | 25.8 ± 1.1 | 0.0 | 10.1 ± 0.4 | 4.4 ± 0.9 | 26.1 ± 1.3 | 26.2 ± 1.4 | 0.2 ± 0.0 |
| P19 + DGAT1 + WRI1 | 22.7 ± 0.9 | 0.0 | 10.1 ± 0.4 | 14.9 ± 0.5 | 27.9 ± 1.3 | 18.5 ± 0.8 | 0.3 ± 0.1 |
| P19 + DGAT1 + FUS3 | 23.9 ± 0.7 | 0.2 ± 0.1 | 7.6 ± 0.4 | 5.3 ± 0.7 | 29.1 ± 0.8 | 26.8 ± 0.7 | 0.4 ± 0.1 |
| P19 + DGAT1 + LEC1 | 24.9 ± 0.4 | 0.1 ± 0.2 | 11.1 ± 0.2 | 4.0 ± 0.1 | 25.9 ± 0.5 | 26.1 ± 0.6 | 0.1 ± 0.0 |
| P19 + DGAT1 + MYB73 | 25.8 ± 0.3 | 0.0 | 10.9 ± 0.7 | 4.3 ± 1.0 | 26.2 ± 0.8 | 25.2 ± 1.8 | 0.1 ± 0.0 |
| P19 | 34.2 ± 4.9 | 0.0 | 10.6 ± 3.1 | 8.3 ± 4.1 | 19.5 ± 1.4 | 23.2 ± 0.8 | 0.1 ± 0.1 |
| P19 + DGAT1 | 27.7 ± 0.1 | 0.3 ± 0.1 | 9.9 ± 1.1 | 4.2 ± 0.3 | 26.4 ± 1.8 | 22.5 ± 0.4 | 0.2 ± 0.1 |
| P19 + DGAT1 + WRI1 | 24.8 ± 1.0 | 0.2 ± 0.0 | 8.8 ± 1.0 | 14.7 ± 0.6 | 27.6 ± 1.0 | 17.2 ± 0.3 | 0.4 ± 0.1 |
| P19 + DGAT1 + bZIP53 | 29.3 ± 0.8 | 0.1 ± 0.2 | 8.7 ± 0.4 | 2.9 ± 0.3 | 22.0 ± 0.5 | 25.9 ± 0.5 | 0.1 ± 0.1 |
| P19 + DGAT1 + AGL15 | 29.2 ± 1.4 | 0.2 ± 0.0 | 4.9 ± 0.9 | 7.0 ± 1.9 | 19.8 ± 0.8 | 30.0 ± 1.3 | 0.3 ± 0.1 |
| P19 + DGAT1 + MYB118 | 31.6 ± 1.7 | 0.2 ± 0.1 | 5.8 ± 1.2 | 4.8 ± 0.8 | 20.7 ± 0.3 | 28.2 ± 1.6 | 0.2 ± 0.1 |
| P19 | 27.4 ± 1.2 | 0.0 | 6.9 ± 1.0 | 4.8 ± 2.6 | 20.0 ± 1.5 | 39.0 ± 4.1 | 0.1 ± 0.0 |
| P19 + DGAT1 | 26.0 ± 1.1 | 0.0 | 8.0 ± 0.6 | 4.2 ± 1.6 | 22.3 ± 2.4 | 33.9 ± 4.3 | 0.2 ± 0.0 |
| P19 + DGAT1 + WRI1 | 23.4 ± 0.8 | 0.1 ± 0.1 | 8.5 ± 0.6 | 17.0 ± 2.4 | 23.3 ± 1.8 | 23.3 ± 4.3 | 0.5 ± 0.1 |
| P19 + DGAT1 + MYB115 | 26.3 ± 0.4 | 0.1 ± 0.1 | 6.6 ± 0.3 | 2.8 ± 0.4 | 22.5 ± 1.8 | 35.7 ± 2.9 | 0.2 ± 0.0 |
| P19 + DGAT1 + TANMEI | 25.6 ± 0.9 | 0.1 ± 0.2 | 8.5 ± 1.2 | 2.6 ± 0.5 | 21.9 ± 2.0 | 35.3 ± 3.8 | 0.2 ± 0.0 |

TABLE 27-continued

TAG level (% leaf dry weight) and fatty acid profile of infiltrated *N. benthamiana* leaves.

|  | C16:0 | C16:1 | C18:0 | C18:1 | C18:2 | C18:3 | TAG |
|---|---|---|---|---|---|---|---|
| P19 + DGAT1 + WUS | 24.3 ± 0.9 | 0.1 ± 0.1 | 5.5 ± 0.6 | 1.7 ± 0.2 | 16.8 ± 1.6 | 47.9 ± 3.3 | 0.2 ± 0.0 |
| P19 | 30.5 ± 1.3 | 0.0 | 8.1 ± 0.9 | 8.2 ± 6.0 | 21.8 ± 1.2 | 28.3 ± 7.3 | 0.1 ± 0.1 |
| P19 + DGAT1 + WRI1 | 25.9 ± 1.7 | 0.2 ± 0.0 | 8.3 ± 0.7 | 19.9 ± 2.8 | 24.5 ± 1.1 | 16.0 ± 0.6 | 0.8 ± 0.1 |
| P19 + DGAT1 + WRI1 + BBM | 27.7 ± 0.7 | 0.2 ± 0.0 | 6.7 ± 0.2 | 21.2 ± 0.7 | 19.8 ± 0.5 | 18.5 ± 0.6 | 0.5 ± 0.1 |
| P19 + DGAT1 + WRI1 + GFR2a1 | 29.2 ± 1.3 | 0.4 ± 0.0 | 6.1 ± 0.1 | 12.9 ± 1.5 | 24.3 ± 0.4 | 20.9 ± 0.5 | 0.4 ± 0.1 |
| P19 + DGAT1 + WRI1 + GFR2a2 | 29.9 ± 2.4 | 0.4 ± 0.1 | 5.5 ± 0.6 | 13.5 ± 2.7 | 23.0 ± 0.5 | 21.3 ± 1.2 | 0.5 ± 0.1 |
| P19 + DGAT1 + WRI1 + PHR1 | 26.2 ± 0.3 | 0.2 ± 0.0 | 4.9 ± 0.0 | 7.6 ± 0.2 | 19.2 ± 0.3 | 36.0 ± 0.7 | 0.3 ± 0.0 |
| P19 | 32.0 ± 1.9 | 1.6 ± 2.7 | 11.1 ± 2.7 | 5.5 ± 2.2 | 23.3 ± 1.1 | 25.4 ± 3.3 | 0.0 |
| P19 + DGAT1 + WRI1 | 27.5 ± 1.2 | 0.7 ± 0.8 | 6.8 ± 0.4 | 16.6 ± 2.1 | 26.7 ± 0.8 | 16.5 ± 0.3 | 1.2 ± 0.2 |
| P19 + DGAT1 + WRI1 + FUS3 | 23.6 ± 1.1 | 2.1 ± 3.5 | 6.5 ± 0.5 | 13.3 ± 0.9 | 32.1 ± 2.6 | 15.6 ± 1.5 | 1.6 ± 0.1 |

For stable transformation of plants using genes encoding the alternative transcription factors, the following binary constructs are made. The genes for expression of the transcription factors use either the SSU promoter or the SAG12 promoter. Over-expression of embryogenic transcription factors such as LEC1 and LEC2 has been shown to induce a variety of pleotropic effects, undesirable in the present context, including somatic embryogenesis (Feeney et al. (2012); Santos-Mendoza et al. (2005); Stone et al. (2008); Stone et al. (2001); Shen et al. (2010)). To minimize possible negative impact on plant development and biomass yield, tissue or developmental-stage specific promoters are preferred over constitutive promoters to drive the ectopic expression of master regulators of embryogenesis.

Example 10. Stem-Specific Expression of a Gene Encoding a Transcription Factor Leaves of *N. tabacum* plants expressing transgenes encoding WRI1, DGAT and Oleosin contain about 1600 TAG at seed setting stage of development. However, the TAG levels were much lower in stems (1%) and roots (1.4%) of the plants (Vanhercke et al., 2014). The inventors considered whether the lower TAG levels in stems and roots were due to poor promoter activity of the Rubisco SSU promoter used to express the gene encoding WRI1 in the transgenic plants. The DGAT transgene in the T-DNA of pJP3502 was expressed by the CaMV35S promoter which is expressed more strongly in stems and roots and therefore was unlikely to be the limiting factor for TAG accumulation in stems and roots.

In an attempt to increase TAG biosynthesis in stem tissue, a construct was designed in which the gene encoding WRI1 was placed under the control of an *A. thaliana* SDP1 promoter. A 3.156 kb synthetic DNA fragment was synthesized comprising 1.5 kb of the *A. thaliana* SDP1 promoter (SEQ ID NO: 175) (Kelly et al., 2013), followed by the coding region for the *A. thaliana* WRI1 polypeptide and the *G. max* lectin terminator/polyadenylation region. This fragment was inserted between the SacI and NotI sites of pJP3303. The resulting vector was designated pOIL050, which was then used to transform cells from the *N. tabacum* plants homozygous for the T-DNA from pJP3502 by *Agrobacterium*-mediated transformation. Transgenic plants were selected for hygromycin resistance and a total of 86 independent transgenic plants were grown to maturity in the glasshouse. Samples were taken from transgenic leaf and stem tissue at seed setting stage and contain increased TAG levels compared to the *N. tabacum* parental plants transformed with pJP3502.

Example 11. Effect of Oil Body Protein Expression on Plant Traits

*N. tabacum* plants transformed with the T-DNA of pJP3502 and expressing transgenes encoding *A. thaliana* WRI1, DGAT1 and *S. indicum* Oleosin had increased TAG levels in vegetative tissues. As shown in Example 2 above, when the endogenous gene encoding SDP1 TAG lipase was silenced in those plants, the leaf TAG levels further increased, which indicated to the inventors that substantial TAG turnover was occurring in the plants that retained SDP1 activity. Therefore, the level of expression of the transgenes in the plants was determined. While Northern hybridisation blotting confirmed strong WRI1 and DGAT1 expression and some oleosin mRNA expression, expression analysis by digital PCR and qRT-PCR detected only very low levels of oleosin transcripts. The expression analysis revealed that the gene encoding the Oleosin was poorly expressed compared to the WRI1 and DGAT1 transgenes. From these experiments, the inventors concluded that the oil bodies in the leaf tissue were not completely protected from TAG breakdown because of inadequate production of Oleosin protein when encoded by the T-DNA in pJP3502. To improve stable accumulation of TAG throughout plant development, several pJP3502 modifications were designed in which the Oleosin gene was substituted. These modified constructs were as follows.

1. pJP3502 contains a gene (SEQ ID NO:176 provides the sequence of its complement) encoding the *S. indicum* oleosin which was poorly expressed. That gene has an internal UBQ10 intron which might be reducing the expression level. To test this, a 502 bp synthetic DNA fragment containing the *S. indicum* oleosin gene and lacking the internal UBQ10 intron was synthesized and inserted into pJP3502 as a NodI fragment, to substitute the oleosin gene containing the intron in pJP3502. The resultant plasmid was designated pOIL040.
2. The Rubisco small subunit (SSU) promoter driving expression of the oleosin gene in pJP3502 was replaced by the constitutive enTCUP2 promoter. To this end, a 2321 bp fragment containing the enTCUP2 promoter, Oleosin protein coding region, *G. max* lectin terminator/polyadenylation region and the first 643 bp of the downstream SSU promoter driving wri1 expression was synthesized and subcloned into the AscI and SpeI sites of pJP3502 resulting in pOIL038.
3. A similar strategy was followed for the expression of an engineered version of the *S. indicum* oleosin gene containing 6 introduced cysteine residues (o3-3) under the control of the enTCUP2 promoter (Winichayakul et al., 2013). A 2298 bp fragment containing the enTCUP2 promoter, Oleosin o3-3 protein coding region, *G. max* lectin terminator/polyadenylation region and the first 643 bp of the downstream SSU promoter driving wri1 expression was synthesized and subcloned into the AscI and SpeI sites of pJP3502 resulting in pOIL037.

4. The Nod sites flanking the *S. indicum* oleosin gene in pJP3502 were used to exchange the protein coding region for one encoding peanut Oleosin3 (Accession No. AAU21501.1) (Parthibane et al., 2012a; Parthibane et al., 2012b). A 528 bp fragment containing the oleosin3 gene, flanked by Nod sites, was synthesized and subcloned into the respective site of pJP3502. The resulting vector was designated pOIL041.

5. Similarly, a 1077 bp Nod flanked fragment containing the gene coding for the *A. thaliana* steroleosin (Arab-1) (Accession No. AAM10215.1) (Jolivet et al., 2014) was synthesized and subcloned into the Nod site of pJP3502, resulting in pOIL043.

6. The *Nannochloropsis oceanic* lipid droplet surface protein (LDSP) (Accession No. AFB75402.1) (Vieler et al., 2012) was synthesized as a 504 bp Nod-flanked fragment and subcloned into the Nod site of pJP3502, yielding pOIL044.

7. Finally, the *A. thaliana* caleosin (CLO3) (Accession No. O22788.1) (Shimada et al., 2014) was synthesized as a 612 bp NotI flanked fragment and subcloned into pJP3502, resulting in pOIL042.

Each of these constructs was introduced into *N. benthamiana* leaf cells as described in Example 1. Transient expression of both pJP3502 and pOIL040 in *N. benthamiana* leaf tissue resulted in elevated TAG levels and similar changes in the TAG fatty acid profile but pOIL040 increased the TAG level more (1.3% compared to 0.9%). Each of the constructs pOIL037, pOIL038, pOIL041, pOIL042 and pOIL043 were used to stably transform *N. tabacum* plants (cultivar W38) by *Agrobacterium*-mediated methods. Transgenic plants were selected on the basis of kanamycin resistance and are grown to maturity in the glasshouse. Samples are taken from transgenic leaf tissue at different stages during plant development and contain increased TAG levels compared to wild-type *N. tabacum* and *N. tabacum* plants transformed with pJP3502.

Cloning and Characterisation of LDAP Polypeptides from *Sapium sebiferum*

Oleosins are not highly expressed in non-seed oil accumulating plant tissues such as the mesocarp of olive, oil palm, and avocado (Murphy, 2012). Instead, lipid droplet associated proteins (LDAP) have been identified in these tissues that may play a similar role to that of oleosin in seed tissues (Horn et al., 2013). The inventors therefore considered it possible that oleosin might not be the optimal packaging protein to protect the accumulated oil from TAG lipase or other cytosolic enzyme activities in vegetative tissues of plants. LDAP polypeptides were therefore identified and evaluated for enhancement of TAG accumulation, as follows.

The fruit of Chinese tallow tree, *Sapium sebiferum*, a member of the family Euphorbiaceae, was of particular interest to the inventors as it contains an oil-rich tissue outside of the seed. A recent study (Divi et al, submitted for publication) indicated that this oleoginous tissue, called a tallow layer, might be derived from the mesocarp of its fruit. Therefore, the inventors queried the transcriptome of *S. sebiferum* for LDAP sequences. A comparative analysis of expressed genes in the fruit coat and seed tissues revealed a group of three previously unidentified LDAP genes which were highly expressed in the tallow layer.

Nucleotide sequences encoding the three LDAPs were obtained by RT-PCR using RNAs derived from tallow tissue using three pairs of primers. The primer sequences were based on the DNA sequences flanking the entire coding region of each of the three genes. The primer sequences were: for LDAP1, 5'-TTTTAACGATATCCGCTAAAGG-3' (SEQ ID NO: 236) and 5'-AATGAATGAACAAGAAT-TAAGTC-3' (SEQ ID NO: 237) AT-3'; LDAP2, 5'-CTTTTCTCACACCGTATCTCCG-3' (SEQ ID NO: 238) and 5'-AGCATGATATA CTTGTCGAGAAAGC-3' (SEQ ID NO: 239); LDAP3, 5'-GCGACAGTGTAGCGTTTT-3' (SEQ ID NO: 240) and 5'-ATACATAAAATGAAAACTAT-TGTGC-3' (SEQ ID NO: 241).

Analysis of the *S. sebiferum* transcriptome revealed multiple orthologs for each of the LDAP genes, including eight LDAP1, six LDAP2, and six LDAP3 genes, with less than 10% sequence divergence within each gene family. The putative peptide sequences were aligned and a phylogenetic tree was constructed using Genious software (FIG. 16), together with LDAPs homologs from other plant species, including two from avocado (Pam), one from oil palm, one from *Parthenium argentatum* (Par), two from *Arabidopsis* (Ath), five from *Taraxacum brevicorniculatum* (Tbr), three from *Hevea brasiliensis* (Hbr), as presented in FIG. 16. The phylogenetic tree was revealed that the SsLDAP3 shared greater amino acid sequence identity to the LDAP1 and LDAP2 polypeptides from avocado and the LDAP from oil palm, while the SsLDAP1 and SsLDAP2 polypeptides were more divergent.

Genetic Constructs for Over-Expression of LDAP

In order to test the function of the LDAPs from *S. sebiferum*, expression vectors were made to express each of these polypeptides under the control of the 35S promoter in leaf cells. The full length SsLDAP cDNA sequences were inserted into the pDONR207 destination vector by recombination reactions, replacing the CcdB and Cm(R) regions of the destination vector with the SsLDAP cDNA fragments. Following confirmation by restriction digestion analysis and DNA sequencing, the constructs were introduced into *Agrobacterium tumefaciens* strain AGL1 and used for both transient expression in *N. benthamiana* leaf cells and stable transformation of *N. tabacum*.

The expression of each of the three SsLDAP genes under the transcriptional control of the 35S promoter in *N. benthamiana* leaves in combination with the expression of 35S::AtDGAT1 and 35S::AtWRI1 yielded substantially higher levels of TAG accumulation relative to the cells infiltrated with the 35S::AtDGAT1 and 35S::AtWRI1 genes without the LDAP construct. The TAG level was increased about 2-fold above the TAG level in the control cells. A significant increase in the level of α-linolenic acid (ALA) and a reduced level of saturated fatty acids was observed in the cells receiving the combination of genes, relative to the control cells.

Co-Localisation of YFP-Fused LDAP Polypeptides with Lipid Droplets in Leaf Cells In order to characterise SsLDAPs in vivo and observe their dynamic behaviour, expression constructs were made for expression of fusion polypeptides consisting of the LDAP polypeptides fused to yellow fluorescent protein (YFP). For each fusion polypeptide, the YFP was fused in-frame to the C-terminus of the SsLDAP. The full open reading frame of each of the three LDAP genes without a stop codon, at its 3' end, was fused to the YFP sequence and the chimeric genes inserted into pDONR207. Following confirmation of the resultant constructs by restriction digestion and DNA sequencing, the constructs were introduced into *A. tumefaciens* strain AGL1 and used for both transient expression in *N. benthamiana* leaf cells and stable transformation of *N. tabacum*. Three days following infiltration of the leaf cells with the LDAP-YFP constructs, leaf discs from the infiltrated zones were stained with Nile Red, which positively stained lipid droplets, and observed under a confocal microscope to detect both the red stain (lipid droplets) and fluorescence from the YFP polypeptide. Co-localisation of LDAP-YFP with the lipid droplets was observed, indicating that the LDAP associated with the lipid droplets in the leaf cells.

Example 12. Silencing of TGD Genes in Plants

Li-Beisson et al. (2013) estimated that in *Arabidopsis* leaves (a 16:3 plant), approximately 40% of the fatty acids synthesized in chloroplasts enter the prokaryotic pathway, whereas 60% were exported to enter the eukaryotic pathway. After they were desaturated in the ER, about half of these exported fatty acids are returned to the plastid to support galactolipid synthesis for thylakoid membranes. The transport (import) of the fatty acids as DAG or phospholipids into the plastid involves TGD1, a permease-like protein of the inner chloroplast envelope. The *Arabidopsis* ABC lipid transporter comprising TGD1, 2, and 3 proteins was identified by Benning et al. (2008 and 2009) and more recently by Roston et al. (2012). This protein complex is localized in the inner chloroplast envelope membrane and is proposed to mediate the transfer of phosphatidate across this membrane. TGD2 polypeptide is a phosphatidic-binding protein, and TGD3 an ATPase. A novel *Arabidopsis* protein, TGD4, was identified by a genetic approach (Xu et al., 2008) and inactivation of the TGD4 gene also blocked lipid transfer from the ER to plastids. Recent biochemical data indicate that TGD4 is phosphatidate binding protein residing in the outer chloroplast envelope membrane (Wang and Benning, 2012).

Xu et al. (2005) described leaky tgd1 alleles in *A. thaliana* resulting in reduced plant growth and high occurrence of embryo abortion. Leaf tissue of *A. thaliana* tgd1 mutants contained increased TAG levels, likely as cytosol oil droplets. In addition, elevated TAG levels were also found in roots of tgd1 mutants. No difference in seed oil content was detected. Similar TAG accumulation in leaf tissue has been reported for *A. thaliana* tgd2 (Awai et al., 2006), tgd3 (Lu et al., 2007) and tgd4 mutants (Xu et al., 2008). All tgd mutant alleles were either sufficiently leaky or severely impairing in plant development.

TGD1 Silencing

A silencing construct directed against the TGD1 plastidial importer was generated based on a full length mRNA transcript identified in the *N. benthamiana* transcriptome. A 685 bp fragment was amplified from *N. benthamiana* leaf cDNA while incorporating a PmlI site at the 5' end. The TGD1 fragment was first cloned into pENTR/D-TOPO (Invitrogen) and subsequently inserted into the pHELLS-GATE12 destination vector via LR cloning (Gateway). The resulting expression vector was designated pOIL025 and is transiently expressed in *N. benthamiana* to assess the effect of TGD1 gene silencing on leaf TAG levels. The TGD1 hairpin construct is placed under the control of the *A. niger* inducible alcA promotor by subcloning as a PmlI-EcoRV fragment into the NheI (klenow)-SfoI sites of pOIL020 (below). The resulting vector, designated pOIL026, is super- transformed into a homozygous *N. tabacum* pJP3502 line to further increase leaf oil levels.

Further constructs are made for expressing hairpin RNA for reducing expression of the TGD-2, -3, -4 and -5 genes. Transformed plants are produced using these constructs and oil content determined in the transformants. The transformed plants are crossed with the transformants generated with pJP3502 or other combinations of genes as described above.

Example 13. Expression of Gene Combinations in Potato Tubers

Construction of pJP3506

A genetic construct containing three genes for expression in potato tubers was made and used for potato transformation. This construct was designated as pJP3506 and was based on an existing vector pJP3502 (WO2013/096993) with replacement of promoters to provide for tuber-specific expression. pJP3506 contained (i) an NPTII kanamycin resistance gene driven by 35S promoter with duplicated enhancer region (e35S) as the selectable marker gene and three gene expression cassettes, which were (ii) 35S::AtDGAT1 encoding the *Arabidopsis thaliana* DGAT1, (iii) B33::AtWRI1 encoding the *Arabidopsis thaliana* WRI1, and (iv) B33::sesame oleosin, encoding the oleosin from *Sesame indicum*. The nucleotide sequences encoding these polypeptides were as in pJP3502. The patatin B33 promoter (B33) was a tuber specific promoter derived from *Solanum tuberosum*, which was provided by Dr Alisdair Fernie, Max Planck Institute of Molecular Plant Physiology, Potsdam, Germany. A circular plasmid map of pJP3506 is presented in FIG. 17.

The *S. tuberosum* Patatin B33 promoter sequence used in the pJP3506 construct was a truncated version having 183 nucleotides deleted from the 5' end and 261 nucleotides deleted from the 3' end relative to GenBank Accession No. X14483. The nucleotide sequence of the patatin B33 promoter as used in pJP3506 is given as SEQ ID NO: 202.

Transformation of Potato

Potato seedlings (*Solanum tuberosum*) of cultivar Atlantic which had been grown aseptically in tissue culture were purchased from Toolangi Elite, Victorian Certified Seed Potato Authority (ViCSPA), Victoria, Australia. Stem internodes were excised into pieces of approximately 1 cm in length under a suspension of *Agrobacterium tumefaciens* strain LBA4404 containing pJP3506. The *Agrobacterium* cells had been grown to an OD of 0.2 and diluted with an equal volume MS medium. Excess *Agrobacterium* suspension was removed by brief blotting the stem pieces on sterile filter paper, which were then plated onto MS medium and maintained at 24° C. for two days (co-cultivation). The internodes were then transferred onto fresh MS medium supplemented with 200 µg/L NAA, 2 mg/L BAP and 250 mg/L Cefetaxime. Selection of transgenic calli was initiated 10 days later when the internodes were transferred onto fresh MS medium supplemented with 2 mg/L BAP, 5 mg/L GA3, 50 mg/L kanamycin and 250 mg/L Cefetaxime. Shoots regenerated from calli were excised and placed onto plain MS medium for root induction prior to transplanting into a 15 cm diameter pot containing potting mix and grown in the greenhouse until plant maturity including tuber growth.

DNA Extraction and Molecular Identification of the Transgenic Plants by PCR

Disks of about 1 cm in diameter were obtained from potato leaves from the plants in the greenhouse. These were placed in a deep-well microtiter plate and freeze dried for 48 hr. The freeze dried leaf samples were then ground into powder by adding a steel ball bearing to each well and shaking the plate in a Reicht tissue lyser (Qiagen) at a maximum frequency of 28/sec for 2 min each side of the microtiter plate. 375 μL of extraction buffer containing 0.1 M Tris-HCl pH8.0, 0.05 M EDTA and 1.25% SDS was added to each well containing the powdered leaf tissue. Following 1 hr incubation at 65° C., 187 μL of 6M ammonium acetate was added to each well and the mixtures stored at 4° C. for 30 min prior to centrifugation of the plates for 30 min at 3000 rpm. 340 μL supernatant from each well was transferred into a new deep well microtiter plate containing 220 μL isopropanol and maintained for 5 min at room temperature prior to centrifugation at 3000 rpm for 30 min. The precipitated DNA pellets were washed with 70% ethanol, air dried and resuspended in 225 μL H$_2$O per sample.

Two μL from each leaf sample DNA preparation was added to a 20 μL PCR reaction mix using the HotStar PCR system (Qiagen). A pair of oligonucleotide primers based on 5' and 3' sequences from the *Arabidopsis thaliana* WRI1 gene, codon-optimized for tobacco, was used in the PCR reactions. Their sequences were: Nt-Wri-P3: 5'-CACTCGTGCTTTCCATCATC-3' (SEQ ID NO: 203) and Nt-Wri-P1: 5'-GAAGGCTGAGCAACAAGAGG-3' (SEQ ID NO: 204). A pair of oligonucleotide primers based on the *Arabidopsis thaliana* DGAT1 gene, codon-optimized for tobacco, was also used in a separate PCR reaction on each DNA sample. Their sequences were: Nt-DGAT-P2: 5'-GGCGATTTTGGATTCTGC-3' (SEQ ID NO: 205) and Nt-DGAT-P3: 5'-CCCAACCCTTCCGTATACAT-3' (SEQ ID NO: 206). Amplification was carried out with an initial cycle at 95° C. for 15 min, followed by 40 cycles of 95° C. for 30 sec, 57° C. for 30 sec and 72° C. for 60 sec. The PCR products were electrophoresed on a 1% agarose gel to detect specific amplification products.

Lipid Analysis of Potato Tubers

Thin slices of tubers harvested from regenerated potato plants, for confirmed transgenic plants and non-transformed controls, were freeze-dried for 72 hr and analysed for lipid content and composition. Total lipids were extracted from the dried tuber tissues using chloroform:methanol:0.1 M KCl (2:1:1 v/v/v) as follows. The freeze-dried tuber tissues were first homogenized in chloroform:methanol (2:1, v/v) in an eppendorf tube containing a metallic ball using a Reicht tissue lyser (Qiagen) for 3 min at a frequency of 29 per sec. After mixing each homogenate with a Vibramax 10 (Heidolph) at 2,000 rpm for 15 min, 1/3 volume of 0.1 M KCl solution was added to each sample and mixed further. Following centrifugation at 10,000 g for 5 min, the lower phase containing lipids from each sample was collected and evaporated completely using N$_2$ flow. Each lipid preparation was dissolved in 3 μL of CHCl$_3$ per milligram of tuber dry weight. Aliquots of the lipid preparations were loaded on a thin layer chromatography (TLC) plate (20 cm×20 cm, Silica gel 60, Merck) and developed in hexane:diethyl ether:acetic acid (70:30:1, v/v/v). The TLC plate was sprayed with Primuline and visualized under UV to show lipid spots. TAG and PL were recovered by scraping the silica of the appropriate bands and converted to fatty acid methyl esters (FAME) by incubating the material in 1 N methanolic-HCl (Supelco, Bellefonte, PA) at 80° C. for 2 hr together with known amount of Triheptadecanoin (Nu-Chek PREP, Inc. USA) as internal standard for lipid quantification. FAME were analysed by GC-FID (7890A GC, Agilent Technologies, Palo Alto, CA) equipped with a 30 m BPX70 column (0.25 mm inner diameter, 0.25 mm film thickness, SGE, Austin, USA) as described previously (Petrie et al., 2012). Peaks were integrated with Agilent Technologies ChemStation software (Rev B.04.03).

Among the approximately 100 individual transgenic lines regenerated, analysis of lipids derived from young potato tubers of about 2 cm in diameter revealed increased levels in total lipids, TAG and phospholipids fractions in tubers from many of the transgenic plants, with a range observed between no increase to substantial increases. The first analysis of the potato tuber lipids indicated that a typical wild-type potato tuber at its early stage of development (about 2 cm in diameter) contained about the 0.03% TAG on dry weight basis.

The content of total lipids was increased to 0.5-4.7% by weight (dry weight) in tubers of 21 individual transgenic plants, representing 16 independently transformed lines (Table 29). Tubers of line #69 showed the highest TAG accumulation at an average 3.3% on dry weight basis. This was approximately a 100-fold increase relative to the wild-type tubers at the same developmental stage. Tubers of the same transgenic line also accumulated the highest observed levels of phospholipids at 1.0% by weight in the young tubers on a dry weight basis (Table 30). The enhanced lipid accumulation was also accompanied by an altered fatty acid composition in transgenic tubers. The transgenic tubers consistently accumulated higher percentages of saturated and monounsaturated fatty acids (MUFA) and lower level of polyunsaturated fatty acids (PUFA) in both the total fatty acid content and in the TAG fraction of the total fatty acid content (Table 29), particularly a reduced level of 18:3 (ALA) which was reduced from about 17% in the wild-type to less than 10% in the transgenic tubers. The level of oleic acid (18:1) in the total fatty acid content increased from about 1% in the wild-type to more than 5% in many of the lines and more than 15% in some of the tubers. Although palmitic acid levels were increased, the stearic acid (18:0) levels decreased in the best transgenic lines (Tables 28 and 29).

TABLE 28

Total lipid yield (% weight of potato tuber dry weight) and its fatty acid composition in representative young potato tubers transformed with the T-DNA of pJP3506, prior to flowering of the plants. Tubers of line 65 were equivalent to the wild-type (non-transgenic) tubers.

| Sample | C14:0 | C16:0 | C16:1 | C16:3 | C18:0 | C18:1 | C18:1d11 | C18:2 | C18:3 | C20:0 | C20:1 | C22:0 | C24:0 | % TFA |
|---|---|---|---|---|---|---|---|---|---|---|---|---|---|---|
| 4-2 | 0.2 | 16.1 | 0.2 | 0.0 | 5.8 | 0.5 | 11.7 | 55.5 | 5.5 | 2.1 | 0.2 | 0.6 | 1.5 | 1.4 |
| 19 | 0.2 | 18.1 | 0.2 | 0.0 | 5.8 | 0.4 | 12.9 | 52.2 | 5.9 | 2.0 | 0.2 | 0.7 | 1.5 | 1.5 |
| 27-2 | 0.2 | 18.9 | 0.3 | 0.0 | 6.5 | 0.5 | 5.5 | 55.0 | 8.0 | 2.0 | 0.2 | 0.8 | 2.1 | 0.7 |
| 27-4 | 0.2 | 19.0 | 0.3 | 0.0 | 6.5 | 5.4 | 0.5 | 57.0 | 7.9 | 1.6 | 0.0 | 0.5 | 1.1 | 0.6 |
| 27-5 | 0.2 | 17.8 | 0.6 | 0.0 | 6.4 | 2.2 | 0.4 | 57.6 | 11.7 | 1.5 | 0.0 | 0.4 | 1.2 | 0.7 |
| 27-6 | 0.2 | 18.7 | 0.4 | 0.0 | 6.9 | 6.3 | 0.5 | 55.9 | 8.2 | 1.6 | 0.0 | 0.4 | 0.9 | 0.8 |
| 55 | 0.2 | 17.8 | 0.6 | 0.0 | 6.4 | 7.9 | 0.5 | 55.7 | 8.6 | 1.4 | 0.0 | 0.3 | 0.7 | 1.0 |
| 65 | 0.2 | 19.4 | 0.4 | 0.0 | 5.7 | 1.2 | 0.5 | 53.6 | 17.2 | 0.9 | 0.0 | 0.0 | 1.0 | 0.5 |
| 69 | 0.3 | 19.8 | 0.1 | 0.0 | 3.2 | 16.5 | 0.9 | 53.2 | 3.7 | 1.1 | 0.3 | 0.4 | 0.6 | 4.7 |

TABLE 28-continued

Total lipid yield (% weight of potato tuber dry weight) and its fatty acid composition in representative young potato tubers
transformed with the T-DNA of pJP3506, prior to flowering of the plants. Tubers of line 65 were equivalent to the wild-type (non-transgenic) tubers.

| Sample | C14:0 | C16:0 | C16:1 | C16:3 | C18:0 | C18:1 | C18:1d11 | C18:2 | C18:3 | C20:0 | C20:1 | C22:0 | C24:0 | % TFA |
|---|---|---|---|---|---|---|---|---|---|---|---|---|---|---|
| 78 | 0.2 | 19.5 | 0.5 | 0.0 | 5.3 | 4.9 | 0.5 | 54.7 | 11.7 | 1.2 | 0.0 | 0.4 | 1.0 | 0.9 |
| 83 | 0.2 | 16.7 | 0.4 | 0.0 | 6.5 | 7.3 | 0.5 | 56.2 | 8.5 | 1.7 | 0.6 | 0.5 | 0.9 | 1.3 |
| 95-1 | 0.3 | 21.0 | 0.2 | 0.1 | 3.1 | 15.2 | 0.8 | 52.8 | 4.2 | 1.1 | 0.2 | 0.3 | 0.7 | 3.0 |
| 95-2 | 0.4 | 21.3 | 0.3 | 0.1 | 4.1 | 7.1 | 1.0 | 56.1 | 7.3 | 1.2 | 0.2 | 0.3 | 0.7 | 2.7 |
| 95-3 | 0.4 | 21.4 | 0.3 | 0.0 | 4.3 | 8.5 | 0.9 | 54.5 | 7.4 | 1.3 | 0.0 | 0.3 | 0.7 | 1.5 |
| 100 | 0.4 | 19.0 | 0.5 | 0.0 | 5.4 | 7.6 | 0.8 | 55.5 | 7.3 | 1.4 | 0.5 | 0.5 | 0.9 | 1.0 |
| 104 | 0.2 | 18.0 | 0.2 | 0.0 | 6.1 | 0.5 | 6.8 | 56.1 | 7.6 | 2.3 | 0.1 | 0.6 | 1.5 | 0.9 |
| 106 | 0.2 | 19.7 | 0.2 | 0.1 | 4.6 | 0.9 | 10.7 | 54.1 | 5.7 | 1.7 | 0.1 | 0.6 | 1.3 | 1.3 |

TABLE 29

TAG yield (% weight of potato tuber dry weight) and its fatty acid composition in
representative young potato tubers, transformed with the T-DNA of pJP3506, prior to flowering of the plants.

| Sample | C14:0 | C16:0 | C16:1 | C16:3 | C18:0 | C18:1 | C18:1d11 | C18:2 | C18:3 | C20:0 | C20:1 | C22:0 | C24:0 | % TAG |
|---|---|---|---|---|---|---|---|---|---|---|---|---|---|---|
| WT | 0.4 | 13.4 | 0.0 | 0.0 | 4.6 | 5.5 | 0.5 | 59.9 | 15.7 | 0.0 | 0.0 | 0.0 | 0.0 | 0.03 |
| 4-2 | 0.3 | 15.4 | 0.2 | 0.0 | 7.0 | 0.6 | 16.4 | 52.5 | 3.1 | 2.6 | 0.2 | 0.6 | 1.1 | 0.5 |
| 19 | 0.2 | 16.3 | 0.1 | 0.0 | 7.2 | 18.0 | 0.5 | 50.9 | 3.6 | 1.9 | 0.2 | 0.4 | 0.6 | 0.8 |
| 27-2 | 0.0 | 19.0 | 0.0 | 0.0 | 11.2 | 9.8 | 0.0 | 52.8 | 4.4 | 2.8 | 0.0 | 0.0 | 0.0 | 0.2 |
| 27-4 | 0.4 | 17.4 | 0.0 | 0.0 | 10.2 | 9.4 | 0.0 | 55.4 | 4.7 | 2.6 | 0.0 | 0.0 | 0.0 | 0.2 |
| 27-5 | 0.0 | 17.9 | 0.0 | 0.0 | 12.5 | 4.4 | 0.0 | 54.9 | 7.1 | 3.2 | 0.0 | 0.0 | 0.0 | 0.1 |
| 27-6 | 0.0 | 17.1 | 0.0 | 0.0 | 9.9 | 10.6 | 0.0 | 55.0 | 4.9 | 2.5 | 0.0 | 0.0 | 0.0 | 0.2 |
| 55 | 0.3 | 17.6 | 0.5 | 0.0 | 8.5 | 12.5 | 0.6 | 52.5 | 5.2 | 1.9 | 0.0 | 0.0 | 0.6 | 0.5 |
| 65 | 0.0 | 18.1 | 0.0 | 0.0 | 12.0 | 0.0 | 0.0 | 55.6 | 14.4 | 0.0 | 0.0 | 0.0 | 0.0 | 0.0 |
| 69 | 0.3 | 20.1 | 0.6 | 0.0 | 3.8 | 20.3 | 1.0 | 49.4 | 2.2 | 1.3 | 0.2 | 0.3 | 0.5 | 3.3 |
| 78 | 0.0 | 19.1 | 0.0 | 0.0 | 8.2 | 9.4 | 0.0 | 52.5 | 8.4 | 2.4 | 0.0 | 0.0 | 0.0 | 0.2 |
| 83 | 0.3 | 16.4 | 0.2 | 0.0 | 8.7 | 11.1 | 0.6 | 53.4 | 5.4 | 2.6 | 0.0 | 0.5 | 0.7 | 0.5 |
| 95-1 | 0.3 | 21.7 | 0.4 | 0.1 | 3.6 | 18.5 | 1.0 | 50.1 | 2.8 | 0.9 | 0.2 | 0.2 | 0.3 | 2.2 |
| 95-2 | 0.6 | 23.4 | 0.4 | 0.0 | 5.1 | 10.1 | 1.2 | 51.9 | 5.3 | 1.4 | 0.0 | 0.0 | 0.5 | 0.9 |
| 95-3 | 0.3 | 17.2 | 0.3 | 0.0 | 7.7 | 0.6 | 11.6 | 49.7 | 8.9 | 2.5 | 0.0 | 0.0 | 1.1 | 0.1 |
| 100 | 0.0 | 18.8 | 0.5 | 0.0 | 8.0 | 12.0 | 0.8 | 54.0 | 3.9 | 2.0 | 0.0 | 0.0 | 0.0 | 0.4 |
| 104 | 0.3 | 17.7 | 0.0 | 0.0 | 8.4 | 0.6 | 11.0 | 52.1 | 4.7 | 3.2 | 0.0 | 0.7 | 1.3 | 0.3 |
| 106 | 0.4 | 20.1 | 0.3 | 0.0 | 5.4 | 15.5 | 1.1 | 51.8 | 3.6 | 1.4 | 0.0 | 0.0 | 0.4 | 0.7 |

TABLE 30

Phospholipids yield (% weight of potato tuber dry weight) and its fatty acid composition in
representative young potato tubers, transformed with the T-DNA of pJP3506, prior to flowering.

| Sample | C14:0 | C16:0 | C16:1 | C16:3 | C18:0 | C18:1 | C18:1d11 | C18:2 | C18:3 | C20:0 | C20:1 | C22:0 | C24:0 | % PL |
|---|---|---|---|---|---|---|---|---|---|---|---|---|---|---|
| 4-2 | 0.2 | 21.2 | 0.2 | 0.0 | 4.6 | 0.4 | 3.8 | 57.8 | 9.3 | 0.9 | 0.0 | 0.0 | 1.7 | 0.3 |
| 19 | 0.1 | 22.7 | 0.2 | 0.0 | 4.4 | 5.1 | 0.3 | 54.9 | 8.9 | 0.7 | 1.0 | 0.5 | 1.2 | 0.4 |
| 27-2 | 0.2 | 21.0 | 0.3 | 0.0 | 5.2 | 2.8 | 0.4 | 56.9 | 9.3 | 0.9 | 1.3 | 0.4 | 1.4 | 0.4 |
| 27-4 | 0.0 | 22.9 | 0.0 | 0.0 | 6.0 | 2.3 | 0.0 | 57.2 | 8.8 | 1.1 | 0.0 | 0.0 | 1.6 | 0.3 |
| 27-5 | 0.0 | 19.6 | 0.5 | 0.0 | 5.0 | 1.2 | 0.0 | 58.7 | 12.6 | 1.0 | 0.0 | 0.0 | 1.4 | 0.4 |
| 27-6 | 0.0 | 22.9 | 0.0 | 0.0 | 6.3 | 2.6 | 0.0 | 56.3 | 9.3 | 1.2 | 0.0 | 0.0 | 1.5 | 0.3 |
| 55 | 0.1 | 21.2 | 0.4 | 0.0 | 5.1 | 2.1 | 0.0 | 57.8 | 11.4 | 0.7 | 0.0 | 0.0 | 1.0 | 0.4 |
| 65 | 0.0 | 21.4 | 0.4 | 0.0 | 5.9 | 1.1 | 0.0 | 53.2 | 15.7 | 1.0 | 0.0 | 0.0 | 1.3 | 0.3 |
| 69 | 0.2 | 21.5 | 0.2 | 0.0 | 2.3 | 3.7 | 0.6 | 61.9 | 7.9 | 0.6 | 0.0 | 0.4 | 0.8 | 1.0 |
| 78 | 0.0 | 22.1 | 0.4 | 0.0 | 4.4 | 2.7 | 0.4 | 55.6 | 12.2 | 0.8 | 0.0 | 0.0 | 1.3 | 0.4 |
| 83 | 0.2 | 21.1 | 0.3 | 0.0 | 5.0 | 2.9 | 0.4 | 57.1 | 10.7 | 0.8 | 0.0 | 0.4 | 1.1 | 0.5 |
| 95-1 | 0.2 | 24.8 | 0.5 | 0.0 | 2.6 | 3.5 | 0.6 | 59.1 | 7.6 | 0.6 | 0.0 | 0.0 | 0.6 | 0.6 |
| 95-2 | 0.3 | 22.1 | 0.0 | 0.0 | 2.7 | 2.1 | 0.6 | 61.0 | 9.6 | 0.7 | 0.0 | 0.0 | 0.9 | 0.6 |
| 95-3 | 0.2 | 23.2 | 0.5 | 0.0 | 3.1 | 3.6 | 0.7 | 57.7 | 9.3 | 0.7 | 0.0 | 0.0 | 0.9 | 0.5 |
| 100 | 0.0 | 23.3 | 0.5 | 0.0 | 4.6 | 3.0 | 0.4 | 57.2 | 9.0 | 0.8 | 0.0 | 0.0 | 1.1 | 0.4 |
| 104 | 0.0 | 21.3 | 0.0 | 0.0 | 4.8 | 2.7 | 0.0 | 58.3 | 10.1 | 1.0 | 0.0 | 0.0 | 1.7 | 0.4 |
| 106 | 0.2 | 23.2 | 0.2 | 0.0 | 3.8 | 3.0 | 0.6 | 57.1 | 8.6 | 0.7 | 1.0 | 0.4 | 1.1 | 0.4 |

The transgenic potato plants were maintained in the glasshouse to allow for continued growth of the tubers. Larger tubers of line #69 contained greater levels of TFA and TAG than the tubers of about 2 cm in diameter.

Further increased levels of TFA and TAG are obtained in potato tubers by addition of a chimeric gene that encodes a silencing RNA for down-regulating the expression of the endogenous SDP1 gene, in combination with the WRI1 and DGAT genes.

Further Gene Combinations for Transformation of Potato

Total RNA from fresh developing potato (*Solanum tuberosum* L. cv. Atlantic) tubers was extracted by the TRIzol method (Invitrogen). Selected regions of the cDNAs encoding potato AGPase small subunit and SDP1 were obtained through RT-PCR using the following primers: st-AGPs1: 5'-ACAGACATGTCTAGACCCAGATG-3' (SEQ ID NO: 242), st-AGPa1: 5'-CACTCTCATCC-CAAGTGAAGTTGC-3' (SEQ ID NO: 243); st-SDP1-s1: 5'-CTGAGATGGAAGTGAAGCACAGATG-3' (SEQ ID NO: 244), and st-SDP1-al: 5'-CCATTGT-TAGTCCTTTCAGTC-3' (SEQ ID NO: 245). The PCR products were then purified and ligated to pGEMT Easy.

Following verification by DNA sequencing, the cloned PCR products were either directly used as the target gene sequence to make a hairpin RNAi construct or fused by overlapping PCR. Three PCR fragments (SDP1, AGPase, SDP+AGP) were subsequently cloned into the pKannibal vector that contained specific restriction sites to clone the desired fragment in sense and antisense orientation. The restriction sites selected were BamHI and HindIII for cloning the fragment in the sense orientation and KpnI and XhoI for inserting the fragment in the antisense orientation. Primers sets used for amplification of the three target gene fragments were altered by addition of restriction sites which direct the fragment into cloning sites of pKannibal. The expression cassettes containing the target DNA fragment between the 35S promoter and OCS terminator in pKannibal were released with Not1 and cloned into a binary vector pWBVec2 with hygromycin as the plant selectable marker. Such binary vectors were introduced into *A. tumefaciens* AGL1 strain and used for potato transformation as described above.

Example 14. Modifying Traits in Monocotyledonous Plants

Expression in Endosperm

The oil content in the endosperm of the monocotyledonous plant species *Triticum aestivum* (wheat) and therefore in the grain of the plants was increased by expressing a combination of genes encoding WRI1, DGAT and Oleosin in the endosperm during grain development using endosperm-specific promoters. The construct (designated pOIL-Endo2) contained the chimeric genes: (a) the promoter of the Glu1 gene of *Brachypodium distachyon*: protein coding region of the *Zea mays* gene encoding the ZmWRI1 polypeptide (SEQ ID NO:35)::terminator/polyadenylation region from the *Glycine max* lectin gene, (b) the promoter of the Bx17 glutenin gene of *Triticum aestivum*::protein coding region of the *A. thaliana* gene encoding the AtDGAT1 polypeptide (SEQ ID NO:1)::terminator/polyadenylation region from the *Agrobacterium tumefaciens* Nos gene, (c) the promoter of the GluB4 gene of *Oryza sativa*::protein coding region of the *Sesame indicum* gene encoding the Oleosin polypeptide::terminator/polyadenylation region from the *Glycine max* lectin gene and (d) a 35S promoter:: hygromycin resistance coding region as a selectable marker gene. The construct was used to transform immature embryos of *T. aestivum* (cv. Fielder) by *Agrobacterium*-mediated transformation. The inoculated immature embryos were exposed to hygromycin to select transformed shoots and then transferred to rooting medium to form roots, before transfer to soil.

Thirty transformed plants were obtained which set T1 seed and contained the T-DNA from pOIL-Endo2. Mature seeds were harvested from all 30 plants, and 6 seed of each family cut in half. The halves containing the embryo were stored for later germination; the other half containing mainly endosperm was extracted and tested for oil content. The T-DNA inserted into the wheat genome was still segregating in the T1 seeds from these plants, so the T1 seeds were a mixture of homozygous transformed, heterozygous transformed and nulls for the T-DNA. Increased oil content was observed in the endosperm of some of the grains, with some grains showing greater than a 5-fold increase in TAG levels. The endosperm halves of six wild-type grains (cv. Fielder) had a TAG content of about 0.47% by weight (range 0.37% to 0.60%), compared to a TAG content of 2.5% in some grains. Some families had all six grains with TAG in excess of 1.7%; others were evidently segregating with both wild type and elevated content of TAG. In endosperms with elevated TAG content the fatty acid composition was also altered, showing increases in the percentages of oleic acid and palmitic acid, and a decrease in the percentage of linoleic acid (Table 31). The T1 grain germinated without difficulty at the same rate as the corresponding wild-type grain and plants representing both high oil and low oil individuals from 14 T0 families were grown to maturity. These plants were fully male and female fertile.

TABLE 31

Fatty acid composition (% of total fatty acids) of TAG content and the total TAG content (% oil by weight of half endosperms) in transgenic wheat endosperm

| Sample | C14:0 | C16:0 | C16:1 | C16:3 |
|---|---|---|---|---|
| Control 1 | 0.3 | 16.9 | 0.1 | 0.0 |
| Control 2 | 0.3 | 16.0 | 0.1 | 0.1 |
| F5.3 | 0.1 | 20.1 | 0.1 | 0.1 |
| F16.3 | 0.1 | 19.1 | 0.1 | 0.1 |

| Sample | C18:0 | C18:1 | C18:1d11 | C18:2 |
|---|---|---|---|---|
| Control 1 | 1.6 | 15.6 | 0.6 | 60.4 |
| Control 2 | 1.6 | 15.1 | 0.6 | 61.3 |
| F5.3 | 2.6 | 23.5 | 0.6 | 48.5 |
| F16.3 | 2.8 | 24.2 | 0.6 | 48.1 |

| Sample | C18:3n3 | C20:0 | C20:1 | C22:0 |
|---|---|---|---|---|
| Control 1 | 4.0 | 0.1 | 0.4 | 0.0 |
| Control 2 | 4.3 | 0.1 | 0.3 | 0.0 |
| F5.3 | 2.4 | 0.8 | 0.7 | 0.3 |
| F16.3 | 2.9 | 0.7 | 0.5 | 0.3 |

| Sample | C24:0 | % oil by wt. |
|---|---|---|
| Control 1 | 0.0 | 0.5 |
| Control 2 | 0.0 | 0.49 |
| F5.3 | 0.4 | 2.5 |
| F16.3 | 0.4 | 1.8 |

220 T2 seed from 22 selected T1 plants were analysed, plus 40 plants from 3 different parental Fielder plants. In most cases ten T2 seed from each T1 plant were tested. Some of the selected T1 plants were nulls with wild type endosperm TAG levels. Some of the results for endosperm half seed analyses are represented in FIG. 18. The high endosperm oil T1 plants produced T2 grain many of which had increased endosperm oil, whereas the control Fielder and null segregant T1 plants produced grain with similar levels of endosperm oil (total fatty acid, TFA).

The grain is useful for preparing food products for human consumption or as animal feed, providing grain with an increased energy content per unit weight (energy density) and resulting in increased growth rates in the animals such as, for example, poultry, pigs, cattle, sheep and horses.

The construct pOIL-Endo2 is also used to transform corn (*Zea mays*) and rice (*Oryza sativa*) to obtain transgenic plants which have increased TAG content in endosperm and therefore in grain.

Expression in Leaves and Stems

A series of binary expression vectors was designed for *Agrobacterium*-mediated transformation of sorghum (*S. bicolor*) and wheat (*Triticum aestivum*) to increase the oil content in vegetative tissues. The starting vectors for the constructions were pOIL093-095, pOIL134 and pOIL100-104 (see Example 5). Firstly, a DNA fragment encoding the *Z. mays* WRI1 polypeptide was amplified by PCR using pOIL104 as a template and primers containing KpnI restriction sites. This fragment was subcloned downstream of the constitutive *Oryza sativa* Actin1 promoter of pOIL095, using the KpnI site. The resulting vector was designated pOIL154. The DNA fragment encoding the *Umbelopsis ramanniana* DGAT2a under the control of the *Z. mays* ubiquitin promoter (pZmUbi) was isolated from pOIL134 as a NotI fragment and inserted into the NotI site of pOIL154, resulting in pOIL155. An expression cassette consisting of the PAT coding region under the control of the pZmUbi promoter and flanked at the 3' end by the *A. tumefaciens* NOS terminator/polyadenylation region was constructed by amplifying the PAT coding region using pJP3416 as a template. Primers were designed to incorporate BamHI and SacI restriction sites at the 5' and 3' ends, respectively. After BamHI+SacI double digestion, the PAT fragment was cloned into the respective sites of pZLUbi1casNK. The resulting intermediate was designated pOIL141. Next, the PAT selectable marker cassette was introduced into the pOIL155 backbone. To this end, pOIL141 was first cut with NotI, blunted with Klenow fragment of DNA polymerase I and subsequently digested with AscI. This 2622 bp fragment was then subcloned into the ZraI-AscI sites of pOIL155, resulting in pOIL156. Finally, the Actin1 promoter driving WRI1 expression in pOIL156 was exchanged for the *Z. mays* Rubisco small subunit promoter (pZmSSU) resulting in pOIL157. This vector was obtained by PCR amplification of the *Z. mays* SSU promoter using pOIL104 as a template and flanking primers containing AsiSI and PmlI restriction sites. The resulting amplicon was then cut with SpeI+MluI and subcloned into the respective sites of pOIL156.

These vectors therefore contained the following expression cassettes:

pOIL156: promoter *O. sativa* Actin1::*Z. mays* WRI1, promoter *Z. mays* Ubiquitin::*U. rammaniana* DGAT2a and promoter *Z. mays* Ubiquitin::PAT pOIL157: promoter *Z. mays* SSU::*Z. mays* WRI1, promoter *Z. mays* Ubiquitin::*U. rammaniana* DGAT2a and *Z. mays* Ubiquitin::PAT.

A second series of binary expression vectors containing the *Z. mays* SEE1 senescence promoter (Robson et al., 2004, see Example 5), *Z. mays* LEC1 transcription factor (Shen et al., 2010) and a *S. bicolor* SDP1 hpRNAi fragment were constructed as follows. First, a matrix attachment region (MAR) was introduced into pORE04 by AatII+SnaBI digest of pDCOT and subcloning into the AatII+EcoRV sites of pORE04. The resulting intermediate vector was designated pOIL158. Next, the PAT selectable marker gene under the control of the *Z. mays* Ubiquitin promoter was subcloned into pOIL158. To this end, pOIL141 was first digested with NotI, treated with Klenow fragment of DNA polymerase I and finally digested with AscI. The resulting fragment was inserted into the AscI+ZraI sites of pOIL158, resulting in pOIL159. The original RK2 oriV origin of replication in pOIL159 was exchanged for the RiA4 origin by SwaI+SpeI restriction digestion of pJP3416, followed by subcloning into the SwaI+AvrII sites of pOIL159. The resulting vector was designated pOIL160. A 10.019 kb 'Monocot senescence part1' fragment containing the following expression cassettes was synthesized: *O. sativa* Actin1::*A. thaliana* DGAT1, codon optimized for *Z. mays* expression, *Z. mays* SEE1::*Z. mays* WRI1, *Z. mays* SEE1::*Z. mays* LEC1. This fragment was subcloned as a SpeI-EcoRV fragment into the SpeI-StuI sites of pOIL160, resulting in pOIL161. A second 7.967 kb 'Monocot senescence part2' fragment was synthesized and contains the following elements: MAR, *Z. mays* Ubiquitin::hpRNAi fragment targeted against *S. bicolor/T. aestivum* SDP1, empty cassette under the control of the *O. sativa* Actin1 promoter. The sequences of two *S. bicolor* SDP1 TAG lipases (Accession Nos. XM_002463620; SEQ ID NO:233 and XM_002458486; SEQ ID NO:169) and one *T. aestivum* SDP1 sequence (Accession No. AK334547) (SEQ ID NO: 234) were obtained by a BLAST search with the *A. thaliana* SDP1 sequence (Accession No. NM_120486). A synthetic hairpin construct (SEQ ID NO:235) was designed including four fragments (67 bp, 90 bp, 50 bp, 59 bp) of the *S. bicolor* XM_002458486 sequence that showed highest degree of identity with the *T. aestivum* SDP1 sequence. In addition, a 278 bp fragment originating from the *S. bicolor* XM_002463620 SDP1 lipase was included to increase silencing efficiency against both *S. bicolor* SDP1 sequences. The 'Monocot senescence part2' fragment is subcloned as a BsiWI-EcoRV fragment into the BsiWI-FspI sites of pOIL161. The resulting vector is designated pOIL162.

The genetic constructs pOIL156 pOIL157, pOIL161 and pOIL162 are used to transform *S. bicolor* and *T. aestivum* using *Agrobacterium*-mediated transformation. Transgenic plants are selected for hygromycin resistance and contain elevated levels of TAG and TFA in vegetative tissues compared to untransformed control plants. Such plants are useful for providing feed for animals as hay or silage, as well as producing grain, or may be used to extract oil.

Further genetic constructs are made for expression of combinations of polypeptides in leaves and stems of monocotyledonous plants, including the C4-photosynthesis plants *S. bicolor* and *Z. mays*. Several constructs are made containing genes for expression of WRI1, DGAT and oleosin, with each gene under the control of a constitutive promoter such as a maize Ubiquitin gene promoter or a rice actin gene promoter, and containing an NPTII gene as selectable marker gene. In one particular construct, the WRI1 is sorghum WRI1. In another, the oleosin is SiOleosinL (see Example 17). In other particular constructs, the oleosin gene is replaced with a gene encoding either LDAP2 or LDAP3 from *S. sebiferum* (Example 11). These constructs are used as the "core constructs" for transformation of *S. bicolor* and *Z. mays* and are deployed on their own or in combination with genetic constructs for expression of a hairpin RNA targeting one or more SDP1 genes in sorghum or maize (see above), a construct encoding Lec2 under the control of a SEE1 promoter (senescence specific), or both. Another construct is made comprising three genes, namely for expression of a hairpin RNA targeting the endogenous TGD5 gene to reduce its expression, a FatA fatty acyl thioesterase and a PDAT, which is used to increase the level of TAG and/or the TTQ parameter for plants transformed with this construct.

Example 15. Extraction of Oil

Extraction of Lipid from Leaves

Transgenic tobacco leaves which had been transformed with the T-DNA from pJP3502 were harvested from plants grown in a glasshouse during the summer months. The leaves were dried and then ground to 1-3 mm sized pieces prior to extraction. The ground material was subject to soxhlet (refluxing) extraction over 24 hours with selected solvents, as described below. 5 g of dried tobacco leaf material and 250 ml of solvent was used in each extraction experiment.

Hexane Solvent Extraction

Hexane is commonly used as a solvent commercially for oil extraction from pressed oil seeds such as canola, extracting neutral (non-polar) lipids, and was therefore tried first. The extracted lipid mass was 1.47 g from 5 g of leaf material, a lipid recovery of 29% by weight. 1H NMR analysis of the hexane extracted lipid in DMSO was preformed. The analysis showed typical signals for long chain triglyceride fatty acids, with no aromatic products being present. The lipid was then subjected to GCMS for identification of major components. Direct GCMS analysis of the hexane extracted lipid proved to be difficult as the boiling point was too high and the material decomposed in the GCMS. In such situations, a common analysis technique is to first make methyl esters of the fatty acids, which was done as follows: 18 mg lipid extract was dissolved in 1 mL toluene, 3 mL of dry 3N methanolic HCL was added and stirred overnight at 60° C. 5 mL of 5% NaCl and 5 mL of hexane were added to the cooled vial and shaken. The organic layer was removed and the extraction was repeated with another 5 mL of hexane. The combined organic fractions were neutralized with 8 mL of 2% KHCO3, separated and dried with Na2SO4. The solvent was evaporated under a stream of N2 and then made up to a concentration of 1 mg/mL in hexane for GCMS analysis. The main fatty acids present were 16:0 (palmitic, 38.9%) and 18:1 (oleic, 31.3%).

| FA | 16:0 | 16:1 | 18:0 | 18:1 | 18:2 | 20:0 | 22:0 |
|---|---|---|---|---|---|---|---|
| % wt | 38.9 | 4.6 | 6.4 | 31.3 | 2.5 | 1.5 | 0.6 |

Acetone Solvent Extraction

Acetone was used as an extraction solvent because its solvent properties should extract almost all lipid from the leaves, i.e. both non-polar and polar lipids. The acetone extracted oil looked similar to the hexane extracted lipid. The extracted lipid mass was 1.59 g from 5 g of tobacco leaf, i.e. 31.8% by weight. 1H NMR analysis of the lipid in DMSO was performed. Signals typical of long chain triglyceride fatty acids were observed, with no signal for aromatic products.

Hot Water Solvent Extraction

Hot water was attempted as an extraction solvent to see if it was suitable to obtain oil from the tobacco leaves. The water extracted material was gel like in appearance and gelled when cooled. The extracted mass was 1.9 g, or 38% by weight. This material was like a thick gel and was likely to have included polar compounds from the leaves such as sugars and other carbohydrates. The 1H NMR analysis of the material in DMSO was preformed. The analysis showed typical signals for long chain triglyceride fatty acids, with no aromatic products being extracted. The left over solid material was extracted with hexane, yielding 20% of lipid by weight, indicating that the water extraction had not efficiently extracted non-polar lipids.

Ethanol Solvent Extraction

Ethanol was used as an extraction solvent to see if it was suitable to obtain oil from the tobacco leaves. The ethanol extracted lipid was similar in appearance to both the water- and hexane-extracted lipid, being yellow-red in colour, had a gel-like appearance and gelled when cooled. The extracted lipid mass was 1.88 g from 5 g tobacco, or 37.6% by weight. The ethanol solvent would also have extracted some of the polar compounds in the tobacco leaves.

Ether Solvent Extraction

Diethyl ether was attempted as an extraction solvent since it was thought that it might extract less impurities than other solvents. The extraction yielded 1.4 g, or 28% by weight. The ether extracted lipid was similar to the hexane extracted material in appearance, was yellowish in colour, and it did appeared a little cleaner than the hexane extract. While the diethyl ether extraction appeared to have given the cleanest oil, the NMR analysis showed a mixture of more organic compounds.

Example 16. Feed Rations for Dairy Cows

Leaves and stems from sorghum or corn plants comprising increased TAG and TFA contents are harvested and chopped into pieces 1-2 cm in size. The processed plant parts are ensiled for at least two weeks and then mixed with other components to produce a feedstuff for dairy cows. The feed mixture for dairy cows comprises: 7.5-10 kg of sorghum or corn silage comprising increase TAG and TFA, 4-5 kg of alfalfa hay, 1 kg brewers grain (about 67% digestible dry matter), 1-2 kg seed meal (canola or soy) or cottonseed, 0.5 kg molasses and mineral supplements such as calcium, phosphorus, magnesium and sulfur. Lipid is optimally present at 5-7% of the total dry matter. Additional amino acids such as lysine and methionine or non-protein nitrogen supplies such as urea may be added, depending on the total protein content. The feedstuff has increased energy density, increased feed value, increased nutritive value and increased digestibility relative to a corresponding feedstuff made with an equivalent amount of wild-type sorghum or corn silage. The increased lipid in the high-oil sorghum or corn silage results in an additional milk production of up to 3 litres per day and an increase of 0.33% in milk fat for each kilogram of lipid eaten.

A heifer will eat the equivalent of about 2.3% of her body weight daily and an adult dry cow will eat the equivalent of about 1.5% of her body weight daily. For example, a 300 kg heifer can eat up to 7 kg dry matter and an adult, dry cow weighing 470 kg will eat about the same amount. Lactating cows have greater feed intakes, up to about 4% of body weight per day. Indeed, feed intake on a weight basis tends to increase with feed quality and palatability.

Example 17. Expression of Oil Body Proteins in Plant Vegetative Tissues

A protein coding region encoding a *Rhodococcus opacus* TadA lipid droplet associated protein (MacEachran et al. 2010; Accession number HM625859), codon optimized for expression in dicotyledonous plants such as *Nicotiana benthamiana*, was synthesised as a NotI-SpeI DNA fragment. The fragment was inserted downstream of the 35S promoter in pJP3343 using the NotI-SpeI sites. The resultant plasmid was designated pOIL380. A protein coding region encoding a *Sesame indicum* OleosinL lipid droplet associated protein (Tai et al. 2002; Accession number AF091840; SEQ ID NO:305) was synthesised as a NotI-SacI DNA fragment and inserted downstream of the 35S promoter in pJP3343 using the same sites. The resultant plasmid was designated pOIL382. A protein coding region encoding a *Sesame indicum* OleosinH1 lipid droplet associated protein (Tai et al., 2002; Accession number AF302807) was synthesised as a NotI-SacI DNA fragment and cloned downstream of the 35S promoter in pJP3343 using the same sites. The resultant plasmid was designated pOIL383. A variant of the protein coding region encoding *S. indicum* OleosinH1 having three amino acid substitutions to remove ubiquitination sites (K130R, K143R, K145R) (Hsiao and Tzen, 2011) was generated by targeted mutagenesis. The coding region was inserted downstream of the 35S promoter in pJP3343 as a NotI-SacI fragment. The resultant plasmid was designated pOIL384. A protein coding region encoding a *Vanilla planfolia* leaf OleosinU1 lipid droplet associated protein (Huang and Huang, 2016; Accession number SRX648194) was codon optimized for expression in *N. benthamiana*, synthesised as a SpeI-EcoRI DNA fragment and inserted downstream of the 35S promoter in pJP3343 using the same sites. The resultant plasmid was designated pOIL386. A protein coding region encoding a *Persea americana* mesocarp OleosinM lipid droplet associated protein (Huang and Huang 2016; Accession number SRX627420) was codon optimized for expression in *N. benthamiana*, synthesised as a SpeI-EcoRI DNA fragment and inserted downstream of the 35S promoter in pJP3343 using the same restriction sites. The resultant plasmid was designated pOIL387. A protein coding region encoding an *Arachis hypogaea* Oleosin 3 lipid droplet associated protein (Parthibane et al., 2012a; Accession number AY722696) was codon optimized for expression in *N. benthamiana*, flanked by NotI sites and inserted into the binary expression vector pJP3502. The resulting plasmid, pOIL041, was digested with NotI and the resultant 520 bp DNA fragment was inserted downstream of the 35S promoter of pJP3343. The resultant plasmid was designated pOIL190. Similarly, the protein coding region for the *A. thaliana* Caleosin3 lipid droplet associated protein (Shen et al., 2014; Laibach et al., 2015; Accession number AK317039) was codon optimized for expression in *N. benthamiana*, flanked by NotI sites and inserted into pJP3502. The resulting plasmid, pOIL042, was digested with NotI and the resulting 604 bp DNA fragment was inserted downstream of the 35S promoter of pJP3343. The resultant plasmid was designated pOIL191. A protein coding region encoding an *A. thaliana* steroleosin lipid droplet associated protein (Accession number AT081653) was codon optimized for expression in *N. benthamiana*, flanked by NotI sites and inserted into pJP3502. The resultant plasmid, pOIL043, was digested with NotI and the resultant 1069 bp DNA fragment was inserted downstream of the 35S promoter of pJP3343. The resultant plasmid was designated pOIL192. A protein coding region encoding a *Nannochloropsis oceanica* LSDP oil body protein (Vieler et al., 2012; Accession number JQ268559) was codon optimized for expression in *N. benthamiana*, flanked by NotI sites and inserted into the pJP3502 binary expression vector. The resultant plasmid, pOIL044, was digested with NotI and the 496 bp DNA fragment was inserted downstream of the 35S promoter of pJP3343. The resultant plasmid was designated pOIL193. A protein coding region encoding a *Trichoderma reesei* HFBI hydrophobin (Linder et al., 2005; Accession number Z68124) was codon optimized for expression in *N. benthamiana*, flanked by NotI sites and inserted into pJP3502. The resultant plasmid, pOIL045, was digested with NotI and the 313 bp DNA fragment was inserted downstream of the 35S promoter of pJP3343. The resultant plasmid was designated pOIL194. An ER-targeted variant of the *Trichoderma reesei* HFBI hydrophobin was created by amending the KDEL ER retention peptide to the C-terminus (Gutierrew et al., 2013). This variant was codon optimized for expression in *N. benthamiana* and cloned as a NotI fragment into pJP3502, resulting in pOIL046. Subsequently, pOIL046 was digested with NotI and the 325 bp fragment was inserted into pJP3343. The resulting vector was designated pOIL195.

Each of the genetic constructs encoding the lipid droplet associated polypeptides were introduced into *N. benthamiana* leaves in combination with genetic constructs encoding WRI1, DGAT1 and p19 as described in Example 1 with some minor modifications. *Agrobacterium tumefaciens* cultures containing the gene coding for the p19 silencing suppressor protein and the chimeric genes of interest were mixed such that the final OD600 of each culture was equal to 0.125 prior to infiltration. Samples being compared were located on the same leaf. After infiltration, *N. benthamiana* plants were grown for a further five days before leaf discs were harvested, pooled across three leaves from the same plant, freeze-dried, weighed and stored at −80° C. Total lipids were extracted from freeze-dried tissues using chloroform:methanol:0.1 M KCl (2:1:1 v/v/v) and aliquots loaded on a thin layer chromatography (TLC) plate and developed in hexane:diethyl ether:acetic acid (70:30:1, v/v/v). TAG was recovered, converted to FAME in the presence of a known amount of triheptadecanoin (Nu-Chek PREP, Inc. USA) as internal standard for lipid quantitation, and analysed by GC-FID.

The assays showed a range of TAG levels compared to the WRI1+DGAT1 control. Some constructs encoding lipid droplet associated polypeptides increased the TAG level relative to the control in some assays whereas others did not. A consistent and statistically significant increase in TAG content was observed when the construct expressing SiOleosinL (pOIL382) was introduced (FIG. 20); this construct was superior to all the others tested in these assays. An increase in the levels of C18:2 and C18:1 and a decrease in C16:0 was also observed in the TAG for this construct, relative to the p19+WRI1+DGAT1 control (FIG. 20). Microscopic analyses to visualize lipid droplets in the leaf cells expressing SiOleosinL showed a decrease in lipid droplet size and an increase in abundance compared to the control.

Further assays were carried out using radiolabelled [14C]-acetate to measure the rate of TAG synthesis for the different gene combinations including each of the lipid droplet associated polypeptides. The [14C]-acetate was infiltrated into the same leaf tissues at 3 days post-infiltration of the genetic constructs i.e. after the genes had been expressed for three days. Three hours later, leaf discs were harvested and total lipids in the tissues were extracted and fractionated by TLC. The amount of radioactivity in different lipid types was quantitated using a Fujifilm FLA-5000 phosphorimager. These assays demonstrated an increase in TAG synthesis rates in the leaves expressing SiOleosinL (pOIL382) as well as an increase in PC and PA synthesis rates over the three hours in leaves expressing SiOleosinL. In contrast, the genetic constructs encoding SiOleosinH, vanilla leaf and avocado mesocarp oleosins did not show a significant effect on TAG synthesis rate or content.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Alemanno et al. (2008) Planta 227:853-866.
Almeida and Allshire (2005) TRENDS Cell Biol. 15:251-258.
Alonso et al. (2009) Plant Cell 21: 1747-1761.
Alonso et al. (2010) Green Chem. 12:1493-1513.
Alvarez et al. (2000) Theor. Appl. Genet. 100:319-327.
Andre at al (2012) Proc. Natl. Acad. Sci. U.S.A. 109:10107-10112.
Andrianov et al. (2010) Plant Biotech. J. 8:277-287.
Awai et al (2006) Biochem. Soc. Trans. 34:395-398.
Bartlett et al. (2008) Plant Methods 4:22.
Bates (2016). Biochim et Biophys Acta 1961:1214-1225.
Bates and Browse (2011). Plant J. 68:387-399.
Baud et al. (2007) Plant J. 50:825-838.
Baud and Lepiniec (2010) Progr. Lipid Res. 49: 235-249.
Baumlein et al. (1991) Mol. Gen. Genet. 225:459-467.
Baumlein et al. (1992) Plant J. 2:233-239.
Belide et al. (2013) Plant Cell Tiss. Org. Cult. DOI 10.1007/s11240-013-0295-1.
Ben Saad et al. (2011) Transgenic Res 20: 1003-1018.
Benning et al (2008) Prog. Lipid Res. 47:381-389.
Benning et al (2009) J. Biol. Chem 284:17420-17427.
Bibikova et al. (2002) Genetics 161:1169-1175.
Bihmidine et al. (2015) BMC Plant Biology 15:186.
Bihmidine et al. (2016) Plant Signaling & Behaviour 11: e1117721.
Bligh and Dyer (1959) Canadian Journal of Biochemistry and Physiology 37:911-917.
Bourque (1995) Plant Sci. 105:125-149.
Boutilier et al. (2002) Plant Cell 14:1737-1749.
Bouvier-Nave et al. (2000) European Journal of Biochemistry/FEBS 267:85-96.
Bradford (1976) Anal. Biochem. 72:248-254.
Braun & Slewinski (2010), Plant Physiol 153: 1940.
Broothaerts et al. (2005) Nature 433:629-633.
Broun et al. (1998) Plant J. 13:201-210.
Browse et al. (1986) Biochem J 235: 25-31.
Buchanan-Wollaston (1994) Plant Physiol. 105:839-846.
Busk et al. (1997) Plant J. 11:1285-1295.
Cao et al. (2007) J. Lipid Res. 48:583-591.
Capuano et al. (2007) Biotechnol. Adv. 25:203-206.
Chen et al (2011) Plant Physiol. 155:851-865.
Chikwamba et al. (2003) Proc. Natl. Acad. Sci. U.S.A. 100:11127-11132.
Christie (1993) Advances in Lipid Methodology-Two, Oily Press, Dundee, pp 195-213.
Chung et al. (2006) BMC Genomics 7:120.
Comai et al. (2004) Plant J 37: 778-786.
Cong et al. (2013) Science 339:819-823.
Corrado and Karali (2009) Biotechnol. Adv. 27:733-743.
Coutu et al. (2007) Transgenic Res. 16:771-781.
Dahlqvist et al. (2000), Proc. Natl. Acad. Sci. U.S.A. 97: 6487-6492.
Damaj et al., (2010) Planta 231:1439-1458.
Dandik and Aksoy (1998) Fuel Process Technol. 57: 81-92.
Dauk et al (2007) Plant Sci. 173:43-49.
Dulermo and Nicaud (2011) Metab. Eng. 13:482-491.
Durrett et al. (2008) Plant J. 54:593-607.
Dyer et al. (2002) Plant Physiol. 130:2027-2038.
Eastmond et al. (2006) Plant Cell 18: 665-675.
Ellerstrom et al. (1996) Plant Mol. Biol. 32:1019-1027.
Endalew et al. (2011) Biomass and Bioenergy 35:3787-3809.
Fan et al. (2013) Plant Cell 25: 3506-3518.
Fan et al. (2013) Plant Journal 76: 930-942.
Fan et al. (2014) Plant Cell 26: 4119-4134.
Fan et al. (2015) Plant Cell 27: 2941-2955.
FAO Animal Production and Health Proceedings (2002) Protein sources for the animal feed industry, Expert Consultation and Workshop, Bangkok.
Feeney et al. (2012) Plant Physiol 162: 1881-1896.
Finkelstein et al. (1998) Plant Cell 10:1043-1054.
Froissard et al. (2009) FEMS Yeast Res 9:428-438.
Gan (1995) Molecular characterization and genetic manipulation of plant senescence.
PhD thesis. University of Wisconsin, Madison.
Gan and Amasino (1995) Science 270:1986-1988.
Gazzarrini et al. (2004) Dev. Cell 7:373-385.
Ghosal et al. (2007) Biochimica et Biophysica Acta 1771: 1457-1463.
Ghosh et al. (2009) Plant Physiol. 151:869-881.
Gidda et al (2013) Plant Signaling Behav. 8:e27141.
Girijashankar and Swathisree, (2009) Physiol. Mol. Biol. Plants 15: 287-302.
Gong and Jiang (2011) Biotechnol. Lett. 33:1269-1284.
Gould et al. (1991) Plant Physiol. 95:426-434.
Greenwell et al. (2010) J. R. Soc. Interface 7:703-726.
Guan et al. (2015) Lipids 50:407-416.
Gurel et al. (2009) Plant Cell Rep. 28:429-444.
Gutierrez et al. (2013) BMC Biotechnol. 13: 40.
Hedrich et al. (2015) Curr Opin Plant Biol 25: 63-70.
Hershey and Stoner (1991) Plant Mol. Biol. 17:679-690.
Hinchee et al. (1988) Biotechnology 6:915-922.
Horn et al. (2007) Euphytica 153:27-34.
Hong et al. (2016). Progr Lipid Res 62:55-74.
Horn et al. (2013). Plant Physiol 162:1926-1936.
Horvath et al. (2000) Proc. Natl. Acad. Sci. U.S.A. 97:1914-1919.
Hsiao and Tzen (2011) Plant Physiol. Biochem. 49: 77-81.
Hu et al. (2012) Plant Physiol. 158:1944-1954.
Huang (1996) Plant Physiol. 110:1055-1061.
Huang et al. (2010). In Vitro Biology Meeting and IAPB 12th World Congress 2010, S93-S211
Huang and Huang (2016) Plant Physiol. 171: 1867-1878.
Ichihara et al (1988) Biochim. Biophys. Acta 958:125-129.
Ikeda et al. (2006) Pl Biotech J. 23: 153-161.
Iwabuchi et al. (2003) J. Biol. Chem. 278:4603-4610.
James et al. (2010) Proc. Natl. Acad. Sci. USA 107:17833-17838.
Jepson et al. (1994) Plant Mol. Biol. 26:1855-1866.
Jiang, et al. (2013) Nucleic Acids Research 41(20) e188.
Jolivet et al. (2014) Plant Physiol. Biochem. 42:501-509.
Jones et al. (1995) Plant Cell 7: 359-371.
Karmakar et al. (2010) Bioresource Technology 101:7201-7210.
Kelly et al. (2011) Plant Physiol. 157: 866-875.
Kelly et al (2013a) Plant Biotech. J. 11:355-361.
Kelly et al. (2013b) Plant Physiol. 162:1282-1289.
Kereszt et al. (2007) Nature Protocols 2:948-952.
Kim et al. (1996) Proc. Natl. Acad. Sci. USA 93:1156-1160.
Kim et al. (2016), Plant Physiol 171: 1951-1964.

Klemens et al. (2013) Plant Physiol 163: 1338-1352.
Koziel et al. (1996) Plant Mol. Biol. 32:393-405.
Kuhn et al. (2009) J. Biol. Chem. 284:34092-102.
Kunst et al. (1988) Proc. Natl. Acad. Sci. U.S.A. 85:4143-4147.
Kwong et al. (2003) Plant Cell 15:5-18.
Lacroix et al. (2008) Proc. Natl. Acad. Sci. U.S.A. 105: 15429-15434.
Laemmli (1970) Nature 227: 680-685.
Laibach et al. (2015). J. Biotechnol. 201: 15-27.
Lardizabal et al. (2008) Plant Physiol. 148: 89-96.
Larkin et al. (1996) Transgenic Res. 5:325-335.
Lebrun et al. (1987) Nucl. Acids Res. 15:4360.
Laux et al. (1996) Development 122: 87-96.
Lazo et al. (1991) Bio/Technology 9:963-967.
Lee et al. (1998) Science 280:915-918.
Lee et al., (2003) Proc. Natl. Acad. Sci. U.S.A. 100:2152-2158.
Li-Beisson et al (2013)_The *Arabidopsis* Book, 2013.
Li et al. (1996) FEBS Lett. 379:117-121.
Li et al. (2006) Phytochemistry 67: 904-915.
Li et al. (2016). *Inter. J. Agric. Biol.* doi: 10.17957/IJAB/15.0075.
Lin et al. (2005) Plant Physiol. Biochem. 43:770-776.
Linder et al. (2005). FEMS Microbiol. Rev. 29: 877-896.
Liu and Godwin (2012). *Plant Cell Reports* 31, 999-1007.
Liu et al. (2010) Plant Physiol. Biochem. 48: 9-15.
Liu et al. (2012) J Exp Bot 63: 3727-3740.
Liu et al. (2014) BMC Plant Biol. 14: 73.
Liu et al. (2015). *South African Journal of Botany* 98, 157-160.
Liu et al. (2015b). Plant Cell 27:1512-1528.
Lotan et al. (1998) Cell 93: 1195-1205.
Lu et al (2007)_J. Biol. Chem. 282: 35945-35953.
Lu et al. (2009) Proc Natl Acad of Sci USA 106:18837-18842.
Luerssen et al. (1998) Plant J. 15: 755-764.
Lui et al. (2009) J. Agric. Food Chem. 57: 2308-2313.
Ma et al. (2016) Plant Journal doi: 10.1111/tpj.13244.
MacEachran et al. (2010). Appl. Environ. Microbiol. 76: 7217-7225.
Maher and Bressler (2007) Bioresource Technology 98:2351-2368.
Matsuoka et al. (1994) Plant J. 6:311-319.
Matsuoka and Minami (1989) Eur. J. Biochem. 181: 593-598.
McCleary et al. (2013) J AOAC Int 93:221-233.
McCleary et al. (2015) Starch 67:860-883.
McElroy et al. (1990) Plant Cell 2: 163-171.
McKinley et al. (2016) Plant Journal: doi:10.1111/tpj.13269.
Meier et al. (1997) FEBS Lett. 415:91-95.
Millar and Waterhouse (2005). Funct Integr Genomics 5:129-135.
Miller (1984). *Crop Sci* 24:1224-1224.
Mizuno et al., (2016) Biotechnol Biofuels 9: 127.
Mojica et al. (2000) Mol Microbiol 36:244-246.
Mongrand et al. (1998) Phytochemistry 49:1049-1064.
Morelle et al., (2005). Eukaryot Cell 4:1308-1316.
Moreno-Perez (2012) PNAS 109:10107-10112.
Moyle and Birch (2013) Theor. Appl. Genet. 126:1775-1782.
Mu et al. (2008) Plant Physiol. 148:1042-1054.
Mudge et al., (2013) Plant Biotechnol. J. 11:502-509.
Murashige and Skoog (1962). *Physiol Plant* 15:473-497.
Murphy et al. (2012). Protoplasma 249:541-585.
Naim et al. (2012) PLoS One 7: e52717.
Nakamura et al., (2005). J Biol Chem 280:7469-7476.
Needleman and Wunsch (1970) J. Mol Biol. 45: 443-453.
Nilsson et al. (2012) Physiol. Plantarum 144: 35-47.
Nishida et al (1993) Plant Mol. Biol. 21:267-277.
Nomura et al. (2000) Plant Mol. Biol. 44: 99-106.
Ohlrogge and Browse (1995) Plant Cell 7: 957-970.
Padidam (2003) Curr. Opin. Plant Biol. 6:169-77.
Padidam et al. (2003) Transgenic Res. 12:101-9.
Parthibane et al. (2012a) J. Biol. Chem. 287:1946-1965.
Parthibane et al. (2012b) Plant Physiol. 159:95-104.
Pasquinelli et al. (2005). Curr. Opin. Genet. Develop. 15:200-205.
Pearson and Lipman (1988) Proc. Natl. Acad. Sci. USA 85:2444-2448.
Perez-Vich et al. (1998) J.A.O.C.S. 75:547-555.
Perrin et al. (2000) Mol. Breed. 6:345-352.
Petrie et al. (2012) PLOS One 7: e35214.
Phillips et al. (2002) Journal of Food Composition and Analysis 12:123-142.
Pokotylo et al., 2013. Progr Lipid Res. 52:62-79.
Potenza et al. (2004) In Vitro Cell Dev. Biol. Plant 40:1-22.
Prosky et al. (1985) J AOAC Chem 68:677-679.
Qazi et al. (2012) Journal of Plant Physiology 169: 605-613.
Qiu et al. (2001) J. Biol. Chem. 276:31561-3156.
Robson et al. (2004) Plant Biotechnol J 2:101-112.
Rossell and Pritchard (1991) *Analysis of Oilseeds, Fats and Fatty Foods*. Elsevier
Roston et al (2012) J. Biol. Chem. 287:21406-21415.
Ruuska et al. (2002) Plant Cell 14:1191-1206.
Saha et al. (2006) Plant Physiol. 141:1533-1543.
Sanjaya et al. (2011) Plant Biotechnol J 9:874-883.
Santos-Mendoza et al. (2005) FEBS Lett. 579:4666-4670.
Santos-Mendoza et al. (2008) Plant J. 54:608-620.
Schneider et al. (2012) Plant Biol 14: 325-336.
Schnurr et al. (2002) Plant Physiol 129:1700-1709.
Scott et al. (2010) Plant Biotechnol. J. 8:912-27.
Shaw et al. (1959) J Soil Sci 10:316-326.
Shen et al. (2010) Plant Phys. 153: 980-987.
Shen et al. (2014). Biochem. Biophys. Res. Comm. 448: 365-371.
Semwal et al. (2011) Bioresource Technology 102:2151-2161.
Senior (1998) Biotech. Genet. Engin. Revs. 15:79-119.
Shen et al. (2010) Plant Physiol. 153:980-987.
Shiina et al. (1997) Plant Physiol. 115:477-483.
Shimada and Hara-Nishimura (2010) Biol. Pharm. Bull. 33:360-363.
Shimada et al. (2014) Plant Physiol. 164:105-118.
Shockey et al. (2002) Plant Physiol 129:1710-1722.
Singh et al., (2013). PLoS One 8, e62494.
Slade and Knauf (2005) Transgenic Res. 14: 109-115.
Slocombe et al. (2009) Plant Biotechnol. J. 7: 694-703.
Smith et al. (2000) Nature 407:319-320.
Somerville et al. (2000) Lipids. In BB Buchanan, W Gruissem, R L Jones, eds, Biochemisty and Molecular Biology of Plants. American Society of Plant Physiologists, Rockville, MD, pp 456-527.
Srinivasan et al. (2007) Planta 225:341-51.
Stalker et al. 1988 Science 242: 419-423.
Stone et al. (2001) Proc. Natl. Acad. Sci. U.S.A. 98: 11806-11811.
Stone et al. (2008) Proc. Natl. Acad. Sci. U.S.A. 105: 3151-3156.
Tai et al. (2002). Biosci. Biotechnol. Biochem. 66: 2146-2153.
Tan et al. (2011) Plant Physiol. 156:1577-1588.
Taylor (1997) The Plant Cell 9:1245-1249.
Thillet et al. (1988) J. Biol. Chem 263:12500-12508.

Tingay et al. (1997) Plant J. 11:1369-1376.
Titball 1993. Microbiol Rev 57:347-366.
To et al. (2012) Plant Cell 24:5007-5023.
Ulmasov et al. (1995) Plant Physiol. 108:919-927.
van de Loo et al. (1995) Proc Natl Acad Sci USA. 92:6743-6747.
Vanhercke et al. (2013) FEBS Letters 587:364-369.
Vanhercke et al. (2014). Plant Biotech. J. 12:231-239.
Vieler et al. (2012) Plant Physiol. 158:1562-1569.
Voinnet et al. (2003) Plant J. 33:949-956.
Wang and Benning (2012) Plant J 70:614-623.
Wang et al., (2001). Annu Rev Plant Physiol Plant Mol Biol 52:211-231.
Wang et al. (2002) Plant J 32:831-843.
Wang (2005). Plant Physiol 139:566-573.
Waterhouse et al. (1998). Proc. Natl. Acad. Sci. U.S.A. 95:13959-13964.
Weissbach and Weissbach, (1989) Methods for Plant Mol Biol, Academic Press.
Weissbach et al., In: Methods for Plant Molecular Biology, Academic Press, San Diego, Calif., (1988).
Winichayakul et al. (2013) Plant Physiol. 162:626-639.
Wood et al. (2009) Plant Biotech. J. 7: 914-924.
Wormit et al. (2006) Plant Cell 18: 3476-3490.
Wright et al. (2006) Methods Mol Biol. 343:120-135.
Wu et al. (2014) In Vitro Cellular and Dev. Biol.-Plant 50:9-18.
Xie et al. (2014) Mol. Plant 7:923-926.
Xu et al (2010) Plant and Cell Physiol. 51:1019-1028.
Xu et al (2005) Plant Cell 17:3094-3110.
Xu et al (2008) Plant Cell 20:2190-2204.
Yamagishi et al. (2005) Pl Physiol 139: 163-173.
Yamasaki et al. (2004) Plant Cell 16:3448-3459.
Yang et al. (2003) Planta 216:597-603.
Yang et al. (2010) Proc. Natl. Acad. Sci. U.S.A. 107:12040-12045.
Yen et al. (2002) Proc. Natl. Acad. Sci. U.S.A. 99:8512-8517.
Yen et al. (2005) J. Lipid Res. 46: 1502-1511.
Yokoyama et al. (1994) Mol Gen Genet 244: 15-22.
Zale et al. (2016), Plant Biotech. J. 14: 661-669.
Zheng et al. (2009) Pl Physiol 21: 2563-2577.
Zienkiewicz et al. (2017) Biotechnology for Biofuels 10 doi:http://dx.doi.org/10.1186/s13068-016-0686-8
Zolman et al (2001) Plant Physiol. 127:1266-1274.
Zulu et al. (2017) Biotechnology for Biofuels, 10 doi:https://doi.org/10.1186/s13068-017-0874-1.

---

The invention claimed is:

1. A process for producing extracted lipid, the process comprising the steps of:
   i) harvesting vegetative plant parts from a transgenic *Sorghum* species plant or a transgenic *Zea mays* plant, the vegetative plant parts being transgenic for at least (a) a first exogenous polynucleotide which encodes a plant Wrinkled 1 (WRI1) polypeptide operably linked to a heterologous promoter which is effective to direct expression of the first exogenous polynucleotide in the *Sorghum* species or *Zea mays* vegetative plant parts and increase the level of the WRI1 polypeptide relative to a corresponding wild-type vegetative plant part, and (b) a second exogenous polynucleotide which encodes a plant diacylglycerol acyltransferase (DGAT) polypeptide operably linked to a heterologous promoter which is effective to direct expression of the second exogenous polynucleotide in the *Sorghum* species or *Zea mays* vegetative plant parts and increase the level of the DGAT polypeptide relative to the corresponding wild-type vegetative plant part, whereby the vegetative plant parts comprise a total fatty acid (TFA) content which comprises fatty acids esterified in the form of triacylglycerols (TAG) and fatty acids in the form of lipids other than TAG, wherein the vegetative plant parts comprise a TFA content of between 6% and 20% (w/w dry weight) and a TAG/TFA Quotient (TTQ) of between 0.60 and 0.84, or between 0.84 and 0.95,
   ii) extracting lipid from the vegetative plant parts, and
   iii) recovering the extracted lipid,
   thereby producing the extracted lipid.

2. The process of claim 1, wherein the vegetative plant parts are further transgenic for at least an exogenous polynucleotide which encodes an RNA molecule which is complementary to a portion of an mRNA molecule encoding an endogenous Sugar Dependent 1 (SDP1) TAG lipase polypeptide and which down-regulates production of the endogenous SDP1 TAG lipase polypeptide in the *Sorghum* species or *Zea mays* vegetative plant parts, wherein the exogenous polynucleotide is operably linked to a heterologous promoter which is effective to direct expression of the exogenous polynucleotide in the *Sorghum* species or *Zea mays* vegetative plant parts and the RNA molecule down-regulates production of the endogenous SDP1 TAG lipase polypeptide relative to the corresponding wild-type vegetative plant part.

3. The process of claim 1, wherein the vegetative plant parts have a TTQ of between 0.60 and 0.84.

4. The process of claim 1, wherein the vegetative plant parts have a TTQ of between 0.84 and 0.95.

5. The process of claim 1, wherein the vegetative plant parts are from a transgenic *Sorghum* species plant.

* * * * *